(12) United States Patent
Konthur et al.

(10) Patent No.: US 9,052,312 B2
(45) Date of Patent: Jun. 9, 2015

(54) BIOMARKER FOR THE PREDICTION OF RESPONSIVENESS TO AN ANTI-TUMOUR NECROSIS FACTOR ALPHA (TNF) TREATMENT

(75) Inventors: Zoltán Konthur, Berlin (DE); Hans Lehrach, Berlin (DE); Karl Skriner, Berlin (DE)

(73) Assignee: Max-Planck-Gesellschaft zur Förderung der Wissenschaften e.V., München (DE)

( * ) Notice: Subject to any disclaimer, the term of this patent is extended or adjusted under 35 U.S.C. 154(b) by 924 days.

(21) Appl. No.: 12/740,166

(22) PCT Filed: Oct. 31, 2008

(86) PCT No.: PCT/EP2008/064820
§ 371 (c)(1),
(2), (4) Date: Oct. 22, 2010

(87) PCT Pub. No.: WO2009/056633
PCT Pub. Date: May 7, 2009

(65) Prior Publication Data
US 2011/0045490 A1 Feb. 24, 2011

(30) Foreign Application Priority Data
Oct. 31, 2007 (EP) .................................... 07119810

(51) Int. Cl.
G01N 33/53 (2006.01)
G01N 33/564 (2006.01)
G01N 33/68 (2006.01)

(52) U.S. Cl.
CPC .......... *G01N 33/564* (2013.01); *G01N 33/6854* (2013.01); *G01N 33/6863* (2013.01); *G01N 2333/82* (2013.01); *G01N 2333/91171* (2013.01); *G01N 2333/9121* (2013.01); *G01N 2333/916* (2013.01); *G01N 2800/102* (2013.01); *G01N 2800/52* (2013.01); *G01N 2333/4703* (2013.01); *G01N 2333/705* (2013.01)

(58) Field of Classification Search
None
See application file for complete search history.

(56) References Cited

U.S. PATENT DOCUMENTS

| | | |
|---|---|---|
| 2003/0224486 A1 | 12/2003 | Carman et al. |
| 2003/0228690 A1 | 12/2003 | Baker et al. |
| 2006/0121511 A1 | 6/2006 | Lee et al. |
| 2008/0026485 A1* | 1/2008 | Hueber et al. ............. 436/507 |
| 2011/0045490 A1* | 2/2011 | Konthur et al. ............. 435/7.1 |

FOREIGN PATENT DOCUMENTS

| | | |
|---|---|---|
| WO | WO 02/066045 A2 | 8/2002 |
| WO | WO 2005/014622 A2 | 2/2005 |
| WO | WO 2005/019258 A2 | 3/2005 |
| WO | WO 2007/085240 A1 | 8/2007 |

OTHER PUBLICATIONS

Written Opinion of the International Searching Authority for International Application No. PCT/EP2008/064820, Murielle Giry, pp. 1-15, Apr. 30, 2010.*
Bussow et al. Genomics Apr. 1, 2000; 65(1):1-8.*
Firestein et al., Arthritis & Rheumatism vol. 46, No. 2, Feb. 2002, pp. 298-308.*
Meyer et al., Arthritis Res Ther. 2006; 8(2): R40.*
Leuking et al., Molecular & Cellular Proteomics 4:1382-1390, 2005.*
Horn et al., Proteomics 2006, 6, 605-613.*
Nishimura et al., Ann Intern Med. 2007;146:797-808.*
Verpoort et al., Arthritis & Rheumatism vol. 54, No. 12, Dec. 2006, pp. 3799-3808.*
Braun-Moscovici et al., "Anti-Cyclic Citrullinated Protein Antibodies as a Predictor of Response to Anti-Tumor Necrosis Factor-α Therapy in Patients with Rheumatoid Arthritis", The Journal of Rheumatology, vol. 33, No. 3 (2006), pp. 497-500.
Hueber et al., "Antigen Microarray Profiling of Autoantibodies in Rheumatoid Arthritis", Arthritis & Rheumatism, vol. 52, No. 9 (2005), pp. 2645-2655.
Krenn et al., "Array technology and proteomics in autoimmune diseases", Pathology—Research and Practice, vol. 200, No. 2 (2004), pp. 95-103.
Skriner et al., "Immunomics in Inflammatory Rheumatic Diseases", Annals of the Rheumatic Diseases, vol. 65, No. 1 (2006), pp. A5.
Ho et al., "Tolerizing DNA vaccines for autoimmune arthritis", Autoimmunity, vol. 39, No. 8 (2006), pp. 675-682.
Lequerréet al., "Gene profiling in white blood cells predicts infliximab responsiveness in rheumatoid arthritis", Arthritis Research & Therapy, vol. 8, No. 4 (2006), pp. 1-11.

(Continued)

*Primary Examiner* — Zachary Skelding
(74) *Attorney, Agent, or Firm* — Foley & Lardner LLP

(57) ABSTRACT

The invention refers to a method for diagnosing an individual who is to be subjected to or is being subjected to an anti-tumor necrosis factor alpha (TNFα or TNF) treatment to assess the responsiveness to an anti-TNF treatment which comprises the detection of immunoglobulin(s) against one or more biomarker proteins in a bodily fluid or an excrement of said patient, and sorting the individual into one of two categories based on detection of said immunoglobulin(s), wherein individuals are classified as NON-responder or responder. The invention refers to diagnostic kits comprising said one or more biomarker proteins and the use of these kits for assessing the responsiveness to an anti-TNF treatment of an individual who is to be subjected to or is being subjected to an anti-TNFα treatment.

5 Claims, 126 Drawing Sheets

(56) References Cited

OTHER PUBLICATIONS

Sarah Jesse et al., "Summary of Cerebrospinal Fluid Routine Parameters in Neurodegenerative Diseases," J Neurol (2011) 258, 1034-1041.

Ewa Maria Kratz et al., "Terminal Monosaccharide Screening of Synovial Immunoglobulins G and A for the Early Detection of Rheumatoid Arthritis," Rheumatol Int (2010) 30, 1285-1292.

Yukio Ishiguro et al., "Sensitive Solid Phase Enzyme Immunoassay for Human IgA, Secretory IgA, and Secretory Component," Clinica Chimica Acta (1981), 116, 237-243.

Andrew D. Strand et al., "Gene Expression in Huntington's Disease Skeletal Muscle: A Potential Biomarker," Human Molecular Genetics (2005), 14, 1863-1876.

Jm Woof et al., "Structure and Function Relationships in IgA," Immunology (2011), 4, 590-597.

Xueling Wu et al., "Plasma and Salivary IgA Subclasses and IgM in HIV-1-Infected Individuals," J Clin Immunol (2002) 22, 106-115.

* cited by examiner

Fig. 1

SEQ ID No. 1
RAB11B
>ENSG00000185236|19|protein_coding|ENST00000328024|ENSP00000333547
ATGGGGACCCGGGACGACGAGTACGACTACCTATTCAAAGTGGTGCTCATCGGGGACTCA
GGCGTGGGCAAGAGCAACCTGCTGTCGCGCTTCACCCGCAACGAGTTCAACCTGGAGAGC
AAGAGCACCATCGGCGTGGAGTTCGCCACCCGCAGCATCCAGGTGGACGGCAAGACCATC
AAGGCGCAGATCTGGGACACCGCTGGCCAGGAGCGCTACCGCGCCATCACCTCCGCGTAC
TACCGTGGTGCAGTGGGCGCCCTGCTGGTGTACGACATCGCCAAGCACCTGACCTATGAG
AACGTGGAGCGCTGGCTGAAGGAGCTGCGGGACCACGCAGACAGCAACATCGTCATCATG
CTGGTGGGCAACAAGAGTGACCTGCGCCACCTGCGGGCTGTGCCCACTGACGAGGCCCGC
GCCTTCGCAGAAAAGAACAACTTGTCCTTCATCGAGACCTCAGCCTTGGATTCCACTAAC
GTAGAGGAAGCATTCAAGAACATCCTCACAGAGATCTACCGCATCGTGTCACAGAAACAG
ATCGCAGACCGCGCTGCCCACGACGAGTCCCCGGGGAACAACGTGGTGGACATCAGCGTG
CCGCCCACCACGGACGGACAGAAGCCCAACAAGCTGCAGTGCTGCCAGAACCTGTGA

Fig. 2

SEQ ID No. 2
PPP2R1A
>ENSG00000105568|19|protein_coding|ENST00000391791|ENSP00000375668
ATGAGGACGTTCAGCTTCGCCTCAACAGCATCAAGAAGCTGTCCACCATCGCCTTGGCCC
TTGGGGTTGAAAGGACCCGAAGTGAGCTTCTGCCTTTCCTTACAGATACCATCTATGATG
AAGATGAGGTCCTCCTGGCCCTGGCAGAACAGCTGGGAACCTTCACTACCCTGGTGGGAG
GCCCAGAGTACGTGCACTGCCTGCTGCCTCTTCTCCGTCTGCTACCCCGAGTGTCCAGT
GCTGTGAAGGCGGAACTTCGACAGTACTTCCGGAACCTGTGCTCAGATGACACCCCCATG
GTGCGGCGGGCCGCAGCCTCCAAGCTGGGGGAGTTTGCCAAGGTGCTGGAGCTGGACAAC
GTCAAGAGTGAGATCATCCCCATGTTCTCCAACCTGGCCTCTGACGAGCAGGACTCGGTG
CGGCTGCTGGCGGTGGAGGCGTGCGTGAACATCGCCCAGCTTCTGCCCCAGGAGGATCTG
GAGGCCCTGGTGATGCCCACTCTGCGCCAGGCCGCTGAAGACAAGTCCTGGCGCGTCCGC
TACATGGTGGCTGACAAGTTCACAGAGCTCCAGAAAGCAGTGGGGCCTGAGATCACCAAG
ACAGACCTGGTCCCTGCCTTCCAGAACCTGATGAAAGACTGTGAGGCCGAGGTGAGGGCC
GCAGCCTCCCACAAGGTCAAAGAGTTCTGTGAAAACCTCTCAGCTGACTGTCGGGAGAAT
GTGATCATGTCCCAGATCTTGCCCTGCATCAAGGAGCTGGTGTCCGATGCCAACCAACAT
GTCAAGTCTGCCCTGGCCTCAGTCATCATGGGTCTCTCTCCCATCTTGGGCAAAGACAAC
ACCATCGAGCACCTCTTGCCCCTCTTCCTGGCTCAGCTGAAGGATGAGTGCCCTGAGGTA
CGGCTGAACATCATCTCTAACCTGGACTGTGTGAACGAGGTGATTGGCATCCGGCAGCTG
TCCCAGTCCCTGCTCCCTGCCATTGTGGAGCTGGCTGAGGACGCCAAGTGGCGGGTGCGG
CTGGCCATCATTGAGTACATGCCCCTCCTGGCTGGACAGCTGGGAGTGGAGTTCTTTGAT
GAGAAACTTAACTCCTTGTGCATGGCCTGGCTTGTGGATCATGTATATGCCATCCGCGAG
GCAGCCACCAGCAACCTGAAGAAGCTAGTGGAAAAGTTTGGGAAGGAGTGGGCCCATGCC
ACAATCATCCCCAAGGTCTTGGCCATGTCCGGAGACCCCAACTACCTGCACCGCATGACT
ACGCTCTTCTGCATCAATGTGCTGTCTGAGGTCTGTGGGCAGGACATCACCACCAAGCAC
ATGCTACCCACGGTTCTGCGCATGGCTGGGGACCCGGTTGCCAATGTCCGCTTCAATGTG
GCCAAGTCTCTGCAGAAGATAGGGCCCATCCTGGACAACAGCACCTTGCAGAGTGAAGTC
AAGCCCATCCTAGAGAAGCTGACCCAGGACCAGGATGTGGACGTCAAATACTTTGCCCAG
GAGGCTCTGACTGTTCTGTCTCTCGCCTGA

Fig. 3

SEQ ID No. 3
PPP2R1A
>ENSG00000105568|19|protein_coding|ENST00000322088|ENSP00000324804
ATGGCGGCGGCCGACGGCGACGACTCGCTGTACCCCATCGCGGTGCTCATAGACGAACTC
CGCAATGAGGACGTTCAGCTTCGCCTCAACAGCATCAAGAAGCTGTCCACCATCGCCTTG
GCCCTTGGGGTTGAAAGGACCCGAAGTGAGCTTCTGCCTTTCCTTACAGATACCATCTAT
GATGAAGATGAGGTCCTCCTGGCCCTGGCAGAACAGCTGGGAACCTTCACTACCCTGGTG
GGAGGCCCAGAGTACGTGCACTGCCTGCTGCCACCGCTGGAGTCGCTGGCCACAGTGGAG
GAGACAGTGGTGCGGGACAAGGCAGTGGAGTCCTTACGGGCCATCTCACACGAGCACTCG
CCCTCTGACCTGGAGGCGCACTTTGTGCCGCTAGTGAAGCGGCTGGCGGGCGGCGACTGG
TTCACCTCCCGCACCTCGGCCTGCGGCCTCTTCTCCGTCTGCTACCCCGAGTGTCCAGT
GCTGTGAAGGCGGAACTTCGACAGTACTTCCGGAACCTGTGCTCAGATGACACCCCCATG
GTGCGGCGGGCCGCAGCCTCCAAGCTGGGGGAGTTTGCCAAGGTGCTGGAGCTGGACAAC
GTCAAGAGTGAGATCATCCCCATGTTCTCCAACCTGGCCTCTGACGAGCAGGACTCGGTG
CGGCTGCTGGCGGTGGAGGCGTGCGTGAACATCGCCCAGCTTCTGCCCCAGGAGGATCTG
GAGGCCCTGGTGATGCCCACTCTGCGCCAGGCCGCTGAAGACAAGTCCTGGCGCGTCCGC
TACATGGTGGCTGACAAGTTCACAGAGCTCCAGAAAGCAGTGGGGCCTGAGATCACCAAG
ACAGACCTGGTCCCTGCCTTCCAGAACCTGATGAAAGACTGTGAGGCCGAGGTGAGGGCC
GCAGCCTCCCACAAGGTCAAAGAGTTCTGTGAAAACCTCTCAGCTGACTGTCGGGAGAAT
GTGATCATGTCCCAGATCTTGCCCTGCATCAAGGAGCTGGTGTCCGATGCCAACCAACAT
GTCAAGTCTGCCCTGGCCTCAGTCATCATGGGTCTCTCTCCCATCTTGGGCAAAGACAAC
ACCATCGAGCACCTCTTGCCCCTCTTCCTGGCTCAGCTGAAGGATGAGTGCCCTGAGGTA
CGGCTGAACATCATCTCTAACCTGGACTGTGTGAACGAGGTGATTGGCATCCGGCAGCTG
TCCCAGTCCCTGCTCCCTGCCATTGTGGAGCTGGCTGAGGACGCCAAGTGGCGGGTGCGG
CTGGCCATCATTGAGTACATGCCCCTCCTGGCTGGACAGCTGGGAGTGGAGTTCTTTGAT
GAGAAACTTAACTCCTTGTGCATGGCCTGGCTTGTGGATCATGTATATGCCATCCGCGAG
GCAGCCACCAGCAACCTGAAGAAGCTAGTGGAAAAGTTTGGGAAGGAGTGGGCCCATGCC
ACAATCATCCCCAAGGTCTTGGCCATGTCCGGAGACCCCAACTACCTGCACCGCATGACT
ACGCTCTTCTGCATCAATGTGCTGTCTGAGGTCTGTGGGCAGGACATCACCACCAAGCAC
ATGCTACCCACGGTTCTGCGCATGGCTGGGACCCGGTTGCCAATGTCCGCTTCAATGTG
GCCAAGTCTCTGCAGAAGATAGGGCCCATCCTGGACAACAGCACCTTGCAGAGTGAAGTC
AAGCCCATCCTAGAGAAGCTGACCCAGGACCAGGATGTGGACGTCAAATACTTTGCCCAG
GAGGCTCTGACTGTTCTGTCTCTCGCCTGA

Fig. 4

SEQ ID No. 4
KPNB1
>ENSG00000108424|17|protein_coding|ENST00000290158|ENSP00000290158
ATGGAGCTGATCACCATTCTCGAGAAGACCGTGTCTCCCGATCGGCTGGAGCTGGAAGCG
GCGCAGAAGTTCCTGGAGCGTGCGGCCGTGGAGAACCTGCCCACTTTCCTTGTGGAACTG
TCCAGAGTGCTGGCAAATCCAGGAAACAGTCAGGTTGCCAGAGTTGCAGCTGGTCTACAA
ATCAAGAACTCTTTGACATCTAAAGATCCAGATATCAAGGCACAATATCAGCAGAGGTGG
CTTGCTATTGATGCTAATGCTCGACGAGAAGTCAAGAACTATGTTTTGCAGACATTGGGT
ACAGAAACTTACCGGCCTAGTTCTGCCTCACAGTGTGTGGCTGGTATTGCTTGTGCAGAG
ATCCCAGTAAACCAGTGGCCAGAACTCATTCCTCAGCTGGTGGCCAATGTCACAAACCCC
AACAGCACAGAGCACATGAAGGAGTCGACATTGGAAGCCATCGGTTATATTTGCCAAGAT
ATAGACCCAGAGCAGCTACAAGATAAATCCAATGAGATTCTGACTGCCATAATCCAGGGG
ATGAGGAAAGAAGAGCCTAGTAATAATGTGAAGCTAGCTGCTACGAATGCACTCCTGAAC
TCATTGGAGTTCACCAAAGCAAACTTTGATAAAGAGTCTGAAAGGCACTTTATTATGCAG
GTGGTCTGTGAAGCCACACAGTGTCCAGATACGAGGGTACGAGTGGCTGCTTTACAGAAT
CTGGTGAAGATAATGTCCTTATATTATCAGTACATGGAGACATATATGGGTCCTGCTCTT
TTTGCAATCACAATCGAAGCAATGAAAAGTGACATTGATGAGGTGGCTTTACAAGGGATA
GAATTCTGGTCCAATGTCTGTGATGAGGAAATGGATTTGGCCATTGAAGCTTCAGAGGCA
GCAGAACAAGGACGGCCCCCTGAGCACACCAGCAAGTTTTATGCGAAGGGAGCACTACAG
TATCTGGTTCCAATCCTCACACAGACACTAACTAAACAGGACGAAAATGATGATGACGAT
GACTGGAACCCCTGCAAAGCAGCAGGGGTGTGCCTCATGCTTCTGGCCACCTGCTGTGAA
GATGACATTGTCCCACATGTCCTCCCCTTCATTAAAGAACACATCAAGAACCCAGATTGG
CGGTACCGGGATGCAGCAGTGATGGCTTTTGGTTGTATCTTGGAAGGACCAGAGCCCAGT
CAGCTCAAACCACTAGTTATACAGGCTATGCCCACCCTAATAGAATTAATGAAAGACCCC
AGTGTAGTTGTTCGAGATACAGCTGCATGGACTGTAGGCAGAATTTGTGAGCTGCTTCCT
GAAGCTGCCATCAATGATGTCTACTTGGCTCCCCTGCTACAGTGTCTGATTGAGGGTCTC
AGTGCTGAACCCAGAGTGGCTTCAAATGTGTGCTGGGCTTTCTCCAGTCTGGCTGAAGCT
GCTTATGAAGCTGCAGACGTTGCTGATGATCAGGAAGAACCAGCTACTTACTGCTTATCT
TCTTCATTTGAACTCATAGTTCAGAAGCTCCTAGAGACTACAGACAGACCTGATGGACAC
CAGAACAACCTGAGGAGTTCTGCATATGAATCTCTGATGGAAATTGTGAAAAACAGTGCC
AAGGATTGTTATCCTGCTGTCCAGAAAACGACTTTGGTCATCATGGAACGACTGCAACAG
GTTCTTCAGATGGAGTCACATATCCAGAGCACATCCGATAGAATCCAGTTCAATGACCTT
CAGTCTTTACTCTGTGCAACTCTTCAGAATGTTCTTCGGAAAGTGCAACATCAAGATGCT
TTGCAGATCTCTGATGTGGTTATGGCCTCCCTGTTAAGGATGTTCCAAAGCACAGCTGGG
TCTGGGGGAGTACAAGAGGATGCCCTGATGGCAGTTAGCACACTGGTGGAAGTGTTGGGT
GGTGAATTCCTCAAGTACATGGAGGCCTTTAAACCCTTCCTGGGCATTGGATTAAAAAAT
TATGCTGAATACCAGGTTTGTTTGGCAGCTGTGGGCTTAGTGGGAGACTTGTGCCGTGCC
CTGCAATCCAACATCATACCTTTCTGTGACGAGGTGATGCAGCTGCTTCTGGAAAATTTG
GGGAATGAGAACGTCCACAGGTCTGTGAAGCCGCAGATTCTGTCAGTGTTTGGTGATATT
GCCCTTGCTATTGGAGGAGAGTTTAAAAAATACTTAGAGGTTGTATTGAATACTCTTCAG
CAGGCCTCCCAAGCCCAGGTGGACAAGTCAGACTATGACATGGTGGATTATCTGAATGAG
CTAAGGGAAAGCTGCTTGGAAGCCTATACTGGAATCGTCCAGGGATTAAAGGGGGATCAG
GAGAACGTACACCCGGATGTGATGCTGGTACAACCCAGAGTAGAATTTATTCTGTCTTTC
ATTGACCACATTGCTGGAGATGAGGATCACACAGATGGAGTAGTAGCTTGTGCTGCTGGA
CTAATAGGGGACTTATGTACAGCATTTGGGAAGGATGTACTGAAATTAGTAGAAGCTAGG
CCAATGATCCATGAATTGTTAACTGAAGGGCGGAGATCGAAGACTAACAAAGCAAAAACC
CTTGCTACATGGGCAACAAAAGAACTGAGGAAACTGAAGAACCAAGCTTGA

Fig. 5

SEQ ID No. 5
COG4
>ENSG00000103051|16|protein_coding|ENST00000323786|ENSP00000315775
ATGGGGACCAAGATGGCGGACCTTGATTCGCCTCCGAAGCTGTCAGGGGTGCAGCAGCCG
TCTGAGGGGGTGGGAGGTGGCCGCTGCTCCGAAATCTCCGCTGAGCTCATTCGCTCCCTG
ACAGAGCTGCAGGAGCTGGAGGCTGTATACGAACGGCTCTGCGGCGAGGAGAAAGTGGTG
GAGAGAGAGCTGGATGCTCTTTTGGAACAGCAAAACACCATTGAAAGTAAGATGGTCACT
CTCCACCGAATGGGTCCTAATCTGCAGCTGATTGAGGGAGATGCAAAGCAGCTGGCTGGA
ATGATCACCTTTACCTGCAACCTGGCTGAGAATGTGTCCAGCAAAGTTCGTCAGCTTGAC
CTGGCCAAGAACCGCCTCTATCAGGCCATTCAGAGAGCTGATGACATCTTGGACCTGAAG
TTCTGCATGGATGGAGTTCAGACTGCTTTGAGGAGTGAAGATTATGAGCAGGCTGCAGCA
CATACTCATCGCTACTTGTGCCTGGACAAGTCGGTCATTGAGCTCAGCCGACAGGGCAAA
GAGGGGAGCATGATTGATGCCAACCTGAAATTGCTGCAGGAAGCTGAGCAACGTCTCAAA
GCCATTGTGGCAGAGAAGTTTGCCATTGCCACCAAGGAAGGTGATCTGCCCCAGGTGGAG
CGCTTCTTCAAGATCTTCCCACTGCTGGGTTTGCATGAGGAGGGATTAAGAAAGTTCTCG
GAGTACCTTTGCAAGCAGGTGGCCAGTAAAGCTGAGGAGAATCTGCTCATGGTGCTGGGG
ACAGACATGAGTGATCGGAGAGCTGCAGTCATCTTTGCAGATACACTTACTCTTCTGTTT
GAAGGGATTGCCCGCATTGTGGAGACCCACCAGCCAATAGTGGAGACCTATTATGGGCCA
GGGAGACTCTATACCCTGATCAAATATCTGCAGGTGGAATGTGACAGACAGGTGGAGAAG
GTGGTAGACAAGTTCATCAAGCAAAGGGACTACCACCAGCAGTTCCGGCATGTTCAGAAC
AACCTGATGAGAAATTCTACAACAGAAAAAATCGAACCAAGAGAACTGGACCCCATCCTG
ACTGAGGTCACCCTGATGAATGCCCGCAGTGAGCTATACTTACGCTTCCTCAAGAAGAGG
ATTAGCTCTGATTTTGAGGTGGGAGACTCCATGGCCTCAGAGGAAGTAAAGCAAGAGCAC
CAGAAGTGTCTGGACAAACTCCTCAATAACTGCCTTTTGAGCTGTACCATGCAGGAGCTA
ATTGGCTTATATGTTACCATGGAGGAGTACTTCATGAGGGAGACTGTCAATAAGGCTGTG
GCTCTGGACACCTATGAGAAGGGCCAGCTGACATCCAGCATGGTGGATGATGTCTTCTAC
ATTGTTAAGAAGTGCATTGGGCGGGCTCTGTCCAGCTCCAGCATTGACTGTCTCTGTGCC
ATGATCAACCTCGCCACCACAGAGCTGGAGTCTGACTTCAGGGATGTTCTGTGTAATAAG
CTGCGGATGGGCTTTCCTGCCACCACCTTCCAGGACATCCAGCGCGGGGTGACAAGTGCC
GTGAACATCATGCACAGCAGCCTCCAGCAAGGCAAATTTGACACAAAAGGCATCGAGAGT
ACTGACGAGGCGAAGATGTCCTTCCTGGTGACTCTGAACAACGTGGAAGTCTGCAGTGAA
AACATCTCCACTCTGAAGAAGACACTGGAGAGTGACTGCACCAAGCTCTTCAGCCAGGGC
ATTGGAGGGGAGCAGGCCCAGGCCAAGTTTGACAGCTGCCTTTCTGACTTGGCCGCCGTG
TCCAACAAATTCCGAGACCTCTTGCAGGAAGGGCTGACGGAGCTCAACAGCACAGCCATC
AAGCCACAGGTGCAGCCTTGGATCAACAGCTTTTTCTCCGTCTCCCACAACATCGAGGAG
GAAGAATTCAATGACTATGAGGCCAACGACCCTTGGGTACAACAGTTCATCCTTAACCTG
GAGCAGCAAATGGCAGAGTTCAAGGCCAGCCTGTCCCGGTCATCTACGACAGCCTAACC
GGCCTCATGACTAGCCTTGTTGCCGTCGAGTTGGAGAAAGTGGTGCTGAAATCCACCTTT
AACCGGCTGGGTGGTCTGCAGTTTGACAAGGAGCTGAGGTCGCTCATTGCCTACCTTACC
ACGGTGACCACCTGGACCATCCGAGACAAGTTTGCCCGGCTCTCCCAGATGGCCACCATC
CTCAATCTGGAGCGGGTGACCGAGATCCTCGATTACTGGGGACCCAATTCCGGCCCATTG
ACGTGGCGCCTCACCCCTGCTGAAGTGCGCCAGGTGCTGGCCCTGCGGATAGACTTCCGC
AGTGAAGATATCAAGAGGCTGCGCCTGTAG

Fig. 6

SEQ ID No. 6
COG4
>ENSG00000103051|16|protein_coding|ENST00000393612|ENSP00000377236
ATGGCGGACCTTGATTCGCCTCCGAAGCTGTCAGGGGTGCAGCAGCCGTCTGAGGGGGTG
GGAGGTGGCCGCTGCTCCGAAATCTCCGCTGAGCTCATTCGCTCCCTGACAGAGCTGCAG
GAGCTGGAGGCTGTATACGAACGGCTCTGCGGCGAGGAGAAAGTGGTGGAGAGAGAGCTG
GATGCTCTTTTGGAACAGCAAAACACCATTGAAAGTAAGATGGTCACTCTCCACCGAATG
GGTCCTAATCTGCAGCTGATTGAGGGAGATGCAAAGCAGCTGGCTGGAATGATCACCTTT
ACCTGCAACCTGGCTGAGAATGTGTCCAGCAAAGTTCGTCAGCTTGACCTGGCCAAGAAC
CGCCTCTATCAGGCCATTCAGAGAGCTGATGACATCTTGGACCTGAAGTTCTGCATGGAT
GGAGTTCAGACTGCTTTGAGGAGTGAAGATTATGAGCAGGCTGCAGCACATACTCATCGC
TACTTGTGCCTGGACAAGTCGGTCATTGAGCTCAGCCGACAGGGCAAAGAGGGGAGCATG
ATTGATGCCAACCTGAAATTGCTGCAGGAAGCTGAGCAACGTCTCAAAGCCATTGTGGCA
GAGAAGTTTGCCATTGCCACCAAGGAAGGTGATCTGCCCCAGGTGGAGCGCTTCTTCAAG
ATCTTCCCACTGCTGGGTTTGCATGAGGAGGGATTAAGAAAGTTCTCGGAGTACCTTTGC
AAGCAGGTGGCCAGTAAAGCTGAGGAGAATCTGCTCATGGTGCTGGGGACAGACATGAGT
GATCGGAGAGCTGCAGTCATCTTTGCAGATACACTTACTCTTCTGTTTGAAGGGATTGCC
CGCATTGTGGAGACCCACCAGCCAATAGTGGAGACCTATTATGGGCCAGGGAGACTCTAT
ACCCTGATCAAATATCTGCAGGTGGAATGTGACAGACAGGTGGAGAAGGTGGTAGACAAG
TTCATCAAGCAAAGGGACTACCACCAGCAGAACTTTGTTTTTTCCTTCTTTTGA

Fig. 7

SEQ ID No. 7
COG4
>ENSG00000103051|16|protein_coding|ENST00000338984|ENSP00000345047
ATGGCGGACCTTGATTCGCCTCCGAAGCTGTCAGGGGTGCAGCAGCCGTCTGAGGGGGTG
GGAGGTGGCCGCTGCTCCGAAATCTCCGCTGAGCTCATTCGCTCCCTGACAGAGCTGCAG
GAGCTGGAGGCTGTATACGAACGGCTCTGCGGCGAGGAGAAAGTGGTGGAGAGAGAGCTG
GATGCTCTTTTGGAACAGCAAAACACCATTGAAAGTAAGATGGTCACTCTCCACCGAATG
GGTCCTAATCTGCAGCTGATTGAGGGAGATGCAAAGCAGCTGGCTGGAATGATCACCTTT
ACCTGCAACCTGGCTGAGAATGTGTCCAGCAAAGTTCGTCAGCTTGACCTGGCCAAGAAC
CGCCTCTATCAGGCCATTCAGAGAGCTGATGACATCTTGGACCTGAAGTTCTGCATGGAT
GGAGTTCAGACTGCTTTGAGGAGTGAAGATTATGAGCAGGCTGCAGCACATACTCATCGC
TACTTGTGCCTGGACAAGTCGGTCATTGAGCTCAGCCGACAGGGCAAAGAGGGGAGCATG
ATTGATGCCAACCTGAAATTGCTGCAGGAAGCTGAGCAACGTCTCAAAGCCATTGTGGCA
GAGAAGTTTGCCATTGCCACCAAGGAAGGTGATCTGCCCCAGGTGGAGCGCTTCTTCAAG
ATCTTCCCACTGCTGGGTTTGCATGAGGAGGGATTAAGAAAGTTCTCGGAGTACCTTTGC
AAGCAGGTGGCCAGTAAAGCTGAGGAGAATCTGCTCATGGTGCTGGGGACAGACATGAGT
GATCGGAGAGCTGCAGTCATCTTTGCAGATACACTTACTCTTCTGTTTGAAGGGATTGCC
CGCATTGTGGAGACCCACCAGCCAATAGTGGAGACCTATTATGGGCCAGGGAGACTCTAT
ACCCTGATCAAATATCTGCAGGTGGAATGTGACAGACAGGTGGGAGAAGGTGGTAGACAAG
TTCATCAAGCAAAGGGACTACCACCAGCAGTTCCGGCATGTTCAGAACAACCTGATGAGA
AATTCTACAACAGAAAAAATCGAACCAAGAGAACTGGACCCCATCCTGACTGAGGTCACC
CTGATGAATGCCCGCAGTGAGCTATACTTACGCTTCCTCAAGAAGAGGATTAGCTCTGAT
TTTGAGGTGGGAGACTCCATGGCCTCAGAGGAAGTAAAGCAAGAGCACCAGAAGTGTCTG
GACAAACTCCTCAATAACTGCCTTTTGAGCTGTACCATGCAGGAGCTAATTGGCTTATAT
GTTACCATGGAGGAGTACTTCATGAGGGAGACTGTCAATAAGGCTGTGGCTCTGGACACC
TATGAGAAGGGCCAGCTGACATCCAGCATGGTGGATGATGTCTTCTACATTGTTAAGAAG
TGCATTGGGCGGGCTCTGTCCAGCTCCAGCATTGACTGTCTCTGTGCCATGATCAACCTC
GCCACCACAGAGCTGGAGTCTGACTTCAGGGATGTTCTGTGTAATAAGCTGCGGATGGGC
TTTCCTGCCACCACCTTCCAGGACATCCAGCGCGGGGTGACAAGTGCCGTGAACATCATG
CACAGCAGCCTCCAGCAAGGCAAATTTGACACAAAAGGCATCGAGAGTACTGACGAGGCG
AAGATGTCCTTCCTGGTGACTCTGAACAACGTGGAAGTCTGCAGTGAAAACATCTCCACT
CTGAAGAAGACACTGGAGAGTGACTGCACCAAGCTCTTCAGCCAGGGCATTGGAGGGGAG
CAGGCCCAGGCCAAGTTTGACAGCTGCCTTTCTGACTTGGCCGCCGTGTCCAACAAATTC
CGAGACCTCTTGCAGGAAGGGCTGACGGAGCTCAACAGCACAGCCATCAAGCCACAGGTG
CAGCCTTGGATCAACAGCTTTTTCTCCGTCTCCCACAACATCGAGGAGGAAGAATTCAAT
GACTATGAGGCCAACGACCCTTGGGTACAACAGTTCATCCTTAACCTGGAGCAGCAAATG
GCAGAGTTCAAGGCCAGCCTGTCCCCGGTCATCTACGACAGCCTAACCGGCCTCATGACT
AGCCTTGTTGCCGTCGAGTTGGAGAAAGTGGTGCTGAAATCCACCTTTAACCGGCTGGGT
GGTCTGCAGTTTGACAAGGAGCTGAGGTCGCTCATTGCCTACCTTACCACGGTGACCACC
TGGACCATCCGAGACAAGTTTGCCCGGCTCTCCCAGATGGCCACCATCCTCAATCTGGAG
CGGGTGACCGAGATCCTCGATTACTGGGGACCCAATTCCGGCCCATTGACGTGGCGCCTC
ACCCCTGCTGAAGTGCGCCAGGTGCTGGCCCTGCGGATAGACTTCCGCAGTGAAGATATC
AAGAGGCTGCGCCTGTAG

Fig. 8

SEQ ID No. 8
COG4
>ENSG00000103051|16|protein_coding|ENST00000219329|ENSP00000219329
ATGGGGACCAAGATGGCGGACCTTGATTCGCCTCCGAAGCTGTCAGGGGTGCAGCAGCCG
TCTGAGGGGGTGGGAGGTGGCCGCTGCTCCGAAATCTCCGCTGAGCTCATTCGCTCCCTG
ACAGAGCTGCAGGAGCTGGAGGCTGTATACGAACGGCTCTGCGGCGAGGAGAAAGTGGTG
GAGAGAGAGCTGGATGCTCTTTTGGAACAGCAAAACACCATTGAAAGTAAGATGGTCACT
CTCCACCGAATGGGTCCTAATCTGCAGCTGATTGAGGCCAACCTGAAATTGCTGCAGGAA
GCTGAGCAACGTCTCAAAGCCATTGTGGCAGAGAAGTTTGCCATTGCCACCAAGGAAGGT
GATCTGCCCCAGGTGGAGCGCTTCTTCAAGATCTTCCCACTGCTGGGTTTGCATGAGGAG
GGATTAAGAAAGTTCTCGGAGTACCTTTGCAAGCAGGTGGCCAGTAAAGCTGAGGAGAAT
CTGCTCATGGTGCTGGGGACAGACATGAGTGATCGGAGAGCTGCAGTCATCTTTGCAGAT
ACACTTACTCTTCTGTTTGAAGGGATTGCCCGCATTGTGGAGACCCACCAGCCAATAGTG
GAGACCTATTATGGGCCAGGGAGACTCTATACCCTGATCAAATATCTGCAGGTGGAATGT
GACAGACAGGTGGAGAAGGTGGTAGACAAGTTCATCAAGCAAAGGGACTACCACCAGCAG
TTCCGGCATGTTCAGAACAACCTGATGAGAAATTCTACAACAGAAAAAATCGAACCAAGA
GAACTGGACCCCATCCTGACTGAGGTCACCCTGATGAATGCCCGCAGTGAGCTATACTTA
CGCTTCCTCAAGAAGAGGATTAGCTCTGATTTTGAGGTGGGAGACTCCATGGCCTCAGAG
GAAGTAAAGCAAGAGCACCAGAAGTGTCTGGACAAACTCCTCAATAACTGCCTTTTGAGC
TGTACCATGCAGGAGCTAATTGGCTTATATGTTACCATGGAGGAGTACTTCATGAGGGAG
ACTGTCAATAAGGCTGTGGCTCTGGACACCTATGAGAAGGGCCAGCTGACATCCAGCATG
GTGGATGATGTCTTCTACATTGTTAAGAAGTGCATTGGGCGGGCTCTGTCCAGCTCCAGC
ATTGACTGTCTCTGTGCCATGATCAACCTCGCCACCACAGAGCTGGAGTCTGACTTCAGG
GATGTTCTGTGTAATAAGCTGCGGATGGGCTTTCCTGCCACCACCTTCCAGGACATCCAG
CGCGGGGTGACAAGTGCCGTGAACATCATGCACAGCAGCCTCCAGCAAGGCAAATTTGAC
ACAAAAGGCATCGAGAGTACTGACGAGGCGAAGATGTCCTTCCTGGTGACTCTGAACAAC
GTGGAAGTCTGCAGTGAAAACATCTCCACTCTGAAGAAGACACTGGAGAGTGACTGCACC
AAGCTCTTCAGCCAGGGCATTGGAGGGGAGCAGGCCCAGGCCAAGTTTGACAGCTGCCTT
TCTGACTTGGCCGCCGTGTCCAACAAATTCCGAGACCTCTTGCAGGAAGGGCTGACGGAG
CTCAACAGCACAGCCATCAAGCCACAGGTGCAGCCTTGGATCAACAGCTTTTTCTCCGTC
TCCCACAACATCGAGGAGGAAGAATTCAATGACTATGAGGCCAACGACCCTTGGGTACAA
CAGTTCATCCTTAACCTGGAGCAGCAAATGGCAGAGTTCAAGGCCAGCCTGTCCCCGGTC
ATCTACGACAGCCTAACCGGCCTCATGACTAGCCTTGTTGCCGTCGAGTTGGAGAAAGTG
GTGCTGAAATCCACCTTTAACCGGCTGGGTGGTCTGCAGTTTGACAAGGAGCTGAGGTCG
CTCATTGCCTACCTTACCACGGTGACCACCTGGACCATCCGAGACAAGTTTGCCCGGCTC
TCCCAGATGGCCACCATCCTCAATCTGGAGCGGGTGACCGAGATCCTCGATTACTGGGGA
CCCAATTCCGGCCCATTGACGTGGCGCCTCACCCCTGCTGAAGTGCGCCAGGTGCTGGCC
CTGCGGATAGACTTCCGCAGTGAAGATATCAAGAGGCTGCGCCTGTAG

Fig. 9

SEQ ID No. 9
FDFT1
>ENSG00000079459|8|protein_coding|ENST00000220584|ENSP00000220584
ATGGAGTTCGTGAAATGCCTTGGCCACCCCGAAGAGTTCTACAACCTGGTGCGCTTCCGG
ATCGGGGGCAAGCGGAAGGTGATGCCCAAGATGGACCAGGACTCGCTCAGCAGCAGCCTG
AAAACTTGCTACAAGTATCTCAATCAGACCAGTCGCAGTTTCGCAGCTGTTATCCAGGCG
CTGGATGGGGAAATGCGCAACGCAGTGTGCATATTTTATCTGGTTCTCCGAGCTCTGGAC
ACACTGGAAGATGACATGACCATCAGTGTGGAAAAGAAGGTCCCGCTGTTACACAACTTT
CACTCTTTCCTTTACCAACCAGACTGGCGGTTCATGGAGAGCAAGGAGAAGGATCGCCAG
GTGCTGGAGGACTTCCCAACGATCTCCCTTGAGTTTAGAAATCTGGCTGAGAAATACCAA
ACAGTGATTGCCGACATTTGCCGGAGAATGGGCATTGGGATGGCAGAGTTTTTGGATAAG
CATGTGACCTCTGAACAGGAGTGGGACAAGTACTGCCACTATGTTGCTGGGCTGGTCGGA
ATTGGCCTTTCCCGTCTTTTCTCAGCCTCAGAGTTTGAAGACCCCTTAGTTGGTGAAGAT
ACAGAACGTGCCAACTCTATGGGCCTGTTTTTGCAGAAAACAAACATCATCCGTGACTAT
CTGGAAGACCAGCAAGGAGGAAGAGAGTTCTGGCCTCAAGAGGTTTGGAGCAGGTATGTT
AAGAAGTTAGGGGATTTTGCTAAGCCGGAGAATATTGACTTGGCCGTGCAGTGCCTGAAT
GAACTTATAACCAATGCACTGCACCACATCCCAGATGTCATCACCTACCTTTCGAGACTC
AGAAACCAGAGTGTGTTTAACTTCTGTGCTATTCCACAGGTGATGGCCATTGCCACTTTG
GCTGCCTGTTATAATAACCAGCAGGTGTTCAAAGGGGCAGTGAAGATTCGGAAAGGGCAA
GCAGTGACCCTGATGATGGATGCCACCAATATGCCAGCTGTCAAAGCCATCATATATCAG
TATATGGAAGAGATTTATCATAGAATCCCCGACTCAGACCCATCTTCTAGCAAAACAAGG
CAGATCATCTCCACCATCCGGACGCAGAATCTTCCCAACTGTCAGCTGATTTCCCGAAGC
CACTACTCCCCATCTACCTGTCGTTTGTCATGCTTTTGGCTGCCCTGAGCTGGCAGTAC
CTGACCACTCTCTCCCAGGTAACAGAAGACTATGTTCAGACTGGAGAACACTGA

Fig. 10

SEQ ID No. 10
PECI
>ENSG00000198721|6|protein_coding|ENST00000380125|ENSP00000369468
ATGAGAGCCAGTCAGAAGGACTTTGAAAATTCAATGAATCAAGTGAAACTCTTGAAAAAG
GATCCAGGAAACGAAGTGAAGCTAAAACTCTACGCGCTATATAAGCAGGCCACTGAAGGA
CCTTGTAACATGCCCAAACCAGGTGTATTTGACTTGATCAACAAGGCCAAATGGGACGCA
TGGAATGCCCTTGGCAGCCTGCCCAAGGAAGCTGCCAGGCAGAACTATGTGGATTTGGTG
TCCAGTTTGAGTCCTTCATTGGAATCCTCTAGTCAGGTGGAGCCTGGAACAGACAGGAAA
TCAACTGGGTTTGAAACTCTGGTGGTGACCTCCGAAGATGGCATCACAAAGATCATGTTC
AACCGGCCCAAAAAGAAAAATGCCATAAACACTGAGATGTATCATGAAATTATGCGTGCA
CTTAAAGCTGCCAGCAAGGATGACTCAATCATCACTGTTTTAACAGGAAATGGTGACTAT
TACAGTAGTGGGAATGATCTGACTAACTTCACTGATATTCCCCCTGGTGGAGTAGAGGAG
AAAGCTAAAAATAATGCCGTTTTACTGAGGGAATTTGTGGGCTGTTTTATAGATTTTCCT
AAGCCTCTGATTGCAGTGGTCAATGGTCCAGCTGTGGGCATCTCCGTCACCCTCCTTGGG
CTATTCGATGCCGTGTATGCATCTGACAGGGCAACATTTCATACACCATTTAGTCACCTA
GGCCAAAGTCCGGAAGGATGCTCCTCTTACACTTTTCCGAAGATAATGAGCCCAGCCAAG
GCAACAGAGATGCTTATTTTTGGAAAGAAGTTAACAGCGGGAGAGGCATGTGCTCAAGGA
CTTGTTACTGAAGTTTTCCCTGATAGCACTTTTCAGAAAGAAGTCTGGACCAGGCTGAAG
GCATTTGCAAAGCTTCCCCCAAATGCCTTGAGAATTTCAAAAGAGGTAATCAGGAAAAGA
GAGAGAGAAAAACTACACGCTGTTAATGCTGAAGAATGCAATGTCCTTCAGGGAAGATGG
CTATCAGATGAATGCACAAATGCTGTGGTGAACTTCTTATCCAGAAAATCAAAACTGTGA

Fig. 11

SEQ ID No. 11
PECI
>ENSG00000198721|6|protein_coding|ENST00000380114|ENSP00000369457
ATGTATCATGAAATTATGCGTGCACTTAAAGCTGCCAGCAAGGATGACTCAATCATCACT
GTTTTAACAGGAAATGGTGACTATTACAGTAGTGGGAATGATCTGACTAACTTCACTGAT
ATTCCCCCTGGTGGAGTAGAGGAGAAAGCTAAAAATAATGCCGTTTTACTGAGGGAATTT
GTGGGCTGTTTTATAGATTTTCCTAAGCCTCTGATTGCAGTGGTCAATGGTCCAGCTGTG
GGCATCTCCGTCACCCTCCTTGGGCTATTCGATGCCGTGTATGCATCTGACAGGGCAACA
TTTCATACACCATTTAGTCACCTAGGCCAAAGTCCGGAAGGATGCTCCTCTTACACTTTT
CCGAAGATAATGAGCCCAGCCAAGGCAACAGAGATGCTTATTTTTGGAAAGAAGTTAACA
GCGGGAGAGGCATGTGCTCAAGGACTTGTTACTGAAGTTTTCCCTGATAGCACTTTTCAG
AAAGAAGTCTGGACCAGGCTGAAGGCATTTGCAAAGCTTCCCCCAAATGCCTTGAGAATT
TCAAAAGAGGTAATCAGGAAAAGAGAGAGAGAAAAACTACACGCTGTTAATGCTGAAGAA
TGCAATGTCCTTCAGGGAAGATGGCTATCAGATGAATGCACAAATGCTGTGGTGAACTTC
TTATCCAGAAAATCAAAACTGTGA

Fig. 12

SEQ ID No. 12
PECI
>ENSG00000198721|6|protein_coding|ENST00000380118|ENSP00000369461
ATGGCGATGGCGTACTTGGCTTGGAGACTGGCGCGGCGTTCGTGTCCGAGTTCTCTGCAG
GTCACTAGTTTCCCGGTAGTTCAGCTGCACATGAATAGAACAGCAATGAGAGCCAGTCAG
AAGGACTTTGAAAATTCAATGAATCAAGTGAAACTCTTGAAAAAGGATCCAGGAAACGAA
GTGAAGCTAAAACTCTACGCGCTATATAAGCAGGCCACTGAAGGACCTTGTAACATGCCC
AAACCAGGTGTATTTGACTTGATCAACAAGGCCAAATGGGACGCATGGAATGCCCTTGGC
AGCCTGCCCAAGGAAGCTGCCAGGCAGAACTATGTGGATTTGGTGTCCAGTTTGAGTCCT
TCATTGGAATCCTCTAGTCAGGTGGAGCCTGGAACAGACAGGAAATCAACTGGGTTTGAA
ACTCTGGTGGTGACCTCCGAAGATGGCATCACAAAGATCATGTTCAACCGGCCCAAAAAG
AAAAATGCCATAAACACTGAGATGTATCATGAAATTATGCGTGCACTTAAAGCTGCCAGC
AAGGATGACTCAATCATCACTGTTTTAACAGGAAATGGTGACTATTACAGTAGTGGGAAT
GATCTGACTAACTTCACTGATATTCCCCCTGGTGGAGTAGAGGAGAAAGCTAAAAATAAT
GCCGTTTTACTGAGGGAATTTGTGGGCTGTTTTATAGATTTTCCTAAGCCTCTGATTGCA
GTGGTCAATGGTCCAGCTGTGGGCATCTCCGTCACCCTCCTTGGGCTATTCGATGCCGTG
TATGCATCTGACAGGGCAACATTTCATACACCATTTAGTCACCTAGGCCAAAGTCCGGAA
GGATGCTCCTCTTACACTTTTCCGAAGATAATGAGCCCAGCCAAGGCAACAGAGATGCTT
ATTTTTGGAAAGAAGTTAACAGCGGGAGAGGCATGTGCTCAAGGACTTGTTACTGAAGTT
TTCCCTGATAGCACTTTTCAGAAAGAAGTCTGGACCAGGCTGAAGGCATTTGCAAAGCTT
CCCCCAAATGCCTTGAGAATTTCAAAAGAGGTAATCAGGAAAAGAGAGAGAGAAAAACTA
CACGCTGTTAATGCTGAAGAATGCAATGTCCTTCAGGGAAGATGGCTATCAGATGAATGC
ACAAATGCTGTGGTGAACTTCTTATCCAGAAAATCAAAACTGTGA

Fig. 13

SEQ ID No. 13
PECI
>ENSG00000198721|6|protein_coding|ENST00000361538|ENSP00000354737
ATGAATAGAACAGCAATGAGAGCCAGTCAGAAGGACTTTGAAAATTCAATGAATCAAGTG
AAACTCTTGAAAAAGGATCCAGGAAACGAAGTGAAGCTAAAACTCTACGCGCTATATAAG
CAGGCCACTGAAGGACCTTGTAACATGCCCAAACCAGGTGTATTTGACTTGATCAACAAG
GCCAAATGGGACGCATGGAATGCCCTTGGCAGCCTGCCCAAGGAAGCTGCCAGGCAGAAC
TATGTGGATTTGGTGTCCAGTTTGAGTCCTTCATTGGAATCCTCTAGTCAGGTGGAGCCT
GGAACAGACAGGAAATCAACTGGGTTTGAAACTCTGGTGGTGACCTCCGAAGATGGCATC
ACAAAGATCATGTTCAACCGGCCCAAAAAGAAAAATGCCATAAACACTGAGATGTATCAT
GAAATTATGCGTGCACTTAAAGCTGCCAGCAAGGATGACTCAATCATCACTGTTTTAACA
GGAAATGGTGACTATTACAGTAGTGGGAATGATCTGACTAACTTCACTGATATTCCCCCT
GGTGGAGTAGAGGAGAAAGCTAAAAATAATGCCGTTTTACTGAGGGAATTTGTGGGCTGT
TTTATAGATTTTCCTAAGCCTCTGATTGCAGTGGTCAATGGTCCAGCTGTGGGCATCTCC
GTCACCCTCCTTGGGCTATTCGATGCCGTGTATGCATCTGACAGGGCAACATTTCATACA
CCATTTAGTCACCTAGGCCAAAGTCCGGAAGGATGCTCCTCTTACACTTTTCCGAAGATA
ATGAGCCCAGCCAAGGCAACAGAGATGCTTATTTTTGGAAAGAAGTTAACAGCGGGAGAG
GCATGTGCTCAAGGACTTGTTACTGAAGTTTTCCCTGATAGCACTTTTCAGAAAGAAGTC
TGGACCAGGCTGAAGGCATTTGCAAAGCTTCCCCCAAATGCCTTGAGAATTTCAAAAGAG
GTAATCAGGAAAAGAGAGAGAGAAAAACTACACGCTGTTAATGCTGAAGAATGCAATGTC
CTTCAGGGAAGATGGCTATCAGATGAATGCACAAATGCTGTGGTGAACTTCTTATCCAGA
AAATCAAAACTGTGA

Fig. 14

SEQ ID No. 14
PECI
>ENSG00000198721|6|protein_coding|ENST00000380120|ENSP00000369463
ATGTTCAACCGGCCCAAAAAGAAAAATGCCATAAACACTGAGATGTATCATGAAATTATG
CGTGCACTTAAAGCTGCCAGCAAGGATGACTCAATCATCACTGTTTTAACAGGAAATGGT
GACTATTACAGTAGTGGGAATGATCTGACTAACTTCACTGATATTCCCCCTGGTGGAGTA
GAGGAGAAAGCTAAAAATAATGCCGTTTTACTGAGGGAATTTGTGGGCTGTTTTATAGAT
TTTCCTAAGCCTCTGATTGCAGTGGTCAATGGTCCAGCTGTGGGCATCTCCGTCACCCTC
CTTGGGCTATTCGATGCCGTGTATGCATCTGACAGGGCAACATTTCATACACCATTTAGT
CACCTAGGCCAAAGTCCGGAAGGATGCTCCTCTTACACTTTTCCGAAGATAATGAGCCCA
GCCAAGGCAACAGAGATGCTTATTTTTGGAAAGAAGTTAACAGCGGGAGAGGCATGTGCT
CAAGGACTTGTTACTGAAGTTTTCCCTGATAGCACTTTTCAGAAAGAAGTCTGGACCAGG
CTGAAGGCATTTGCAAAGCTTCCCCCAAATGCCTTGAGAATTTCAAAAGAGGTAATCAGG
AAAAGAGAGAGAGAAAAACTACACGCTGTTAATGCTGAAGAATGCAATGTCCTTCAGGGA
AGATGGCTATCAGATGAATGCACAAATGCTGTGGTGAACTTCTTATCCAGAAAATCAAAA
CTGTGA

Fig. 15

SEQ ID No. 15
CTNND2
>ENSG00000169862|5|protein_coding|ENST00000359640|ENSP00000352661
ATGTTTGCGAGGAAGCCGCCGGGCGCCGCGCCTTTGGGAGCTATGCCTGTTCCAGACCAG
CCTTCATCAGCCTCAGAGAAGACGAGTTCCCTGAGCCCCGGCTTAAACACCTCCAACGGG
GATGGCTCTGAAACAGAAACCACCTCTGCCATCCTCGCCTCAGTCAAAGAACAGGAATTA
CAGTTTGAAAGGCTGACCCGAGAGCTGGAGGCTGAACGGCAGATCGTAGCCAGCCAGCTG
GAGCGATGCAAGCTCGGATCCGAGACTGGCAGCATGAGCAGCATGAGTTCAGCAGAAGAG
CAGTTTCAGTGGCAGTCACAAGATGGTCAAAAAGATATCGAAGATGAGCTTACAACAGGT
CTCGAGCTGGTGGACTCCTGTATTAGGTCACTACAGGAATCAGGAATACTTGACCCACAG
GATTATTCTACAGGTGAAAGGCCCAGCCTGCTCTCCCAGAGTGCACTTCAGCTCAATTCC
AAACCTGAAGGGTCTTTCCAGTATCCGGCCAGCTACCATAGCAACCAGACCCTGCCCCTG
GGGGAAACCACCCCTTCACAGCTCCCGGCCCGAGGCACACAAGCCCGAGCTACGGGCCAG
AGCTTCAGCCAGGGCACGACCAGCCGCGCCGGCCACCTGGCGGGGCCCGAGCCCGCGCCG
CCGCCGCCGCCGCCGCCGCGGGAGCCGTTCGCGCCCAGCCTGGGCAGCGCCTTCCACCTG
CCCGACGCGCCGCCCGCCGCCGCCGCCGCGCTCTACTACTCCAGCTCCACGCTGCCC
GCGCCGCCGCGCGGGGGCTCCCCGCTGGCCGCGCCCCAGGGCGGTTCGCCCACCAAGCTG
CAGCGCGGCGGCTCGGCCCCGAGGGCGCCACCTACGCCGCGCCGCGCGGCTCCTCGCCC
AAGCAGTCGCCCAGCCGCCTGGCCAAGTCCTACAGCACCAGCTCGCCCATCAACATCGTC
GTGTCCTCGGCCGGCCTGTCCCCGATCCGCGTGACCTCGCCCCCACCGTGCAGTCCACC
ATCTCCTCCTCGCCCATCCACCAGCTGAGCTCCACCATCGGCACGTACGCCACCCTGTCG
CCCACCAAGCGCCTGGTCCACGCGTCCGAGCAGTACAGCAAGCACTCGCAGGAGCTGTAT
GCCACGGCCACCCTCCAGAGGCCGGGCAGCCTGGCAGCTGGTTCCGAGCCTCATACAGC
AGCCAGCATGGGCACCTGGGCCCAGAGTTGCGGGCCCTGCAGTCCCCAGAACACCACATA
GATCCCATCTATGAAGACCGCGTCTATCAGAAGCCCCCTATGAGGAGTCTCAGCCAGAGC
CAGGGGGACCCTCTGCCGCCAGCACACACCGGCACCTACCGCACGAGCACAGCCCCATCT
TCCCCTGGTGTCGACTCCGTCCCCTTGCAGCGCACAGGCAGCCAGCACGGCCCACAGAAT
GCCGCCGCGGCCACCTTCCAGAGGGCCAGCTATGCCGCCGGCCCAGCCTCCAATTACGCG
GACCCCTACCGACAGCTGCAGTATTGTCCCTCTGTTGAGTCTCCATACAGCAAATCCGGC
CCTGCTCTCCCGCCTGAAGGCACCTTGGCCAGGTCCCCGTCCATTGATAGCATTCAGAAA
GATCCCAGAGAATTTGGATGGAGAGACCCGGAACTGCCGGAAGTGATTCAGATGTTGCAG
CACCAGTTTCCCTCGGTCCAGTCTAACGCGGCAGCCTACTTGCAACACCTCTGTTTTGGA
GACAACAAAATTAAAGCCGAGATAAGGAGACAAGGAGGCATCCAGCTCCTGGTGGACCTG
TTGGATCATCGGATGACCGAAGTCCACCGTAGTGCCTGTGGAGCTCTGAGAAACCTGGTG
TATGGGAAGGCCAACGATGATAACAAAATTGCCCTGAAAAACTGTGGTGGCATCCCAGCA
CTGGTGAGGTTACTCCGCAAGACGACTGACCTGGAGATCCGGGAGCTGGTCACAGGAGTC
CTTTGGAACCTCTCCTCATGCGATGCACTCAAAATGCCAATCATCCAGGATGCCCTAGCA
GTACTGACCAACGCGGTGATTATCCCCCACTCAGGCTGGGAAAATTCGCCTCTTCAGGAT
GATCGGAAAATACAGCTGCATTCATCACAGGTGCTGCGTAACGCCACCGGGTGCCTAAGG
AATGTTAGTTCGGCCGGAGAGGAGGCCCGCAGAAGGATGAGAGAGTGTGATGGGCTTACG
GATGCCTTGCTGTACGTGATCCAGTCTGCGCTGGGGAGCAGTGAGATCGATAGCAAGACC
GTTGAAAACTGTGTGTGCATTTTAAGGAACCTCTCGTACCGGCTGGCGGCAGAAACGTCT
CAGGGACAGCACATGGGCACGGACGAGCTGGACGGGCTACTCTGTGGCGAGGCCAATGGC
AAGGATGCTGAGAGCTCTGGGTGCTGGGGCAAGAAGAAGAAGAAAAAGAAATCCCAAGAT
CAGTGGTCAGTATATATCCGAGCCGCTGTCCGAAAAGAGAAAGGCCTGCCCATCCTCGTG
GAGCTGCTCCGAATAGACAATGACCGTGTGGTGTGCGCGGTGGCCACTGCGCTGCGGAAC
ATGGCCTTGGACGTCAGAAATAAGGAGCTCATCGGCAAATACGCCATGCGAGACCTAGTC
CACAGGCTTCCAGGAGGGAACAACAGCAACAACACTGCAAGCAAGGCCATGTCGGATGAC
ACAGTGACAGCTGTCTGCTGCACACTGCACGAAGTGATTACCAAGAACATGGAGAACGCC
AAGGCCTTACGGGATGCCGGTGGCATCGAGAAGTTGGTCGGCATCTCCAAAAGCAAAGGA
GATAAACACTCTCCAAAAGTGGTCAAGGCTGCATCTCAGGTCCTCAACAGCATGTGGCAG
TACCGAGATCTGAGGAGTCTCTACAAAAAGGATGGATGGTCACAATACCACTTTGTAGCC
TCGTCTTCAACCATCGAGAGGGACCGGCAAAGGCCCTACTCCTCCTCCCGCACGCCCTCC
ATCTCCCCTGTGCGCGTGTCTCCCAACAACCGCTCAGCAAGTGCCCCAGCTTCACCTCGG
GAAATGATCGCCTCAAAGAAAGGAAAACAGACTGAGTGCACCGGCAGCAACGCCACC
TACCACGGAGCTAAAGGCGAACACACTTCCAGGAAAGATGCCATGACAGCTCAAAACACT
GGAATTTCAACTTTGTATAGGAATTCTTATGGTGCGCCCGCTGAAGACATCAAACACAAC
CAGGTTTCAGCACAGCCAGTCCCACAGGAGCCCAGCAGAAAAGATTACGAGACCTACCAG
CCATTTCAGAATTCCACAAGAAATTACGATGAGTCCTTCTTCGAGGACCAGGTCCACCAT
CGCCCTCCCGCCAGCGAGTACACCATGCACCTGGGTCTCAAGTCCACCGGCAACTACGTT
GACTTCTACTCAGCTGCCCGTCCCTACAGTGAACTGAACTATGAAACGAGCCACTACCCG
GCCTCCCCCGACTCCTGGGTGTGA

Fig. 16

SEQ ID No. 16
CTNND2
>ENSG00000169862|5|protein_coding|ENST00000304623|ENSP00000307134
ATGTTTGCGAGGAAGCCGCCGGGCGCCGCGCCTTTGGGAGCTATGCCTGTTCCAGACCAG
CCTTCATCAGCCTCAGAGAAGACGAGTTCCCTGAGCCCCGGCTTAAACACCTCCAACGGG
GATGGCTCTGAAACAGAAACCACCTCTGCCATCCTCGCCTCAGTCAAAGAACAGGAATTA
CAGTTTGAAAGGCTGACCCGAGAGCTGGAGGCTGAACGGCAGATCGTAGCCAGCCAGCTG
GAGCGATGCAAGCTCGGATCCGAGACTGGCAGCATGAGCAGCATGAGTTCAGCAGAAGAG
CAGTTTCAGTGGCAGTCACAAGATGGTCAAAAAGATATCGAAGATGAGCTTACAACAGGT
CTCGAGCTGGTGGACTCCTGTATTAGGTCACTACAGGAATCAGGAATACTTGACCCACAG
GATTATTCTACAGGTGAAAGGCCCAGCCTGCTCTCCCAGAGTGCACTTCAGCTCAATTCC
AAACCTGAAGGGTCTTTCCAGTATCCGGCCAGCTACCATAGCAACCAGACCCTGGCCCTG
GGGGAAACCACCCCTTCACAGCTCCCGGCCCGAGGCACACAAGCCCGAGCTACGGGCCAG
AGCTTCAGCCAGGGCACGACCAGCCGCGCCGGCCACCTGGCGGGGCCCGAGCCCGCGCCG
CCGCCGCCGCCGCCGCCGCGGGAGCCGTTCGCGCCCAGCCTGGGCAGCGCCTTCCACCTG
CCCGACGCGCCGCCCGCCGCCGCCGCCGCCGCGCTCTACTACTCCAGCTCCACGCTGCCC
GCGCCGCCGCGCGGGGGCTCCCCGCTGGCCGCGCCCCAGGGCGGTTCGCCCACCAAGCTG
CAGCGCGGCGGCTCGGCCCCCGAGGGCGCCACCTACGCCGCGCCGCGCGGCTCCTCGCCC
AAGCAGTCGCCCAGCCGCCTGGCCAAGTCCTACAGCACCAGCTCGCCCATCAACATCGTC
GTGTCCTCGGCCGGCCTGTCCCCGATCCGCGTGACCTCGCCCCCACCGTGCAGTCCACC
ATCTCCTCCTCGCCCATCCACCAGCTGAGCTCCACCATCGGCACGTACGCCACCCTGTCG
CCCACCAAGCGCCTGGTCCACGCGTCCGAGCAGTACAGCAAGCACTCGCAGGAGCTGTAT
GCCACGGCCACCCTCCAGAGGCCGGGCAGCCTGGCAGCTGGTTCCCGAGCCTCATACAGC
AGCCAGCATGGGCACCTGGGCCCAGAGTTGCGGCCCTGCAGTCCCCAGAACACCACATA
GATCCCATCTATGAAGACCGCGTCTATCAGAAGCCCCCTATGAGGAGTCTCAGCCAGAGC
CAGGGGGACCCTCTGCCGCCAGCACACACCGGCACCTACCGCACGAGCACAGCCCCATCT
TCCCCTGGTGTCGACTCCGTCCCCTTGCAGCGCACAGGCAGCCAGCACGGCCCACAGAAT
GCCGCCGCGGCCACCTTCCAGAGGGCCAGCTATGCCGCCGGCCCAGCCTCCAATTACGCG
GACCCCTACCGACAGCTGCAGTATTGTCCCTCTGTTGAGTCTCCATACAGCAAATCCGGC
CCTGCTCTCCCGCCTGAAGGCACCTTGGCCAGGTCCCCGTCCATTGATAGCATTCAGAAA
GATCCCAGAGAATTTGGATGGAGAGACCCGGAACTGCCGGAAGTGATTCAGATGTTGCAG
CACCAGTTTCCCTCGGTCCAGTCTAACGCGGCAGCCTACTTGCAACACCTCTGTTTTGGA
GACAACAAAATTAAAGCCGAGATAAGGAGACAAGGAGGCATCCAGCTCCTGGTGGACCTG
TTGGATCATCGGATGACCGAAGTCCACCGTAGTGCCTGTGGAGCTCTGAGAAACCTGGTG
TATGGGAAGGCCAACGATGATAACAAAATTGCCCTGAAAAACTGTGGTGGCATCCCAGCA
CTGGTGAGGTTACTCCGCAAGACGACTGACCTGGAGATCCGGGAGCTGGTCACAGGAGTC
CTTTGGAACCTCTCCTCATGCGATGCACTCAAAATGCCAATCATCCAGGATGCCCTAGCA
GTACTGACCAACGCGGTGATTATCCCCCACTCAGGCTGGGAAAATTCGCCTCTTCAGGAT
GATCGGAAAATACAGCTGCATTCATCACAGGTGCTGCGTAACGCCACCGGGTGCCTAAGG
AATGTTAGTTCGGCCGGAGAGGAGGCCCGCAGAAGGATGAGAGAGTGTGATGGGCTTACG
GATGCCTTGCTGTACGTGATCCAGTCTGCGCTGGGGAGCAGTGAGATCGATAGCAAGACC
GTTGAAAACTGTGTGTGCATTTTAAGGAACCTCTCGTACCGGCTGGCGGCAGAAACGTCT
CAGGGACAGCACATGGGCACGGACGAGCTGGACGGGCTACTCTGTGGCGAGGCCAATGGC
AAGGATGCTGAGAGCTCTGGGTGCTGGGGCAAGAAGAAGAAGAAAAAGAAATCCCAAGAT
CAGTGGGATGGAGTAGGACCTCTTCCAGACTGTGCTGAACCACCAAAAGGGATCCAGATG
CTGTGGCACCCATCAATAGTCAAACCCTACCTCACACTGCTCTCTGAGTGCTCAAATCCA
GACACGCTGGAAGGGGCGGCAGGCGCCCTGCAGAACTTGGCTGCAGGGAGCTGGAAGTGG
TCAGTATATATCCGAGCCGCTGTCCGAAAAGAGAAAGGCCTGCCCATCCTCGTGGAGCTG
CTCCGAATAGACAATGACCGTGTGGTGTGCGCGGTGGCACTGCGCTGCGGAACATGGCC
TTGGACGTCAGAAATAAGGAGCTCATCGGCAAATACGCCATGCGAGACCTAGTCCACAGG
CTTCCAGGAGGGAACAACAGCAACAACACTGCAAGCAAGGCCATGTCGGATGACACAGTG
ACAGCTGTCTGCTGCACACTGCACGAAGTGATTACCAAGAACATGGAGAACGCCAAGGCC
TTACGGGATGCCGGTGGCATCGAGAAGTTGGTCGGCATCTCCAAAAGCAAAGGAGATAAA
CACTCTCCAAAAGTGGTCAAGGCTGCATCTCAGGTCCTCAACAGCATGTGGCAGTACCGA
GATCTGAGGAGTCTCTACAAAAAGGATGGATGGTCACAATACCACTTTGTAGCCTCGTCT
TCAACCATCGAGAGGGACCGGCAAAGGCCCTACTCCTCCTCCCGCACGCCCTCCATCTCC
CCTGTGCGCGTGTCTCCCAACAACCGCTCAGCAAGTGCCCCAGCTTCACCTCGGGAAATG
ATCAGCCTCAAAGAAAGGAAAACAGACTACGAGTGCACCGGCAGCAACGCCACCTACCAC
GGAGCTAAAGGCGAACACACTTCCAGGAAAGATGCCATGACAGCTCAAAACACTGGAATT
TCAACTTTGTATAGGAATTCTTATGGTGCGCCCGCTGAAGACATCAAACACAACCAGGTT
TCAGCACAGCCAGTCCCACAGGAGCCCAGCAGAAAAGATTACGAGACCTACCAGCCATTT
CAGAATTCCACAAGAAATTACGATGAGTCCTTCTTCGAGGACCAGGTCCACCATCGCCCT

```
CCCGCCAGCGAGTACACCATGCACCTGGGTCTCAAGTCCACCGGCAACTACGTTGACTTC
TACTCAGCTGCCCGTCCCTACAGTGAACTGAACTATGAAACGAGCCACTACCCGGCCTCC
CCCGACTCCTGGGTGTGA
```

SEQ ID No. 17
NSMCE1
>ENSG00000169189|16|protein_coding|ENST00000358787|ENSP00000351638
CCGTATCCGCTAGCGCGGTGGGATGCGCTTGGGCTCCCTGTTCGTTCCCACATGCAGGGC
AGCACAAGGAGAATGGGCGTCATGACTGATGTCCACCGGCGCTTCCTCCAGTTGCTGATG
ACCCATGGCGTGCTAGAGGAATGGGACGTGAAGCGCTTGCAGACGCACTGCTACAAGGTC
CATGACCGCAATGCCACCGTAGATAAGTTGGAGGACTTCATCAACAACATTAACAGTGTC
TTGGAGTCCTTGTATATTGAGATAAAGAGAGGAGTCACGGAAGATGATGGGAGACCCATT
TATGCGTTGGTGAATCTTGCTACAACTTCAATTTCCAAAATGGCTACGGATTTTGCAGAG
AATGAACTGGATTTGTTTAGAAAGGCTCTGGAACTGATTATTGACTCAGAAACCTTGCGT
CTTCCACAAACATATTGA

Fig. 18

SEQ ID No. 18
NSMCE1
>ENSG00000169189|16|protein_coding|ENST00000361439|ENSP00000355077
ATGCAGGGCAGCACAAGGAGAATGGGCGTCATGACTGATGTCCACCGGCGCTTCCTCCAG
TTGCTGATGACCCATGGCGTGCTAGAGGAATGGGACGTGAAGCGCTTGCAGACGCACTGC
TACAAGGTCCATGACCGCAATGCCACCGTAGATAAGTTGGAGGACTTCATCAACAACATT
AACAGTGTCTTGGAGTCCTTGTATATTGAGATAAAGAGAGGAGTCACGGAAGATGATGGG
AGACCCATTTATGCGTTGGTGAATCTTGCTACAACTTCAATTTCCAAAATGGCTACGGAT
TTTGCAGAGAATGAACTGGATTTGTTTAGAAAGGCTCTGGAACTGATTATTGACTCAGAA
ACCGGCTTTGCGTCTTCCACAAACATATTGAACCTGGTTGATCAACTTAAAGGCAAGAAG
ATGAGGAAGAAGGAAGCGGAGCAGGTGCTGCAGAAGTTTGTTCAAAACAAGTGGCTGATT
GAGAAGGAAGGGGAGTTCACCCTGCACGGCCGGGCCATCCTGGAGATGGAGCAATACATC
CGGGAGACGTACCCCGACGCGGTGAAGATCTGCAATATCTGTCACAGCCTCCTCATCCAG
GGTCAAAGCTGCGAAACCTGTGGGATCAGGATGCACTTACCCTGCGTGGCCAAGTACTTC
CAGTCGAATGCTGAACCGCGCTGCCCCCACTGCAACGACTACTGGCCCCACGAGATCCCA
AAAGTCTTCGACCCTGAGAAGGAGAGGGAGTCTGGTGTCTTGAAATCGAACAAAAAGTCC
CTGCGGTCCAGGCAGCATTAG

Fig. 19

SEQ ID No. 19
NSMCE1
>ENSG00000169189|16|protein_coding|ENST00000311505|ENSP00000310853
GTCCACCTTGCGACCGTATCCGCTAGCGCGGCCTGGGATGCGCTTGGGCTCCCTGTTCGT
TCCCACATGCAGGGCAGCACAAGGAGAATGGGCGTCATGACTGATGTCCACCGGCGCTTC
CTCCAGTTGCTGATGACCCATGGCGTGCTAGAGGAATGGGACGTGAAGCGCTTGCAGACG
CACTGCTACAAGGTCCATGACCGCAATGCCACCGTAGATAAGTTGGAGGACTTCATCAAC
AACATTAACAGTGTCTTGGAGTCCTTGTATATTGAGATAAAGAGAGGAGTCACGGAAGAT
GATGGGAGACCCATTTATGCGTTGGTGAATCTTGCTACAACTTCAATTTCCAAAATGGCT
ACGGATTTTGCAGAGAATGAACTGGATTTGTTTAGAAAGGCTCTGGAACTGATTATTGAC
TCAGAAACCGGCTTTGCGTCTTCCACAAACATATTGAACCTGGTTGATCAACTTAAAGGC
AAGAAGATGAGGAAGAAGGAAGCGAGGTGCTGCAGAAGTTTGTTCAAAACAAGTGGCTGA

Fig. 20

SEQ ID No. 20
KTELC1
>ENSG00000163389|3|protein_coding|ENST00000295588|ENSP00000295588
ATGGAGTGGTGGGCTAGCTCGCCGCTTCGGCTCTGGCTGCTGTTGTTCCTCCTGCCCTCA
GCGCAGGGCCGCCAGAAGGAGTCAGGTTCAAAATGGAAAGTATTTATTGACCAAATTAAC
AGGTCTTTGGAGAATTACGAACCATGTTCAAGTCAAAACTGCAGCTGCTACCATGGTGTC
ATAGAAGAGGATCTAACTCCTTTCCGAGGAGGCATCTCCAGGAAGATGATGGCAGAGGTA
GTCAGACGGAAGCTAGGGACCCACTATCAGATCACTAAGAACAGACTGTACCGGGAAAAT
GACTGCATGTTCCCCTCAAGGTGTAGTGGTGTTGAGCACTTTATTTTGGAAGTGATCGGG
CGTCTCCCTGACATGGAGATGGTGATCAATGTACGAGATTATCCTCAGGTTCCTAAATGG
ATGGAGCCTGCCATCCCAGTCTTCTCCTTCAGTAAGACATCAGAGTACCATGATATCATG
TATCCTGCTTGGACATTTTGGGAAGGGGACCTGCTGTTTGGCCAATTTATCCTACAGGT
CTTGGACGGTGGGACCTCTTCAGAGAAGATCTGGTAAGGTCAGCAGCACAGTGGCCATGG
AAAAAGAAAAACTCTACAGCATATTTCCGAGGATCAAGGACAAGTCCAGAACGAGATCCT
CTCATTCTTCTGTCTCGGAAAAACCCAAAACTTGTTGATGCAGAATACACCAAAAACCAG
GCCTGGAAATCTATGAAAGATACCTTAGGAAAGCCAGCTGCTAAGGATGTCCATCTTGTG
GATCACTGCAAATACAAGTATCTGTTTAATTTTCGAGGCGTAGCTGCAAGTTTCCGGTTT
AAACACCTCTTCCTGTGTGGCTCACTTGTTTTCCATGTTGGTGATGAGTGGCTAGAATTC
TTCTATCCACAGCTGAAGCCATGGGTTCACTATATCCCAGTCAAAACAGATCTCTCCAAT
GTCCAAGAGCTGTTACAATTTGTAAAAGCAAATGATGATGTAGCTCAAGAGATTGCTGAA
AGGGGAAGCCAGTTTATTAGGAACCATTTGCAGATGGATGACATCACCTGTTACTGGGAG
AACCTCTTGAGTGAATACTCTAAATTCCTGTCTTATAATGTAACGAGAAGGAAAGGTTAT
GATCAAATTATTCCCAAAATGTTGAAAACTGAACTATAG

Fig. 21

SEQ ID No. 21
HS6ST1
>ENSG00000136720|2|protein_coding|ENST00000259241|ENSP00000259241
ATGCGGCGGCGGCGCGCCGGCGGCAGGACCATGGTTGAGCGCGCCAGCAAGTTCGTGCTG
GTGGTGGCGGGCTCGGTGTGCTTCATGCTCATCTTGTACCAGTACGCGGGCCCAGGACTG
AGCCTGGGCGCGCCCGGCGGCCGCGCGCCGCCCGACGACCTGGACCTGTTCCCCACACCC
GACCCCCACTACGAGAAGAAGTACTACTTCCCGGTCCGCGAGCTGGAGCGCTCGCTGCGC
TTCGACATGAAGGGCGACGACGTGATCGTCTTCCTGCACATCCAGAAGACGGGCGGCACC
ACCTTCGGCCGCCACCTCGTGCAGAACGTACGCCTCGAGGTGCCGTGCGACTGCCGGCCC
GGCCAGAAGAAGTGCACCTGCTACCGGCCCAACCGCCGCGAGACTTGGCTCTTCTCCCGC
TTCTCCACCGGCTGGAGCTGCGGGCTGCACGCCGACTGGACCGAGCTCACCAACTGCGTG
CCCGGCGTGCTGGACCGCCGCGACTCCGCCGCGCTGCGCACGCCCAGGAAGTTCTACTAC
ATCACCCTGCTACGAGACCCCGTGTCCGCTACCTGAGCGAGTGGCGGCATGTGCAGAGG
GGTGCCACGTGGAAGACGTCGTTGCATATGTGTGATGGGCGCACGCCCACGCCTGAGGAG
CTGCCGCCCTGCTACGAGGGCACGGACTGGTCGGGCTGCACGCTACAGGAGTTCATGGAC
TGCCCGTACAACCTGGCCAACAACCGCCAGGTGCGCATGCTGGCCGACCTGAGCCTGGTG
GGCTGCTACAACCTGTCCTTCATCCCCGAGGGCAAGCGGGCCCAGCTGCTGCTCGAGAGC
GCCAAGAAGAACCTGCGGGGCATGGCCTTCTTCGGCCTGACCGAGTTCCAGCGCAAGACG
CAGTACCTGTTCGAGCGGACGTTCAACCTCAAGTTCATCCGGCCCTTCATGCAGTACAAT
AGCACGCGGGCGGGCGGCGTGGAGGTGGATGAAGACACCATCCGGCGCATCGAGGAGCTC
AACGACCTGGACATGCAGCTGTACGACTACGCCAAGGACCTCTTCCAGCAGCGCTACCAG
TACAAGCGGCAGCTGGAGCGCAGGGAGCAGCGCCTGAGGAGCCGCGAGGAGCGTCTGCTG
CACCGGGCCAAGGAGGCACTGCCGCGGGAGGATGCCGACGAGCCGGGCCGCGTGCCCACC
GAGGACTACATGAGCCACATCATTGAGAAGTGGTAG

Fig. 22

SEQ ID No. 22
ARMC6
>ENSG00000105676|19|protein_coding|ENST00000379532|ENSP00000368847
ATGACATCCTGCAGATGCTCAGTGACCTCCAGGAGTCTGTGGCCAGCTCTCGCCCCCAGG
AGGTGTCAGCATACCTCACCCGCTTCTGCGCAGTGCAAACAGGACAAGGCCTGCCGCTTC
CTCGCGGCCCAGAAGGGGGCCTACCCCATCATCTTCACTGCCTGGAAGCTGGCCACTGCA
GGTGACCAGGGCCTTCTGCTCCAGTCCCTCAATGCCCTGTCGGTGCTGACTGATGGACAG
CCAGACCTCCTGGATGCCCAGGGCCTGCAGCTCCTAGTGGCCACGCTGACCCAGAATGCT
GATGAGGCTGACCTGACCTGCTCTGGGATCCGCTGTGTGCGTCACGCTTGCCTGAAACAT
GAACAGAATCGGCAAGACCTGGTGAAAGCTGGCGTGCTGCCTCTGCTGACTGGTGCCATC
ACCCATCATGGCCACCACACTGACGTGGTCAGGGAAGCCTGCTGGGCCCTGCGTGTCATG
ACCTTCGATGACGACATCCGTGTGCCCTTTGGCCATGCCCACAACCATGCCAAGATGATT
GTGCAGGAGAACAAAGGCTTGAAGGTGCTCATCGAAGCCACCAAAGCGTTCCTGGATAAC
CCTGGCATCCTGAGCGAGCTCTGTGGAACCCTGTCCCGCCTGGCCATTCGCAACGAGTTC
TGCCAGGAGGTCGTCGACCTCGGGGGCCTGAGCATTCTGGTGTCCCTGCTAGCCGACTGC
AATGACCACCAGATGAGGGACCAGAGCGGCGTTCAGGAGCTCGTGAAGCAAGTGCTGAGC
ACCCTGCGAGCCATCGCAGGCAACGACGACGTGAAAGATGCTATTGTCCGTGCTGGTGGG
ACGGAGTCCATCGTGGCTGCTATGACCCAGCATCTGACCAGCCCCAGGTGTGTGAGCAG
AGCTGCGCGGCCCTGTGCTTCCTGGCCCTGCGTAAGCCCGACAACAGCCGCATCATCGTG
GAGGGTGGCGGGGCTGTGGCAGCACTGCAGGCCATGAAGGCACACCCGCAGAAGGCCGGC
GTGCAGAAACAGGCTTGCATGCTGATCCGAAACCTGGTGGCCCACAGGCCTTCTCGAAGC
CCATCCTGGACCTGGGGGCTGAGGCACTCATCATGCAGGCCCGATCTGCCCACCGTGACT
GTGAGGACGTGGCCAAGGCCGCCCTGCGGGACCTGGGTTGTCATGTCGAGCTCCGAGAGC
TGTGGACAGGCCAGAGGGGCAACCTGGCGCCATGACCCCAGGCCCAGTCTGGTGACTCTG
GGTGAGTCGTGTGACTCAGGAATGGGGGTAGATCCATGTCCTCCACTGTCCCCCATTAGT
TCTGTCCCCTTCACAATGAGAAGTGTTTTCTGGCAGGCCCTAGGTAAAGGGTCGGGGGAG
GGGGGAGCCTTGTAG

Fig. 23

SEQ ID No. 23
ARMC6
>ENSG00000105676|19|protein_coding|ENST00000392335|ENSP00000376147
ATGGTCTCCAAGCGCATTGCCCAGGAGACCTTTGATGCAGCTGTGCGCGAGAACATCGAG
GAGTTTGCGATGGGGCCAGAGGAGGCAGTGAAAGAGGCCGTGGAGCAGTTTGAATCGCAA
GGGGTTGATCTGAGCAACATTGTAAAGACGGCACCTAAAGTCTCTGCAGACGGATCCCAG
GAGCCCACACATGACATCCTGCAGATGCTCAGTGACCTCCAGGAGTCTGTGGCCAGCTCT
CGCCCCCAGGAGGTGTCAGCATACCTCACCCGCTTCTGCGACCAGTGCAAACAGGACAAG
GCCTGCCGCTTCCTCGCGGCCCAGAAGGGGGCCTACCCCATCATCTTCACTGCCTGGAAG
CTGGCCACTGCAGGTGACCAGGGCCTTCTGCTCCAGTCCCTCAATGCCCTGTCGGTGCTG
ACTGATGGACAGCCAGACCTCCTGGATGCCCAGGGCCTGCAGCTCCTAGTGGCCACGCTG
ACCCAGAATGCTGATGAGGCTGACCTGACCTGCTCTGGGATCCGCTGTGTGCGTCACGCT
TGCCTGAAACATGAACAGAATCGGCAAGACCTGGTGAAAGCTGGCGTGCTGCCTCTGCTG
ACTGGTGCCATCACCCATCATGGCCACCACACTGACGTGGTCAGGGAAGCCTGCTGGGCC
CTGCGTGTCATGACCTTCGATGACGACATCCGTGTGCCCTTTGGCCATGCCCACAACCAT
GCCAAGATGATTGTGCAGGAGAACAAAGGCTTGAAGGTGCTCATCGAAGCCACCAAAGCG
TTCCTGGATAACCCTGGCATCCTGAGCGAGCTCTGTGGAACCCTGTCCCGCCTGGCCATT
CGCAACGAGTTCTGCCAGGAGGTCGTCGACCTCGGGGGCCTGAGCATTCTGGTGTCCCTG
CTAGCCGACTGCAATGACCACCAGATGAGGGACCAGAGCGGCGTTCAGGAGCTCGTGAAG
CAAGTGCTGAGCACCCTGCGAGCCATCGCAGGCAACGACGACGTGAAAGATGCTATTGTC
CGTGCTGGTGGGACGGAGTCCATCGTGGCTGCTATGACCCAGCATCTGACCAGCCCCCAG
GTGTGTGAGCAGAGCTGCGCGGCCCTGTGCTTCCTGGCCCTGCGTAAGCCCGACAACAGC
CGCATCATCGTGGAGGGTGGCGGGGCTGTGGCAGCACTGCAGGCCATGAAGGCACACCCG
CAGAAGGCCGGCGTGCAGAAACAGGCTTGCATGCTGATCCGAAACCTGGTGGCCCACGGC
CAGGCCTTCTCGAAGCCCATCCTGGACCTGGGGGCTGAGGCACTCATCATGCAGGCCCGA
TCTGCCCACCGTGACTGTGAGGACGTGGCCAAGGCCGCCCTGCGGGACCTGGGTTGTCAT
GTCGAGCTCCGAGAGCTGTGGACAGGCCAGAGGGGCAACCTGGCGCCATGA

Fig. 24

SEQ ID No. 24
ARMC6
>ENSG00000105676|19|protein_coding|ENST00000392336|ENSP00000376148
ATGAGTGAACGATGTTGCTCTAGATACAGCTCAGGAGCATCTATCGGCTGCACGCCAACA
TCAACACAGGCGAAGATGGTCTCCAAGCGCATTGCCCAGGAGACCTTTGATGCAGCTGTG
CGCGAGAACATCGAGGAGTTTGCGATGGGGCCAGAGGAGGCAGTGAAAGAGGCCGTGGAG
CAGTTTGAATCGCAAGGGGTTGATCTGAGCAACATTGTAAAGACGGCACCTAAAGTCTCT
GCAGACGGATCCCAGGAGCCCACACATGACATCCTGCAGATGCTCAGTGACCTCCAGGAG
TCTGTGGCCAGCTCTCGCCCCCAGGAGGTGTCAGCATACCTCACCCGCTTCTGCGACCAG
TGCAAACAGGACAAGGCCTGCCGCTTCCTCGCGGCCCAGAAGGGGGCCTACCCCATCATC
TTCACTGCCTGGAAGCTGGCCACTGCAGGTGACCAGGGCCTTCTGCTCCAGTCCCTCAAT
GCCCTGTCGGTGCTGACTGATGGACAGCCAGACCTCCTGGATGCCCAGGGCCTGCAGCTC
CTAGTGGCCACGCTGACCCAGAATGCTGATGAGGCTGACCTGACCTGCTCTGGGATCCGC
TGTGTGCGTCACGCTTGCCTGAAACATGAACAGAATCGGCAAGACCTGGTGAAAGCTGGC
GTGCTGCCTCTGCTGACTGGTGCCATCACCCATCATGGCCACCACACTGACGTGGTCAGG
GAAGCCTGCTGGGCCCTGCGTGTCATGACCTTCGATGACGACATCCGTGTGCCCTTTGGC
CATGCCCACAACCATGCCAAGATGATTGTGCAGGAGAACAAAGGCTTGAAGGTGCTCATC
GAAGCCACCAAAGCGTTCCTGGATAACCCTGGCATCCTGAGCGAGCTCTGTGGAACCCTG
TCCCGCCTGGCCATTCGCAACGAGTTCTGCCAGGAGGTCGTCGACCTCGGGGGCCTGAGC
ATTCTGGTGTCCCTGCTAGCCGACTGCAATGACCACCAGATGAGGGACCAGAGCGGCGTT
CAGGAGCTCGTGAAGCAAGTGCTGAGCACCCTGCGAGCCATCGCAGGCAACGACGACGTG
AAAGATGCTATTGTCCGTGCTGGTGGGACGGAGTCCATCGTGGCTGCTATGACCCAGCAT
CTGACCAGCCCCCAGGTGTGTGAGCAGAGCTGCGCGGCCCTGTGCTTCCTGGCCCTGCGT
AAGCCCGACAACAGCCGCATCATCGTGGAGGGTGGCGGGGCTGTGGCAGCACTGCAGGCC
ATGAAGGCACACCCGCAGAAGGCCGGCGTGCAGAAACAGGCTTGCATGCTGATCCGAAAC
CTGGTGGCCCACGGCCAGGCCTTCTCGAAGCCCATCCTGGACCTGGGGGCTGAGGCACTC
ATCATGCAGGCCCGATCTGCCCACCGTGACTGTGAGGACGTGGCCAAGGCCGCCCTGCGG
GACCTGGGTTGTCATGTCGAGCTCCGAGAGCTGTGGACAGGCCAGAGGGGCAACCTGGCG
CCATGA

Fig. 25

SEQ ID No. 25
ARMC6
>ENSG00000105676|19|protein_coding|ENST00000269932|ENSP00000269932
ATGGTCTCCAAGCGCATTGCCCAGGAGACCTTTGATGCAGCTGTGCGCGAGAACATCGAG
GAGTTTGCGATGGGGCCAGAGGAGGCAGTGAAAGAGGCCGTGGAGCAGTTTGAATCGCAA
GGGGTTGATCTGAGCAACATTGTAAAGACGGCACCTAAAGTCTCTGCAGACGGATCCAG
GAGCCCACACATGACATCCTGCAGATGCTCAGTGACCTCCAGGAGTCTGTGGCCAGCTCT
CGCCCCAGGAGGTGTCAGCATACCTCACCCGCTTCTGCGACCAGTGCAAACAGGACAAG
GCCTGCCGCTTCCTCGCGGCCCAGAAGGGGGCCTACCCCATCATCTTCACTGCCTGGAAG
CTGGCCACTGCAGGTGACCAGGGCCTTCTGCTCCAGTCCCTCAATGCCCTGTCGGTGCTG
ACTGATGGACAGCCAGACCTCCTGGATGCCCAGGGCCTGCAGCTCCTAGTGGCCACGCTG
ACCCAGAATGCTGATGAGGCTGACCTGACCTGCTCTGGGATCCGCTGTGTGCGTCACGCT
TGCCTGAAACATGAACAGAATCGGCAAGACCTGGTGAAAGCTGGCGTGCTGCCTCTGCTG
ACTGGTGCCATCACCCATCATGGCCACCACACTGACGTGGTCAGGGAAGCCTGCTGGGCC
CTGCGTGTCATGACCTTCGATGACGACATCCGTGTGCCCTTTGGCCATGCCCACAACCAT
GCCAAGATGATTGTGCAGGAGAACAAAGGCTTGAAGGTGCTCATCGAAGCCACCAAAGCG
TTCCTGGATAACCCTGGCATCCTGAGCGAGCTCTGTGGAACCCTGTCCCGCCTGGCCATT
CGCAACGAGTTCTGCCAGGAGGTCGTCGACCTCGGGGGCCTGAGCATTCTGGTGTCCCTG
CTAGCCGACTGCAATGACCACCAGATGAGGGACCAGAGCGGCGTTCAGGAGCTCGTGAAG
CAAGTGCTGAGCACCCTGCGAGCCATCGCAGGCAACGACGACGTGAAAGATGCTATTGTC
CGTGCTGGTGGGACGGAGTCCATCGTGGCTGCTATGACCCAGCATCTGACCAGCCCCAG
GTGTGTGAGCAGAGCTGCGCGGCCCTGTGCTTCCTGGCCCTGCGTAAGCCCGACAACAGC
CGCATCATCGTGGAGGGTGGCGGGGCTGTGGCAGCACTGCAGGCCATGAAGGCACACCCG
CAGAAGGCCGGCGTGCAGAAACAGGCTTGCATGCTGATCCGAAACCTGGTGGCCCACGGC
CAGGCCTTCTCGAAGCCCATCCTGGACCTGGGGGCTGAGGCACTCATCATGCAGGCCCGA
TCTGCCCACCGTGACTGTGAGGACGTGGCCAAGGCCGCCCTGCGGGACCTGGGTTGTCAT
GTCGAGCTCCGAGAGCTGTGGACAGGCCAGAGGGGCAACCTGGCGCCATGA

Fig. 26

SEQ ID No. 26
TH1L
>ENSG00000101158|20|protein_coding|ENST00000344018|ENSP00000342300
ATGGCGGGGCCGTGCCGGGCGCCATCATGGACGAGGACTACTACGGGAGCGCGGCCGAG
TGGGGCGACGAGGCTGACGGCGGCCAGCAGGAGGATGATTCTGGAGAAGGAGAGGATGAT
GCGGAGGTTCAGCAAGAATGCCTGCATAAATTTTCCACCCGGGATTATATCATGGAACCC
TCCATCTTCAACACTCTGAAGAGGTATTTTCAGGCAGGAGGGTCTCCAGAGAATGTTATC
CAGCTCTTATCTGAAAACTACACCGCTGTGGCCCAGACTGTGAACCTGCTGGCCGAGTGG
CTCATTCAGACAGGTGTTGAGCCAGTGCAGGTTCAGGAAACTGTGGAAAATCACTTGAAG
AGTTTGCTGATCAAACATTTTGACCCCGCAAAGCAGATTCTATTTTTACTGAAGAAGGA
GAGACCCCAGCGTGGCTGGAACAGATGATTGCACATACCACGTGGCGGGACCTTTTTTAT
AAACTGGCTGAAGCCCATCCAGACTGTTTGATGCTGAACTTCACCGTTAAGCTTATTTCT
GACGCAGGGTACCAGGGGGAGATCACCAGTGTGTCCACAGCATGCCAGCAGCTAGAAGTG
TTCTCGAGAGTGCTCCGGACCTCTCTAGCTACAATTTTAGATGGAGGAGAAGAAAACCTT
GAAAAAAATCTCCCTGAGTTTGCCAAGATGGTGTGCCACGGGAGCACACGTACCTGTTT
GCCCAGGCCATGATGTCCGTGCTGGCCCAGGAGGAGCAGGGGGGCTCCGCTGTGCGCAGG
ATCGCCCAGGAAGTGCAGCGCTTTGCCCAGGAGAAAGGTCATGACGCCAGTCAGATCACA
CTAGCCTTGGGCACAGCTGCCTCCTACCCCAGGGCCTGCCAGGCTCTCGGGGCCATGCTG
TCCAAAGGAGCCCTGAACCCTGCTGACATCACCGTCCTGTTCAAGATGTTCACAAGCATG
GACCCTCCTCCGGTTGAACTTATCCGCGTTCCAGCCTTCCTGGACCTGTTCATGCAGTCA
CTCTTTAAACCAGGGGCTCGGATCAACCAGGACCACAAGCACAAATACATCCACATCTTG
GCGTACGCAGCAAGCGTGGTTGAGACCTGGAAGAAGAACAAGCGAGTGAGCATCAATAAA
GATGAGCTGAAGTCAACGTCAAAAGCTGTCGAAACCGTTCACAATTTGTGTTGCAACGAG
AACAAAGGGGCCTCTGAACTAGTGGCAGAATTGAGCACACTTTATCAGTGTATTAGGTTT
CCAGTGGTAGCAATGGGTGTGCTGAAGTGGGTGGATTGGACTGTATCAGAACCAAGGTAC
TTTCAGCTGCAGACTGACCATACCCCTGTCCACCTGGCGTTGCTGGATGAGATCAGCACC
TGCCACCAGCTCCTGCACCCCCAGGTCCTGCAGCTGCTTGTTAAGCTTTTTGAGACTGAG
CACTCCCAGCTGGACGTGATGGAGCAGCTTGAGTTGAAGAAGACACTGCTGGACAGGATG
GTTCACCTGCTGAGTCGAGGTTATGTACTTCCTGTTGTCAGTTACATCCGAAAGTGTCTG
GAGAAGCTGGACACTGACATTTCACTCATTCGCTATTTTGTCACTGAGGTGCTGGACGTC
ATTGCTCCTCCTTATACCTCTGACTTCGTGCAACTTTTCCTCCCCATCCTGGAGAATGAC
AGCATCGCAGGTACCATCAAAACGGAAGGCGAGCATGACCCTGTGACGGAGTTTATAGCT
CACTGCAAATCTAACTTCATCATGGTGAACTAA

Fig. 27

SEQ ID No. 27
PSME1
>ENSG00000092010|14|protein_coding|ENST00000382708|ENSP00000372155
ATGGCCATGCTCAGGGTCCAGCCCGAGGCCCAAGCCAAGGTGGATGTGTTTCGTGAAGAC
CTCTGTACCAAGACAGAGAACCTGCTCGGGAGCTATTTCCCCAAGAAGATTTCTGAGCTG
GATGCATTTTTAAAGGAGCCAGCTCTCAATGAAGCCAACTTGAGCAATCTGAAGGCCCCA
TTGGACATCCCAGTGCCTGATCCAGTCAAGGAGAAAGAGAAAGAGGAGCGGAAGAAACAG
CAGGAGAAGGAAGACAAGGATGAAAAGAAGAAGGGGGAGGATGAAGACAAAGGTCCTCCC
TGTGGCCCAGTGAACTGCAATGAAAAGATCGTGGTCCTTCTGCAGCGCTTGAAGCCTGAG
ATCAAGGATGTCATTGAGCAGCTCAACCTGGTCACCACCTGGTTGCAGCTGCAGATACCT
CGGATTGAGGATGGTAACAATTTTGGAGTGGCTGTCCAGGAGAAGGTGTTTGAGCTGATG
ACCAGCCTCCACACCAAGCTAGAAGGCTTCCACACTCAAATCTCTAAGTATTTCTCTGAG
CGTGGTGATGCAGTGACTAAAGCAGCCAAGCAGCCCCATGTGGGTGATTATCGGCAGCTG
GTGCACGAGCTGGATGAGGCAGAGTACCGGGACATCCGGCTGATGGTCATGGAGATCCGC
AATGCTTATGTGAGGAGGCAAGGGCAGGGCAGGGGTGGGCAGAGGCAGCTTTCCCAGGCC
ACCCACTCCCTGACCCTGCAGGCTAGGGGTTAA

Fig. 28

SEQ ID No. 28
PSME1
>ENSG00000092010|14|protein_coding|ENST00000206451|ENSP00000206451
ATGGCCATGCTCAGGGTCCAGCCCGAGGCCCAAGCCAAGGTGGATGTGTTTCGTGAAGAC
CTCTGTACCAAGACAGAGAACCTGCTCGGGAGCTATTTCCCCAAGAAGATTTCTGAGCTG
GATGCATTTTTAAAGGAGCCAGCTCTCAATGAAGCCAACTTGAGCAATCTGAAGGCCCCA
TTGGACATCCCAGTGCCTGATCCAGTCAAGGAGAAAGAGAAAGAGGAGCGGAAGAAACAG
CAGGAGAAGGAAGACAAGGATGAAAAGAAGAAGGGGGAGGATGAAGACAAAGGTCCTCCC
TGTGGCCCAGTGAACTGCAATGAAAAGATCGTGGTCCTTCTGCAGCGCTTGAAGCCTGAG
ATCAAGGATGTCATTGAGCAGCTCAACCTGGTCACCACCTGGTTGCAGCTGCAGATACCT
CGGATTGAGGATGGTAACAATTTTGGAGTGGCTGTCCAGGAGAAGGTGTTTGAGCTGATG
ACCAGCCTCCACACCAAGCTAGAAGGCTTCCACACTCAAATCTCTAAGTATTTCTCTGAG
CGTGGTGATGCAGTGACTAAAGCAGCCAAGCAGCCCATGTGGGTGATTATCGGCAGCTG
GTGCACGAGCTGGATGAGGCAGAGTACCGGGACATCCGGCTGATGGTCATGGAGATCCGC
AATGCTTATGCTGTGTTATATGACATCATCCTGAAGAACTTCGAGAAGCTCAAGAAGCCC
AGGGGAGAAACAAAGGGAATGATCTATTGA

Fig. 29

SEQ ID No. 29
GPC1
>ENSG00000063660|2|protein_coding|ENST00000264039|ENSP00000264039
ATGGAGCTCCGGGCCCGAGGCTGGTGGCTGCTATGTGCGGCCGCAGCGCTGGTCGCCTGC
GCCCGCGGGGACCCGGCCAGCAAGAGCCGGAGCTGCGGCGAGGTCCGCCAGATCTACGGA
GCCAAGGGCTTCAGCCTGAGCGACGTGCCCCAGGCGGAGATCTCGGGTGAGCACCTGCGG
ATCTGTCCCCAGGGCTACACCTGCTGCACCAGCGAGATGGAGGAGAACCTGGCCAACCGC
AGCCATGCCGAGCTGGAGACCGCGCTCCGGGACAGCAGCCGCGTCCTGCAGGCCATGCTT
GCCACCCAGCTGCGCAGCTTCGATGACCACTTCCAGCACCTGCTGAACGACTCGGAGCGG
ACGCTGCAGGCCACCTTCCCCGGCGCCTTCGGAGAGCTGTACACGCAGAACGCGAGGGCC
TTCCGGGACCTGTACTCAGAGCTGCGCCTGTACTACCGCGGTGCCAACCTGCACCTGGAG
GAGACGCTGGCCGAGTTCTGGGCCCGCCTGCTCGAGCGCCTCTTCAAGCAGCTGCACCCC
CAGCTGCTGCTGCCTGATGACTACCTGGACTGCCTGGGCAAGCAGGCCGAGGCGCTGCGG
CCCTTCGGGGAGGCCCCGAGAGAGCTGCGCCTGCGGGCCACCCGTGCCTTCGTGGCTGCT
CGCTCCTTTGTGCAGGGCCTGGGCGTGGCCAGCGACGTGGTCCGGAAAGTGGCTCAGGTC
CCCCTGGGCCCGGAGTGCTCGAGAGCTGTCATGAAGCTGGTCTACTGTGCTCACTGCCTG
GGAGTCCCCGGCGCCAGGCCCTGCCCTGACTATTGCCGAAATGTGCTCAAGGGCTGCCTT
GCCAACCAGGCCGACCTGGACGCCGAGTGGAGGAACCTCCTGGACTCCATGGTGCTCATC
ACCGACAAGTTCTGGGGTACATCGGGTGTGGAGAGTGTCATCGGCAGCGTGCACACGTGG
CTGGCGGAGGCCATCAACGCCCTCCAGGACAACAGGGACACGCTCACGGCCAAGGTCATC
CAGGGCTGCGGGAACCCCAAGGTCAACCCCCAGGGCCCCGGGCCTGAGGAGAAGCGGCGC
CGGGGCAAGCTGGCCCCGCGGGAGAGGCCACCTTCAGGCACGCTGGAGAAGCTGGTCTCC
GAAGCCAAGGCCCAGCTCCGCGACGTCCAGGACTTCTGGATCAGCCTCCCAGGGACACTG
TGCAGTGAGAAGATGGCCCTGAGCACTGCCAGTGATGACCGCTGCTGGAACGGGATGGCC
AGAGGCCGGTACCTCCCCGAGGTCATGGGTGACGGCCTGGCCAACCAGATCAACAACCCC
GAGGTGGAGGTGGACATCACCAAGCCGGACATGACCATCCGGCAGCAGATCATGCAGCTG
AAGATCATGACCAACCGGCTGCGCAGCGCCTACAACGGCAACGACGTGGACTTCCAGGAC
GCCAGTGACGACGGCAGCGGCTCGGGCAGCGGTGATGGCTGTCTGGATGACCTCTGCAGC
CGGAAGGTCAGCAGGAAGAGCTCCAGCTCCCGGACGCCCTTGACCCATGCCCTCCCAGGC
CTGTCAGAGCAGGAAGGACAGAAGACCTCGGCTGCCAGCTGCCCCCAGCCCCCGACCTTC
CTCCTGCCCCTCCTCCTCTTCCTGGCCCTTACAGTAGCCAGGCCCCGGTGGCGGTAA

Fig. 30

SEQ ID No. 30
EDC4
>ENSG00000038358|16|protein_coding|ENST00000041337|ENSP00000041337
ATGGCCTCCTGCGCGAGCATCGACATCGAGGACGCCACGCAGCACCTGCGGGACATCCTC
AAGCTGGACCGGCCCGCGGGCGGCCCCAGTGCAGAGAGCCCACGGCCATCCAGTGCCTAC
AATGGGGACCTCAATGGACTTCTGGTCCCAGACCCGCTCTGCTCAGGTGATAGTACCTCA
GCAAACAAGACTGGTCTTCGGACCATGCCACCCATTAACCTGCAAGAGAAGCAGGTCATC
TGTCTCTCAGGAGATGATAGCTCCACCTGCATTGGGATTTTGGCCAAGGAGGTGGAGATT
GTGGCTAGCAGTGACTCTAGCATTTCAAGCAAGGCCCGGGGAAGCAACAAGGTGAAAATT
CAGCCTGTCGCCAAGTATGACTGGGAACAGAAGTACTACTATGGCAACCTGATTGCTGTG
TCTAACTCCTTCTTGGCCTATGCCATTCGGGCTGCCAACAATGGCTCTGCCATGGTGCGG
GTGATCAGCGTCAGCACTTCGGAGCGGACCTTGCTCAAGGGCTTCACAGGCAGTGTGGCT
GATCTGGCTTTCGCGCACCTCAACTCTCCACAGCTGGCCTGCCTGGATGAGGCAGGCAAC
CTGTTCGTGTGGCGCTTGGCTCTGGTTAATGGCAAAATTCAAGAAGAGATCTTGGTCCAT
ATTCGGCAGCCAGAGGGCACGCCACTGAACCACTTTCGCAGGATCATCTGGTGCCCCTTC
ATCCCTGAGGAGAGCGAAGACTGCTGTGAGGAGAGCAGCCCAACAGTGGCCCTGCTGCAT
GAAGACCGGGCTGAGGTGTGGGACCTGGACATGCTCCGCTCCAGCCACAGTACCTGGCCT
GTGGATGTTAGCCAGATCAAGCAGGGCTTCATTGTGGTAAAAGGTCATAGCACGTGCCTC
AGTGAAGGAGCCCTCTCTCCTGATGGGACTGTGCTGGCTACTGCGAGCCACGATGGCTAT
GTCAAGTTCTGGCAGATCTACATTGAGGGCAAGATGAGCCAAGGTGTCTGCACGAGTGG
AAACCTCATGATGGGCGGCCCCTCTCCTGCCTCCTGTTCTGTGACAACCATAAGAAACAA
GACCCTGATGTCCCTTTCTGGAGGTTCCTTATTACTGGTGCTGACCAGAACCGAGAGTTA
AAGATGTGGTGTACAGTATCCTGGACCTGCCTGCAGACTATTCGCTTCTCCCCAGATATC
TTCAGCTCAGTGAGTGTGCCCCCTAGCCTCAAGGTTTGCTTGGACCTCTCAGCAGAATAC
CTGATTCTCAGCGATGTGCAACGGAAGGTCCTCTATGTGATGGAGCTGCTGCAAAACCAG
GAGGAGGGCCACGCCTGCTTCAGCTCCATCTCGGAGTTCCTGCTCACCCACCCTGTGCTG
AGCTTTGGTATCCAGGTTGTGAGTCGCTGCCGGCTACGGCACACTGAGGTGCTGCCTGCC
GAAGAGGAAAATGACAGCCTGGGTGCTGATGGTACCCATGGAGCCGGTGCCATGGAGTCT
GCGGCCGGTGTGCTCATCAAGCTCTTTTGTGTGCATACTAAGGCACTGCAAGATGTGCAG
ATCCGCTTCCAGCCACAGCTGAACCCTGATGTGGTGGCCCCACTGCCCACCCACACTGCC
CACGAGGACTTCACATTTGGAGAGTCTCGGCCCGAACTGGGCTCTGAGGGCCTGGGGTCA
GCCGCTCACGGCTCCCAGCCTGACCTCCGACGAATCGTGGAGCTGCCTGCACCTGCCGAC
TTCCTCAGTCTGAGCAGTGAGACCAAGCCCAAGTTGATGACACCTGACGCCTTCATGACA
CCTAGCGCCTCCTTGCAGCAGATCACTGCCTCTCCCAGCAGCAGCAGCAGCGGTAGCAGC
AGCAGCAGCAGCAGTAGCAGCAGCTCCCTTACAGCTGTGTCTGCCATGAGCAGCACCTCA
GCTGTGGACCCCTCCTTGACCAGGCCACCTGAGGAGCTGACCTTGAGCCCCAAGCTGCAG
CTGGATGGCAGCCTGACAATGAGCAGCAGTGGCAGCCTTCAGGCAAGCCCGCGTGGCCTC
CTGCCTGGCCTGCTCCCAGCCCCAGCTGACAAACTGACTCCCAAGGGGCCGGGCCAGGTG
CCTACTGCCACCTCTGCACTGTCCCTGGAGCTGCAGGAAGTGGAGCCCCTGGGGCTACCC
CAAGCCTCCCCTAGCCGCACTCGTTCCCCTGATGTCATCTCCTCAGCTTCCACTGCCCTG
TCCCAGGACATCCCTGAGATTGCATCTGAGGCCCTGTCCCGTGGTTTTGGCTCCTCTGCA
CCAGAGGGCCTTGAGCCAGACAGTATGGCTTCAGCCGCCTCGGCACTGCACCTGCTGTCC
CCACGGCCCCGGCCAGGGCCCGAGCTCGGCCCCCAGCTCGGGCTTGATGGAGGCCCTGGG
GATGGAGATCGGCATAATACCCCTCCCTCCTGGAGGCAGCCTTGACCCAGGAGGCCTCG
ACTCCTGACAGTCAGGTTTGGCCCACAGCACCTGACATTACTCGTGAGACCTGCAGCACC
CTGGCAGAAAGCCCCAGGAATGGCCTTCAGGAAAAGCACAAGAGCCTGGCCTTCCACCGA
CCACCATATCACCTGCTGCAGCAACGTGACAGCCAGGATGCCAGTGCTGAGCAAAGTGAC
CATGATGATGAGGTGGCCAGCCTTGCCTCTGCTTCAGGAGGCTTTGGCACCAAAGTTCCT
GCTCCACGGCTGCCTGCCAAGGACTGGAAGACCAAGGGATCCCCTCGAACCTCACCCAAG
CTCAAGAGGAAAAGCAAGAAGGATGATGGGGATGCAGCCATGGGATCCCGGCTCACAGAG
CACCAGGTGGCAGAGCCCCTGAGGACTGGCCAGCACTAATTTGGCAACAGCAGAGAGAG
CTGGCAGAGCTGCGGCACAGCCAGGAAGAGCTGCTGCAGCGTCTGTGTACCCAACTCGAA
GGCCTGCAGAGCACAGTCACAGGCCACGTAGAACGTGCCCTTGAGACTCGGCACGAGCAG
GAACAGCGGCGGCTGGAGCGAGCACTGGCTGAGGGGCAGCAGCGGGGAGGGCAGCTGCAG
GAGCAGCTGACACAACAGTTGTCCCAAGCACTGTCGTCAGCTGTAGCTGGGCGGCTAGAG
CGCAGCATACGGGATGAGATCAAGAAGACAGTCCCTCCATGTGTCTCAAGGAGTCTGGAG
CCTATGGCAGGCCAACTGAGCAACTCAGTGGCTACCAAGCTCACAGCTGTGGAGGGCAGC
ATGAAAGAGAACATCTCCAAGCTGCTCAAGTCCAAGAACTTGACTGATGCCATCGCCCGA
GCAGCTGCAGACACATTACAAGGGCCGATGCAGGCTGCCTACCGGGAAGCCTTCCAGAGT
GTGGTGCTGCCGGCCTTTGAGAAGAGCTGCCAGGCCATGTTCCAGCAAATCAATGATAGC
TTCCGGCTGGGGACACAGGAATACTTGCAGCAGCTAGAAAGCCACATGAAGAGCCGGAAG
GCACGGGAACAGGAGGCCAGGGAGCCTGTGCTAGCCCAGCTGCGGGGCCTGGTCAGCACA

```
CTGCAGAGTGCCACTGAGCAGATGCCACCGTGGCCGGCAGTGTTCGTGCTGAGGTGCAGC
ACCAGCTGCATGTGGCTGTGGGCAGCCTGCAGGAGTCCATTTTAG
```

SEQ ID No. 31
EDC4
>ENSG00000038358|16|protein_coding|ENST00000358933|ENSP00000351811
ATGGCCTCCTGCGCGAGCATCGACATCGAGGACGCCACGCAGCACCTGCGGGACATCCTC
AAGCTGGACCGGCCCGCGGGCGGCCCCAGTGCAGAGAGCCCACGGCCATCCAGTGCCTAC
AATGGGGACCTCAATGGACTTCTGGTCCCAGACCCGCTCTGCTCAGGTGATAGTACCTCA
GCAAACAAGACTGGTCTTCGGACCATGCCACCCATTAACCTGCAAGAGAAGCAGGTCATC
TGTCTCTCAGGAGATGATAGCTCCACCTGCATTGGGATTTTGGCCAAGGAGGTGGAGATT
GTGGCTAGCAGTGACTCTAGCATTTCAAGCAAGGCCCGGGGAAGCAACAAGGTGAAAATT
CAGCCTGTCGCCAAGTATGACTGGGAACAGAAGTACTACTATGGCAACCTGATTGCTGTG
TCTAACTCCTTCTTGGCCTATGCCATTCGGGCTGCCAACAATGGCTCTGCCATGGTGCGG
GTGATCAGCGTCAGCACTTCGGAGCGGACCTTGCTCAAGGGCTTCACAGGCAGTGTGGCT
GATCTGGCTTTCGCGCACCTCAACTCTCCACAGCTGGCCTGCCTGGATGAGGCAGGCAAC
CTGTTCGTGTGGCGCTTGGCTCTGGTTAATGGCAAAATTCAAGAAGAGATCTTGGTCCAT
ATTCGGCAGCCAGAGGGCACGCCACTGAACCACTTTCGCAGGATCATCTGGTGCCCCTTC
ATCCCTGAGGAGAGCGAAGACTGCTGTGAGGAGAGCAGCCCAACAGTGGCCCTGCTGCAT
GAAGACCGGGCTGAGGTGTGGGACCTGGACATGCTCCGCTCCAGCCACAGTACCTGGCCT
GTGGATGTTAGCCAGATCAAGCAGGGCTTCATTGTGGTAAAAGGTCATAGCACGTGCCTC
AGTGAAGGAGCCCTCTCTCCTGATGGGACTGTGCTGGCTACTGCGAGCCACGATGGCTAT
GTCAAGTTCTGGCAGATCTACATTGAGGGCAAGATGAGCCAAGGTGTCTGCACGAGTGG
AAACCTCATGATGGGCGGCCCCTCTCCTGCCTCCTGTTCTGTGACAACCATAAGAAACAA
GACCCTGATGTCCCCTTTCTGGAGGTTCCTTATTACTGGTGCTGACCAGAACCGAGAGTTA
AAGATGTGGTGTACAGTATCCTGGACCTGCCTGCAGACTATTCGCTTCTCCCCAGATATC
TTCAGCTCAGTGAGTGTGCCCCCTAGCCTCAAGGTTTGCTTGGACCTCTCAGCAGAATAC
CTGATTCTCAGCGATGTGCAACGGAAGGTCCTCTATGTGATGGAGCTGCTGCAAAACCAG
GAGGAGGGCCACGCCTGCTTCAGCTCCATCTCGGAGTTCCTGCTCACCCACCCTGTGCTG
AGCTTTGGTATCCAGGTTGTGAGTCGCTGCCGGCTACGGCACACTGAGGTGCTGCCTGCC
GAAGAGGAAAATGACAGCCTGGGTGCTGATGGTACCCATGGAGCCGGTGCCATGGAGTCT
GCGGCCGGTGTGCTCATCAAGCTCTTTTGTGTGCATACTAAGGCACTGCAAGATGTGCAG
ATCCGCTTCCAGCCACAGCTGAACCCTGATGTGGTGGCCCCACTGCCCACCCACACTGCC
CACGAGGACTTCACATTTGGAGAGTCTCGGCCCGAACTGGGCTCTGAGGGCCTGGGGTCA
GCCGCTCACGGCTCCCAGCCTGACCTCCGACGAATCGTGGAGCTGCCTGCCACCTGCCGAC
TTCCTCAGTCTGAGCAGTGAGACCAAGCCCAAGTTGATGACACCTGACGCCTTCATGACA
CCTAGCGCCTCCTTGCAGCAGATCACTGCCTCTCCCAGCAGCAGCAGCAGCGGTAGCAGC
AGCAGCAGCAGCAGTAGCAGCAGCTCCCTTACAGCTGTGTCTGCCATGAGCAGCACCTCA
GCTGTGGACCCCTCCTTGACCAGGCCACCTGAGGAGCTGACCTTGAGCCCCAAGCTGCAG
CTGGATGGCAGCCTGACAATGAGCAGCAGTGGCAGCCTTCAGGCAAGCCCGCGTGGCCTC
CTGCCTGGCCTGCTCCCAGCCCCAGCTGACAAACTGACTCCCAAGGGGCCGGGCCAGGTG
CCTACTGCCACCTCTGCACTGTCCCTGGAGCTGCAGGAAGTGGAGCCCCTGGGGCTACCC
CAAGCCTCCCCTAGCCGCACTCGTTCCCCTGATGTCATCTCCTCAGCTTCCACTGCCCTG
TCCCAGGACATCCCTGAGATTGCATCTGAGGCCCTGTCCCGTGGTTTTGGCTCCTCTGCA
CCAGAGGGCCTTGAGCCAGACAGTATGGCTTCAGCCGCCTCGGCACTGCACCTGCTGTCC
CCACGGCCCCGGCCAGGGCCCGAGCTCGGCCCCAGCTCGGGCTTGATGGAGGCCCTGGG
GATGGAGATCGGCATAATACCCCCTCCCTCCTGGAGGCAGCCTTGACCCAGGAGGCCTCG
ACTCCTGACAGTCAGGTTTGGCCCACAGCACCTGACATTACTCGTGAGACCTGCAGCACC
CTGGCAGAAAGCCCCAGGAATGGCCTTCAGGAAAAGCACAAGAGCCTGGCCTTCCACCGA
CCACCATATCACCTGCTGCAGCAACGTGACAGCCAGGATGCCAGTGCTGAGCAAAGTGAC
CATGATGATGAGGTGGCCAGCCTTGCCTCTGCTTCAGGAGGCTTTGGCACCAAAGTTCCT
GCTCCACGGCTGCCTGCCAAGGACTGGAAGACCAAGGGATCCCCTCGAACCTCACCCAAG
CTCAAGAGGAAAAGCAAGAAGGATGATGGGGATGCAGCCATGGGATCCCGGCTCACAGAG
CACCAGGTGGCAGAGCCCCTGAGGACTGGCCAGCACTAATTTGGCAACAGCAGAGAGAG
CTGGCAGAGCTGCGGCACAGCCAGGAAGAGCTGCTGCAGCGTCTGTGTACCCAACTCGAA
GGCCTGCAGAGCACAGTCACAGGCCACGTAGAACGTGCCCTTGAGACTCGGCACGAGCAG
GAACAGCGGCGGCTGGAGCGAGCACTGGCTGAGGGGCAGCAGCGGGGAGGGCAGCTGCAG
GAGCAGCTGACACAACAGTTGTCCCAAGCACTGTCGTCAGCTGTAGCTGGGCGGCTAGAG
CGCAGCATACGGGATGAGATCAAGAAGACAGTCCCTCCATGTGTCTCAAGGAGTCTGGAG
CCTATGGCAGGCCAACTGAGCAACTCAGTGGCTACCAAGCTCACAGCTGTGGAGGGCAGC
ATGAAAGAGAACATCTCCAAGCTGCTCAAGTCCAAGAACTTGACTGATGCCATCGCCCGA
GCAGCTGCAGACACATTACAAGGGCCGATGCAGGCTGCCTACCGGGAAGCCTTCCAGAGT
GTGGTGCTGCCGGCCTTTGAGAAGAGCTGCCAGGCCATGTTCCAGCAAATCAATGATAGC
TTCCGGCTGGGGACACAGGAATACTTGCAGCAGCTAGAAAGCCACATGAAGAGCCGGAAG
GCACGGGAACAGGAGGCCAGGGAGCCTGTGCTAGCCCAGCTGCGGGCCTGGTCAGCACA

```
CTGCAGAGTGCCACTGAGCAGATGGCAGCCACCGTGGCCGGCAGTGTTCGTGCTGAGGTG
CAGCACCAGCTGCATGTGGCTGTGGGCAGCCTGCAGGAGTCCATTTTAGCACAGGTACAG
CGCATCGTTAAGGGTGAGGTGAGTGTGGCGCTCAAGGAGCAGCAGGCCGCCGTCACCTCC
AGCATCATGCAGGCCATGCGCTCAGCTGCTGGCACACCTGTCCCCTCTGCCCACCTTGAC
TGCCAGGCCCAGCAAGCCCATATCCTGCAGCTGCTGCAGCAGGGCCACCTCAATCAGGCC
TTCCAGCAGGCGCTGACAGCTGCTGACCTGAACCTGGTGCTGTATGTGTGTGAAACTGTG
GACCCAGCCCAGGTTTTTGGGCAGCCACCCTGCCCGCTCTCCCAGCCTGTGCTCCTTTCC
CTCATCCAGCAGCTGGCATCTGACCTTGGCACTCGAACTGACCTCAAGCTCAGCTACCTG
GAAGAGGCCGTGATGCACCTGGACCACAGTGACCCCATCACTCGGGACCACATGGGCTCC
GTTATGGCCCAGGTGCGCCAAAAGCTTTTTCAGTTCCTGCAGGCTGAGCCACACAACTCA
CTTGGCAAAGCAGCTCGGCGTCTCAGCCTCATGCTGCATGGCCTCGTGACCCCCAGCCTC
CCTTAG
```

SEQ ID No. 32
PRC1
>ENSG00000198901|15|protein_coding|ENST00000361188|ENSP00000354679
ACGAGGCTTCGCCCCGTGGCGCGGTTTGAAATTTTGCGGGGCTCAACGGCTCGCGGAGCG
GCTACGCGGAGTGACATCGCCGGTGTTTGCGGGTGGTTGTTGCTCTCGGGGCCGTGTGGA
GTAGGTCTGGACCTGGACTCACGGCTGCTTGGAGCGTCCGCCATGAGGAGAAGTGAGGTG
CTGGCGGAGGAGTCCATAGTATGTCTGCAGAAAGCCCTAAATCACCTTCGGGAAATATGG
GAGCTAATTGGGATTCCAGAGGACCAGCGGTTACAAAGAACTGAGGTGGTAAAGAAGCAT
ATCAAGGAACTCCTGGATATGATGATTGCTGAAGAGGAAAGCCTGAAGGAAAGACTCATC
AAAAGCATATCCGTCTGTCAGAAAGAGCTGAACACTCTGTGCAGCGAGTTACATGTTGAG
CCATTTCAGGAAGAAGGAGAGACGACCATCTTGCAACTAGAAAAGATTTGCGCACCCAA
GTGGAATTGATGCGAAAACAGAAAAGGAGAGAAAACAGGAACTGAAGCTACTTCAAGAG
CAAGATCAAGAACTGTGCGAAATTCTTTGTATGCCCCACTATGATATTGACAGTGCCTCA
GTGCCCAGCTTAGAAGAGCTGAACCAGTTCAGGCAACATGTGACAACTTTGAGGGAAACA
AAGGCTTCTAGGCGTGAGGAGTTTGTCAGTATAAAGAGACAGATCATACTGTGTATGGAA
GCATTAGACCACACCCCAGACACAAGCTTTGAAAGAGATGTGGTGTGTGAAGACGAAGAT
GCCTTTTGTTTGTCTTTGGAGAATATTGCAACACTACAAAAGTTGCTACGGCAGCTGGAA
ATGCAGAAATCACAAAATGAAGCAGTGTGTGAGGGGCTGCGTACTCAAATCCGAGAGCTC
TGGGACAGGTTGCAAATACCTGAAGAAGAAAGAGAAGCTGTGGCCACCATTATGTCTGGG
TCAAAGGCCAAGGTCCGGAAAGCGCTGCAATTAGAAGTGGATCGGTTGGAAGAACTGAAA
ATGCAAAACATGAAGAAAGTGATTGAGGCAATTCGAGTGGAGCTGGTTCAGTACTGGGAC
CAGTGCTTTTATAGCCAGGAGCAGAGACAAGCTTTTGCCCCTTTCTGTGCTGAGGACTAC
ACAGAAAGTCTGCTCCAGCTCCACGATGCTGAGATTGTGCGGTTAAAAAACTACTATGAA
GTTCACAAGGAACTCTTTGAAGGTGTCCAGAAGTGGGAAGAAACCTGGAGGCTTTTCTTA
GAGTTTGAGAGAAAAGCTTCAGATCCAAATCGATTTACAAACCGAGGAGGAAATCTTCTA
AAAGAAGAAAAACAACGAGCCAAGCTCCAGAAAATGCTGCCCAAGCTGGAAGAAGAGTTG
AAGGCACGAATTGAATTGTGGGAACAGGAACATTCAAAGGCATTTATGGTGAATGGGCAG
AAATTCATGGAGTATGTGGCAGAACAATGGGAGATGCATCGATTGGAGAAAGAGAGAGCC
AAGCAGGAAAGACAACTGAAGAACAAAAAACAGACAGAGACAGAGATGCTGTATGGCAGC
GCTCCTCGAACACCTAGCAAGCGGCGAGGACTGGCTCCCAATACACCGGGCAAAGCACGT
AAGCTGAACACTACCACCATGTCCAATGCTACGGCCAATAGTAGCATTCGGCCTATCTTT
GGAGGGACAGTCTACCACTCCCCGTGTCTCGACTTCCTCCTTCTGGCAGCAAGCCAGTC
GCTGCTTCCACCTGTTCAGGGAAGAAAACACCCCGTACTGGCAGGCATGGAGCCAACAAG
GAGAACCTGGAGCTCAACGGCAGCATCCTGAGTGGTGGGTACCCTGGCTCGGCCCCCCTC
CAGCGCAACTTCAGCATTAATTCTGTTGCCAGCACCTATTCTGAGTTTGCGCGAGAACTT
TCAAAGGCTTCCAAATCTGATGCTACTTCTGGAATCCTCAATTCAACCAACATCCAGTCC
TGA

Fig. 33

SEQ ID No. 33
PRC1
>ENSG00000198901|15|protein_coding|ENST00000394249|ENSP00000377793
ACGAGGCTTCGCCCCGTGGCGCGGTTTGAAATTTTGCGGGGCTCAACGGCTCGCGGAGCG
GCTACGCGGAGTGACATCGCCGGTGTTTGCGGGTGGTTGTTGCTCTCGGGCCGTGTGGA
GTAGGTCTGGACCTGGACTCACGGCTGCTTGGAGCGTCCGCCATGAGGAGAAGTGAGGTG
CTGGCGGAGGAGTCCATAGTATGTCTGCAGAAAGCCCTAAATCACCTTCGGGAAATATGG
GAGCTAATTGGGATTCCAGAGGACCAGCGGTTACAAAGAACTGAGGTGGTAAAGAAGCAT
ATCAAGGAACTCCTGGATATGATGATTGCTGAAGAGGAAAGCCTGAAGGAAAGACTCATC
AAAAGCATATCCGTCTGTCAGAAAGAGCTGAACACTCTGTGCAGCGAGTTACATGTTGAG
CCATTTCAGGAAGAAGGAGAGACGACCATCTTGCAACTAGAAAAAGATTTGCGCACCCAA
GTGGAATTGATGCGAAAACAGAAAAAGGAGAGAAAACAGGAACTGAAGCTACTTCAAGAG
CAAGATCAAGAACTGTGCGAAATTCTTTGTATGCCCCACTATGATATTGACAGTGCCTCA
GTGCCCAGCTTAGAAGAGCTGAACCAGTTCAGGCAACATGTGACAACTTTGAGGGAAACA
AAGGCTTCTAGGCGTGAGGAGTTTGTCAGTATAAAGAGACAGATCATACTGTGTATGGAA
GCATTAGACCACACCCCAGACACAAGCTTTGAAAGAGATGTGGTGTGTGAAGACGAAGAT
GCCTTTTGTTTGTCTTTGGAGAATATTGCAACACTACAAAAGTTGCTACGGCAGCTGGAA
ATGCAGAAATCACAAAATGAAGCAGTGTGTGAGGGGCTGCGTACTCAAATCCGAGAGCTC
TGGGACAGGTTGCAAATACCTGAAGAAGAAAGAGAAGCTGTGGCCACCATTATGTCTGGG
TCAAAGGCCAAGGTCCGGAAAGCGCTGCAATTAGAAGTGGATCGGTTGGAAGAACTGAAA
ATGCAAAACATGAAGAAAGTGATTGAGGCAATTCGAGTGGAGCTGGTTCAGTACTGGGAC
CAGTGCTTTTATAGCCAGGAGCAGAGACAAGCTTTTGCCCCTTTCTGTGCTGAGGACTAC
ACAGAAAGTCTGCTCCAGCTCCACGATGCTGAGATTGTGCGGTTAAAAAACTACTATGAA
GTTCACAAGGAACTCTTTGAAGGTGTCCAGAAGTGGGAAGAAACCTGGAGGCTTTTCTTA
GAGTTTGAGAGAAAAGCTTCAGATCCAAATCGATTTACAAACCGAGGAGGAAATCTTCTA
AAAGAAGAAAAACAACGAGCCAAGCTCCAGAAAATGCTGCCCAAGCTGGAAGAAGAGTTG
AAGGCACGAATTGAATTGTGGGAACAGGAACATTCAAAGGCATTTATGGTGAATGGGCAG
AAATTCATGGAGTATGTGGCAGAACAATGGGAGATGCATCGATTGGAGAAAGAGAGAGCC
AAGCAGGAAAGACAACTGAAGAACAAAAAACAGACAGAGACAGAGATGCTGTATGGCAGC
GCTCCTCGAACACCTAGCAAGCGGCGAGGACTGGCTCCCAATACACCGGGCAAAGCACGT
AAGCTGAACACTACCACCATGTCCAATGCTACGGCCAATAGTAGCATTCGGCCTATCTTT
GGAGGGACAGTCTACCACTCCCCCGTGTCTCGACTTCCTCCTTCTGGCAGCAAGCCAGTC
GCTGCTTCCACCTGTTCAGGGAAGAAAACACCCCGTACTGGCAGGCATGGAGCCAACAAG
GAGAACCTGGAGCTCAACGGCAGCATCCTGAGTGGTGGGTACCCTGGCTCGGCCCCCCTC
CAGCGCAACTTCAGCATTAATTCTGTTGCCAGCACCTATTCTGAGTTTGCGAAGGATCCG
TCCCTCTCTGACAGTTCCACTGTTGGGCTTCAGCGAGAACTTTCAAAGGCTTCCAAATCT
GATGCTACTTCTGGAATCCTCAATTCAACCAACATCCAGTCCTGA

Fig. 34

SEQ ID No. 34
PRC1
>ENSG00000198901|15|protein_coding|ENST00000361919|ENSP00000354618
ATGAGGAGAAGTGAGGTGCTGGCGGAGGAGTCCATAGTATGTCTGCAGAAAGCCCTAAAT
CACCTTCGGGAAATATGGGAGCTAATTGGGATTCCAGAGGACCAGCGGTTACAAAGAACT
GAGGTGGTAAAGAAGCATATCAAGGAACTCCTGGATATGATGATTGCTGAAGAGGAAAGC
CTGAAGGAAAGACTCATCAAAAGCATATCCGTCTGTCAGAAAGAGCTGAACACTCTGTGC
AGCGAGTTACATGTTGAGCCATTTCAGGAAGAAGGAGAGACGACCATCTTGCAACTAGAA
AAAGATTTGCGCACCCAAGTGGAATTGATGCGAAAACAGAAAAAGGAGAGAAAACAGGAA
CTGAAGCTACTTCAAGAGCAAGATCAAGAACTGTGCGAAATTCTTTGTATGCCCCACTAT
GATATTGACAGTGCCTCAGTGCCCAGCTTAGAAGAGCTGAACCAGTTCAGGCAACATGTG
ACAACTTTGAGGGAAACAAAGGCTTCTAGGCGTGAGGAGTTTGTCAGTATAAAGAGACAG
ATCATACTGTGTATGGAAGCATTAGACCACACCCCAGACACAAGCTTTGAAAGAGATGTG
GTGTGTGAAGACGAAGATGCCTTTTGTTTGTCTTTGGAGAATATTGCAACACTACAAAAG
TTGCTACGGCAGCTGGAAATGCAGAAATCACAAAATGAAGCAGTGTGTGAGGGGCTGCGT
ACTCAAATCCGAGAGCTCTGGGACAGGTTGCAAATACCTGAAGAAGAAAGAGAAGCTGTG
GCCACCATTATGTCTGGGTCAAAGGCCAAGGTCCGGAAAGCGCTGCAATTAGAAGTGGAT
CGGTTGGAAGAACTGAAAATGCAAAACATGAAGAAAGTGATTGAGGCAATTCGAGTGGAG
CTGGTTCAGTACTGGGACCAGTGCTTTTATAGCCAGGAGCAGAGACAAGCTTTTGCCCCT
TTCTGTGCTGAGGACTACACAGAAAGTCTGCTCCAGCTCCACGATGCTGAGATTGTGCGG
TTAAAAAACTACTATGAAGTTCACAAGGAACTCTTTGAAGGTGTCCAGAAGTGGGAAGAA
ACCTGGAGGCTTTTCTTAGAGTTTGAGAGAAAAGCTTCAGATCCAAATCGATTTACAAAC
CGAGGAGGAAATCTTCTAAAAGAAGAAAAACAACGAGCCAAGCTCCAGAAAATGCTGCCC
AAGCTGGAAGAAGAGTTGAAGGCACGAATTGAATTGTGGGAACAGGAACATTCAAAGGCA
TTTATGGTGAATGGGCAGAAATTCATGGAGTATGTGGCAGAACAATGGGAGATGCATCGA
TTGGAGAAAGAGAGAGCCAAGCAGGAAAGACAACTGAAGAACAAAAAACAGACAGAGACA
GAGATGCTGTATGGCAGCGCTCCTCGAACACCTAGCAAGCGGCGAGGACTGGCTCCCAAT
ACACCGGGCAAAGCACGTAAGCTGAACACTACCACCATGTCCAATGCTACGGCCAATAGT
AGCATTCGGCCTATCTTTGGAGGGACAGTCTACCACTCCCCGTGTCTCGACTTCCTCCT
TCTGGCAGCAAGCCAGTCGCTGCTTCCACCTGTTCAGGGAAGAAAACACCCCGTACTGGC
AGGCATGGAGCCAACAAGGAGAACCTGGAGCTCAACGGCAGCATCCTGAGTGGTGGGTAC
CCTGGCTCGGCCCCCCTCCAGCGCAACTTCAGCATTAATTCTGTTGCCAGCACCTATTCT
GAGTTTGCGAAGGATCCGTCCCTCTCTGACAGTTCCACTGTTGGGCTTCAGCGAGAACTT
TCAAAGGCTTCCAAATCTGATGCTACTTCTGGAATCCTCAATTCAACCAACATCCAGTCC
TGA

Fig. 35

SEQ ID No. 35
NAT6
>ENSG00000186792|3|protein_coding|ENST00000359051|ENSP00000351946
ATGACCACGCAACTGGGCCCAGCCCTGGTGCTGGGGGTGGCCCTGTGCCTGGGTTGTGGC
CAGCCCCTACCACAGGTCCCTGAACGCCCCTTCTCTGTGCTGTGGAATGTACCCTCAGCA
CACTGTGAGGCCCGCTTTGGTGTGCACCTGCCACTCAATGCTCTGGGCATCATAGCCAAC
CGTGGCCAGCATTTTCACGGTCAGAACATGACCATTTTCTACAAGAACCAACTCGGCCTC
TATCCCTACTTTGGACCCAGGGGCACAGCTCACAATGGGGGCATCCCCCAGGCTTTGCCC
CTTGACCGCCACCTGGCACTGGCTGCCTACCAGATCCACCACAGCCTGAGACCTGGCTTT
GCTGGCCCAGCAGTGCTGGATTGGGAGGAGTGGTGTCCACTCTGGGCTGGGAACTGGGGC
CGCCGCCGAGCTTATCAGGCAGCCTCTTGGGCTTGGGCACAGCAGGTATTCCCTGACCTG
GACCCTCAGGAGCAGCTCTACAAGGCCTATACTGGCTTTGAGCAGGCGGCCCGTGCACTG
ATGGAGGATACGCTGCGGGTGGCCCAGGCACTACGGCCCCATGGACTCTGGGGCTTCTAT
CACTACCCAGCCTGTGGCAATGGCTGGCATAGTATGGCTTCCAACTATACCGGCCGCTGC
CATGCAGCCACCCTTGCCCGCAACACTCAACTGCATTGGCTCTGGGCCGCCTCCAGTGCC
CTCTTCCCCAGCATCTACCTCCCACCCAGGCTGCCACCTGCCCACCACCAGGCCTTTGTC
CGACATCGCCTGGAGGAGGCCTTCCGTGTGGCCCTTGTTGGGCACCGACATCCCCTGCCT
GTCCTGGCCTATGTCCGCCTCACACACCGGAGATCTGGGAGGTTCCTGTCCCAGGAGGAG
TGCTGGCATCTCCATGACTACCTGGTGGACACCTTGGGCCCCTATGTGATCAATGTGACC
AGGGCAGCGATGGCCTGCAGTCACCAGCGGTGCCATGGCCACGGGCGCTGTGCCCGGCGA
GATCCAGGACAGATGGAAGCCTTTCTACACCTGTGGCCAGACGGCAGCCTTGGAGATTGG
AAGTCCTTCAGCTGCCACTGTTACTGGGGCTGGGCTGGCCCCACCTGCCAGGAGCCCAGG
CCTGGGCCTAAAGAAGCAGTATAA

Fig. 36

SEQ ID No. 36
NAT6
>ENSG00000186792|3|protein_coding|ENST00000066014|ENSP00000066014
ATGACCACGCAACTGGGCCCAGCCCTGGTGCTGGGGGTGGCCCTGTGCCTGGGTTGTGGC
CAGCCCCTACCACAGGTCCCTGAACGCCCCTTCTCTGTGCTGTGGAATGTACCCTCAGCA
CACTGTGAGGCCCGCTTTGGTGTGCACCTGCCACTCAATGCTCTGGGCATCATAGCCAAC
CGTGGCCAGCATTTTCACGGTCAGAACATGACCATTTTCTACAAGAACCAACTCGGCCTC
TATCCCTACTTTGGACCCAGGGGCACAGCTCACAATGGGGGCATCCCCCAGGCTTTGCCC
CTTGACCGCCACCTGGCACTGGCTGCCTACCAGATCCACCACAGCCTGAGACCTGGCTTT
GCTGGCCCAGCAGTGCTGGATTGGGAGGAGTGGTGTCCACTCTGGGCTGGGAACTGGGGC
CGCCGCCGAGCTTATCAGGCAGCCTCTTGGGCTTGGGCACAGCAGGTATTCCCTGACCTG
GACCCTCAGGAGCAGCTCTACAAGGCCTATACTGGCTTTGAGCAGGCGGCCCGTGCACTG
ATGGAGGATACGCTGCGGGTGGCCCAGGCACTACGGCCCCATGGACTCTGGGGCTTCTAT
CACTACCCAGCCTGTGGCAATGGCTGGCATAGTATGGCTTCCAACTATACCGGCCGCTGC
CATGCAGCCACCCTTGCCCGCAACACTCAACTGCATTGGCTCTGGGCCGCCTCCAGTGCC
CTCTTCCCCAGCATCTACCTCCCACCCAGGCTGCCACCTGCCCACCACCAGGCCTTTGTC
CGACATCGCCTGGAGGAGGCCTTCCGTGTGGCCCTTGTTGGGCACCGACATCCCCTGCCT
GTCCTGGCCTATGTCCGCCTCACACACCGGAGATCTGGGAGGTTCCTGTCCCAGGATGAC
CTTGTGCAGTCCATTGGTGTGAGTGCAGCACTAGGGGCAGCCGGCGTGGTGCTCTGGGGG
GACCTGAGCCTCTCCAGCTCTGAGGAGGAGTGCTGGCATCTCCATGACTACCTGGTGGAC
ACCTTGGGCCCCTATGTGATCAATGTGACCAGGGCAGCGATGGCCTGCAGTCACCAGCGG
TGCCATGGCCACGGGCGCTGTGCCCGGCGAGATCCAGGACAGATGGAAGCCTTTCTACAC
CTGTGGCCAGACGGCAGCCTTGGAGATTGGAAGTCCTTCAGCTGCCACTGTTACTGGGGC
TGGGCTGGCCCCACCTGCCAGGAGCCCCTGGGCCTAAAGAAGCAGTATAAAGCCAGGGCC
CCTGCCACTGCCTCTTCTTTTCCCTGCTGCCACTTTTCCAGTCCTGGAACTACTCTGTCC
CACTCTTGCTCTATTCAGTTTACAGTCAACCCTCCCAAGCACACACCCCGCTTCCCTTGG
AATCCCTGA

Fig. 37

SEQ ID No. 37
NAT6
>ENSG00000186792|3|protein_coding|ENST00000336307|ENSP00000337425
ATGACCACGCAACTGGGCCCAGCCCTGGTGCTGGGGGTGGCCCTGTGCCTGGGTTGTGGC
CAGCCCCTACCACAGGTCCCTGAACGCCCCTTCTCTGTGCTGTGGAATGTACCCTCAGCA
CACTGTGAGGCCCGCTTTGGTGTGCACCTGCCACTCAATGCTCTGGGCATCATAGCCAAC
CGTGGCCAGCATTTTCACGGTCAGAACATGACCATTTTCTACAAGAACCAACTCGGCCTC
TATCCCTACTTTGGACCCAGGGGCACAGCTCACAATGGGGGCATCCCCCAGGCTTTGCCC
CTTGACCGCCACCTGGCACTGGCTGCCTACCAGATCCACCACAGCCTGAGACCTGGCTTT
GCTGGCCCAGCAGTGCTGGATTGGGAGGAGTGGTGTCCACTCTGGGCTGGGAACTGGGGC
CGCCGCCGAGCTTATCAGGCAGCCTCTTGGGCTTGGGCACAGCAGGTATTCCCTGACCTG
GACCCTCAGGAGCAGCTCTACAAGGCCTATACTGGCTTTGAGCAGGCGGCCCGTGCACTG
ATGGAGGATACGCTGCGGGTGGCCCAGGCACTACGGCCCCATGGACTCTGGGGCTTCTAT
CACTACCCAGCCTGTGGCAATGGCTGGCATAGTATGGCTTCCAACTATACCGGCCGCTGC
CATGCAGCCACCCTTGCCCGCAACACTCAACTGCATTGGCTCTGGGCCGCCTCCAGTGCC
CTCTTCCCCAGCATCTACCTCCCACCCAGGCTGCCACCTGCCCACCACCAGGCCTTTGTC
CGACATCGCCTGGAGGAGGCCTTCCGTGTGGCCCTTGTTGGGCACCGACATCCCCTGCCT
GTCCTGGCCTATGTCCGCCTCACACACCGGAGATCTGGGAGGTTCCTGTCCCAGGATGAC
CTTGTGCAGTCCATTGGTGTGAGTGCAGCACTAGGGGCAGCCGGCGTGGTGCTCTGGGGG
GACCTGAGCCTCTCCAGCTCTGAGGAGGAGTGCTGGCATCTCCATGACTACCTGGTGGAC
ACCTTGGGCCCCTATGTGATCAATGTGACCAGGGCAGCGATGGCCTGCAGTCACCAGCGG
TGCCATGGCCACGGGCGCTGTGCCCGGCGAGATCCAGGACAGATGGAAGCCTTTCTACAC
CTGTGGCCAGACGGCAGCCTTGGAGATTGGAAGTCCTTCAGCTGCCACTGTTACTGGGGC
TGGGCTGGCCCCACCTGCCAGGAGCCCAGGCCTGGGCCTAAAGAAGCAGTATAA

Fig. 38

SEQ ID No. 38
EEF1AL3
>ENSG00000185637|9|protein_coding|ENST00000329018|ENSP00000332874
ATGGGAAAGGAAAAGACTCATATCAACATTGTCGTCATTGGACACGTAGATTCGGGCAAG
TCCACCACTACTGGCCATCTGATCTATAAATGCGGTGGCATCGACAAAAGAACCATTGAA
AAATTTGAGAAGGAGGCTGCTGAGATGGGAAAGGGCTCCTTCAAGTATGCCTGGGTCTTG
GATAAACTGAAAGCTGAGCGTGAACGTGGTATCACCATTGATATCTCCTTGTGGAAATTT
GAGACCAGCAAGTACTATGTGACTATCATTGATGCCCCAGGACACAGAGACTTCATCAAA
AACATGATTACAGGGACATCTCAGGCTGACTGTGCTGTCCTGATTGTTGCTGCTGGTGTT
GGTGAATTTGAAGCTGGTATCTCCAAGAATGGGCAGACCCGAGAGCATGCCCTTCTGGCT
TACACACTGGGTGTGAAACAACTAATTGTCGGTGTTAACAAAATGGATTCCACTGAGCCA
CCCTACAGCCAGAAGAGATATGAGGAAATTGTTAAGGAAGTCAGCACTTACATTAAGAAA
ATTGGCTACAACCCCGACACAGTAGCATTTGTGCCAATTTCTGGTTGGAATGGTGACAAC
ATGCTGGAGCCAAGTGCTAACATGCCTTGGTTCAAGGGATGGAAAGTCACCCGTAAGGAT
GGCAATGCCAGTGGAACCACGCTGCTTGAGGCTCTGGACTGCATCCTACCACCAACTCGC
CCAACTGACAAGCCCTTGCGCCTGCCTCTCCAGGATGTCTACAAAATTGGTGGTATTGGT
ACTGTTCCTGTTGGCCGAGTGGAGACTGGTGTTCTCAAACCCGGTATGGTGGTCACCTTT
GCTCCAGTCAACGTTACAACGGAAGTAAAATCTGTCGAAATGCACCATGAAGCTTTGAGT
GAAGCTCTTCCTGGGGACAATGTGGGCTTCAAGGTCAAGAATGTGTCTGTCAAGGATGTT
CGTCGTGGCAACGTTGCTGGTGACAGCAAAAATGACCCACCAATGGAAGCAGCTGGCTTC
ACTGCTCAGGTGATTATCCTGAACCATCCAGGCCAAATAAGCGCCGGCTATGCCCCTGTA
TTGGATTGCCACATGGCTCACATTGCATGCAAGTTTGCTGAGCTGAAGGAAAAGATTGAT
CGCCGTTCTGGTAAAAAGCTGGAAGATGGCCCTAAATTCTTGAAGTCTGGTGATGCTGCC
ATTGTTGATATGGTTCCTGGCAAGCCCATGTGTGTTGAGAGCTTCTCAGACTATCCACCT
TTGGGTCGCTTTGCTGTTCGTGATATGAGACAGACAGTTGCGGTGGGTGTCATCAAAGCA
GTGGACAAGAAGGCTGCTGGAGCTGGCAAGGTCACCAAGTCTGCCCAGAAAGCTCAGAAG
GCTAAATGA

Fig. 39

SEQ ID No. 39
NP_612480.1
>ENSG00000168005|11|protein_coding|ENST00000294244|ENSP00000294244
ATGGCCCTAAAGGCCGAGGGCGCCGCACTCGACTGCTTCGAGGTGACGCTGAAATGCGAG
GAAGGGGAGGACGAGGAGGAGGCCATGGTGGTGGCCGTAATTCCGCGGCCCGAGCCGATG
CTCAGAGTGACCCAACAGGAGAAGACCCCACCGCCTAGACCCAGCCCGCTAGAGGCAGGC
AGTGATGGCTGTGAGGAGCCGAAGCAGCAGGTGTCTTGGGAGCAGGAGTTCCTGGTGGGC
AGCAGCCCAGGAGGCAGCGGGCGGGCACTGTGCATGGTGTGTGGCGCTGAGATCCGGGCA
CCCTCGGCCGACACAGCTCGCTCGCACATCTTGGAGCAGCACCCTCACACCTTGGACCTG
AGCCCTTCTGAGAAGAGCAATATCCTGGAGGCCTGGAGTGAAGGGGTGGCCCTCTTGCAA
GACGTGAGAGCTGAGCAGCCGTCCCCACCCAACTCAGACTCGGGCCAGGATGCCCACCCA
GACCCAGACGCCAACCCAGACGCTGCCAGAATGCCAGCCGAAATCGTCGTTCTCCTTGAC
TCTGAGGATAACCCATCCCTCCCTAAAAGGAGCCGGCCCAGGGGACTCCGCCCCCTCGAG
CTTCCTGCTGTCCCTGCCACAGAGCCAGGAAATAAGAAGCCCCGTGGTCAGAGATGGAAG
GAACCCCCAGGGGAAGAGCCAGTCAGAAAGAAAAGAGGCAGACCTATGACCAAAAACCTG
GACCCTGACCCAGAGCCCCCATCGCCAGACTCGCCCACGGAGACTTTCGCAGCACCAGCC
GAGGTCCGACACTTCACTGACGGCAGCTTCCCCGCCGGCTTCGTCTTGCAGCTCTTCTCC
CACACCCAGCTCAGGGGCCCAGACAGCAAGGACTCACCCAAAGACAGGGAAGTGGCAGAA
GGAGGCCTTCCCCGGGCGGAGAGCCCCTCTCCAGCTCCCCCTCCGGGGCTCCGCGGGACA
CTGGATCTCCAGGTTATCCGCGTGCGGATGGAGGAGCCCCCAGCGGTCAGCCTCCTGCAA
GACTGGTCCAGGCACCCCCAGGGCACCAAGCGTGTGGGAGCAGGTGACACCTCAGACTGG
CCCACAGTTCTGTCAGAATCCAGCACCACTGTGGCAGGGAAGCCGGAAAAAGGGAATGGA
GTGTAA

Fig. 40

SEQ ID No. 40
PLXNA2
>ENSG00000076356|1|protein_coding|ENST00000321063|ENSP00000323194
ATGAGCACACACAGGAGCCGTCTCCTCACCGCCGCCCCTCTCAGCATGGAACAGAGGCGG
CCCTGGCCCCGGGCCCTGGAGGTGGACAGCCGCTCTGTGGTCCTGCTCTCAGTGGTCTGG
GTGCTGCTGGCCCCCCCAGCAGCCGGCATGCCTCAGTTCAGCACCTTCCACTCTGAGAAT
CGTGACTGGACCTTCAACCACTTGACCGTCCACCAAGGGACGGGGGCCGTCTATGTGGGG
GCCATCAACCGGGTCTATAAGCTGACAGGCAACCTGACCATCCAGGTGGCTCATAAGACA
GGGCCAGAAGAGGACAACAAGTCTTGTTACCCGCCCCTCATCGTGCAGCCCTGCAGCGAA
GTGCTCACCCTCACCAACAATGTCAACAAGCTGCTCATCATTGACTACTCTGAGAACCGC
CTGCTGGCCTGTGGGAGCCTCTACCAGGGGGTCTGCAAGCTGCTGCGGCTGGATGACCTC
TTCATCCTGGTGGAGCCATCCCACAAGAAGGAGCACTACCTGTCCAGTGTCAACAAGACG
GGCACCATGTACGGGGTGATTGTGCGCTCTGAGGGTGAGGATGGCAAGCTCTTCATCGGC
ACGGCTGTGGATGGGAAGCAGGATTACTTCCCGACCCTGTCCAGCCGGAAGCTGCCCCGA
GACCCTGAGTCCTCAGCCATGCTCGACTATGAGCTACACAGCGATTTTGTCTCCTCTCTC
ATCAAGATCCCTTCAGACACCCTGGCCCTGGTCTCCCACTTTGACATCTTCTACATCTAC
GGCTTTGCTAGTGGGGGCTTTGTCTACTTTCTCACTGTCCAGCCCGAGACCCCTGAGGGT
GTGGCCATCAACTCCGCTGGAGACCTCTTCTACACCTCACGCATCGTGCGGCTCTGCAAG
GATGACCCCAAGTTCCACTCATACGTGTCCCTGCCCTTCGGCTGCACCCGGGCCGGGGTG
GAATACCGCCTCCTGCAGGCTGCTTACCTGGCCAAGCCTGGGGACTCACTGGCCCAGGCC
TTCAATATCACCAGCCAGGACGATGTACTCTTTGCCATCTTCTCCAAAGGGCAGAAGCAG
TATCACCACCCGCCCGATGACTCTGCCCTGTGTGCCTTCCCTATCCGGGCCATCAACTTG
CAGATCAAGGAGCGCCTGCAGTCCTGCTACCAGGGCGAGGGCAACCTGGAGCTCAACTGG
CTGCTGGGGAAGGACGTCCAGTGCACCAAGGCGCCTGTCCCCATCGATGATAACTTCTGT
GGACTGGACATCAACCAGCCCCTGGGAGGCTCAACTCCAGTGGAGGGCCTGACCCTGTAC
ACCACCAGCAGGGACCGCATGACCTCTGTGGCCTCCTACGTTTACAACGGCTACAGCGTG
GTTTTTGTGGGGACTAAGAGTGGCAAGCTGAAAAAGATTCGGGCCGACGGTCCCCCCCAT
GGTGGGGTCCAGTACGAGATGGTCTCTGTGCTCAAGGACGGAAGCCCCATCCTCCGGGAC
ATGGCCTTCTCCATTGATCAGCGCTACCTGTACGTCATGTCTGAGAGACAGGTCACCAGG
GTCCCCGTGGAGTCATGTGAGCAGTATACGACTTGTGGGGAGTGCCTGAGCTCTGGGGAC
CCTCACTGTGGCTGGTGTGCCCTGCACAACATGTGCTCCCGCAGGGACAAATGCCAACAG
GCCTGGGAACCTAATCGATTTGCTGCCAGCATCAGCCAGTGTGTGAGCCTTGCAGTGCAT
CCCAGCAGCATCTCAGTATCTGAGCACAGCCGGTTGCTTAGCCTGGTAGTGAGTGATGCT
CCTGATCTATCTGCGGGTATCGCCTGTGCCTTTGGGAACCTGACAGAGGTGGAGGGGCAG
GTGTCCGGGAGCCAGGTCATCTGCATCTCACCTGGGCCCAAGGATGTCCCTGTCATCCCG
CTGGATCAAGACTGGTTTGGGCTGGAGCTACAGCTGAGGTCCAAGGAGACAGGGAAGATA
TTTGTCAGCACCGAGTTCAAGTTTTACAACTGCAGTGCCCACCAACTGTGCCTGTCCTGT
GTCAACAGCGCCTTCCGCTGCCATTGGTGCAAGTACCGCAACCTCTGCACTCATGACCCC
ACCACCTGCTCCTTCCAGGAGGGCCGGATCAATATTTCAGAGGACTGTCCCCAGCTGGTG
CCCACAGAGGAGATCTTGATTCCAGTCGGGGAGGTAAAGCCAATCACCCTTAAGGCGCGA
AATCTGCCCCAGCCGCAGTCCGGCCAGCGAGGCTATGAGTGTGTCCTCAACATACAAGGA
GCCATCCACCGGGTCCCCGCTCTGCGCTTCAACAGCTCCAGCGTTCAGTGTCAGAACAGC
TCGTACCAGTATGATGGCATGGACATCAGCAATCTGGCCGTGGATTTCGCTGTGGTGTGG
AACGGCAATTTCATCATTGACAACCCTCAGGACCTGAAAGTCCATCTCTACAAGTGTGCA
GCCCAGCGGGAGAGCTGCGGCCTCTGCCTCAAGGCCGACCGGAAGTTTGAGTGTGGCTGG
TGCAGCGGCGAGCGCAGGTGCACCCTCCACCAGCACTGTACCAGCCCTTCCAGCCCCTGG
CTCGACTGGTCCAGCCACAATGTCAAGTGCTCCAACCCTCAAATCACCGAGATTTTGACG
GTGTCTGGACCGCCGGAAGGAGGGACGCGAGTGACCATCCATGGCGTGAACCTGGGTCTG
GACTTCTCCGAGATCGCCCACCATGTGCAGGTGGCTGGGGTGCCCTGCAGCCCCTCCCA
GGGGAATACATCATCGCTGAGCAGATTGTCTGTGAGATGGGCCATGCCCTCGTGGGAACC
ACCTCCGGGCCAGTACGCCTGTGTATTGGCGAGTGTAAGCCAGAGTTCATGACGAAGTCC
CATCAGCAGTACACCTTCGTGAACCCTTCTGTGCTGTCACTCAACCCAATCCGAGGTCCC
GAGTCAGGAGGCACTATGGTGACCATTACCGGCCATTACCTTGGGGCTGGGAGCAGCGTG
GCAGTCTACCTGGGCAACCAGACCTGCGAGTTCTACGGGAGGTCAATGAGTGAGATCGTG
TGTGTCTCACCCCCATCATCCAATGGCCTTGGCCCGGTCCCTGTTTCTGTGAGTGTCGAC
CGAGCCCATGTGGATAGCAACCTGCAGTTTGAGTACATAGATGACCCTCGGGTCCAGCGC
ATCGAGCCAGAGTGGAGCATTGCCAGTGGCCACACACCCCTGACCATCACAGGCTTCAAC
CTGGATGTCATTCAGGAGCCAAGGATCCGAGTCAAATTCAATGGCAAAGAATCTGTCAAT
GTGTGTAAAGTTGTGAACACAACCACCCTCACCTGCCTGGCACCCTCTCTGACCACGGAC
TACCGCCCTGGCCTGGACACTGTGGAACGCCAGATGAGTTTGGATTTGTCTTTAACAAT
GTCCAATCCTTGCTAATTTACAACGACACCAAGTTTATCTACTACCCCAACCCGACCTTT
GAACTGCTTAGCCCTACTGGAGTCTTGGATCAAAAGCCAGGATCGCCCATCATTCTGAAG

```
GGCAAAAACCTCTGCCCTCCTGCCTCTGGAGGGGCCAAACTCAACTACACTGTGCTCATC
GGAGAGACCCCTTGTGCTGTCACCGTATCTGAGACCCAGCTTCTCTGCGAGCCTCCCAAC
CTCACCGGGCAGCACAAGGTCATGGTTCACGTGGGCGGGATGGTGTTCTCGCCTGGCTCG
GTGAGTGTCATCTCAGACAGCTTGCTGACCCTGCCAGCCATCGTCAGCATCGCGGCCGGC
GGCAGCCTCCTCCTCATCATCGTCATCATCGTCCTCATTGCCTACAAGCGCAAGTCTCGA
GAAAATGACCTCACTCTCAAGCGGCTGCAAATGCAGATGGACAATCTGGAGTCCCGTGTG
GCCTTGGAGTGCAAGGAAGCTTTTGCTGAGCTCCAGACGGATATCAATGAGTTGACCAGT
GACCTGGACCGCTCAGGAATCCCTTACCTGGACTATCGTACCTACGCTATGCGAGTCCTG
TTCCCGGGCATCGAGGACCACCCCGTCCTGCGGGAGCTGGAGGTACAAGGAAACGGGCAG
CAGCACGTGGAGAAGGCCCTGAAGCTCTTTGCCCAGCTCATCAACAACAAGGTGTTCCTG
CTGACCTTCATCCGCACCCTGGAGCTGCAGCGCAGTTTCTCCATGCGCGACCGGGGCAAC
GTGGCTTCGCTCATCATGACCGGCCTGCAGGGCCGCCTGGAATATGCCACTGATGTCCTC
AAGCAGCTGCTCTCTGACCTCATCGATAAGAACCTGGAGAACAAGAACCACCCCAAGCTG
CTACTCCGGAGGACAGAGTCTGTGGCTGAAAAGATGCTGACCAATTGGTTCGCCTTCCTC
CTGCACAAGTTCCTAAAGGAGTGCGCAGGGGAGCCACTCTTCATGCTATACTGTGCCATC
AAGCAGCAGATGGAGAAGGGCCCCATTGATGCCATCACGGGCGAGGCCCGCTACTCCCTG
AGCGAGGACAAGCTCATCCGGCAGCAGATCGAGTACAAGACCCTGATCCTGAACTGCGTC
AACCCTGACAACGAGAACAGTCCAGAGATCCCAGTGAAGGTGTTAAACTGTGACACCATC
ACACAGGTCAAGGAGAAGATTCTTGATGCCGTGTATAAGAATGTGCCCTATTCCCAGCGG
CCGAGGGCAGTGGACATGGACTTGGAGTGGCGCCAAGGCCGGATCGCCCGGGTCGTGCTG
CAAGATGAGGACATCACCACCAAGATTGAGGGTGACTGGAAGCGGCTCAACACACTGATG
CATTATCAGGTGTCAGACAGGTCGGTGGTGGCTCTGGTCCCCAAACAGACCTCCTCCTAC
AACATCCCTGCCTCTGCCAGCATCTCCCGGACGTCCATCAGCAGATACGACTCCTCCTTC
AGGTATACGGGCAGCCCCGACAGCCTGCGGTCCCGGGCCCGATGATCACCCCAGACCTG
GAAAGTGGGGTCAAGGTGTGGCATCTGGTGAAGAACCATGACCACGGTGACCAGAAGGAG
GGTGACCGGGGCAGCAAGATGGTGTCCGAGATCTACCTGACCCGGCTACTGGCCACCAAG
GGCACCCTGCAGAAGTTTGTGGACGACTTGTTTGAGACCTTGTTCAGCACTGTGCACCGG
GGCAGCGCTCTCCCCCTGGCCATCAAGTACATGTTTGATTTCCTAGATGAGCAGGCAGAC
AGGCACAGCATCCATGACACAGATGTGCGGCACACCTGGAAAAGCAACTGCCTCCCTCTG
CGCTTCTGGGTGAACGTGATTAAGAACCCCCAGTTCGTGTTTGACATCCACAAGGGCAGC
ATCACGGACGCCTGCCTCTCTGTGGTGGCCCAGACCTTCATGGACTCTTGTTCAACGTCA
GAGCACCGGCTGGGCAAGGACTCCCCCTCCAACAAGCTGCTCTATGCCAAGGACATCCCC
AGCTACAAGAGCTGGGTGGAGAGATACTACGCAGACATCGCCAAGCTCCCAGCCATCAGT
GACCAGGACATGAATGCCTACCTCGCCGAGCAGTCCCGCCTGCACGCCGTGGAGTTCAAC
ATGCTGAGTGCCCTCAATGAGATCTACTCCTATGTCAGCAAGTATAGTGAGGAGCTCATC
GGGGCCCTAGAGCAGGATGAGCAGGCACGGCGGCAGCGGCTGGCTTATAAGGTGGAGCAG
CTCATTAATGCCATGTCCATTGAGAGCTGA
```

SEQ ID No. 41
PLXNA2
>ENSG00000076356|1|protein_coding|ENST00000367033|ENSP00000356000
ATGGAACAGAGGCGGCCCTGGCCCCGGGCCCTGGAGGTGGACAGCCGCTCTGTGGTCCTG
CTCTCAGTGGTCTGGGTGCTGCTGGCCCCCCCAGCAGCCGGCATGCCTCAGTTCAGCACC
TTCCACTCTGAGAATCGTGACTGGACCTTCAACCACTTGACCGTCCACCAAGGGACGGGG
GCCGTCTATGTGGGGGCCATCAACCGGGTCTATAAGCTGACAGGCAACCTGACCATCCAG
GTGGCTCATAAGACAGGGCCAGAAGAGGACAACAAGTCTTGTTACCCGCCCCTCATCGTG
CAGCCCTGCAGCGAAGTGCTCACCCTCACCAACAATGTCAACAAGCTGCTCATCATTGAC
TACTCTGAGAACCGCCTGCTGGCCTGTGGGAGCCTCTACCAGGGGGTCTGCAAGCTGCTG
CGGCTGGATGACCTCTTCATCCTGGTGGAGCCATCCCACAAGAAGGAGCACTACCTGTCC
AGTGTCAACAAGACGGGCACCATGTACGGGGTGATTGTGCGCTCTGAGGGTGAGGATGGC
AAGCTCTTCATCGGCACGGCTGTGGATGGGAAGCAGGATTACTTCCCGACCCTGTCCAGC
CGGAAGCTGCCCCGAGACCCTGAGTCCTCAGCCATGCTCGACTATGAGCTACACAGCGAT
TTTGTCTCCTCTCTCATCAAGATCCCTTCAGACACCCTGGCCCTGGTCTCCCACTTTGAC
ATCTTCTACATCTACGGCTTTGCTAGTGGGGCTTTGTCTACTTTCTCACTGTCCAGCCC
GAGACCCCTGAGGGTGTGGCCATCAACTCCGCTGGAGACCTCTTCTACACCTCACGCATC
GTGCGGCTCTGCAAGGATGACCCCAAGTTCCACTCATACGTGTCCCTGCCCTTCGGCTGC
ACCCGGCCGGGGTGGAATACCGCCTCCTGCAGGCTGCTTACCTGGCCAAGCCTGGGGAC
TCACTGGCCCAGGCCTTCAATATCACCAGCCAGGACGATGTACTCTTTGCCATCTTCTCC
AAAGGGCAGAAGCAGTATCACCACCCGCCCGATGACTCTGCCCTGTGTGCCTTCCCTATC
CGGGCCATCAACTTGCAGATCAAGGAGCGCCTGCAGTCCTGCTACCAGGGCGAGGGCAAC
CTGGAGCTCAACTGGCTGCTGGGGAAGGACGTCCAGTGCACCAAGGCGCCTGTCCCCATC
GATGATAACTTCTGTGGACTGGACATCAACCAGCCCCTGGGAGGCTCAACTCCAGTGGAG
GGCCTGACCCTGTACACCACCAGCAGGGACCGCATGACCTCTGTGGCCTCCTACGTTTAC
AACGGCTACAGCGTGGTTTTTGTGGGGACTAAGAGTGGCAAGCTGAAAAAGATTCGGGCC
GACGGTCCCCCCATGGTGGGGTCCAGTACGAGATGGTCTCTGTGCTCAAGGACGGAAGC
CCCATCCTCCGGGACATGGCCTTTCTCCATTGATCAGCGCTACCTGTACGTCATGTCTGAG
AGACAGGTCACCAGGGTCCCCGTGGAGTCATGTGAGCAGTATACGACTTGTGGGGAGTGC
CTGAGCTCTGGGGACCCTCACTGTGGCTGGTGTGCCCTGCACAACATGTGCTCCCGCAGG
GACAAATGCCAACAGGCCTGGGAACCTAATCGATTTGCTGCCAGCATCAGCCAGTGTGTG
AGCCTTGCAGTGCATCCCAGCAGCATCTCAGTATCTGAGCACAGCCGGTTGCTTAGCCTG
GTAGTGAGTGATGCTCCTGATCTATCTGCGGGTATCGCCTGTGCCTTTGGGAACCTGACA
GAGGTGGAGGGGCAGGTGTCCGGGAGCCAGGTCATCTGCATCTCACCTGGGCCCAAGGAT
GTCCCTGTCATCCCGCTGGATCAAGACTGGTTTGGGCTGGAGCTACAGCTGAGGTCCAAG
GAGACAGGGAAGATATTTGTCAGCACCGAGTTCAAGTTTTACAACTGCAGTGCCCACCAA
CTGTGCCTGTCCTGTGTCAACAGCGCCTTCCGCTGCCATTGGTGCAAGTACCGCAACCTC
TGCACTCATGACCCCACCACCTGCTCCTTCCAGGAGGGCCGGATCAATATTTCAGAGGAC
TGTCCCCAGCTGGTGCCCACAGAGGAGATCTTGATTCCAGTCGGGGAGGTAAAGCCAATC
ACCCTTAAGGCGCGAAATCTGCCCCAGCCGCAGTCCGGCCAGCGAGGCTATGAGTGTGTC
CTCAACATACAAGGAGCCATCCACCGGGTCCCCGCTCTGCGCTTCAACAGCTCCAGCGTT
CAGTGTCAGAACAGCTCGTACCAGTATGATGGCATGGACATCAGCAATCTGGCCGTGGAT
TTCGCTGTGGTGTGGAACGGCAATTTCATCATTGACAACCCTCAGGACCTGAAAGTCCAT
CTCTACAAGTGTGCAGCCCAGCGGGAGAGCTGCGGCCTCTGCCTCAAGGCCGACCGGAAG
TTTGAGTGTGGCTGGTGCAGCGGCGAGCGCAGGTGCACCCTCCACCAGCACTGTACCAGC
CCTTCCAGCCCCTGGCTCGACTGGTCCAGCCACAATGTCAAGTGCTCCAACCCTCAAATC
ACCGAGATTTTGACGGTGTCTGGACCGCCGGAAGGAGGGACGCGAGTGACCATCCATGGC
GTGAACCTGGGTCTGGACTTCTCCGAGATCGCCCACCATGTGCAGGTGGCTGGGGTGCCC
TGCACGCCCCTCCCAGGGGAATACATCATCGCTGAGCAGATTGTCTGTGAGATGGGCCAT
GCCCTCGTGGGAACCACCTCCGGGCCAGTACGCCTGTGTATTGGCGAGTGTAAGCCAGAG
TTCATGACGAAGTCCCATCAGCAGTACACCTTCGTGAACCCTTCTGTGCTGTCACTCAAC
CCAATCCGAGGTCCCGAGTCAGGAGGCACTATGGTGACCATTACCGGCCATTACCTTGGG
GCTGGGAGCAGCGTGGCAGTCTACCTGGGCAACCAGACCTGCGAGTTCTACGGGAGGTCA
ATGAGTGAGATCGTGTGTGTCTCACCCCCATCATCCAATGGCCTTGCCCGGTCCCTGTT
TCTGTGAGTGTCGACCGAGCCCATGTGGATAGCAACCTGCAGTTTGAGTACATAGATGAC
CCTCGGGTCCAGCGCATCGAGCCAGAGTGGAGCATTGCCAGTGGCCACACACCCCTGACC
ATCACAGGCTTCAACCTGGATGTCATTCAGGAGCCAAGGATCCGAGTCAAATTCAATGGC
AAAGAATCTGTCAATGTGTGTAAAGTTGTGAACACAACCACCCTCACCTGCCTGGCACCC
TCTCTGACCACGGACTACCGCCCTGGCCTGGACACTGTGGAACGCCCAGATGAGTTTGGA
TTTGTCTTTAACAATGTCCAATCCTTGCTAATTTACAACGACACCAAGTTTATCTACTAC
CCCAACCCGACCTTTGAACTGCTTAGCCCTACTGGAGTCTTGGATCAAAAGCCAGGATCG
CCCATCATTCTGAAGGGCAAAAACCTCTGCCCTCCTGCCTCTGGAGGGGCCAAACTCAAC

```
TACACTGTGCTCATCGGAGAGACCCCTTGTGCTGTCACCGTATCTGAGACCCAGCTTCTC
TGCGAGCCTCCCAACCTCACCGGGCAGCACAAGGTCATGGTTCACGTGGGCGGGATGGTG
TTCTCGCCTGGCTCGGTGAGTGTCATCTCAGACAGCTTGCTGACCCTGCCAGCCATCGTC
AGCATCGCGGCCGGCGGCAGCCTCCTCCTCATCATCGTCATCATCGTCCTCATTGCCTAC
AAGCGCAAGTCTCGAGAAAATGACCTCACTCTCAAGCGGCTGCAAATGCAGATGGACAAT
CTGGAGTCCCGTGTGGCCTTGGAGTGCAAGGAAGCTTTTGCTGAGCTCCAGACGGATATC
AATGAGTTGACCAGTGACCTGGACCGCTCAGGAATCCCTTACCTGGACTATCGTACCTAC
GCTATGCGAGTCCTGTTCCCGGGCATCGAGGACCACCCCGTCCTGCGGGAGCTGGAGGTA
CAAGGAAACGGGCAGCAGCACGTGGAGAAGGCCCTGAAGCTCTTTGCCCAGCTCATCAAC
AACAAGGTGTTCCTGCTGACCTTCATCCGCACCCTGGAGCTGCAGCGCAGTTTCTCCATG
CGCGACCGGGGCAACGTGGCTTCGCTCATCATGACCGGCCTGCAGGGCCGCCTGGAATAT
GCCACTGATGTCCTCAAGCAGCTGCTCTCTGACCTCATCGATAAGAACCTGGAGAACAAG
AACCACCCCAAGCTGCTACTCCGGAGGACAGAGTCTGTGGCTGAAAAGATGCTGACCAAT
TGGTTCGCCTTCCTCCTGCACAAGTTCCTAAAGGAGTGCGCAGGGGAGCCACTCTTCATG
CTATACTGTGCCATCAAGCAGCAGATGGAGAAGGGCCCCATTGATGCCATCACGGGCGAG
GCCCGCTACTCCCTGAGCGAGGACAAGCTCATCCGGCAGCAGATCGAGTACAAGACCCTG
ATCCTGAACTGCGTCAACCCTGACAACGAGAACAGTCCAGAGATCCCAGTGAAGGTGTTA
AACTGTGACACCATCACACAGGTCAAGGAGAAGATTCTTGATGCCGTGTATAAGAATGTG
CCCTATTCCCAGCGGCCGAGGGCAGTGGACATGGACTTGGAGTGGCGCCAAGGCCGGATC
GCCCGGGTCGTGCTGCAAGATGAGGACATCACCACCAAGATTGAGGGTGACTGGAAGCGG
CTCAACACACTGATGCATTATCAGGTGTCAGACAGGTCGGTGGTGGCTCTGGTCCCCAAA
CAGACCTCCTCCTACAACATCCCTGCCTCTGCCAGCATCTCCCGGACGTCCATCAGCAGA
TACGACTCCTCCTTCAGGTATACGGGCAGCCCGACAGCCTGCGGTCCCGGGCCCCGATG
ATCACCCCAGACCTGGAAAGTGGGGTCAAGGTGTGGCATCTGGTGAAGAACCATGACCAC
GGTGACCAGAAGGAGGGTGACCGGGGCAGCAAGATGGTGTCCGAGATCTACCTGACCCGG
CTACTGGCCACCAAGGGCACCCTGCAGAAGTTTGTGGACGACTTGTTTGAGACCTTGTTC
AGCACTGTGCACCGGGGCAGCGCTCTCCCCCTGGCCATCAAGTACATGTTTGATTTCCTA
GATGAGCAGGCAGACAGGCACAGCATCCATGACACAGATGTGCGGCACACCTGGAAAAGC
AACTGCCTCCCTCTGCGCTTCTGGGTGAACGTGATTAAGAACCCCCAGTTCGTGTTTGAC
ATCCACAAGGGCAGCATCACGGACGCCTGCCTCTCTGTGGTGGCCCAGACCTTCATGGAC
TCTTGTTCAACGTCAGAGCACCGGCTGGGCAAGGACTCCCCCTCCAACAAGCTGCTCTAT
GCCAAGGACATCCCCAGCTACAAGAGCTGGGTGGAGAGATACTACGCAGACATCGCCAAG
CTCCCAGCCATCAGTGACCAGGACATGAATGCCTACCTCGCCGAGCAGTCCCGCCTGCAC
GCCGTGGAGTTCAACATGCTGAGTGCCCTCAATGAGATCTACTCCTATGTCAGCAAGTAT
AGTGAGGAGCTCATCGGGGCCCTAGAGCAGGATGAGCAGGCACGGCGGCAGCGGCTGGCT
TATAAGGTGGAGCAGCTCATTAATGCCATGTCCATTGAGAGCTGA
```

SEQ ID No. 42
ELMO2
>ENSG00000062598|20|protein_coding|ENST00000290246|ENSP00000290246
ATGCCACCACCGTCAGACATTGTCAAAGTGGCCATTGAGTGGCCAGGTGCTAACGCCCAG
CTCCTTGAAATCGACCAGAAACGGCCCCTGGCATCCATTATCAAGGAAGTTTGTGATGGG
TGGTCGTTGCCAAACCCAGAGTATTATACCCTCCGTTATGCAGATGGTCCTCAGCTGTAC
ATCACCGAACAGACTCGCAGTGACATTAAGAATGGGACAATCTTACAACTGGCTATCTCC
CCGTCCCGGGCTGCACGCCAGCTGATGGAGAGGACCCAGTCATCCAACATGGAGACCCGG
CTGGATGCCATGAAGGAGCTGGCCAAGCTCTCTGCCGACGTGACTTTCGCTACTGAGTTC
ATCAACATGGATGGCATCATTGTGCTGACAAGGCTCGTGGAAAGTGGAACCAAGCTCTTG
TCCCACTACAGTGAGATGCTGGCATTCACCCTGACTGCCTTCCTAGAGCTCATGGACCAT
GGCATTGTCTCCTGGGACATGGTTTCAATCACCTTTATTAAGCAGATTGCAGGGTATGTG
AGCCAGCCCATGGTGGACGTGTCAATCCTTCAGAGGTCCCTGGCCATCCTGGAGAGCATG
GTCTTGAACAGCCAGAGTCTGTACCAGAAGATAGCCGAGGAAATCACCGTGGGACAGCTC
ATCTCACACCTCCAGGTCTCCAACCAGGAGATTCAGACCTACGCCATTGCACTGATTAAT
GCACTTTTTCTGAAGGCTCCTGAGGACAAACGACAGGATATGGCAAATGCATTTGCACAG
AAGCATCTCCGGTCTATAATCCTGAATCATGTGATCCGAGGGAACCGCCCCATCAAAACT
GAGATGGCCCATCAGCTATATGTCCTTCAAGTCCTAACCTTTAACCTTCTGGAAGAAAGG
ATGATGACCAAGATGGACCCCAATGACCAGGCTCAAAGGGACATCATATTTGAACTGAGG
AGGATTGCATTTGACGCAGAGTCTGATCCTAGCAATGCCCCTGGGAGTGGGACCGAAAAA
CGCAAAGCCATGTACACAAAGGACTACAAAATGCTGGGATTTACCAACCACATCAATCCA
GCCATGGACTTTACCCAGACTCCTCCTGGAATGCTGGCCTTGGACAACATGCTGTACTTG
GCTAAAGTCCACCAGGACACCTACATCCGGATTGTCTTGGAGAACAGTAGCCGGGAAGAC
AAACATGAATGCCCCTTTGGCCGCAGTGCCATTGAGCTCACCAAAATGCTCTGTGAAATC
CTGCAGGTTGGGGAACTACCAAATGAAGGACGCAATGACTACCACCCGATGTTCTTTACC
CATGACCGAGCCTTTGAAGAGCTCTTTGGAATCTGCATCCAGCTGTTGAACAAGACCTGG
AAGGAGATGAGGGCAACAGCAGAGGACTTCAACAAGGTTATGCAAGTCGTCCGAGAGCAA
ATCACTCGAGCTTTGCCCTCCAAACCCAACTCTTTGGATCAGTTCAAGAGCAAATTGCGT
AGCCTGAGTTACTCTGAGATTCTACGACTGCGCCAGTCTGAGAGGATGAGTCAGGATGAC
TTCCAGTCCCGCCAATTGTGGAGCTGAGGGAGAAGATCCAGCCCGAGATCCTTGAGCTG
ATCAAGCAGCAGCGCCTGAACCGGCTCTGTGAGGGCAGCAGCTTCCGAAAGATTGGGAAC
CGCCGAAGGCAAGAACGGTTCTGGTACTGCCGGTTGGCACTGAACCACAAGGTCCTTCAC
TATGGTGACTTGGATGACAACCCACAAGGGGAGGTGACATTTGAATCCCTGCAGGAGAAA
ATTCCTGTTGCAGACATTAAGGCCATTGTCACTGGGAAAGATTGTCCCCACATGAAAGAG
AAAAGTGCTCTGAAACAGAACAAGGAGGTGTTGGAATTGGCCTTCTCCATCCTGTATGAC
CCTGATGAGACCTTAAACTTCATCGCACCTAATAAATATGAGTACTGCATCTGGATTGAT
GGCCTCAGTGCCCTTCTGGGGAAGGACATGTCCAGTGAGCTGACCAAGAGTGACCTGGAC
ACCCTGCTGAGCATGGAGATGAAGCTGCGGCTCCTGGACCTGGAGAACATCCAGATTCCC
GAAGCCCCACCCCCCATCCCCAAGGAGCCCAGCAGCTATGACTTTGTCTATCACTATGGC
TGA

Fig. 43

SEQ ID No. 43
ELMO2
>ENSG00000062598|20|protein_coding|ENST00000396391|ENSP00000379673
ATGCCACCACCGTCAGACATTGTCAAAGTGGCCATTGAGTGGCCAGGTGCTAACGCCCAG
CTCCTTGAAATCGACCAGAAACGGCCCCTGGCATCCATTATCAAGGAAGTTTGTGATGGG
TGGTCGTTGCCAAACCCAGAGTATTATACCCTCCGTTATGCAGATGGTCCTCAGCTGTAC
ATCACCGAACAGACTCGCAGTGACATTAAGAATGGGACAATCTTACAACTGGCTATCTCC
CCGTCCCGGGCTGCACGCCAGCTGATGGAGAGGACCCAGTCATCCAACATGGAGACCCGG
CTGGATGCCATGAAGGAGCTGGCCAAGCTCTCTGCCGACGTGACTTTCGCTACTGAGTTC
ATCAACATGGATGGCATCATTGTGCTGACAAGGCTCGTGGAAAGTGGAACCAAGCTCTTG
TCCCACTACAGTGAGATGCTGGCATTCACCCTGACTGCCTTCCTAGAGCTCATGGACCAT
GGCATTGTCTCCTGGGACATGGTTTCAATCACCTTTATTAAGCAGATTGCAGGGTATGTG
AGCCAGCCCATGGTGGACGTGTCAATCCTTCAGAGGTCCCTGGCCATCCTGGAGAGCATG
GTCTTGAACAGCCAGAGTCTGTACCAGAAGATAGCCGAGGAAATCACCGTGGGACAGCTC
ATCTCACACCTCCAGGTCTCCAACCAGGAGATTCAGACCTACGCCATTGCACTGATTAAT
GCACTTTTTCTGAAGGCTCCTGAGGACAAACGACAGGATATGGCAAATGCATTTGCACAG
AAGCATCTCCGGTCTATAATCCTGAATCATGTGATCCGAGGGAACCGCCCCATCAAAACT
GAGATGGCCCATCAGCTATATGTCCTTCAAGTCCTAACCTTTAACCTTCTGGAAGAAAGG
ATGATGACCAAGATGGACCCCAATGACCAGGCTCAAAGGGACATCATATTTGAACTGAGG
AGGATTGCATTTGACGCAGAGTCTGATCCTAGCAATGCCCCTGGGAGTGGGACCGAAAAA
CGCAAAGCCATGTACACAAAGGACTACAAAATGCTGGGATTTACCAACCACATCAATCCA
GCCATGGACTTTACCCAGACTCCTCCTGGAATGCTGGCCTTGGACAACATGCTGTACTTG
GCTAAAGTCCACCAGGACACCTACATCCGGATTGTCTTGGAGAACAGTAGCCGGGAAGAC
AAACATGAATGCCCCTTTGGCCGCAGTGCCATTGAGCTCACCAAAATGCTCTGTGAAATC
CTGCAGGTTGGGGAACTACCAAATGAAGGACGCAATGACTACCACCCGATGTTCTTTACC
CATGACCGAGCCTTTGAAGAGCTCTTTGGAATCTGCATCCAGCTGTTGAACAAGACCTGG
AAGGAGATGAGGGCAACAGCAGAGGACTTCAACAAGGTTATGCAAGTCGTCCGAGAGCAA
ATCACTCGAGCTTTGCCCTCCAAACCCAACTCTTTGGATCAGTTCAAGAGCAAATTGCGT
AGCCTGAGTTACTCTGAGATTCTACGACTGCGCCAGTCTGAGAGGATGAGTCAGGATGAC
TTCCAGTCCCCGCCAATTGTGGAGCTGAGGGAGAAGATCCAGCCCGAGATCCTTGAGCTG
ATCAAGCAGCAGCGCCTGAACCGGCTCTGTGAGGGCAGCAGCTTCCGAAAGATTGGGAAC
CGCCGAAGGCAAGAACGGTTCTGGTACTGCCGGTTGGCACTGAACCACAAGGTCCTTCAC
TATGGTGACTTGGATGACAACCCACAAGGGGAGGTGACATTTGAATCCCTGCAGGAGAAA
ATTCCTGTTGCAGACATTAAGGCCATTGTCACTGGGAAGATTGTCCCCACATGAAAGAG
AAAAGTGCTCTGAAACAGAACAAGGAGGTGTTGGAATTGGCCTTCTCCATCCTGTATGAC
CCTGATGAGACCTTAAACTTCATCGCACCTAATAAATATGAGTACTGCATCTGGATTGAT
GGCCTCAGTGCCCTTCTGGGGAAGGACATGTCCAGTGAGCTGACCAAGAGTGACCTGGAC
ACCCTGCTGAGCATGGAGATGAAGCTGCGGCTCCTGGACCTGGAGAACATCCAGATTCCC
GAAGCCCCACCCCCCATCCCCAAGGAGCCCAGCAGCTATGACTTTGTCTATCACTATGGC
TGA

Fig. 44

SEQ ID No. 44
ELMO2
>ENSG00000062598|20|protein_coding|ENST00000372176|ENSP00000361249
ATGGAGAGGACCCAGTCATCCAACATGGAGACCCGGCTGGATGCCATGAAGGAGCTGGCC
AAGCTCTCTGCCGACGTGACTTTCGCTACTGAGTTCATCAACATGGATGGCATCATTGTG
CTGACAAGGCTCGTGGAAAGTGGAACCAAGCTCTTGTCCCACTACAGTGAGATGCTGGCA
TTCACCCTGACTGCCTTCCTAGAGCTCATGGACCATGGCATTGTCTCCTGGGACATGGTT
TCAATCACCTTTATTAAGCAGATTGCAGGGTATGTGAGCCAGCCCATGGTGGACGTGTCA
ATCCTTCAGAGGTCCCTGGCCATCCTGGAGAGCATGGTCTTGAACAGCCAGAGTCTGTAC
CAGAAGATAGCCGAGGAAATCACCGTGGGACAGCTCATCTCACACCTCCAGGTCTCCAAC
CAGGAGATTCAGACCTACGCCATTGCACTGATTAATGCACTTTTTCTGAAGGCTCCTGAG
GACAAACGACAGGATATGGCAAATGCATTTGCACAGAAGCATCTCCGGTCTATAATCCTG
AATCATGTGATCCGAGGGAACCGCCCCATCAAAACTGAGATGGCCCATCAGCTATATGTC
CTTCAAGTCCTAACCTTTAACCTTCTGGAAGAAAGGATGATGACCAAGATGGACCCCAAT
GACCAGGCTCAAAGGGACATCATATTTGAACTGAGGAGGATTGCATTTGACGCAGAGTCT
GATCCTAGCAATGCCCCTGGGAGTGGGACCGAAAAACGCAAAGCCATGTACACAAAGGAC
TACAAAATGCTGGGATTTACCAACCACATCAATCCAGCCATGGACTTTACCCAGACTCCT
CCTGGAATGCTGGCCTTGGACAACATGCTGTACTTGGCTAAAGTCCACCAGGACACCTAC
ATCCGGATTGTCTTGGAGAACAGTAGCCGGGAAGACAAACATGAATGCCCCTTTGGCCGC
AGTGCCATTGAGCTCACCAAAATGCTCTGTGAAATCCTGCAGGTTGGGGAACTACCAAAT
GAAGGACGCAATGACTACCACCCGATGTTCTTTACCCATGACCGAGCCTTTGAAGAGCTC
TTTGGAATCTGCATCCAGCTGTTGAACAAGACCTGGAAGGAGATGAGGGCAACAGCAGAG
GACTTCAACAAGGTTATGCAAGTCGTCCGAGAGCAAATCACTCGAGCTTTGCCCTCCAAA
CCCAACTCTTTGGATCAGTTCAAGAGCAAATTGCGTAGCCTGAGTTACTCTGAGATTCTA
CGACTGCGCCAGTCTGAGAGGATGAGTCAGGATGACTTCCAGTCCCCGCCAATTGTGGAG
CTGAGGGAGAAGATCCAGCCCGAGATCCTTGAGCTGATCAAGCAGCAGCGCCTGAACCGG
CTCTGTGAGGGCAGCAGCTTCCGAAAGATTGGGAACCGCCGAAGGCAAGAACGGTTCTGG
TACTGCCGGTTGGCACTGAACCACAAGGTCCTTCACTATGGTGACTTGGATGACAACCCA
CAAGGGGAGGTGACATTTGAATCCCTGCAGGAGAAAATTCCTGTTGCAGACATTAAGGCC
ATTGTCACTGGGAAAGATTGTCCCCACATGAAAGAGAAAGTGCTCTGAAACAGAACAAG
GAGGTGTTGGAATTGGCCTTCTCCATCCTGTATGACCCTGATGAGACCTTAAACTTCATC
GCACCTAATAAATATGAGTACTGCATCTGGATTGATGGCCTCAGTGCCCTTCTGGGGAAG
GACATGTCCAGTGAGCTGACCAAGAGTGACCTGGACACCCTGCTGAGCATGGAGATGAAG
CTGCGGCTCCTGGACCTGGAGAACATCCAGATTCCCGAAGCCCCACCCCCCATCCCCAAG
GAGCCCAGCAGCTATGACTTTGTCTATCACTATGGCTGA

Fig. 45

SEQ ID No. 45
ELMO2
>ENSG00000062598|20|protein_coding|ENST00000352077|ENSP00000326172
ATGCCACCACCGTCAGACATTGTCAAAGTGGCCATTGAGTGGCCAGGTGCTAACGCCCAG
CTCCTTGAAATCGACCAGAAACGGCCCCTGGCATCCATTATCAAGGAAGTTTGTGATGGG
TGGTCGTTGCCAAACCCAGAGTATTATACCCTCCGTTATGCAGATGGTCCTCAGCTGTAC
ATCACCGAACAGACTCGCAGTGACATTAAGAATGGGACAATCTTACAACTGGCTATCTCC
CCGTCCCGGGCTGCACGCCAGCTGATGGAGAGGACCCAGTCATCCAACATGGAGACCCGG
CTGGATGCCATGAAGGAGCTGGCCAAGCTCTCTGCCGACGTGACTTTCGCTACTGAGTTC
ATCAACATGGATGGCATCATTGTGCTGACAAGGCTCGTGGAAAGTGGAACCAAGCTCTTG
TCCCATGAGATGCTGGCATTCACCCTGACTGCCTTCCTAGAGCTCATGGACCATGGCATT
GTCTCCTGGGACATGGTTTCAATCACCTTTATTAAGCAGATTGCAGGGTATGTGAGCCAG
CCCATGGTGGACGTGTCAATCCTTCAGAGGTCCCTGGCCATCCTGGAGAGCATGGTCTTG
AACAGCCAGAGTCTGTACCAGAAGATAGCCGAGGAAATCACCGTGGGACAGCTCATCTCA
CACCTCCAGGTCTCCAACCAGGAGATTCAGACCTACGCCATTGCACTGATTAATGCACTT
TTTCTGAAGGCTCCTGAGGACAAACGACAGGATATGGCAAATGCATTTGCACAGAAGCAT
CTCCGGTCTATAATCCTGAATCATGTGATCCGAGGGAACCGCCCCATCAAAACTGAGATG
GCCCATCAGCTATATGTCCTTCAAGTCCTAACCTTTAACCTTCTGGAAGAAAGGATGATG
ACCAAGATGGACCCCAATGACCAGGCTCAAAGGGACATCATATTTGAACTGAGGAGGATT
GCATTTGACGCAGAGTCTGATCCTAGCAATGCCCCTGGGAGTGGGACCGAAAAACGCAAA
GCCATGTACACAAAGGACTACAAAATGCTGGGATTTACCAACCACATCAATCCAGCCATG
GACTTTACCCAGACTCCTCCTGGAATGCTGGCCTTGGACAACATGCTGTACTTGGCTAAA
GTCCACCAGGACACCTACATCCGGATTGTCTTGGAGAACAGTAGCCGGGAAGACAAACAT
GAATGCCCCTTTGGCCGCAGTGCCATTGAGCTCACCAAAATGCTCTGTGAAATCCTGCAG
GTTGGGGAACTACCAAATGAAGGACGCAATGACTACCACCCGATGTTCTTTACCCATGAC
CGAGCCTTTGAAGAGCTCTTTGGAATCTGCATCCAGCTGTTAACAAGACCTGGAAGGAG
ATGAGGGCAACAGCAGAGGACTTCAACAAGGTTATGCAAGTCGTCCGAGAGCAAATCACT
CGAGCTTTGCCCTCCAAACCCAACTCTTTGGATCAGTTCAAGAGCAAATTGCGTAGCCTG
AGTTACTCTGAGATTCTACGACTGCGCCAGTCTGAGAGGATGAGTCAGGATGACTTCCAG
TCCCCGCCAATTGTGGAGCTGAGGGAGAAGATCCAGCCCGAGATCCTTGAGCTGATCAAG
CAGCAGCGCCTGAACCGGCTCTGTGAGGGCAGCAGCTTCCGAAAGATTGGGAACCGCCGA
AGGCAAGAACGGTTCTGGTACTGCCGGTTGGCACTGAACCACAAGGTCCTTCACTATGGT
GACTTGGATGACAACCCACAAGGGGAGGTGACATTTGAATCCCTGCAGGAGAAAATTCCT
GTTGCAGACATTAAGGCCATTGTCACTGGGAAGATTGTCCCCACATGAAAGAGAAAGT
GCTCTGAAACAGAACAAGGAGGTGTTGGAATTGGCCTTCTCCATCCTGTATGACCCTGAT
GAGACCTTAAACTTCATCGCACCTAATAAATATGAGTACTGCATCTGGATTGATGGCCTC
AGTGCCCTTCTGGGGAAGGACATGTCCAGTGAGCTGACCAAGAGTGACCTGGACACCCTG
CTGAGCATGGAGATGAAGCTGCGGCTCCTGGACCTGGAGAACATCCAGATTCCCGAAGCC
CCACCCCCCATCCCCAAGGAGCCCAGCAGCTATGACTTTGTCTATCACTATGGCTGA

Fig. 46

SEQ ID No. 46
NDUFS2
>ENSG00000158864|1|protein_coding|ENST00000367993|ENSP00000356972
ATGGCGGCGCTGAGGGCTTTGTGCGGCTTCCGGGGCGTCGCGGCCCAGGTGCTGCGGCCT
GGGGCTGGAGTCCGATTGCCGATTCAGCCCAGCAGAGGTGTTCGGCAGTGGCAGCCAGAT
GTGGAATGGGCACAGCAGTTTGGGGGAGCTGTTATGTACCCAAGCAAAGAAACAGCCCAC
TGGAAGCCTCCACCTTGGAATGATGTGGACCCTCCAAAGGACACAATTGTGAAGAACATT
ACCCTGAACTTTGGGCCCCAACACCCAGCAGCGCATGGTGTCCTGCGACTAGTGATGGAA
TTGAGTGGGGAGATGGTGCGGAAGTGTGATCCTCACATCGGGCTCCTGCACCGAGGCACT
GAGAAGCTCATTGAATACAAGACCTATCTTCAGGCCCTTCCATACTTTGACCGGCTAGAC
TATGTGTCCATGATGTGTAACGAACAGGCCTATTCTCAGCTGTGGAGAAGTTGCTAAAC
ATCCGGCCTCCTCCTCGGGCACAGTGGATCCGAGTGCTGTTTGGAGAAATCACACGTTTG
TTGAACCACATCATGGCTGTGACCACACATGCCCTGGACCTTGGGGCCATGACCCCTTTC
TTCTGGCTGTTTGAAGAAAGGGAGAAGATGTTTGAGTTCTACGAGCGAGTGTCTGGAGCC
CGAATGCATGCTGCTTATATCCGGCCAGGAGGAGTGCACCAGGACCTACCCCTTGGGCTT
ATGGATGACATTTATCAGTTTTCTAAGAACTTCTCTCTTCGGCTTGATGAGTTGGAGGAG
TTGCTGACCAACAATAGGATCTGGCGAAATCGGACAATTGACATTGGGGTTGTAACAGCA
GAAGAAGCACTTAACTATGGTTTTAGTGGAGTGATGCTTCGGGGCTCAGGCATCCAGTGG
GACCTGCGGAAGACCCAGCCCTATGATGTTTACGACCAGGTTGAGTTTGATGTTCCTGTT
GGTTCTCGAGGGGACTGCTATGATAGGTACCTGTGCCGGGTGGAGGAGATGCGCCAGTCC
CTGAGAATTATCGCACAGTGTCTAAACAAGATGCCTCCTGGGGAGATCAAGGTTGATGAT
GCCAAAGTGTCTCCACCTAAGCGAGCAGAGATGAAGACTTCCATGGAGTCACTGATTCAT
CACTTTAAGTTGTATACTGAGGGCTACCAAGTTCCTCCAGGAGCCACATATACTGCCATT
GAGGCTCCCAAGGGAGAGTTTGGGGTGTACCTGGTGTCTGATGGCAGCAGCCGCCCTTAT
CGATGCAAGATCAAGGCTCCTGGTTTTGCCCATCTGGCTGGTTTGGACAAGATGTCTAAG
GGACACATGTTGGCAGATGTCGTTGCCATCATAGGTACCCAAGATATTGTATTTGGAGAA
GTAGATCGGTGA

Fig. 47

SEQ ID No. 47
NDUFS2
>ENSG00000158864|1|protein_coding|ENST00000392179|ENSP00000376018
ATGGCGGCGCTGAGGGCTTTGTGCGGCTTCCGGGGCGTCGCGGCCCAGGTGCTGCGGCCT
GGGGCTGGAGTCCGATTGCCGATTCAGCCCAGCAGAGGTGTTCGGCAGTGGCAGCCAGAT
GTGGAATGGGCACAGCAGTTTGGGGGAGCTGTTATGTACCCAAGCAAAGAAACAGCCCAC
TGGAAGCCTCCACCTTGGAATGATGTGGACCCTCCAAAGGACACAATTGTGAAGAACATT
ACCCTGAACTTTGGGCCCCAACACCCAGCAGCGCATGGTGTCCTGCGACTAGTGATGGAA
TTGAGTGGGGAGATGGTGCGGAAGTGTGATCCTCACATCGGGCTCCTGCACCGAGGCACT
GAGAAGCTCATTGAATACAAGACCTATCTTCAGGCCCTTCCATACTTTGACCGGCTAGAC
TATGTGTCCATGATGTGTAACGAACAGGCCTATTCTCTAGCTGTGGAGAAGTTGCTAAAC
ATCCGGCCTCCTCCTCGGGCACAGTGGATCCGAGTGCTGTTTGGAGAAATCACACGTTTG
TTGAACCACATCATGGCTGTGACCACACATGCCCTGGACCTTGGGGCCATGACCCCTTTC
TTCTGGCTGTTTGAAGAAAGGGAGAAGATGTTTGAGTTCTACGAGCGAGTGTCTGGAGCC
CGAATGCATGCTGCTTATATCCGGCCAGGAGGAGTGCACCAGGACCTACCCCTTGGGCTT
ATGGATGACATTTATCAGTTTTCTAAGAACTTCTCTCTTCGGCTTGATGAGTTGGAGGAG
TTGCTGACCAACAATAGGATCTGGCGAAATCGGACAATTGACATTGGGGTTGTAACAGCA
GAAGAAGCACTTAACTATGGTTTTAGTGGAGTGATGCTTCGGGGCTCAGGCATCCAGTGG
GACCTGCGGAAGACCCAGCCCTATGATGTTTACGACCAGGTTGAGTTTGATGTTCCTGTT
GGTTCTCGAGGGGACTGCTATGATAGGTACCTGTGCCGGGTGGAGGAGATGCGCCAGTCC
CTGAGAATTATCGCACAGTGTCTAAACAAGATGCCTCCTGGGGAGATCAAGGTTGATGAT
GCCAAAGTGTCTCCACCTAAGCGAGCAGAGATGAAGACTTCCATGGAGTCACTGATTCAT
CACTTTAAGTTGTATACTGAGGGCTACCAAGTTCCTCCAGGAGCCACATATACTGCCATT
GAGGCTCCCAAGGGAGAGTTTGGGGTGTACCTGGTGTCTGATGGCAGCAGCCGCCCTTAT
CGATGCAAGATCAAGGCTCCTGGTTTTGCCCATCTGGCTGGTTTGGACAAGATGTCTAAG
GGACACATGTTGGCAGATGTCGTTGCCATCATAGGTACCCAAGATATTGTATTTGGAGAA
GTAGATCGGTGA

Fig. 48

SEQ ID No. 48
IRAK1
>ENSG00000184216|X|protein_coding|ENST00000369980|ENSP00000358997
ATGGCCGGGGGCCGGGCCCGGGGGAGCCCGCAGCCCCCGGCGCCCAGCACTTCTTGTAC
GAGGTGCCGCCCTGGGTCATGTGCCGCTTCTACAAAGTGATGGACGCCCTGGAGCCCGCC
GACTGGTGCCAGTTCGCCGCCCTGATCGTGCGCGACCAGACCGAGCTGCGGCTGTGCGAG
CGCTCCGGGCAGCGCACGGCCAGCGTCCTGTGGCCCTGGATCAACCGCAACGCCCGTGTG
GCCGACCTCGTGCACATCCTCACGCACCTGCAGCTGCTCCGTGCGCGGGACATCATCACA
GCCTGGCACCCTCCCGCCCGCTTCCGTCCCCAGGCACCACTGCCCCGAGGCCCAGCAGC
ATCCCTGCACCCGCCGAGGCCGAGGCCTGGAGCCCCGGAAGTTGCCATCCTCAGCCTCC
ACCTTCCTCTCCCCAGCTTTTCCAGGCTCCCAGACCCATTCAGGGCCTGAGCTCGGCCTG
GTCCCAAGCCCTGCTTCCCTGTGGCCTCCACCGCCATCTCCAGCCCCTTCTTCTACCAAG
CCAGGCCCAGAGAGCTCAGTGTCCCTCCTGCAGGGAGCCCGCCCCTTTCCGTTTTGCTGG
CCCCTCTGTGAGATTTCCCGGGGCACCCACAACTTCTCGGAGGAGCTCAAGATCGGGGAG
GGTGGCTTTGGGTGCGTGTACCGGGCGGTGATGAGGAACACGGTGTATGCTGTGAAGAGG
CTGAAGGAGAACGCTGACCTGGAGTGGACTGCAGTGAAGCAGAGCTTCCTGACCGAGGTG
GAGCAGCTGTCCAGGTTTCGTCACCCAAACATTGTGGACTTTGCTGGCTACTGTGCTCAG
AACGGCTTCTACTGCCTGGTGTACGGCTTCCTGCCCAACGGCTCCCTGGAGGACCGTCTC
CACTGCCAGACCCAGGCCTGCCCACCTCTCTCCTGGCCTCAGCGACTGGACATCCTTCTG
GGTACAGCCCGGGCAATTCAGTTTCTACATCAGGACAGCCCCAGCCTCATCCATGGAGAC
ATCAAGAGTTCCAACGTCCTTCTGGATGAGAGGCTGACACCCAAGCTGGGAGACTTTGGC
CTGGCCCGGTTCAGCCGCTTTGCCGGGTCCAGCCCCAGCCAGAGCAGCATGGTGGCCCGG
ACACAGACAGTGCGGGGCACCCTGGCCTACCTGCCCGAGGAGTACATCAAGACGGGAAGG
CTGGCTGTGGACACGGACACCTTCAGCTTTGGGGTGGTAGTGCTAGAGACCTTGGCTGGT
CAGAGGGCTGTGAAGACGCACGGTGCCAGGACCAAGTATCTGAAAGACCTGGTGGAAGAG
GAGGCTGAGGAGGCTGGAGTGGCTTTGAGAAGCACCCAGAGCACACTGCAAGCAGGTCTG
GCTGCAGATGCCTGGGCTGCTCCCATCGCCATGCAGATCTACAAGAAGCACCTGGACCCC
AGGCCCGGGCCCTGCCCACCTGAGCTGGGCCTGGGCCTGGGCCAGCTGGCCTGCTGCTGC
CTGCACCGCCGGGCCAAAAGGAGGCCTCCTATGACCCAGGTGTACGAGAGGCTAGAGAAG
CTGCAGGCAGTGGTGGCGGGGGTGCCCGGGCATTCGGAGGCCGCCAGCTGCATCCCCCCT
TCCCCGCAGGAGAACTCCTACGTGTCCAGCACTGGCAGAGCCCACAGTGGGGCTGCTCCA
TGGCAGCCCCTGGCAGCGCCATCAGGAGCCAGTGCCCAGGCAGCAGAGCAGCTGCAGAGA
GGCCCCAACCAGCCCGTGGAGAGTGACGAGAGCCTAGGCGGCCTCTCTGCTGCCCTGCGC
TCCTGGCACTTGACTCCAAGCTGCCCTCTGGACCCAGCACCCCTCAGGGAGGCCGGCTGT
CCTCAGGGGGACACGGCAGGAGAATCGAGCTGGGGGAGTGGCCCAGGATCCCGGCCCACA
GCCGTGGAAGGACTGGCCCTTGGCAGCTCTGCATCATCGTCGTCAGAGCCACCGCAGATT
ATCATCAACCCTGCCCGACAGAAGATGGTCCAGAAGCTGGCCCTGTACGAGGATGGGGCC
CTGGACAGCCTGCAGCTGCTGTCGTCCAGCTCCCTCCCAGGCTTGGGCCTGGAACAGGAC
AGGCAGGGGCCCGAAGAAAGTGATGAATTTCAGAGCTGA

Fig. 49

SEQ ID No. 49
IRAK1
>ENSG00000184216|X|protein_coding|ENST00000369973|ENSP00000358990
ATGGCCGGGGGGCCGGGCCCGGGGGAGCCCGCAGCCCCCGGCGCCCAGCACTTCTTGTAC
GAGGTGCCGCCCTGGGTCATGTGCCGCTTCTACAAAGTGATGGACGCCCTGGAGCCCGCC
GACTGGTGCCAGTTCGGTGGGTGGCGGCGGGCTGCCGGGGGGCGGGAGGCGCGCGGGCTC
CTGGCGCCGACGCCTGACGCCCCCGCCCCGCAGCCGCCCTGATCGTGCGCGACCAGACC
GAGCTGCGGCTGTGCGAGCGCTCCGGGCAGCGCACGGCCAGCGTCCTGTGGCCCTGGATC
AACCGCAACGCCCGTGTGGCCGACCTCGTGCACATCCTCACGCACCTGCAGCTGCTCCGT
GCGCGGGACATCATCACAGCCTGGCACCCTCCCGCCCCGCTTCCGTCCCCAGGCACCACT
GCCCCGAGGCCCAGCAGCATCCCTGCACCCGCCGAGGCCGAGGCCTGGAGCCCCCGGAAG
TTGCCATCCTCAGCCTCCACCTTCCTCTCCCAGCTTTTCCAGGCTCCCAGACCCATTCA
GGGCCTGAGCTCGGCCTGGTCCCAAGCCCTGCTTCCCTGTGGCCTCCACCGCCATCTCCA
GCCCCTTCTTCTACCAAGCCAGGCCCAGAGAGCTCAGTGTCCCTCCTGCAGGGAGCCCGC
CCCTTTCCGTTTTGCTGGCCCCTCTGTGAGATTTCCCGGGGCACCCACAACTTCTCGGAG
GAGCTCAAGATCGGGGAGGGTGGCTTTGGGTGCGTGTACCGGGCGGTGATGAGGAACACG
GTGTATGCTGTGAAGAGGCTGAAGGAGAACGCTGACCTGGAGTGGACTGCAGTGAAGCAG
AGCTTCCTGACCGAGGTGGAGCAGCTGTCCAGGTTTCGTCACCCAAACATTGTGGACTTT
GCTGGCTACTGTGCTCAGAACGGCTTCTACTGCCTGGTGTACGGCTTCCTGCCCAACGGC
TCCCTGGAGGACCGTCTCCACTGCCAGACCCAGGCCTGCCCACCTCTCTCCTGGCCTCAG
CGACTGGACATCCTTCTGGGTACAGCCCGGGCAATTCAGTTTCTACATCAGGACAGCCCC
AGCCTCATCCATGGAGACATCAAGAGTTCCAACGTCCTTCTGGATGAGAGGCTGACACCC
AAGCTGGGAGACTTTGGCCTGGCCCGGTTCAGCCGCTTTGCCGGGTCCAGCCCCAGCCAG
AGCAGCATGGTGGCCCGGACACAGACAGTGCGGGGCACCCTGGCCTACCTGCCCGAGGAG
TACATCAAGACGGGAAGGCTGGCTGTGGACACGGACACCTTCAGCTTTGGGGTGGTAGTG
CTAGAGACCTTGGCTGGTCAGAGGGCTGTGAAGACGCACGGTGCCAGGACCAAGTATCTG
AAAGACCTGGTGGAAGAGGAGGCTGAGGAGGCTGGAGTGGCTTTGAGAAGCACCCAGAGC
ACACTGCAAGCAGGTCTGGCTGCAGATGCCTGGGCTGCTCCCATCGCCATGCAGATCTAC
AAGAAGCACCTGGACCCCAGGCCCGGGCCCTGCCCACCTGAGCTGGGCCTGGGCCTGGGC
CAGCTGGCCTGCTGCTGCCTGCACCGCCGGGCCAAAAGGAGGCCTCCTATGACCCAGGAG
AACTCCTACGTGTCCAGCACTGGCAGAGCCCACAGTGGGCTGCTCCATGGCAGCCCCTG
GCAGCGCCATCAGGAGCCAGTGCCCAGGCAGCAGAGCAGCTGCAGAGAGGCCCCAACCAG
CCCGTGGAGAGTGACGAGAGCCTAGGCGGCCTCTCTGCTGCCCTGCGCTCCTGGCACTTG
ACTCCAAGCTGCCCTCTGGACCCAGCACCCCTCAGGGAGGCCGGCTGTCCTCAGGGGGAC
ACGGCAGGAGAATCGAGCTGGGGGAGTGGCCCAGGATCCCGGCCCACAGCCGTGGAAGGA
CTGGCCCTTGGCAGCTCTGCATCATCGTCGTCAGAGCCACCGCAGATTATCATCAACCCT
GCCCGACAGAAGATGGTCCAGAAGCTGGCCCTGTACGAGGATGGGGCCCTGGACAGCCTG
CAGCTGCTGTCGTCCAGCTCCCTCCCAGGCTTGGGCCTGGAACAGGACAGGCAGGGGCCC
GAAGAAAGTGATGAATTTCAGAGCTGA

Fig. 50

SEQ ID No. 50
IRAK1
>ENSG00000184216|X|protein_coding|ENST00000369974|ENSP00000358991
ATGGCCGGGGGCCGGGCCCGGGGGAGCCCGCAGCCCCGGCGCCCAGCACTTCTTGTAC
GAGGTGCCGCCCTGGGTCATGTGCCGCTTCTACAAAGTGATGGACGCCCTGGAGCCCGCC
GACTGGTGCCAGTTCGCCGCCCTGATCGTGCGCGACCAGACCGAGCTGCGGCTGTGCGAG
CGCTCCGGGCAGCGCACGGCCAGCGTCCTGTGGCCCTGGATCAACCGCAACGCCCGTGTG
GCCGACCTCGTGCACATCCTCACGCACCTGCAGCTGCTCCGTGCGCGGGACATCATCACA
GCCTGGCACCCTCCCGCCCCGCTTCCGTCCCCAGGCACCACTGCCCCGAGGCCCAGCAGC
ATCCCTGCACCCGCCGAGGCCGAGGCCTGGAGCCCCGGAAGTTGCCATCCTCAGCCTCC
ACCTTCCTCTCCCCAGCTTTTCCAGGCTCCCAGACCCATTCAGGGCCTGAGCTCGGCCTG
GTCCCAAGCCCTGCTTCCCTGTGGCCTCCACCGCCATCTCCAGCCCCTTCTTCTACCAAG
CCAGGCCCAGAGAGCTCAGTGTCCCTCCTGCAGGGAGCCCGCCCCTTTCCGTTTTGCTGG
CCCCTCTGTGAGATTTCCCGGGGCACCCACAACTTCTCGGAGGAGCTCAAGATCGGGGAG
GGTGGCTTTGGGTGCGTGTACCGGGCGGTGATGAGGAACACGGTGTATGCTGTGAAGAGG
CTGAAGGAGAACGCTGACCTGGAGTGGACTGCAGTGAAGCAGAGCTTCCTGACCGAGGTG
GAGCAGCTGTCCAGGTTTCGTCACCCAAACATTGTGGACTTTGCTGGCTACTGTGCTCAG
AACGGCTTCTACTGCCTGGTGTACGGCTTCCTGCCCAACGGCTCCCTGGAGGACCGTCTC
CACTGCCAGACCCAGGCCTGCCCACCTCTCTCCTGGCCTCAGCGACTGGACATCCTTCTG
GGTACAGCCCGGGCAATTCAGTTTCTACATCAGGACAGCCCCAGCCTCATCCATGGAGAC
ATCAAGAGTTCCAACGTCCTTCTGGATGAGAGGCTGACACCCAAGCTGGGAGACTTTGGC
CTGGCCCGGTTCAGCCGCTTTGCCGGGTCCAGCCCCAGCCAGAGCAGCATGGTGGCCCGG
ACACAGACAGTGCGGGCACCCTGGCCTACCTGCCCGAGGAGTACATCAAGACGGGAAGG
CTGGCTGTGGACACGGACACCTTCAGCTTTGGGGTGGTAGTGCTAGAGACCTTGGCTGGT
CAGAGGGCTGTGAAGACGCACGGTGCCAGGACCAAGTATCTGGTGTACGAGAGGCTAGAG
AAGCTGCAGGCAGTGGTGGCGGGGGTGCCCGGGCATTCGGAGGCCGCCAGCTGCATCCCC
CCTTCCCCGCAGGAGAACTCCTACGTGTCCAGCACTGGCAGAGCCCACAGTGGGGCTGCT
CCATGGCAGCCCCTGGCAGCGCCATCAGGAGCCAGTGCCCAGGCAGCAGAGCAGCTGCAG
AGAGGCCCCAACCAGCCCGTGGAGAGTGACGAGAGCCTAGGCGGCCTCTCTGCTGCCCTG
CGCTCCTGGCACTTGACTCCAAGCTGCCCTCTGGACCCAGCACCCCTCAGGGAGGCCGGC
TGTCCTCAGGGGGACACGGCAGGAGAATCGAGCTGGGGAGTGGCCCAGGATCCCGGCCC
ACAGCCGTGGAAGGACTGGCCCTTGGCAGCTCTGCATCATCGTCGTCAGAGCCACCGCAG
ATTATCATCAACCCTGCCCGACAGAAGATGGTCCAGAAGCTGGCCCTGTACGAGGATGGG
GCCCTGGACAGCCTGCAGCTGCTGTCGTCCAGCTCCCTCCCAGGCTTGGGCCTGGAACAG
GACAGGCAGGGGCCCGAAGAAAGTGATGAATTTCAGAGCTGA

Fig. 51

SEQ ID No. 51
IRAK1
>ENSG00000184216|X|protein_coding|ENST00000393682|ENSP00000377287
ATGGCCGGGGGGCCGGGCCCGGGGGAGCCCGCAGCCCCCGGCGCCCAGCACTTCTTGTAC
GAGGTGCCGCCCTGGGTCATGTGCCGCTTCTACAAAGTGATGGACGCCCTGGAGCCCGCC
GACTGGTGCCAGTTCGGTGGGTGGCGGCGGGCTGCCGGGGGGCGGGAGGCGCGCGGGCTC
CTGGCGCCGACGCCTGACGCCCCCGCCCCGCAGCCGCCCTGATCGTGCGCGACCAGACC
GAGCTGCGGCTGTGCGAGCGCTCCGGGCAGCGCACGGCCAGCGTCCTGTGGCCCTGGATC
AACCGCAACGCCCGTGTGGCCGACCTCGTGCACATCCTCACGCACCTGCAGCTGCTCCGT
GCGCGGGACATCATCACAGCCTGGCACCCTCCCGCCCCGCTTCCGTCCCCAGGCACCACT
GCCCCGAGGCCCAGCAGCATCCCTGCACCCGCCGAGGCCGAGGCCTGGAGCCCCCGGAAG
TTGCCATCCTCAGCCTCCACCTTCCTCTCCCAGCTTTTCCAGGCTCCCAGACCCATTCA
GGGCCTGAGCTCGGCCTGGTCCCAAGCCCTGCTTCCCTGTGGCCTCCACCGCCATCTCCA
GCCCCTTCTTCTACCAAGCCAGGCCCAGAGAGCTCAGTGTCCCTCCTGCAGGGAGCCCGC
CCCTTTCCGTTTTGCTGGCCCCTCTGTGAGATTTCCCGGGGCACCCACAACTTCTCGGAG
GAGCTCAAGATCGGGGAGGGTGGCTTTGGGTGCGTGTACCGGGCGGTGATGAGGAACACG
GTGTATGCTGTGAAGAGGCTGAAGGAGAACGCTGACCTGGAGTGGACTGCAGTGAAGCAG
AGCTTCCTGACCGAGGTGGAGCAGCTGTCCAGGTTTCGTCACCCAAACATTGTGGACTTT
GCTGGCTACTGTGCTCAGAACGGCTTCTACTGCCTGGTGTACGGCTTCCTGCCCAACGGC
TCCCTGGAGGACCGTCTCCACTGCCAGACCCAGGCCTGCCCACCTCTCTCCTGGCCTCAG
CGACTGGACATCCTTCTGGGTACAGCCCGGGCAATTCAGTTTCTACATCAGGACAGCCCC
AGCCTCATCCATGGAGACATCAAGAGTTCCAACGTCCTTCTGGATGAGAGGCTGACACCC
AAGCTGGGAGACTTTGGCCTGGCCCGGTTCAGCCGCTTTGCCGGGTCCAGCCCCAGCCAG
AGCAGCATGGTGGCCCGGACACAGACAGTGCGGGCACCCTGGCCTACCTGCCCGAGGAG
TACATCAAGACGGGAAGGCTGGCTGTGGACACGGACACCTTCAGCTTTGGGGTGGTAGTG
CTAGAGACCTTGGCTGGTCAGAGGGCTGTGAAGACGCACGGTGCCAGGACCAAGTATCTG
AAAGACCTGGTGGAAGAGGAGGCTGAGGAGGCTGGAGTGGCTTTGAGAAGCACCCAGAGC
ACACTGCAAGCAGGTCTGGCTGCAGATGCCTGGGCTGCTCCCATCGCCATGCAGATCTAC
AAGAAGCACCTGGGCCAGCTGGCCTGCTGCTGCCTGCACCGCCGGGCCAAAAGGAGGCCT
CCTATGACCCAGGAGAACTCCTACGTGTCCAGCACTGGCAGAGCCCACAGTGGGCTGCT
CCATGGCAGCCCCTGGCAGCGCCATCAGGAGCCAGTGCCCAGGCAGCAGAGCAGCTGCAG
AGAGGCCCAACCAGCCCGTGGAGAGTGACGAGAGCCTAGGCGGCCTCTCTGCTGCCCTG
CGCTCCTGGCACTTGACTCCAAGCTGCCCTCTGGACCCAGCACCCCTCAGGGAGGCCGGC
TGTCCTCAGGGGGACACGGCAGGAGAATCGAGCTGGGGGAGTGGCCCAGGATCCCGGCCC
ACAGCCGTGGAAGGACTGGCCCTTGGCAGCTCTGCATCATCGTCGTCAGAGCCACCGCAG
ATTATCATCAACCCTGCCCGACAGAAGATGGTCCAGAAGCTGGCCCTGTACGAGGATGGG
GCCCTGGACAGCCTGCAGCTGCTGTCGTCCAGCTCCCTCCCAGGCTTGGGCCTGGAACAG
GACAGGCAGGGGCCCGAAGAAAGTGATGAATTTCAGAGCTGA

Fig. 52

SEQ ID No. 52
IRAK1
>ENSG00000184216|X|protein_coding|ENST00000393687|ENSP00000377291
ATGGCCGGGGGCCGGGCCCGGGGGAGCCCGCAGCCCCGGCGCCCAGCACTTCTTGTAC
GAGGTGCCGCCCTGGGTCATGTGCCGCTTCTACAAAGTGATGGACGCCCTGGAGCCCGCC
GACTGGTGCCAGTTCGCCGCCCTGATCGTGCGCGACCAGACCGAGCTGCGGCTGTGCGAG
CGCTCCGGGCAGCGCACGGCCAGCGTCCTGTGGCCCTGGATCAACCGCAACGCCCGTGTG
GCCGACCTCGTGCACATCCTCACGCACCTGCAGCTGCTCCGTGCGCGGGACATCATCACA
GCCTGGCACCCTCCCGCCCCGCTTCCGTCCCCAGGCACCACTGCCCCGAGGCCCAGCAGC
ATCCCTGCACCCGCCGAGGCCGAGGCCTGGAGCCCCCGGAAGTTGCCATCCTCAGCCTCC
ACCTTCCTCTCCCCAGCTTTTCCAGGCTCCCAGACCCATTCAGGGCCTGAGCTCGGCCTG
GTCCCAAGCCCTGCTTCCCTGTGGCCTCCACCGCCATCTCCAGCCCCTTCTTCTACCAAG
CCAGGCCCAGAGAGCTCAGTGTCCCTCCTGCAGGGAGCCCGCCCCTTTCCGTTTTGCTGG
CCCCTCTGTGAGATTTCCCGGGGCACCCACAACTTCTCGGAGGAGCTCAAGATCGGGGAG
GGTGGCTTTGGGTGCGTGTACCGGGCGGTGATGAGGAACACGGTGTATGCTGTGAAGAGG
CTGAAGGAGAACGCTGACCTGGAGTGGACTGCAGTGAAGCAGAGCTTCCTGACCGAGGTG
GAGCAGCTGTCCAGGTTTCGTCACCCAAACATTGTGGACTTTGCTGGCTACTGTGCTCAG
AACGGCTTCTACTGCCTGGTGTACGGCTTCCTGCCCAACGGCTCCCTGGAGGACCGTCTC
CACTGCCAGACCCAGGCCTGCCCACCTCTCTCCTGGCCTCAGCGACTGGACATCCTTCTG
GGTACAGCCCGGGCAATTCAGTTTCTACATCAGGACAGCCCCAGCCTCATCCATGGAGAC
ATCAAGAGTTCCAACGTCCTTCTGGATGAGAGGCTGACACCCAAGCTGGGAGACTTTGGC
CTGGCCCGGTTCAGCCGCTTTGCCGGGTCCAGCCCCAGCCAGAGCAGCATGGTGGCCCGG
ACACAGACAGTGCGGGGCACCCTGGCCTACCTGCCCGAGGAGTACATCAAGACGGGAAGG
CTGGCTGTGGACACGGACACCTTCAGCTTTGGGGTGGTAGTGCTAGAGACCTTGGCTGGT
CAGAGGGCTGTGAAGACGCACGGTGCCAGGACCAAGTATCTGAAAGACCTGGTGGAAGAG
GAGGCTGAGGAGGCTGGAGTGGCTTTGAGAAGCACCCAGAGCACACTGCAAGCAGGTCTG
GCTGCAGATGCCTGGGCTGCTCCCATCGCCATGCAGATCTACAAGAAGCACCTGGACCCC
AGGCCCGGGCCCTGCCCACCTGAGCTGGGCCTGGGCCTGGGCCAGCTGGCCTGCTGCTGC
CTGCACCGCCGGGCCAAAAGGAGGCCTCCTATGACCCAGGAGAACTCCTACGTGTCCAGC
ACTGGCAGAGCCCACAGTGGGGCTGCTCCATGGCAGCCCTGGCAGCGCCATCAGGAGCC
AGTGCCCAGGCAGCAGAGCAGCTGCAGAGAGGCCCCAACCAGCCCGTGGGAGAGTGACGAG
AGCCTAGGCGGCCTCTCTGCTGCCCTGCGCTCCTGGCACTTGACTCCAAGCTGCCCTCTG
GACCCAGCACCCCTCAGGGAGGCCGGCTGTCCTCAGGGGACACGGCAGGAGAATCGAGC
TGGGGGAGTGGCCCAGGATCCCGGCCCACAGCCGTGGAAGGACTGGCCCTTGGCAGCTCT
GCATCATCGTCGTCAGAGCCACCGCAGATTATCATCAACCCTGCCCGACAGAAGATGGTC
CAGAAGCTGGCCCTGTACGAGGATGGGGCCCTGGACAGCCTGCAGCTGCTGTCGTCCAGC
TCCCTCCCAGGCTTGGGCCTGGAACAGGACAGGCAGGGGCCCGAAGAAAGTGATGAATTT
CAGAGCTGA

Fig. 53

SEQ ID No. 53
C20orf149
>ENSG00000125534|20|protein_coding|ENST00000370177|ENSP00000359196
ATGGCGGCCATCCCCTCCAGCGGCTCGCTCGTGGCCACCCACGACTACTACCGGCGCCGC
CTGGGTTCCACTTCCAGCAACAGCTCCTGCAGCAGTACCGAGTGCCCCGGGGAAGCCATT
CCCCACCCCCCAGGTGAGTGCAGGATCGCCCCTTTCTCCCCCCGCTCCTCCAGGAGCTGG
CAGCATCAAGACCCCACTTCGCTTCTCTCAGGTCTCCCCAAGGCTGACCCGGGTCATTGG
TGGGCCAGCTTCTTTTTCGGGAAGTCCACCCTCCCGTTCATGGCCACGGTGTTGGAGTCC
GCAGAGCACTCGGAACCTCCCCAGGCCTCCAGCAGCATGACCGCCTGTGGCCTGGCTCGG
GACGCCCCGAGGAAGCAGCCCGGCGGTCAGTCCAGCACAGCCAGCGCTGGGCCCCCGTCC
TGA

Fig. 54

SEQ ID No. 54
C20orf149
>ENSG00000125534|20|protein_coding|ENST00000370178|ENSP00000359197
ATGGCGGCCATCCCCTCCAGCGGCTCGCTCGTGGCCACCCACGACTACTACCGGCGCCGC
CTGGGTTCCACTTCCAGCAACAGCTCCTGCAGCAGTACCGAGTGCCCCGGGGAAGCCATT
CCCCACCCCCCAGGTCTCCCCAAGGCTGACCCGGGTCATTGGTGGGCCAGCTTCTTTTTC
GGGAAGTCCACCCTCCCACCCCCCACCCTGTAA

Fig. 55

SEQ ID No. 55
C20orf149
>ENSG00000125534|20|protein_coding|ENST00000370179|ENSP00000359198
ATGGCGGCCATCCCCTCCAGCGGCTCGCTCGTGGCCACCCACGACTACTACCGGCGCCGC
CTGGGTTCCACTTCCAGCAACAGCTCCTGCAGCAGTACCGAGTGCCCCGGGGAAGCCATT
CCCCACCCCCCAGGTCTCCCCAAGGCTGACCCGGGTCATTGGTGGGCCAGCTTCTTTTTC
GGGAAGTCCACCCTCCCGTTCATGGCCACGGTGTTGGAGTCCGCAGAGCACTCGGAACCT
CCCCAGGCCTCCAGCAGCATGACCGCCTGTGGCCTGGCTCGGGACGCCCCGAGGAAGCAG
CCCGGCGGTCAGTCCAGCACAGCCAGCGCTGGGCCCCGTCCTGA

Fig. 56

SEQ ID No. 56
PSCD2L
>ENSG00000105443|19|protein_coding|ENST00000325139|ENSP00000314566
ATGGAGGACGGCGTCTATGAACCCCAGACCTGACTCCGGAGGAGCGGATGGAGCTGGAG
AACATCCGGCGGCGGAAGCAGGAGCTGCTGGTGGAGATTCAGCGCCTGCGGGAGGAGCTC
AGTGAAGCCATGAGCGAGGTGGAGGGGCTGGAGGCCAATGAGGGCAGTAAGACCTTGCAA
CGGAACCGGAAGATGGCAATGGGCAGGAAGAAGTTCAACATGGACCCCAAGAAGGGGATC
CAGTTCTTGGTGGAGAATGAACTGCTGCAGAACACACCCGAGGAGATCGCCCGCTTCCTG
TACAAGGGCGAGGGGCTGAACAAGACAGCCATCGGGGACTACCTGGGGGAGAGGGAAGAA
CTGAACCTGGCAGTGCTCCATGCTTTTGTGGATCTGCATGAGTTCACCGACCTCAATCTG
GTGCAGGCCCTCAGGCAGTTTCTATGGAGCTTTCGCCTACCCGGAGAGGCCCAGAAAATT
GACCGGATGATGGAGGCCTTCGCCCAGCGATACTGCCTGTGCAACCCTGGGGTTTTCCAG
TCCACAGACACGTGCTATGTGCTGTCCTTCGCCGTCATCATGCTCAACACCAGTCTCCAC
AATCCCAATGTCCGGGACAAGCCGGGCCTGGAGCGCTTTGTGGCCATGAACCGGGGCATC
AACGAGGGCGGGGACCTGCCTGAGGAGCTGCTCAGGAACCTGTACGACAGCATCCGAAAT
GAGCCCTTCAAGATTCCTGAGGATGACGGGAATGACCTGACCCACACCTTCTTCAACCCG
GACCGGGAGGGCTGGCTCCTGAAGCTGGGTAGGGGCCGGGTGAAGACGTGGAAGCGGCGC
TGGTTTATCCTCACAGACAACTGCCTCTACTACTTTGAGTACACCACGGACAAGGAGCCC
CGAGGAATCATCCCCCTGGAGAATCTGAGCATCCGAGAGGTGGACGACCCCCGGAAACCG
AACTGCTTTGAACTTTACATCCCCAACAACAAGGGGCAGCTCATCAAAGCCTGCAAAACT
GAGGCGGACGGCCGAGTGGTGGAGGGAAACCACATGGTGTACCGGATCTCGGCCCCCACG
CAGGAGGAGAAGGACGAGTGGATCAAGTCCATCCAGGCGGCTGTGAGTGTGGACCCCTTC
TATGAGATGCTGGCAGCGAGAAAGAAGCGGATTTCAGTCAAGAAGAAGCAGGAGCAGCCC
TGA

Fig. 57

SEQ ID No. 57
PSCD2L
>ENSG00000105443|19|protein_coding|ENST00000391881|ENSP00000375753
ATGGAGGACGGCGTCTATGAACCCCAGACCTGACTCCGGAGGAGCGGATGGAGCTGGAG
AACATCCGGCGGCGGAAGCAGGAGCTGCTGGTGGAGATTCAGCGCCTGCGGGAGGAGCTC
AGTGAAGCCATGAGCGAGGTGGAGGGGCTGGAGGCCAATGAGGGCAGTAAGACCTTGCAA
CGGAACCGGAAGATGGCAATGGGCAGGAAGAAGTTCAACATGGACCCCAAGAAGGGGATC
CAGTTCTTGGTGGAGAATGAACTGCTGCAGAACACACCCGAGGAGATCGCCCGCTTCCTG
TACAAGGGCGAGGGGCTGAACAAGACAGCCATCGGGGACTACCTGGGGGAGAGGGAAGAA
CTGAACCTGGCAGTGCTCCATGCTTTTGTGGATCTGCATGAGTTCACCGACCTCAATCTG
GTGCAGGCCCTCAGGCAGTTTCTATGGAGCTTTCGCCTACCCGGAGAGGCCCAGAAAATT
GACCGGATGATGGAGGCCTTCGCCCAGCGATACTGCCTGTGCAACCCTGGGGTTTTCCAG
TCCACAGACACGTGCTATGTGCTGTCCTTCGCCGTCATCATGCTCAACACCAGTCTCCAC
AATCCCAATGTCCGGGACAAGCCGGGCCTGGAGCGCTTTGTGGCCATGAACCGGGGCATC
AACGAGGGCGGGGACCTGCCTGAGGAGCTGCTCAGGAACCTGTACGACAGCATCCGAAAT
GAGCCCTTCAAGATTCCTGAGGATGACGGGAATGACCTGACCCACACCTTCTTCAACCCG
GACCGGGAGGGCTGGCTCCTGAAGCTGGGGGGCCGGGTGAAGACGTGGAAGCGGCGCTGG
TTTATCCTCACAGACAACTGCCTCTACTACTTTGAGTACACCACGGACAAGGAGCCCCGA
GGAATCATCCCCCTGGAGAATCTGAGCATCCGAGAGGTGGACGACCCCCGGAAACCGAAC
TGCTTTGAACTTTACATCCCCAACAACAAGGGGCAGCTCATCAAAGCCTGCAAAACTGAG
GCGGACGGCCGAGTGGTGGAGGGAAACCACATGGTGTACCGGATCTCGGCCCCACGCAG
GAGGAGAAGGACGAGTGGATCAAGTCCATCCAGGCGGCTGTGAGTGTGGACCCCTTCTAT
GAGATGCTGGCAGCGAGAAGAAGCGGATTTCAGTCAAGAAGAAGCAGGAGCAGCCCTGA

Fig. 58

SEQ ID No. 58
PPIA
>ENSG00000198618|21|protein_coding|ENST00000358455|ENSP00000351238
ATGGTCAACCCCACCGTGTTCTTCGACATTGCCGTCGACGGCGAGCCCTTGGGCCGCGTC
TCCTTTGAGCTGTTTGCAGACAAGGTCCCAAAGACAGCAGAAAATTTTCGTGCTCTGAGC
ACTGGAGAGAAAGGATTTGGTTATAAGGGTTCCTGCTTTCACAGAATTATTCCAGGGTTT
ATGTGTCAGGGTGGTGACTTCACACGCCATAATGGCACTGGTGGCAAGTCCATCTATGGG
GAGAAATTTGAAGATGAGAACTTCATCCTAAAGCATACAGGTCCTGGCATCTTGTCCATG
GCAAATGCTGGACCCAACACAAATGGATCCCAGTTTTTCATCTGCACTGCCAAGACTGAG
TGGTTGGATGGCAAGCATGTGGTGTTTGGCAAAGTGAAAGAAGGCATGAATATTGTGGAG
GCCATGGAGCGCTTTGGGTCCAGGAATGGCAAGACCAGCAAGAAGATCACCATTGCTGAC
TGTGGACAACTCGAATAA

Fig. 59

SEQ ID No. 59
MGTRDDEYDYLFKVVLIGDSGVGKSNLLSRFTRNEFNLESKSTIGVEFATRSIQVDGKTI
KAQIWDTAGQERYRAITSAYYRGAVGALLVYDIAKHLTYENVERWLKELRDHADSNIVIM
LVGNKSDLRHLRAVPTDEARAFAEKNNLSFIETSALDSTNVEEAFKNILTEIYRIVSQKQ
IADRAAHDESPGNNVVDISVPPTTDGQKPNKLQCCQNL*

Fig. 60

SEQ ID No. 60
MAAADGDDSLYPIAVLIDELRNEDVQLRLNSIKKLSTIALALGVERTRSELLPFLTDTIY
DEDEVLLALAEQLGTFTTLVGGPEYVHCLLPPLESLATVEETVVRDKAVESLRAISHEHS
PSDLEAHFVPLVKRLAGGDWFTSRTSACGLFSVCYPRVSSAVKAELRQYFRNLCSDDTPM
VRRAAASKLGEFAKVLELDNVKSEIIPMFSNLASDEQDSVRLLAVEACVNIAQLLPQEDL
EALVMPTLRQAAEDKSWRVRYMVADKFTELQKAVGPEITKTDLVPAFQNLMKDCEAEVRA
AASHKVKEFCENLSADCRENVIMSQILPCIKELVSDANQHVKSALASVIMGLSPILGKDN
TIEHLLPLFLAQLKDECPEVRLNIISNLDCVNEVIGIRQLSQSLLPAIVELAEDAKWRVR
LAIIEYMPLLAGQLGVEFFDEKLNSLCMAWLVDHVYAIREAATSNLKKLVEKFGKEWAHA
TIIPKVLAMSGDPNYLHRMTTLFCINVLSEVCGQDITTKHMLPTVLRMAGDPVANVRFNV
AKSLQKIGPILDNSTLQSEVKPILEKLTQDQDVDVKYFAQEALTVLSLA*

Fig. 61

SEQ ID No. 61
MRTFSFASTASRSCPPSPWPLGLKGPEVSFCLSLQIPSMMKMRSSWPWQNSWEPSLPWWE
AQSTCTACCLFSVCYPRVSSAVKAELRQYFRNLCSDDTPMVRRAAASKLGEFAKVLELDN
VKSEIIPMFSNLASDEQDSVRLLAVEACVNIAQLLPQEDLEALVMPTLRQAAEDKSWRVR
YMVADKFTELQKAVGPEITKTDLVPAFQNLMKDCEAEVRAAASHKVKEFCENLSADCREN
VIMSQILPCIKELVSDANQHVKSALASVIMGLSPILGKDNTIEHLLPLFLAQLKDECPEV
RLNIISNLDCVNEVIGIRQLSQSLLPAIVELAEDAKWRVRLAIIEYMPLLAGQLGVEFFD
EKLNSLCMAWLVDHVYAIREAATSNLKKLVEKFGKEWAHATIIPKVLAMSGDPNYLHRMT
TLFCINVLSEVCGQDITTKHMLPTVLRMAGDPVANVRFNVAKSLQKIGPILDNSTLQSEV
KPILEKLTQDQDVDVKYFAQEALTVLSLA*

Fig. 62

SEQ ID No. 62
MELITILEKTVSPDRLELEAAQKFLERAAVENLPTFLVELSRVLANPGNSQVARVAAGLQ
IKNSLTSKDPDIKAQYQQRWLAIDANARREVKNYVLQTLGTETYRPSSASQCVAGIACAE
IPVNQWPELIPQLVANVTNPNSTEHMKESTLEAIGYICQDIDPEQLQDKSNEILTAIIQG
MRKEEPSNNVKLAATNALLNSLEFTKANFDKESERHFIMQVVCEATQCPDTRVRVAALQN
LVKIMSLYYQYMETYMGPALFAITIEAMKSDIDEVALQGIEFWSNVCDEEMDLAIEASEA
AEQGRPPEHTSKFYAKGALQYLVPILTQTLTKQDENDDDDWNPCKAAGVCLMLLATCCE
DDIVPHVLPFIKEHIKNPDWRYRDAAVMAFGCILEGPEPSQLKPLVIQAMPTLIELMKDP
SVVVRDTAAWTVGRICELLPEAAINDVYLAPLLQCLIEGLSAEPRVASNVCWAFSSLAEA
AYEAADVADDQEEPATYCLSSSFELIVQKLLETTDRPDGHQNNLRSSAYESLMEIVKNSA
KDCYPAVQKTTLVIMERLQQVLQMESHIQSTSDRIQFNDLQSLLCATLQNVLRKVQHQDA
LQISDVVMASLLRMFQSTAGSGGVQEDALMAVSTLVEVLGGEFLKYMEAFKPFLGIGLKN
YAEYQVCLAAVGLVGDLCRALQSNIIPFCDEVMQLLLENLGNENVHRSVKPQILSVFGDI
ALAIGGEFKKYLEVVLNTLQQASQAQVDKSDYDMVDYLNELRESCLEAYTGIVQGLKGDQ
ENVHPDVMLVQPRVEFILSFIDHIAGDEDHTDGVVACAAGLIGDLCTAFGKDVLKLVEAR
PMIHELLTEGRRSKTNKAKTLATWATKELRKLKNQA*

Fig. 64

SEQ ID No. 64
MGTKMADLDSPPKLSGVQQPSEGVGGGRCSEISAELIRSLTELQELEAVYERLCGEEKVV
ERELDALLEQQNTIESKMVTLHRMGPNLQLIEGDAKQLAGMITFTCNLAENVSSKVRQLD
LAKNRLYQAIQRADDILDLKFCMDGVQTALRSEDYEQAAAHTHRYLCLDKSVIELSRQGK
EGSMIDANLKLLQEAEQRLKAIVAEKFAIATKEGDLPQVERFFKIFPLLGLHEEGLRKFS
EYLCKQVASKAEENLLMVLGTDMSDRRAAVIFADTLTLLFEGIARIVETHQPIVETYYGP
GRLYTLIKYLQVECDRQVEKVVDKFIKQRDYHQQFRHVQNNLMRNSTTEKIEPRELDPIL
TEVTLMNARSELYLRFLKKRISSDFEVGDSMASEEVKQEHQKCLDKLLNNCLLSCTMQEL
IGLYVTMEEYFMRETVNKAVALDTYEKGQLTSSMVDDVFYIVKKCIGRALSSSSIDCLCA
MINLATTELESDFRDVLCNKLRMGFPATTFQDIQRGVTSAVNIMHSSLQQGKFDTKGIES
TDEAKMSFLVTLNNVEVCSENISTLKKTLESDCTKLFSQGIGGEQAQAKFDSCLSDLAAV
SNKFRDLLQEGLTELNSTAIKPQVQPWINSFFSVSHNIEEEEFNDYEANDPWVQQFILNL
EQQMAEFKASLSPVIYDSLTGLMTSLVAVELEKVVLKSTFNRLGGLQFDKELRSLIAYLT
TVTTWTIRDKFARLSQMATILNLERVTEILDYWGPNSGPLTWRLTPAEVRQVLALRIDFR
SEDIKRLRL*

Fig. 65

SEQ ID No. 65
MADLDSPPKLSGVQQPSEGVGGGRCSEISAELIRSLTELQELEAVYERLCGEEKVVEREL
DALLEQQNTIESKMVTLHRMGPNLQLIEGDAKQLAGMITFTCNLAENVSSKVRQLDLAKN
RLYQAIQRADDILDLKFCMDGVQTALRSEDYEQAAAHTHRYLCLDKSVIELSRQGKEGSM
IDANLKLLQEAEQRLKAIVAEKFAIATKEGDLPQVERFFKIFPLLGLHEEGLRKFSEYLC
KQVASKAEENLLMVLGTDMSDRRAAVIFADTLTLLFEGIARIVETHQPIVETYYGPGRLY
TLIKYLQVECDRQVEKVVDKFIKQRDYHQQFRHVQNNLMRNSTTEKIEPRELDPILTEVT
LMNARSELYLRFLKKRISSDFEVGDSMASEEVKQEHQKCLDKLLNNCLLSCTMQELIGLY
VTMEEYFMRETVNKAVALDTYEKGQLTSSMVDDVFYIVKKCIGRALSSSSIDCLCAMINL
ATTELESDFRDVLCNKLRMGFPATTFQDIQRGVTSAVNIMHSSLQQGKFDTKGIESTDEA
KMSFLVTLNNVEVCSENISTLKKTLESDCTKLFSQGIGGEQAQAKFDSCLSDLAAVSNKF
RDLLQEGLTELNSTAIKPQVQPWINSFFSVSHNIEEEEFNDYEANDPWVQQFILNLEQQM
AEFKASLSPVIYDSLTGLMTSLVAVELEKVVLKSTFNRLGGLQFDKELRSLIAYLTTVTT
WTIRDKFARLSQMATILNLERVTEILDYWGPNSGPLTWRLTPAEVRQVLALRIDFRSEDI
KRLRL*

Fig. 66

SEQ ID No. 66
MADLDSPPKLSGVQQPSEGVGGGRCSEISAELIRSLTELQELEAVYERLCGEEKVVEREL
DALLEQQNTIESKMVTLHRMGPNLQLIEGDAKQLAGMITFTCNLAENVSSKVRQLDLAKN
RLYQAIQRADDILDLKFCMDGVQTALRSEDYEQAAAHTHRYLCLDKSVIELSRQGKEGSM
IDANLKLLQEAEQRLKAIVAEKFAIATKEGDLPQVERFFKIFPLLGLHEEGLRKFSEYLC
KQVASKAEENLLMVLGTDMSDRRAAVIFADTLTLLFEGIARIVETHQPIVETYYGPGRLY
TLIKYLQVECDRQVEKVVDKFIKQRDYHQQNFVFSFF*

Fig. 67

SEQ ID No. 67
MGTKMADLDSPPKLSGVQQPSEGVGGGRCSEISAELIRSLTELQELEAVYERLCGEEKVV
ERELDALLEQQNTIESKMVTLHRMGPNLQLIEANLKLLQEAEQRLKAIVAEKFAIATKEG
DLPQVERFFKIFPLLGLHEEGLRKFSEYLCKQVASKAEENLLMVLGTDMSDRRAAVIFAD
TLTLLFEGIARIVETHQPIVETYYGPGRLYTLIKYLQVECDRQVEKVVDKFIKQRDYHQQ
FRHVQNNLMRNSTTEKIEPRELDPILTEVTLMNARSELYLRFLKKRISSDFEVGDSMASE
EVKQEHQKCLDKLLNNCLLSCTMQELIGLYVTMEEYFMRETVNKAVALDTYEKGQLTSSM
VDDVFYIVKKCIGRALSSSSIDCLCAMINLATTELESDFRDVLCNKLRMGFPATTFQDIQ
RGVTSAVNIMHSSLQQGKFDTKGIESTDEAKMSFLVTLNNVEVCSENISTLKKTLESDCT
KLFSQGIGGEQAQAKFDSCLSDLAAVSNKFRDLLQEGLTELNSTAIKPQVQPWINSFFSV
SHNIEEEEFNDYEANDPWVQQFILNLEQQMAEFKASLSPVIYDSLTGLMTSLVAVELEKV
VLKSTFNRLGGLQFDKELRSLIAYLTTVTTWTIRDKFARLSQMATILNLERVTEILDYWG
PNSGPLTWRLTPAEVRQVLALRIDFRSEDIKRLRL*

Fig. 68

SEQ ID No. 68
MEFVKCLGHPEEFYNLVRFRIGGKRKVMPKMDQDSLSSSLKTCYKYLNQTSRSFAAVIQA
LDGEMRNAVCIFYLVLRALDTLEDDMTISVEKKVPLLHNFHSFLYQPDWRFMESKEKDRQ
VLEDFPTISLEFRNLAEKYQTVIADICRRMGIGMAEFLDKHVTSEQEWDKYCHYVAGLVG
IGLSRLFSASEFEDPLVGEDTERANSMGLFLQKTNIIRDYLEDQQGGREFWPQEVWSRYV
KKLGDFAKPENIDLAVQCLNELITNALHHIPDVITYLSRLRNQSVFNFCAIPQVMAIATL
AACYNNQQVFKGAVKIRKGQAVTLMMDATNMPAVKAIIYQYMEEIYHRIPDSDPSSSKTR
QIISTIRTQNLPNCQLISRSHYSPIYLSFVMLLAALSWQYLTTLSQVTEDYVQTGEH*

Fig. 69

SEQ ID No. 69
MRASQKDFENSMNQVKLLKKDPGNEVKLKLYALYKQATEGPCNMPKPGVFDLINKAKWDA
WNALGSLPKEAARQNYVDLVSSLSPSLESSSQVEPGTDRKSTGFETLVVTSEDGITKIMF
NRPKKKNAINTEMYHEIMRALKAASKDDSIITVLTGNGDYYSSGNDLTNFTDIPPGGVEE
KAKNNAVLLREFVGCFIDFPKPLIAVVNGPAVGISVTLLGLFDAVYASDRATFHTPFSHL
GQSPEGCSSYTFPKIMSPAKATEMLIFGKKLTAGEACAQGLVTEVFPDSTFQKEVWTRLK
AFAKLPPNALRISKEVIRKREREKLHAVNAEECNVLQGRWLSDECTNAVVNFLSRKSKL*

Fig. 70

SEQ ID No. 70
MYHEIMRALKAASKDDSIITVLTGNGDYYSSGNDLTNFTDIPPGGVEEKAKNNAVLLREF
VGCFIDFPKPLIAVVNGPAVGISVTLLGLFDAVYASDRATFHTPFSHLGQSPEGCSSYTF
PKIMSPAKATEMLIFGKKLTAGEACAQGLVTEVFPDSTFQKEVWTRLKAFAKLPPNALRI
SKEVIRKREREKLHAVNAEECNVLQGRWLSDECTNAVVNFLSRKSKL*

Fig. 71

SEQ ID No. 71
MAMAYLAWRLARRSCPSSLQVTSFPVVQLHMNRTAMRASQKDFENSMNQVKLLKKDPGNE
VKLKLYALYKQATEGPCNMPKPGVFDLINKAKWDAWNALGSLPKEAARQNYVDLVSSLSP
SLESSSQVEPGTDRKSTGFETLVVTSEDGITKIMFNRPKKKNAINTEMYHEIMRALKAAS
KDDSIITVLTGNGDYYSSGNDLTNFTDIPPGGVEEKAKNNAVLLREFVGCFIDFPKPLIA
VVNGPAVGISVTLLGLFDAVYASDRATFHTPFSHLGQSPEGCSSYTFPKIMSPAKATEML
IFGKKLTAGEACAQGLVTEVFPDSTFQKEVWTRLKAFAKLPPNALRISKEVIRKREREKL
HAVNAEECNVLQGRWLSDECTNAVVNFLSRKSKL*

Fig. 72

SEQ ID No. 72
MNRTAMRASQKDFENSMNQVKLLKKDPGNEVKLKLYALYKQATEGPCNMPKPGVFDLINK
AKWDAWNALGSLPKEAARQNYVDLVSSLSPSLESSSQVEPGTDRKSTGFETLVVTSEDGI
TKIMFNRPKKKNAINTEMYHEIMRALKAASKDDSIITVLTGNGDYYSSGNDLTNFTDIPP
GGVEEKAKNNAVLLREFVGCFIDFPKPLIAVVNGPAVGISVTLLGLFDAVYASDRATFHT
PFSHLGQSPEGCSSYTFPKIMSPAKATEMLIFGKKLTAGEACAQGLVTEVFPDSTFQKEV
WTRLKAFAKLPPNALRISKEVIRKREREKLHAVNAEECNVLQGRWLSDECTNAVVNFLSR
KSKL*

Fig. 73

SEQ ID No. 73
MFNRPKKKNAINTEMYHEIMRALKAASKDDSIITVLTGNGDYYSSGNDLTNFTDIPPGGV
EEKAKNNAVLLREFVGCFIDFPKPLIAVVNGPAVGISVTLLGLFDAVYASDRATFHTPFS
HLGQSPEGCSSYTFPKIMSPAKATEMLIFGKKLTAGEACAQGLVTEVFPDSTFQKEVWTR
LKAFAKLPPNALRISKEVIRKREREKLHAVNAEECNVLQGRWLSDECTNAVVNFLSRKSK
L*

Fig. 74

SEQ ID No. 74
MFARKPPGAAPLGAMPVPDQPSSASEKTSSLSPGLNTSNGDGSETETTSAILASVKEQEL
QFERLTRELEAERQIVASQLERCKLGSETGSMSSMSSAEEQFQWQSQDGQKDIEDELTTG
LELVDSCIRSLQESGILDPQDYSTGERPSLLSQSALQLNSKPEGSFQYPASYHSNQTLAL
GETTPSQLPARGTQARATGQSFSQGTTSRAGHLAGPEPAPPPPPPREPFAPSLGSAFHL
PDAPPAAAAAALYYSSSTLPAPPRGGSPLAAPQGGSPTKLQRGGSAPEGATYAAPRGSSP
KQSPSRLAKSYSTSSPINIVVSSAGLSPIRVTSPPTVQSTISSSPIHQLSSTIGTYATLS
PTKRLVHASEQYSKHSQELYATATLQRPGSLAAGSRASYSSQHGHLGPELRALQSPEHHI
DPIYEDRVYQKPPMRSLSQSQGDPLPPAHTGTYRTSTAPSSPGVDSVPLQRTGSQHGPQN
AAAATFQRASYAAGPASNYADPYRQLQYCPSVESPYSKSGPALPPEGTLARSPSIDSIQK
DPREFGWRDPELPEVIQMLQHQFPSVQSNAAAYLQHLCFGDNKIKAEIRRQGGIQLLVDL
LDHRMTEVHRSACGALRNLVYGKANDDNKIALKNCGGIPALVRLLRKTTDLEIRELVTGV
LWNLSSCDALKMPIIQDALAVLTNAVIIPHSGWENSPLQDDRKIQLHSSQVLRNATGCLR
NVSSAGEEARRRMRECDGLTDALLYVIQSALGSSEIDSKTVENCVCILRNLSYRLAAETS
QGQHMGTDELDGLLCGEANGKDAESSGCWGKKKKKKKSQDQWDGVGPLPDCAEPPKGIQM
LWHPSIVKPYLTLLSECSNPDTLEGAAGALQNLAAGSWKWSVYIRAAVRKEKGLPILVEL
LRIDNDRVVCAVATALRNMALDVRNKELIGKYAMRDLVHRLPGGNNSNNTASKAMSDDTV
TAVCCTLHEVITKNMENAKALRDAGGIEKLVGISKSKGDKHSPKVVKAASQVLNSMWQYR
DLRSLYKKDGWSQYHFVASSSTIERDRQRPYSSSRTPSISPVRVSPNNRSASAPASPREM
ISLKERKTDYECTGSNATYHGAKGEHTSRKDAMTAQNTGISTLYRNSYGAPAEDIKHNQV
SAQPVPQEPSRKDYETYQPFQNSTRNYDESFFEDQVHHRPPASEYTMHLGLKSTGNYVDF
YSAARPYSELNYETSHYPASPDSWV*

Fig. 75

SEQ ID No. 75
MFARKPPGAAPLGAMPVPDQPSSASEKTSSLSPGLNTSNGDGSETETTSAILASVKEQEL
QFERLTRELEAERQIVASQLERCKLGSETGSMSSMSSAEEQFQWQSQDGQKDIEDELTTG
LELVDSCIRSLQESGILDPQDYSTGERPSLLSQSALQLNSKPEGSFQYPASYHSNQTLAL
GETTPSQLPARGTQARATGQSFSQGTTSRAGHLAGPEPAPPPPPPREPFAPSLGSAFHL
PDAPPAAAAAALYYSSSTLPAPPRGGSPLAAPQGGSPTKLQRGGSAPEGATYAAPRGSSP
KQSPSRLAKSYSTSSPINIVVSSAGLSPIRVTSPPTVQSTISSSPIHQLSSTIGTYATLS
PTKRLVHASEQYSKHSQELYATATLQRPGSLAAGSRASYSSQHGHLGPELRALQSPEHHI
DPIYEDRVYQKPPMRSLSQSQGDPLPPAHTGTYRTSTAPSSPGVDSVPLQRTGSQHGPQN
AAAATFQRASYAAGPASNYADPYRQLQYCPSVESPYSKSGPALPPEGTLARSPSIDSIQK
DPREFGWRDPELPEVIQMLQHQFPSVQSNAAAYLQHLCFGDNKIKAEIRRQGGIQLLVDL
LDHRMTEVHRSACGALRNLVYGKANDDNKIALKNCGGIPALVRLLRKTTDLEIRELVTGV
LWNLSSCDALKMPIIQDALAVLTNAVIIPHSGWENSPLQDDRKIQLHSSQVLRNATGCLR
NVSSAGEEARRRMRECDGLTDALLYVIQSALGSSEIDSKTVENCVCILRNLSYRLAAETS
QGQHMGTDELDGLLCGEANGKDAESSGCWGKKKKKKKSQDQWSVYIRAAVRKEKGLPILV
ELLRIDNDRVVCAVATALRNMALDVRNKELIGKYAMRDLVHRLPGGNNSNNTASKAMSDD
TVTAVCCTLHEVITKNMENAKALRDAGGIEKLVGISKSKGDKHSPKVVKAASQVLNSMWQ
YRDLRSLYKKDGWSQYHFVASSSTIERDRQRPYSSSRTPSISPVRVSPNNRSASAPASPR
EMISLKERKTDYECTGSNATYHGAKGEHTSRKDAMTAQNTGISTLYRNSYGAPAEDIKHN
QVSAQPVPQEPSRKDYETYQPFQNSTRNYDESFFEDQVHHRPPASEYTMHLGLKSTGNYV
DFYSAARPYSELNYETSHYPASPDSWV*

Fig. 76

SEQ ID No. 76
MQGSTRRMGVMTDVHRRFLQLLMTHGVLEEWDVKRLQTHCYKVHDRNATVDKLEDFINNI
NSVLESLYIEIKRGVTEDDGRPIYALVNLATTSISKMATDFAENELDLFRKALELIIDSE
TGFASSTNILNLVDQLKGKKMRKKEAEQVLQKFVQNKWLIEKEGEFTLHGRAILEMEQYI
RETYPDAVKICNICHSLLIQGQSCETCGIRMHLPCVAKYFQSNAEPRCPHCNDYWPHEIP
KVFDPEKERESGVLKSNKKSLRSRQH*

Fig. 77

SEQ ID No. 77
PYPLARWDALGLPVRSHMQGSTRRMGVMTDVHRRFLQLLMTHGVLEEWDVKRLQTHCYKV
HDRNATVDKLEDFINNINSVLESLYIEIKRGVTEDDGRPIYALVNLATTSISKMATDFAE
NELDLFRKALELIIDSETLRLPQTY*

Fig. 78

SEQ ID No. 78
VHLATVSASAAWDALGLPVRSHMQGSTRRMGVMTDVHRRFLQLLMTHGVLEEWDVKRLQT
HCYKVHDRNATVDKLEDFINNINSVLESLYIEIKRGVTEDDGRPIYALVNLATTSISKMA
TDFAENELDLFRKALELIIDSETGFASSTNILNLVDQLKGKKMRKKEARCCRSLFKTSG*

Fig. 79

SEQ ID No. 79
MEWWASSPLRLWLLLFLLPSAQGRQKESGSKWKVFIDQINRSLENYEPCSSQNCSCYHGV
IEEDLTPFRGGISRKMMAEVVRRKLGTHYQITKNRLYRENDCMFPSRCSGVEHFILEVIG
RLPDMEMVINVRDYPQVPKWMEPAIPVFSFSKTSEYHDIMYPAWTFWEGGPAVWPIYPTG
LGRWDLFREDLVRSAAQWPWKKKNSTAYFRGSRTSPERDPLILLSRKNPKLVDAEYTKNQ
AWKSMKDTLGKPAAKDVHLVDHCKYKYLFNFRGVAASFRFKHLFLCGSLVFHVGDEWLEF
FYPQLKPWVHYIPVKTDLSNVQELLQFVKANDDVAQEIAERGSQFIRNHLQMDDITCYWE
NLLSEYSKFLSYNVTRRKGYDQIIPKMLKTEL*

Fig. 80

SEQ ID No. 80
MRRRRAGGRTMVERASKFVLVVAGSVCFMLILYQYAGPGLSLGAPGGRAPPDDLDLFPTP
DPHYEKKYYFPVRELERSLRFDMKGDDVIVFLHIQKTGGTTFGRHLVQNVRLEVPCDCRP
GQKKCTCYRPNRRETWLFSRFSTGWSCGLHADWTELTNCVPGVLDRRDSAALRTPRKFYY
ITLLRDPVSRYLSEWRHVQRGATWKTSLHMCDGRTPTPEELPPCYEGTDWSGCTLQEFMD
CPYNLANNRQVRMLADLSLVGCYNLSFIPEGKRAQLLLESAKKNLRGMAFFGLTEFQRKT
QYLFERTFNLKFIRPFMQYNSTRAGGVEVDEDTIRRIEELNDLDMQLYDYAKDLFQQRYQ
YKRQLERREQRLRSREERLLHRAKEALPREDADEPGRVPTEDYMSHIIEKW*

Fig. 81

SEQ ID No. 81
MTSCRCSVTSRSLWPALAPRRCQHTSPASAQCKQDKACRFLAAQKGAYPIIFTAWKLATA
GDQGLLLQSLNALSVLTDGQPDLLDAQGLQLLVATLTQNADEADLTCSGIRCVRHACLKH
EQNRQDLVKAGVLPLLTGAITHHGHHTDVVREACWALRVMTFDDDIRVPFGHAHNHAKMI
VQENKGLKVLIEATKAFLDNPGILSELCGTLSRLAIRNEFCQEVVDLGGLSILVSLLADC
NDHQMRDQSGVQELVKQVLSTLRAIAGNDDVKDAIVRAGGTESIVAAMTQHLTSPQVCEQ
SCAALCFLALRKPDNSRIIVEGGGAVAALQAMKAHPQKAGVQKQACMLIRNLVAHRPSRS
PSWTWGLRHSSCRPDLPTVTVRTWPRPPCGTWVVMSSSESCGQARGATWRHDPRPSLVTL
GESCDSGMGVDPCPPLSPISSVPFTMRSVFWQALGKGSGEGGAL*

Fig. 82

SEQ ID No. 82
MSERCCSRYSSGASIGCTPTSTQAKMVSKRIAQETFDAAVRENIEEFAMGPEEAVKEAVE
QFESQGVDLSNIVKTAPKVSADGSQEPTHDILQMLSDLQESVASSRPQEVSAYLTRFCDQ
CKQDKACRFLAAQKGAYPIIFTAWKLATAGDQGLLLQSLNALSVLTDGQPDLLDAQGLQL
LVATLTQNADEADLTCSGIRCVRHACLKHEQNRQDLVKAGVLPLLTGAITHHGHHTDVVR
EACWALRVMTFDDDIRVPFGHAHNHAKMIVQENKGLKVLIEATKAFLDNPGILSELCGTL
SRLAIRNEFCQEVVDLGGLSILVSLLADCNDHQMRDQSGVQELVKQVLSTLRAIAGNDDV
KDAIVRAGGTESIVAAMTQHLTSPQVCEQSCAALCFLALRKPDNSRIIVEGGGAVAALQA
MKAHPQKAGVQKQACMLIRNLVAHGQAFSKPILDLGAEALIMQARSAHRDCEDVAKAALR
DLGCHVELRELWTGQRGNLAP*

Fig. 83

SEQ ID No. 83
MVSKRIAQETFDAAVRENIEEFAMGPEEAVKEAVEQFESQGVDLSNIVKTAPKVSADGSQ
EPTHDILQMLSDLQESVASSRPQEVSAYLTRFCDQCKQDKACRFLAAQKGAYPIIFTAWK
LATAGDQGLLLQSLNALSVLTDGQPDLLDAQGLQLLVATLTQNADEADLTCSGIRCVRHA
CLKHEQNRQDLVKAGVLPLLTGAITHHGHHTDVVREACWALRVMTFDDDIRVPFGHAHNH
AKMIVQENKGLKVLIEATKAFLDNPGILSELCGTLSRLAIRNEFCQEVVDLGGLSILVSL
LADCNDHQMRDQSGVQELVKQVLSTLRAIAGNDDVKDAIVRAGGTESIVAAMTQHLTSPQ
VCEQSCAALCFLALRKPDNSRIIVEGGGAVAALQAMKAHPQKAGVQKQACMLIRNLVAHG
QAFSKPILDLGAEALIMQARSAHRDCEDVAKAALRDLGCHVELRELWTGQRGNLAP*

Fig. 84

SEQ ID No. 84
MVSKRIAQETFDAAVRENIEEFAMGPEEAVKEAVEQFESQGVDLSNIVKTAPKVSADGSQ
EPTHDILQMLSDLQESVASSRPQEVSAYLTRFCDQCKQDKACRFLAAQKGAYPIIFTAWK
LATAGDQGLLLQSLNALSVLTDGQPDLLDAQGLQLLVATLTQNADEADLTCSGIRCVRHA
CLKHEQNRQDLVKAGVLPLLTGAITHHGHHTDVVREACWALRVMTFDDDIRVPFGHAHNH
AKMIVQENKGLKVLIEATKAFLDNPGILSELCGTLSRLAIRNEFCQEVVDLGGLSILVSL
LADCNDHQMRDQSGVQELVKQVLSTLRAIAGNDDVKDAIVRAGGTESIVAAMTQHLTSPQ
VCEQSCAALCFLALRKPDNSRIIVEGGGAVAALQAMKAHPQKAGVQKQACMLIRNLVAHG
QAFSKPILDLGAEALIMQARSAHRDCEDVAKAALRDLGCHVELRELWTGQRGNLAP*

Fig. 85

SEQ ID No. 85
MAGAVPGAIMDEDYYGSAAEWGDEADGGQQEDDSGEGEDDAEVQQECLHKFSTRDYIMEP
SIFNTLKRYFQAGGSPENVIQLLSENYTAVAQTVNLLAEWLIQTGVEPVQVQETVENHLK
SLLIKHFDPRKADSIFTEEGETPAWLEQMIAHTTWRDLFYKLAEAHPDCLMLNFTVKLIS
DAGYQGEITSVSTACQQLEVFSRVLRTSLATILDGGEENLEKNLPEFAKMVCHGEHTYLF
AQAMMSVLAQEEQGGSAVRRIAQEVQRFAQEKGHDASQITLALGTAASYPRACQALGAML
SKGALNPADITVLFKMFTSMDPPPVELIRVPAFLDLFMQSLFKPGARINQDHKHKYIHIL
AYAASVVETWKKNKRVSINKDELKSTSKAVETVHNLCCNENKGASELVAELSTLYQCIRF
PVVAMGVLKWVDWTVSEPRYFQLQTDHTPVHLALLDEISTCHQLLHPQVLQLLVKLFETE
HSQLDVMEQLELKKTLLDRMVHLLSRGYVLPVVSYIRKCLEKLDTDISLIRYFVTEVLDV
IAPPYTSDFVQLFLPILENDSIAGTIKTEGEHDPVTEFIAHCKSNFIMVN*

Fig. 86

SEQ ID No. 86
MAMLRVQPEAQAKVDVFREDLCTKTENLLGSYFPKKISELDAFLKEPALNEANLSNLKAP
LDIPVPDPVKEKEKEERKKQQEKEDKDEKKKGEDEDKGPPCGPVNCNEKIVVLLQRLKPE
IKDVIEQLNLVTTWLQLQIPRIEDGNNFGVAVQEKVFELMTSLHTKLEGFHTQISKYFSE
RGDAVTKAAKQPHVGDYRQLVHELDEAEYRDIRLMVMEIRNAYVRRQGQGRGGQRQLSQA
THSLTLQARG*

Fig. 87

SEQ ID No. 87
MAMLRVQPEAQAKVDVFREDLCTKTENLLGSYFPKKISELDAFLKEPALNEANLSNLKAP
LDIPVPDPVKEKEKEERKKQQEKEDKDEKKKGEDEDKGPPCGPVNCNEKIVVLLQRLKPE
IKDVIEQLNLVTTWLQLQIPRIEDGNNFGVAVQEKVFELMTSLHTKLEGFHTQISKYFSE
RGDAVTKAAKQPHVGDYRQLVHELDEAEYRDIRLMVMEIRNAYAVLYDIILKNFEKLKKP
RGETKGMIY*

Fig. 88

SEQ ID No. 88
MELRARGWWLLCAAAALVACARGDPASKSRSCGEVRQIYGAKGFSLSDVPQAEISGEHLR
ICPQGYTCCTSEMEENLANRSHAELETALRDSSRVLQAMLATQLRSFDDHFQHLLNDSER
TLQATFPGAFGELYTQNARAFRDLYSELRLYYRGANLHLEETLAEFWARLLERLFKQLHP
QLLLPDDYLDCLGKQAEALRPFGEAPRELRLRATRAFVAARSFVQGLGVASDVVRKVAQV
PLGPECSRAVMKLVYCAHCLGVPGARPCPDYCRNVLKGCLANQADLDAEWRNLLDSMVLI
TDKFWGTSGVESVIGSVHTWLAEAINALQDNRDTLTAKVIQGCGNPKVNPQGPGPEEKRR
RGKLAPRERPPSGTLEKLVSEAKAQLRDVQDFWISLPGTLCSEKMALSTASDDRCWNGMA
RGRYLPEVMGDGLANQINNPEVEVDITKPDMTIRQQIMQLKIMTNRLRSAYNGNDVDFQD
ASDDGSGSGSGDGCLDDLCSRKVSRKSSSSRTPLTHALPGLSEQEGQKTSAASCPQPPTF
LLPLLLFLALTVARPRWR*

Fig. 89

SEQ ID No. 89
MASCASIDIEDATQHLRDILKLDRPAGGPSAESPRPSSAYNGDLNGLLVPDPLCSGDSTS
ANKTGLRTMPPINLQEKQVICLSGDDSSTCIGILAKEVEIVASSDSSISSKARGSNKVKI
QPVAKYDWEQKYYYGNLIAVSNSFLAYAIRAANNGSAMVRVISVSTSERTLLKGFTGSVA
DLAFAHLNSPQLACLDEAGNLFVWRLALVNGKIQEEILVHIRQPEGTPLNHFRRIIWCPF
IPEESEDCCEESSPTVALLHEDRAEVWDLDMLRSSHSTWPVDVSQIKQGFIVVKGHSTCL
SEGALSPDGTVLATASHDGYVKFWQIYIEGQDEPRCLHEWKPHDGRPLSCLLFCDNHKKQ
DPDVPFWRFLITGADQNRELKMWCTVSWTCLQTIRFSPDIFSSVSVPPSLKVCLDLSAEY
LILSDVQRKVLYVMELLQNQEEGHACFSSISEFLLTHPVLSFGIQVVSRCRLRHTEVLPA
EEENDSLGADGTHGAGAMESAAGVLIKLFCVHTKALQDVQIRFQPQLNPDVVAPLPTHTA
HEDFTFGESRPELGSEGLGSAAHGSQPDLRRIVELPAPADFLSLSSETKPKLMTPDAFMT
PSASLQQITASPSSSSSGSSSSSSSSSSSLTAVSAMSSTSAVDPSLTRPPEELTLSPKLQ
LDGSLTMSSSGSLQASPRGLLPGLLPAPADKLTPKGPGQVPTATSALSLELQEVEPLGLP
QASPSRTRSPDVISSASTALSQDIPEIASEALSRGFGSSAPEGLEPDSMASAASALHLLS
PRPRPGPELGPQLGLDGGPGDGDRHNTPSLLEAALTQEASTPDSQVWPTAPDITRETCST
LAESPRNGLQEKHKSLAFHRPPYHLLQQRDSQDASAEQSDHDDEVASLASASGGFGTKVP
APRLPAKDWKTKGSPRTSPKLKRKSKKDDGDAAMGSRLTEHQVAEPPEDWPALIWQQQRE
LAELRHSQEELLQRLCTQLEGLQSTVTGHVERALETRHEQEQRRLERALAEGQQRGGQLQ
EQLTQQLSQALSSAVAGRLERSIRDEIKKTVPPCVSRSLEPMAGQLSNSVATKLTAVEGS
MKENISKLLKSKNLTDAIARAAADTLQGPMQAAYREAFQSVVLPAFEKSCQAMFQQINDS
FRLGTQEYLQQLESHMKSRKAREQEAREPVLAQLRGLVSTLQSATEQMPPWPAVFVLRCS
TSCMWLWAACRSPF*

Fig. 90

SEQ ID No. 90
MASCASIDIEDATQHLRDILKLDRPAGGPSAESPRPSSAYNGDLNGLLVPDPLCSGDSTS
ANKTGLRTMPPINLQEKQVICLSGDDSSTCIGILAKEVEIVASSDSSISSKARGSNKVKI
QPVAKYDWEQKYYYGNLIAVSNSFLAYAIRAANNGSAMVRVISVSTSERTLLKGFTGSVA
DLAFAHLNSPQLACLDEAGNLFVWRLALVNGKIQEEILVHIRQPEGTPLNHFRRIIWCPF
IPEESEDCCEESSPTVALLHEDRAEVWDLDMLRSSHSTWPVDVSQIKQGFIVVKGHSTCL
SEGALSPDGTVLATASHDGYVKFWQIYIEGQDEPRCLHEWKPHDGRPLSCLLFCDNHKKQ
DPDVPFWRFLITGADQNRELKMWCTVSWTCLQTIRFSPDIFSSVSVPPSLKVCLDLSAEY
LILSDVQRKVLYVMELLQNQEEGHACFSSISEFLLTHPVLSFGIQVVSRCRLRHTEVLPA
EEENDSLGADGTHGAGAMESAAGVLIKLFCVHTKALQDVQIRFQPQLNPDVVAPLPTHTA
HEDFTFGESRPELGSEGLGSAAHGSQPDLRRIVELPAPADFLSLSSETKPKLMTPDAFMT
PSASLQQITASPSSSSSGSSSSSSSSSSSLTAVSAMSSTSAVDPSLTRPPEELTLSPKLQ
LDGSLTMSSSGSLQASPRGLLPGLLPAPADKLTPKGPGQVPTATSALSLELQEVEPLGLP
QASPSRTRSPDVISSASTALSQDIPEIASEALSRGFGSSAPEGLEPDSMASAASALHLLS
PRPRPGPELGPQLGLDGGPGDGDRHNTPSLLEAALTQEASTPDSQVWPTAPDITRETCST
LAESPRNGLQEKHKSLAFHRPPYHLLQQRDSQDASAEQSDHDDEVASLASASGGFGTKVP
APRLPAKDWKTKGSPRTSPKLKRKSKKDDGDAAMGSRLTEHQVAEPPEDWPALIWQQQRE
LAELRHSQEELLQRLCTQLEGLQSTVTGHVERALETRHEQEQRRLERALAEGQQRGGQLQ
EQLTQQLSQALSSAVAGRLERSIRDEIKKTVPPCVSRSLEPMAGQLSNSVATKLTAVEGS
MKENISKLLKSKNLTDAIARAAADTLQGPMQAAYREAFQSVVLPAFEKSCQAMFQQINDS
FRLGTQEYLQQLESHMKSRKAREQEAREPVLAQLRGLVSTLQSATEQMAATVAGSVRAEV
QHQLHVAVGSLQESILAQVQRIVKGEVSVALKEQQAAVTSSIMQAMRSAAGTPVPSAHLD
CQAQQAHILQLLQQGHLNQAFQQALTAADLNLVLYVCETVDPAQVFGQPPCPLSQPVLLS
LIQQLASDLGTRTDLKLSYLEEAVMHLDHSDPITRDHMGSVMAQVRQKLFQFLQAEPHNS
LGKAARRLSLMLHGLVTPSLP*

Fig. 91

SEQ ID No. 91
MRRSEVLAEESIVCLQKALNHLREIWELIGIPEDQRLQRTEVVKKHIKELLDMMIAEEES
LKERLIKSISVCQKELNTLCSELHVEPFQEEGETTILQLEKDLRTQVELMRKQKKERKQE
LKLLQEQDQELCEILCMPHYDIDSASVPSLEELNQFRQHVTTLRETKASRREEFVSIKRQ
IILCMEALDHTPDTSFERDVVCEDEDAFCLSLENIATLQKLLRQLEMQKSQNEAVCEGLR
TQIRELWDRLQIPEEEREAVATIMSGSKAKVRKALQLEVDRLEELKMQNMKKVIEAIRVE
LVQYWDQCFYSQEQRQAFAPFCAEDYTESLLQLHDAEIVRLKNYYEVHKELFEGVQKWEE
TWRLFLEFERKASDPNRFTNRGGNLLKEEKQRAKLQKMLPKLEEELKARIELWEQEHSKA
FMVNGQKFMEYVAEQWEMHRLEKERAKQERQLKNKKQTETEMLYGSAPRTPSKRRGLAPN
TPGKARKLNTTTMSNATANSSIRPIFGGTVYHSPVSRLPPSGSKPVAASTCSGKKTPRTG
RHGANKENLELNGSILSGGYPGSAPLQRNFSINSVASTYSEFAKDPSLSDSSTVGLQREL
SKASKSDATSGILNSTNIQS*

Fig. 92

SEQ ID No. 92
TRLRPVARFEILRGSTARGAATRSDIAGVCGWLLLSGPCGVGLDLDSRLLGASAMRRSEV
LAEESIVCLQKALNHLREIWELIGIPEDQRLQRTEVVKKHIKELLDMMIAEEESLKERLI
KSISVCQKELNTLCSELHVEPFQEEGETTILQLEKDLRTQVELMRKQKKERKQELKLLQE
QDQELCEILCMPHYDIDSASVPSLEELNQFRQHVTTLRETKASRREEFVSIKRQIILCME
ALDHTPDTSFERDVVCEDEDAFCLSLENIATLQKLLRQLEMQKSQNEAVCEGLRTQIREL
WDRLQIPEEEREAVATIMSGSKAKVRKALQLEVDRLEELKMQNMKKVIEAIRVELVQYWD
QCFYSQEQRQAFAPFCAEDYTESLLQLHDAEIVRLKNYYEVHKELFEGVQKWEETWRLFL
EFERKASDPNRFTNRGGNLLKEEKQRAKLQKMLPKLEEELKARIELWEQEHSKAFMVNGQ
KFMEYVAEQWEMHRLEKERAKQERQLKNKKQTETEMLYGSAPRTPSKRRGLAPNTPGKAR
KLNTTTMSNATANSSIRPIFGGTVYHSPVSRLPPSGSKPVAASTCSGKKTPRTGRHGANK
ENLELNGSILSGGYPGSAPLQRNFSINSVASTYSEFAKDPSLSDSSTVGLQRELSKASKS
DATSGILNSTNIQS*

Fig. 93

SEQ ID No. 93
TRLRPVARFEILRGSTARGAATRSDIAGVCGWLLLSGPCGVGLDLDSRLLGASAMRRSEV
LAEESIVCLQKALNHLREIWELIGIPEDQRLQRTEVVKKHIKELLDMMIAEEESLKERLI
KSISVCQKELNTLCSELHVEPFQEEGETTILQLEKDLRTQVELMRKQKKERKQELKLLQE
QDQELCEILCMPHYDIDSASVPSLEELNQFRQHVTTLRETKASRREEFVSIKRQIILCME
ALDHTPDTSFERDVVCEDEDAFCLSLENIATLQKLLRQLEMQKSQNEAVCEGLRTQIREL
WDRLQIPEEEREAVATIMSGSKAKVRKALQLEVDRLEELKMQNMKKVIEAIRVELVQYWD
QCFYSQEQRQAFAPFCAEDYTESLLQLHDAEIVRLKNYYEVHKELFEGVQKWEETWRLFL
EFERKASDPNRFTNRGGNLLKEEKQRAKLQKMLPKLEEELKARIELWEQEHSKAFMVNGQ
KFMEYVAEQWEMHRLEKERAKQERQLKNKKQTETEMLYGSAPRTPSKRRGLAPNTPGKAR
KLNTTTMSNATANSSIRPIFGGTVYHSPVSRLPPSGSKPVAASTCSGKKTPRTGRHGANK
ENLELNGSILSGGYPGSAPLQRNFSINSVASTYSEFARELSKASKSDATSGILNSTNIQS
*

Fig. 94

SEQ ID No. 94
MTTQLGPALVLGVALCLGCGQPLPQVPERPFSVLWNVPSAHCEARFGVHLPLNALGIIAN
RGQHFHGQNMTIFYKNQLGLYPYFGPRGTAHNGGIPQALPLDRHLALAAYQIHHSLRPGF
AGPAVLDWEEWCPLWAGNWGRRRAYQAASWAWAQQVFPDLDPQEQLYKAYTGFEQAARAL
MEDTLRVAQALRPHGLWGFYHYPACGNGWHSMASNYTGRCHAATLARNTQLHWLWAASSA
LFPSIYLPPRLPPAHHQAFVRHRLEEAFRVALVGHRHPLPVLAYVRLTHRRSGRFLSQDD
LVQSIGVSAALGAAGVVLWGDLSLSSSEEECWHLHDYLVDTLGPYVINVTRAAMACSHQR
CHGHGRCARRDPGQMEAFLHLWPDGSLGDWKSFSCHCYWGWAGPTCQEPRPGPKEAV*

Fig. 95

SEQ ID No. 95
MTTQLGPALVLGVALCLGCGQPLPQVPERPFSVLWNVPSAHCEARFGVHLPLNALGIIAN
RGQHFHGQNMTIFYKNQLGLYPYFGPRGTAHNGGIPQALPLDRHLALAAYQIHHSLRPGF
AGPAVLDWEEWCPLWAGNWGRRRAYQAASWAWAQQVFPDLDPQEQLYKAYTGFEQAARAL
MEDTLRVAQALRPHGLWGFYHYPACGNGWHSMASNYTGRCHAATLARNTQLHWLWAASSA
LFPSIYLPPRLPPAHHQAFVRHRLEEAFRVALVGHRHPLPVLAYVRLTHRRSGRFLSQDD
LVQSIGVSAALGAAGVVLWGDLSLSSSEEECWHLHDYLVDTLGPYVINVTRAAMACSHQR
CHGHGRCARRDPGQMEAFLHLWPDGSLGDWKSFSCHCYWGWAGPTCQEPLGLKKQYKARA
PATASSFPCCHFSSPGTTLSHSCSIQFTVNPPKHTPRFPWNP*

Fig. 96

SEQ ID No. 96
MTTQLGPALVLGVALCLGCGQPLPQVPERPFSVLWNVPSAHCEARFGVHLPLNALGIIAN
RGQHFHGQNMTIFYKNQLGLYPYFGPRGTAHNGGIPQALPLDRHLALAAYQIHHSLRPGF
AGPAVLDWEEWCPLWAGNWGRRRAYQAASWAWAQQVFPDLDPQEQLYKAYTGFEQAARAL
MEDTLRVAQALRPHGLWGFYHYPACGNGWHSMASNYTGRCHAATLARNTQLHWLWAASSA
LFPSIYLPPRLPPAHHQAFVRHRLEEAFRVALVGHRHPLPVLAYVRLTHRRSGRFLSQEE
CWHLHDYLVDTLGPYVINVTRAAMACSHQRCHGHGRCARRDPGQMEAFLHLWPDGSLGDW
KSFSCHCYWGWAGPTCQEPRPGPKEAV*

Fig. 97

SEQ ID No. 97
MGKEKTHINIVVIGHVDSGKSTTTGHLIYKCGGIDKRTIEKFEKEAAEMGKGSFKYAWVL
DKLKAERERGITIDISLWKFETSKYYVTIIDAPGHRDFIKNMITGTSQADCAVLIVAAGV
GEFEAGISKNGQTREHALLAYTLGVKQLIVGVNKMDSTEPPYSQKRYEEIVKEVSTYIKK
IGYNPDTVAFVPISGWNGDNMLEPSANMPWFKGWKVTRKDGNASGTTLLEALDCILPPTR
PTDKPLRLPLQDVYKIGGIGTVPVGRVETGVLKPGMVVTFAPVNVTTEVKSVEMHHEALS
EALPGDNVGFKVKNVSVKDVRRGNVAGDSKNDPPMEAAGFTAQVIILNHPGQISAGYAPV
LDCHMAHIACKFAELKEKIDRRSGKKLEDGPKFLKSGDAAIVDMVPGKPMCVESFSDYPP
LGRFAVRDMRQTVAVGVIKAVDKKAAGAGKVTKSAQKAQKAK*

Fig. 98

SEQ ID No. 98
MALKAEGAALDCFEVTLKCEEGEDEEEAMVVAVIPRPEPMLRVTQQEKTPPPRPSPLEAG
SDGCEEPKQQVSWEQEFLVGSSPGGSGRALCMVCGAEIRAPSADTARSHILEQHPHTLDL
SPSEKSNILEAWSEGVALLQDVRAEQPSPPNSDSGQDAHPDPDANPDAARMPAEIVVLLD
SEDNPSLPKRSRPRGLRPLELPAVPATEPGNKKPRGQRWKEPPGEEPVRKKRGRPMTKNL
DPDPEPPSPDSPTETFAAPAEVRHFTDGSFPAGFVLQLFSHTQLRGPDSKDSPKDREVAE
GGLPRAESPSPAPPPGLRGTLDLQVIRVRMEEPPAVSLLQDWSRHPQGTKRVGAGDTSDW
PTVLSESSTTVAGKPEKGNGV*

Fig. 99

SEQ ID No. 99
MSTHRSRLLTAAPLSMEQRRPWPRALEVDSRSVVLLSVVWVLLAPPAAGMPQFSTFHSEN
RDWTFNHLTVHQGTGAVYVGAINRVYKLTGNLTIQVAHKTGPEEDNKSCYPPLIVQPCSE
VLTLTNNVNKLLIIDYSENRLLACGSLYQGVCKLLRLDDLFILVEPSHKKEHYLSSVNKT
GTMYGVIVRSEGEDGKLFIGTAVDGKQDYFPTLSSRKLPRDPESSAMLDYELHSDFVSSL
IKIPSDTLALVSHFDIFYIYGFASGGFVYFLTVQPETPEGVAINSAGDLFYTSRIVRLCK
DDPKFHSYVSLPFGCTRAGVEYRLLQAAYLAKPGDSLAQAFNITSQDDVLFAIFSKGQKQ
YHHPPDDSALCAFPIRAINLQIKERLQSCYQGEGNLELNWLLGKDVQCTKAPVPIDDNFC
GLDINQPLGGSTPVEGLTLYTTSRDRMTSVASYVYNGYSVVFVGTKSGKLKKIRADGPPH
GGVQYEMVSVLKDGSPILRDMAFSIDQRYLYVMSERQVTRVPVESCEQYTTCGECLSSGD
PHCGWCALHNMCSRRDKCQQAWEPNRFAASISQCVSLAVHPSSISVSEHSRLLSLVVSDA
PDLSAGIACAFGNLTEVEGQVSGSQVICISPGPKDVPVIPLDQDWFGLELQLRSKETGKI
FVSTEFKFYNCSAHQLCLSCVNSAFRCHWCKYRNLCTHDPTTCSFQEGRINISEDCPQLV
PTEEILIPVGEVKPITLKARNLPQPQSGQRGYECVLNIQGAIHRVPALRFNSSSVQCQNS
SYQYDGMDISNLAVDFAVVWNGNFIIDNPQDLKVHLYKCAAQRESCGLCLKADRKFECGW
CSGERRCTLHQHCTSPSSPWLDWSSHNVKCSNPQITEILTVSGPPEGGTRVTIHGVNLGL
DFSEIAHHVQVAGVPCTPLPGEYIIAEQIVCEMGHALVGTTSGPVRLCIGECKPEFMTKS
HQQYTFVNPSVLSLNPIRGPESGGTMVTITGHYLGAGSSVAVYLGNQTCEFYGRSMSEIV
CVSPPSSNGLGPVPVSVSVDRAHVDSNLQFEYIDDPRVQRIEPEWSIASGHTPLTITGFN
LDVIQEPRIRVKFNGKESVNVCKVVNTTTLTCLAPSLTTDYRPGLDTVERPDEFGFVFNN
VQSLLIYNDTKFIYYPNPTFELLSPTGVLDQKPGSPIILKGKNLCPPASGGAKLNYTVLI
GETPCAVTVSETQLLCEPPNLTGQHKVMVHVGGMVFSPGSVSVISDSLLTLPAIVSIAAG
GSLLLIIVIIVLIAYKRKSRENDLTLKRLQMQMDNLESRVALECKEAFAELQTDINELTS
DLDRSGIPYLDYRTYAMRVLFPGIEDHPVLRELEVQGNGQQHVEKALKLFAQLINNKVFL
LTFIRTLELQRSFSMRDRGNVASLIMTGLQGRLEYATDVLKQLLSDLIDKNLENKNHPKL
LLRRTESVAEKMLTNWFAFLLHKFLKECAGEPLFMLYCAIKQQMEKGPIDAITGEARYSL
SEDKLIRQQIEYKTLILNCVNPDNENSPEIPVKVLNCDTITQVKEKILDAVYKNVPYSQR
PRAVDMDLEWRQGRIARVVLQDEDITTKIEGDWKRLNTLMHYQVSDRSVVALVPKQTSSY
NIPASASISRTSISRYDSSFRYTGSPDSLRSRAPMITPDLESGVKVWHLVKNHDHGDQKE
GDRGSKMVSEIYLTRLLATKGTLQKFVDDLFETLFSTVHRGSALPLAIKYMFDFLDEQAD
RHSIHDTDVRHTWKSNCLPLRFWVNVIKNPQFVFDIHKGSITDACLSVVAQTFMDSCSTS
EHRLGKDSPSNKLLYAKDIPSYKSWVERYYADIAKLPAISDQDMNAYLAEQSRLHAVEFN
MLSALNEIYSYVSKYSEELIGALEQDEQARRQRLAYKVEQLINAMSIES*

Fig. 100

SEQ ID No. 100
MEQRRPWPRALEVDSRSVVLLSVVWVLLAPPAAGMPQFSTFHSENRDWTFNHLTVHQGTG
AVYVGAINRVYKLTGNLTIQVAHKTGPEEDNKSCYPPLIVQPCSEVLTLTNNVNKLLIID
YSENRLLACGSLYQGVCKLLRLDDLFILVEPSHKKEHYLSSVNKTGTMYGVIVRSEGEDG
KLFIGTAVDGKQDYFPTLSSRKLPRDPESSAMLDYELHSDFVSSLIKIPSDTLALVSHFD
IFYIYGFASGGFVYFLTVQPETPEGVAINSAGDLFYTSRIVRLCKDDPKFHSYVSLPFGC
TRAGVEYRLLQAAYLAKPGDSLAQAFNITSQDDVLFAIFSKGQKQYHHPPDDSALCAFPI
RAINLQIKERLQSCYQGEGNLELNWLLGKDVQCTKAPVPIDDNFCGLDINQPLGGSTPVE
GLTLYTTSRDRMTSVASYVYNGYSVVFVGTKSGKLKKIRADGPPHGGVQYEMVSVLKDGS
PILRDMAFSIDQRYLYVMSERQVTRVPVESCEQYTTCGECLSSGDPHCGWCALHNMCSRR
DKCQQAWEPNRFAASISQCVSLAVHPSSISVSEHSRLLSLVVSDAPDLSAGIACAFGNLT
EVEGQVSGSQVICISPGPKDVPVIPLDQDWFGLELQLRSKETGKIFVSTEFKFYNCSAHQ
LCLSCVNSAFRCHWCKYRNLCTHDPTTCSFQEGRINISEDCPQLVPTEEILIPVGEVKPI
TLKARNLPQPQSGQRGYECVLNIQGAIHRVPALRFNSSSVQCQNSSYQYDGMDISNLAVD
FAVVWNGNFIIDNPQDLKVHLYKCAAQRESCGLCLKADRKFECGWCSGERRCTLHQHCTS
PSSPWLDWSSHNVKCSNPQITEILTVSGPPEGGTRVTIHGVNLGLDFSEIAHHVQVAGVP
CTPLPGEYIIAEQIVCEMGHALVGTTSGPVRLCIGECKPEFMTKSHQQYTFVNPSVLSLN
PIRGPESGGTMVTITGHYLGAGSSVAVYLGNQTCEFYGRSMSEIVCVSPPSSNGLGPVPV
SVSVDRAHVDSNLQFEYIDDPRVQRIEPEWSIASGHTPLTITGFNLDVIQEPRIRVKFNG
KESVNVCKVVNTTTLTCLAPSLTTDYRPGLDTVERPDEFGFVFNNVQSLLIYNDTKFIYY
PNPTFELLSPTGVLDQKPGSPIILKGKNLCPPASGGAKLNYTVLIGETPCAVTVSETQLL
CEPPNLTGQHKVMVHVGGMVFSPGSVSVISDSLLTLPAIVSIAAGGSLLLIIVIIVLIAY
KRKSRENDLTLKRLQMQMDNLESRVALECKEAFAELQTDINELTSDLDRSGIPYLDYRTY
AMRVLFPGIEDHPVLRELEVQGNGQQHVEKALKLFAQLINNKVFLLTFIRTLELQRSFSM
RDRGNVASLIMTGLQGRLEYATDVLKQLLSDLIDKNLENKNHPKLLLRRTESVAEKMLTN
WFAFLLHKFLKECAGEPLFMLYCAIKQQMEKGPIDAITGEARYSLSEDKLIRQQIEYKTL
ILNCVNPDNENSPEIPVKVLNCDTITQVKEKILDAVYKNVPYSQRPRAVDMDLEWRQGRI
ARVVLQDEDITTKIEGDWKRLNTLMHYQVSDRSVVALVPKQTSSYNIPASASISRTSISR
YDSSFRYTGSPDSLRSRAPMITPDLESGVKVWHLVKNHDHGDQKEGDRGSKMVSEIYLTR
LLATKGTLQKFVDDLFETLFSTVHRGSALPLAIKYMFDFLDEQADRHSIHDTDVRHTWKS
NCLPLRFWVNVIKNPQFVFDIHKGSITDACLSVVAQTFMDSCSTSEHRLGKDSPSNKLLY
AKDIPSYKSWVERYYADIAKLPAISDQDMNAYLAEQSRLHAVEFNMLSALNEIYSYVSKY
SEELIGALEQDEQARRQRLAYKVEQLINAMSIES*

Fig. 101

SEQ ID No. 101
MPPPSDIVKVAIEWPGANAQLLEIDQKRPLASIIKEVCDGWSLPNPEYYTLRYADGPQLY
ITEQTRSDIKNGTILQLAISPSRAARQLMERTQSSNMETRLDAMKELAKLSADVTFATEF
INMDGIIVLTRLVESGTKLLSHYSEMLAFTLTAFLELMDHGIVSWDMVSITFIKQIAGYV
SQPMVDVSILQRSLAILESMVLNSQSLYQKIAEEITVGQLISHLQVSNQEIQTYAIALIN
ALFLKAPEDKRQDMANAFAQKHLRSIILNHVIRGNRPIKTEMAHQLYVLQVLTFNLLEER
MMTKMDPNDQAQRDIIFELRRIAFDAESDPSNAPGSGTEKRKAMYTKDYKMLGFTNHINP
AMDFTQTPPGMLALDNMLYLAKVHQDTYIRIVLENSSREDKHECPFGRSAIELTKMLCEI
LQVGELPNEGRNDYHPMFFTHDRAFEELFGICIQLLNKTWKEMRATAEDFNKVMQVVREQ
ITRALPSKPNSLDQFKSKLRSLSYSEILRLRQSERMSQDDFQSPPIVELREKIQPEILEL
IKQQRLNRLCEGSSFRKIGNRRRQERFWYCRLALNHKVLHYGDLDDNPQGEVTFESLQEK
IPVADIKAIVTGKDCPHMKEKSALKQNKEVLELAFSILYDPDETLNFIAPNKYEYCIWID
GLSALLGKDMSSELTKSDLDTLLSMEMKLRLLDLENIQIPEAPPPIPKEPSSYDFVYHYG
*

Fig. 102

SEQ ID No. 102
MPPPSDIVKVAIEWPGANAQLLEIDQKRPLASIIKEVCDGWSLPNPEYYTLRYADGPQLY
ITEQTRSDIKNGTILQLAISPSRAARQLMERTQSSNMETRLDAMKELAKLSADVTFATEF
INMDGIIVLTRLVESGTKLLSHYSEMLAFTLTAFLELMDHGIVSWDMVSITFIKQIAGYV
SQPMVDVSILQRSLAILESMVLNSQSLYQKIAEEITVGQLISHLQVSNQEIQTYAIALIN
ALFLKAPEDKRQDMANAFAQKHLRSIILNHVIRGNRPIKTEMAHQLYVLQVLTFNLLEER
MMTKMDPNDQAQRDIIFELRRIAFDAESDPSNAPGSGTEKRKAMYTKDYKMLGFTNHINP
AMDFTQTPPGMLALDNMLYLAKVHQDTYIRIVLENSSREDKHECPFGRSAIELTKMLCEI
LQVGELPNEGRNDYHPMFFTHDRAFEELFGICIQLLNKTWKEMRATAEDFNKVMQVVREQ
ITRALPSKPNSLDQFKSKLRSLSYSEILRLRQSERMSQDDFQSPPIVELREKIQPEILEL
IKQQRLNRLCEGSSFRKIGNRRRQERFWYCRLALNHKVLHYGDLDDNPQGEVTFESLQEK
IPVADIKAIVTGKDCPHMKEKSALKQNKEVLELAFSILYDPDETLNFIAPNKYEYCIWID
GLSALLGKDMSSELTKSDLDTLLSMEMKLRLLDLENIQIPEAPPPIPKEPSSYDFVYHYG
*

Fig. 103

SEQ ID No. 103
MPPPSDIVKVAIEWPGANAQLLEIDQKRPLASIIKEVCDGWSLPNPEYYTLRYADGPQLY
ITEQTRSDIKNGTILQLAISPSRAARQLMERTQSSNMETRLDAMKELAKLSADVTFATEF
INMDGIIVLTRLVESGTKLLSHEMLAFTLTAFLELMDHGIVSWDMVSITFIKQIAGYVSQ
PMVDVSILQRSLAILESMVLNSQSLYQKIAEEITVGQLISHLQVSNQEIQTYAIALINAL
FLKAPEDKRQDMANAFAQKHLRSIILNHVIRGNRPIKTEMAHQLYVLQVLTFNLLEERMM
TKMDPNDQAQRDIIFELRRIAFDAESDPSNAPGSGTEKRKAMYTKDYKMLGFTNHINPAM
DFTQTPPGMLALDNMLYLAKVHQDTYIRIVLENSSREDKHECPFGRSAIELTKMLCEILQ
VGELPNEGRNDYHPMFFTHDRAFEELFGICIQLLNKTWKEMRATAEDFNKVMQVVREQIT
RALPSKPNSLDQFKSKLRSLSYSEILRLRQSERMSQDDFQSPPIVELREKIQPEILELIK
QQRLNRLCEGSSFRKIGNRRRQEREWYCRLALNHKVLHYGDLDDNPQGEVTFESLQEKIP
VADIKAIVTGKDCPHMKEKSALKQNKEVLELAFSILYDPDETLNFIAPNKYEYCIWIDGL
SALLGKDMSSELTKSDLDTLLSMEMKLRLLDLENIQIPEAPPPIPKEPSSYDFVYHYG*

Fig. 104

SEQ ID No. 104
MERTQSSNMETRLDAMKELAKLSADVTFATEFINMDGIIVLTRLVESGTKLLSHYSEMLA
FTLTAFLELMDHGIVSWDMVSITFIKQIAGYVSQPMVDVSILQRSLAILESMVLNSQSLY
QKIAEEITVGQLISHLQVSNQEIQTYAIALINALFLKAPEDKRQDMANAFAQKHLRSIIL
NHVIRGNRPIKTEMAHQLYVLQVLTFNLLEERMMTKMDPNDQAQRDIIFELRRIAFDAES
DPSNAPGSGTEKRKAMYTKDYKMLGFTNHINPAMDFTQTPPGMLALDNMLYLAKVHQDTY
IRIVLENSSREDKHECPFGRSAIELTKMLCEILQVGELPNEGRNDYHPMFFTHDRAFEEL
FGICIQLLNKTWKEMRATAEDFNKVMQVVREQITRALPSKPNSLDQFKSKLRSLSYSEIL
RLRQSERMSQDDFQSPPIVELREKIQPEILELIKQQRLNRLCEGSSFRKIGNRRRQERFW
YCRLALNHKVLHYGDLDDNPQGEVTFESLQEKIPVADIKAIVTGKDCPHMKEKSALKQNK
EVLELAFSILYDPDETLNFIAPNKYEYCIWIDGLSALLGKDMSSELTKSDLDTLLSMEMK
LRLLDLENIQIPEAPPPIPKEPSSYDFVYHYG*

Fig. 105

SEQ ID No. 105
  MAALRALCGFRGVAAQVLRPGAGVRLPIQPSRGVRQWQPDVEWAQQFGGAVMYPSKETAH
WKPPPWNDVDPPKDTIVKNITLNFGPQHPAAHGVLRLVMELSGEMVRKCDPHIGLLHRGT
EKLIEYKTYLQALPYFDRLDYVSMMCNEQAYSLAVEKLLNIRPPPRAQWIRVLFGEITRL
LNHIMAVTTHALDLGAMTPFFWLFEEREKMFEFYERVSGARMHAAYIRPGGVHQDLPLGL
MDDIYQFSKNFSLRLDELEELLTNNRIWRNRTIDIGVVTAEEALNYGFSGVMLRGSGIQW
DLRKTQPYDVYDQVEFDVPVGSRGDCYDRYLCRVEEMRQSLRIIAQCLNKMPPGEIKVDD
AKVSPPKRAEMKTSMESLIHHFKLYTEGYQVPPGATYTAIEAPKGEFGVYLVSDGSSRPY
RCKIKAPGFAHLAGLDKMSKGHMLADVVAIIGTQDIVFGEVDR*

Fig. 106

SEQ ID No. 106
MAALRALCGFRGVAAQVLRPGAGVRLPIQPSRGVRQWQPDVEWAQQFGGAVMYPSKETAH
WKPPPWNDVDPPKDTIVKNITLNFGPQHPAAHGVLRLVMELSGEMVRKCDPHIGLLHRGT
EKLIEYKTYLQALPYFDRLDYVSMMCNEQAYSLAVEKLLNIRPPPRAQWIRVLFGEITRL
LNHIMAVTTHALDLGAMTPFFWLFEEREKMFEFYERVSGARMHAAYIRPGGVHQDLPLGL
MDDIYQFSKNFSLRLDELEELLTNNRIWRNRTIDIGVVTAEEALNYGFSGVMLRGSGIQW
DLRKTQPYDVYDQVEFDVPVGSRGDCYDRYLCRVEEMRQSLRIIAQCLNKMPPGEIKVDD
AKVSPPKRAEMKTSMESLIHHFKLYTEGYQVPPGATYTAIEAPKGEFGVYLVSDGSSRPY
RCKIKAPGFAHLAGLDKMSKGHMLADVVAIIGTQDIVFGEVDR*

Fig. 107

SEQ ID No. 107
MAGGPGPGEPAAPGAQHFLYEVPPWVMCRFYKVMDALEPADWCQFGGWRRAAGGREARGL
LAPTPDAPRPAAALIVRDQTELRLCERSGQRTASVLWPWINRNARVADLVHILTHLQLLR
ARDIITAWHPPAPLPSPGTTAPRPSSIPAPAEAEAWSPRKLPSSASTFLSPAFPGSQTHS
GPELGLVPSPASLWPPPPSPAPSSTKPGPESSVSLLQGARPFPFCWPLCEISRGTHNFSE
ELKIGEGGFGCVYRAVMRNTVYAVKRLKENADLEWTAVKQSFLTEVEQLSRFRHPNIVDF
AGYCAQNGFYCLVYGFLPNGSLEDRLHCQTQACPPLSWPQRLDILLGTARAIQFLHQDSP
SLIHGDIKSSNVLLDERLTPKLGDFGLARFSRFAGSSPSQSSMVARTQTVRGTLAYLPEE
YIKTGRLAVDTDTFSFGVVVLETLAGQRAVKTHGARTKYLKDLVEEEAEEAGVALRSTQS
TLQAGLAADAWAAPIAMQIYKKHLGQLACCCLHRRAKRRPPMTQENSYVSSTGRAHSGAA
PWQPLAAPSGASAQAAEQLQRGPNQPVESDESLGGLSAALRSWHLTPSCPLDPAPLREAG
CPQGDTAGESSWGSGPGSRPTAVEGLALGSSASSSSEPPQIIINPARQKMVQKLALYEDG
ALDSLQLLSSSSLPGLGLEQDRQGPEESDEFQS*

Fig. 108

SEQ ID No. 108
MAGGPGPGEPAAPGAQHFLYEVPPWVMCRFYKVMDALEPADWCQFAALIVRDQTELRLCE
RSGQRTASVLWPWINRNARVADLVHILTHLQLLRARDIITAWHPPAPLPSPGTTAPRPSS
IPAPAEAEAWSPRKLPSSASTFLSPAFPGSQTHSGPELGLVPSPASLWPPPPSPAPSSTK
PGPESSVSLLQGARPFPFCWPLCEISRGTHNFSEELKIGEGGFGCVYRAVMRNTVYAVKR
LKENADLEWTAVKQSFLTEVEQLSRFRHPNIVDFAGYCAQNGFYCLVYGFLPNGSLEDRL
HCQTQACPPLSWPQRLDILLGTARAIQFLHQDSPSLIHGDIKSSNVLLDERLTPKLGDFG
LARFSRFAGSSPSQSSMVARTQTVRGTLAYLPEEYIKTGRLAVDTDTFSFGVVVLETLAG
QRAVKTHGARTKYLKDLVEEEAEEAGVALRSTQSTLQAGLAADAWAAPIAMQIYKKHLDP
RPGPCPPELGLGLGQLACCCLHRRAKRRPPMTQVYERLEKLQAVVAGVPGHSEAASCIPP
SPQENSYVSSTGRAHSGAAPWQPLAAPSGASAQAAEQLQRGPNQPVESDESLGGLSAALR
SWHLTPSCPLDPAPLREAGCPQGDTAGESSWGSGPGSRPTAVEGLALGSSASSSSEPPQI
IINPARQKMVQKLALYEDGALDSLQLLSSSSLPGLGLEQDRQGPEESDEFQS*

Fig. 109

SEQ ID No. 109
MAGGPGPGEPAAPGAQHFLYEVPPWVMCRFYKVMDALEPADWCQFAALIVRDQTELRLCE
RSGQRTASVLWPWINRNARVADLVHILTHLQLLRARDIITAWHPPAPLPSPGTTAPRPSS
IPAPAEAEAWSPRKLPSSASTFLSPAFPGSQTHSGPELGLVPSPASLWPPPPSPAPSSTK
PGPESSVSLLQGARPFPFCWPLCEISRGTHNFSEELKIGEGGFGCVYRAVMRNTVYAVKR
LKENADLEWTAVKQSFLTEVEQLSRFRHPNIVDFAGYCAQNGFYCLVYGFLPNGSLEDRL
HCQTQACPPLSWPQRLDILLGTARAIQFLHQDSPSLIHGDIKSSNVLLDERLTPKLGDFG
LARFSRFAGSSPSQSSMVARTQTVRGTLAYLPEEYIKTGRLAVDTDTFSFGVVVLETLAG
QRAVKTHGARTKYLKDLVEEEAEEAGVALRSTQSTLQAGLAADAWAAPIAMQIYKKHLDP
RPGPCPPELGLGLGQLACCCLHRRAKRRPPMTQENSYVSSTGRAHSGAAPWQPLAAPSGA
SAQAAEQLQRGPNQPVESDESLGGLSAALRSWHLTPSCPLDPAPLREAGCPQGDTAGESS
WGSGPGSRPTAVEGLALGSSASSSSEPPQIIINPARQKMVQKLALYEDGALDSLQLLSSS
SLPGLGLEQDRQGPEESDEFQS*

Fig. 110

SEQ ID No. 110
MAGGPGPGEPAAPGAQHFLYEVPPWVMCRFYKVMDALEPADWCQFAALIVRDQTELRLCE
RSGQRTASVLWPWINRNARVADLVHILTHLQLLRARDIITAWHPPAPLPSPGTTAPRPSS
IPAPAEAEAWSPRKLPSSASTFLSPAFPGSQTHSGPELGLVPSPASLWPPPPSPAPSSTK
PGPESSVSLLQGARPFPFCWPLCEISRGTHNFSEELKIGEGGFGCVYRAVMRNTVYAVKR
LKENADLEWTAVKQSFLTEVEQLSRFRHPNIVDFAGYCAQNGFYCLVYGFLPNGSLEDRL
HCQTQACPPLSWPQRLDILLGTARAIQFLHQDSPSLIHGDIKSSNVLLDERLTPKLGDFG
LARFSRFAGSSPSQSSMVARTQTVRGTLAYLPEEYIKTGRLAVDTDTFSFGVVVLETLAG
QRAVKTHGARTKYLVYERLEKLQAVVAGVPGHSEAASCIPPSPQENSYVSSTGRAHSGAA
PWQPLAAPSGASAQAAEQLQRGPNQPVESDESLGGLSAALRSWHLTPSCPLDPAPLREAG
CPQGDTAGESSWGSGPGSRPTAVEGLALGSSASSSSEPPQIIINPARQKMVQKLALYEDG
ALDSLQLLSSSSLPGLGLEQDRQGPEESDEFQS*

Fig. 111

SEQ ID No. 111
MAGGPGPGEPAAPGAQHFLYEVPPWVMCRFYKVMDALEPADWCQFGGWRRAAGGREARGL
LAPTPDAPRPAAALIVRDQTELRLCERSGQRTASVLWPWINRNARVADLVHILTHLQLLR
ARDIITAWHPPAPLPSPGTTAPRPSSIPAPAEAEAWSPRKLPSSASTFLSPAFPGSQTHS
GPELGLVPSPASLWPPPPSPAPSSTKPGPESSVSLLQGARPFPFCWPLCEISRGTHNFSE
ELKIGEGGFGCVYRAVMRNTVYAVKRLKENADLEWTAVKQSFLTEVEQLSRFRHPNIVDF
AGYCAQNGFYCLVYGFLPNGSLEDRLHCQTQACPPLSWPQRLDILLGTARAIQFLHQDSP
SLIHGDIKSSNVLLDERLTPKLGDFGLARFSRFAGSSPSQSSMVARTQTVRGTLAYLPEE
YIKTGRLAVDTDTFSFGVVVLETLAGQRAVKTHGARTKYLKDLVEEEAEEAGVALRSTQS
TLQAGLAADAWAAPIAMQIYKKHLDPRPGPCPPELGLGLGQLACCCLHRRAKRRPPMTQE
NSYVSSTGRAHSGAAPWQPLAAPSGASAQAAEQLQRGPNQPVESDESLGGLSAALRSWHL
TPSCPLDPAPLREAGCPQGDTAGESSWGSGPGSRPTAVEGLALGSSASSSSEPPQIIINP
ARQKMVQKLALYEDGALDSLQLLSSSSLPGLGLEQDRQGPEESDEFQS*

Fig. 112

SEQ ID No. 112
MAAIPSSGSLVATHDYYRRRLGSTSSNSSCSSTECPGEAIPHPPGECRIAPFSPRSSRSW
QHQDPTSLLSGLPKADPGHWWASFFFGKSTLPFMATVLESAEHSEPPQASSSMTACGLAR
DAPRKQPGGQSSTASAGPPS*

Fig. 113

SEQ ID No. 113
MAAIPSSGSLVATHDYYRRRLGSTSSNSSCSSTECPGEAIPHPPGLPKADPGHWWASFFF
GKSTLPPPTL*

Fig. 114

SEQ ID No. 114
MAAIPSSGSLVATHDYYRRRLGSTSSNSSCSSTECPGEAIPHPPGLPKADPGHWWASFFF
GKSTLPFMATVLESAEHSEPPQASSSMTACGLARDAPRKQPGGQSSTASAGPPS*

Fig. 115

SEQ ID No. 115
MEDGVYEPPDLTPEERMELENIRRRKQELLVEIQRLREELSEAMSEVEGLEANEGSKTLQ
RNRKMAMGRKKFNMDPKKGIQFLVENELLQNTPEEIARFLYKGEGLNKTAIGDYLGEREE
LNLAVLHAFVDLHEFTDLNLVQALRQFLWSFRLPGEAQKIDRMMEAFAQRYCLCNPGVFQ
STDTCYVLSFAVIMLNTSLHNPNVRDKPGLERFVAMNRGINEGGDLPEELLRNLYDSIRN
EPFKIPEDDGNDLTHTFFNPDREGWLLKLGRGRVKTWKRRWFILTDNCLYYFEYTTDKEP
RGIIPLENLSIREVDDPRKPNCFELYIPNNKGQLIKACKTEADGRVVEGNHMVYRISAPT
QEEKDEWIKSIQAAVSVDPFYEMLAARKKRISVKKKQEQP*

Fig. 116

SEQ ID No. 116
MEDGVYEPPDLTPEERMELENIRRRKQELLVEIQRLREELSEAMSEVEGLEANEGSKTLQ
RNRKMAMGRKKFNMDPKKGIQFLVENELLQNTPEEIARFLYKGEGLNKTAIGDYLGEREE
LNLAVLHAFVDLHEFTDLNLVQALRQFLWSFRLPGEAQKIDRMMEAFAQRYCLCNPGVFQ
STDTCYVLSFAVIMLNTSLHNPNVRDKPGLERFVAMNRGINEGGDLPEELLRNLYDSIRN
EPFKIPEDDGNDLTHTFFNPDREGWLLKLGGRVKTWKRRWFILTDNCLYYFEYTTDKEPR
GIIPLENLSIREVDDPRKPNCFELYIPNNKGQLIKACKTEADGRVVEGNHMVYRISAPTQ
EEKDEWIKSIQAAVSVDPFYEMLAARKKRISVKKKQEQP*

Fig. 117

SEQ ID No. 117
MVNPTVFFDIAVDGEPLGRVSFELFADKVPKTAENFRALSTGEKGFGYKGSCFHRIIPGF
MCQGGDFTRHNGTGGKSIYGEKFEDENFILKHTGPGILSMANAGPNTNGSQFFICTAKTE
WLDGKHVVFGKVKEGMNIVEAMERFGSRNGKTSKKITIADCGQLE*

Fig. 118

SEQ ID No. 118
TAEEEASSEACAGPATRSPGWGDPGISHRDCCRRKAEWGTAESR*

Fig. 119

SEQ ID No. 119
EAELPDRGGAAVQVSSPKHCGLCWLLCSERLLLPGVRLPAQRLPGGPSPLPDPGLPTSLL
ASATGHPSGYSPGNSVSTSGQPQPHPWRHQEFQRPSG*

Fig. 120

SEQ ID 120
LRGLAPPSPPPVIVRRGPRGVAAQIPPASKLKHGGHPLQRLARGHPRLLPAPPGFHFQQQ
LLQQYRVPRGSHSPPPRSPQG*

Fig. 121

SEQ ID No. 121
APWPSAPVPATRDRAPRPARGRRPDPTSQQAKAWRPSPPAARSWPPTTTTGAAWVPLPAT
APAAVPSAPGKPFPTPQVSPRLTRVIGGPASFSGSPPSRSWPRCWSPQSTRNLPRPPAA*

Fig. 122

SEQ ID No. 122
WTCSPHPTPTTRRSTTSRSASWSARCAST*

BIOMARKER FOR THE PREDICTION OF RESPONSIVENESS TO AN ANTI-TUMOUR NECROSIS FACTOR ALPHA (TNF) TREATMENT

The invention refers to a method for diagnosing an individual who is to be subjected to or is being subjected to an anti-tumour necrosis factor alpha (TNFα or TNF) treatment to assess the responsiveness to an anti-TNF treatment which comprises the detection of immunoglobulin(s) against one or more biomarker proteins in a bodily fluid or an excrement of said patient, and sorting the individual into one of two categories based on detection of said immunoglobulin(s), wherein individuals are classified as NON-responder or responder. The invention refers to diagnostic kits comprising said one or more biomarker proteins and the use of these kits for assessing the responsiveness to an anti-TNF treatment of an individual who is to be subjected to or is being subjected to an anti-TNFα treatment.

BACKGROUND

Rheumatic diseases are the most common chronic inflammatory disorders. In Germany alone, one million patients suffer from immunologically mediated rheumatic diseases including rheumatoid arthritis (RA), spondyloarthropathies (SpA) and systemic autoimmune diseases like systemic lupus erythematosus (SLE), while additional five million individuals have osteoarthritis (OA), a primarily degenerative joint disease, which, however, in its active phases is also dominated by inflammatory processes. Rheumatoid arthritis leads to severe pain, loss of function and serious impairment of the quality of life. Besides these deleterious consequences for the individual patient, there is a striking socio-economic impact leading to direct and indirect costs of about 20 billion Euros in Germany per year. The demographic development clearly indicates that rheumatic diseases will dramatically increase over the next decades and will be equal in importance to cardiovascular diseases and cancer. Already now, rheumatic disorders dominate the number of patient visits in the General Practitioner's office and are the leading cause of absence from work and premature invalidity. In recognition of the tremendous impact of arthritic and bone diseases, the World Health Organization has announced the current decade as the "Decade of Bone and Joint Diseases".

A range of therapies for rheumatoid arthritis is available based on standard disease-modifying antirheumatic drugs (DMARDs), such as Methotrexate (MTX) and on biologicals, such as TNF inhibitors/antagonists. Chronically elevated levels of TNF have been implicated as a pathogenic component in rheumatoid arthritis. TNF inhibitors are biologicals which bind to soluble and cell membrane-associated form of TNFα and neutralise the proinflammatory effect of TNFα by preventing the binding of TNFα to the TNF-RI/II cell-surface receptors. TNFa-inhibiting biological agents comprise e.g. therapeutic antibodies (Adalimumab® & Infliximab®) and soluble receptor constructs (Etanercept®). These biologicals are currently used to treat active rheumatoid arthritis, all of which effectively reduce the signs and symptoms of the disease and inhibit radiographic joint damage progression. Currently ~10% of patients in Germany, but up to 30% in Scandinavian countries are treated with TNF-α inhibitors and the numbers are continuously growing. Anti-TNF-α antibodies (Adalimumab®; Humira) account for 90% of all biologicals in current use of rheumatoid arthritis therapy.

However, only 70% of rheumatoid arthritis patients benefit from a treatment with anti-TNFα, while 30% (~10.000 patients in Germany in 2006) remain non-responders. An anti-TNFα therapy costs currently ~20.000 € in Germany and hence, the costs of unsuccessful therapies account for 200 Mia € /year in Germany alone.

Next to rheumatoid arthritis, chronically elevated levels of TNF have been implicated as a pathogenic component in a number of other disease states—primarily autoimmune conditions—such as psoriasis, psoriatic arthritis, ankylosing spondylitis, Crohn's disease, ulcerative colitis, etc.

Currently, there are no biomarkers available, which can predict the outcome of a treatment with anti-TNF agents (e.g. TNF antagonists/inhibitors) prior treatment. Only reduction of all isotype levels of rheumatoid factors during and after treatment is associated with a positive response and outcome of the treatment (van Laar J M. Nat Clin Pract Rheumatol. 2007 October; 3(10):544-5. PMID: 17726429). However, high level of IgA rheumatoid factor in sera of patients with rheumatoid arthritis has been suggested to identify a subgroup of patients at risk of a poor clinical response to treatment with anti-TNFα antibodies (Bobbio-Pallavicini F. et al. Ann Rheum Dis. 2007 March; 66(3):302-7. PMID: 17079248; Bobbio-Pallavicini F. et al. Ann NY Acad Sci. 2007 August; 1109:287-95. PMID: 17785317; van Laar J M. Nat Clin Pract Rheumatol. 2007 October; 3(10):544-5. PMID: 17726429). The nature of anti-CCP antibodies suggested as a predictor for therapy efficacy is controversial (Braun-Moscovici Y et al. J Rheumatol. 2006 March; 33(3): 497-500. PMID: 16511906; Bobbio-Pallavicini F et al. Ann NY Acad Sci. 2007 August; 1109:287-95. PMID: 17785317; van Laar J M. Nat Clin Pract Rheumatol. 2007 October; 3(10):544-5. PMID: 17726429).

Thus, there is a need in the art for markers, which can predict the outcome of an anti-TNFα therapy prior to and during treatment. There is a need for stratification of patients who are to be subjected to or are being subjected to an anti-TNFα treatment and distinguishing between anti-TNFα treatment responder and Non-responder patients.

Subject of the present invention is a method for diagnosing an individual who is to be subjected to or is being subjected to an anti-TNFα treatment to assess the responsiveness to an anti-TNF treatment prior, during and/or after anti-TNFα treatment which comprises:
  a. Detection of immunoglobulin(s) against one or more biomarker proteins in a bodily fluid or excrement of said patient, wherein the one or more biomarker is indicative for the responsiveness to an anti-TNF treatment prior, during and after anti-TNFα treatment.
  b. Sorting the individual into responder or NON-responder based on detection of said immunoglobulin(s).

Thus, the invention provides for the first time marker which can predict the outcome of an anti-TNFα treatment prior to treatment in addition to during and/or after treatment. Anti-TNFalpha treatment may be conducted by administration of TNF inhibitors, e.g. TNF antagonists. These markers are not related to IgA rheumatoid factor. The marker according to the present invention can either be indicative of responder or of NON-responder as will be outlined below in detail. It is preferred that the responsiveness is assessed prior to treatment.

Subject of the present invention is a method for diagnosing an individual who is to be subjected to or is being subjected to an anti-TNFα treatment to assess the responsiveness to an anti-TNF treatment which comprises:
  Detection of immunoglobulin(s) against one or more biomarker proteins in a bodily fluid or excrement of said patient, wherein a biomarker protein is an expression product encoded by a gene selected from the group comprising RAB11B, PPP2R1A, KPNB1, COG4 and FDFT1, wherein an individual positive for at least one of said immunoglobulin(s) is classified as NON-responder.

In a preferred embodiment of the above-identified method the individual is sorted into one of two categories based on detection of said immunoglobulin(s), wherein an individual positive for at least one of said immunoglobulin(s) is classified as NON-responder and, wherein an individual negative for any of said detected immunoglobulin(s) is classified as responder.

In a preferred embodiment of the inventive method at least two of the biomarker proteins of the protein marker group are detected wherein a biomarker protein is an expression product encoded by a gene selected from the group comprising RAB11B, PPP2R1A, KPNB1, COG4 and FDFT1 (Protein Set 1=RAB11B, PPP2R1A, KPNB1, COG4 and FDFT1). In another preferred embodiment of the inventive method at least expression products encoded by genes RAB11B, PPP2R1A, KPNB1, COG4 and FDFT1 are detected. In another preferred embodiment only expression products encoded by genes RAB11B, PPP2R1A, KPNB1, COG4 and FDFT1 are detected. In another preferred embodiment each and only the expression products encoded by genes RAB11B, PPP2R1A, KPNB1, COG4 and FDFT1 are detected.

In another preferred embodiment of the method for diagnosing an individual who is to be subjected to or is being subjected to an anti-TNFα treatment according to the invention the biomarker protein group additionally comprises at least one other expression product encoded by a gene selected from the group comprising PECI, CTNND2, NSMCE1, KTELC1, HS6ST1, ARMC6, TH1L, PSME1, GPC1, EDC4 (Protein Set 2) and at least one of the proteins of the entire group 1 and 2 (Protein Set 1 and 2) is detected. In a preferred embodiment of the invention at least one protein from Protein Set 1 is detected and additionally at least one of Protein Set 2 is detected. In another preferred embodiment at least two of the proteins of Protein Set 1 and additionally at least one of Protein Set 2 are detected. In another preferred embodiment Protein Set 1 and Protein Set 2 are detected.

In another preferred embodiment additionally to the above cited combinations of marker proteins a protein of Protein Set 3 is detected: the Protein Set 3 comprises the expression products encoded by genes PRC1, NAT6, EEF1AL3, NP_612480.1, PLXNA2, ELMO2 and NDUFS2.

In another preferred embodiment of the invention at least two marker proteins are selected from the group comprising the marker from protein sets 1, 2 and 3 for the method for diagnosing an individual who is to be subjected to or is being subjected to an anti-TNFα treatment to assess the responsiveness to an anti-TNF treatment prior, during and/or after anti-TNFα treatment. This means in this embodiment at least two marker are selected from the group comprising RAB11B, PPP2R1A, KPNB1, COG4, FDFT1, PECI, CTNND2, NSMCE1, KTELC1, HS6ST1, ARMC6, TH1L, PSME1, GPC1, EDC4, PRC1, NAT6, EEF1AL3, NP_612480.1, PLXNA2, ELMO2 and NDUFS2.

In another preferred embodiment at least three marker proteins are selected, more preferably four or five protein marker.

According to the present invention biomarker proteins of the present invention may be peptides, protein fragments, full length or splice variants or synthetically modified derivatives or post-translationally modified versions of the proteins encoded by aforementioned genes. Preferably, said protein fragments have a length of more than nine amino acids, more preferably at least n twelve or more than twelve amino acids. Modification of proteins may be but are not limited to deimination, deamidation and/or transglutamination. Additionally, they can be artificial polypeptides being expression products derived from incorrect reading frames within the gene. An examples for such an expression product derived from incorrect reading frames within the gene is shown in FIG. 122 which is a protein sequence derived from an incorrect reading frame of the gene HS6SP1. Another example is shown in FIG. 121 which is a protein sequence derived from an incorrect reading frame of the gene C20orf149. Yet another example is shown in FIG. 120 which is a protein sequence derived from an incorrect reading frame of the gene IRAK1.

This means when for example IRAK1 is mentioned in the context of the present application it may concern the peptides, protein fragments, full length or splice variants or synthetically modified derivatives and/or post-translationally modified versions of IRAK1 and/or a protein sequence derived from an incorrect reading frame of the gene IRAK1.

A biomarker protein encompasses also variants thereof, such as peptides, protein fragments, artificial polypeptides, full length or splice variants, synthetically modified derivatives or post-translationally modified versions of the proteins encoded by aforementioned genes which are characterized in that these variants exhibit essentially the same ability to be recognized by the respective immunoglobulin as the biomarker proteins that are subject of the invention.

In particular, according to the present inventions biomarker proteins are encompassed wherein the sequences involved in binding to the respective immunoglobulin exhibit at least 80%, preferred at least 90%, more preferred at least 95% degree of sequence identity on the amino acid level to the sequences involved in binding of the biomarker proteins defined in SEQ ID No.s 59-122 as well as peptides, protein fragments, full length or splice variants, synthetically modified derivatives or post-translationally modified versions thereof exhibiting the same ability.

In context of the present invention a DNA sequence of a gene is defined by comprising all exons of a gene necessary to represent the protein coding sequence (CDS) or all splice variants thereof, as well as the exons representing the 5' untranslated region (UTR) and the 3' UTR.

According to the present invention all DNA sequences are encompassed which encode the before-mentioned biomarker proteins.

In particular, according to the present inventions furthermore DNA sequences are encompassed which exhibit referred to the sequence encoding a stretch which is involved in the binding region at least 80%, preferred at least 90%, more preferred at least 95% degree of sequence identity on the nucleic acid level to the DNA sequences encoding a stretch which is involved in the binding region defined in SEQ ID No.s 1-58 as well as fragments thereof encoding the biomarkers according to the present invention.

The before mentioned definitions for biomarker proteins and for genes encoding said biomarker proteins apply to every single embodiment of this inventions, any specific method, kit etc.

The determination of percent identity between two sequences is accomplished using the mathematical algorithm of Karlin and Altschul (1993) Proc. Natl. Acad. Sci. USA 90: 5873-5877. Such an algorithm is incorporated into the BLASTN and BLASTP programs of Altschul et al. (1990) J. Mol. Biol. 215: 403-410. BLAST nucleotide searches may be performed with the BLASTN program, score=100, word length=12, to obtain nucleotide sequences homologous to variant polypeptide encoding nucleic acids. BLAST protein searches are performed with the BLASTP program, score=50, wordlength=3, to obtain amino acid sequences homologous to the variant polypeptide, respectively. To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used.

The immunoglobulin(s) to be detected may be selected from IgA, IgD, IgG and IgM. In a preferred embodiment the immunoglobulin(s) to be detected is IgA or IgG. In the most preferred embodiment the immunoglobulin is IgA. The immunoglobulin(s) to be detected is not related to IgA rheumatoid factor.

In another preferred embodiment subsets of biomarker proteins may be used to assess the responsiveness to an anti-TNF treatment prior, during and/or after anti-TNFα treatment.

The respective set of proteins can not only predict responsiveness before, but also during treatment. Thus, a diagnostic assay based on one or more protein of the set will help the clinician in treatment decisions and the identification of anti-TNF therapy responders and non-responders a priory.

The bodily fluid and/or excrement from the individual to be assessed may be selected from a group comprising: blood, saliva, tears, synovial and spinal fluid, plasma, urine and stool.

An individual who is to be subjected to or is being subjected to an anti-TNFα treatment may suffer autoimmune conditions such as Crohn's disease, ulcerative colitis, psoriasis, psoriatic arthritis, ankylosing spondylitis, spondyloarthropathies, rheumatoid arthritis etc.

The method of the invention is especially suited for individuals suffering from rheumatoid arthritis.

Subject of the present invention is furthermore a kit for diagnosing an individual who is to be subjected to or is being subjected to an anti-TNFα treatment to assess the responsiveness to an anti-TNF treatment which comprises one or more biomarker proteins, wherein a biomarker protein is an expression product encoded by a gene selected from the group comprising RAB11B, PPP2R1A, KPNB1, COG4 and FDFT1. In a preferred embodiment the kit comprises at least those proteins encoded by a gene selected from the group comprising RAB11B, PPP2R1A, KPNB1, COG4 and FDFT1.

In a preferred embodiment of the inventive kit at least two of the biomarker proteins of the protein marker group are detected wherein a biomarker protein is an expression product encoded by a gene selected from the group comprising RAB11B, PPP2R1A, KPNB1, COG4 and FDFT1 (Protein Set 1=RAB11B, PPP2R1A, KPNB1, COG4 and FDFT1). In another preferred embodiment of the inventive kit at least one expression product encoded by genes RAB11B, PPP2R1A, KPNB1, COG4 and FDFT1 are detected. In another preferred embodiment only expression products encoded by genes RAB11B, PPP2R1A, KPNB1, COG4 and FDFT1 are detected. In another preferred embodiment each and only the expression products encoded by genes RAB11B, PPP2R1A, KPNB1, COG4 and FDFT1 are detected.

In another preferred embodiment of the kit for diagnosing an individual who is to be subjected to or is being subjected to an anti-TNFα treatment according to the invention the biomarker protein group additionally comprises at least one other expression product encoded by a gene selected from the group comprising PECI, CTNND2, NSMCE1, KTELC1, HS6ST1, ARMC6, TH1L, PSME1, GPC1, EDC4 (Protein Set 2) and at least one of the proteins of the entire group 1 and 2 (Protein Set 1 and 2) is detected. In a preferred embodiment of the invention at least one protein from Protein Set 1 is detected and additionally at least one of Protein Set 2 is detected. In another preferred embodiment at least two of the proteins of Protein Set 1 and additionally at least one of Protein Set 2 are detected. In another preferred embodiment Protein Set 1 and Protein Set 2 are detected.

In another preferred embodiment additionally to the above cited combinations of marker proteins a protein of Protein Set 3 is detected: the Protein Set 3 comprises the expression products encoded by genes PRC1, NAT6, EEF1AL3, NP_612480.1, PLXNA2, ELMO2 and NDUFS2.

In another preferred embodiment of the kit the biomarker protein group additionally comprises at least one expression product encoded by genes PECI, CTNND2, NSMCE1, KTELC1, HS6ST1, ARMC6, TH1L, PSME1, GPC1, EDC4, PRC1, NAT6, EEF1AL3, NP_612480.1, PLXNA2, ELMO2 and NDUFS2.

Another preferred embodiment of the invention is a kit for diagnosing an individual who is to be subjected to or is being subjected to an anti-TNFα treatment to assess the responsiveness to an anti-TNF treatment which comprises at least two biomarker proteins, wherein a biomarker protein is an expression product encoded by a gene selected from the group comprising RAB11B, PPP2R1A, KPNB1, COG4, FDFT1, PECI, CTNND2, NSMCE1, KTELC1, HS6ST1, ARMC6, TH1L, PSME1, GPC1, EDC4, PRC1, NAT6, EEF1AL3, NP_612480.1, PLXNA2, ELMO2 and NDUFS2.

As outlined above subject of the present invention is a method, wherein markers are detected and used to identify non-responder. A further embodiment of the present invention is the provision of marker(s), wherein the detection of those marker(s) is indicative for responder.

Thus, subject of the present invention is further a method for diagnosing an individual who is to be subjected to or is being subjected to an anti-TNFα treatment to assess the responsiveness to an anti-TNF treatment which comprises:
    Detection of immunoglobulin(s) against one or more biomarker proteins in a bodily fluid or excrement of said patient, wherein a biomarker protein is an artificial peptides deduced from an expression product in an incorrect reading frame of a gene selected from the group comprising IRAK1 and C20orf149, wherein an individual positive for at least one of said immunoglobulin(s) is classified as responder.

In a preferred embodiment of the above-identified method the individual is sorted into one of two categories based on detection of said immunoglobulin(s), wherein an individual positive for at least one of said immunoglobulin(s) is classified as responder and, wherein an individual negative for any of said detected immunoglobulin(s) is classified as NON-responder.

In a preferred embodiment of the present invention the method for diagnosing an individual who is to be subjected to or is being subjected to an anti-TNFα treatment the biomarker protein group additionally comprises at least one other expression product encoded by a gene selected from a group comprising PSCD2L and PPIA.

In another preferred embodiment all members of the biomarker group are detected, the group comprising either artificial peptides deduced from an expression product in an incorrect reading frame of a gene or the expression products encoded by the following genes IRAK1 and C20orf149 as well as PSCD2L and PPIA.

The immunoglobulin(s) to be detected may be selected from IgA, IgD, IgG and IgM. In a preferred embodiment the immunoglobulin(s) to be detected is IgA or IgG. In the most preferred embodiment the immunoglobulin is IgG. The immunoglobulin(s) to be detected is not related to IgA rheumatoid factor.

Subject of the method of the present invention is a method for diagnosing an individual who is to be subjected to or is being subjected to an anti-TNFα treatment, wherein the immunoglobulin(s) is IgA and/or IgG. IgG is especially preferred in the context of a method for diagnosing an individual who is to be subjected to or is being subjected to an anti-TNFα treatment to assess the responsiveness to an anti-TNF treatment, wherein an individual positive for at least one of before said immunoglobulin(s) is classified as responder.

The respective set of proteins can not only predict responsiveness before, but also during treatment. Thus, a diagnostic assay based on one or more protein of the set will help the clinician in treatment decisions and the identification of anti-TNF therapy responders and non-responders a priory.

The bodily fluid and/or excrement from the individual to be assessed may be selected from a group comprising: blood, saliva, tears, synovial and spinal fluid, plasma, urine and stool.

An individual who is to be subjected to or is being subjected to an anti-TNFα treatment may suffer autoimmune conditions such as Crohn's disease, ulcerative colitis, psoriasis, psoriatic arthritis, ankylosing spondylitis, spondyloarthropathies, rheumatoid arthritis etc.

The method of the invention is especially suited for individuals suffering from rheumatoid arthritis.

Subject of the present invention is also a kit for diagnosing an individual who is to be subjected to or is being subjected to an anti-TNFα treatment to assess the responsiveness to an anti-TNF treatment which comprises one or more biomarker proteins, wherein a biomarker protein is an artificial peptides deduced from an expression product in an incorrect reading frame of a gene selected from the group comprising IRAK1 and C20orf149.

In a preferred embodiment of the present invention the kit for diagnosing an individual who is to be subjected to or is being subjected to an anti-TNFα treatment the biomarker protein group additionally comprises at least one other expression product encoded by a gene selected from a group comprising PSCD2L and PPIA.

In another preferred embodiment all members of the biomarker group are detected, the group to comprising either artificial peptides deduced from an expression product in an incorrect reading frame of a gene or the expression products encoded by the following genes IRAK1 and C20orf149 as well as PSCD2L and PPIA.

In another embodiment of the invention the kit and the method according to the present invention is may additionally comprise one or more known diagnostic markers e.g. for autoimmune disorders. In a preferred embodiment the kit may also comprise other known diagnostic markers for rheumatoid arthritis.

The proteins, protein sets/kits may be conducted in different assay types known to a person skilled in the art.

The immunoglobulins to be detected are in or isolated from body fluids and excrements, such as blood, saliva, tears, synovial and spinal fluid, plasma, urine and stool, etc.

The diagnostic assay can be of any type applied in the field of diagnostics, including but not restricted to assays methods based on
  enzymatic reactions
  luminescence
  fluorescence
  radiochemicals The preferred detection methods comprise strip tests, radioimmunoassay, chemiluminescence- and fluorescence-immunoassay, Immunoblot assay, Enzyme-linked immunoassay (ELISA), Luminex-based bead arrays, and protein microarray assay.

The assay types can further be microliter plate-based, chip-based, bead-based, wherein the biomarker proteins can be attached to the surface or in solution.

The assays can be homogenous or heterogeneous assays, sandwich assays, competitive and non-competitive assays (The Immunoassay Handbook, Ed. David Wild, Elsevier LTD, Oxford; 3rd ed. (May 2005), ISBN-13: 978-0080445267; Hultschig C et al., Curr Opin Chem Biol. 2006 February; 10(1):4-10. PMID: 16376134).

TNFα treatment is conducted by administration of a TNF inhibitor to an individual in need thereof. TNF inhibitors are biologicals which bind to soluble and cell membrane-associated form of TNFα and neutralise the proinflammatory effect of TNF by preventing the binding of TNFα to the TNF-RI/II cell-surface receptors. The TNF inhibitors can be anti-TNFα antibodies or receptor molecules but also of other types. The essential of a TNF inhibitor according to the present invention is the ability to capture TNF before it binds to the TNF receptor on the cells.

Subject to the present invention is also the use of the biomarker proteins and/or protein sets and the kits comprising these biomarker proteins and/or protein sets according to the present invention for assessing the responsiveness to an anti-TNFα treatment of an individual who is to be subjected to or is being subjected to an anti-TNFα treatment.

FIGURE DESCRIPTION

FIG. 1 shows SEQ ID No. 1 which is a DNA sequence of the gene RAB11B (Table 1, No. 1)

FIG. 2 shows SEQ ID No. 2 which is a DNA sequence of the gene PPP2R1A (Table 1, No. 2)

FIG. 3 shows SEQ ID No. 3 which is a DNA sequence of the gene PPP2R1A (Table 1, No. 2)

FIG. 4 shows SEQ ID No. 4 which is a DNA sequence of the gene KPNB1 (Table 1, No. 3)

FIG. 5 shows SEQ ID No. 5 which is a DNA sequence of the gene COG4 (Table 1, No. 4)

FIG. 6 shows SEQ ID No. 6 which is a DNA sequence of the gene COG4 (Table 1, No. 4)

FIG. 7 shows SEQ ID No. 7 which is a DNA sequence of the gene COG4 (Table 1, No. 4)

FIG. 8 shows SEQ ID No. 8 which is a DNA sequence of the gene COG4 (Table 1, No. 4)

FIG. 9 shows SEQ ID No. 9 which is a DNA sequence of the gene FDFT1 (Table 1, No. 5)

FIG. 10 shows SEQ ID No. 10 which is a DNA sequence of the gene PECI (Table 1, No. 6)

FIG. 11 shows SEQ ID No. 11 which is a DNA sequence of the gene PECI (Table 1, No. 6)

FIG. 12 shows SEQ ID No. 12 which is a DNA sequence of the gene PECI (Table 1, No. 6)

FIG. 13 shows SEQ ID No. 13 which is a DNA sequence of the gene PECI (Table 1, No. 6)

FIG. 14 shows SEQ ID No. 14 which is a DNA sequence of the gene PECI (Table 1, No. 6)

FIG. 15 shows SEQ ID No. 15 which is a DNA sequence of the gene CTNND2 (Table 1, No. 7)

FIG. 16 shows SEQ ID No. 16 which is a DNA sequence of the gene CTNND2 (Table 1, No. 7)

FIG. 17 shows SEQ ID No. 17 which is a DNA sequence of the gene NSMCE1 (Table 1, No. 8)

FIG. 18 shows SEQ ID No. 18 which is a DNA sequence of the gene NSMCE1 (Table 1, No. 8)

FIG. 19 shows SEQ ID No. 19 which is a DNA sequence of the gene NSMCE1 (Table 1, No. 8)

FIG. 20 shows SEQ ID No. 20 which is a DNA sequence of the gene KTELC1 (Table 1, No. 9)

FIG. 21 shows SEQ ID No. 21 which is a DNA sequence of the gene HS6ST1 (Table 1, No. 10)

FIG. 22 shows SEQ ID No. 22 which is a DNA sequence of the gene ARMC6 (Table 1, No. 11)

FIG. 23 shows SEQ ID No. 23 which is a DNA sequence of the gene ARMC6 (Table 1, No. 11)

FIG. 24 shows SEQ ID No. 24 which is a DNA sequence of the gene ARMC6 (Table 1, No. 11)

FIG. 25 shows SEQ ID No. 25 which is a DNA sequence of the gene ARMC6 (Table 1, No. 11)

FIG. 26 shows SEQ ID No. 26 which is a DNA sequence of the gene TH1L (Table 1, No. 12)

FIG. 27 shows SEQ ID No. 27 which is a DNA sequence of the gene PSME1 (Table 1, No. 13)

FIG. 28 shows SEQ ID No. 28 which is a DNA sequence of the gene PSME1 (Table 1, No. 13)

FIG. 29 shows SEQ ID No. 29 which is a DNA sequence of the gene GPC1 (Table 1, No. 14)

FIG. 30 shows SEQ ID No. 30 which is a DNA sequence of the gene EDC4 (Table 1, No. 15)

FIG. 31 shows SEQ ID No. 31 which is a DNA sequence of the gene EDC4 (Table 1, No. 15)

FIG. 32 shows SEQ ID No. 32 which is a DNA sequence of the gene PRC1 (Table 1, No. 16)

FIG. 33 shows SEQ ID No. 33 which is a DNA sequence of the gene PRC1 (Table 1, No. 16)

FIG. 34 shows SEQ ID No. 34 which is a DNA sequence of the gene PRC1 (Table 1, No. 16)

FIG. 35 shows SEQ ID No. 35 which is a DNA sequence of the gene NAT6 (Table 1, No. 17)

FIG. 36 shows SEQ ID No. 36 which is a DNA sequence of the gene NAT6 (Table 1, No. 17)

FIG. 37 shows SEQ ID No. 37 which is a DNA sequence of the gene NAT6 (Table 1, No. 17)

FIG. 38 shows SEQ ID No. 38 which is a DNA sequence of the gene EEF1AL3 (Table 1, No. 18)

FIG. 39 shows SEQ ID No. 39 which is a DNA sequence of the gene NP_612480.1 (Table 1, No. 19)

FIG. 40 shows SEQ ID No. 40 which is a DNA sequence of the gene PLXNA2 (Table 1, No. 20)

FIG. 41 shows SEQ ID No. 41 which is a DNA sequence of the gene PLXNA2 (Table 1, No. 20)

FIG. 42 shows SEQ ID No. 42 which is a DNA sequence of the gene ELMO2 (Table 1, No. 21)

FIG. 43 shows SEQ ID No. 43 which is a DNA sequence of the gene ELMO2 (Table 1, No. 21)

FIG. 44 shows SEQ ID No. 44 which is a DNA sequence of the gene ELMO2 (Table 1, No. 21)

FIG. 45 shows SEQ ID No. 45 which is a DNA sequence of the gene ELMO2 (Table 1, No. 21)

FIG. 46 shows SEQ ID No. 46 which is a DNA sequence of the gene NDUFS2 (Table 1, No. 22)

FIG. 47 shows SEQ ID No. 47 which is a DNA sequence of the gene NDUFS2 (Table 1, No. 22)

FIG. 48 shows SEQ ID No. 48 which is a DNA sequence of the gene IRAK1 (Table 1, No. 23)

FIG. 49 shows SEQ ID No. 49 which is a DNA sequence of the gene IRAK1 (Table 1, No. 23)

FIG. 50 shows SEQ ID No. 50 which is a DNA sequence of the gene IRAK1 (Table 1, No. 23)

FIG. 51 shows SEQ ID No. 51 which is a DNA sequence of the gene IRAK1 (Table 1, No. 23)

FIG. 52 shows SEQ ID No. 52 which is a DNA sequence of the gene IRAK1 (Table 1, No. 23)

FIG. 53 shows SEQ ID No. 53 which is a DNA sequence of the gene C20orf149 (Table 1, No. 24)

FIG. 54 shows SEQ ID No. 54 which is a DNA sequence of the gene C20orf149 (Table 1, No. 24)

FIG. 55 shows SEQ ID No. 55 which is a DNA sequence of the gene C20orf149 (Table 1, No. 24)

FIG. 56 shows SEQ ID No. 56 which is a DNA sequence of the gene PCSD2L (Table 1, No. 25)

FIG. 57 shows SEQ ID No. 57 which is a DNA sequence of the gene PCSD2L (Table 1, No. 25)

FIG. 58 shows SEQ ID No. 58 which is a DNA sequence of the gene PPIA (Table 1, No. 26)

FIG. 59 shows SEQ ID No. 59 which is a Protein sequence of the gene RAB11B (Table 1, No. 1)

FIG. 60 shows SEQ ID No. 60 which is a Protein sequence of the gene PPP2R1A (Table 1, No. 2)

FIG. 61 shows SEQ ID No. 61 which is a Protein sequence of the gene PPP2R1A (Table 1, No. 2)

FIG. 62 shows SEQ ID No. 62 which is a Protein sequence of the gene KPNB1 (Table 1, No. 3)

FIG. 64 shows SEQ ID No. 64 which is a Protein sequence of the gene COG4 (Table 1, No. 4)

FIG. 65 shows SEQ ID No. 65 which is a Protein sequence of the gene COG4 (Table 1, No. 4)

FIG. 66 shows SEQ ID No. 66 which is a Protein sequence of the gene COG4 (Table 1, No. 4)

FIG. 67 shows SEQ ID No. 67 which is a Protein sequence of the gene COG4 (Table 1, No. 4)

FIG. 68 shows SEQ ID No. 68 which is a Protein sequence of the gene FDFT1 (Table 1, No. 5)

FIG. 69 shows SEQ ID No. 69 which is a Protein sequence of the gene PECI (Table 1, No. 6)

FIG. 70 shows SEQ ID No. 70 which is a Protein sequence of the gene PECI (Table 1, No. 6)

FIG. 71 shows SEQ ID No. 71 which is a Protein sequence of the gene PECI (Table 1, No. 6)

FIG. 72 shows SEQ ID No. 72 which is a Protein sequence of the gene PECI (Table 1, No. 6)

FIG. 73 shows SEQ ID No. 73 which is a Protein sequence of the gene PECI (Table 1, No. 6)

FIG. 74 shows SEQ ID No. 74 which is a Protein sequence of the gene CTNND2 (Table 1, No. 7)

FIG. 75 shows SEQ ID No. 75 which is a Protein sequence of the gene CTNND2 (Table 1, No. 7)

FIG. 76 shows SEQ ID No. 76 which is a Protein sequence of the gene NSMCE1 (Table 1, No. 8)

FIG. 77 shows SEQ ID No. 77 which is a Protein sequence of the gene NSMCE1 (Table 1, No. 8)

FIG. 78 shows SEQ ID No. 78 which is a Protein sequence of the gene NSMCE1 (Table 1, No. 8)

FIG. 79 shows SEQ ID No. 79 which is a Protein sequence of the gene KTELC1 (Table 1, No. 9)

FIG. 80 shows SEQ ID No. 80 which is a Protein sequence of the gene HS6ST1 (Table 1, No. 10)

FIG. 81 shows SEQ ID No. 81 which is a Protein sequence of the gene ARMC6 (Table 1, No. 11)

FIG. 82 shows SEQ ID No. 82 which is a Protein sequence of the gene ARMC6 (Table 1, No. 11)

FIG. 83 shows SEQ ID No. 83 which is a Protein sequence of the gene ARMC6 (Table 1, No. 11)

FIG. 84 shows SEQ ID No. 84 which is a Protein sequence of the gene ARMC6 (Table 1, No. 11)

FIG. 85 shows SEQ ID No. 85 which is a Protein sequence of the gene TH1L (Table 1, No. 12)

FIG. 86 shows SEQ ID No. 86 which is a Protein sequence of the gene PSME1 (Table 1, No. 13)

FIG. 87 shows SEQ ID No. 87 which is a Protein sequence of the gene PSME1 (Table 1, No. 13)

FIG. 88 shows SEQ ID No. 88 which is a Protein sequence of the gene GPC1 (Table 1, No. 14)

FIG. 89 shows SEQ ID No. 89 which is a Protein sequence of the gene EDC4 (Table 1, No. 15)

FIG. 90 shows SEQ ID No. 90 which is a Protein sequence of the gene EDC4 (Table 1, No. 15)

FIG. 91 shows SEQ ID No. 91 which is a Protein sequence of the gene PRC1 (Table 1, No. 16)

FIG. 92 shows SEQ ID No. 92 which is a Protein sequence of the gene PRC1 (Table 1, No. 16)

FIG. 93 shows SEQ ID No. 93 which is a Protein sequence of the gene PRC1 (Table 1, No. 16)

FIG. 94 shows SEQ ID No. 94 which is a Protein sequence of the gene NAT6 (Table 1, No. 17)

FIG. 95 shows SEQ ID No. 95 which is a Protein sequence of the gene NAT6 (Table 1, No. 17)

FIG. 96 shows SEQ ID No. 96 which is a Protein sequence of the gene NAT6 (Table 1, No. 17)

FIG. 97 shows SEQ ID No. 97 which is a Protein sequence of the gene EEF1AL3 (Table 1, No. 18)

FIG. 98 shows SEQ ID No. 98 which is a Protein sequence of the gene NP_612480.1 (Table 1, No. 19)

FIG. 99 shows SEQ ID No. 99 which is a Protein sequence of the gene PLXNA2 (Table 1, No. 20)

FIG. 100 shows SEQ ID No. 100 which is a Protein sequence of the gene PLXNA2 (Table 1, No. 20)

FIG. 101 shows SEQ ID No. 101 which is a Protein sequence of the gene ELMO2 (Table 1, No. 21)

FIG. 102 shows SEQ ID No. 102 which is a Protein sequence of the gene ELMO2 (Table 1, No. 21)

FIG. 103 shows SEQ ID No. 103 which is a Protein sequence of the gene ELMO2 (Table 1, No. 21)

FIG. 104 shows SEQ ID No. 104 which is a Protein sequence of the gene ELMO2 (Table 1, No. 21)

FIG. 105 shows SEQ ID No. 105 which is a Protein sequence of the gene NDUFS2 (Table 1, No. 22)

FIG. 106 shows SEQ ID No. 106 which is a Protein sequence of the gene NDUFS2 (Table 1, No. 22)

FIG. 107 shows SEQ ID No. 107 which is a Protein sequence of the gene IRAK1 (Table 1, No. 23)

FIG. 108 shows SEQ ID No. 108 which is a Protein sequence of the gene IRAK1 (Table 1, No. 23)

FIG. 109 shows SEQ ID No. 109 which is a Protein sequence of the gene IRAK1 (Table 1, No. 23)

FIG. 110 shows SEQ ID No. 110 which is a Protein sequence of the gene IRAK1 (Table 1, No. 23)

FIG. 111 shows SEQ ID No. 111 which is a Protein sequence of the gene IRAK1 (Table 1, No. 23)

FIG. 112 shows SEQ ID No. 112 which is a Protein sequence of the gene C20orf149 (Table 1, No. 24)

FIG. 113 shows SEQ ID No. 113 which is a Protein sequence of the gene C20orf149 (Table 1, No. 24)

FIG. 114 shows SEQ ID No. 114 which is a Protein sequence of the gene C20orf149 (Table 1, No. 24)

FIG. 115 shows SEQ ID No. 115 which is a Protein sequence of the gene PCSD2L (Table 1, No. 25)

FIG. 116 shows SEQ ID No. 116 which is a Protein sequence of the gene PCSD2L (Table 1, No. 25)

FIG. 117 shows SEQ ID No. 117 which is a Protein sequence of the gene PPIA (Table 1, No. 26)

FIG. 118 shows SEQ ID No. 118 which is a Protein sequence derived from an incorrect reading frame of the gene HS6ST1 (Table 1, No. 10)

FIG. 119 shows SEQ ID No. 119 which is a Protein sequence derived from an incorrect reading frame of the gene IRAK1 (Table 1, No. 23)

FIG. 120 shows SEQ ID No. 120 which is a Protein sequence derived from an incorrect reading frame of the gene C20orf149 (Table 1, No. 24)

FIG. 121 shows SEQ ID No. 121 which is a Protein sequence derived from an incorrect reading frame of the gene C20orf149 (Table 1, No. 24)

FIG. 122 shows SEQ ID No. 122 which is a Protein sequence derived from an incorrect reading frame of the gene HS6SP1 (Table 1, No. 10)

EXAMPLES

The set of proteins which are subject of the present invention have been found by conducting serum screening experiments on protein macroarrays. The protein macroarrays consist of >38.000 individual *E. coli* clones expressing human gene fragments cloned from a foetal brain cDNA library. These fragments can be full length proteins and fragments thereof, as well as artificial peptides resulting from translation products in the incorrect reading frame. The technology for screening was developed at the MPI for Molecular Genetics and constitutes prior art; Büssow K, et al. Nucleic Acids Res. 1998 Nov. 1; 26(20:5007-8. PMID: 9776767; Büssow K, et al. Genomics 2000 Apr. 1; 65(1):1-8. PMID: 10777659) and has been applied since then in multiple scientific publications (e.g. Horn S, et al. Proteomics. 2006 January; 6(2):605-13. PMID: 16419013; Lueking A, et al. Mol Cell Proteomics. 2005 September; 4(9):1382-90. PMID: 15939964). The only amendment to the method described in the original paper is the incubation with patient serum and the use of specific secondary antibodies directed against different immunoglobulin isotypes such as IgG, IgA, IgM and IgD as described beneath:

Patient serum was diluted 1:40 in blocking buffer (3% Milk powder/TBST) and incubated overnight at room temperature, kept in slow motion on an orbital shaker. After incubation filters are washed 3×20 min. in TBST, followed by a second incubation for 1 h at room temperature with anti human IgG or anti human IgA secondary antibody (mouse) conjugated with alkaline phosphatase, 1:1000 in blocking buffer. Positive signals on the macroarray (PVDF filter) were recorded as described and correlated to the original *E. coli* clones stored in 384-well microtitre plates. *E. coli* clones corresponding with the signals on the macroarray were sequenced to obtain information of the insert, and hence the gene fragment of which the translation product is recognised by the patient sera. These fragments can be full length proteins and fragments thereof, as well as artificial peptides resulting from out-of frame-translation products.

The protein macroarrays were screened with pools of anti-TNFα treatment (Adalimumab®; Humira) responder and non-responder patient sera before and after therapy. Responder and non-responder patients were categorised according to the clinical response evaluated after 1 year (or at drop-out) in accordance with the European League Against Rheumatism criteria using the modified disease activity score that includes 28 joints (DAS 28). The DAS28 score and the European League Against Rheumatism (EULAR) response criteria are widely used to record disease activity and therapeutic response in patients with RA (Van Gestel A M et al. Arthritis Rheum 1996; 39:34-40. PMID:

The DAS28 was developed and validated for patients with RA, and in addition to disease activity it also reflects the patient's satisfaction with reasonable accuracy. This composite index comprises 4 items, namely, swollen joint count (SJC), tender joint count (TJC), a visual analog scale (VAS) of the patient's assessment of general health (GH), and erythrocyte sedimentation rate (ESR; first hour), which are also part of the American College of Rheumatology (ACR) response criteria.

Description of the Used Patient Sera:

DAS28 values from 2 RA patient cohorts comprising 3 patients each were compared and sera of these patients before and after therapy were used for screening the protein macroarrays. RA cohort 1 (RA1) consisted of therapy responder patients and the RA cohort 2 (RA2) consisted of of age- and sex-matched patients seen during the same period who were therapy non-responders. Item weighting, factor loading, and internal consistency were assessed by factor analysis, principal component analysis, and calculation of Cronbach's alpha. The range of DAS 28 scores in the responder group initially before treatment was from 4.4-6 with a mean value of 4.83 and in the non responder group 4.1-8.6 with a mean value 6.2. Responder had a mean change of 2.36 during therapy while there was no mean change in the DAS28 in the non responder group.

Table 1 (consisting of Table 1 A and Table 1 B) shows a summary list of genes of which the expression products represent biomarker proteins and artificial peptides resulting from translation products in the incorrect reading frame found to be predictive for responsiveness to anti-TNFα antibody treatment (Adalimumab; Humira) of the patient groups described above having been subjected to an anti-TNFα treatment.

TABLE 1 A

List of candidate genes encoding a biomarker set detected by immunoglobulins of TNF inhibitor therapy NON-RESPONDER patients

| No. | Importance | frame offset | ENSEMBL gene identifier | HGNC gene symbol | gene description and alternative identifiers |
|---|---|---|---|---|---|
| 1 | 1: High | 0 | ENSG00000185236 | RAB11B | Ras-related protein Rab-11B (GTP-binding protein YPT3). [Source: Uniprot/SWISSPROT; Acc: Q15907] |
| 2 | 1: High | 0 | ENSG00000105568 | PPP2R1A | Serine/threonine-protein phosphatase 2A 65 kDa regulatory subunit A alpha isoform (PP2A, subunit A, PR65-alpha isoform) (PP2A, subunit A, R1-alpha isoform) (Medium tumor antigen-associated 61 kDa protein). [Source: Uniprot/SWISSPROT; Acc: P30153] |
| 3 | 1: High | 0 | ENSG00000108424 | KPNB1 | Importin beta-1 subunit (Karyopherin beta-1 subunit) (Nuclear factor P97) (Importin 90). [Source: Uniprot/SWISSPROT; Acc: Q14974] |
| 4 | 1: High | 0 | ENSG00000103051 | COG4 | Conserved oligomeric Golgi complex component 4. [Source: Uniprot/SWISSPROT; Acc: Q9H9E3] |
| 5 | 1: High | 0 | ENSG00000079459 | FDFT1 | Squalene synthetase (EC 2.5.1.21) (SQS) (SS) (Farnesyl-diphosphate farnesyltransferase) (FPP:FPP farnesyltransferase). [Source: Uniprot/SWISSPROT; Acc: P37268] |
| 6 | 2: Medium | 0 | ENSG00000198721 | PECI | Peroxisomal 3,2-trans-enoyl-CoA isomerase (EC 5.3.3.8) (Dodecenoyl-CoA isomerase) (Delta(3),delta(2)-enoyl-CoA isomerase) (D3,D2-enoyl-CoA isomerase) (DBI-related protein 1) (DRS-1) (Hepatocellular carcinoma-associated antigen 88) (Renal carcinoma antige |
| 7 | 2: Medium | 0 | ENSG00000169862 | CTNND2 | Catenin delta-2 (Delta-catenin) (Neural plakophilin-related ARM-repeat protein) (NPRAP) (Neurojungin) (GT24). [Source: Uniprot/SWISSPROT; Acc: Q9UQB3] chromosome NCBI36:5:11024952-11957110:-1 |
| 8 | 2: Medium | 0 | ENSG00000169189 | NSMCE1 | non-SMC element 1 homolog [Source: RefSeq_peptide; Acc: NP_659547] chromosome_NCBI36:16:27143817-27187586:-1 |
| 9 | 2: Medium | 0 | ENSG00000163389 | KTELC1 | KTEL motif-containing protein 1 precursor (CAP10-like 46 kDa protein) (Myelodysplastic syndromes relative protein). [Source: Uniprot/SWISSPROT; Acc: Q8NBL1] |
| 10 | 2: Medium | -1 | ENSG00000136720 | HS6ST1 | Heparan-sulfate 6-O-sulfotransferase 1 (EC 2.8.2.—) (HS6ST-1). [Source: Uniprot/SWISSPROT; Acc: O60243] |
| 11 | 2: Medium | 0 | ENSG00000105676 | ARMC6 | Armadillo repeat-containing protein 6. [Source: Uniprot/SWISSPROT; Acc: Q6NXE6]chromosome_NCBI36:19:19005538-19029985:1 |
| 12 | 2: Medium | 0 | ENSG00000101158 | TH1L | Negative elongation factor C/D (NELF-C/D) (TH1-like protein). [Source: Uniprot/SWISSPROT; Acc: Q8IXH7] |
| 13 | 2: Medium | 0 | ENSG00000092010 | PSME1 | Proteasome activator complex subunit 1 (Proteasome activator 28-alpha subunit) (PA28alpha) (PA28a) (Activator of multicatalytic protease subunit 1) (11S regulator complex subunit alpha) (REG-alpha) (Interferon gamma up-regulated I-5111 protein) (IGUP I-51 |
| 14 | 2: Medium | 0 | ENSG00000063660 | GPC1 | Glypican-1 precursor. [Source: Uniprot/SWISSPROT; Acc: P35052] |
| 15 | 2: Medium | 0 | ENSG00000038358 | EDC4 | autoantigen RCD8 [Source: RefSeq_peptide; Acc: NP_055144] chromosome_NCBI36:16:66464500-66475906:1 |
| 16 | 3: Low | 0 | ENSG00000198901 | PRC1 | Protein regulator of cytokinesis 1. [Source: Uniprot/SWISSPROT; Acc: O43663] chromosome_NCBI36:15:89310279-89338808:-1 |
| 17 | 3: Low | 0 | ENSG00000186792 | NAT6 | Hyaluronidase-3 precursor (EC 3.2.1.35) (Hyal-3) (Hyaluronoglucosaminidase-3) (LUCA-3). [Source: Uniprot/SWISSPROT; Acc: O43820] chromosome_NCBI36:3:50300178-50311903:-1 |
| 18 | 3: Low | 0 | ENSG00000185637 | EEF1AL3 | Eukaryotic translation elongation factor 1 alpha 1 (Fragment). [Source: Uniprot/SPTREMBL; Acc: Q5JR01] chromosome_NCBI36:9:134884631-134886374:1 |
| 19 | 3: Low | 0 | ENSG00000168005 | NP_612480.1 | chromosome_NCBI36:11:63337436-63351727:1 |
| 20 | 3: Low | 0 | ENSG00000076356 | PLXNA2 | Plexin-A2 precursor (Semaphorin receptor OCT). [Source: Uniprot/SWISSPROT; Acc: O75051] chromosome_NCBI36:1:206262210-206484288:-1 |

TABLE 1 A-continued

List of candidate genes encoding a biomarker set detected by immunoglobulins of TNF inhibitor therapy NON-RESPONDER patients

| No. | Importance | frame offset | ENSEMBL gene identifier | HGNC gene symbol | gene description and alternative identifiers |
|---|---|---|---|---|---|
| 21 | 3: Low | 0 | ENSG00000062598 | ELMO2 | Engulfment and cell motility protein 2 (CED-12 homolog A) (hCED-12A). [Source: Uniprot/SWISSPROT; Acc: Q96JJ3] chromosome_NCBI36:20:44428096-44468678:-1 |
| 22 | 3: Low | 0 | ENSG00000158864 | NDUFS2 | NADH-ubiquinone oxidoreductase 49 kDa subunit, mitochondrial precursor (EC 1.6.5.3) (EC 1.6.99.3) (Complex I-49 KD) (CI-49 KD). [Source: Uniprot/SWISSPROT; Acc: O75306] |

TABLE 1 B

List of candidate genes encoding a biomarker set detected by immunoglobulins of TNF inhibitor therapy RESPONDER patients

| No. | Importance | frame offset | ENSEMBL identifier | HGNC gene symbol | gene description and alternative identifiers |
|---|---|---|---|---|---|
| 23 | 1: High | -1 | ENSG00000184216 | IRAK1 | Interleukin-1 receptor-associated kinase 1 (EC 2.7.11.1) (IRAK-1). [Source: Uniprot/SWISSPROT; Acc: P51617] |
| 24 | 1: High | -1 | ENSG00000125534 | C20orf149 | UPF0362 protein C20orf149. [Source: Uniprot/SWISSPROT; Acc: Q9H3Y8] |
| 25 | 2: Medium | 0 | ENSG00000105443 | PSCD2L | Cytohesin-2 (ARF nucleotide-binding site opener) (ARNO protein) (ARF exchange factor). [Source: Uniprot/SWISSPROT; Acc: Q99418] chromosome_NCBI36:19:53664424-53674457:1 |
| 26 | 3: Low | 0 | ENSG00000198618 | PPIA | Peptidyl-prolyl cis-trans isomerase A (EC 5.2.1.8) (PPIase A) (Rotamase A) (Cyclophilin A) (Cyclosporin A-binding protein). [Source: Uniprot/SWISSPROT; Acc: P62937] chromosome_NCBI36:21:19151917-19152651:1 |

The invention claimed is:

1. A method for diagnosing whether an individual suffering from rheumatoid arthritis will be non-responsive to anti-TNFα treatment, comprising:
   (i) obtaining a biological sample from the individual;
   (ii) providing a surface comprising one or more biomarker proteins, wherein the biomarker protein(s) comprises one or more sequences selected from the group consisting of SEQ ID NO. 59, SEQ ID NO. 60, SEQ ID NO. 61, SEQ ID NO. 62, SEQ ID NO. 63, SEQ ID NO. 64, SEQ ID NO. 65, SEQ ID NO. 66, SEQ ID NO. 67, and SEQ ID NO. 68 attached to said surface;
   (iii) incubating said surface with said biological sample;
   (iv) washing the product of step (iii), and incubating with an antibody that binds the IgA isotype;
   (v) wherein the presence of IgA isotype immunoglobulin(s) that bind to one or more of said biomarker proteins classifies the individual as a NON-Responder to anti-TNFα treatment.

2. The method of claim 1, wherein the biomarker protein group additionally comprises at least one other expression product encoded by a gene selected from the group comprising PECI, CTNND2, NSMCE1, KTELC1, HS6ST1, ARMC6, TH1L, PSME1, GPC1, EDC4, PRC1, NAT6, EEF1AL3, NP_612480.1, PLXNA2, ELMO2 and NDUFS2; wherein the biomarker protein comprises the sequence selected from the group consisting of SEQ ID NO. 69 to SEQ ID NO. 79, SEQ ID NO. 81 to SEQ ID NO. 106, and SEQ ID NO. 118.

3. The method of claim 1, wherein the biological sample is selected from the group consisting of blood, saliva, tears, synovial fluid, spinal fluid, plasma, urine, and stool.

4. The method of claim 1, further comprising treating an individual classified as a NON-responder with therapy that does not include anti-TNFα treatment.

5. The method of claim 1, further comprising treating an individual not classified as a NON-responder with therapy that does include anti-TNFα treatment.

* * * * *

SEQUENCE LISTING

<160> NUMBER OF SEQ ID NOS: 122

<210> SEQ ID NO 1
<211> LENGTH: 657
<212> TYPE: DNA
<213> ORGANISM: Human

<400> SEQUENCE: 1

```
atggggaccc gggacgacga gtacgactac ctattcaaag tggtgctcat cggggactca      60
ggcgtgggca agagcaacct gctgtcgcgc ttcacccgca acgagttcaa cctggagagc     120
aagagcacca tcggcgtgga gttcgccacc cgcagcatcc aggtggacgg caagaccatc     180
aaggcgcaga tctgggacac cgctggccag gagcgctacc gcgccatcac ctccgcgtac     240
taccgtggtg cagtgggcgc cctgctggtg tacgacatcg ccaagcacct gacctatgag     300
aacgtggagc gctggctgaa ggagctgcgg gaccacgcag acagcaacat cgtcatcatg     360
ctggtgggca acaagagtga cctgcgccac ctgcgggctg tgcccactga cgaggcccgc     420
gccttcgcag aaaagaacaa cttgtccttc atcgagacct cagccttgga ttccactaac     480
gtagaggaag cattcaagaa catcctcaca gagatctacc gcatcgtgtc acagaaacag     540
atcgcagacc gcgctgccca cgacgagtcc ccggggaaca acgtggtgga catcagcgtg     600
ccgcccacca cggacggaca gaagcccaac aagctgcagt gctgccagaa cctgtga       657
```

<210> SEQ ID NO 2
<211> LENGTH: 1530
<212> TYPE: DNA
<213> ORGANISM: Human

<400> SEQUENCE: 2

```
atgaggacgt tcagcttcgc ctcaacagca tcaagaagct gtccaccatc gccttggccc    60
ttggggttga aaggacccga agtgagcttc tgcctttcct tacagatacc atctatgatg   120
aagatgaggt cctcctggcc ctggcagaac agctgggaac cttcactacc ctggtgggag   180
gcccagagta cgtgcactgc ctgctgcctc ttctccgtct gctaccccg agtgtccagt    240
gctgtgaagg cggaacttcg acagtacttc cggaacctgt gctcagatga caccccatg    300
gtgcggcggg ccgcagcctc caagctgggg gagtttgcca aggtgctgga gctggacaac   360
gtcaagagtg agatcatccc catgttctcc aacctggcct ctgacgagca ggactcggtg   420
cggctgctgg cggtggaggc gtgcgtgaac atcgcccagc ttctgcccca ggaggatctg   480
gaggccctgg tgatgcccac tctgcgccag gccgctgaag acaagtcctg gcgcgtccgc   540
tacatggtgg ctgacaagtt cacagagctc cagaaagcag tggggcctga gatcaccaag   600
acagacctgg tccctgcctt ccagaacctg atgaaagact gtgaggccga ggtgagggcc   660
gcagcctccc acaaggtcaa agagttctgt gaaaacctct cagctgactg tcggagaat   720
gtgatcatgt cccagatctt gccctgcatc aaggagctgg tgtccgatgc caaccaacat   780
gtcaagtctg ccctggcctc agtcatcatg ggtctctctc ccatcttggg caaagacaac   840
accatcgagc acctcttgcc cctcttcctg gctcagctga aggatgagtg ccctgaggta   900
cggctgaaca tcatctctaa cctggactgt gtgaacgagg tgattggcat ccggcagctg   960
tcccagtccc tgctccctgc cattgtggag ctggctgagg acgccaagtg gcgggtgcgg  1020
ctggccatca ttgagtacat gcccctcctg gctggacagc tgggagtgga gttctttgat  1080
gagaaactta actccttgtg catggcctgg cttgtggatc atgtatatgc catccgcgag  1140
gcagccacca gcaacctgaa gaagctagtg aaaagtttg gaaggagtg ggcccatgcc    1200
acaatcatcc caaggtcttt ggccatgtcc ggagaccca actacctgca ccgcatgact   1260
acgctcttct gcatcaatgt gctgtctgag gtctgtgggc aggacatcac caccaagcac  1320
atgctaccca cggttctgcg catggctggg gacccggttg ccaatgtccg cttcaatgtg  1380
gccaagtctc tgcagaagat agggcccatc ctggacaaca gcaccttgca gagtgaagtc  1440
aagcccatcc tagagaagct gacccaggac caggatgtgg acgtcaaata ctttgcccag  1500
gaggctctga ctgttctgtc tctcgcctga                                   1530
```

<210> SEQ ID NO 3
<211> LENGTH: 1770
<212> TYPE: DNA
<213> ORGANISM: Human

<400> SEQUENCE: 3

```
atggcggcgg ccgacggcga cgactcgctg taccccatcg cggtgctcat agacgaactc    60
cgcaatgagg acgttcagct tcgcctcaac agcatcaaga agctgtccac catcgccttg   120
gcccttgggg ttgaaaggac ccgaagtgag cttctgcctt ccttacagat accatctat   180
gatgaagatg aggtcctcct ggccctggca gaacagctgg gaaccttcac taccctggtg   240
ggaggcccag agtacgtgca ctgcctgctg ccaccgctgg agtcgctggc cacagtggag   300
gagacagtgt gcgggacaa gcagtggag tccttacggg ccatctcaca cgagcactcg    360
ccctctgacc tggaggcgca ctttgtgccg ctagtgaagc ggctggcggg cggcgactgg   420
ttcacctccc gcacctcggc ctgcggcctc ttctccgtct gctaccccg agtgtccagt    480
gctgtgaagg cggaacttcg acagtacttc cggaacctgt gctcagatga caccccatg    540
gtgcggcggg ccgcagcctc caagctgggg gagtttgcca aggtgctgga gctggacaac   600
```

```
gtcaagagtg agatcatccc catgttctcc aacctggcct ctgacgagca ggactcggtg    660
cggctgctgg cggtggaggc gtgcgtgaac atcgcccagc ttctgcccca ggaggatctg    720
gaggccctgg tgatgcccac tctgcgccag gccgctgaag acaagtcctg gcgcgtccgc    780
tacatggtgg ctgacaagtt cacagagctc cagaaagcag tggggcctga gatcaccaag    840
acagacctgg tccctgcctt ccagaacctg atgaaagact gtgaggccga ggtgagggcc    900
gcagcctccc acaaggtcaa agagttctgt gaaaacctct cagctgactg tcggagaat    960 gtgatcatgt cccagatctt gccctgcatc aaggagctgg tgtccgatgc aaccaacat    1020 gtcaagtctg ccctggcctc agtcatcatg ggtctctctc ccatcttggg caaagacaac    1080
accatcgagc acctcttgcc cctcttcctg gctcagctga aggatgagtg ccctgaggta    1140
cggctgaaca tcatctctaa cctggactgt gtgaacgagg tgattggcat ccggcagctg    1200
tcccagtccc tgctccctgc cattgtggag ctggctgagg acgccaagtg gcgggtgcgg    1260
ctggccatca ttgagtacat gcccctcctg gctggacagc tgggagtgga gttctttgat    1320
gagaaactta actccttgtg catggcctgg cttgtggatc atgtatatgc catccgcgag    1380
gcagccacca gcaacctgaa gaagctagtg aaaagtttg gaaggagtg ggcccatgcc    1440 acaatcatcc ccaaggtctt ggccatgtcc ggagaccca actacctgca ccgcatgact    1500
acgctcttct gcatcaatgt gctgtctgag gtctgtgggc aggacatcac caccaagcac    1560
atgctaccca cggttctgcg catggctggg gacccggttg ccaatgtccg cttcaatgtg    1620
gccaagtctc tgcagaagat agggcccatc ctggacaaca gcaccttgca gagtgaagtc    1680
aagcccatcc tagagaagct gacccaggac caggatgtgg acgtcaaata ctttgcccag    1740
gaggctctga ctgttctgtc tctcgcctga                                    1770
```

<210> SEQ ID NO 4
<211> LENGTH: 2631
<212> TYPE: DNA
<213> ORGANISM: Human

<400> SEQUENCE: 4

```
atggagctga tcaccattct cgagaagacc gtgtctcccg atcggctgga gctggaagcg     60
gcgcagaagt tcctggagcg tgcggccgtg gagaacctgc ccactttcct tgtggaactg    120
tccagagtgc tggcaaatcc aggaaacagt caggttgcca gagttgcagc tggtctacaa    180
atcaagaact cttttgacat ctaaagatcca gatatcaagg cacaatatca gcagaggtgg    240
cttgctattg atgctaatgc tcgacgagaa gtcaagaact atgttttgca gacattgggt    300
acagaaactt accggcctag ttctgcctca cagtgtgtgg ctggtattgc ttgtgcagag    360
atcccagtaa accagtggcc agaactcatt cctcagctgg tggccaatgt cacaaacccc    420
aacagcacag agcacatgaa ggagtcgaca ttggaagcca tcggttatat ttgccaagat    480
atagacccag agcagctaca agataaatcc aatgagattc tgactgccat aatccagggg    540
atgaggaaag aagagcctag taataatgtg aagctagctg ctacgaatgc actcctgaac    600
tcattggagt tcaccaaagc aaactttgat aaagagtctg aaaggcactt tattatgcag    660
gtggtctgtg aagccacaca gtgtccagat acgagggtac gagtggctgc tttacagaat    720
ctggtgaaga taatgtcctt atattatcag tacatggaga catatatggg tcctgctctt    780
tttgcaatca caatcgaagc aatgaaaagt gacattgatg aggtggcttt acaagggata    840
gaattctggt ccaatgtctg tgatgaggaa atggatttgg ccattgaagc ttcagaggca    900
```

| | |
|---|---|
| gcagaacaag gacggccccc tgagcacacc agcaagtttt atgcgaaggg agcactacag | 960 |
| tatctggttc caatcctcac acagacacta actaaacagg acgaaaatga tgatgacgat | 1020 |
| gactggaacc cctgcaaagc agcaggggtg tgcctcatgc ttctggccac ctgctgtgaa | 1080 |
| gatgacattg tcccacatgt cctccccttc attaaagaac acatcaagaa cccagattgg | 1140 |
| cggtaccggg atgcagcagt gatggctttt ggttgtatct tggaaggacc agagcccagt | 1200 |
| cagctcaaac cactagttat acaggctatg cccacccctaa tagaattaat gaaagacccc | 1260 |
| agtgtagttg ttcgagatac agctgcatgg actgtaggca gaatttgtga gctgcttcct | 1320 |
| gaagctgcca tcaatgatgt ctacttggct cccctgctac agtgtctgat tgagggtctc | 1380 |
| agtgctgaac ccagagtggc ttcaaatgtg tgctgggctt tctccagtct ggctgaagct | 1440 |
| gcttatgaag ctgcagacgt tgctgatgat caggaagaac cagctactta ctgcttatct | 1500 |
| tcttcatttg aactcatagt tcagaagctc ctagagacta cagacagacc tgatggacac | 1560 |
| cagaacaacc tgaggagttc tgcatatgaa tctctgatgg aaattgtgaa aaacagtgcc | 1620 |
| aaggattgtt atcctgctgt ccagaaaacg actttggtca tcatgaacg actgcaacag | 1680 |
| gttcttcaga tggagtcaca tatccagagc acatccgata aatccagtt caatgacctt | 1740 |
| cagtctttac tctgtgcaac tcttcagaat gttcttcgga agtgcaaca tcaagatgct | 1800 |
| ttgcagatct ctgatgtggt tatggcctcc ctgttaagga tgttccaaag cacagctggg | 1860 |
| tctgggggag tacaagagga tgccctgatg gcagttagca cactggtgga agtgttgggt | 1920 |
| ggtgaattcc tcaagtacat ggaggccttt aaacccttcc tgggcattgg attaaaaaat | 1980 |
| tatgctgaat accaggtttg tttggcagct gtgggcttag tgggagactt gtgccgtgcc | 2040 |
| ctgcaatcca acatcatacc tttctgtgac gaggtgatgc agctgcttct ggaaaatttg | 2100 |
| gggaatgaga acgtccacag gtctgtgaag ccgcagattc tgtcagtgtt tggtgatatt | 2160 |
| gcccttgcta ttggaggaga gtttaaaaaa tacttagagg ttgtattgaa tactcttcag | 2220 |
| caggcctccc aagcccaggt ggacaagtca gactatgaca tggtggatta tctgaatgag | 2280 |
| ctaagggaaa gctgcttgga agcctatact ggaatcgtcc aggattaaa ggggatcag | 2340 |
| gagaacgtac acccggatgt gatgctggta caacccagag tagaatttat tctgtctttc | 2400 |
| attgaccaca ttgctggaga tgaggatcac acagatggag tagtagcttg tgctgctgga | 2460 |
| ctaatagggg acttatgtac agcatttggg aaggatgtac tgaaattagt agaagctagg | 2520 |
| ccaatgatcc atgaattgtt aactgaaggg cggagatcga agactaacaa agcaaaaacc | 2580 |
| cttgctacat gggcaacaaa agaactgagg aaactgaaga accaagcttg a | 2631 |

<210> SEQ ID NO 5
<211> LENGTH: 2370
<212> TYPE: DNA
<213> ORGANISM: Human

<400> SEQUENCE: 5

| | |
|---|---|
| atggggacca agatggcgga ccttgattcg cctccgaagc tgtcagggt gcagcagccg | 60 |
| tctgaggggg tgggaggtgg ccgctgctcc gaaatctccg ctgagctcat tcgctccctg | 120 |
| acagagctgc aggagctgga ggctgtatac aacggctct cggcgagga aaagtggtg | 180 |
| gagagagagc tggatgctct tttggaacag caaaacacca ttgaaagtaa gatggtcact | 240 |
| ctccaccgaa tggtcctaa tctgcagctg attgagggag atgcaaagca gctggctgga | 300 |
| atgatcacct ttacctgcaa cctggctgag aatgtgtcca gcaaagttcg tcagcttgac | 360 |
| ctggccaaga accgcctcta tcaggccatt cagagagctg atgacatctt ggacctgaag | 420 |

```
ttctgcatgg atggagttca gactgctttg aggagtgaag attatgagca ggctgcagca    480
catactcatc gctacttgtg cctggacaag tcggtcattg agctcagccg acagggcaaa    540
gaggggagca tgattgatgc caacctgaaa ttgctgcagg aagctgagca acgtctcaaa    600
gccattgtgg cagagaagtt tgccattgcc accaaggaag tgatctgcc  ccaggtggag    660
cgcttcttca agatcttccc actgctgggt tgcatgagg  agggattaag aaagttctcg    720
gagtaccttt gcaagcaggt ggccagtaaa gctgaggaga tctgctcat  ggtgctgggg    780
acagacatga gtgatcggag agctgcagtc atctttgcag atacacttac tcttctgttt    840
gaagggattg cccgcattgt ggagacccac cagccaatag tggagaccta ttatgggcca    900
gggagactct ataccctgat caaatatctg caggtggaat gtgacagaca ggtggagaag    960
gtggtagaca agttcatcaa gcaaagggac taccaccagc agttccggca tgttcagaac   1020
aacctgatga gaaattctac aacagaaaaa atcgaaccaa gagaactgga ccccatcctg   1080
actgaggtca ccctgatgaa tgcccgcagt gagctatact tacgcttcct caagaagagg   1140
attagctctg attttgaggt gggagactcc atggcctcag aggaagtaaa gcaagagcac   1200
cagaagtgtc tggacaaact cctcaataac tgccttttga gctgtaccat gcaggagcta   1260
attggcttat atgttaccat ggaggagtac ttcatgaggg agactgtcaa taaggctgtg   1320
gctctggaca cctatgagaa gggccagctg acatccagca tggtggatga tgtcttctac   1380
attgttaaga agtgcattgg gcgggctctg tccagctcca gcattgactg tctctgtgcc   1440
atgatcaacc tcgccaccac agagctggag tctgacttca gggatgttct gtgtaataag   1500
ctgcggatgg gctttcctgc caccaccttc caggacatcc agcgcggggt gacaagtgcc   1560
gtgaacatca tgcacagcag cctccagcaa ggcaaatttg acacaaaagg catcgagagt   1620
actgacgagg cgaagatgtc cttcctggtg actctgaaca cgtggaagt  ctgcagtgaa   1680
aacatctcca ctctgaagaa gacactggag agtgactgca ccaagctctt cagccagggc   1740
attggagggg agcaggccca ggccaagttt gacagctgcc tttctgactt ggccgccgtg   1800
tccaacaaat tccgagacct cttgcaggaa gggctgacgg agctcaacag cacagccatc   1860
aagccacagg tgcagccttg gatcaacagc tttttctccg tctcccacaa catcgaggag   1920
gaagaattca tgactatga  ggccaacgac ccttgggtac aacagttcat ccttaacctg   1980
gagcagcaaa tggcagagtt caaggccagc ctgtccccgg tcatctacga cagcctaacc   2040
ggcctcatga ctagccttgt tgccgtcgag ttggagaaag tggtgctgaa atccaccttt   2100
aaccggctgg tgctgtctgca gtttgacaag gagctgaggt cgctcattgc ctaccttacc   2160
acggtgacca cctggaccat ccgagacaag tttgcccggc tctcccagat ggccaccatc   2220
ctcaatctgg agcgggtgac cgagatcctc gattactggg gacccaattc cggcccattg   2280
acgtggcgcc tcacccctgc tgaagtgcgc caggtgctgg ccctgcggat agacttccgc   2340
agtgaagata tcaagaggct gcgcctgtag                                      2370
```

<210> SEQ ID NO 6
<211> LENGTH: 1014
<212> TYPE: DNA
<213> ORGANISM: Human

<400> SEQUENCE: 6

```
atggcggacc ttgattcgcc tccgaagctg tcaggggtgc agcagccgtc tgaggggtg     60
ggaggtggcc gctgctccga aatctccgct gagctcattc gctccctgac agagctgcag    120
```

| | |
|---|---|
| gagctggagg ctgtatacga acggctctgc ggcgaggaga aagtggtgga gagagagctg | 180 |
| gatgctcttt tggaacagca aaacaccatt gaaagtaaga tggtcactct ccaccgaatg | 240 |
| ggtcctaatc tgcagctgat tgagggagat gcaaagcagc tggctggaat gatcacctttt | 300 |
| acctgcaacc tggctgagaa tgtgtccagc aaagttcgtc agcttgacct ggccaagaac | 360 |
| cgcctctatc aggccattca gagagctgat gacatcttgg acctgaagtt ctgcatggat | 420 |
| ggagttcaga ctgctttgag gagtgaagat tatgagcagg ctgcagcaca tactcatcgc | 480 |
| tacttgtgcc tggacaagtc ggtcattgag ctcagccgac agggcaaaga ggggagcatg | 540 |
| attgatgcca acctgaaatt gctgcaggaa gctgagcaac gtctcaaagc cattgtggca | 600 |
| gagaagtttg ccattgccac caaggaaggt gatctgcccc aggtggagcg cttcttcaag | 660 |
| atcttcccac tgctgggttt gcatgaggag ggattaagaa agttctcgga gtacctttgc | 720 |
| aagcaggtgg ccagtaaagc tgaggagaat ctgctcatgg tgctggggac agacatgagt | 780 |
| gatcggagag ctgcagtcat ctttgcagat acacttactc ttctgtttga agggattgcc | 840 |
| cgcattgtgg agacccacca gccaatagtg gagacctatt atgggccagg agactctat | 900 |
| accctgatca aatatctgca ggtggaatgt gacagacagg tggagaaggt ggtagacaag | 960 |
| ttcatcaagc aaagggacta ccaccagcag aactttgttt tttccttctt ttga | 1014 |

<210> SEQ ID NO 7
<211> LENGTH: 2358
<212> TYPE: DNA
<213> ORGANISM: Human

<400> SEQUENCE: 7

| | |
|---|---|
| atggcggacc ttgattcgcc tccgaagctg tcaggggtgc agcagccgtc tgaggggtg | 60 |
| ggaggtggcc gctgctccga aatctccgct gagctcattc gctccctgac agagctgcag | 120 |
| gagctggagg ctgtatacga acggctctgc ggcgaggaga aagtggtgga gagagagctg | 180 |
| gatgctcttt tggaacagca aaacaccatt gaaagtaaga tggtcactct ccaccgaatg | 240 |
| ggtcctaatc tgcagctgat tgagggagat gcaaagcagc tggctggaat gatcaccttt | 300 |
| acctgcaacc tggctgagaa tgtgtccagc aaagttcgtc agcttgacct ggccaagaac | 360 |
| cgcctctatc aggccattca gagagctgat gacatcttgg acctgaagtt ctgcatggat | 420 |
| ggagttcaga ctgctttgag gagtgaagat tatgagcagg ctgcagcaca tactcatcgc | 480 |
| tacttgtgcc tggacaagtc ggtcattgag ctcagccgac agggcaaaga ggggagcatg | 540 |
| attgatgcca acctgaaatt gctgcaggaa gctgagcaac gtctcaaagc cattgtggca | 600 |
| gagaagtttg ccattgccac caaggaaggt gatctgcccc aggtggagcg cttcttcaag | 660 |
| atcttcccac tgctgggttt gcatgaggag ggattaagaa agttctcgga gtacctttgc | 720 |
| aagcaggtgg ccagtaaagc tgaggagaat ctgctcatgg tgctggggac agacatgagt | 780 |
| gatcggagag ctgcagtcat ctttgcagat acacttactc ttctgtttga agggattgcc | 840 |
| cgcattgtgg agacccacca gccaatagtg gagacctatt atgggccagg agactctat | 900 |
| accctgatca aatatctgca ggtggaatgt gacagacagg tggagaaggt ggtagacaag | 960 |
| ttcatcaagc aaagggacta ccaccagcag ttccggcatg ttcagaacaa cctgatgaga | 1020 |
| aattctacaa cagaaaaaat cgaaccaaga gaactggacc ccatcctgac tgaggtcacc | 1080 |
| ctgatgaatg cccgcagtga gctatactta cgcttcctca agaagaggat tagctctgat | 1140 |
| tttgaggtgg gagactccat ggcctcagag gaagtaaagc aagagcacca gaagtgtctg | 1200 |
| gacaaactcc tcaataactg ccttttgagc tgtaccatgc aggagctaat tggcttatat | 1260 |

```
gttaccatgg aggagtactt catgagggag actgtcaata aggctgtggc tctggacacc    1320
tatgagaagg gccagctgac atccagcatg gtggatgatg tcttctacat tgttaagaag    1380
tgcattgggc gggctctgtc cagctccagc attgactgtc tctgtgccat gatcaacctc    1440
gccaccacag agctggagtc tgacttcagg gatgttctgt gtaataagct gcggatgggc    1500
tttcctgcca ccaccttcca ggacatccag cgcggggtga caagtgccgt gaacatcatg    1560
cacagcagcc tccagcaagg caaatttgac acaaaaggca tcgagagtac tgacgaggcg    1620
aagatgtcct tcctggtgac tctgaacaac gtggaagtct gcagtgaaaa catctccact    1680
ctgaagaaga cactggagag tgactgcacc aagctcttca gccagggcat ggaggggag    1740
caggcccagg ccaagtttga cagctgcctt tctgacttgg ccgccgtgtc caacaaattc    1800
cgagacctct gcaggaagg gctgacggag ctcaacagca cagccatcaa gccacaggtg    1860
cagccttgga tcaacagctt tttctccgtc tcccacaaca tcgaggagga agaattcaat    1920
gactatgagg ccaacgaccc ttgggtacaa cagttcatcc ttaacctgga gcagcaaatg    1980
gcagagttca aggccagcct gtccccggtc atctacgaca gcctaaccgg cctcatgact    2040
agccttgttg ccgtcgagtt ggagaaagtg gtgctgaaat ccacctttaa ccggctgggt    2100
ggtctgcagt ttgacaagga gctgaggtcg ctcattgcct accttaccac ggtgaccacc    2160
tggaccatcc gagacaagtt tgcccggctc tcccagatgg ccaccatcct caatctggag    2220
cgggtgaccg agatcctcga ttactgggga cccaattccg gcccattgac gtggcgcctc    2280
accccctgctg aagtgcgcca ggtgctggcc ctgcggatag acttccgcag tgaagatatc    2340
aagaggctgc gcctgtag                                                 2358

<210> SEQ ID NO 8
<211> LENGTH: 2088
<212> TYPE: DNA
<213> ORGANISM: Human

<400> SEQUENCE: 8
atggggacca agatggcgga ccttgattcg cctccgaagc tgtcagggg gcagcagccg     60
tctgagggg tgggaggtgg ccgctgctcc gaaatctccg ctgagctcat cgctccctg    120
acagagctgc aggagctgga ggctgtatac gaacggctct gcggcgagga gaaagtggtg    180
gagagagagc tggatgctct tttggaacag caaaacacca ttgaaagtaa gatggtcact    240
ctccaccgaa tgggtcctaa tctgcagctg attgaggcca acctgaaatt gctgcaggaa    300
gctgagcaac gtctcaaagc cattgtggca gagaagtttg ccattgccac caaggaaggt    360
gatctgcccc aggtggagcg cttcttcaag atcttcccac tgctgggttt gcatgaggag    420
ggattaagaa agttctcgga gtacctttgc aagcaggtgg ccagtaaagc tgaggagaat    480
ctgctcatgg tgctggggac agacatgagt gatcggagag ctgcagtcat ctttgcagat    540
acacttactc ttctgtttga agggattgcc cgcattgtgg agacccacca gccaatagtg    600
gagacctatt atgggccagg gagactctat accctgatca aatatctgca ggtggaatgt    660
gacagacagg tggagaaggt ggtagacaag ttcatcaagc aaagggacta ccaccagcag    720
ttccggcatg ttcagaacaa cctgatgaga aattctacaa cagaaaaaat cgaaccaaga    780
gaactggacc ccatcctgac tgaggtcacc ctgatgaatg cccgcagtga gctatactta    840
cgcttcctca gaagaggat tagctctgat tttgaggtgg gagactccat ggcctcagag    900
gaagtaaagc aagagcacca gaagtgtctg acaaactcc tcaataactg ccttttgagc    960
```

```
tgtaccatgc aggagctaat tggcttatat gttaccatgg aggagtactt catgagggag    1020
actgtcaata aggctgtggc tctggacacc tatgagaagg ccagctgac atccagcatg     1080 gtggatgatg tcttctacat tgttaagaag tgcattgggc gggctctgtc cagctccagc   1140
attgactgtc tctgtgccat gatcaacctc gccaccacag agctggagtc tgacttcagg   1200
gatgttctgt gtaataagct gcggatgggc tttcctgcca ccaccttcca ggacatccag   1260
cgcggggtga caagtgccgt gaacatcatg cacagcagcc tccagcaagg caaatttgac   1320
acaaaaggca tcgagagtac tgacgaggcg aagatgtcct tcctggtgac tctgaacaac   1380
gtggaagtct gcagtgaaaa catctccact ctgaagaaga cactggagag tgactgcacc   1440
aagctcttca gccagggcat tggaggggag caggcccagg ccaagtttga cagctgcctt   1500
tctgacttgg ccgccgtgtc caacaaattc cgagacctct gcaggaagg gctgacggag    1560 ctcaacagca cagccatcaa gccacaggtg cagccttgga tcaacagctt tttctccgtc   1620
tcccacaaca tcgaggagga agaattcaat gactatgagg ccaacgaccc ttgggtacaa   1680
cagttcatcc ttaacctgga gcagcaaatg gcagagttca aggccagcct gtccccggtc   1740
atctacgaca gcctaaccgg cctcatgact agccttgttg ccgtcgagtt ggagaaagtg   1800
gtgctgaaat ccacctttaa ccggctgggt ggtctgcagt ttgacaagga gctgaggtcg   1860
ctcattgcct accttaccac ggtgaccacc tggaccatcc gagacaagtt gcccggctc    1920 tcccagatgg ccaccatcct caatctggag cgggtgaccg agatcctcga ttactgggga   1980
cccaattccg gcccattgac gtggcgcctc accctgctg aagtgcgcca ggtgctggcc    2040
ctgcggatag acttccgcag tgaagatatc aagaggctgc gcctgtag                 2088

<210> SEQ ID NO 9
<211> LENGTH: 1254
<212> TYPE: DNA
<213> ORGANISM: Human

<400> SEQUENCE: 9
atggagttcg tgaaatgcct tggccacccc gaagagttct acaacctggt gcgcttccgg     60
atcgggggca gcggaaggt gatgcccaag atggaccagg actcgctcag cagcagcctg    120
aaaacttgct acaagtatct caatcagacc agtcgcagtt cgcagctgt tatccaggcg    180 ctggatgggg aaatgcgcaa cgcagtgtgc atatttatc tggttctccg agctctggac    240
acactggaag atgacatgac catcagtgtg gaaaagaagg tcccgctgtt acacaacttt   300 cactcttttcc tttaccaacc agactggcgg ttcatggaga gcaaggagaa ggatcgccag   360
gtgctggagg acttcccaac gatctcccct gagtttagaa atctggctga aaataccaa    420 acagtgattg ccgacatttg ccggagaatg ggcattggga tggcagagtt tttggataag   480 catgtgaccct ctgaacagga gtgggacaag tactgccact atgttgctgg gctggtcgga   540
attggccttt cccgtctttt ctcagcctca gagtttgaag accccttagt tggtgaagat    600
acagaacgtg ccaactctat gggcctgttt ttgcagaaaa caaacatcat ccgtgactat    660
ctggaagacc agcaaggagg aagagagttc tggcctcaag aggtttggag caggtatgtt    720
aagaagttag gggattttgc taagccggag aatattgact tggccgtgca gtgcctgaat    780
gaacttataa ccaatgcact gcaccacatc ccagatgtca tcacctacct ttcgagactc    840
agaaaccaga gtgtgtttaa cttctgtgct attccacagg tgatggccat tgccactttg   900
gctgcctgtt ataataacca gcaggtgttc aaggggcag tgaagattcg gaaagggcaa    960
gcagtgaccc tgatgatgga tgccaccaat atgccagctg tcaaagccat catatatcag   1020
```

| | | | |
|---|---|---|---|
| tatatggaag | agatttatca | tagaatcccc | gactcagacc  catcttctag  caaaacaagg | 1080 |
| cagatcatct | ccaccatccg | gacgcagaat | cttcccaact  gtcagctgat  ttcccgaagc | 1140 |
| cactactccc | ccatctacct | gtcgtttgtc | atgctttggg  ctgccctgag  ctggcagtac | 1200 |
| ctgaccactc | tctcccaggt | aacagaagac | tatgttcaga  ctggagaaca  ctga | 1254 |

<210> SEQ ID NO 10
<211> LENGTH: 1080
<212> TYPE: DNA
<213> ORGANISM: Human

<400> SEQUENCE: 10

| | | | |
|---|---|---|---|
| atgagagcca | gtcagaagga | ctttgaaaat | tcaatgaatc  aagtgaaact  cttgaaaaag | 60 |
| gatccaggaa | acgaagtgaa | gctaaaactc | tacgcgctat  ataagcaggc  cactgaagga | 120 |
| ccttgtaaca | tgcccaaacc | aggtgtattt | gacttgatca  caaggccaa  atgggacgca | 180 |
| tggaatgccc | ttggcagcct | gcccaaggaa | gctgccaggc  agaactatgt  ggatttggtg | 240 |
| tccagtttga | gtccttcatt | ggaatcctct | agtcaggtgg  agcctggaac  agacaggaaa | 300 |
| tcaactgggt | ttgaaactct | ggtggtgacc | tccgaagatg  gcatcacaaa  gatcatgttc | 360 |
| aaccggccca | aaagaaaaa | tgccataaac | actgagatgt  atcatgaaat  tatgcgtgca | 420 |
| cttaaagctg | ccagcaagga | tgactcaatc | atcactgttt  taacaggaaa  tggtgactat | 480 |
| tacagtagtg | ggaatgatct | gactaacttc | actgatattc  ccctggtgg  agtagaggag | 540 |
| aaagctaaaa | ataatgccgt | tttactgagg | gaatttgtgg  gctgttttat  agattttcct | 600 |
| aagcctctga | ttgcagtggt | caatggtcca | gctgtgggca  tctccgtcac  cctccttggg | 660 |
| ctattcgatg | ccgtgtatgc | atctgacagg | gcaacatttc  atacaccatt  tagtcaccta | 720 |
| ggccaaagtc | cggaaggatg | ctcctcttac | acttttccga  agataatgag  cccagccaag | 780 |
| gcaacagaga | tgcttatttt | tggaaagaag | ttaacagcgg  gagaggcatg  tgctcaagga | 840 |
| cttgttactg | aagttttccc | tgatagcact | tttcagaaag  aagtctggac  caggctgaag | 900 |
| gcatttgcaa | agcttccccc | aaatgccttg | agaatttcaa  agaggtaat  caggaaaaga | 960 |
| gagagagaaa | aactacacgc | tgttaatgct | gaagaatgca  atgtccttca  gggaagatgg | 1020 |
| ctatcagatg | aatgcacaaa | tgctgtggtg | aacttcttat  ccagaaaatc  aaaactgtga | 1080 |

<210> SEQ ID NO 11
<211> LENGTH: 684
<212> TYPE: DNA
<213> ORGANISM: Human

<400> SEQUENCE: 11

| | | | |
|---|---|---|---|
| atgtatcatg | aaattatgcg | tgcacttaaa | gctgccagca  aggatgactc  aatcatcact | 60 |
| gttttaacag | gaaatggtga | ctattacagt | agtgggaatg  atctgactaa  cttcactgat | 120 |
| attcccctg | gtggagtaga | ggagaaagct | aaaaataatg  ccgttttact  gagggaattt | 180 |
| gtgggctgtt | ttatagattt | tcctaagcct | ctgattgcag  tggtcaatgg  tccagctgtg | 240 |
| ggcatctccg | tcaccctcct | tgggctattc | gatgccgtgt  atgcatctga  cagggcaaca | 300 |
| tttcatacac | catttagtca | cctaggccaa | agtccggaag  gatgctcctc  ttacactttt | 360 |
| ccgaagataa | tgagcccagc | caaggcaaca | gagatgctta  ttttggaaa  gaagttaaca | 420 |
| gcgggagagg | catgtgctca | aggacttgtt | actgaagttt  tccctgatag  cacttttcag | 480 |
| aaagaagtct | ggaccaggct | gaaggcattt | gcaaagcttc  ccccaaatgc  cttgagaatt | 540 |

| | |
|---|---|
| tcaaaagagg taatcaggaa aagagagaga gaaaaactac acgctgttaa tgctgaagaa | 600 |
| tgcaatgtcc ttcagggaag atggctatca gatgaatgca caaatgctgt ggtgaacttc | 660 |
| ttatccagaa aatcaaaact gtga | 684 |

<210> SEQ ID NO 12
<211> LENGTH: 1185
<212> TYPE: DNA
<213> ORGANISM: Human

<400> SEQUENCE: 12

| | |
|---|---|
| atggcgatgg cgtacttggc ttggagactg gcgcggcgtt cgtgtccgag ttctctgcag | 60 |
| gtcactagtt tcccggtagt tcagctgcac atgaatagaa cagcaatgag agccagtcag | 120 |
| aaggactttg aaaattcaat gaatcaagtg aaactcttga aaaaggatcc aggaaacgaa | 180 |
| gtgaagctaa aactctacgc gctatataag caggccactg aaggaccttg taacatgccc | 240 |
| aaaccaggtg tatttgactt gatcaacaag gccaaatggg acgcatggaa tgcccttggc | 300 |
| agcctgccca aggaagctgc caggcagaac tatgtggatt tggtgtccag tttgagtcct | 360 |
| tcattggaat cctctagtca ggtggagcct ggaacagaca ggaaatcaac tgggtttgaa | 420 |
| actctggtgg tgacctccga agatggcatc acaaagatca tgttcaaccg gcccaaaaag | 480 |
| aaaaatgcca taacactga gatgtatcat gaaattatgc gtgcacttaa agctgccagc | 540 |
| aaggatgact caatcatcac tgttttaaca ggaaatggtg actattacag tagtgggaat | 600 |
| gatctgacta acttcactga tattcccccct ggtggagtag aggagaaagc taaaaataat | 660 |
| gccgttttac tgagggaatt tgtgggctgt tttatagatt ttcctaagcc tctgattgca | 720 |
| gtggtcaatg gtccagctgt gggcatctcc gtcaccctcc ttgggctatt cgatgccgtg | 780 |
| tatgcatctg acagggcaac atttcataca ccatttagtc acctaggcca agtccggaa | 840 |
| ggatgctcct cttacacttt tccgaagata atgagcccag ccaaggcaac agagatgctt | 900 |
| atttttggaa agaagttaac agcggggagag gcatgtgctc aaggacttgt tactgaagtt | 960 |
| ttccctgata gcacttttca gaaagaagtc tggaccaggc tgaaggcatt tgcaaagctt | 1020 |
| cccccaaatg ccttgagaat ttcaaaagag gtaatcagga aagagagag agaaaaacta | 1080 |
| cacgctgtta atgctgaaga atgcaatgtc cttcagggaa gatggctatc agatgaatgc | 1140 |
| acaaatgctg tggtgaactt cttatccaga aaatcaaaac tgtga | 1185 |

<210> SEQ ID NO 13
<211> LENGTH: 1095
<212> TYPE: DNA
<213> ORGANISM: Human

<400> SEQUENCE: 13

| | |
|---|---|
| atgaatagaa cagcaatgag agccagtcag aaggactttg aaaattcaat gaatcaagtg | 60 |
| aaactcttga aaaaggatcc aggaaacgaa gtgaagctaa aactctacgc gctatataag | 120 |
| caggccactg aaggaccttg taacatgccc aaaccaggtg tatttgactt gatcaacaag | 180 |
| gccaaatggg acgcatggaa tgcccttggc agcctgccca aggaagctgc caggcagaac | 240 |
| tatgtggatt tggtgtccag tttgagtcct tcattggaat cctctagtca ggtggagcct | 300 |
| ggaacagaca ggaaatcaac tgggtttgaa actctggtgg tgacctccga agatggcatc | 360 |
| acaaagatca tgttcaaccg gcccaaaaag aaaaatgcca taacactga gatgtatcat | 420 |
| gaaattatgc gtgcacttaa agctgccagc aaggatgact caatcatcac tgttttaaca | 480 |
| ggaaatggtg actattacag tagtgggaat gatctgacta acttcactga tattcccccct | 540 |

```
ggtggagtag aggagaaagc taaaaataat gccgttttac tgagggaatt tgtgggctgt    600
tttatagatt ttcctaagcc tctgattgca gtggtcaatg gtccagctgt gggcatctcc    660
gtcaccctcc ttgggctatt cgatgccgtg tatgcatctg acagggcaac atttcataca    720
ccatttagtc acctaggcca aagtccggaa ggatgctcct cttacacttt tccgaagata    780
atgagcccag ccaaggcaac agagatgctt attttggaa agaagttaac agcgggagag    840
gcatgtgctc aaggacttgt tactgaagtt ttccctgata gcacttttca gaaagaagtc    900
tggaccaggc tgaaggcatt tgcaaagctt cccccaaatg ccttgagaat ttcaaaagag    960
gtaatcagga aaagagagag agaaaaacta cacgctgtta atgctgaaga atgcaatgtc   1020
cttcagggaa gatggctatc agatgaatgc acaaatgctg tggtgaactt cttatccaga   1080
aaatcaaaac tgtga                                                    1095

<210> SEQ ID NO 14
<211> LENGTH: 726
<212> TYPE: DNA
<213> ORGANISM: Human

<400> SEQUENCE: 14
atgttcaacc ggcccaaaaa gaaaaatgcc ataaacactg agatgtatca tgaaattatg     60
cgtgcactta agctgccag caaggatgac tcaatcatca ctgttttaac aggaaatggt    120
gactattaca gtagtgggaa tgatctgact aacttcactg atattccccc tggtggagta    180
gaggagaaag ctaaaaataa tgccgtttta ctgagggaat tgtgggctg ttttatagat    240 tttcctaagc tctgattgc agtggtcaat ggtccagctg tgggcatctc cgtcaccctc    300
cttgggctat cgatgccgt gtatgcatct gacagggcaa catttcatac accatttagt    360
cacctaggcc aaagtccgga aggatgctcc tcttacactt ttccgaagat aatgagccca    420
gccaaggcaa cagagatgct tattttgga agaagttaa cagcgggaga ggcatgtgct    480
caaggacttg ttactgaagt tttccctgat agcacttttc agaaagaagt ctggaccagg    540
ctgaaggcat tgcaaagct ccccccaaat gccttgagaa tttcaaaaga ggtaatcagg    600
aaaagagaga gagaaaaact acacgctgtt aatgctgaag aatgcaatgt ccttcaggga    660
agatggctat cagatgaatg cacaaatgct gtggtgaact tcttatccag aaaatcaaaa    720
ctgtga                                                              726

<210> SEQ ID NO 15
<211> LENGTH: 3504
<212> TYPE: DNA
<213> ORGANISM: Human

<400> SEQUENCE: 15
atgtttgcga ggaagccgcc gggcgccgcg cctttgggag ctatgcctgt tccagaccag     60
ccttcatcag cctcagagaa gacgagttcc ctgagcccg gcttaaacac tccaacggg    120 gatggctctg aaacagaaac cacctctgcc atcctcgcct cagtcaaaga acaggaatta    180
cagtttgaaa ggctgacccg agagctggag gctgaacggc agatcgtagc cagccagctg    240
gagcgatgca agctcggatc cgagactggc agcatgagca gcatgagttc agcagaagag    300
cagtttcagt ggcagtcaca agatggtcaa aaagatatcg aagatgagct tacaacaggt    360
ctcgagctgg tggactcctg tattaggtca ctacaggaat caggaatact tgacccacag    420
gattattcta caggtgaaag gcccagcctg ctctcccaga gtgcacttca gctcaattcc    480
```

```
aaacctgaag ggtctttcca gtatccggcc agctaccata gcaaccagac cctggccctg    540
ggggaaacca ccccttcaca gctcccggcc cgaggcacac aagcccgagc tacgggccag    600
agcttcagcc agggcacgac cagccgcgcc ggccacctgg cggggcccga gcccgcgccg    660
ccgccgccgc cgccgccgcg ggagccgttc gcgcccagcc tgggcagcgc cttccacctg    720
cccgacgcgc cgcccgccgc cgccgccgcc gcgctctact actccagctc cacgctgccc    780
gcgccgccgc gcggggggctc cccgctggcc gcgcccagg gcggttcgcc caccaagctg    840
cagcgcggcg gctcggcccc cgagggcgcc acctacgccg cgccgcgcgg ctcctcgccc    900
aagcagtcgc ccagccgcct ggccaagtcc tacagcacca gctcgcccat caacatcgtc    960
gtgtcctcgg ccggcctgtc cccgatccgc gtgacctcgc cccccaccgt gcagtccacc   1020
atctcctcct cgcccatcca ccagctgagc tccaccatcg gcacgtacgc caccctgtcg   1080
cccaccaagc gcctggtcca cgcgtccgag cagtacagca agcactcgca ggagctgtat   1140
gccacggcca ccctccagag gccgggcagc ctggcagctg gttcccgagc tcatacagc    1200
agccagcatg ggcacctggg cccagagttg cgggccctgc agtccccaga acaccacata   1260
gatcccatct atgaagaccg cgtctatcag aagcccccta tgaggagtct cagccagagc   1320
caggggggacc ctctgccgcc agcacacacc ggcacctacc gcacgagcac agccccatct   1380
tcccctggtg tcgactccgt ccccttgcag cgcacaggca gccagcacgg cccacagaat   1440
gccgccgcgg ccaccttcca gagggccagc tatgccgccg gccagcctc caattacgcg   1500
gaccectace gacagetgea gtattgtece tetgttgagt etecatacag eaaateegge   1560
cctgctctcc cgcctgaagg caccttggcc aggtccccgt ccattgatag cattcagaaa   1620
gatcccagag aatttggatg gagagacccg gaactgccgg aagtgattca gatgttgcag   1680
caccagtttc cctcggtcca gtctaacgcg gcagcctact gcaacaccct ctgttttgga   1740
gacaacaaaa ttaaagccga gataaggaga caaggaggca tccagctcct ggtggacctg   1800
ttggatcatc ggatgaccga agtccaccgt agtgcctgtg gagctctgag aaacctggtg   1860
tatgggaagg ccaacgatga taacaaaatt gccctgaaaa actgtggtgg catcccagca   1920
ctggtgaggt tactccgcaa gacgactgac ctggagatcc gggagctggt cacaggagtc   1980
cttttggaacc tctcctcatg cgatgcactc aaaatgccaa tcatccagga tgccctagca   2040
gtactgacca acgcggtgat tatcccccac tcaggctggg aaaattcgcc tcttcaggat   2100
gatcggaaaa tacagctgca ttcatcacag gtgctgcgta acgccaccgg gtgcctaagg   2160
aatgttagtt cggccggaga ggaggcccgc agaaggatga gagagtgtga tgggcttacg   2220
gatgccttgc tgtacgtgat ccagtctgcg ctggggagca gtgagatcga tagcaagacc   2280
gttgaaaact gtgtgtgcat tttaaggaac ctctcgtacc ggctggcggc agaaacgtct   2340
cagggacagc acatgggcac ggacgagctg gacgggctac tctgtggcga ggccaatggc   2400
aaggatgctg agagctctgg gtgctggggc aagaagaaga gaaaaagaa atcccaagat   2460
cagtggtcag tatatatccg agccgctgtc cgaaaagaga aaggcctgcc catcctcgtg   2520
gagctgctcc gaatagacaa tgaccgtgtg gtgtgcgcgg tggccactgc gctgcggaac   2580
atggccttgg acgtcagaaa taaggagctc atcggcaaat acgccatgcg agacctagtc   2640
cacaggcttc caggagggaa caacagcaac aacactgcaa gcaaggccat gtcggatgac   2700
acagtgacag ctgtctgctg cacactgcac gaagtgatta ccaagaacat ggagaacgcc   2760
aaggccttac gggatgccgg tggcatcgag aagttggtcg gcatctccaa aagcaaagga   2820
gataaacact ctccaaaagt ggtcaaggct gcatctcagg tcctcaacag catgtggcag   2880
```

-continued

| | | |
|---|---|---|
| taccgagatc tgaggagtct ctacaaaaag gatggatggt cacaatacca ctttgtagcc | 2940 |
| tcgtcttcaa ccatcgagag ggaccggcaa aggcccctact cctcctcccg cacgccctcc | 3000 |
| atctcccctg tgcgcgtgtc tcccaacaac cgctcagcaa gtgccccagc ttcacctcgg | 3060 |
| gaaatgatca gcctcaaaga aggaaaaaca gactacgagt gcaccggcag caacgccacc | 3120 |
| taccacggag ctaaaggcga acacacttcc aggaaagatg ccatgacagc tcaaaacact | 3180 |
| ggaatttcaa ctttgtatag gaattcttat ggtgcgccg ctgaagacat caaacacaac | 3240 |
| caggtttcag cacagccagt cccacaggag cccagcagaa aagattacga gacctaccag | 3300 |
| ccatttcaga attccacaag aaattacgat gagtccttct tcgaggacca ggtccaccat | 3360 |
| cgccctcccg ccagcgagta caccatgcac ctgggtctca gtccaccgg caactacgtt | 3420 |
| gacttctact cagctgcccg tccctacagt gaactgaact atgaaacgag ccactacccg | 3480 |
| gcctcccccg actcctgggt gtga | 3504 |

<210> SEQ ID NO 16
<211> LENGTH: 3678
<212> TYPE: DNA
<213> ORGANISM: Human

<400> SEQUENCE: 16

| | | |
|---|---|---|
| atgtttgcga ggaagccgcc gggcgccgcg cctttgggag ctatgcctgt tccagaccag | 60 |
| ccttcatcag cctcagagaa gacgagttcc ctgagccccg gcttaaacac ctccaacggg | 120 |
| gatggctctg aaacagaaac cacctctgcc atcctcgcct cagtcaaaga acaggaatta | 180 |
| cagtttgaaa ggctgacccg agagctggag gctgaacggc agatcgtagc cagccagctg | 240 |
| gagcgatgca gctcggatc cgagactggc agcatgagca gcatgagttc agcagaagag | 300 |
| cagtttcagt ggcagtcaca agatggtcaa aaagatatcg aagatgagct acaacaggt | 360 |
| ctcgagctgg tggactcctg tattaggtca ctacaggaat caggaatact tgacccacag | 420 |
| gattattcta caggtgaaag gcccagcctg ctctcccaga gtgcacttca gctcaattcc | 480 |
| aaacctgaag ggtcttttcca gtatccggcc agctaccata gcaaccagac cctggccctg | 540 |
| ggggaaacca cccttcaca gctcccggcc cgaggcacac aagcccgagc tacgggccag | 600 |
| agcttcagcc agggcacgac cagccgcgcc ggccacctgg cggggcccga gcccgcgccg | 660 |
| ccgccgccgc cgccgccgcg ggagccgttc gcgcccagcc tgggcagcgc cttccacctg | 720 |
| cccgacgcgc cgcccgccgc cgccgccgcc gcgctctact actccagctc cacgctgccc | 780 |
| gcgccgccgc gcgggggctc cccgctggcc gcgcccagg gcggttcgcc caccaagctg | 840 |
| cagcgcggcg gctcggcccc cgagggcgcc acctacgccg cgccgcgcgg ctcctcgccc | 900 |
| aagcagtcgc ccagccgcct ggccaagtcc tacagcacca gctcgcccat caacatcgtc | 960 |
| gtgtcctcgg ccggcctgtc cccgatccgc gtgacctcgc cccccaccgt gcagtccacc | 1020 |
| atctcctcct cgcccatcca ccagctgagc tccaccatcg gcacgtacgc cacccctgtcg | 1080 |
| cccaccaagc gcctggtcca gcgtccgag cagtacagca agcactcgca ggagctgtat | 1140 |
| gccacggcca ccctccagag gccgggcagc ctggcagctg gttcccgagc ctcatacagc | 1200 |
| agccagcatg gcacctgggg cccagagttg cgggccctgc agtccccaga acaccacata | 1260 |
| gatcccatct atgaagaccg cgtctatcag aagcccccta tgaggagtct cagccagagc | 1320 |
| cagggggacc ctctgccgcc agcacacacc ggcacctacc gcacgagcac agccccatct | 1380 |
| tcccctggtg tcgactccgt cccccttgcag cgcacaggca gccagcacgg cccacagaat | 1440 |

-continued

| | |
|---|---|
| gccgccgcgg ccaccttcca gagggccagc tatgccgccg gcccagcctc caattacgcg | 1500 |
| gaccCctacc gacagctgca gtattgtccc tctgttgagt ctccatacag caaatccggc | 1560 |
| cctgctctcc cgcctgaagg caccttggcc aggtccccgt ccattgatag cattcagaaa | 1620 |
| gatcccagag aatttggatg gagagacccg gaactgccgg aagtgattca gatgttgcag | 1680 |
| caccagtttc cctcggtcca gtctaacgcg gcagcctact tgcaacacct ctgttttgga | 1740 |
| gacaacaaaa ttaaagccga gataaggaga caaggaggca tccagctcct ggtgacctg | 1800 |
| ttggatcatc ggatgaccga agtccaccgt agtgcctgtg gagctctgag aaacctggtg | 1860 |
| tatgggaagg ccaacgatga taacaaaatt gccctgaaaa actgtggtgg catcccagca | 1920 |
| ctggtgaggt tactccgcaa gacgactgac ctggagatcc gggagctggt cacaggagtc | 1980 |
| ctttggaacc tctcctcatg cgatgcactc aaaatgccaa tcatccagga tgccctagca | 2040 |
| gtactgacca acgcggtgat tatcccccac tcaggctggg aaaattcgcc tcttcaggat | 2100 |
| gatcggaaaa tacagctgca ttcatcacag gtgctgcgta acgccaccgg gtgcctaagg | 2160 |
| aatgttagtt cggccggaga ggaggcccgc agaaggatga gagagtgtga tgggcttacg | 2220 |
| gatgccttgc tgtacgtgat ccagtctgcg ctggggagca gtgagatcga tagcaagacc | 2280 |
| gttgaaaact gtgtgtgcat tttaaggaac ctctcgtacc ggctggcggc agaaacgtct | 2340 |
| cagggacagc acatgggcac ggacgagctg acgggctac tctgtggcga ggccaatggc | 2400 |
| aaggatgctg agagctctgg gtgctggggc aagaagaaga agaaaaagaa atcccaagat | 2460 |
| cagtgggatg gagtaggacc tcttccagac tgtgctgaac caccaaaagg gatccagatg | 2520 |
| ctgtggcacc catcaatagt caaaccctac ctcacactgc tctctgagtg ctcaaatcca | 2580 |
| gacacgctgg aaggggcggc aggcgccctg cagaacttgg ctgcagggag ctggaagtgg | 2640 |
| tcagtatata tccgagccgc tgtccgaaaa gagaaaggcc tgcccatcct cgtggagctg | 2700 |
| ctccgaatag acaatgaccg tgtggtgtgc gcggtggcca ctgcgctgcg gaacatggcc | 2760 |
| ttggacgtca gaaataagga gctcatcggc aaatacgcca tgcgagacct agtccacagg | 2820 |
| cttccaggag ggaacaacag caacaacact gcaagcaagg ccatgtcgga tgacacagtg | 2880 |
| acagctgtct gctgcacact gcacgaagtg attaccaaga acatggagaa cgccaaggcc | 2940 |
| ttacgggatg ccggtggcat cgagaagttg gtcggcatct ccaaaagcaa aggagataaa | 3000 |
| cactctccaa aagtggtcaa ggctgcatct caggtcctca acagcatgtg gcagtaccga | 3060 |
| gatctgagga gtctctacaa aaaggatgga tggtcacaat accactttgt agcctcgtct | 3120 |
| tcaaccatcg agagggaccg gcaaaggccc tactcctcct cccgcacgcc ctccatctcc | 3180 |
| cctgtgcgcg tgtctcccaa caaccgctca gcaagtgccc cagcttcacc tcgggaaatg | 3240 |
| atcagcctca agaaaggaa aacagactac gagtgcaccg gcagcaacgc cacctaccac | 3300 |
| ggagctaaag gcgaacacac ttccaggaaa gatgccatga cagctcaaaa cactggaatt | 3360 |
| tcaactttgt ataggaattc ttatggtgcg cccgctgaag catcaaaaca caaccaggtt | 3420 |
| tcagcacagc cagtcccaca ggagcccagc agaaaagatt cgagaccta ccagccattt | 3480 |
| cagaattcca caagaaatta cgatgagtcc ttcttcgagg accaggtcca ccatcgccct | 3540 |
| cccgccagcg agtacaccat gcacctgggt ctcaagtcca ccgcaacta cgttgacttc | 3600 |
| tactcagctg cccgtcccta cagtgaactg aactatgaaa cgagccacta cccggcctcc | 3660 |
| cccgactcct gggtgtga | 3678 |

<210> SEQ ID NO 17
<211> LENGTH: 438

```
<212> TYPE: DNA
<213> ORGANISM: Human

<400> SEQUENCE: 17
ccgtatccgc tagcgcggtg ggatgcgctt gggctccctg ttcgttccca catgcagggc      60
agcacaagga gaatgggcgt catgactgat gtccaccggc gcttcctcca gttgctgatg     120
acccatggcg tgctagagga atgggacgtg aagcgcttgc agacgcactg ctacaaggtc     180
catgaccgca atgccaccgt agataagttg gaggacttca tcaacaacat taacagtgtc     240
ttggagtcct tgtatattga gataaagaga ggagtcacgg aagatgatgg gagacccatt     300
tatgcgttgg tgaatcttgc tacaacttca atttccaaaa tggctacgga ttttgcagag     360
aatgaactgg atttgtttag aaaggctctg gaactgatta ttgactcaga aaccttgcgt     420
cttccacaaa catattga                                                   438

<210> SEQ ID NO 18
<211> LENGTH: 801
<212> TYPE: DNA
<213> ORGANISM: Human

<400> SEQUENCE: 18
atgcagggca gcacaaggag aatgggcgtc atgactgatg tccaccggcg cttcctccag      60
ttgctgatga cccatggcgt gctagaggaa tgggacgtga agcgcttgca gacgcactgc     120
tacaaggtcc atgaccgcaa tgccaccgta gataagttgg aggacttcat caacaacatt     180
aacagtgtct tggagtcctt gtatattgag ataaagagag gagtcacgga agatgatggg     240
agacccattt atgcgttggt gaatcttgct acaacttcaa tttccaaaat ggctacggat     300
tttgcagaga atgaactgga tttgtttaga aaggctctgg aactgattat tgactcagaa     360
accggctttg cgtcttccac aaacatattg aacctggttg atcaacttaa aggcaagaag     420
atgaggaaga aggaagcgga gcaggtgctg cagaagtttg ttcaaaacaa gtggctgatt     480
gagaaggaag gggagttcac cctgcacggc cgggccatcc tggagatgga gcaatacatc     540
cgggagacgt accccgacgc ggtgaagatc tgcaatatct gtcacagcct cctcatccag     600
ggtcaaagct gcgaaacctg tgggatcagg atgcacttac cctgcgtggc caagtacttc     660
cagtcgaatg ctgaaccgcg ctgcccccac tgcaacgact actggcccca cgagatccca     720
aaagtcttcg accctgagaa ggagagggag tctggtgtct gaaatcgaac aaaaagtcc     780
ctgcggtcca ggcagcatta g                                              801

<210> SEQ ID NO 19
<211> LENGTH: 540
<212> TYPE: DNA
<213> ORGANISM: Human

<400> SEQUENCE: 19
gtccaccttg cgaccgtatc cgctagcgcg gcctgggatg cgcttgggct ccctgttcgt      60
tcccacatgc agggcagcac aaggagaatg ggcgtcatga ctgatgtcca ccggcgcttc     120
ctccagttgc tgatgaccca tggcgtgcta gaggaatggg acgtgaagcg cttgcagacg     180
cactgctaca aggtccatga ccgcaatgcc accgtagata agttggagga cttcatcaac     240
aacattaaca gtgtcttgga gtccttgtat attgagataa agagaggagt cacggaagat     300
gatgggagac ccatttatgc gttggtgaat cttgctacaa cttcaatttc caaaatggct     360
acggattttg cagagaatga actggatttg tttagaaagg ctctggaact gattattgac     420
```

```
tcagaaaccg gctttgcgtc ttccacaaac atattgaacc tggttgatca acttaaaggc    480
aagaagatga ggaagaagga agcgaggtgc tgcagaagtt tgttcaaaac aagtggctga    540
```

<210> SEQ ID NO 20
<211> LENGTH: 1179
<212> TYPE: DNA
<213> ORGANISM: Human

<400> SEQUENCE: 20

```
atggagtggt gggctagctc gccgcttcgg ctctggctgc tgttgttcct cctgccctca     60
gcgcagggcc gccagaagga gtcaggttca aatggaaag tatttattga ccaaattaac    120
aggtctttgg agaattacga accatgttca agtcaaaact gcagctgcta ccatggtgtc    180
atagaagagg atctaactcc tttccgagga ggcatctcca ggaagatgat ggcagaggta    240
gtcagacgga agctagggac ccactatcag atcactaaga acagactgta ccgggaaaat    300
gactgcatgt tcccctcaag gtgtagtggt gttgagcact ttattttgga agtgatcggg    360
cgtctccctg acatggagat ggtgatcaat gtacgagatt atcctcaggt tcctaaatgg    420
atggagcctg ccatcccagt cttctccttc agtaagacat cagagtacca tgatatcatg    480
tatcctgctt ggacattttg gaaggggga cctgctgttt ggccaattta tcctacaggt    540
cttggacggt gggacctctt cagagaagat ctggtaaggt cagcagcaca gtggccatgg    600
aaaaagaaaa actctacagc atatttccga ggatcaagga caagtccaga acgagatcct    660
ctcattcttc tgtctcggaa aaacccaaaa cttgttgatg cagaatacac caaaaaccag    720
gcctggaaat ctatgaaaga taccttagga aagccagctg ctaaggatgt ccatcttgtg    780
gatcactgca atacaagta tctgtttaat tttcgaggcg tagctgcaag tttccggttt    840
aaacacctct tcctgtgtgg ctcacttgtt ttccatgttg gtgatgagtg ctagaattc    900 ttctatccac agctgaagcc atgggttcac tatatcccag tcaaaacaga tctctccaat    960
gtccaagagc tgttacaatt tgtaaaagca aatgatgatg tagctcaaga gattgctgaa   1020
aggggaagcc agtttattag gaaccatttg cagatggatg acatcacctg ttactgggag   1080
aacctcttga gtgaatactc taaattcctg tcttataatg taacgagaag gaaaggttat   1140
gatcaaatta ttcccaaaat gttgaaaact gaactatag                           1179
```

<210> SEQ ID NO 21
<211> LENGTH: 1236
<212> TYPE: DNA
<213> ORGANISM: Human

<400> SEQUENCE: 21

```
atgcggcggc ggcgcgccgg cggcaggacc atggttgagc gcgccagcaa gttcgtgctg     60
gtggtggcgg gctcggtgtg cttcatgctc atcttgtacc agtacgcggg cccaggactg    120
agcctgggcg cgcccggcgg ccgcgcgccc cccgacgacc tggacctgtt ccccacaccc    180 gaccccact acgagaagaa gtactacttc ccggtccgcg agctggagcg ctcgctgcgc    240
ttcgacatga agggcgacga cgtgatcgtc ttcctgcaca tccagaagac gggcggcacc    300
accttcggcc gccacctcgt gcagaacgta cgcctcgagg tgccgtgcga ctgccggccc    360
ggccagaaga agtgcaccct ctaccggccc aaccgccgcg agacttggct cttctcccgc    420
ttctccaccg gctggagctg cgggctgcac gccgactgga ccgagctcac caactgcgtg    480 cccgcgtgc tggaccgccg cgactccgcc gcgctgcgca cgcccaggaa gttctactac    540
atcaccctgc tacgagaccc cgtgtcccgc tacctgagcg agtggcggca tgtgcagagg    600
```

```
ggtgccacgt ggaagacgtc gttgcatatg tgtgatgggc gcacgcccac gcctgaggag      660
ctgccgccct gctacgaggg cacggactgg tcgggctgca cgctacagga gttcatggac      720
tgcccgtaca acctggccaa caaccgccag gtgcgcatgc tggccgacct gagcctggtg      780
ggctgctaca acctgtcctt catccccgag ggcaagcggg cccagctgct gctcgagagc      840
gccaagaaga acctgcgggg catggccttc ttcggcctga ccgagttcca gcgcaagacg      900
cagtacctgt tcgagcggac gttcaacctc aagttcatcc ggcccttcat gcagtacaat      960
agcacgcggg cgggcggcgt ggaggtggat gaagacacca tccggcgcat cgaggagctc     1020
aacgacctgg acatgcagct gtacgactac gccaaggacc tcttccagca gcgctaccag     1080
tacaagcggc agctggagcg cagggagcag cgcctgagga gccgcgagga gcgtctgctg     1140
caccgggcca aggaggcact gccgcgggag gatgccgacg agccgggccg cgtgcccacc     1200
gaggactaca tgagccacat cattgagaag tggtag                                1236

<210> SEQ ID NO 22
<211> LENGTH: 1395
<212> TYPE: DNA
<213> ORGANISM: Human

<400> SEQUENCE: 22
atgacatcct gcagatgctc agtgacctcc aggagtctgt ggccagctct cgccccagg        60 aggtgtcagc atacctcacc cgcttctgcg cagtgcaaac aggacaaggc ctgccgcttc      120
ctcgcggccc agaaggggc ctaccccatc atcttcactg cctggaagct ggccactgca      180
ggtgaccagg gccttctgct ccagtccctc aatgccctgt cggtgctgac tgatggacag      240
ccagacctcc tggatgccca gggcctgcag ctcctagtgg ccacgctgac ccagaatgct      300
gatgaggctg acctgacctg ctctgggatc cgctgtgtgc gtcacgcttg cctgaaacat      360
gaacagaatc ggcaagacct ggtgaaagct ggcgtgctgc ctctgctgac tggtgccatc      420
acccatcatg gccaccacac tgacgtggtc agggaagcct gctgggccct gcgtgtcatg      480
accttcgatg acgacatccg tgtgcccttt ggccatgccc acaaccatgc caagatgatt      540
gtgcaggaga acaaaggctt gaaggtgctc atcgaagcca ccaaagcgtt cctggataac      600
cctggcatcc tgagcgagct ctgtggaacc ctgtcccgcc tggccattcg caacgagttc      660
tgccaggagg tcgtcgacct cggggggcctg agcattctgg tgtccctgct agccgactgc      720
aatgaccacc agatgaggga ccagagcggc gttcaggagc tcgtgaagca agtgctgagc      780
accctgcgag ccatcgcagg caacgacgac gtgaaagatg ctattgtccg tgctggtggg      840
acggagtcca tcgtggctgc tatgacccag catctgacca gccccaggt gtgtgagcag      900 agctgcgcg cctgtgctt cctggccctg cgtaagcccg acaacagccg catcatcgtg      960
gagggtggcg gggctgtggc agcactgcag gccatgaagg cacacccgca gaaggccggc     1020
gtgcagaaac aggcttgcat gctgatccga aacctggtgg cccacaggcc ttctcgaagc     1080
ccatcctgga cctgggggct gaggcactca tcatgcaggc ccgatctgcc caccgtgact     1140
gtgaggacgt ggccaaggcc gccctgcggg acctgggttg tcatgtcgag ctccgagagc     1200
tgtggacagg ccagagggc aacctggcgc catgacccca ggcccagtct ggtgactctg     1260
ggtgagtcgt gtgactcagg aatgggggta gatccatgtc ctccactgtc ccccattagt     1320
tctgtcccct tcacaatgag aagtgttttc tggcaggccc taggtaaagg gtcggggag     1380 gggggagcct tgtag                                                       1395
```

```
<210> SEQ ID NO 23
<211> LENGTH: 1431
<212> TYPE: DNA
<213> ORGANISM: Human

<400> SEQUENCE: 23
atggtctcca agcgcattgc ccaggagacc tttgatgcag ctgtgcgcga aacatcgag      60 gagtttgcga tggggccaga ggaggcagtg aaagaggccg tggagcagtt tgaatcgcaa    120
ggggttgatc tgagcaacat tgtaaagacg gcacctaaag tctctgcaga cggatcccag    180
gagcccacac atgacatcct gcagatgctc agtgacctcc aggagtctgt ggccagctct    240 cgccccccagg aggtgtcagc atacctcacc cgcttctgcg accagtgcaa acaggacaag    300
gcctgccgct cctcgcggc ccagaagggg gcctacccca tcatcttcac tgcctggaag    360
ctggccactg caggtgacca gggccttctg ctccagtccc tcaatgccct gtcggtgctg    420
actgatggac agccagacct cctggatgcc cagggcctgc agctcctagt ggccacgctg    480
acccagaatg ctgatgaggc tgacctgacc tgctctggga tccgctgtgt gcgtcacgct    540
tgcctgaaac atgaacagaa tcggcaagac ctggtgaaag ctggcgtgct gcctctgctg    600
actggtgcca tcacccatca tggccaccac actgacgtgg tcagggaagc ctgctgggcc    660
ctgcgtgtca tgaccttcga tgacgacatc cgtgtgccct tggccatgc ccacaaccat    720 gccaagatga ttgtgcagga aacaaaggc ttgaaggtgc tcatcgaagc caccaaagcg    780
ttcctggata accctggcat cctgagcgag ctctgtggaa ccctgtcccg cctggccatt    840
cgcaacgagt ctgccagga ggtcgtcgac ctcgggggcc tgagcattct ggtgtccctg    900
ctagccgact gcaatgacca ccagatgagg gaccagagcg gcgttcagga gctcgtgaag    960
caagtgctga gcaccctgcg agccatcgca ggcaacgacg acgtgaaaga tgctattgtc   1020
cgtgctggtg ggacggagtc catcgtggct gctatgaccc agcatctgac cagccccag   1080 gtgtgtgagc agagctgcgc ggccctgtgc ttcctggccc tgcgtaagcc cgacaacagc   1140
cgcatcatcg tggagggtgg cggggctgtg gcagcactgc aggccatgaa gcacacccg   1200 cagaaggccg gcgtgcagaa acaggcttgc atgctgatcc gaaacctggt ggcccacggc   1260
caggccttct cgaagcccat cctggacctg ggggctgagg cactcatcat gcaggcccga   1320
tctgcccacc gtgactgtga ggacgtggcc aaggccgccc tgcgggacct gggttgtcat   1380
gtcgagctcc gagagctgtg gacaggccag aggggcaacc tggcgccatg a            1431

<210> SEQ ID NO 24
<211> LENGTH: 1506
<212> TYPE: DNA
<213> ORGANISM: Human

<400> SEQUENCE: 24
atgagtgaac gatgttgctc tagatacagc tcaggagcat ctatcggctg cacgccaaca     60
tcaacacagg cgaagatggt ctccaagcgc attgcccagg agacctttga tgcagctgtg    120
cgcgagaaca tcgaggagtt tgcgatgggg ccagaggagg cagtgaaaga ggccgtggag    180
cagtttgaat cgcaagggt tgatctgagc aacattgtaa agacggcacc taaagtctct    240
gcagacggat cccaggagcc cacacatgac atcctgcaga tgctcagtga cctccaggag    300
tctgtggcca gctctcgccc ccaggaggtg tcagcatacc tcacccgctt ctgcgaccag    360
tgcaaacagg acaaggcctg ccgcttcctc gcggcccaga ggggggccta ccccatcatc    420
ttcactgcct ggaagctggc cactgcaggt gaccagggcc ttctgctcca gtccctcaat    480
```

```
gccctgtcgg tgctgactga tggacagcca gacctcctgg atgcccaggg cctgcagctc      540
ctagtggcca cgctgaccca gaatgctgat gaggctgacc tgacctgctc tgggatccgc      600
tgtgtgcgtc acgcttgcct gaaacatgaa cagaatcggc aagacctggt gaaagctggc      660
gtgctgcctc tgctgactgg tgccatcacc catcatggcc accacactga cgtggtcagg      720
gaagcctgct gggccctgcg tgtcatgacc ttcgatgacg catccgtgt gcccttggc      780 catgcccaca accatgccaa gatgattgtg caggagaaca aaggcttgaa ggtgctcatc      840
gaagccacca agcgttcct ggataaccct ggcatcctga gcgagctctg tggaaccctg      900
tcccgcctgg ccattcgcaa cgagttctgc caggaggtcg tcgacctcgg ggcctgagc      960 attctggtgt ccctgctagc cgactgcaat gaccaccaga tgagggacca gagcggcgtt     1020
caggagctcg tgaagcaagt gctgagcacc ctgcgagcca tcgcaggcaa cgacgacgtg     1080
aaagatgcta ttgtccgtgc tggtgggacg gagtccatcg tggctgctat gacccagcat     1140
ctgaccagcc cccaggtgtg tgagcagagc tgcgcggccc tgtgcttcct ggccctgcgt     1200
aagcccgaca acagccgcat catcgtggag ggtggcgggg ctgtggcagc actgcaggcc     1260
atgaaggcac acccgcagaa ggccggcgtg cagaaacagg cttgcatgct gatccgaaac     1320
ctggtggccc acggccaggc cttctcgaag cccatcctgg acctgggggc tgaggcactc     1380
atcatgcagg cccgatctgc ccaccgtgac tgtgaggacg tggccaaggc cgccctgcgg     1440
gacctgggtt gtcatgtcga gctccagagc ctgtggacag gccagagggg caacctggcg     1500
ccatga                                                                1506

<210> SEQ ID NO 25
<211> LENGTH: 1431
<212> TYPE: DNA
<213> ORGANISM: Human

<400> SEQUENCE: 25
atggtctcca agcgcattgc ccaggagacc tttgatgcag ctgtgcgcga aacatcgag       60 gagtttgcga tggggccaga ggaggcagtg aaagaggccg tggagcagtt tgaatcgcaa     120
ggggttgatc tgagcaacat tgtaaagacg gcacctaaag tctctgcaga cggatcccag     180
gagcccacac atgacatcct gcagatgctc agtgacctcc aggagtctgt ggccagctct     240
cgcccccagg aggtgtcagc atacctcacc cgcttctgcg accagtgcaa acaggacaag     300
gcctgccgct tcctcgcggc ccagaagggg gcctaccccca tcatcttcac tgcctggaag     360
ctggccactg caggtgacca gggccttctg ctccagtccc tcaatgccct gtcggtgctg     420
actgatggac agccagacct cctggatgcc cagggcctgc agctcctagt ggccacgctg     480
acccagaatg ctgatgaggc tgacctgacc tgctctggga tccgctgtgt gcgtcacgct     540
tgcctgaaaa catgaacagaa tcggcaagac ctggtgaaag ctggcgtgct gcctctgctg     600
actggtgcca tcacccatca tggccaccac actgacgtgg tcaggaagc ctgctgggcc     660 ctgcgtgtca tgaccttcga tgacgacatc cgtgtgccct ttggccatgc ccacaaccat     720
gccaagatga ttgtgcagga aacaaaggc ttgaaggtgc tcatcgaagc caccaaagcg     780
ttcctggata accctggcat cctgagcgag ctctgtggaa ccctgtcccg cctggccatt     840
cgcaacgagt tctgccagga ggtcgtcgac ctcgggggcc tgagcattct ggtgtccctg     900
ctagccgact gcaatgacca ccagatgagg accagagcg cgttcagga gctcgtgaag     960 caagtgctga gcaccctgcg agccatcgca ggcaacgacg acgtgaaaga tgctattgtc    1020
```

```
cgtgctggtg ggacggagtc catcgtggct gctatgaccc agcatctgac cagcccccag   1080
gtgtgtgagc agagctgcgc ggccctgtgc ttcctggccc tgcgtaagcc cgacaacagc   1140
cgcatcatcg tggagggtgg cggggctgtg gcagcactgc aggccatgaa ggcacacccg   1200
cagaaggccg gcgtgcagaa acaggcttgc atgctgatcc gaaacctggt ggcccacggc   1260
caggccttct cgaagcccat cctggacctg ggggctgagg cactcatcat gcaggcccga   1320
tctgcccacc gtgactgtga ggacgtggcc aaggccgccc tgcgggacct gggttgtcat   1380
gtcgagctcc gagagctgtg gacaggccag aggggcaacc tggcgccatg a           1431

<210> SEQ ID NO 26
<211> LENGTH: 1773
<212> TYPE: DNA
<213> ORGANISM: Human

<400> SEQUENCE: 26
atggcggggg ccgtgccggg cgccatcatg acgaggact actacgggag cgcggccgag    60
tggggcgacg aggctgacgg cggccagcag gaggatgatt ctggagaagg agaggatgat   120
gcggaggttc agcaagaatg cctgcataaa ttttccaccc gggattatat catggaaccc   180
tccatcttca acactctgaa gaggtatttt caggcaggag ggtctccaga gaatgttatc   240
cagctcttat ctgaaaacta caccgctgtg gcccagactg tgaacctgct ggccgagtgg   300
ctcattcaga caggtgttga gccagtgcag gttcaggaaa ctgtggaaaa tcacttgaag   360
agtttgctga tcaaacattt tgaccccgc aaagcagatt ctatttttac tgaagaagga   420
gagaccccag cgtggctgga acagatgatt gcacatacca cgtggcggga cctttttttat   480
aaactggctg aagcccatcc agactgtttg atgctgaact tcaccgttaa gcttatttct   540
gacgcagggt accagggga gatcaccagt gtgtccacag catgccagca gctagaagtg   600
ttctcgagag tgctccggac ctctctagct acaatttag atggaggaga agaaaacctt   660
gaaaaaaatc tccctgagtt tgccaagatg gtgtgccacg gggagcacac gtacctgttt   720
gcccaggcca tgatgtccgt gctggcccag gaggagcagg ggggctccgc tgtgcgcagg   780
atcgcccagg aagtgcagcg cttgccccag gagaaaggtc atgacgccag tcagatcaca   840
ctagccttgg gcacagctgc ctcctacccc agggcctgcc aggctctcgg ggccatgctg   900
tccaaaggag ccctgaaccc tgctgacatc accgtcctgt tcaagatgtt cacaagcatg   960
gaccctcctc cggttgaact tatccgcgtt ccagccttcc tggacctgtt catgcagtca  1020
ctctttaaac caggggctcg gatcaaccag gaccacaagc acaaatacat ccacatcttg  1080
gcgtacgcag caagcgtggt tgagacctgg aagaagaaca agcgagtgag catcaataaa  1140
gatgagctga agtcaacgtc aaaagctgtc gaaaccgttc acaattgtgt ttgcaacgag  1200
aacaaagggg cctctgaact agtggcagaa ttgagcacac tttatcagtg tattaggttt  1260
ccagtggtag caatgggtgt gctgaagtgg gtggattgga ctgtatcaga accaaggtac  1320
tttcagctgc agactgacca taccctgtc cacctggcgt tgctggatga atcagcacc   1380
tgccaccagc tcctgcaccc ccaggtcctg cagctgcttg ttaagctttt tgagactgag  1440
cactcccagc tggacgtgat ggagcagctt gagttgaaga agacactgct ggacaggatg  1500
gttcacctgc tgagtcgagg ttatgtactt cctgttgtca gttacatccg aaagtgtctg  1560
gagaagctgg acactgacat ttcactcatt cgctattttg tcactgaggt gctgacgtc   1620
attgctcctc cttatacctc tgacttcgtg caacttttcc tccccatcct ggagaatgac  1680
agcatcgcag gtaccatcaa aacggaaggc gagcatgacc ctgtgacgga gtttatagct  1740
```
cactgcaaat ctaacttcat catggtgaac taa         1773

<210> SEQ ID NO 27
<211> LENGTH: 753
<212> TYPE: DNA
<213> ORGANISM: Human

<400> SEQUENCE: 27
atggccatgc tcagggtcca gcccgaggcc caagccaagg tggatgtgtt tcgtgaagac      60
ctctgtacca agacagagaa cctgctcggg agctatttcc ccaagaagat ttctgagctg     120
gatgcatttt taaaggagcc agctctcaat gaagccaact tgagcaatct gaaggcccca     180
ttggacatcc cagtgcctga tccagtcaag gagaaagaga agaggagcg gaagaaacag     240
caggagaagg aagacaagga tgaaaagaag aaggggagg atgaagacaa aggtcctccc     300
tgtggcccag tgaactgcaa tgaaaagatc gtggtccttc tgcagcgctt gaagcctgag     360
atcaaggatg tcattgagca gctcaacctg gtcaccacct ggttgcagct gcagatacct     420
cggattgagg atggtaacaa ttttggagtg gctgtccagg agaaggtgtt tgagctgatg     480
accagcctcc acaccaagct agaaggcttc cacactcaaa tctctaagta tttctctgag     540
cgtggtgatg cagtgactaa agcagccaag cagccccatg tgggtgatta tcggcagctg     600
gtgcacgagc tggatgaggc agagtaccgg gacatccggc tgatggtcat ggagatccgc     660
aatgcttatg tgaggaggca agggcagggc aggggtgggc agaggcagct ttcccaggcc     720
acccactccc tgaccctgca ggctagggt taa                                   753

<210> SEQ ID NO 28
<211> LENGTH: 750
<212> TYPE: DNA
<213> ORGANISM: Human

<400> SEQUENCE: 28
atggccatgc tcagggtcca gcccgaggcc caagccaagg tggatgtgtt tcgtgaagac      60
ctctgtacca agacagagaa cctgctcggg agctatttcc ccaagaagat ttctgagctg     120
gatgcatttt taaaggagcc agctctcaat gaagccaact tgagcaatct gaaggcccca     180
ttggacatcc cagtgcctga tccagtcaag gagaaagaga agaggagcg gaagaaacag     240
caggagaagg aagacaagga tgaaaagaag aaggggagg atgaagacaa aggtcctccc     300
tgtggcccag tgaactgcaa tgaaaagatc gtggtccttc tgcagcgctt gaagcctgag     360
atcaaggatg tcattgagca gctcaacctg gtcaccacct ggttgcagct gcagatacct     420
cggattgagg atggtaacaa ttttggagtg gctgtccagg agaaggtgtt tgagctgatg     480
accagcctcc acaccaagct agaaggcttc cacactcaaa tctctaagta tttctctgag     540
cgtggtgatg cagtgactaa agcagccaag cagccccatg tgggtgatta tcggcagctg     600
gtgcacgagc tggatgaggc agagtaccgg gacatccggc tgatggtcat ggagatccgc     660
aatgcttatg ctgtgttata tgacatcatc ctgaagaact cgagaagct caagaagccc     720
aggggagaaa caagggaat gatctattga                                       750

<210> SEQ ID NO 29
<211> LENGTH: 1677
<212> TYPE: DNA
<213> ORGANISM: Human

<400> SEQUENCE: 29

```
atggagctcc gggcccgagg ctggtggctg ctatgtgcgg ccgcagcgct ggtcgcctgc    60
gcccgcgggg acccgccag caagagccgg agctgcggcg aggtccgcca gatctacgga   120
gccaagggct tcagcctgag cgacgtgccc caggcggaga tctcgggtga gcacctgcgg   180
atctgtcccc agggctacac ctgctgcacc agcgagatgg aggagaacct ggccaaccgc   240
agccatgccg agctggagac cgcgctccgg gacagcagcc gcgtcctgca ggccatgctt   300
gccacccagc tgcgcagctt cgatgaccac ttccagcacc tgctgaacga ctcggagcgg   360
acgctgcagg ccaccttccc cggcgccttc ggagagctgt acacgcagaa cgcgagggcc   420
ttccgggacc tgtactcaga gctgcgcctg tactaccgcg tgccaacct gcacctggag   480
gagacgctgg ccgagttctg ggcccgcctg ctcgagcgcc tcttcaagca gctgcacccc   540
cagctgctgc tgcctgatga ctacctggac tgcctgggca gcaggccga ggcgctgcgg   600
cccttcgggg aggccccgag agagctgcgc ctgcgggcca cccgtgcctt cgtggctgct   660
cgctcctttg tgcagggcct gggcgtggcc agcgacgtgg tccggaaagt ggctcaggtc   720
cccctgggcc cggagtgctc gagagctgtc atgaagctgg tctactgtgc tcactgcctg   780
ggagtccccg cgccaggcc ctgcctgac tattgccgaa atgtgctcaa gggctgcctt   840
gccaaccagc ccgacctgga cgccgagtgg aggaacctcc tggactccat ggtgctcatc   900
accgacaagt ctgggggtac atcgggtgtg gagagtgtca tcggcagcgt gcacacgtgg   960
ctggcggagg ccatcaacgc cctccaggac aacaggaca cgctcacggc caaggtcatc  1020
cagggctgcg ggaacccaa ggtcaacccc cagggccccg ggcctgagga aagcggcgc  1080
cggggcaagc tggccccgcg ggagaggcca ccttcaggca cgctggagaa gctggtctcc  1140
gaagccaagg cccagctccg cgacgtccag gacttctgga tcagcctccc agggacactg  1200
tgcagtgaga agatggccct gagcactgcc agtgatgacc gctgctggaa cgggatggcc  1260
agaggccggt acctccccga ggtcatgggt gacggcctgg ccaaccagat caacaacccc  1320
gaggtggagg tggacatcac caagccggac atgaccatcc ggcagcagat catgcagctg  1380
aagatcatga ccaaccggct gcgcagcgcc tacaacggca cgacgtgga cttccaggac  1440
gccagtgacg acggcagcgg ctcgggcagc ggtgatggc gtctggatga cctctgcagc  1500
cggaaggtca gcaggaagag ctccagctcc cggacgccct tgacccatgc cctcccaggc  1560
ctgtcagagc aggaaggaca gaagacctcg gctgccagct gccccagcc ccgaccttc  1620
ctcctgcccc tcctcctctt cctggcccttt acagtagcca ggccccggtg gcggtaa    1677

<210> SEQ ID NO 30
<211> LENGTH: 3645
<212> TYPE: DNA
<213> ORGANISM: Human

<400> SEQUENCE: 30
atggcctcct gcgcgagcat cgacatcgag gacgccacgc agcacctgcg ggacatcctc    60
aagctggacc ggcccgcggg cggccccagt gcagagagcc acggccatc cagtgcctac   120
aatggggacc tcaatggact tctggtccca gacccgctct gctcaggtga tagtacctca   180
gcaaacaaga ctggtcttcg gaccatgcca cccattaacc tgcaagagaa gcaggtcatc   240
tgtctctcag gagatgatag ctccacctgc attgggattt tggccaagga ggtggagatt   300
gtggctagca gtgactctag catttcaagc aaggcccggg gaagcaacaa ggtgaaaatt   360
cagcctgtcg ccaagtatga ctgggaacag aagtactact atggcaacct gattgctgtg   420
tctaactcct tcttggccta tgccattcgg gctgccaaca atggctctgc catggtgcgg   480
```

| | |
|---|---|
| gtgatcagcg tcagcacttc ggagcggacc ttgctcaagg cttcacagg cagtgtggct | 540 |
| gatctggctt tcgcgcacct caactctcca cagctggcct gctggatga ggcaggcaac | 600 |
| ctgttcgtgt ggcgcttggc tctggttaat ggcaaaattc aagaagagat cttggtccat | 660 |
| attcggcagc cagagggcac gccactgaac cactttcgca ggatcatctg gtgcccttc | 720 |
| atccctgagg agagcgaaga ctgctgtgag gagagcagcc aacagtggc cctgctgcat | 780 |
| gaagaccggg ctgaggtgtg ggacctggac atgctccgct ccagccacag tacctggcct | 840 |
| gtggatgtta gccagatcaa gcagggcttc attgtggtaa aaggtcatag cacgtgcctc | 900 |
| agtgaaggag ccctctctcc tgatgggact gtgctggcta ctgcgagcca cgatggctat | 960 |
| gtcaagttct ggcagatcta cattgagggg caagatgagc caaggtgtct gcacgagtgg | 1020 |
| aaacctcatg atgggcggcc cctctcctgc ctcctgttct gtgacaacca taagaaacaa | 1080 |
| gaccctgatg tcccttcctg gaggttcctt attactggtg ctgaccagaa ccgagagtta | 1140 |
| aagatgtggt gtacagtatc ctggacctgc ctgcagacta ttcgcttctc cccagatatc | 1200 |
| ttcagctcag tgagtgtgcc ccctagcctc aaggtttgct tggacctctc agcagaatac | 1260 |
| ctgattctca gcgatgtgca acggaaggtc ctctatgtga tggagctgct gcaaaaccag | 1320 |
| gaggagggcc acgcctgctt cagctccatc tcggagttcc tgctcaccca ccctgtgctg | 1380 |
| agctttggta tccaggttgt gagtcgctgc cggctacggc acactgaggt gctgcctgcc | 1440 |
| gaagaggaaa atgacagcct gggtgctgat ggtacccatg gagccggtgc catggagtct | 1500 |
| gcggccggtg tgctcatcaa gctcttttgt gtgcatacta aggcactgca agatgtgcag | 1560 |
| atccgcttcc agccacagct gaaccctgat gtggtggccc cactgccac ccacactgcc | 1620 |
| cacgaggact tcacatttgg agagtctcgg cccgaactgg gctctgaggg cctggggtca | 1680 |
| gccgctcacg gctcccagcc tgacctccga cgaatcgtgg agctgcctgc acctgccgac | 1740 |
| ttcctcagtc tgagcagtga gaccaagccc aagttgatga cacctgacgc cttcatgaca | 1800 |
| cctagcgcct ccttgcagca gatcactgcc tctcccagca gcagcagcag cggtagcagc | 1860 |
| agcagcagca gcagtagcag cagctcccct acagctgtgt ctgccatgag cagcacctca | 1920 |
| gctgtggacc cctccttgac caggccacct gaggagctga ccttgagccc caagctgcag | 1980 |
| ctggatggca gcctgacaat gagcagcagt ggcagccttc aggcaagccc gcgtggcctc | 2040 |
| ctgcctggcc tgctcccagc cccagctgac aaactgactc caaggggcc gggccaggtg | 2100 |
| cctactgcca cctctgcact gtccctggag ctgcaggaag tggagcccct ggggctaccc | 2160 |
| caagcctccc ctagccgcac tcgttcccct gatgtcatct cctcagcttc cactgccctg | 2220 |
| tcccaggaca tccctgagat tgcatctgag gccctgtccc gtggttttgg ctcctctgca | 2280 |
| ccagagggcc ttgagccaga cagtatggct tcagccgcct cggcactgca cctgctgtcc | 2340 |
| ccacggcccc ggccagggcc cgagctcggc ccccagctcg gcttgatgg aggccctggg | 2400 |
| gatggagatc ggcataatac cccctccctc tggaggcag ccttgaccca ggaggcctcg | 2460 |
| actcctgaca gtcaggtttg gcccacagca cctgacatta ctcgtgagac ctgcagcacc | 2520 |
| ctggcagaaa gccccaggaa tggccttcag gaaaagcaca agagcctggc cttccaccga | 2580 |
| ccaccatatc acctgctgca gcaacgtgac agccaggatg ccagtgctga gcaaagtgac | 2640 |
| catgatgatg aggtggccag ccttgcctct gcttcaggag gctttggcac caaagttcct | 2700 |
| gctccacggc tgcctgccaa ggactggaag accaagggat cccctcgaac ctcacccaag | 2760 |
| ctcaagagga aaagcaagaa ggatgatggg gatgcagcca tgggatcccg gctcacagag | 2820 |

| | | |
|---|---|---|
| caccaggtgg cagagccccc tgaggactgg ccagcactaa tttggcaaca gcagagagag | 2880 | |
| ctggcagagc tgcggcacag ccaggaagag ctgctgcagc gtctgtgtac ccaactcgaa | 2940 | |
| ggcctgcaga gcacagtcac aggccacgta gaacgtgccc ttgagactcg gcacgagcag | 3000 | |
| gaacagcggc ggctggagcg agcactggct gaggggcagc agcggggagg gcagctgcag | 3060 | |
| gagcagctga cacaacagtt gtcccaagca ctgtcgtcag ctgtagctgg gcggctagag | 3120 | |
| cgcagcatac gggatgagat caagaagaca gtccctccat gtgtctcaag gagtctggag | 3180 | |
| cctatggcag gccaactgag caactcagtg gctaccaagc tcacagctgt ggagggcagc | 3240 | |
| atgaaagaga acatctccaa gctgctcaag tccaagaact tgactgatgc catcgcccga | 3300 | |
| gcagctgcag acacattaca agggccgatg caggctgcct accgggaagc cttccagagt | 3360 | |
| gtggtgctgc cggcctttga aaagagctgc caggccatgt tccagcaaat caatgatagc | 3420 | |
| ttccggctgg ggacacagga atacttgcag cagctagaaa gccacatgaa gagccggaag | 3480 | |
| gcacgggaac aggaggccag ggagcctgtg ctagcccagc tgcggggcct ggtcagcaca | 3540 | |
| ctgcagagtg ccactgagca gatgccaccg tggccggcag tgttcgtgct gaggtgcagc | 3600 | |
| accagctgca tgtggctgtg ggcagcctgc aggagtccat tttag | 3645 | |

<210> SEQ ID NO 31
<211> LENGTH: 4206
<212> TYPE: DNA
<213> ORGANISM: Human

<400> SEQUENCE: 31

| | | |
|---|---|---|
| atggcctcct gcgcgagcat cgacatcgag gacgccacgc agcacctgcg ggacatcctc | 60 | |
| aagctggacc ggcccgcggg cggccccagt gcagagagcc cacggccatc cagtgcctac | 120 | |
| aatggggacc tcaatggact tctggtccca gacccgctct gctcaggtga tagtacctca | 180 | |
| gcaaacaaga ctggtcttcg gaccatgcca cccattaacc tgcaagagaa gcaggtcatc | 240 | |
| tgtctctcag gagatgatag ctccacctgc attgggattt tggccaagga ggtggagatt | 300 | |
| gtggctagca gtgactctag catttcaagc aaggcccggg gaagcaacaa ggtgaaaatt | 360 | |
| cagcctgtcg ccaagtatga ctgggaacag aagtactact atggcaacct gattgctgtg | 420 | |
| tctaactcct tcttggccta tgccattcgg gctgccaaca atggctctgc catggtgcgg | 480 | |
| gtgatcagcg tcagcacttc ggagcggacc ttgctcaagg gcttcacagg cagtgtggct | 540 | |
| gatctggctt tcgcgcacct caactctcca cagctggcct gcctggatga ggcaggcaac | 600 | |
| ctgttcgtgt ggcgcttggc tctggttaat ggcaaaattc aagaagagat cttggtccat | 660 | |
| attcggcagc cagagggcac gccactgaac cactttcgca ggatcatctg gtgccccttc | 720 | |
| atccctgagg agagcgaaga ctgctgtgag gagagcagcc caacagtggc cctgctgcat | 780 | |
| gaagaccggg ctgaggtgtg ggacctggac atgctccgct ccagccacag tacctggcct | 840 | |
| gtggatgtta gccagatcaa gcagggcttc attgtggtaa aggtcatag cacgtgcctc | 900 | |
| agtgaaggag ccctctctcc tgatgggact gtgctggcta ctgcgagcca cgatggctat | 960 | |
| gtcaagttct ggcagatcta cattgagggg caagatgagc caaggtgtct gcacgagtgg | 1020 | |
| aaacctcatg atgggcggcc cctctcctgc ctcctgttct gtgacaacca taagaaacaa | 1080 | |
| gaccctgatg tccctttctg gaggttcctt attactggtg ctgaccagaa ccgagagtta | 1140 | |
| aagatgtggt gtacagtatc ctggacctgc ctgcagacta ttcgcttctc cccagatatc | 1200 | |
| ttcagctcag tgagtgtgcc ccctagcctc aaggtttgct tggacctctc agcagaatac | 1260 | |
| ctgattctca gcgatgtgca acggaaggtc ctctatgtga tggagctgct gcaaaaccag | 1320 | |

```
gaggagggcc acgcctgctt cagctccatc tcggagttcc tgctcaccca ccctgtgctg   1380
agctttggta tccaggttgt gagtcgctgc cggctacggc acactgaggt gctgcctgcc   1440
gaagaggaaa atgacagcct gggtgctgat ggtacccatg gagccggtgc catggagtct   1500
gcggccggtg tgctcatcaa gctcttttgt gtgcatacta aggcactgca agatgtgcag   1560
atccgcttcc agccacagct gaaccctgat gtggtggccc cactgcccac ccacactgcc   1620
cacgaggact tcacatttgg agagtctcgg cccgaactgg gctctgaggg cctggggtca   1680
gccgctcacg gctcccagcc tgacctccga cgaatcgtgg agctgcctgc acctgccgac   1740
ttcctcagtc tgagcagtga gaccaagccc aagttgatga cacctgacgc cttcatgaca   1800
cctagcgcct ccttgcagca gatcactgcc tctcccagca gcagcagcag cggtagcagc   1860
agcagcagca gcagtagcag cagctccctt acagctgtgt ctgccatgag cagcacctca   1920
gctgtggacc cctccttgac caggccacct gaggagctga ccttgagccc caagctgcag   1980
ctggatggca gcctgacaat gagcagcagt ggcagccttc aggcaagccc gcgtggcctc   2040
ctgcctggcc tgctcccagc cccagctgac aaactgactc ccaaggggcc gggccaggtg   2100
cctactgcca cctctgcact gtccctggag ctgcaggaag tggagcccct ggggctaccc   2160
caagcctccc ctagccgcac tcgttcccct gatgtcatct cctcagcttc cactgccctg   2220
tcccaggaca tccctgagat tgcatctgag gccctgtccc gtggttttgg ctcctctgca   2280
ccagagggcc ttgagccaga cagtatggct tcagccgcct cggcactgca cctgctgtcc   2340
ccacggcccc ggccagggcc cgagctcggc ccccagctcg gcttgatgg aggccctggg   2400 gatggagatc ggcataatac cccctccctc ctggaggcag ccttgaccca ggaggcctcg   2460
actcctgaca gtcaggtttg gcccacagca cctgacatta tcgtgagac ctgcagcacc   2520 ctggcagaaa gccccaggaa tggccttcag gaaaagcaca gagcctggc cttccaccga   2580 ccaccatatc acctgctgca gcaacgtgac agccaggatg ccagtgctga gcaaagtgac   2640
catgatgatg aggtggccag ccttgcctct gcttcaggag gctttggcac caaagttcct   2700
gctccacggc tgcctgccaa ggactggaag accaagggat cccctcgaac ctcacccaag   2760
ctcaagagga aaagcaagaa ggatgatggg gatgcagcca tgggatcccg gctcacagag   2820
caccaggtgg cagagccccc tgaggactgg ccagcactaa tttggcaaca gcagagagag   2880
ctggcagagc tgcggcacag ccaggaagag ctgctgcagc gtctgtgtac ccaactcgaa   2940
ggcctgcaga gcacagtcac aggccacgta gaacgtgccc ttgagactcg gcacgagcag   3000
gaacagcggc ggctggagcg agcactggct gaggggcagc agcggggagg gcagctgcag   3060
gagcagctga cacaacagtt gtcccaagca ctgtcgtcag ctgtagctgg gcggctagag   3120
cgcagcatac gggatgagat caagaagaca gtccctccat gtgtctcaag gagtctggag   3180
cctatggcag gccaactgag caactcagtg gctaccaagc tcacagctgt ggagggcagc   3240
atgaaagaga acatctccaa gctgctcaag tccaagaact tgactgatgc catcgcccga   3300
gcagctgcag acacattaca agggccgatg caggctgcct accgggaagc cttccagagt   3360
gtggtgctgc cggcctttga aaagagctgc caggccatgt ccagcaaat caatgatagc   3420 ttccggctgg gacacaggaa atacttgcag cagctagaaa gccacatgaa gagccggaag   3480
gcacgggaac aggaggccag ggagcctgtg ctagcccagc tgcggggcct ggtcagcaca   3540
ctgcagagtg ccactgagca gatggcagcc accgtggccg gcagtgttcg tgctgaggtg   3600
cagcaccagc tgcatgtggc tgtgggcagc ctgcaggagt ccattttagc acaggtacag   3660
```

```
cgcatcgtta agggtgaggt gagtgtggcg ctcaaggagc agcaggccgc cgtcacctcc    3720
agcatcatgc aggccatgcg ctcagctgct ggcacacctg tccctctgc ccaccttgac      3780 tgccaggccc agcaagccca tatcctgcag ctgctgcagc agggccacct caatcaggcc    3840
ttccagcagg cgctgacagc tgctgacctg aacctggtgc tgtatgtgtg tgaaactgtg    3900
gacccagccc aggttttttgg gcagccaccc tgcccgctct cccagcctgt gctcctttcc   3960
ctcatccagc agctggcatc tgaccttggc actcgaactg acctcaagct cagctacctg   4020
gaagaggccg tgatgcacct ggaccacagt gaccccatca ctcgggacca catgggctcc   4080 gttatgccc aggtgcgcca aaagctttttt cagttcctgc aggctgagcc acacaactca    4140
cttggcaaag cagctcggcg tctcagcctc atgctgcatg gcctcgtgac ccccagcctc   4200
ccttag                                                              4206
```

<210> SEQ ID NO 32  
<211> LENGTH: 1983  
<212> TYPE: DNA  
<213> ORGANISM: Human

<400> SEQUENCE: 32

```
acgaggcttc gccccgtggc gcggtttgaa attttgcggg gctcaacggc tcgcggagcg     60
gctacgcgga gtgacatcgc cggtgttttgc gggtggttgt tgctctcggg gccgtgtgga   120
gtaggtctgg acctggactc acggctgctt ggagcgtccg ccatgaggag aagtgaggtg   180
ctggcggagg agtccatagt atgtctgcag aaagccctaa atcaccttcg ggaaatatgg   240
gagctaattg ggattccaga ggaccagcgg ttacaaagaa ctgaggtggt aaagaagcat   300
atcaaggaac tcctggatat gatgattgct gaagaggaaa gcctgaagga aagactcatc   360
aaaagcatat ccgtctgtca gaaagagctg aacactctgt gcagcgagtt acatgttgag   420
ccatttcagg aagaaggaga gacgaccatc ttgcaactag aaaagatttt gcgcacccaa   480
gtggaattga tgcgaaaaca gaaaaaggag agaaaacagg aactgaagct acttcaagag   540
caagatcaag aactgtgcga aattctttgt atgccccact atgatattga cagtgcctca   600
gtgcccagct agaagagct gaaccagttc aggcaacatg tgacaacttt gagggaaaca   660
aaggcttcta ggcgtgagga gtttgtcagt ataaagagac agatcatact gtgtatggaa   720
gcattagacc acaccccaga cacaagcttt gaaagagatg tggtgtgtga agacgaagat   780
gccttttgtt tgtctttgga gaatattgca acactacaaa agttgctacg gcagctggaa   840
atgcagaaat cacaaaatga agcagtgtgt gaggggctgc gtactcaaat ccgagagctc   900
tgggacaggt tgcaaatacc tgaagaagaa agagaagctg tggccaccat tatgtctggg   960
tcaaaggcca aggtccggaa agcgctgcaa ttagaagtgg atcggttgga agaactgaaa   1020
atgcaaaaca tgaagaaagt gattgaggca attcgagtgg agctggttca gtactgggac   1080
cagtgctttt atagccagga gcagagacaa gcttttgccc cttctctgtgc tgaggactac   1140 acagaaagtc tgctccagct ccacgatgct gagattgtgg ggttaaaaaa ctactatgaa   1200
gttcacaagg aactctttga aggtgtccag aagtgggaag aaacctggag cttttcttta   1260
gagtttgaga gaaaagcttc agatccaaat cgatttacaa accgaggagg aaatcttcta   1320
aaagaagaaa acaacgagc caagctccag aaaatgctgc ccaagctgga agaagagttg   1380
aaggcacgaa ttgaattgtg ggaacaggaa cattcaaagg catttatggt gaatgggcag   1440
aaattcatgg agtatgtggc agaacaatgg gagatgcatc gattggagaa agagagagcc   1500
aagcaggaaa gacaactgaa gaacaaaaaa cagacagaga cagagatgct gtatggcagc   1560
```

```
gctcctcgaa cacctagcaa gcggcgagga ctggctccca atacaccggg caaagcacgt    1620
aagctgaaca ctaccaccat gtccaatgct acggccaata gtagcattcg gcctatcttt    1680
ggagggacag tctaccactc ccccgtgtct cgacttcctc cttctggcag caagccagtc    1740
gctgcttcca cctgttcagg gaagaaaaca ccccgtactg gcaggcatgg agccaacaag    1800
gagaacctgg agctcaacgg cagcatcctg agtggtgggt accctggctc ggcccccctc    1860
cagcgcaact tcagcattaa ttctgttgcc agcacctatt ctgagtttgc gcgagaactt    1920
tcaaaggctt ccaaatctga tgctacttct ggaatcctca attcaaccaa catccagtcc    1980
tga                                                                   1983

<210> SEQ ID NO 33
<211> LENGTH: 2025
<212> TYPE: DNA
<213> ORGANISM: Human

<400> SEQUENCE: 33
acgaggcttc gccccgtggc gcggtttgaa attttgcggg gctcaacggc tcgcggagcg      60
gctacgcgga gtgacatcgc cggtgtttgc gggtggttgt tgctctcggg gccgtgtgga    120
gtaggtctgg acctggactc acggctgctt ggagcgtccg ccatgaggag aagtgaggtg    180
ctggcggagt agtccatagt atgtctgcag aaagccctaa atcaccttcg ggaaatatgg    240
gagctaattg ggattccaga ggaccagcgg ttacaaagaa ctgaggtggt aaagaagcat    300
atcaaggaac tcctggatat gatgattgct gaagaggaaa gcctgaagga aagactcatc    360
aaaagcatat ccgtctgtca gaaagagctg aacactctgt gcagcgagtt acatgttgag    420
ccatttcagg aagaaggaga gacgaccatc ttgcaactag aaaagagattt gcgcacccaa    480 gtggaattga tgcgaaaaca gaaaaggag agaaaacagg aactgaagct acttcaagag    540
caagatcaag aactgtgcga aattctttgt atgccccact atgatattga cagtgcctca    600
gtgcccagct tagaagagct gaaccagttc aggcaacatg tgacaacttt gagggaaaca    660
aaggcttcta gcgtgagga gtttgtcagt ataaagagac agatcatact gtgtatggaa    720
gcattagacc acaccccaga cacaagcttt gaaagagatg tggtgtgtga agacgaagat    780 gcctttttgtt tgtctttgga gaatattgca acactacaaa agttgctacg gcagctggaa    840
atgcagaaat cacaaaatga agcagtgtgt gaggggctgc gtactcaaat ccagagagctc    900 tgggacaggt tgcaaatacc tgaagaagaa agagaagctg tggccaccat tatgtctggg    960
tcaaaggcca aggtccggaa agcgctgcaa ttagaagtgg atcggttgga agaactgaaa   1020
atgcaaaaca tgaagaaagt gattgaggca attcgagtgg agctggttca gtactgggac   1080
cagtgctttt atagccagga gcagagacaa gcttttgccc ctttctgtgc tgaggactac   1140
acagaaagtc tgctccagct ccacgatgct gagattgtgc ggttaaaaaa ctactatgaa   1200
gttcacaagg aactctttga aggtgtccag aagtgggaag aaacctggag cttttcttta   1260
gagtttgaga gaaaagcttc agatccaaat cgatttacaa accgaggagg aaatcttcta   1320
aaagaagaaa acaacgagc caagctccag aaaatgctgc ccaagctgga agaagagttg   1380
aaggcacgaa ttgaattgtg ggaacaggaa cattcaaagg catttatggt gaatgggcag   1440
aaattcatgg agtatgtggc agaacaatgg gagatgcatc gattggagaa agagagagcc   1500
aagcaggaaa gacaactgaa gaacaaaaaa cagacagaga cagagatgct gtatggcagc   1560
gctcctcgaa cacctagcaa gcggcgagga ctggctccca atacaccggg caaagcacgt   1620
```

-continued

| | |
|---|---|
| aagctgaaca ctaccaccat gtccaatgct acggccaata gtagcattcg gcctatcttt | 1680 |
| ggagggacag tctaccactc ccccgtgtct cgacttcctc cttctggcag caagccagtc | 1740 |
| gctgcttcca cctgttcagg aagaaaaca ccccgtactg gcaggcatgg agccaacaag | 1800 |
| gagaacctgg agctcaacgg cagcatcctg agtggtgggt accctggctc ggccccctc | 1860 |
| cagcgcaact tcagcattaa ttctgttgcc agcaccatt ctgagtttgc gaaggatccg | 1920 |
| tccctctctg acagttccac tgttgggctt cagcgagaac tttcaaaggc ttccaaatct | 1980 |
| gatgctactt ctggaatcct caattcaacc aacatccagt cctga | 2025 |

<210> SEQ ID NO 34
<211> LENGTH: 1863
<212> TYPE: DNA
<213> ORGANISM: Human

<400> SEQUENCE: 34

| | |
|---|---|
| atgaggagaa gtgaggtgct ggcggaggag tccatagtat gtctgcagaa agccctaaat | 60 |
| caccttcggg aaatatggga gctaattggg attccagagg accagcggtt acaaagaact | 120 |
| gaggtggtaa agaagcatat caaggaactc ctggatatga tgattgctga gaggaaagc | 180 |
| ctgaaggaaa gactcatcaa agcatatcc gtctgtcaga aagagctgaa cactctgtgc | 240 |
| agcgagttac atgttgagcc atttcaggaa gaaggagaga cgaccatctt gcaactagaa | 300 |
| aaagatttgc gcacccaagt ggaattgatg cgaaaacaga aaaaggagag aaaacaggaa | 360 |
| ctgaagctac ttcaagagca agatcaagaa ctgtgcgaaa ttctttgtat gccccactat | 420 |
| gatattgaca gtgcctcagt gcccagctta gaagagctga accagttcag gcaacatgtg | 480 |
| acaactttga gggaaacaaa ggcttctagg cgtgaggagt ttgtcagtat aaagagacag | 540 |
| atcatactgt gtatggaagc attagaccac accccagaca caagctttga agagatgtg | 600 |
| gtgtgtgaag acgaagatgc cttttgtttg tctttggaga atattgcaac actacaaaag | 660 |
| ttgctacggc agctggaaat gcagaaatca caaaatgaag cagtgtgtga ggggctgcgt | 720 |
| actcaaatcc gagagctctg gacaggttg caaataccg aagaagaaag agaagctgtg | 780 |
| gccaccatta tgtctgggtc aaaggccaag gtccggaaag cgctgcaatt agaagtggat | 840 |
| cggttggaag aactgaaaat gcaaaacatg aagaaagtga ttgaggcaat tcgagtggag | 900 |
| ctggttcagt actgggacca gtgcttttat agccaggagc agagacaagc ttttgcccct | 960 |
| ttctgtgctg aggactacac agaaagtctg ctccagctcc acgatgctga gattgtgcgg | 1020 |
| ttaaaaaact actatgaagt tcacaaggaa ctctttgaag tgtccagaa gtgggaagaa | 1080 |
| acctggaggc ttttcttaga gtttgagaga aaagcttcag atccaaatcg atttacaaac | 1140 |
| cgaggaggaa atcttctaaa agaagaaaaa caacgagcca agctccagaa atgctgccc | 1200 |
| aagctggaag aagagttgaa ggcacgaatt gaattgtggg aacaggaaca ttcaaaggca | 1260 |
| tttatggtga tgggcagaa attcatggag tatgtggcag aacaatggga gatgcatcga | 1320 |
| ttggagaaag agagagccaa gcaggaaaga caactgaaga caaaaaaaca gacagagaca | 1380 |
| gagatgctgt atggcagcgc tcctcgaaca cctagcaagc ggcgaggact ggctcccaat | 1440 |
| acaccgggca agcacgtaa gctgaacact accaccatgt ccaatgctac ggccaatagt | 1500 |
| agcattcggc ctatctttgg agggacagtc taccactccc ccgtgtctcg acttcctcct | 1560 |
| tctggcagca agccagtcgc tgcttccacc tgttcaggga agaaaacacc cgtactggc | 1620 |
| aggcatggag ccaacaagga gaacctggag ctcaacggca gcatcctgag tggtgggtac | 1680 |
| cctggctcgg ccccctcca gcgcaacttc agcattaatt ctgttgccag cacctattct | 1740 |

-continued

| | |
|---|---|
| gagtttgcga aggatccgtc cctctctgac agttccactg ttgggcttca gcgagaactt | 1800 |
| tcaaaggctt ccaaatctga tgctacttct ggaatcctca attcaaccaa catccagtcc | 1860 |
| tga | 1863 |

<210> SEQ ID NO 35
<211> LENGTH: 1164
<212> TYPE: DNA
<213> ORGANISM: Human

<400> SEQUENCE: 35

| | |
|---|---|
| atgaccacgc aactgggccc agccctggtg ctggggtgg ccctgtgcct gggttgtggc | 60 |
| cagcccctac acaggtccc tgaacgcccc ttctctgtgc tgtggaatgt accctcagca | 120 |
| cactgtgagg cccgctttgg tgtgcacctg ccactcaatg ctctgggcat catagccaac | 180 |
| cgtggccagc attttcacgg tcagaacatg accattttct acaagaacca actcggcctc | 240 |
| tatccctact ttggacccag ggcacagct cacaatgggg gcatccccca ggctttgccc | 300 |
| cttgaccgcc acctggcact ggctgcctac cagatccacc acagcctgag acctggcttt | 360 |
| gctggcccag cagtgctgga ttgggaggag tggtgtccac tctgggctgg aactggggc | 420 |
| cgccgccgag cttatcaggc agcctcttgg gcttgggcac agcaggtatt ccctgacctg | 480 |
| gaccctcagg agcagctcta caaggcctat actggctttg agcaggcggc ccgtgcactg | 540 |
| atggaggata cgctgcgggt ggcccaggca ctacggcccc atggactctg ggcttctat | 600 |
| cactacccag cctgtggcaa tggctggcat agtatggctt ccaactatac cggccgctgc | 660 |
| catgcagcca cccttgcccg caacactcaa ctgcattggc tctgggccgc ctccagtgcc | 720 |
| ctcttcccca gcatctacct cccacccagg ctgccacctg ccaccacca ggcctttgtc | 780 |
| cgacatcgcc tggaggaggc cttccgtgtg gcccttgttg ggcaccgaca tccctgcct | 840 |
| gtcctggcct atgtccgcct cacacaccgg agatctggga ggttcctgtc ccaggaggag | 900 |
| tgctggcatc tccatgacta cctggtggac accttgggcc ctatgtgat caatgtgacc | 960 |
| agggcagcga tggcctgcag tcaccagcgg tgccatggcc acgggcgctg tgcccggcga | 1020 |
| gatccaggac agatggaagc ctttctacac ctgtggccag acggcagcct ggagattgg | 1080 |
| aagtccttca gctgccactg ttactggggc tgggctggcc ccacctgcca ggagcccagg | 1140 |
| cctgggccta agaagcagt ataa | 1164 |

<210> SEQ ID NO 36
<211> LENGTH: 1389
<212> TYPE: DNA
<213> ORGANISM: Human

<400> SEQUENCE: 36

| | |
|---|---|
| atgaccacgc aactgggccc agccctggtg ctggggtgg ccctgtgcct gggttgtggc | 60 |
| cagcccctac acaggtccc tgaacgcccc ttctctgtgc tgtggaatgt accctcagca | 120 |
| cactgtgagg cccgctttgg tgtgcacctg ccactcaatg ctctgggcat catagccaac | 180 |
| cgtggccagc attttcacgg tcagaacatg accattttct acaagaacca actcggcctc | 240 |
| tatccctact ttggacccag ggcacagct cacaatgggg gcatccccca ggctttgccc | 300 |
| cttgaccgcc acctggcact ggctgcctac cagatccacc acagcctgag acctggcttt | 360 |
| gctggcccag cagtgctgga ttgggaggag tggtgtccac tctgggctgg aactggggc | 420 |
| cgccgccgag cttatcaggc agcctcttgg gcttgggcac agcaggtatt ccctgacctg | 480 |

| | |
|---|---:|
| gaccctcagg agcagctcta caaggcctat actggctttg agcaggcggc ccgtgcactg | 540 |
| atggaggata cgctgcgggt ggcccaggca ctacggcccc atggactctg gggcttctat | 600 |
| cactacccag cctgtggcaa tggctggcat agtatggctt ccaactatac cggccgctgc | 660 |
| catgcagcca cccttgcccg caacactcaa ctgcattggc tctgggccgc ctccagtgcc | 720 |
| ctcttcccca gcatctacct cccacccagg ctgccacctg ccaccacca ggcctttgtc | 780 |
| cgacatcgcc tggaggaggc cttccgtgtg gcccttgttg ggcaccgaca tccctgcct | 840 |
| gtcctggcct atgtccgcct cacacaccgg agatctggga ggttcctgtc ccaggatgac | 900 |
| cttgtgcagt ccattggtgt gagtgcagca ctaggggcag ccggcgtggt gctctggggg | 960 |
| gacctgagcc tctccagctc tgaggaggag tgctggcatc tccatgacta cctggtggac | 1020 |
| acctggggcc cctatgtgat caatgtgacc agggcagcga tggcctgcag tcaccagcgg | 1080 |
| tgccatggcc acgggcgctg tgcccggcga gatccaggac agatggaagc ctttctacac | 1140 |
| ctgtggccag acggcagcct ggagattgg aagtccttca gctgccactg ttactgggc | 1200 |
| tgggctggcc ccacctgcca ggagcccctg gcctaaaga agcagtataa agccagggcc | 1260 |
| cctgccactg cctcttcttt tccctgctgc cacttttcca gtcctggaac tactctgtcc | 1320 |
| cactcttgct ctattcagtt tacagtcaac cctcccaagc acacacccg cttcccttgg | 1380 |
| aatccctga | 1389 |

<210> SEQ ID NO 37
<211> LENGTH: 1254
<212> TYPE: DNA
<213> ORGANISM: Human

<400> SEQUENCE: 37

| | |
|---|---:|
| atgaccacgc aactgggccc agccctggtg ctggggtgg ccctgtgcct gggttgtggc | 60 |
| cagcccctac acaggtccc tgaacgcccc ttctctgtgc tgtggaatgt accctcagca | 120 |
| cactgtgagg cccgctttgg tgtgcacctg ccactcaatg ctctgggcat catagccaac | 180 |
| cgtggccagc attttcacgg tcagaacatg accattttct acaagaacca actcggcctc | 240 |
| tatccctact ttggacccag gggcacagct cacaatgggg gcatccccca ggctttgccc | 300 |
| cttgaccgcc acctggcact ggctgcctac cagatccacc acagcctgag acctggcttt | 360 |
| gctgccccag cagtgctgga ttgggaggag tggtgtccac tctgggctgg gaactggggc | 420 |
| cgccgccgag cttatcaggc agcctcttgg gcttgggcac agcaggtatt ccctgacctg | 480 |
| gaccctcagg agcagctcta caaggcctat actggctttg agcaggcggc ccgtgcactg | 540 |
| atggaggata cgctgcgggt ggcccaggca ctacggcccc atggactctg gggcttctat | 600 |
| cactacccag cctgtggcaa tggctggcat agtatggctt ccaactatac cggccgctgc | 660 |
| catgcagcca cccttgcccg caacactcaa ctgcattggc tctgggccgc ctccagtgcc | 720 |
| ctcttcccca gcatctacct cccacccagg ctgccacctg ccaccacca ggcctttgtc | 780 |
| cgacatcgcc tggaggaggc cttccgtgtg gcccttgttg ggcaccgaca tccctgcct | 840 |
| gtcctggcct atgtccgcct cacacaccgg agatctggga ggttcctgtc ccaggatgac | 900 |
| cttgtgcagt ccattggtgt gagtgcagca ctaggggcag ccggcgtggt gctctggggg | 960 |
| gacctgagcc tctccagctc tgaggaggag tgctggcatc tccatgacta cctggtggac | 1020 |
| acctggggcc cctatgtgat caatgtgacc agggcagcga tggcctgcag tcaccagcgg | 1080 |
| tgccatggcc acgggcgctg tgcccggcga gatccaggac agatggaagc ctttctacac | 1140 |
| ctgtggccag acggcagcct ggagattgg aagtccttca gctgccactg ttactgggc | 1200 |

```
tgggctggcc ccacctgcca ggagcccagg cctgggccta agaagcagt ataa         1254
```

<210> SEQ ID NO 38
<211> LENGTH: 1389
<212> TYPE: DNA
<213> ORGANISM: Human

<400> SEQUENCE: 38

```
atgggaaagg aaaagactca tatcaacatt gtcgtcattg acacgtaga ttcgggcaag    60
tccaccacta ctggccatct gatctataaa tgcggtggca tcgacaaaag aaccattgaa   120
aaatttgaga aggaggctgc tgagatggga aagggctcct tcaagtatgc ctgggtcttg   180
gataaactga agctgagcg tgaacgtggt atcaccattg atatctcctt gtggaaattt   240
gagaccagca agtactatgt gactatcatt gatgccccag acacagaga cttcatcaaa   300
aacatgatta caggacatc tcaggctgac tgtgctgtcc tgattgttgc tgctggtgtt   360
ggtgaatttg aagctggtat ctccaagaat gggcagaccc gagagcatgc ccttctggct   420
tacacactgg gtgtgaaaca actaattgtc ggtgttaaca aaatggattc cactgagcca   480
ccctacagcc agaagagata tgaggaaatt gttaaggaag tcagcactta cattaagaaa   540
attggctaca ccccgacac agtagcattt gtgccaattt ctggttggaa tggtgacaac   600
atgctggagc aagtgctaa catgccttgg ttcaagggat ggaaagtcac ccgtaaggat   660
ggcaatgcca gtggaaccac gctgcttgag gctctggact gcatcctacc accaactcgc   720
ccaactgaca agcccttgcg cctgcctctc caggatgtct acaaaattgg tggtattggt   780
actgttcctg ttggccgagt ggagactggt gttctcaaac ccggtatggt ggtcaccttt   840
gctccagtca cgttacaac ggaagtaaaa tctgtcgaaa tgcaccatga agctttgagt   900
gaagctcttc ctggggacaa tgtgggcttc aaggtcaaga atgtgtctgt caaggatgtt   960
cgtcgtggca cgttgctgg tgacagcaaa aatgacccac caatggaagc agctggcttc  1020
actgctcagg tgattatcct gaaccatcca ggccaaataa gcgccggcta tgcccctgta  1080
ttggattgcc acatggctca cattgcatgc aagtttgctg agctgaagga aaagattgat  1140
cgccgttctg gtaaaaagct ggaagatggc cctaaattct gaagtctgg tgatgctgcc  1200
attgttgata tggttcctgg caagcccatg tgtgttgaga gcttctcaga ctatccacct  1260
ttgggtcgct ttgctgttcg tgatatgaga cagacagttg cggtgggtgt catcaaagca  1320
gtggacaaga aggctgctgg agctggcaag gtcaccaagt ctgcccagaa agctcagaag  1380
gctaaatga                                                          1389
```

<210> SEQ ID NO 39
<211> LENGTH: 1146
<212> TYPE: DNA
<213> ORGANISM: Human

<400> SEQUENCE: 39

```
atggccctaa aggccgaggg cgccgcactc gactgcttcg aggtgacgct gaaatgcgag    60
gaagggagg acgaggagga ggccatggtg gtggccgtaa ttccgcggcc cgagccgatg   120
ctcagagtga cccaacagga gaagacccca ccgcctagac ccagcccgct agaggcaggc   180
agtgatggct gtgaggagcc gaagcagcag gtgtcttggg agcaggagtt cctggtgggc   240
agcagcccag gaggcagcgg gcgggcactg tgcatggtgt gtggcgctga gatccgggca   300
ccctcggccg acacagctcg ctcgcacatc ttggagcagc accctcacac cttggacctg   360
```

| | |
|---|---|
| agcccttctg agaagagcaa tatcctggag gcctggagtg aaggggtggc cctcttgcaa | 420 |
| gacgtgagag ctgagcagcc gtccccaccc aactcagact cgggccagga tgcccaccca | 480 |
| gacccagacg ccaacccaga cgctgccaga atgccagccg aaatcgtcgt tctccttgac | 540 |
| tctgaggata acccatccct ccctaaaagg agccggccca gggactccg cccctcgag | 600 |
| cttcctgctg tccctgccac agagccagga aataagaagc cccgtggtca gagatggaag | 660 |
| gaacccccag gggaagagcc agtcagaaag aaaagaggca gacctatgac caaaaacctg | 720 |
| gaccctgacc cagagccccc atcgccagac tcgcccacgg agactttcgc agcaccagcc | 780 |
| gaggtccgac acttcactga cggcagcttc cccgccggct tcgtcttgca gctcttctcc | 840 |
| cacacccagc tcaggggccc agacagcaag gactcaccca agacaggga agtggcagaa | 900 |
| ggaggccttc cccgggcgga gagcccctct ccagctcccc ctccggggct ccgcgggaca | 960 |
| ctggatctcc aggttatccg cgtgcggatg gaggagcccc cagcggtcag cctcctgcaa | 1020 |
| gactggtcca gcaccccca gggcaccaag cgtgtgggag caggtgacac ctcagactgg | 1080 |
| cccacagttc tgtcagaatc cagcaccact gtggcaggga agccggaaaa agggaatgga | 1140 |
| gtgtaa | 1146 |

<210> SEQ ID NO 40
<211> LENGTH: 5730
<212> TYPE: DNA
<213> ORGANISM: Human

<400> SEQUENCE: 40

| | |
|---|---|
| atgagcacac acaggagccg tctcctcacc gccgccctc tcagcatgga acagaggcgg | 60 |
| ccctggcccc gggccctgga ggtggacagc cgctctgtgg tcctgctctc agtggtctgg | 120 |
| gtgctgctgg ccccccagc agccggcatg cctcagttca gcaccttcca ctctgagaat | 180 |
| cgtgactgga ccttcaacca cttgaccgtc caccaaggga cggggccgt ctatgtgggg | 240 |
| gccatcaacc gggtctataa gctgacaggc aacctgacca tccaggtggc tcataagaca | 300 |
| gggccagaag aggacaacaa gtcttgttac ccgcccctca tcgtgcagcc ctgcagcgaa | 360 |
| gtgctcaccc tcaccaacaa tgtcaacaag ctgctcatca ttgactactc tgagaaccgc | 420 |
| ctgctggcct gtgggagcct ctaccagggg gtctgcaagc tgctgcggct ggatgacctc | 480 |
| ttcatcctgg tggagccatc ccacaagaag gagcactacc tgtccagtgt caacaagacg | 540 |
| ggcaccatgt acgggtgat tgtgcgctct gagggtgagg atgcaagct cttcatcggc | 600 |
| acggctgtgg atgggaagca ggattacttc ccgaccctgt ccagccggaa gctgccccga | 660 |
| gaccctgagt cctcagccat gctcgactat gagctacaca gcgattttgt ctcctctctc | 720 |
| atcaagatcc cttcagacac cctggccctg gtctcccact ttgacatctt ctacatctac | 780 |
| ggctttgcta gtgggggctt tgtctacttt ctcactgtcc agcccgagac cctgagggt | 840 |
| gtggccatca actccgctgg agacctcttc tacctcac gcatcgtgcg gctctgcaag | 900 |
| gatgacccca agttccactc atacgtgtcc ctgcccttcg gctgcacccg gccggggtg | 960 |
| gaataccgcc tcctgcaggc tgcttacctg gccaagcctg ggactcact ggcccaggcc | 1020 |
| ttcaatatca ccagccagga cgatgtactc tttgccatct ctccaaagg gcagaagcag | 1080 |
| tatcaccacc cgcccgatga ctctgccctg tgtgccttcc ctatccgggc catcaacttg | 1140 |
| cagatcaagg agcgcctgca gtcctgctac caggcgagg gcaacctgga gctcaactgg | 1200 |
| ctgctgggga aggacgtcca gtgcaccaag gcgcctgtcc ccatcgatga taacttctgt | 1260 |
| ggactggaca tcaaccagcc cctgggaggc tcaactccag tggagggcct gacctgtac | 1320 |

```
accaccagca gggaccgcat gacctctgtg gcctcctacg tttacaacgg ctacagcgtg    1380
gtttttgtgg ggactaagag tggcaagctg aaaaagattc gggccgacgg tcccccccat    1440
ggtggggtcc agtacgagat ggtctctgtg ctcaaggacg gaagcccat cctccgggac     1500 atggccttct ccattgatca cgctacctg tacgtcatgt ctgagagaca ggtcaccagg     1560
gtccccgtgg agtcatgtga gcagtatacg acttgtgggg agtgcctgag ctctggggac    1620
cctcactgtg gctggtgtgc cctgcacaac atgtgctccc gcagggacaa atgccaacag    1680
gcctgggaac ctaatcgatt tgctgccagc atcagccagt gtgtgagcct gcagtgcat    1740 cccagcagca tctcagtatc tgagcacagc cggttgctta gctggtagt gagtgatgct     1800 cctgatctat ctgcgggtat cgcctgtgcc tttgggaacc tgacagaggt ggaggggcag    1860
gtgtccggga gccaggtcat ctgcatctca cctgggccca aggatgtccc tgtcatcccg    1920
ctggatcaag actggtttgg gctggagcta cagctgaggt ccaaggagac agggaagata    1980
tttgtcagca ccgagttcaa gttttacaac tgcagtgccc accaactgtg cctgtcctgt    2040
gtcaacagcg ccttccgctg ccattggtgc aagtaccgca acctctgcac tcatgacccc    2100
accacctgct ccttccagga gggccggatc aatatttcag aggactgtcc ccagctggtg    2160
cccacagagg agatcttgat tccagtcggg gaggtaaagc caatcaccct taaggcgcga    2220
aatctgcccc agccgcagtc cggccagcga ggctatgagt gtgtcctcaa catacaagga    2280
gccatccacc gggtccccgc tctgcgcttc aacagctcca gcgttcagtg tcagaacagc    2340
tcgtaccagt atgatggcat ggacatcagc aatctggccg tggatttcgc gtggtgtgg    2400 aacggcaatt tcatcattga caaccctcag gacctgaaag tccatctcta caagtgtgca    2460
gcccagcggg agagctgcgg cctctgcctc aaggccgacc ggaagtttga gtgtggctgg    2520
tgcagcggcg agcgcaggtg caccctccac cagcactgta ccagcccttc cagcccctgg    2580
ctcgactggt ccagccacaa tgtcaagtgc tccaaccctc aaatcaccga gattttgacg    2640
gtgtctggac cgccggaagg agggacgcga gtgaccatcc atggcgtgaa cctgggtctg    2700
gacttctccg agatcgccca ccatgtgcag gtggctgggg tgcctgcac gcccctccca    2760 ggggaataca tcatcgctga gcagattgtc tgtgagatgg ccatgccct cgtgggaacc    2820 acctccgggc cagtacgcct gtgtattggc gagtgtaagc cagagttcat gacgaagtcc    2880
catcagcagt acaccttcgt gaaccttct gtgctgtcac tcaacccaat ccgaggtccc    2940
gagtcaggag gcactatggt gaccattacc ggccattacc ttggggctgg gagcagcgtg    3000
gcagtctacc tgggcaacca gacctgcgag ttctacggga ggtcaatgag tgagatcgtg    3060
tgtgtctcac ccccatcatc caatggcctt ggcccggtcc ctgtttctgt gagtgtcgac    3120
cgagcccatg tggatagcaa cctgcagttt gagtacatag atgaccctcg ggtccagcgc    3180
atcgagccag agtggagcat tgccagtggc cacacacccc tgaccatcac aggcttcaac    3240
ctggatgtca ttcaggagcc aaggatccga gtcaaattca atggcaaaga atctgtcaat    3300
gtgtgtaaag ttgtgaacac aaccaccctc acctgcctgg caccctctct gaccacggac    3360
taccgccctg gcctggacac tgtggaacgc ccagatgagt ttggatttgt ctttaacaat    3420
gtccaatcct tgctaatttta caacgacacc aagtttatct actaccccaa cccgaccttt    3480
gaactgctta gcctactgg agtcttggat caaaagccag atcgcccat cattctgaag    3540 ggcaaaaacc tctgccctcc tgcctctgga ggggccaaac tcaactacac tgtgctcatc    3600
ggagagaccc cttgtgctgt caccgtatct gagacccagc ttctctgcga gcctcccaac    3660
```

-continued

| | |
|---|---|
| ctcaccgggc agcacaaggt catggttcac gtgggcggga tggtgttctc gcctggctcg | 3720 |
| gtgagtgtca tctcagacag cttgctgacc ctgccagcca tcgtcagcat cgcggccggc | 3780 |
| ggcagcctcc tcctcatcat cgtcatcatc gtcctcattg cctacaagcg caagtctcga | 3840 |
| gaaaatgacc tcactctcaa gcggctgcaa atgcagatgg acaatctgga gtcccgtgtg | 3900 |
| gccttggagt gcaaggaagc ttttgctgag ctccagacgg atatcaatga gttgaccagt | 3960 |
| gacctggacc gctcaggaat cccttacctg gactatcgta cctacgctat gcgagtcctg | 4020 |
| ttcccgggca tcgaggacca ccccgtcctg cgggagctgg aggtacaagg aaacgggcag | 4080 |
| cagcacgtgg agaaggccct gaagctcttt gcccagctca tcaacaacaa ggtgttcctg | 4140 |
| ctgaccttca tccgcaccct ggagctgcag cgcagtttct ccatgcgcga ccggggcaac | 4200 |
| gtggcttcgc tcatcatgac cggcctgcag ggccgcctgg aatatgccac tgatgtcctc | 4260 |
| aagcagctgc tctctgacct catcgataag aacctggaga caagaaccac ccccaagctg | 4320 |
| ctactccgga ggacagagtc tgtggctgaa aagatgctga ccaattggtt cgccttcctc | 4380 |
| ctgcacaagt tcctaaagga gtgcgcaggg gagccactct tcatgctata ctgtgccatc | 4440 |
| aagcagcaga tggagaaggg ccccattgat gccatcacgg gcgaggcccg ctactccctg | 4500 |
| agcgaggaca agctcatccg gcagcagatc gagtacaaga ccctgatcct gaactgcgtc | 4560 |
| aaccctgaca acgagaacag tccagagatc ccagtgaagg tgttaaactg tgacaccatc | 4620 |
| acacaggtca aggagaagat tcttgatgcc gtgtataaga atgtgcccta ttcccagcgg | 4680 |
| ccgagggcag tggacatgga cttggagtgg cgccaaggcc ggatcgcccg ggtcgtgctg | 4740 |
| caagatgagg acatcaccac caagattgag ggtgactgga gcggctcaa cacactgatg | 4800 |
| cattatcagg tgtcagacag gtcggtggtg gctctggtcc ccaaacagac ctcctcctac | 4860 |
| aacatccctg cctctgccag catctcccgg acgtccatca gcagatacga ctcctccttc | 4920 |
| aggtatacgg gcagccccga cagcctgcgg tcccgggccc cgatgatcac cccagacctg | 4980 |
| gaaagtgggg tcaaggtgtg gcatctggtg aagaaccatg accacggtga ccagaaggag | 5040 |
| ggtgaccggg gcagcaagat ggtgtccgag atctacctga cccggctact ggccaccaag | 5100 |
| ggcaccctgc agaagtttgt ggacgacttg tttgagacct tgttcagcac tgtgcaccgg | 5160 |
| ggcagcgctc tcccccctggc catcaagtac atgtttgatt cctagatga gcaggcagac | 5220 |
| aggcacagca tccatgacac agatgtgcgg cacacctgga aaagcaactg cctccctctg | 5280 |
| cgcttctggg tgaacgtgat taagaacccc cagttcgtgt ttgacatcca caagggcagc | 5340 |
| atcacggacg cctgcctctc tgtggtggcc cagaccttca tggactcttg ttcaacgtca | 5400 |
| gagcaccggc tgggcaagga ctccccctcc aacaagctgc tctatgccaa ggacatcccc | 5460 |
| agctacaaga gctgggtgga gagatactac gcagacatcg ccaagctccc agccatcagt | 5520 |
| gaccaggaca tgaatgccta cctcgccgag cagtcccgcc tgcacgccgt ggagttcaac | 5580 |
| atgctgagtg ccctcaatga gatctactcc tatgtcagca gtatagtgga ggagctcatc | 5640 |
| ggggccctag agcaggatga gcaggcacgg cggcagcggc tggcttataa ggtggagcag | 5700 |
| ctcattaatg ccatgtccat tgagagctga | 5730 |

<210> SEQ ID NO 41
<211> LENGTH: 5685
<212> TYPE: DNA
<213> ORGANISM: Human

<400> SEQUENCE: 41

| | |
|---|---|
| atggaacaga ggcggccctg gccccggggcc ctggaggtgg acagccgctc tgtggtcctg | 60 |

```
ctctcagtgg tctgggtgct gctggccccc ccagcagccg gcatgcctca gttcagcacc      120
ttccactctg agaatcgtga ctggaccttc aaccacttga ccgtccacca agggacgggg      180
gccgtctatg tgggggccat caaccgggtc tataagctga caggcaacct gaccatccag      240
gtggctcata agacagggcc agaagaggac aacaagtctt gttacccgcc cctcatcgtg      300
cagccctgca gcgaagtgct caccctcacc aacaatgtca acaagctgct catcattgac      360
tactctgaga accgcctgct ggcctgtggg agcctctacc aggggtctg caagctgctg       420 cggctggatg acctcttcat cctggtggag ccatcccaca agaaggagca ctacctgtcc      480
agtgtcaaca agacgggcac catgtacggg gtgattgtgc gctctgaggg tgaggatggc      540
aagctcttca tcggcacggc tgtggatggg aagcaggatt acttcccgac cctgtccagc      600
cggaagctgc cccgagaccc tgagtcctca gccatgctcg actatgagct acacagcgat      660
tttgtctcct ctctcatcaa gatcccttca gacaccctgg ccctggtctc ccactttgac      720
atcttctaca tctacggctt tgctagtggg ggctttgtct actttctcac tgtccagccc      780
gagacccctg agggtgtggc catcaactcc gctggagacc tcttctacac ctcacgcatc      840
gtgcggctct gcaaggatga cccccaagttc cactcatacg tgtccctgcc cttcggctgc      900
acccgggccg gggtggaata ccgcctcctg caggctgctt acctggccaa gcctggggac      960
tcactggccc aggccttcaa tatcaccagc caggacgatg tactctttgc catcttctcc      1020
aaagggcaga agcagtatca ccacccgccc gatgactctg ccctgtgtgc cttccctatc      1080
cgggccatca acttgcagat caaggagcgc ctgcagtcct gctaccaggg cgagggcaac      1140
ctggagctca actggctgct ggggaaggac gtccagtgca ccaaggcgcc tgtccccatc      1200
gatgataact tctgtggact ggacatcaac cagcccctgg gaggctcaac tccagtggag      1260
ggcctgaccc tgtacaccac cagcagggac cgcatgacct ctgtggcctc ctacgtttac      1320
aacggctaca gcgtggtttt tgtggggact aagagtggca agctgaaaaa gattcgggcc      1380
gacggtcccc cccatggtgg ggtccagtac gagatggtct ctgtgctcaa ggacggaagc      1440
cccatcctcc gggacatggc cttctccatt gatcagcgct acctgtacgt catgtctgag      1500
agacaggtca ccagggtccc cgtggagtca tgtgagcagt atacgacttg tggggagtgc      1560
ctgagctctg ggaccctca ctgtggctgg tgtgccctgc acaacatgtg ctcccgcagg      1620
gacaaatgcc aacaggcctg gaacctaat cgatttgctg ccagcatcag ccagtgtgtg      1680
agccttgcag tgcatcccag cagcatctca gtatctgagc acagccggtt gcttagcctg      1740
gtagtgagtg atgctcctga tctatctgcg ggtatcgcct gtgcctttgg gaacctgaca      1800
gaggtggagg ggcaggtgtc cgggagccag gtcatctgca tctcacctgg gcccaaggat      1860
gtccctgtca tcccgctgga tcaagactgg tttgggctgg agctacagct gaggtccaag      1920
gagacaggga agatatttgt cagcaccgag ttcaagtttt acaactgcag tgcccaccaa      1980
ctgtgcctgt cctgtgtcaa cagcgccttc gctgccatt ggtgcaagta ccgcaacctc       2040
tgcactcatg accccaccac ctgctcctc caggagggcc ggatcaatat ttcagaggac       2100
tgtccccagc tggtgcccac agaggagatc ttgattccag tcggggaggt aaagccaatc      2160 accccttaagg cgcgaaatct gccccagccg cagtccggcc agcgaggcta tgagtgtgtc      2220
ctcaacatac aaggagccat ccaccgggtc cccgctctgc gcttcaacag ctccagcgtt     2280
cagtgtcaga acagctcgta ccagtatgat ggcatggaca tcagcaatct ggccgtggat     2340
ttcgctgtgg tgtggaacgg caatttcatc attgacaacc ctcaggacct gaaagtccat     2400
```

```
ctctacaagt gtgcagccca gcgggagagc tgcggcctct gcctcaaggc cgaccggaag    2460
tttgagtgtg gctggtgcag cggcgagcgc aggtgcaccc tccaccagca ctgtaccagc    2520
ccttccagcc cctggctcga ctggtccagc acaatgtca agtgctccaa ccctcaaatc    2580
accgagattt tgacggtgtc tggaccgccg aaggaggga cgcgagtgac catccatggc    2640
gtgaacctgg gtctggactt ctccgagatc gcccaccatg tgcaggtggc tggggtgccc    2700
tgcacgcccc tcccagggga atacatcatc gctgagcaga ttgtctgtga gatgggccat    2760
gccctcgtgg gaaccacctc cgggccagta cgcctgtgta ttggcgagtg taagccagag    2820
ttcatgacga agtcccatca gcagtacacc ttcgtgaacc cttctgtgct gtcactcaac    2880
ccaatccgag gtcccgagtc aggaggcact atggtgacca ttaccggcca ttaccttggg    2940
gctgggagca gcgtggcagt ctacctgggc aaccagacct gcgagttcta cgggaggtca    3000
atgagtgaga tcgtgtgtgt ctcaccccca tcatccaatg gccttggccc ggtccctgtt    3060
tctgtgagtg tcgaccgagc ccatgtggat agcaacctgc agtttgagta catagatgac    3120
cctcgggtcc agcgcatcga gccagagtgg agcattgcca gtggccacac accccctgacc    3180
atcacaggct tcaacctgga tgtcattcag gagccaagga tccgagtcaa attcaatggc    3240
aaagaatctg tcaatgtgtg taaagttgtg aacacaacca ccctcacctg cctggcaccc    3300
tctctgacca cggactaccg ccctggcctg gacactgtgg aacgcccaga tgagtttgga    3360
tttgtcttta caatgtcca atccttgcta atttacaacg acaccaagtt tatctactac    3420
cccaacccga cctttgaact gcttagccct actggagtct ggatcaaaaa gccaggatcg    3480
cccatcattc tgaagggcaa aaacctctgc cctcctgcct ctggaggggc caaactcaac    3540
tacactgtgc tcatcggaga gacccccttgt gctgtcaccg tatctgagac ccagcttctc    3600
tgcgagcctc ccaacctcac cgggcagcac aaggtcatgg ttcacgtggg cgggatggtg    3660
ttctcgcctg gctcggtgag tgtcatctca gacagcttgc tgaccctgcc agccatcgtc    3720
agcatcgcgg ccggcggcag cctcctcctc atcatcgtca tcatcgtcct cattgcctac    3780
aagcgcaagt ctcgagaaaa tgacctcact ctcaagcggc tgcaaatgca gatggacaat    3840
ctggagtccc gtgtggcctt ggagtgcaag gaagcttttg ctgagctcca gacggatatc    3900
aatgagttga ccagtgacct ggaccgctca ggaatcccctt acctggacta tcgtacctac    3960
gctatgcgag tcctgttccc gggcatcgag gaccaccccg tcctgcggga gctgaggta    4020
caaggaaacg ggcagcagca cgtggagaag gccctgaagc tctttgccca gctcatcaac    4080
aacaaggtgt tcctgctgac cttcatccgc ccccctggagc tgcagcgcag tttctccatg    4140
cgcgaccggg gcaacgtggc ttcgctcatc atgaccggcc tgcagggccg cctggaatat    4200
gccactgatg tcctcaagca gctgctctct gacctcatcg ataagaacct ggagaacaag    4260
aaccacccca gctgctact ccggaggaca gagtctgtgg ctgaaaagat gctgaccaat    4320
tggttcgcct tcctcctgca caagttccta aaggagtgcg caggggagcc actcttcatg    4380
ctatactgtg ccatcaagca gcagatggag aagggcccca ttgatgccat cacgggcgag    4440
gcccgctact ccctgagcga ggacaagctc atccggcagc agatcgagta caagaccctg    4500
atcctgaact cgtcaacccc tgacaacgag aacagtccag agatcccagt gaaggtgtta    4560
aactgtgaca ccatcacaca ggtcaaggag aagattcttg atgccgtgta taagaatgtg    4620
ccctattccc agcggccgag ggcagtggac atggacttgg agtggcgcca aggccggatc    4680
gcccgggtcg tgctgcaaga tgaggacatc accaccaaga ttgagggtga ctggaagcgg    4740
ctcaacacac tgatgcatta tcaggtgtca gacaggtcgg tggtggctct ggtccccaaa    4800
```

```
cagacctcct cctacaacat ccctgcctct gccagcatct cccggacgtc catcagcaga    4860
tacgactcct ccttcaggta tacgggcagc cccgacagcc tgcggtcccg ggcccccgatg   4920 atcaccccag acctggaaag tggggtcaag gtgtggcatc tggtgaagaa ccatgaccac    4980
ggtgaccaga aggagggtga ccggggcagc aagatggtgt ccgagatcta cctgacccgg    5040
ctactggcca ccaagggcac cctgcagaag tttgtggacg acttgtttga gaccttgttc    5100
agcactgtgc accggggcag cgctctcccc ctggccatca agtacatgtt tgatttccta    5160
gatgagcagg cagacaggca cagcatccat gacacagatg tgcggcacac ctggaaaagc    5220
aactgcctcc ctctgcgctt ctgggtgaac gtgattaaga accccagtt cgtgtttgac     5280 atccacaagg gcagcatcac ggacgcctgc ctctctgtgg tggcccagac cttcatggac    5340
tcttgttcaa cgtcagagca ccggctgggc aaggactccc cctccaacaa gctgctctat    5400
gccaaggaca tccccagcta caagagctgg gtggagagat actacgcaga catcgccaag    5460
ctcccagcca tcagtgacca ggacatgaat gcctacctcg ccgagcagtc ccgcctgcac    5520
gccgtggagt tcaacatgct gagtgccctc aatgagatct actcctatgt cagcaagtat    5580
agtgaggagc tcatcggggc cctagagcag gatgagcagg cacggcggca gcggctggct    5640
tataaggtgg agcagctcat taatgccatg tccattgaga gctga                    5685
```

<210> SEQ ID NO 42
<211> LENGTH: 2163
<212> TYPE: DNA
<213> ORGANISM: Human

<400> SEQUENCE: 42

```
atgccaccac cgtcagacat tgtcaaagtg gccattgagt ggccaggtgc taacgcccag      60
ctccttgaaa tcgaccagaa acggcccctg gcatccatta tcaaggaagt ttgtgatggg     120
tggtcgttgc caaacccaga gtattatacc ctccgttatg cagatggtcc tcagctgtac    180
atcaccgaac agactcgcag tgacattaag aatgggacaa tcttacaact ggctatctcc    240
ccgtcccggg ctgcacgcca gctgatggag aggacccagt catccaacat ggagacccgg    300
ctggatgcca tgaaggagct ggccaagctc tctgccgacg tgactttcgc tactgagttc    360
atcaacatgg atggcatcat tgtgctgaca aggctcgtgg aaagtggaac caagctcttg    420
tcccactaca gtgagatgct ggcattcacc ctgactgcct tcctagagct catggaccat    480
ggcattgtct cctgggacat ggtttcaatc accctttatta gcagattgc agggtatgtg    540 agccagccca tggtggacgt gtcaatcctt cagaggtccc tggccatcct ggagagcatg    600
gtcttgaaca gccagagtct gtaccagaag atagccgagg aaatcaccgt gggacagctc    660
atctcacacc tccaggtctc caaccaggag attcagacct acgccattgc actgattaat    720 gcacttttc tgaaggctcc tgaggacaaa cgacaggata tggcaaatgc atttgcacag    780
aagcatctcc ggtctataat cctgaatcat gtgatccgag ggaaccgccc catcaaaact    840
gagatggccc atcagctata tgtccttcaa gtcctaacct ttaaccttct ggaagaaagg    900
atgatgacca agatggaccc caatgaccag gctcaaaggg acatcatatt tgaactgagg    960
aggattgcat ttgacgcaga gtctgatcct agcaatgccc ctgggagtgg gaccgaaaaa    1020
cgcaaagcca tgtacacaaa ggactacaaa atgctgggat taccaaccca tcaatccca    1080 gccatggact ttacccagac tcctcctgga atgctggcct tggacaacat gctgtacttg    1140
gctaaagtcc accaggacac ctacatccgg attgtcttgg agaacagtag ccgggaagac    1200
```

```
aaacatgaat gccnctttgg ccgcagtgcc attgagctca ccaaaatgct ctgtgaaatc    1260
ctgcaggttg gggaactacc aaatgaagga cgcaatgact accacccgat gttctttacc    1320
catgaccgag cctttgaaga gctctttgga atctgcatcc agctgttgaa caagacctgg    1380
aaggagatga gggcaacagc agaggacttc aacaaggtta tgcaagtcgt ccgagagcaa    1440
atcactcgag ctttgccctc caaacccaac tctttggatc agttcaagag caaattgcgt    1500
agcctgagtt actctgagat tctacgactg cgccagtctg agaggatgag tcaggatgac    1560
ttccagtccc cgccaattgt ggagctgagg gagaagatcc agcccgagat ccttgagctg    1620
atcaagcagc agcgcctgaa ccggctctgt gagggcagca gcttccgaaa gattgggaac    1680
cgccgaaggc aagaacggtt ctggtactgc cggttggcac tgaaccacaa ggtccttcac    1740
tatggtgact tggatgacaa cccacaaggg gaggtgacat ttgaatccct gcaggagaaa    1800
attcctgttg cagacattaa ggccattgtc actgggaaag attgtcccca catgaaagag    1860
aaaagtgctc tgaaacagaa caaggaggtg ttggaattgg ccttctccat cctgtatgac    1920
cctgatgaga ccttaaactt catcgcacct aataaatatg agtactgcat ctggattgat    1980
ggcctcagtg cccttctggg aaggacatg tccagtgagc tgaccaagag tgacctggac    2040
accctgctga gcatggagat gagctgcgg ctcctggacc tggagaacat ccagattccc    2100
gaagccccac cccccatccc caaggagccc agcagctatg actttgtcta tcactatggc    2160
tga                                                                  2163

<210> SEQ ID NO 43
<211> LENGTH: 2163
<212> TYPE: DNA
<213> ORGANISM: Human

<400> SEQUENCE: 43
atgccaccac cgtcagacat tgtcaaagtg gccattgagt ggccaggtgc taacgcccag      60
ctccttgaaa tcgaccagaa acggcccctg gcatccatta tcaaggaagt ttgtgatggg     120
tggtcgttgc caaacccaga gtattatacc ctccgttatg cagatggtcc tcagctgtac     180
atcaccgaac agactcgcag tgacattaag aatgggacaa tcttacaact ggctatctcc     240
ccgtcccggg ctgcacgcca gctgatggag aggacccagt catccaacat ggagacccgg     300
ctggatgcca tgaaggagct ggccaagctc tctgccgacg tgactttcgc tactgagttc     360
atcaacatgg atggcatcat tgtgctgaca aggctcgtgg aaagtggaac caagctcttg     420
tcccactaca gtgagatgct ggcattcacc ctgactgcct tcctagagct catgaccat     480 ggcattgtct cctgggacat ggtttcaatc acctttatta gcagattgc agggtatgtg     540 agccagccca tggtggacgt gtcaatcctt cagaggtccc tggccatcct ggagagcatg     600
gtcttgaaca gccagagtct gtaccagaag atagccgagg aaatcaccgt gggacagctc     660
atctcacacc tccaggtctc caaccaggag attcagacct acgccattgc actgattaat     720
gcactttttc tgaaggctcc tgaggacaaa cgacaggata tggcaaatgc atttgcacag     780
aagcatctcc ggtctataat cctgaatcat gtgatccgag ggaaccgccc catcaaaact     840
gagatggccc atcagctata tgtccttcaa gtcctaacct taaccttct ggaagaaagg     900 atgatgacca agatggaccc caatgaccag gctcaaaggg acatcatatt tgaactgagg    960
aggattgcat ttgacgcaga gtctgatcct agcaatgccc tgggagtgg accgaaaaa    1020 cgcaaagcca tgtacacaaa ggactacaaa atgctgggat ttaccaacca catcaatcca    1080
gccatggact ttacccagac tcctcctgga atgctggcct tggacaacat gctgtacttg    1140
```

```
gctaaagtcc accaggacac ctacatccgg attgtcttgg agaacagtag ccgggaagac    1200
aaacatgaat gccccttggg ccgcagtgcc attgagctca ccaaaatgct ctgtgaaatc    1260
ctgcaggttg ggaactacc aaatgaagga cgcaatgact accacccgat gttctttacc     1320
catgaccgag cctttgaaga gctctttgga atctgcatcc agctgttgaa caagacctgg    1380
aaggagatga gggcaacagc agaggacttc aacaaggtta tgcaagtcgt ccgagagcaa    1440
atcactcgag ctttgccctc caaacccaac tctttggatc agttcaagag caaattgcgt    1500
agcctgagtt actctgagat tctacgactg cgccagtctg agaggatgag tcaggatgac    1560
ttccagtccc cgccaattgt ggagctgagg agaagatcc agcccgagat ccttgagctg     1620
atcaagcagc agcgcctgaa ccggctctgt gagggcagca gcttccgaaa gattgggaac    1680
cgccgaaggc aagaacggtt ctggtactgc cggttggcac tgaaccacaa ggtccttcac    1740
tatggtgact tggatgacaa cccacaaggg gaggtgacat ttgaatccct gcaggagaaa    1800
attcctgttg cagacattaa ggccattgtc actgggaaag attgtcccca catgaaagag    1860
aaaagtgctc tgaaacagaa caaggaggtg ttggaattgg ccttctccat cctgtatgac    1920
cctgatgaga ccttaaactt catcgcacct aataaatatg agtactgcat ctggattgat    1980
ggcctcagtg cccttctggg gaaggacatg tccagtgagc tgaccaagag tgacctggac    2040
accctgctga gcatggagat gaagctgcgg ctcctggacc tggagaacat ccagattccc    2100
gaagccccac cccccatccc caaggagccc agcagctatg actttgtcta tcactatggc    2160
tga                                                                  2163

<210> SEQ ID NO 44
<211> LENGTH: 1899
<212> TYPE: DNA
<213> ORGANISM: Human

<400> SEQUENCE: 44
atggagagga cccagtcatc caacatggag acccggctgg atgccatgaa ggagctggcc      60
aagctctctg ccgacgtgac tttcgctact gagttcatca acatggatgg catcattgtg     120
ctgacaaggc tcgtggaaag tggaaccaag ctccttgtcc actacagtga gatgctggca    180
ttcaccctga ctgccttcct agagctcatg gaccatggca ttgtctcctg ggacatggtt    240
tcaatcacct ttattaagca gattgcaggg tatgtgagcc agcccatggt ggacgtgtca    300
atccttcaga ggtccctggc catcctggag agcatggtct tgaacagcca gagtctgtac    360
cagaagatag ccgaggaaat caccgtggga cagctcatct cacacctcca ggtctccaac    420
caggagattc agacctacgc cattgcactg attaatgcac tttttctgaa ggctcctgag    480
gacaaacgac aggatatggc aaatgcattt gcacagaagc atctccggtc tataatcctg    540
aatcatgtga tccgagggaa ccgccccatc aaaactgaga tggcccatca gctatatgtc    600
cttcaagtcc taacctttaa ccttctggaa gaaaggatga tgaccaagat ggaccccaat    660
gaccaggctc aaagggacat catatttgaa ctgaggagga ttgcatttga cgcagagtct    720
gatcctagca atgcccctgg gagtgggacc gaaaaacgca aagccatgta cacaaaggac    780
tacaaaatgc tgggatttac caaccacatc aatccagcca tggactttac ccagactcct    840
cctggaatgc tggccttgga caacatgctg tacttggcta aagtccacca ggacacctac    900
atccggattc tcttggagaa cagtagccgg aagacaaac atgaatgccc ctttggccgc    960
agtgccattg agctcaccaa aatgctctgt gaaatcctgc aggttgggga actaccaaat    1020
```

```
gaaggacgca atgactacca cccgatgttc tttacccatg accgagcctt tgaagagctc   1080
tttggaatct gcatccagct gttgaacaag acctggaagg agatgagggc aacagcagag   1140
gacttcaaca aggttatgca agtcgtccga gagcaaatca ctcgagcttt gccctccaaa   1200
cccaactctt tggatcagtt caagagcaaa ttgcgtagcc tgagttactc tgagattcta   1260
cgactgcgcc agtctgagag gatgagtcag gatgacttcc agtccccgcc aattgtggag   1320
ctgagggaga agatccagcc cgagatcctt gagctgatca agcagcagcg cctgaaccgg   1380
ctctgtgagg gcagcagctt ccgaaagatt gggaaccgcc gaaggcaaga acggttctgg   1440
tactgccggt tggcactgaa ccacaaggtc cttcactatg gtgacttgga tgacaaccca   1500
caaggggagg tgacatttga atccctgcag gagaaaattc ctgttgcaga cattaaggcc   1560
attgtcactg ggaaagattg tccccacatg aaagagaaaa gtgctctgaa acagaacaag   1620
gaggtgttgg aattggcctt ctccatcctg tatgaccctg atgagacctt aaacttcatc   1680
gcacctaata aatatgagta ctgcatctgg attgatggcc tcagtgccct tctggggaag   1740
gacatgtcca gtgagctgac caagagtgac ctggacaccc tgctgagcat ggagatgaag   1800
ctgcggctcc tggacctgga gaacatccag attcccgaag ccccacccc catccccaag   1860 gagcccagca gctatgactt tgtctatcac tatggctga                          1899

<210> SEQ ID NO 45
<211> LENGTH: 2157
<212> TYPE: DNA
<213> ORGANISM: Human

<400> SEQUENCE: 45
atgccaccac cgtcagacat tgtcaaagtg gccattgagt ggccaggtgc taacgcccag     60
ctccttgaaa tcgaccagaa acggcccctg gcatccatta tcaaggaagt ttgtgatggg    120
tggtcgttgc aaacccaga gtattatacc ctccgttatg cagatggtcc tcagctgtac    180
atcaccgaac agactcgcag tgacattaag aatgggacaa tcttacaact ggctatctcc    240
ccgtcccggg ctgcacgcca gctgatggag aggacccagt catccaacat ggagacccgg    300
ctggatgcca tgaaggagct ggccaagctc tctgccgacg tgactttcgc tactgagttc    360
atcaacatgg atggcatcat tgtgctgaca aggctcgtgg aaagtggaac caagctcttg    420
tcccatgaga tgctggcatt cacccctgact gccttcctag agctcatgga ccatggcatt    480
gtctcctggg acatggtttc aatcaccttt attaagcaga ttgcagggta tgtgagccag    540
cccatggtgg acgtgtcaat ccttcagagg tccctggcca tcctggagag catggtcttg    600
aacagccaga gtctgtacca agatagcc gaggaaatca ccgtgggaca gctcatctca    660
cacctccagg tctccaacca ggagattcag acctacgcca ttgcactgat taatgcactt    720
tttctgaagg ctccctgagga caaacgacag gatatggcaa atgcatttgc acagaagcat    780
ctccggtcta taatcctgaa tcatgtgatc cgagggaacc gccccatcaa aactgagatg    840
gcccatcagc tatatgtcct tcaagtccta acctttaacc ttctggaaga aggatgatga    900
accaagatgg accccaatga ccaggctcaa agggacatca tatttgaact gaggaggatt    960
gcatttgacg cagagtctga tcctagcaat gcccctggga gtgggaccga aaaacgcaaa   1020
gccatgtaca caaaggacta caaaatgctg ggatttacca ccacatcaa tccagccatg   1080 gactttaccc cagactcctcc tggaatgctg gccttggaca catgctgta cttggctaaa   1140 gtccaccagg acacctacat ccggattgtc ttggagaaca gtagccggga agacaaaaat   1200
gaatgcccct ttggccgcag tgccattgag ctcaccaaaa tgctctgtga aatcctgcag   1260
```

```
gttggggaac taccaaatga aggacgcaat gactaccacc cgatgttctt tacccatgac    1320
cgagcctttg aagagctctt tggaatctgc atccagctgt tgaacaagac ctggaaggag    1380
atgagggcaa cagcagagga cttcaacaag gttatgcaag tcgtccgaga gcaaatcact    1440
cgagctttgc cctccaaacc caactctttg gatcagttca agagcaaatt gcgtagcctg    1500
agttactctg agattctacg actgcgccag tctgagagga tgagtcagga tgacttccag    1560
tccccgccaa ttgtggagct gagggagaag atccagcccg agatccttga gctgatcaag    1620
cagcagcgcc tgaaccggct ctgtgagggc agcagcttcc gaaagattgg gaaccgccga    1680
aggcaagaac ggtctctggta ctgccggttg gcactgaacc acaaggtcct tcactatggt    1740
gacttggatg acaacccaca aggggaggtg acatttgaat ccctgcagga gaaaattcct    1800
gttgcagaca ttaaggccat tgtcactggg aaagattgtc cccacatgaa agagaaaagt    1860
gctctgaaac agaacaagga ggtgttggaa ttggccttct ccatcctgta tgaccctgat    1920
gagaccttaa acttcatcgc acctaataaa tatgagtact gcatctggat tgatggcctc    1980
agtgcccttc tggggaagga catgtccagt gagctgacca agagtgacct ggacaccctg    2040
ctgagcatgg agatgaagct gcggctcctg gacctggaga acatccagat tcccgaagcc    2100
ccacccccca tccccaagga gcccagcagc tatgactttg tctatcacta tggctga      2157
```

<210> SEQ ID NO 46
<211> LENGTH: 1392
<212> TYPE: DNA
<213> ORGANISM: Human

<400> SEQUENCE: 46

```
atggcggcgc tgagggcttt gtgcggcttc cggggcgtcg cggcccaggt gctgcggcct      60
ggggctggag tccgattgcc gattcagccc agcagaggtg ttcggcagtg cagccagat     120 gtggaatggg cacagcagtt tgggggagct gttatgtacc caagcaaaga aacagcccac     180
tggaagcctc caccttggaa tgatgtggac cctccaaagg acacaattgt gaagaacatt     240
accctgaact ttgggcccca acacccagca gcgcatggtg tcctgcgact agtgatggaa     300
ttgagtgggg agatggtgcg gaagtgtgat cctcacatcg ggctcctgca ccgaggcact     360
gagaagctca ttgaatacaa gacctatctt caggcccttc catactttga ccggctagac     420
tatgtgtcca tgatgtgtaa cgaacaggcc tattctctag ctgtggagaa gttgctaaac     480
atccggcctc ctcctcgggc acagtggatc cgagtgctgt ttggagaaat cacacgtttg     540
ttgaaccaca tcatggctgt gaccacacat gccctggacc ttggggccat gaccccttc     600 ttctggctgt tgaagaaag ggagaagatg tttgagttct acgagcgagt gtctggagcc     660
cgaatgcatg ctgcttatat ccggccagga ggagtgcacc aggacctacc ccttgggctt     720
atggatgaca tttatcagtt ttctaagaac ttctctcttc ggcttgatga gttggaggag     780
ttgctgacca acaataggat ctggcgaaat cggacaattg acattggggt tgtaacagca     840
gaagaagcac ttaactatgg ttttagtgga gtgatgcttc ggggctcagg catccagtgg     900
gacctgcgga agacccagcc ctatgatgtt tacgaccagg ttgagtttga tgttcctgtt     960
ggttctcgag gggactgcta tgataggtac ctgtgccggg tggaggagat gcgccagtcc    1020
ctgagaatta tcgcacagtg tctaaacaag atgcctcctg gggagatcaa ggttgatgat    1080
gccaaagtgt ctccacctaa gcgagcagag atgaagactt ccatggagtc actgattcat    1140
cactttaagt tgtatactga gggctaccaa gttcctccag gagccacata tactgccatt    1200
```

| | |
|---|---|
| gaggctccca agggagagtt tggggtgtac ctggtgtctg atggcagcag ccgcccttat | 1260 |
| cgatgcaaga tcaaggctcc tggttttgcc catctggctg gtttggacaa gatgtctaag | 1320 |
| ggacacatgt tggcagatgt cgttgccatc ataggtaccc aagatattgt atttggagaa | 1380 |
| gtagatcggt ga | 1392 |

<210> SEQ ID NO 47
<211> LENGTH: 1392
<212> TYPE: DNA
<213> ORGANISM: Human

<400> SEQUENCE: 47

| | |
|---|---|
| atggcggcgc tgagggcttt gtgcggcttc cggggcgtcg cggcccaggt gctgcggcct | 60 |
| ggggctggag tccgattgcc gattcagccc agcagaggtg ttcggcagtg cagccagat | 120 |
| gtggaatggg cacagcagtt tggggagct gttatgtacc aagcaaaga aacagcccac | 180 |
| tggaagcctc cacctggaa tgatgtggac cctccaaagg acacaattgt gaagaacatt | 240 |
| accctgaact ttgggcccca cacccagca gcgcatggtc tcctgcgact agtgatggaa | 300 |
| ttgagtgggg agatggtgcg gaagtgtgat cctcacatcg gctcctgca ccgaggcact | 360 |
| gagaagctca ttgaatacaa gacctatctt caggcccttc catactttga ccggctagac | 420 |
| tatgtgtcca tgatgtgtaa cgaacaggcc tattctctag ctgtggagaa gttgctaaac | 480 |
| atccggcctc ctcctcgggc acagtggatc cgagtgctgt ttggagaaat cacacgtttg | 540 |
| ttgaaccaca tcatggctgt gaccacacat gccctggacc ttggggccat gaccccttc | 600 |
| ttctggctgt ttgaagaaag ggagaagatg tttgagttct acgagcgagt gtctggagcc | 660 |
| cgaatgcatg ctgcttatat ccggccagga ggagtgcacc aggacctacc ccttgggctt | 720 |
| atggatgaca tttatcagtt ttctaagaac ttctctcttc ggcttgatga gttgaggag | 780 |
| ttgctgacca caataggat ctggcgaaat cggacaattg acattggggt tgtaacagca | 840 |
| gaagaagcac ttaactatgg ttttagtgga gtgatgcttc ggggctcagg catccagtgg | 900 |
| gacctgcgga agacccagcc ctatgatgtt tacgaccagg ttgagtttga tgttcctgtt | 960 |
| ggttctcgag gggactgcta tgataggtac ctgtgccggg tggaggagat cgccagtcc | 1020 |
| ctgagaatta tcgcacagtg tctaaacaag atgcctcctg gggagatcaa ggttgatgat | 1080 |
| gccaaagtgt ctccacctaa gcgagcgag atgaagactt ccatggagtc actgattcat | 1140 |
| cactttaagt tgtatactga gggctaccaa gttcctccag gagccacata tactgccatt | 1200 |
| gaggctccca agggagagtt tggggtgtac ctggtgtctg atggcagcag ccgcccttat | 1260 |
| cgatgcaaga tcaaggctcc tggttttgcc catctggctg gtttggacaa gatgtctaag | 1320 |
| ggacacatgt tggcagatgt cgttgccatc ataggtaccc aagatattgt atttggagaa | 1380 |
| gtagatcggt ga | 1392 |

<210> SEQ ID NO 48
<211> LENGTH: 2139
<212> TYPE: DNA
<213> ORGANISM: Human

<400> SEQUENCE: 48

| | |
|---|---|
| atggccgggg ggccgggccc gggggagccc gcagcccccg gcgcccagca cttcttgtac | 60 |
| gaggtgccgc cctgggtcat gtgccgcttc tacaaagtga tggacgccct ggagcccgcc | 120 |
| gactggtgcc agttcgccgc cctgatcgtg cgcgaccaga ccgagctgcg gctgtgcgag | 180 |
| cgctccgggc agcgcacggc cagcgtcctg tggccctgga tcaaccgcaa cgcccgtgtg | 240 |

```
gccgacctcg tgcacatcct cacgcacctg cagctgctcc gtgcgcggga catcatcaca    300
gcctggcacc ctcccgcccc gcttccgtcc ccaggcacca ctgccccgag cccagcagc     360 atccctgcac ccgccgaggc cgaggcctgg agccccggga agttgccatc ctcagcctcc    420
accttcctct ccccagcttt tccaggctcc agacccatt cagggcctga gctcggcctg     480
gtcccaagcc ctgcttccct gtggcctcca ccgccatctc agccccttc ttctaccaag     540 ccaggcccag agagctcagt gtccctcctg cagggagccc gcccctttcc gttttgctgg    600
cccctctgtg agatttcccg gggcacccac aacttctcgg aggagctcaa gatcggggag    660
ggtggctttg ggtgcgtgta ccgggcgtg atgaggaaca cggtgtatgc tgtgaagagg     720
ctgaaggaga acgctgacct ggagtggact gcagtgaagc agagcttcct gaccgaggtg    780
gagcagctgt ccaggtttcg tcacccaaac attgtggact tgctggcta ctgtgctcag     840 aacggcttct actgcctggt gtacggcttc ctgcccaacg gctccctgga ggaccgtctc    900
cactgccaga cccaggcctg cccacctctc tcctggcctc agcgactgga catccttctg    960
ggtacagccc gggcaattca gtttctacat caggacagcc ccagcctcat ccatggagac    1020
atcaagagtt ccaacgtcct tctggatgag aggctgacac ccaagctggg agactttggc    1080
ctggcccggt tcagccgctt tgccgggtcc agccccagcc agagcagcat ggtggcccgg    1140
acacagacag tgcggggcac cctggcctac ctgcccgagg agtacatcaa gacgggaagg    1200
ctggctgtgg acacggacac cttcagcttt ggggtggtag tgctagagac cttggctggt    1260
cagagggctg tgaagacgca cggtgccagg accaagtatc tgaaagacct ggtggaagag    1320
gaggctgagg aggctggagt ggctttgaga agcacccaga gcacactgca agcaggtctg    1380
gctgcagatg cctgggctgc tcccatcgcc atgcagatct acaagaagca cctggacccc    1440
aggcccgggc cctgcccacc tgagctgggc ctgggcctgg ccagctggc ctgctgctgc     1500 ctgcaccgcc gggccaaaag gaggcctcct atgacccagg tgtacgagag ctagagaag     1560 ctgcaggcag tggtggcggg ggtgcccggg cattcggagg ccgccagctg catccccct    1620 tccccgcagg agaactccta cgtgtccagc actggcagag cccacagtgg gctgctcca    1680 tggcagcccc tggcagcgcc atcaggagcc agtgcccagg cagcagagca gctgcagaga    1740
ggccccaacc agcccgtgga gagtgacgag agcctaggcg gcctctctgc tgccctgcgc    1800
tcctggcact tgactccaag ctgccctctg gacccagcac cctcaggga ggccggctgt     1860 cctcaggggg acacggcagg agaatcgagc tgggggagtg gcccaggatc ccggcccaca    1920
gccgtggaag gactggccct tggcagctct gcatcatcgt cgtcagagcc accgcagatt    1980
atcatcaacc tgcccgaca gaagatggtc cagaagctgg ccctgtacga ggatggggcc    2040
ctggacagcc tgcagctgct gtcgtccagc tccctcccag gcttgggcct ggaacaggac    2100
aggcaggggc ccgaagaaag tgatgaattt cagagctga                          2139
```

<210> SEQ ID NO 49
<211> LENGTH: 2127
<212> TYPE: DNA
<213> ORGANISM: Human

<400> SEQUENCE: 49

```
atggccgggg ggccgggccc gggggagccc gcagccccg gcgcccagca cttcttgtac      60
gaggtgccgc cctgggtcat gtgccgcttc tacaaagtga tggacgccct ggagcccgcc    120
gactggtgcc agttcggtgg gtggcggcgg gctgccgggg ggcgggaggc gcgcgggctc    180
```

```
ctggcgccga cgcctgacgc ccccgcccc gcagccgccc tgatcgtgcg cgaccagacc      240
gagctgcggc tgtgcgagcg ctccgggcag cgcacggcca cgtcctgtg ccctggatc       300 aaccgcaacg cccgtgtggc cgacctcgtg cacatcctca cgcacctgca gctgctccgt     360
gcgcgggaca tcatcacagc ctggcaccct cccgccccgc ttccgtcccc aggcaccact     420
gccccgaggc ccagcagcat ccctgcaccc gccgaggccg aggcctggag ccccggaag     480 ttgccatcct cagcctccac cttcctctcc ccagcttttc caggctccca gacccattca    540
gggcctgagc tcggcctggt cccaagccct gcttccctgt ggcctccacc gccatctcca    600
gccccttctt ctaccaagcc aggcccgaga agctcagtgt ccctcctgca gggagcccgc    660 cccttccgt tttgctggcc cctctgtgag atttcccggg gcacccacaa cttctcggag     720
gagctcaaga tcggggaggg tggctttggg tgcgtgtacc gggcggtgat gaggaacacg    780
gtgtatgctg tgaagaggct gaaggagaac gctgacctgg agtggactgc agtgaagcag    840
agcttcctga ccgaggtgga gcagctgtcc aggtttcgtc acccaaacat tgtggacttt    900
gctggctact gtgctcagaa cggcttctac tgcctggtgt acgcttcct gcccaacggc     960 tccctggagg accgtctcca ctgccagacc caggcctgcc cacctctctc ctggcctcag   1020
cgactggaca tccttctggg tacagcccgg gcaattcagt ttctacatca ggacagcccc   1080
agcctcatcc atgagacat caagagttcc aacgtcctc tggatgagag gctgacaccc    1140 aagctggag actttggcct ggcccggttc agccgctttg ccgggtccag ccccagccag   1200
agcagcatgg tggcccggac acagacagtg cggggcaccc tggcctacct gcccgaggag   1260
tacatcaaga cgggaaggct ggctgtggac acggacacct tcagctttgg ggtggtagtg   1320
ctagagacct tggctggtca gagggctgtg aagacgcacg gtgccaggac caagtatctg   1380
aaagacctgg tggaagagga ggctgaggag gctggagtgg cttgagaag cacccagagc    1440 acactgcaag caggtctggc tgcagatgcc tgggctgctc ccatcgccat gcagatctac   1500
aagaagcacc tggaccccag gcccgggccc tgcccacctg agctgggcct gggcctgggc   1560
cagctggcct gctgctgcct gcaccgccgg gccaaaagga ggcctcctat gacccaggag   1620
aactcctacg tgtccagcac tggcagagcc cacagtgggg ctgctccatg gcagcccctg   1680
gcagcgccat caggagccag tgcccaggca gcagagcagc tgcagagagg ccccaaccag   1740
cccgtggaga gtgacgagag cctaggcggc ctctctgctg ccctgcgctc ctggcacttg   1800
actccaagct gccctctgga cccagcaccc ctcagggagg ccggctgtcc tcagggggac   1860
acggcaggag aatcgagctg ggggagtggc ccaggatccc ggcccacagc cgtggaagga   1920
ctggcccttg gcagctctgc atcatcgtcg tcagagccac cgcagattat catcaaccct   1980
gcccgacaga agatggtcca gaagctggcc ctgtacgagg atggggccct ggacagcctg   2040
cagctgctgt cgtccagctc cctcccaggc ttgggcctgg aacaggacag gcaggggccc   2100
gaagaaagtg atgaatttca gagctga                                       2127

<210> SEQ ID NO 50
<211> LENGTH: 1902
<212> TYPE: DNA
<213> ORGANISM: Human

<400> SEQUENCE: 50
atggccgggg ggccgggccc gggggagccc gcagccccg cgcccagca cttcttgtac       60 gaggtgccgc cctgggtcat gtgccgcttc tacaaagtga tggacgccct ggagcccgcc    120
gactggtgcc agttcgccgc cctgatcgtg cgcgaccaga ccgagctgcg gctgtgcgag    180
```

```
cgctccgggc agcgcacggc cagcgtcctg tggccctgga tcaaccgcaa cgcccgtgtg     240
gccgacctcg tgcacatcct cacgcacctg cagctgctcc gtgcgcggga catcatcaca     300
gcctggcacc ctcccgcccc gcttccgtcc ccaggcacca ctgccccgag gcccagcagc     360
atccctgcac ccgccgaggc cgaggcctgg agccccggga gttgccatc ctcagcctcc      420 accttcctct ccccagcttt tccaggctcc cagacccatt cagggcctga gctcggcctg     480
gtcccaagcc ctgcttccct gtggcctcca ccgccatctc cagcccttc ttctaccaag      540 ccaggcccag agagctcagt gtccctcctg cagggagccc gcccctttcc gttttgctgg     600
cccctctgtg agatttcccg gggcacccac aacttctcgg aggagctcaa gatcggggag     660
ggtggctttg ggtgcgtgta ccgggcggtg atgaggaaca cggtgtatgc tgtgaagagg     720
ctgaaggaga cgctgacctg gagtggact gcagtgaagc agagcttcct gaccgaggtg      780
gagcagctgt ccaggtttcg tcacccaaac attgtggact ttgctggcta ctgtgctcag     840
aacggcttct actgcctggt gtacggcttc ctcccaacg gctccctgga ggaccgtctc      900
cactgccaga cccaggcctg cccacctctc tcctggcctc agcgactgga catccttctg     960
ggtacagccc gggcaattca gtttctacat caggacagcc ccagcctcat ccatggagac    1020
atcaagagtt ccaacgtcct tctggatgag aggctgacac ccaagctggg agactttggc    1080
ctggcccggt tcagccgctt tgccgggtcc agccccagcc agagcagcat ggtggcccgg    1140
acacagacag tgcggggcac cctggcctac ctgcccgagg agtacatcaa gacgggaagg    1200
ctggctgtgg acacggacac cttcagcttt ggggtggtag tgctagagac cttggctggt    1260
cagagggctg tgaagacgca cggtgccagg accaagtatc tggtgtacga gaggctagag    1320
aagctgcagg cagtggtggc gggggtgccc gggcattcgg aggccgccag ctgcatcccc    1380
ccttccccgc aggagaactc ctacgtgtcc agcactggca gagcccacag tggggctgct    1440
ccatggcagc ccctggcagc gccatcagga gccagtgccc aggcagcaga gcagctgcag    1500
agaggcccca accagcccgt ggagagtgac gagagcctag gcggcctctc tgctgccctg    1560
cgctcctggc acttgactcc aagctgccct ctggacccag cacccctcag ggaggccggc    1620
tgtcctcagg gggacacggc aggagaatcg agctggggga gtggcccagg atcccggccc    1680
acagccgtgg aaggactggc ccttggcagc tctgcatcat cgtcgtcaga gccaccgcag    1740
attatcatca cccctgcccg acagaagatg gtccagaagc tggcccttgta cgaggatggg     1800 gccctggaca gctgcagct gctgtcgtcc agctccctcc caggcttggg cctggaacag     1860
gacaggcagg ggcccgaaga aagtgatgaa tttcagagct ga                      1902
```

<210> SEQ ID NO 51
<211> LENGTH: 2082
<212> TYPE: DNA
<213> ORGANISM: Human

<400> SEQUENCE: 51

```
atggccgggg ggccgggccc gggggagccc gcagcccccg cgcccagca cttcttgtac       60 gaggtgccgc cctgggtcat gtgccgcttc tacaaagtga tggacgccct ggagcccgcc     120
gactggtgca gttccgtgg gtgcggcggc gctgccgggg gcggaggc gcgcgggctc        180 ctggcgccga cgcctgacgc ccccgcccc cagccgcccc tgatcgtgcg cgaccagacc     240
gagctgcggg tgtgcgagcg ctccgggcag cgcacggcca cgtcctgtg gccctggatc     300 aaccgcaacg cccgtgtggc cgacctcgtg cacatcctca cgcacctgca gctgctccgt     360
```

| | |
|---|---|
| gcgcgggaca tcatcacagc ctggcaccct cccgccccgc ttccgtcccc aggcaccact | 420 |
| gccccgaggc ccagcagcat ccctgcaccc gccgaggccg aggcctggag ccccgggaag | 480 |
| ttgccatcct cagcctccac cttcctctcc ccagcttttc caggctccca gaccattca | 540 |
| gggcctgagc tcggcctggt cccaagccct gcttccctgt ggcctccacc gccatctcca | 600 |
| gccccttctt ctaccaagcc aggcccagag agctcagtgt ccctcctgca gggagcccgc | 660 |
| cccttttccgt tttgctggcc cctctgtgag atttcccggg gcacccacaa cttctcggag | 720 |
| gagctcaaga tcggggaggg tggctttggg tgcgtgtacc gggcggtgat gaggaacacg | 780 |
| gtgtatgctg tgaagaggct gaaggagaac gctgacctgg agtggactgc agtgaagcag | 840 |
| agcttcctga ccgaggtgga gcagctgtcc aggtttcgtc acccaaacat tgtggacttt | 900 |
| gctggctact gtgctcagaa cggcttctac tgcctggtgt acggcttcct gcccaacggc | 960 |
| tccctggagg accgtctcca ctgccagacc caggcctgcc acctctctc ctggcctcag | 1020 |
| cgactggaca tccttctggg tacagcccgg gcaattcagt ttctacatca ggacagcccc | 1080 |
| agcctcatcc atggagacat caagagttcc aacgtccttc tggatgagag gctgacaccc | 1140 |
| aagctgggag actttggcct ggcccggttc agccgctttg ccgggtccag ccccagccag | 1200 |
| agcagcatgg tgcccggac acagacagtg cggggcaccc tggcctacct gcccgaggag | 1260 |
| tacatcaaga cgggaaggct ggctgtggac acggacacct tcagctttgg ggtggtagtg | 1320 |
| ctagagacct tggctggtca gagggctgtg aagacgcacg tgccaggac caagtatctg | 1380 |
| aaagacctgg tggaagagga ggctgaggag gctggagtgg ctttgagaag cacccagagc | 1440 |
| acactgcaag caggtctggc tgcagatgcc tgggctgctc ccatcgccat gcagatctac | 1500 |
| aagaagcacc tgggccagct ggcctgctgc tgcctgcacc gccgggccaa aaggaggcct | 1560 |
| cctatgaccc aggagaactc ctacgtgtcc agcactggca gagcccacag tggggctgct | 1620 |
| ccatggcagc ccctggcagc gccatcagga gccagtgccc aggcagcaga gcagctgcag | 1680 |
| agaggcccca accagcccgt ggagagtgac gagagcctag cggcctctc tgctgccctg | 1740 |
| cgctcctggc acttgactcc aagctgccct ctggacccag caccctcag ggaggccggc | 1800 |
| tgtcctcagg gggacacggc aggagaatcg agctggggga gtggcccagg atccggccc | 1860 |
| acagccgtgg aaggactggc ccttggcagc tctgcatcat cgtcgtcaga gccaccgcag | 1920 |
| attatcatca cccctgcccg acagaagatg gtccagaagc tggccctgta cgaggatggg | 1980 |
| gccctggaca gcctgcagct gctgtcgtcc agctccctcc caggcttggg cctggaacag | 2040 |
| gacaggcagg ggcccgaaga aagtgatgaa tttcagagct ga | 2082 |

<210> SEQ ID NO 52
<211> LENGTH: 2049
<212> TYPE: DNA
<213> ORGANISM: Human

<400> SEQUENCE: 52

| | |
|---|---|
| atggccgggg ggccgggccc ggggagccc gcagccccg cgcccagca cttcttgtac | 60 |
| gaggtgccgc cctgggtcat gtgccgcttc tacaaagtga tggacgccct ggagcccgcc | 120 |
| gactggtgcc agttcgccgc cctgatcgtg cgcgaccaga ccgagctgcg gctgtgcgag | 180 |
| cgctccgggc agcgcacggc cagcgtcctg tggccctgga tcaaccgcaa cgcccgtgtg | 240 |
| gccgacctcg tgcacatcct cacgcacctg cagctgctcc gtgcgcggga tcatcatcaca | 300 |
| gcctggcacc ctcccgcccc gcttccgtcc ccaggcacca ctgccccgag gcccagcagc | 360 |
| atccctgcac ccgccgaggc cgaggcctgg agccccggga agttgccatc ctcagcctcc | 420 |

-continued

| | |
|---|---|
| accttcctct cccagcttt tccaggctcc cagacccatt cagggcctga gctcggcctg | 480 |
| gtcccaagcc ctgcttccct gtggcctcca ccgccatctc cagcccttc ttctaccaag | 540 |
| ccaggcccag agagctcagt gtccctcctg cagggagccc gccctttcc gttttgctgg | 600 |
| cccctctgtg agatttcccg gggcacccac aacttctcgg aggagctcaa gatcggggag | 660 |
| ggtggctttg ggtgcgtgta ccgggcggtg atgaggaaca cggtgtatgc tgtgaagagg | 720 |
| ctgaaggaga cgctgacct ggagtggact gcagtgaagc agagcttcct gaccgaggtg | 780 |
| gagcagctgt ccaggtttcg tcacccaaac attgtggact ttgctggcta ctgtgctcag | 840 |
| aacggcttct actgcctggt gtacggcttc ctgcccaacg gctccctgga ggaccgtctc | 900 |
| cactgccaga cccaggcctg cccacctctc tcctggcctc agcgactgga catccttctg | 960 |
| ggtacagccc gggcaattca gtttctacat caggacagcc ccagcctcat ccatggagac | 1020 |
| atcaagagtt ccaacgtcct tctggatgag aggctgacac caagctgggg agactttggc | 1080 |
| ctggcccggt tcagccgctt tgccgggtcc agccccagcc agagcagcat ggtggcccgg | 1140 |
| acacagacag tgcggggcac cctggcctac ctgcccgagg agtacatcaa gacgggaagg | 1200 |
| ctggctgtgg acacgacac cttcagcttt ggggtggtag tgctagagac cttggctggt | 1260 |
| cagagggctg tgaagacgca cggtgccagg accaagtatc tgaaagacct ggtggaagag | 1320 |
| gaggctgagg aggctggagt ggctttgaga agcacccaga gcacactgca agcaggtctg | 1380 |
| gctgcagatg cctgggctgc tcccatcgcc atgcagatct acaagaagca cctggacccc | 1440 |
| aggcccgggc cctgcccacc tgagctgggc ctgggcctgg gccagctggc ctgctgctgc | 1500 |
| ctgcaccgcc gggccaaaag gaggcctcct atgacccagg agaactccta cgtgtccagc | 1560 |
| actggcagag cccacagtgg ggctgctcca tggcagcccc tggcagcgcc atcaggagcc | 1620 |
| agtgcccagg cagcagagca gctgcagaga ggccccaacc agcccgtgga gagtgacgag | 1680 |
| agcctaggcg gcctctctgc tgccctgcgc tcctggcact tgactccaag ctgccctctg | 1740 |
| gacccagcac ccctcaggga ggccggctgt cctcagggg acacggcagg agaatcgagc | 1800 |
| tgggggagtg gccaggatc ccggcccaca gccgtggaag gactggccct tggcagctct | 1860 |
| gcatcatcgt cgtcagagcc accgcagatt atcatcaacc ctgcccgaca gaagatggtc | 1920 |
| cagaagctgg ccctgtacga ggatggggcc ctggacagcc tgcagctgct gtcgtccagc | 1980 |
| tccctcccag gcttgggcct ggaacaggac aggcagggc ccgaagaaag tgatgaattt | 2040 |
| cagagctga | 2049 |

<210> SEQ ID NO 53
<211> LENGTH: 423
<212> TYPE: DNA
<213> ORGANISM: Human

<400> SEQUENCE: 53

| | |
|---|---|
| atggcggcca tcccctccag cggctcgctc gtggccaccc acgactacta ccggcgccgc | 60 |
| ctgggttcca cttccagcaa cagctcctgc agcagtaccg agtgccccgg ggaagccatt | 120 |
| cccccaccccc caggtgagtg caggatcgcc cctttctccc ccgctcctc caggagctgg | 180 |
| cagcatcaag accccacttc gcttctctca ggtctcccca aggctgaccc gggtcattgg | 240 |
| tgggccagct tcttttcgg gaagtccacc ctcccgttca tggccacggt gttggagtcc | 300 |
| gcagagcact cggaacctcc ccaggcctcc agcagcatga ccgcctgtgg cctggctcgg | 360 |
| gacgccccga ggaagcagcc cggcggtcag tccagcacag ccagcgctgg gccccgtcc | 420 |

<210> SEQ ID NO 54
<211> LENGTH: 213
<212> TYPE: DNA
<213> ORGANISM: Human

<400> SEQUENCE: 54

```
atggcggcca tcccctccag cggctcgctc gtggccaccc acgactacta ccggcgccgc    60
ctgggttcca cttccagcaa cagctcctgc agcagtaccg agtgccccgg ggaagccatt   120
ccccaccccc caggtctccc caaggctgac ccgggtcatt ggtgggccag cttctttttc   180
gggaagtcca ccctcccacc ccccaccctg taa                                213
```

<210> SEQ ID NO 55
<211> LENGTH: 345
<212> TYPE: DNA
<213> ORGANISM: Human

<400> SEQUENCE: 55

```
atggcggcca tcccctccag cggctcgctc gtggccaccc acgactacta ccggcgccgc    60
ctgggttcca cttccagcaa cagctcctgc agcagtaccg agtgccccgg ggaagccatt   120
ccccaccccc caggtctccc caaggctgac ccgggtcatt ggtgggccag cttctttttc   180
gggaagtcca ccctcccgtt catggccacg tgttggagt ccgcagagca ctcggaacct   240
ccccaggcct ccagcagcat gaccgcctgt ggcctggctc gggacgcccc gaggaagcag   300
cccggcggtc agtccagcac agccagcgct gggcccccgt cctga                  345
```

<210> SEQ ID NO 56
<211> LENGTH: 1203
<212> TYPE: DNA
<213> ORGANISM: Human

<400> SEQUENCE: 56

```
atggaggacg gcgtctatga acccccagac ctgactccgg aggagcggat ggagctggag    60
aacatccggc ggcggaagca ggagctgctg gtggagattc agcgcctgcg ggaggagctc   120
agtgaagcca tgagcgaggt ggaggggctg gaggccaatg agggcagtaa gaccttgcaa   180
cggaaccgga gatggcaat gggcaggaag aagttcaaca tggaccccaa gaaggggatc   240
cagttcttgg tggagaatga actgctgcag aacacacccg aggagatcgc ccgcttcctg   300
tacaagggcg aggggctgaa caagacagcc atcgggact acctggggga gggaagaa   360
ctgaacctgg cagtgctcca tgcttttgtg gatctgcatg agttcaccga cctcaatctg   420
gtgcaggccc tcaggcagtt tctatggagc tttcgcctac ccggagaggc ccagaaaatt   480
gaccggatga tggaggcctt cgcccagcga tactgcctgt gcaaccctgg ggttttccag   540
tccacagaca cgtgctatgt gctgtccttc gccgtcatca tgctcaacac cagtctccac   600
aatcccaatg tccgggacaa gccgggcctg gagcgctttg tggccatgaa ccggggcatc   660
aacgagggcg ggacctgcc tgaggagctg ctcaggaacc tgtacgacag catccgaaat   720
gagcccttca gattcctga ggatgacggg aatgacctga cccacacctt cttcaacccg   780
gaccgggagg gctggctcct gaagctgggt aggggccggg tgaagacgtg aagcggcgc   840
tggtttatcc tcacagacaa ctgcctctac tactttgagt acaccacgga caaggagccc   900
cgaggaatca tcccctgga gaatctgagc atcgagagg tggacgaccc ccggaaaccg   960
aactgctttg aactttacat cccaacaac aaggggcagc tcatcaaagc ctgcaaaact  1020
```

| | | |
|---|---|---|
| gaggcggacg gccgagtggt ggagggaaac cacatggtgt accggatctc ggcccccacg | 1080 | |
| caggaggaga aggacgagtg gatcaagtcc atccaggcgg ctgtgagtgt ggaccccttc | 1140 | |
| tatgagatgc tggcagcgag aaagaagcgg atttcagtca agaagaagca ggagcagccc | 1200 | |
| tga | 1203 | |

<210> SEQ ID NO 57
<211> LENGTH: 1200
<212> TYPE: DNA
<213> ORGANISM: Human

<400> SEQUENCE: 57

| | |
|---|---|
| atggaggacg gcgtctatga acccccagac ctgactccgg aggagcggat ggagctggag | 60 |
| aacatccggc ggcggaagca ggagctgctg gtggagattc agcgcctgcg ggaggagctc | 120 |
| agtgaagcca tgagcgaggt ggaggggctg gaggccaatg agggcagtaa gaccttgcaa | 180 |
| cggaaccgga gatggcaatg ggcaggaag aagttcaaca tggaccccaa gaagggatc | 240 |
| cagttcttgg tggagaatga actgctgcag aacacacccg aggagatcgc ccgcttcctg | 300 |
| tacaagggcg aggggctgaa caagacagcc atcggggact acctggggga gagggaagaa | 360 |
| ctgaacctgg cagtgctcca tgcttttgtg atctgcatg agttcaccga cctcaatctg | 420 |
| gtgcaggccc tcaggcagtt tctatggagc tttcgcctac ccggagaggc ccagaaaatt | 480 |
| gaccggatga tggaggcctt cgcccagcga tactgcctgt gcaaccctgg ggttttccag | 540 |
| tccacagaca cgtgctatgt gctgtccttc gccgtcatca tgctcaacac cagtctccac | 600 |
| aatcccaatg tccgggacaa gccgggcctg agcgctttg tggccatgaa ccggggcatc | 660 |
| aacgagggcg ggaccctgcc tgaggagctg ctcaggaacc tgtacgacag catccgaaat | 720 |
| gagcccttca gattcctga ggatgacggg aatgacctga cccacacctt cttcaacccg | 780 |
| gaccgggagg ctggctcct gaagctgggg ggccgggtga agacgtggaa gcggcgctgg | 840 |
| tttatcctca gacaactg cctctactac tttgagtaca ccacggacaa ggagccccga | 900 |
| ggaatcatcc ccctggagaa tctgagcatc cgagaggtgg acgaccccg gaaaccgaac | 960 |
| tgctttgaac tttacatccc caacaacaag gggcagctca tcaaagcctg caaaactgag | 1020 |
| gcggacggcc gagtggtgga gggaaaccac atggtgtacc ggatctcggc ccccacgcag | 1080 |
| gaggagaagg acgagtggat caagtccatc caggcggctg tgagtgtgga ccccttctat | 1140 |
| gagatgctgg cagcgagaaa gaagcggatt tcagtcaaga gaagcagga gcagccctga | 1200 |

<210> SEQ ID NO 58
<211> LENGTH: 498
<212> TYPE: DNA
<213> ORGANISM: Human

<400> SEQUENCE: 58

| | |
|---|---|
| atggtcaacc ccaccgtgtt cttcgacatt gccgtcgacg gcgagcccct gggccgcgtc | 60 |
| tcctttgagc tgtttgcaga caaggtccca agacagcag aaaattttcg tgctctgagc | 120 |
| actggagaga aaggatttgg ttataagggt tcctgctttc acagaattat tccagggttt | 180 |
| atgtgtcagg tggtgacttc acacgccat aatggcactg tggcaagtc catctatggg | 240 |
| gagaaatttg aagatgagaa cttcatccta aagcatacag gtcctggcat cttgtccatg | 300 |
| gcaaatgctg acccaacac aaatggatcc cagttttca tctgcactgc caagactgag | 360 |
| tggttggatg gcaagcatgt ggtgtttggc aaagtgaaag aaggcatgaa tattgtggag | 420 |

```
gccatggagc gctttgggtc caggaatggc aagaccagca agaagatcac cattgctgac      480
tgtggacaac tcgaataa                                                    498
```

<210> SEQ ID NO 59
<211> LENGTH: 218
<212> TYPE: PRT
<213> ORGANISM: Human

<400> SEQUENCE: 59

```
Met Gly Thr Arg Asp Asp Glu Tyr Asp Tyr Leu Phe Lys Val Val Leu
1               5                   10                  15

Ile Gly Asp Ser Gly Val Gly Lys Ser Asn Leu Leu Ser Arg Phe Thr
            20                  25                  30

Arg Asn Glu Phe Asn Leu Glu Ser Lys Ser Thr Ile Gly Val Glu Phe
        35                  40                  45

Ala Thr Arg Ser Ile Gln Val Asp Gly Lys Thr Ile Lys Ala Gln Ile
    50                  55                  60

Trp Asp Thr Ala Gly Gln Glu Arg Tyr Arg Ala Ile Thr Ser Ala Tyr
65                  70                  75                  80

Tyr Arg Gly Ala Val Gly Ala Leu Leu Val Tyr Asp Ile Ala Lys His
                85                  90                  95

Leu Thr Tyr Glu Asn Val Glu Arg Trp Leu Lys Glu Leu Arg Asp His
            100                 105                 110

Ala Asp Ser Asn Ile Val Ile Met Leu Val Gly Asn Lys Ser Asp Leu
        115                 120                 125

Arg His Leu Arg Ala Val Pro Thr Asp Glu Ala Arg Ala Phe Ala Glu
    130                 135                 140

Lys Asn Asn Leu Ser Phe Ile Glu Thr Ser Ala Leu Asp Ser Thr Asn
145                 150                 155                 160

Val Glu Glu Ala Phe Lys Asn Ile Leu Thr Glu Ile Tyr Arg Ile Val
                165                 170                 175

Ser Gln Lys Gln Ile Ala Asp Arg Ala Ala His Asp Glu Ser Pro Gly
            180                 185                 190

Asn Asn Val Val Asp Ile Ser Val Pro Pro Thr Thr Asp Gly Gln Lys
        195                 200                 205

Pro Asn Lys Leu Gln Cys Cys Gln Asn Leu
    210                 215
```

<210> SEQ ID NO 60
<211> LENGTH: 589
<212> TYPE: PRT
<213> ORGANISM: Human

<400> SEQUENCE: 60

```
Met Ala Ala Ala Asp Gly Asp Asp Ser Leu Tyr Pro Ile Ala Val Leu
1               5                   10                  15

Ile Asp Glu Leu Arg Asn Glu Asp Val Gln Leu Arg Leu Asn Ser Ile
            20                  25                  30

Lys Lys Leu Ser Thr Ile Ala Leu Ala Leu Gly Val Glu Arg Thr Arg
        35                  40                  45

Ser Glu Leu Leu Pro Phe Leu Thr Asp Thr Ile Tyr Asp Glu Asp Glu
    50                  55                  60

Val Leu Leu Ala Leu Ala Glu Gln Leu Gly Thr Phe Thr Thr Leu Val
65                  70                  75                  80

Gly Gly Pro Glu Tyr Val His Cys Leu Leu Pro Pro Leu Glu Ser Leu
                85                  90                  95
```

```
Ala Thr Val Glu Glu Thr Val Val Arg Asp Lys Ala Val Glu Ser Leu
            100                 105                 110

Arg Ala Ile Ser His Glu His Ser Pro Ser Asp Leu Glu Ala His Phe
            115                 120                 125

Val Pro Leu Val Lys Arg Leu Ala Gly Gly Asp Trp Phe Thr Ser Arg
130                 135                 140

Thr Ser Ala Cys Gly Leu Phe Ser Val Cys Tyr Pro Arg Val Ser Ser
145                 150                 155                 160

Ala Val Lys Ala Glu Leu Arg Gln Tyr Phe Arg Asn Leu Cys Ser Asp
                165                 170                 175

Asp Thr Pro Met Val Arg Arg Ala Ala Ser Lys Leu Gly Glu Phe
                180                 185                 190

Ala Lys Val Leu Glu Leu Asp Asn Val Lys Ser Glu Ile Ile Pro Met
            195                 200                 205

Phe Ser Asn Leu Ala Ser Asp Glu Gln Asp Ser Val Arg Leu Leu Ala
            210                 215                 220

Val Glu Ala Cys Val Asn Ile Ala Gln Leu Leu Pro Gln Glu Asp Leu
225                 230                 235                 240

Glu Ala Leu Val Met Pro Thr Leu Arg Gln Ala Ala Glu Asp Lys Ser
                245                 250                 255

Trp Arg Val Arg Tyr Met Val Ala Asp Lys Phe Thr Glu Leu Gln Lys
                260                 265                 270

Ala Val Gly Pro Glu Ile Thr Lys Thr Asp Leu Val Pro Ala Phe Gln
            275                 280                 285

Asn Leu Met Lys Asp Cys Glu Ala Val Arg Ala Ala Ser His
            290                 295                 300

Lys Val Lys Glu Phe Cys Glu Asn Leu Ser Ala Asp Cys Arg Glu Asn
305                 310                 315                 320

Val Ile Met Ser Gln Ile Leu Pro Cys Ile Lys Glu Leu Val Ser Asp
                325                 330                 335

Ala Asn Gln His Val Lys Ser Ala Leu Ala Ser Val Ile Met Gly Leu
            340                 345                 350

Ser Pro Ile Leu Gly Lys Asp Asn Thr Ile Glu His Leu Leu Pro Leu
            355                 360                 365

Phe Leu Ala Gln Leu Lys Asp Glu Cys Pro Glu Val Arg Leu Asn Ile
370                 375                 380

Ile Ser Asn Leu Asp Cys Val Asn Glu Val Ile Gly Ile Arg Gln Leu
385                 390                 395                 400

Ser Gln Ser Leu Leu Pro Ala Ile Val Glu Leu Ala Glu Asp Ala Lys
                405                 410                 415

Trp Arg Val Arg Leu Ala Ile Ile Glu Tyr Met Pro Leu Leu Ala Gly
                420                 425                 430

Gln Leu Gly Val Glu Phe Phe Asp Glu Lys Leu Asn Ser Leu Cys Met
            435                 440                 445

Ala Trp Leu Val Asp His Val Tyr Ala Ile Arg Glu Ala Ala Thr Ser
            450                 455                 460

Asn Leu Lys Lys Leu Val Glu Lys Phe Gly Lys Glu Trp Ala His Ala
465                 470                 475                 480

Thr Ile Ile Pro Lys Val Leu Ala Met Ser Gly Asp Pro Asn Tyr Leu
                485                 490                 495

His Arg Met Thr Thr Leu Phe Cys Ile Asn Val Leu Ser Glu Val Cys
                500                 505                 510
```

```
Gly Gln Asp Ile Thr Thr Lys His Met Leu Pro Thr Val Leu Arg Met
            515                 520                 525

Ala Gly Asp Pro Val Ala Asn Val Arg Phe Asn Val Ala Lys Ser Leu
530                 535                 540

Gln Lys Ile Gly Pro Ile Leu Asp Asn Ser Thr Leu Gln Ser Glu Val
545                 550                 555                 560

Lys Pro Ile Leu Glu Lys Leu Thr Gln Asp Gln Asp Val Asp Val Lys
            565                 570                 575

Tyr Phe Ala Gln Glu Ala Leu Thr Val Leu Ser Leu Ala
                580                 585

<210> SEQ ID NO 61
<211> LENGTH: 509
<212> TYPE: PRT
<213> ORGANISM: Human

<400> SEQUENCE: 61

Met Arg Thr Phe Ser Phe Ala Ser Thr Ala Ser Arg Ser Cys Pro Pro
1               5                   10                  15

Ser Pro Trp Pro Leu Gly Leu Lys Gly Pro Glu Val Ser Phe Cys Leu
            20                  25                  30

Ser Leu Gln Ile Pro Ser Met Met Lys Met Arg Ser Ser Trp Pro Trp
        35                  40                  45

Gln Asn Ser Trp Glu Pro Ser Leu Pro Trp Trp Glu Ala Gln Ser Thr
    50                  55                  60

Cys Thr Ala Cys Cys Leu Phe Ser Val Cys Tyr Pro Arg Val Ser Ser
65                  70                  75                  80

Ala Val Lys Ala Glu Leu Arg Gln Tyr Phe Arg Asn Leu Cys Ser Asp
                85                  90                  95

Asp Thr Pro Met Val Arg Arg Ala Ala Ser Lys Leu Gly Glu Phe
            100                 105                 110

Ala Lys Val Leu Glu Leu Asp Asn Val Lys Ser Glu Ile Ile Pro Met
        115                 120                 125

Phe Ser Asn Leu Ala Ser Asp Glu Gln Asp Ser Val Arg Leu Leu Ala
    130                 135                 140

Val Glu Ala Cys Val Asn Ile Ala Gln Leu Leu Pro Gln Glu Asp Leu
145                 150                 155                 160

Glu Ala Leu Val Met Pro Thr Leu Arg Gln Ala Ala Glu Asp Lys Ser
                165                 170                 175

Trp Arg Val Arg Tyr Met Val Ala Asp Lys Phe Thr Glu Leu Gln Lys
            180                 185                 190

Ala Val Gly Pro Glu Ile Thr Lys Thr Asp Leu Val Pro Ala Phe Gln
        195                 200                 205

Asn Leu Met Lys Asp Cys Glu Ala Glu Val Arg Ala Ala Ala Ser His
    210                 215                 220

Lys Val Lys Glu Phe Cys Glu Asn Leu Ser Ala Asp Cys Arg Glu Asn
225                 230                 235                 240

Val Ile Met Ser Gln Ile Leu Pro Cys Ile Lys Glu Leu Val Ser Asp
                245                 250                 255

Ala Asn Gln His Val Lys Ser Ala Leu Ala Ser Val Ile Met Gly Leu
            260                 265                 270

Ser Pro Ile Leu Gly Lys Asp Asn Thr Ile Glu His Leu Leu Pro Leu
        275                 280                 285

Phe Leu Ala Gln Leu Lys Asp Glu Cys Pro Glu Val Arg Leu Asn Ile
    290                 295                 300
```

-continued

```
Ile Ser Asn Leu Asp Cys Val Asn Glu Val Ile Gly Ile Arg Gln Leu
305                 310                 315                 320

Ser Gln Ser Leu Leu Pro Ala Ile Val Glu Leu Ala Glu Asp Ala Lys
            325                 330                 335

Trp Arg Val Arg Leu Ala Ile Ile Glu Tyr Met Pro Leu Leu Ala Gly
        340                 345                 350

Gln Leu Gly Val Glu Phe Phe Asp Glu Lys Leu Asn Ser Leu Cys Met
    355                 360                 365

Ala Trp Leu Val Asp His Val Tyr Ala Ile Arg Glu Ala Ala Thr Ser
370                 375                 380

Asn Leu Lys Lys Leu Val Glu Lys Phe Gly Lys Glu Trp Ala His Ala
385                 390                 395                 400

Thr Ile Ile Pro Lys Val Leu Ala Met Ser Gly Asp Pro Asn Tyr Leu
                405                 410                 415

His Arg Met Thr Thr Leu Phe Cys Ile Asn Val Leu Ser Glu Val Cys
            420                 425                 430

Gly Gln Asp Ile Thr Thr Lys His Met Leu Pro Thr Val Leu Arg Met
        435                 440                 445

Ala Gly Asp Pro Val Ala Asn Val Arg Phe Asn Val Ala Lys Ser Leu
    450                 455                 460

Gln Lys Ile Gly Pro Ile Leu Asp Asn Ser Thr Leu Gln Ser Glu Val
465                 470                 475                 480

Lys Pro Ile Leu Glu Lys Leu Thr Gln Asp Gln Asp Val Asp Val Lys
                485                 490                 495

Tyr Phe Ala Gln Glu Ala Leu Thr Val Leu Ser Leu Ala
            500                 505

<210> SEQ ID NO 62
<211> LENGTH: 876
<212> TYPE: PRT
<213> ORGANISM: Human

<400> SEQUENCE: 62

Met Glu Leu Ile Thr Ile Leu Glu Lys Thr Val Ser Pro Asp Arg Leu
1               5                   10                  15

Glu Leu Glu Ala Ala Gln Lys Phe Leu Glu Arg Ala Ala Val Glu Asn
            20                  25                  30

Leu Pro Thr Phe Leu Val Glu Leu Ser Arg Val Leu Ala Asn Pro Gly
        35                  40                  45

Asn Ser Gln Val Ala Arg Val Ala Ala Gly Leu Gln Ile Lys Asn Ser
    50                  55                  60

Leu Thr Ser Lys Asp Pro Asp Ile Lys Ala Gln Tyr Gln Gln Arg Trp
65                  70                  75                  80

Leu Ala Ile Asp Ala Asn Ala Arg Arg Glu Val Lys Asn Tyr Val Leu
                85                  90                  95

Gln Thr Leu Gly Thr Glu Thr Tyr Arg Pro Ser Ser Ala Ser Gln Cys
            100                 105                 110

Val Ala Gly Ile Ala Cys Ala Glu Ile Pro Val Asn Gln Trp Pro Glu
        115                 120                 125

Leu Ile Pro Gln Leu Val Ala Asn Val Thr Asn Pro Asn Ser Thr Glu
    130                 135                 140

His Met Lys Glu Ser Thr Leu Glu Ala Ile Gly Tyr Ile Cys Gln Asp
145                 150                 155                 160

Ile Asp Pro Glu Gln Leu Gln Asp Lys Ser Asn Glu Ile Leu Thr Ala
```

-continued

```
            165                 170                 175
Ile Ile Gln Gly Met Arg Lys Glu Glu Pro Ser Asn Asn Val Lys Leu
            180                 185                 190
Ala Ala Thr Asn Ala Leu Leu Asn Ser Leu Glu Phe Thr Lys Ala Asn
            195                 200                 205
Phe Asp Lys Glu Ser Glu Arg His Phe Ile Met Gln Val Val Cys Glu
    210                 215                 220
Ala Thr Gln Cys Pro Asp Thr Arg Val Arg Val Ala Ala Leu Gln Asn
225                 230                 235                 240
Leu Val Lys Ile Met Ser Leu Tyr Tyr Gln Tyr Met Glu Thr Tyr Met
                245                 250                 255
Gly Pro Ala Leu Phe Ala Ile Thr Ile Glu Ala Met Lys Ser Asp Ile
                260                 265                 270
Asp Glu Val Ala Leu Gln Gly Ile Glu Phe Trp Ser Asn Val Cys Asp
            275                 280                 285
Glu Glu Met Asp Leu Ala Ile Glu Ala Ser Glu Ala Ala Glu Gln Gly
        290                 295                 300
Arg Pro Pro Glu His Thr Ser Lys Phe Tyr Ala Lys Gly Ala Leu Gln
305                 310                 315                 320
Tyr Leu Val Pro Ile Leu Thr Gln Thr Leu Thr Lys Gln Asp Glu Asn
                325                 330                 335
Asp Asp Asp Asp Asp Trp Asn Pro Cys Lys Ala Ala Gly Val Cys Leu
                340                 345                 350
Met Leu Leu Ala Thr Cys Cys Glu Asp Asp Ile Val Pro His Val Leu
            355                 360                 365
Pro Phe Ile Lys Glu His Ile Lys Asn Pro Asp Trp Arg Tyr Arg Asp
    370                 375                 380
Ala Ala Val Met Ala Phe Gly Cys Ile Leu Glu Gly Pro Glu Pro Ser
385                 390                 395                 400
Gln Leu Lys Pro Leu Val Ile Gln Ala Met Pro Thr Leu Ile Glu Leu
                405                 410                 415
Met Lys Asp Pro Ser Val Val Arg Asp Thr Ala Ala Trp Thr Val
                420                 425                 430
Gly Arg Ile Cys Glu Leu Leu Pro Glu Ala Ala Ile Asn Asp Val Tyr
            435                 440                 445
Leu Ala Pro Leu Leu Gln Cys Leu Ile Glu Gly Leu Ser Ala Glu Pro
        450                 455                 460
Arg Val Ala Ser Asn Val Cys Trp Ala Phe Ser Ser Leu Ala Glu Ala
465                 470                 475                 480
Ala Tyr Glu Ala Ala Asp Val Ala Asp Asp Gln Glu Pro Ala Thr
                485                 490                 495
Tyr Cys Leu Ser Ser Ser Phe Glu Leu Ile Val Gln Lys Leu Leu Glu
            500                 505                 510
Thr Thr Asp Arg Pro Asp Gly His Gln Asn Asn Leu Arg Ser Ser Ala
        515                 520                 525
Tyr Glu Ser Leu Met Glu Ile Val Lys Asn Ser Ala Lys Asp Cys Tyr
    530                 535                 540
Pro Ala Val Gln Lys Thr Thr Leu Val Ile Met Glu Arg Leu Gln Gln
545                 550                 555                 560
Val Leu Gln Met Glu Ser His Ile Gln Ser Thr Ser Asp Arg Ile Gln
                565                 570                 575
Phe Asn Asp Leu Gln Ser Leu Leu Cys Ala Thr Leu Gln Asn Val Leu
            580                 585                 590
```

Arg Lys Val Gln His Gln Asp Ala Leu Gln Ile Ser Asp Val Val Met
            595                 600                 605

Ala Ser Leu Leu Arg Met Phe Gln Ser Thr Ala Gly Ser Gly Gly Val
        610                 615                 620

Gln Glu Asp Ala Leu Met Ala Val Ser Thr Leu Val Glu Val Leu Gly
625                 630                 635                 640

Gly Glu Phe Leu Lys Tyr Met Glu Ala Phe Lys Pro Phe Leu Gly Ile
                645                 650                 655

Gly Leu Lys Asn Tyr Ala Glu Tyr Gln Val Cys Leu Ala Ala Val Gly
            660                 665                 670

Leu Val Gly Asp Leu Cys Arg Ala Leu Gln Ser Asn Ile Ile Pro Phe
        675                 680                 685

Cys Asp Glu Val Met Gln Leu Leu Leu Glu Asn Leu Gly Asn Glu Asn
690                 695                 700

Val His Arg Ser Val Lys Pro Gln Ile Leu Ser Val Phe Gly Asp Ile
705                 710                 715                 720

Ala Leu Ala Ile Gly Gly Glu Phe Lys Lys Tyr Leu Glu Val Val Leu
                725                 730                 735

Asn Thr Leu Gln Gln Ala Ser Gln Ala Gln Val Asp Lys Ser Asp Tyr
            740                 745                 750

Asp Met Val Asp Tyr Leu Asn Glu Leu Arg Glu Ser Cys Leu Glu Ala
        755                 760                 765

Tyr Thr Gly Ile Val Gln Gly Leu Lys Gly Asp Gln Glu Asn Val His
770                 775                 780

Pro Asp Val Met Leu Val Gln Pro Arg Val Glu Phe Ile Leu Ser Phe
785                 790                 795                 800

Ile Asp His Ile Ala Gly Asp Glu Asp His Thr Asp Gly Val Val Ala
                805                 810                 815

Cys Ala Ala Gly Leu Ile Gly Asp Leu Cys Thr Ala Phe Gly Lys Asp
            820                 825                 830

Val Leu Lys Leu Val Glu Ala Arg Pro Met Ile His Glu Leu Leu Thr
        835                 840                 845

Glu Gly Arg Arg Ser Lys Thr Asn Lys Ala Lys Thr Leu Ala Thr Trp
850                 855                 860

Ala Thr Lys Glu Leu Arg Lys Leu Lys Asn Gln Ala
865                 870                 875

<210> SEQ ID NO 63

<400> SEQUENCE: 63

000

<210> SEQ ID NO 64
<211> LENGTH: 789
<212> TYPE: PRT
<213> ORGANISM: Human

<400> SEQUENCE: 64

Met Gly Thr Lys Met Ala Asp Leu Asp Ser Pro Pro Lys Leu Ser Gly
1               5                   10                  15

Val Gln Gln Pro Ser Glu Gly Val Gly Gly Arg Cys Ser Glu Ile
            20                  25                  30

Ser Ala Glu Leu Ile Arg Ser Leu Thr Glu Leu Gln Glu Leu Glu Ala
        35                  40                  45

-continued

```
Val Tyr Glu Arg Leu Cys Gly Glu Glu Lys Val Val Glu Arg Glu Leu
 50                  55                  60

Asp Ala Leu Leu Glu Gln Gln Asn Thr Ile Glu Ser Lys Met Val Thr
 65                  70                  75                  80

Leu His Arg Met Gly Pro Asn Leu Gln Leu Ile Glu Gly Asp Ala Lys
                 85                  90                  95

Gln Leu Ala Gly Met Ile Thr Phe Thr Cys Asn Leu Ala Glu Asn Val
                100                 105                 110

Ser Ser Lys Val Arg Gln Leu Asp Leu Ala Lys Asn Arg Leu Tyr Gln
             115                 120                 125

Ala Ile Gln Arg Ala Asp Asp Ile Leu Asp Leu Lys Phe Cys Met Asp
130                 135                 140

Gly Val Gln Thr Ala Leu Arg Ser Glu Asp Tyr Glu Gln Ala Ala Ala
145                 150                 155                 160

His Thr His Arg Tyr Leu Cys Leu Asp Lys Ser Val Ile Glu Leu Ser
                165                 170                 175

Arg Gln Gly Lys Glu Gly Ser Met Ile Asp Ala Asn Leu Lys Leu Leu
            180                 185                 190

Gln Glu Ala Glu Gln Arg Leu Lys Ala Ile Val Ala Glu Lys Phe Ala
        195                 200                 205

Ile Ala Thr Lys Glu Gly Asp Leu Pro Gln Val Glu Arg Phe Phe Lys
210                 215                 220

Ile Phe Pro Leu Leu Gly Leu His Glu Glu Gly Leu Arg Lys Phe Ser
225                 230                 235                 240

Glu Tyr Leu Cys Lys Gln Val Ala Ser Lys Ala Glu Glu Asn Leu Leu
                245                 250                 255

Met Val Leu Gly Thr Asp Met Ser Asp Arg Arg Ala Ala Val Ile Phe
            260                 265                 270

Ala Asp Thr Leu Thr Leu Leu Phe Glu Gly Ile Ala Arg Ile Val Glu
        275                 280                 285

Thr His Gln Pro Ile Val Glu Thr Tyr Tyr Gly Pro Gly Arg Leu Tyr
290                 295                 300

Thr Leu Ile Lys Tyr Leu Gln Val Glu Cys Asp Arg Gln Val Glu Lys
305                 310                 315                 320

Val Val Asp Lys Phe Ile Lys Gln Arg Asp Tyr His Gln Gln Phe Arg
                325                 330                 335

His Val Gln Asn Asn Leu Met Arg Asn Ser Thr Thr Glu Lys Ile Glu
            340                 345                 350

Pro Arg Glu Leu Asp Pro Ile Leu Thr Glu Val Thr Leu Met Asn Ala
        355                 360                 365

Arg Ser Glu Leu Tyr Leu Arg Phe Leu Lys Lys Arg Ile Ser Ser Asp
370                 375                 380

Phe Glu Val Gly Asp Ser Met Ala Ser Glu Glu Val Lys Gln Glu His
385                 390                 395                 400

Gln Lys Cys Leu Asp Lys Leu Leu Asn Asn Cys Leu Leu Ser Cys Thr
                405                 410                 415

Met Gln Glu Leu Ile Gly Leu Tyr Val Thr Met Glu Glu Tyr Phe Met
            420                 425                 430

Arg Glu Thr Val Asn Lys Ala Val Ala Leu Asp Thr Tyr Glu Lys Gly
        435                 440                 445

Gln Leu Thr Ser Ser Met Val Asp Asp Val Phe Tyr Ile Val Lys Lys
450                 455                 460

Cys Ile Gly Arg Ala Leu Ser Ser Ser Ile Asp Cys Leu Cys Ala
```

```
            465                 470                 475                 480
        Met Ile Asn Leu Ala Thr Thr Glu Leu Glu Ser Asp Phe Arg Asp Val
                        485                 490                 495

Leu Cys Asn Lys Leu Arg Met Gly Phe Pro Ala Thr Thr Phe Gln Asp
                    500                 505                 510

Ile Gln Arg Gly Val Thr Ser Ala Val Asn Ile Met His Ser Ser Leu
                515                 520                 525

Gln Gln Gly Lys Phe Asp Thr Lys Gly Ile Glu Ser Thr Asp Glu Ala
            530                 535                 540

Lys Met Ser Phe Leu Val Thr Leu Asn Asn Val Glu Val Cys Ser Glu
        545                 550                 555                 560

Asn Ile Ser Thr Leu Lys Lys Thr Leu Glu Ser Asp Cys Thr Lys Leu
                        565                 570                 575

Phe Ser Gln Gly Ile Gly Gly Glu Gln Ala Gln Ala Lys Phe Asp Ser
                    580                 585                 590

Cys Leu Ser Asp Leu Ala Ala Val Ser Asn Lys Phe Arg Asp Leu Leu
                595                 600                 605

Gln Glu Gly Leu Thr Glu Leu Asn Ser Thr Ala Ile Lys Pro Gln Val
            610                 615                 620

Gln Pro Trp Ile Asn Ser Phe Phe Ser Val Ser His Asn Ile Glu Glu
        625                 630                 635                 640

Glu Glu Phe Asn Asp Tyr Glu Ala Asn Asp Pro Trp Val Gln Gln Phe
                        645                 650                 655

Ile Leu Asn Leu Glu Gln Gln Met Ala Glu Phe Lys Ala Ser Leu Ser
                    660                 665                 670

Pro Val Ile Tyr Asp Ser Leu Thr Gly Leu Met Thr Ser Leu Val Ala
                675                 680                 685

Val Glu Leu Glu Lys Val Val Leu Lys Ser Thr Phe Asn Arg Leu Gly
            690                 695                 700

Gly Leu Gln Phe Asp Lys Glu Leu Arg Ser Leu Ile Ala Tyr Leu Thr
        705                 710                 715                 720

Thr Val Thr Thr Trp Thr Ile Arg Asp Lys Phe Ala Arg Leu Ser Gln
                        725                 730                 735

Met Ala Thr Ile Leu Asn Leu Glu Arg Val Thr Glu Ile Leu Asp Tyr
                    740                 745                 750

Trp Gly Pro Asn Ser Gly Pro Leu Thr Trp Arg Leu Thr Pro Ala Glu
                755                 760                 765

Val Arg Gln Val Leu Ala Leu Arg Ile Asp Phe Arg Ser Glu Asp Ile
            770                 775                 780

Lys Arg Leu Arg Leu
        785

<210> SEQ ID NO 65
<211> LENGTH: 785
<212> TYPE: PRT
<213> ORGANISM: Human

<400> SEQUENCE: 65

Met Ala Asp Leu Asp Ser Pro Pro Lys Leu Ser Gly Val Gln Gln Pro
        1               5                   10                  15

Ser Glu Gly Val Gly Gly Gly Arg Cys Ser Glu Ile Ser Ala Glu Leu
                        20                  25                  30

Ile Arg Ser Leu Thr Glu Leu Gln Glu Leu Glu Ala Val Tyr Glu Arg
                    35                  40                  45
```

```
Leu Cys Gly Glu Glu Lys Val Val Glu Arg Glu Leu Asp Ala Leu Leu
 50                  55                  60

Glu Gln Gln Asn Thr Ile Glu Ser Lys Met Val Thr Leu His Arg Met
 65                  70                  75                  80

Gly Pro Asn Leu Gln Leu Ile Glu Gly Asp Ala Lys Gln Leu Ala Gly
                 85                  90                  95

Met Ile Thr Phe Thr Cys Asn Leu Ala Glu Asn Val Ser Ser Lys Val
                100                 105                 110

Arg Gln Leu Asp Leu Ala Lys Asn Arg Leu Tyr Gln Ala Ile Gln Arg
                115                 120                 125

Ala Asp Asp Ile Leu Asp Leu Lys Phe Cys Met Asp Gly Val Gln Thr
130                 135                 140

Ala Leu Arg Ser Glu Asp Tyr Glu Gln Ala Ala His Thr His Arg
145                 150                 155                 160

Tyr Leu Cys Leu Asp Lys Ser Val Ile Glu Leu Ser Arg Gln Gly Lys
                165                 170                 175

Glu Gly Ser Met Ile Asp Ala Asn Leu Lys Leu Leu Gln Glu Ala Glu
                180                 185                 190

Gln Arg Leu Lys Ala Ile Val Ala Glu Lys Phe Ala Ile Ala Thr Lys
                195                 200                 205

Glu Gly Asp Leu Pro Gln Val Glu Arg Phe Phe Lys Ile Phe Pro Leu
                210                 215                 220

Leu Gly Leu His Glu Glu Gly Leu Arg Lys Phe Ser Glu Tyr Leu Cys
225                 230                 235                 240

Lys Gln Val Ala Ser Lys Ala Glu Glu Asn Leu Leu Met Val Leu Gly
                245                 250                 255

Thr Asp Met Ser Asp Arg Arg Ala Ala Val Ile Phe Ala Asp Thr Leu
                260                 265                 270

Thr Leu Leu Phe Glu Gly Ile Ala Arg Ile Val Glu Thr His Gln Pro
                275                 280                 285

Ile Val Glu Thr Tyr Tyr Gly Pro Gly Arg Leu Tyr Thr Leu Ile Lys
                290                 295                 300

Tyr Leu Gln Val Glu Cys Asp Arg Gln Val Glu Lys Val Val Asp Lys
305                 310                 315                 320

Phe Ile Lys Gln Arg Asp Tyr His Gln Phe Arg His Val Gln Asn
                325                 330                 335

Asn Leu Met Arg Asn Ser Thr Thr Glu Lys Ile Glu Pro Arg Glu Leu
                340                 345                 350

Asp Pro Ile Leu Thr Glu Val Thr Leu Met Asn Ala Arg Ser Glu Leu
                355                 360                 365

Tyr Leu Arg Phe Leu Lys Lys Arg Ile Ser Ser Asp Phe Glu Val Gly
                370                 375                 380

Asp Ser Met Ala Ser Glu Glu Val Lys Gln Glu His Gln Lys Cys Leu
385                 390                 395                 400

Asp Lys Leu Leu Asn Asn Cys Leu Leu Ser Cys Thr Met Gln Glu Leu
                405                 410                 415

Ile Gly Leu Tyr Val Thr Met Glu Glu Tyr Phe Met Arg Glu Thr Val
                420                 425                 430

Asn Lys Ala Val Ala Leu Asp Thr Tyr Glu Lys Gly Gln Leu Thr Ser
                435                 440                 445

Ser Met Val Asp Asp Val Phe Tyr Ile Val Lys Lys Cys Ile Gly Arg
450                 455                 460

Ala Leu Ser Ser Ser Ser Ile Asp Cys Leu Cys Ala Met Ile Asn Leu
```

```
            465                 470                 475                 480
        Ala Thr Thr Glu Leu Glu Ser Asp Phe Arg Asp Val Leu Cys Asn Lys
                        485                 490                 495

Leu Arg Met Gly Phe Pro Ala Thr Thr Phe Gln Asp Ile Gln Arg Gly
                    500                 505                 510

Val Thr Ser Ala Val Asn Ile Met His Ser Ser Leu Gln Gln Gly Lys
                    515                 520                 525

Phe Asp Thr Lys Gly Ile Glu Ser Thr Asp Glu Ala Lys Met Ser Phe
                    530                 535                 540

Leu Val Thr Leu Asn Asn Val Glu Val Cys Ser Glu Asn Ile Ser Thr
        545                 550                 555                 560

Leu Lys Lys Thr Leu Glu Ser Asp Cys Thr Lys Leu Phe Ser Gln Gly
                        565                 570                 575

Ile Gly Gly Glu Gln Ala Gln Ala Lys Phe Asp Ser Cys Leu Ser Asp
                    580                 585                 590

Leu Ala Ala Val Ser Asn Lys Phe Arg Asp Leu Leu Gln Glu Gly Leu
                    595                 600                 605

Thr Glu Leu Asn Ser Thr Ala Ile Lys Pro Gln Val Gln Pro Trp Ile
                    610                 615                 620

Asn Ser Phe Phe Ser Val Ser His Asn Ile Glu Glu Glu Phe Asn
        625                 630                 635                 640

Asp Tyr Glu Ala Asn Asp Pro Trp Val Gln Gln Phe Ile Leu Asn Leu
                        645                 650                 655

Glu Gln Gln Met Ala Glu Phe Lys Ala Ser Leu Ser Pro Val Ile Tyr
                    660                 665                 670

Asp Ser Leu Thr Gly Leu Met Thr Ser Leu Val Ala Val Glu Leu Glu
                    675                 680                 685

Lys Val Val Leu Lys Ser Thr Phe Asn Arg Leu Gly Gly Leu Gln Phe
                    690                 695                 700

Asp Lys Glu Leu Arg Ser Leu Ile Ala Tyr Leu Thr Thr Val Thr Thr
        705                 710                 715                 720

Trp Thr Ile Arg Asp Lys Phe Ala Arg Leu Ser Gln Met Ala Thr Ile
                        725                 730                 735

Leu Asn Leu Glu Arg Val Thr Glu Ile Leu Asp Tyr Trp Gly Pro Asn
                    740                 745                 750

Ser Gly Pro Leu Thr Trp Arg Leu Thr Pro Ala Glu Val Arg Gln Val
                    755                 760                 765

Leu Ala Leu Arg Ile Asp Phe Arg Ser Glu Asp Ile Lys Arg Leu Arg
                    770                 775                 780

Leu
        785

<210> SEQ ID NO 66
<211> LENGTH: 337
<212> TYPE: PRT
<213> ORGANISM: Human

<400> SEQUENCE: 66

Met Ala Asp Leu Asp Ser Pro Pro Lys Leu Ser Gly Val Gln Gln Pro
        1               5                   10                  15

Ser Glu Gly Val Gly Gly Gly Arg Cys Ser Glu Ile Ser Ala Glu Leu
                        20                  25                  30

Ile Arg Ser Leu Thr Glu Leu Gln Glu Leu Glu Ala Val Tyr Glu Arg
                    35                  40                  45
```

Leu Cys Gly Glu Glu Lys Val Val Glu Arg Glu Leu Asp Ala Leu Leu
            50                  55                  60

Glu Gln Gln Asn Thr Ile Glu Ser Lys Met Val Thr Leu His Arg Met
65                  70                  75                  80

Gly Pro Asn Leu Gln Leu Ile Glu Gly Asp Ala Lys Gln Leu Ala Gly
                85                  90                  95

Met Ile Thr Phe Thr Cys Asn Leu Ala Glu Asn Val Ser Ser Lys Val
            100                 105                 110

Arg Gln Leu Asp Leu Ala Lys Asn Arg Leu Tyr Gln Ala Ile Gln Arg
            115                 120                 125

Ala Asp Asp Ile Leu Asp Leu Lys Phe Cys Met Asp Gly Val Gln Thr
130                 135                 140

Ala Leu Arg Ser Glu Asp Tyr Glu Gln Ala Ala His Thr His Arg
145                 150                 155                 160

Tyr Leu Cys Leu Asp Lys Ser Val Ile Glu Leu Ser Arg Gln Gly Lys
                165                 170                 175

Glu Gly Ser Met Ile Asp Ala Asn Leu Lys Leu Leu Gln Glu Ala Glu
            180                 185                 190

Gln Arg Leu Lys Ala Ile Val Ala Glu Lys Phe Ala Ile Ala Thr Lys
            195                 200                 205

Glu Gly Asp Leu Pro Gln Val Glu Arg Phe Phe Lys Ile Phe Pro Leu
210                 215                 220

Leu Gly Leu His Glu Glu Gly Leu Arg Lys Phe Ser Glu Tyr Leu Cys
225                 230                 235                 240

Lys Gln Val Ala Ser Lys Ala Glu Glu Asn Leu Leu Met Val Leu Gly
                245                 250                 255

Thr Asp Met Ser Asp Arg Arg Ala Ala Val Ile Phe Ala Asp Thr Leu
            260                 265                 270

Thr Leu Leu Phe Glu Gly Ile Ala Arg Ile Val Glu Thr His Gln Pro
            275                 280                 285

Ile Val Glu Thr Tyr Tyr Gly Pro Gly Arg Leu Tyr Thr Leu Ile Lys
            290                 295                 300

Tyr Leu Gln Val Glu Cys Asp Arg Gln Val Glu Lys Val Val Asp Lys
305                 310                 315                 320

Phe Ile Lys Gln Arg Asp Tyr His Gln Asn Phe Val Phe Ser Phe
                325                 330                 335

Phe

<210> SEQ ID NO 67
<211> LENGTH: 695
<212> TYPE: PRT
<213> ORGANISM: Human

<400> SEQUENCE: 67

Met Gly Thr Lys Met Ala Asp Leu Asp Ser Pro Pro Lys Leu Ser Gly
1               5                   10                  15

Val Gln Gln Pro Ser Glu Gly Val Gly Gly Arg Cys Ser Glu Ile
                20                  25                  30

Ser Ala Glu Leu Ile Arg Ser Leu Thr Glu Leu Gln Glu Leu Glu Ala
            35                  40                  45

Val Tyr Glu Arg Leu Cys Gly Glu Glu Lys Val Val Glu Arg Glu Leu
        50                  55                  60

Asp Ala Leu Leu Glu Gln Gln Asn Thr Ile Glu Ser Lys Met Val Thr
65                  70                  75                  80

-continued

```
Leu His Arg Met Gly Pro Asn Leu Gln Leu Ile Glu Ala Asn Leu Lys
                 85                  90                  95
Leu Leu Gln Glu Ala Glu Gln Arg Leu Lys Ala Ile Val Ala Glu Lys
            100                 105                 110
Phe Ala Ile Ala Thr Lys Glu Gly Asp Leu Pro Gln Val Glu Arg Phe
        115                 120                 125
Phe Lys Ile Phe Pro Leu Leu Gly Leu His Glu Gly Leu Arg Lys
    130                 135                 140
Phe Ser Glu Tyr Leu Cys Lys Gln Val Ala Ser Lys Ala Glu Glu Asn
145                 150                 155                 160
Leu Leu Met Val Leu Gly Thr Asp Met Ser Asp Arg Arg Ala Ala Val
                165                 170                 175
Ile Phe Ala Asp Thr Leu Thr Leu Phe Glu Gly Ile Ala Arg Ile
            180                 185                 190
Val Glu Thr His Gln Pro Ile Val Glu Thr Tyr Tyr Gly Pro Gly Arg
        195                 200                 205
Leu Tyr Thr Leu Ile Lys Tyr Leu Gln Val Glu Cys Asp Arg Gln Val
    210                 215                 220
Glu Lys Val Val Asp Lys Phe Ile Lys Gln Arg Asp Tyr His Gln Gln
225                 230                 235                 240
Phe Arg His Val Gln Asn Asn Leu Met Arg Asn Ser Thr Thr Glu Lys
                245                 250                 255
Ile Glu Pro Arg Glu Leu Asp Pro Ile Leu Thr Glu Val Thr Leu Met
            260                 265                 270
Asn Ala Arg Ser Glu Leu Tyr Leu Arg Phe Leu Lys Lys Arg Ile Ser
        275                 280                 285
Ser Asp Phe Glu Val Gly Asp Ser Met Ala Ser Glu Glu Val Lys Gln
    290                 295                 300
Glu His Gln Lys Cys Leu Asp Lys Leu Leu Asn Asn Cys Leu Leu Ser
305                 310                 315                 320
Cys Thr Met Gln Glu Leu Ile Gly Leu Tyr Val Thr Met Glu Glu Tyr
                325                 330                 335
Phe Met Arg Glu Thr Val Asn Lys Ala Val Ala Leu Asp Thr Tyr Glu
            340                 345                 350
Lys Gly Gln Leu Thr Ser Ser Met Val Asp Asp Val Phe Tyr Ile Val
        355                 360                 365
Lys Lys Cys Ile Gly Arg Ala Leu Ser Ser Ser Ile Asp Cys Leu
    370                 375                 380
Cys Ala Met Ile Asn Leu Ala Thr Thr Glu Leu Glu Ser Asp Phe Arg
385                 390                 395                 400
Asp Val Leu Cys Asn Lys Leu Arg Met Gly Phe Pro Ala Thr Phe
                405                 410                 415
Gln Asp Ile Gln Arg Gly Val Thr Ser Ala Val Asn Ile Met His Ser
            420                 425                 430
Ser Leu Gln Gln Gly Lys Phe Asp Thr Lys Gly Ile Glu Ser Thr Asp
        435                 440                 445
Glu Ala Lys Met Ser Phe Leu Val Thr Leu Asn Asn Val Glu Val Cys
    450                 455                 460
Ser Glu Asn Ile Ser Thr Leu Lys Lys Thr Leu Glu Ser Asp Cys Thr
465                 470                 475                 480
Lys Leu Phe Ser Gln Gly Ile Gly Gly Glu Gln Ala Gln Ala Lys Phe
                485                 490                 495
Asp Ser Cys Leu Ser Asp Leu Ala Ala Val Ser Asn Lys Phe Arg Asp
```

```
                500                 505                 510
Leu Leu Gln Glu Gly Leu Thr Glu Leu Asn Ser Thr Ala Ile Lys Pro
            515                 520                 525
Gln Val Gln Pro Trp Ile Asn Ser Phe Phe Ser Val Ser His Asn Ile
        530                 535                 540
Glu Glu Glu Glu Phe Asn Asp Tyr Glu Ala Asn Asp Pro Trp Val Gln
545                 550                 555                 560
Gln Phe Ile Leu Asn Leu Glu Gln Gln Met Ala Glu Phe Lys Ala Ser
                565                 570                 575
Leu Ser Pro Val Ile Tyr Asp Ser Leu Thr Gly Leu Met Thr Ser Leu
            580                 585                 590
Val Ala Val Glu Leu Glu Lys Val Val Leu Lys Ser Thr Phe Asn Arg
        595                 600                 605
Leu Gly Gly Leu Gln Phe Asp Lys Glu Leu Arg Ser Leu Ile Ala Tyr
    610                 615                 620
Leu Thr Thr Val Thr Thr Trp Thr Ile Arg Asp Lys Phe Ala Arg Leu
625                 630                 635                 640
Ser Gln Met Ala Thr Ile Leu Asn Leu Glu Arg Val Thr Glu Ile Leu
                645                 650                 655
Asp Tyr Trp Gly Pro Asn Ser Gly Pro Leu Thr Trp Arg Leu Thr Pro
            660                 665                 670
Ala Glu Val Arg Gln Val Leu Ala Leu Arg Ile Asp Phe Arg Ser Glu
        675                 680                 685
Asp Ile Lys Arg Leu Arg Leu
    690                 695

<210> SEQ ID NO 68
<211> LENGTH: 417
<212> TYPE: PRT
<213> ORGANISM: Human

<400> SEQUENCE: 68

Met Glu Phe Val Lys Cys Leu Gly His Pro Glu Glu Phe Tyr Asn Leu
1               5                   10                  15
Val Arg Phe Arg Ile Gly Gly Lys Arg Lys Val Met Pro Lys Met Asp
            20                  25                  30
Gln Asp Ser Leu Ser Ser Ser Leu Lys Thr Cys Tyr Lys Tyr Leu Asn
        35                  40                  45
Gln Thr Ser Arg Ser Phe Ala Ala Val Ile Gln Ala Leu Asp Gly Glu
    50                  55                  60
Met Arg Asn Ala Val Cys Ile Phe Tyr Leu Val Leu Arg Ala Leu Asp
65                  70                  75                  80
Thr Leu Glu Asp Asp Met Thr Ile Ser Val Glu Lys Lys Val Pro Leu
                85                  90                  95
Leu His Asn Phe His Ser Phe Leu Tyr Gln Pro Asp Trp Arg Phe Met
            100                 105                 110
Glu Ser Lys Glu Lys Asp Arg Gln Val Leu Glu Asp Phe Pro Thr Ile
        115                 120                 125
Ser Leu Glu Phe Arg Asn Leu Ala Glu Lys Tyr Gln Thr Val Ile Ala
    130                 135                 140
Asp Ile Cys Arg Arg Met Gly Ile Gly Met Ala Glu Phe Leu Asp Lys
145                 150                 155                 160
His Val Thr Ser Glu Gln Glu Trp Asp Lys Tyr Cys His Tyr Val Ala
                165                 170                 175
```

```
Gly Leu Val Gly Ile Gly Leu Ser Arg Leu Phe Ser Ala Ser Glu Phe
            180                 185                 190

Glu Asp Pro Leu Val Gly Asp Thr Glu Arg Ala Asn Ser Met Gly
        195                 200                 205

Leu Phe Leu Gln Lys Thr Asn Ile Ile Arg Asp Tyr Leu Glu Asp Gln
    210                 215                 220

Gln Gly Gly Arg Glu Phe Trp Pro Gln Glu Val Trp Ser Arg Tyr Val
225                 230                 235                 240

Lys Lys Leu Gly Asp Phe Ala Lys Pro Glu Asn Ile Asp Leu Ala Val
                245                 250                 255

Gln Cys Leu Asn Glu Leu Ile Thr Asn Ala Leu His His Ile Pro Asp
                260                 265                 270

Val Ile Thr Tyr Leu Ser Arg Leu Arg Asn Gln Ser Val Phe Asn Phe
            275                 280                 285

Cys Ala Ile Pro Gln Val Met Ala Ile Ala Thr Leu Ala Ala Cys Tyr
        290                 295                 300

Asn Asn Gln Gln Val Phe Lys Gly Ala Val Lys Ile Arg Lys Gly Gln
305                 310                 315                 320

Ala Val Thr Leu Met Met Asp Ala Thr Asn Met Pro Ala Val Lys Ala
                325                 330                 335

Ile Ile Tyr Gln Tyr Met Glu Glu Ile Tyr His Arg Ile Pro Asp Ser
                340                 345                 350

Asp Pro Ser Ser Ser Lys Thr Arg Gln Ile Ile Ser Thr Ile Arg Thr
            355                 360                 365

Gln Asn Leu Pro Asn Cys Gln Leu Ile Ser Arg Ser His Tyr Ser Pro
370                 375                 380

Ile Tyr Leu Ser Phe Val Met Leu Leu Ala Ala Leu Ser Trp Gln Tyr
385                 390                 395                 400

Leu Thr Thr Leu Ser Gln Val Thr Glu Asp Tyr Val Gln Thr Gly Glu
                405                 410                 415

His

<210> SEQ ID NO 69
<211> LENGTH: 359
<212> TYPE: PRT
<213> ORGANISM: Human

<400> SEQUENCE: 69

Met Arg Ala Ser Gln Lys Asp Phe Glu Asn Ser Met Asn Gln Val Lys
1               5                   10                  15

Leu Leu Lys Lys Asp Pro Gly Asn Glu Val Lys Leu Lys Leu Tyr Ala
                20                  25                  30

Leu Tyr Lys Gln Ala Thr Glu Gly Pro Cys Asn Met Pro Lys Pro Gly
            35                  40                  45

Val Phe Asp Leu Ile Asn Lys Ala Lys Trp Asp Ala Trp Asn Ala Leu
    50                  55                  60

Gly Ser Leu Pro Lys Glu Ala Ala Arg Gln Asn Tyr Val Asp Leu Val
65                  70                  75                  80

Ser Ser Leu Ser Pro Ser Leu Glu Ser Ser Gln Val Glu Pro Gly
                85                  90                  95

Thr Asp Arg Lys Ser Thr Gly Phe Glu Thr Leu Val Val Thr Ser Glu
                100                 105                 110

Asp Gly Ile Thr Lys Ile Met Phe Asn Arg Pro Lys Lys Lys Asn Ala
            115                 120                 125
```

```
Ile Asn Thr Glu Met Tyr His Glu Ile Met Arg Ala Leu Lys Ala Ala
    130                 135                 140

Ser Lys Asp Asp Ser Ile Ile Thr Val Leu Thr Gly Asn Gly Asp Tyr
145                 150                 155                 160

Tyr Ser Ser Gly Asn Asp Leu Thr Asn Phe Thr Asp Ile Pro Pro Gly
                165                 170                 175

Gly Val Glu Glu Lys Ala Lys Asn Asn Ala Val Leu Leu Arg Glu Phe
            180                 185                 190

Val Gly Cys Phe Ile Asp Phe Pro Lys Pro Leu Ile Ala Val Val Asn
            195                 200                 205

Gly Pro Ala Val Gly Ile Ser Val Thr Leu Leu Gly Leu Phe Asp Ala
210                 215                 220

Val Tyr Ala Ser Asp Arg Ala Thr Phe His Thr Pro Phe Ser His Leu
225                 230                 235                 240

Gly Gln Ser Pro Glu Gly Cys Ser Ser Tyr Thr Phe Pro Lys Ile Met
                245                 250                 255

Ser Pro Ala Lys Ala Thr Glu Met Leu Ile Phe Gly Lys Lys Leu Thr
                260                 265                 270

Ala Gly Glu Ala Cys Ala Gln Gly Leu Val Thr Glu Val Phe Pro Asp
            275                 280                 285

Ser Thr Phe Gln Lys Glu Val Trp Thr Arg Leu Lys Ala Phe Ala Lys
290                 295                 300

Leu Pro Pro Asn Ala Leu Arg Ile Ser Lys Glu Val Ile Arg Lys Arg
305                 310                 315                 320

Glu Arg Glu Lys Leu His Ala Val Asn Ala Glu Glu Cys Asn Val Leu
                325                 330                 335

Gln Gly Arg Trp Leu Ser Asp Glu Cys Thr Asn Ala Val Val Asn Phe
            340                 345                 350

Leu Ser Arg Lys Ser Lys Leu
            355

<210> SEQ ID NO 70
<211> LENGTH: 227
<212> TYPE: PRT
<213> ORGANISM: Human

<400> SEQUENCE: 70

Met Tyr His Glu Ile Met Arg Ala Leu Lys Ala Ala Ser Lys Asp Asp
1               5                   10                  15

Ser Ile Ile Thr Val Leu Thr Gly Asn Gly Asp Tyr Tyr Ser Ser Gly
                20                  25                  30

Asn Asp Leu Thr Asn Phe Thr Asp Ile Pro Pro Gly Gly Val Glu Glu
            35                  40                  45

Lys Ala Lys Asn Asn Ala Val Leu Leu Arg Glu Phe Val Gly Cys Phe
50                  55                  60

Ile Asp Phe Pro Lys Pro Leu Ile Ala Val Val Asn Gly Pro Ala Val
65                  70                  75                  80

Gly Ile Ser Val Thr Leu Leu Gly Leu Phe Asp Ala Val Tyr Ala Ser
                85                  90                  95

Asp Arg Ala Thr Phe His Thr Pro Phe Ser His Leu Gly Gln Ser Pro
            100                 105                 110

Glu Gly Cys Ser Ser Tyr Thr Phe Pro Lys Ile Met Ser Pro Ala Lys
        115                 120                 125

Ala Thr Glu Met Leu Ile Phe Gly Lys Lys Leu Thr Ala Gly Glu Ala
130                 135                 140
```

```
Cys Ala Gln Gly Leu Val Thr Glu Val Phe Pro Asp Ser Thr Phe Gln
145                 150                 155                 160

Lys Glu Val Trp Thr Arg Leu Lys Ala Phe Ala Lys Leu Pro Pro Asn
            165                 170                 175

Ala Leu Arg Ile Ser Lys Glu Val Ile Arg Lys Arg Glu Arg Glu Lys
            180                 185                 190

Leu His Ala Val Asn Ala Glu Glu Cys Asn Val Leu Gln Gly Arg Trp
            195                 200                 205

Leu Ser Asp Glu Cys Thr Asn Ala Val Val Asn Phe Leu Ser Arg Lys
            210                 215                 220

Ser Lys Leu
225

<210> SEQ ID NO 71
<211> LENGTH: 394
<212> TYPE: PRT
<213> ORGANISM: Human

<400> SEQUENCE: 71

Met Ala Met Ala Tyr Leu Ala Trp Arg Leu Ala Arg Arg Ser Cys Pro
1               5                   10                  15

Ser Ser Leu Gln Val Thr Ser Phe Pro Val Val Gln Leu His Met Asn
            20                  25                  30

Arg Thr Ala Met Arg Ala Ser Gln Lys Asp Phe Glu Asn Ser Met Asn
            35                  40                  45

Gln Val Lys Leu Leu Lys Lys Asp Pro Gly Asn Glu Val Lys Leu Lys
50                  55                  60

Leu Tyr Ala Leu Tyr Lys Gln Ala Thr Glu Gly Pro Cys Asn Met Pro
65                  70                  75                  80

Lys Pro Gly Val Phe Asp Leu Ile Asn Lys Ala Lys Trp Asp Ala Trp
            85                  90                  95

Asn Ala Leu Gly Ser Leu Pro Lys Glu Ala Ala Arg Gln Asn Tyr Val
            100                 105                 110

Asp Leu Val Ser Ser Leu Ser Pro Ser Leu Glu Ser Ser Ser Gln Val
            115                 120                 125

Glu Pro Gly Thr Asp Arg Lys Ser Thr Gly Phe Glu Thr Leu Val Val
            130                 135                 140

Thr Ser Glu Asp Gly Ile Thr Lys Ile Met Phe Asn Arg Pro Lys Lys
145                 150                 155                 160

Lys Asn Ala Ile Asn Thr Glu Met Tyr His Glu Ile Met Arg Ala Leu
            165                 170                 175

Lys Ala Ala Ser Lys Asp Asp Ser Ile Ile Thr Val Leu Thr Gly Asn
            180                 185                 190

Gly Asp Tyr Tyr Ser Ser Gly Asn Asp Leu Thr Asn Phe Thr Asp Ile
            195                 200                 205

Pro Pro Gly Gly Val Glu Glu Lys Ala Lys Asn Ala Val Leu Leu
            210                 215                 220

Arg Glu Phe Val Gly Cys Phe Ile Asp Phe Pro Lys Pro Leu Ile Ala
225                 230                 235                 240

Val Val Asn Gly Pro Ala Val Gly Ile Ser Val Thr Leu Leu Gly Leu
            245                 250                 255

Phe Asp Ala Val Tyr Ala Ser Asp Arg Ala Thr Phe His Thr Pro Phe
            260                 265                 270

Ser His Leu Gly Gln Ser Pro Glu Gly Cys Ser Ser Tyr Thr Phe Pro
```

```
               275                 280                 285
Lys Ile Met Ser Pro Ala Lys Ala Thr Glu Met Leu Ile Phe Gly Lys
    290                 295                 300
Lys Leu Thr Ala Gly Glu Ala Cys Ala Gln Gly Leu Val Thr Glu Val
305                 310                 315                 320
Phe Pro Asp Ser Thr Phe Gln Lys Glu Val Trp Thr Arg Leu Lys Ala
                325                 330                 335
Phe Ala Lys Leu Pro Pro Asn Ala Leu Arg Ile Ser Lys Glu Val Ile
            340                 345                 350
Arg Lys Arg Glu Arg Glu Lys Leu His Ala Val Asn Ala Glu Glu Cys
        355                 360                 365
Asn Val Leu Gln Gly Arg Trp Leu Ser Asp Glu Cys Thr Asn Ala Val
    370                 375                 380
Val Asn Phe Leu Ser Arg Lys Ser Lys Leu
385                 390

<210> SEQ ID NO 72
<211> LENGTH: 364
<212> TYPE: PRT
<213> ORGANISM: Human

<400> SEQUENCE: 72

Met Asn Arg Thr Ala Met Arg Ala Ser Gln Lys Asp Phe Glu Asn Ser
1               5                   10                  15
Met Asn Gln Val Lys Leu Leu Lys Lys Asp Pro Gly Asn Glu Val Lys
            20                  25                  30
Leu Lys Leu Tyr Ala Leu Tyr Lys Gln Ala Thr Glu Gly Pro Cys Asn
        35                  40                  45
Met Pro Lys Pro Gly Val Phe Asp Leu Ile Asn Lys Ala Lys Trp Asp
    50                  55                  60
Ala Trp Asn Ala Leu Gly Ser Leu Pro Lys Glu Ala Ala Arg Gln Asn
65                  70                  75                  80
Tyr Val Asp Leu Val Ser Ser Leu Ser Pro Ser Leu Glu Ser Ser Ser
                85                  90                  95
Gln Val Glu Pro Gly Thr Asp Arg Lys Ser Thr Gly Phe Glu Thr Leu
            100                 105                 110
Val Val Thr Ser Glu Asp Gly Ile Thr Lys Ile Met Phe Asn Arg Pro
        115                 120                 125
Lys Lys Lys Asn Ala Ile Asn Thr Glu Met Tyr His Glu Ile Met Arg
    130                 135                 140
Ala Leu Lys Ala Ala Ser Lys Asp Asp Ser Ile Ile Thr Val Leu Thr
145                 150                 155                 160
Gly Asn Gly Asp Tyr Tyr Ser Ser Gly Asn Asp Leu Thr Asn Phe Thr
                165                 170                 175
Asp Ile Pro Pro Gly Val Glu Glu Lys Ala Lys Asn Asn Ala Val
            180                 185                 190
Leu Leu Arg Glu Phe Val Gly Cys Phe Ile Asp Phe Pro Lys Pro Leu
        195                 200                 205
Ile Ala Val Val Asn Gly Pro Ala Val Gly Ile Ser Val Thr Leu Leu
    210                 215                 220
Gly Leu Phe Asp Ala Val Tyr Ala Ser Asp Arg Ala Thr Phe His Thr
225                 230                 235                 240
Pro Phe Ser His Leu Gly Gln Ser Pro Glu Gly Cys Ser Ser Tyr Thr
                245                 250                 255
```

```
Phe Pro Lys Ile Met Ser Pro Ala Lys Ala Thr Glu Met Leu Ile Phe
                260                 265                 270

Gly Lys Lys Leu Thr Ala Gly Glu Ala Cys Ala Gln Gly Leu Val Thr
            275                 280                 285

Glu Val Phe Pro Asp Ser Thr Phe Gln Lys Glu Val Trp Thr Arg Leu
        290                 295                 300

Lys Ala Phe Ala Lys Leu Pro Pro Asn Ala Leu Arg Ile Ser Lys Glu
305                 310                 315                 320

Val Ile Arg Lys Arg Glu Arg Glu Lys Leu His Ala Val Asn Ala Glu
                325                 330                 335

Glu Cys Asn Val Leu Gln Gly Arg Trp Leu Ser Asp Glu Cys Thr Asn
            340                 345                 350

Ala Val Val Asn Phe Leu Ser Arg Lys Ser Lys Leu
            355                 360

<210> SEQ ID NO 73
<211> LENGTH: 241
<212> TYPE: PRT
<213> ORGANISM: Human

<400> SEQUENCE: 73

Met Phe Asn Arg Pro Lys Lys Lys Asn Ala Ile Asn Thr Glu Met Tyr
1               5                   10                  15

His Glu Ile Met Arg Ala Leu Lys Ala Ala Ser Lys Asp Asp Ser Ile
                20                  25                  30

Ile Thr Val Leu Thr Gly Asn Gly Asp Tyr Tyr Ser Ser Gly Asn Asp
            35                  40                  45

Leu Thr Asn Phe Thr Asp Ile Pro Pro Gly Gly Val Glu Glu Lys Ala
        50                  55                  60

Lys Asn Asn Ala Val Leu Leu Arg Glu Phe Val Gly Cys Phe Ile Asp
65                  70                  75                  80

Phe Pro Lys Pro Leu Ile Ala Val Val Asn Gly Pro Ala Val Gly Ile
                85                  90                  95

Ser Val Thr Leu Leu Gly Leu Phe Asp Ala Val Tyr Ala Ser Asp Arg
                100                 105                 110

Ala Thr Phe His Thr Pro Phe Ser His Leu Gly Gln Ser Pro Glu Gly
            115                 120                 125

Cys Ser Ser Tyr Thr Phe Pro Lys Ile Met Ser Pro Ala Lys Ala Thr
        130                 135                 140

Glu Met Leu Ile Phe Gly Lys Lys Leu Thr Ala Gly Glu Ala Cys Ala
145                 150                 155                 160

Gln Gly Leu Val Thr Glu Val Phe Pro Asp Ser Thr Phe Gln Lys Glu
                165                 170                 175

Val Trp Thr Arg Leu Lys Ala Phe Ala Lys Leu Pro Pro Asn Ala Leu
            180                 185                 190

Arg Ile Ser Lys Glu Val Ile Arg Lys Arg Glu Arg Glu Lys Leu His
        195                 200                 205

Ala Val Asn Ala Glu Glu Cys Asn Val Leu Gln Gly Arg Trp Leu Ser
    210                 215                 220

Asp Glu Cys Thr Asn Ala Val Val Asn Phe Leu Ser Arg Lys Ser Lys
225                 230                 235                 240

Leu

<210> SEQ ID NO 74
<211> LENGTH: 1225
```

<212> TYPE: PRT
<213> ORGANISM: Human

<400> SEQUENCE: 74

```
Met Phe Ala Arg Lys Pro Gly Ala Ala Pro Leu Gly Ala Met Pro
1               5                   10                  15

Val Pro Asp Gln Pro Ser Ser Ala Ser Glu Lys Thr Ser Ser Leu Ser
            20                  25                  30

Pro Gly Leu Asn Thr Ser Asn Gly Asp Gly Ser Glu Thr Glu Thr Thr
            35                  40                  45

Ser Ala Ile Leu Ala Ser Val Lys Glu Gln Glu Leu Gln Phe Glu Arg
        50                  55                  60

Leu Thr Arg Glu Leu Glu Ala Glu Arg Gln Ile Val Ala Ser Gln Leu
65                  70                  75                  80

Glu Arg Cys Lys Leu Gly Ser Glu Thr Gly Ser Met Ser Ser Met Ser
                85                  90                  95

Ser Ala Glu Glu Gln Phe Gln Trp Gln Ser Gln Asp Gly Gln Lys Asp
            100                 105                 110

Ile Glu Asp Glu Leu Thr Thr Gly Leu Glu Leu Val Asp Ser Cys Ile
            115                 120                 125

Arg Ser Leu Gln Glu Ser Gly Ile Leu Asp Pro Gln Asp Tyr Ser Thr
130                 135                 140

Gly Glu Arg Pro Ser Leu Leu Ser Gln Ser Ala Leu Gln Leu Asn Ser
145                 150                 155                 160

Lys Pro Glu Gly Ser Phe Gln Tyr Pro Ala Ser Tyr His Ser Asn Gln
                165                 170                 175

Thr Leu Ala Leu Gly Glu Thr Thr Pro Ser Gln Leu Pro Ala Arg Gly
            180                 185                 190

Thr Gln Ala Arg Ala Thr Gly Gln Ser Phe Ser Gln Gly Thr Thr Ser
            195                 200                 205

Arg Ala Gly His Leu Ala Gly Pro Glu Pro Ala Pro Pro Pro Pro
210                 215                 220

Pro Pro Arg Glu Pro Phe Ala Pro Ser Leu Gly Ser Ala Phe His Leu
225                 230                 235                 240

Pro Asp Ala Pro Pro Ala Ala Ala Ala Ala Leu Tyr Tyr Ser Ser
                245                 250                 255

Ser Thr Leu Pro Ala Pro Pro Arg Gly Gly Ser Pro Leu Ala Ala Pro
            260                 265                 270

Gln Gly Gly Ser Pro Thr Lys Leu Gln Arg Gly Gly Ser Ala Pro Glu
            275                 280                 285

Gly Ala Thr Tyr Ala Ala Pro Arg Gly Ser Ser Pro Lys Gln Ser Pro
            290                 295                 300

Ser Arg Leu Ala Lys Ser Tyr Ser Thr Ser Ser Pro Ile Asn Ile Val
305                 310                 315                 320

Val Ser Ser Ala Gly Leu Ser Pro Ile Arg Val Thr Ser Pro Pro Thr
                325                 330                 335

Val Gln Ser Thr Ile Ser Ser Ser Pro Ile His Gln Leu Ser Ser Thr
            340                 345                 350

Ile Gly Thr Tyr Ala Thr Leu Ser Pro Thr Lys Arg Leu Val His Ala
            355                 360                 365

Ser Glu Gln Tyr Ser Lys His Ser Gln Glu Leu Tyr Ala Thr Ala Thr
            370                 375                 380

Leu Gln Arg Pro Gly Ser Leu Ala Ala Gly Ser Arg Ala Ser Tyr Ser
385                 390                 395                 400
```

```
Ser Gln His Gly His Leu Gly Pro Glu Leu Arg Ala Leu Gln Ser Pro
                405                 410                 415
Glu His His Ile Asp Pro Ile Tyr Glu Asp Arg Val Tyr Gln Lys Pro
            420                 425                 430
Pro Met Arg Ser Leu Ser Gln Ser Gln Gly Asp Pro Leu Pro Pro Ala
        435                 440                 445
His Thr Gly Thr Tyr Arg Thr Ser Thr Ala Pro Ser Ser Pro Gly Val
    450                 455                 460
Asp Ser Val Pro Leu Gln Arg Thr Gly Ser Gln His Gly Pro Gln Asn
465                 470                 475                 480
Ala Ala Ala Thr Phe Gln Arg Ala Ser Tyr Ala Ala Gly Pro Ala
                485                 490                 495
Ser Asn Tyr Ala Asp Pro Tyr Arg Gln Leu Gln Tyr Cys Pro Ser Val
                500                 505                 510
Glu Ser Pro Tyr Ser Lys Ser Gly Pro Ala Leu Pro Pro Glu Gly Thr
            515                 520                 525
Leu Ala Arg Ser Pro Ser Ile Asp Ser Ile Gln Lys Asp Pro Arg Glu
        530                 535                 540
Phe Gly Trp Arg Asp Pro Glu Leu Pro Glu Val Ile Gln Met Leu Gln
545                 550                 555                 560
His Gln Phe Pro Ser Val Gln Ser Asn Ala Ala Ala Tyr Leu Gln His
                565                 570                 575
Leu Cys Phe Gly Asp Asn Lys Ile Lys Ala Glu Ile Arg Arg Gln Gly
                580                 585                 590
Gly Ile Gln Leu Leu Val Asp Leu Leu Asp His Arg Met Thr Glu Val
            595                 600                 605
His Arg Ser Ala Cys Gly Ala Leu Arg Asn Leu Val Tyr Gly Lys Ala
        610                 615                 620
Asn Asp Asp Asn Lys Ile Ala Leu Lys Asn Cys Gly Gly Ile Pro Ala
625                 630                 635                 640
Leu Val Arg Leu Leu Arg Lys Thr Thr Asp Leu Glu Ile Arg Glu Leu
                645                 650                 655
Val Thr Gly Val Leu Trp Asn Leu Ser Ser Cys Asp Ala Leu Lys Met
                660                 665                 670
Pro Ile Ile Gln Asp Ala Leu Ala Val Leu Thr Asn Ala Val Ile Ile
            675                 680                 685
Pro His Ser Gly Trp Glu Asn Ser Pro Leu Gln Asp Asp Arg Lys Ile
        690                 695                 700
Gln Leu His Ser Ser Gln Val Leu Arg Asn Ala Thr Gly Cys Leu Arg
705                 710                 715                 720
Asn Val Ser Ser Ala Gly Glu Glu Ala Arg Arg Met Arg Glu Cys
                725                 730                 735
Asp Gly Leu Thr Asp Ala Leu Leu Tyr Val Ile Gln Ser Ala Leu Gly
            740                 745                 750
Ser Ser Glu Ile Asp Ser Lys Thr Val Glu Asn Cys Val Cys Ile Leu
        755                 760                 765
Arg Asn Leu Ser Tyr Arg Leu Ala Ala Glu Thr Ser Gln Gly Gln His
    770                 775                 780
Met Gly Thr Asp Glu Leu Asp Gly Leu Leu Cys Gly Glu Ala Asn Gly
785                 790                 795                 800
Lys Asp Ala Glu Ser Ser Gly Cys Trp Gly Lys Lys Lys Lys Lys
                805                 810                 815
```

-continued

Lys Ser Gln Asp Gln Trp Asp Gly Val Gly Pro Leu Pro Asp Cys Ala
                820                 825                 830

Glu Pro Pro Lys Gly Ile Gln Met Leu Trp His Pro Ser Ile Val Lys
            835                 840                 845

Pro Tyr Leu Thr Leu Leu Ser Glu Cys Ser Asn Pro Asp Thr Leu Glu
        850                 855                 860

Gly Ala Ala Gly Ala Leu Gln Asn Leu Ala Ala Gly Ser Trp Lys Trp
865                 870                 875                 880

Ser Val Tyr Ile Arg Ala Ala Val Arg Lys Glu Lys Gly Leu Pro Ile
                885                 890                 895

Leu Val Glu Leu Leu Arg Ile Asp Asn Asp Arg Val Val Cys Ala Val
            900                 905                 910

Ala Thr Ala Leu Arg Asn Met Ala Leu Asp Val Arg Asn Lys Glu Leu
        915                 920                 925

Ile Gly Lys Tyr Ala Met Arg Asp Leu Val His Arg Leu Pro Gly Gly
        930                 935                 940

Asn Asn Ser Asn Asn Thr Ala Ser Lys Ala Met Ser Asp Asp Thr Val
945                 950                 955                 960

Thr Ala Val Cys Cys Thr Leu His Glu Val Ile Thr Lys Asn Met Glu
                965                 970                 975

Asn Ala Lys Ala Leu Arg Asp Ala Gly Gly Ile Glu Lys Leu Val Gly
            980                 985                 990

Ile Ser Lys Ser Lys Gly Asp Lys His Ser Pro Lys Val Val Lys Ala
            995                 1000                1005

Ala Ser Gln Val Leu Asn Ser Met Trp Gln Tyr Arg Asp Leu Arg
    1010                1015                1020

Ser Leu Tyr Lys Lys Asp Gly Trp Ser Gln Tyr His Phe Val Ala
    1025                1030                1035

Ser Ser Ser Thr Ile Glu Arg Asp Arg Gln Arg Pro Tyr Ser Ser
    1040                1045                1050

Ser Arg Thr Pro Ser Ile Ser Pro Val Arg Val Ser Pro Asn Asn
    1055                1060                1065

Arg Ser Ala Ser Ala Pro Ala Ser Pro Arg Glu Met Ile Ser Leu
    1070                1075                1080

Lys Glu Arg Lys Thr Asp Tyr Glu Cys Thr Gly Ser Asn Ala Thr
    1085                1090                1095

Tyr His Gly Ala Lys Gly Glu His Thr Ser Arg Lys Asp Ala Met
    1100                1105                1110

Thr Ala Gln Asn Thr Gly Ile Ser Thr Leu Tyr Arg Asn Ser Tyr
    1115                1120                1125

Gly Ala Pro Ala Glu Asp Ile Lys His Asn Gln Val Ser Ala Gln
    1130                1135                1140

Pro Val Pro Gln Glu Pro Ser Arg Lys Asp Tyr Glu Thr Tyr Gln
    1145                1150                1155

Pro Phe Gln Asn Ser Thr Arg Asn Tyr Asp Glu Ser Phe Phe Glu
    1160                1165                1170

Asp Gln Val His His Arg Pro Pro Ala Ser Glu Tyr Thr Met His
    1175                1180                1185

Leu Gly Leu Lys Ser Thr Gly Asn Tyr Val Asp Phe Tyr Ser Ala
    1190                1195                1200

Ala Arg Pro Tyr Ser Glu Leu Asn Tyr Glu Thr Ser His Tyr Pro
    1205                1210                1215

Ala Ser Pro Asp Ser Trp Val

<210> SEQ ID NO 75
<211> LENGTH: 1167
<212> TYPE: PRT
<213> ORGANISM: Human

<400> SEQUENCE: 75

```
Met Phe Ala Arg Lys Pro Pro Gly Ala Ala Pro Leu Gly Ala Met Pro
1               5                   10                  15

Val Pro Asp Gln Pro Ser Ser Ala Ser Glu Lys Thr Ser Ser Leu Ser
            20                  25                  30

Pro Gly Leu Asn Thr Ser Asn Gly Asp Gly Ser Glu Thr Glu Thr Thr
        35                  40                  45

Ser Ala Ile Leu Ala Ser Val Lys Glu Gln Glu Leu Gln Phe Glu Arg
    50                  55                  60

Leu Thr Arg Glu Leu Glu Ala Glu Arg Gln Ile Val Ala Ser Gln Leu
65                  70                  75                  80

Glu Arg Cys Lys Leu Gly Ser Glu Thr Gly Ser Met Ser Ser Met Ser
                85                  90                  95

Ser Ala Glu Glu Gln Phe Gln Trp Gln Ser Gln Asp Gly Gln Lys Asp
            100                 105                 110

Ile Glu Asp Glu Leu Thr Thr Gly Leu Glu Leu Val Asp Ser Cys Ile
        115                 120                 125

Arg Ser Leu Gln Glu Ser Gly Ile Leu Asp Pro Gln Asp Tyr Ser Thr
    130                 135                 140

Gly Glu Arg Pro Ser Leu Leu Ser Gln Ser Ala Leu Gln Leu Asn Ser
145                 150                 155                 160

Lys Pro Glu Gly Ser Phe Gln Tyr Pro Ala Ser Tyr His Ser Asn Gln
                165                 170                 175

Thr Leu Ala Leu Gly Glu Thr Thr Pro Ser Gln Leu Pro Ala Arg Gly
            180                 185                 190

Thr Gln Ala Arg Ala Thr Gly Gln Ser Phe Ser Gln Gly Thr Thr Ser
        195                 200                 205

Arg Ala Gly His Leu Ala Gly Pro Glu Pro Ala Pro Pro Pro Pro Pro
    210                 215                 220

Pro Pro Arg Glu Pro Phe Ala Pro Ser Leu Gly Ser Ala Phe His Leu
225                 230                 235                 240

Pro Asp Ala Pro Pro Ala Ala Ala Ala Ala Leu Tyr Tyr Ser Ser
                245                 250                 255

Ser Thr Leu Pro Ala Pro Pro Arg Gly Gly Ser Pro Leu Ala Ala Pro
            260                 265                 270

Gln Gly Gly Ser Pro Thr Lys Leu Gln Arg Gly Gly Ser Ala Pro Glu
        275                 280                 285

Gly Ala Thr Tyr Ala Ala Pro Arg Gly Ser Ser Pro Lys Gln Ser Pro
    290                 295                 300

Ser Arg Leu Ala Lys Ser Tyr Ser Thr Ser Ser Pro Ile Asn Ile Val
305                 310                 315                 320

Val Ser Ser Ala Gly Leu Ser Pro Ile Arg Val Thr Ser Pro Pro Thr
                325                 330                 335

Val Gln Ser Thr Ile Ser Ser Ser Pro Ile His Gln Leu Ser Ser Thr
            340                 345                 350

Ile Gly Thr Tyr Ala Thr Leu Ser Pro Thr Lys Arg Leu Val His Ala
        355                 360                 365
```

-continued

```
Ser Glu Gln Tyr Ser Lys His Ser Gln Glu Leu Tyr Ala Thr Ala Thr
370                 375                 380

Leu Gln Arg Pro Gly Ser Leu Ala Ala Gly Ser Arg Ala Ser Tyr Ser
385                 390                 395                 400

Ser Gln His Gly His Leu Gly Pro Glu Leu Arg Ala Leu Gln Ser Pro
                405                 410                 415

Glu His His Ile Asp Pro Ile Tyr Glu Asp Arg Val Tyr Gln Lys Pro
            420                 425                 430

Pro Met Arg Ser Leu Ser Gln Ser Gln Gly Asp Pro Leu Pro Pro Ala
        435                 440                 445

His Thr Gly Thr Tyr Arg Thr Ser Thr Ala Pro Ser Ser Pro Gly Val
450                 455                 460

Asp Ser Val Pro Leu Gln Arg Thr Gly Ser Gln His Gly Pro Gln Asn
465                 470                 475                 480

Ala Ala Ala Ala Thr Phe Gln Arg Ala Ser Tyr Ala Ala Gly Pro Ala
                485                 490                 495

Ser Asn Tyr Ala Asp Pro Tyr Arg Gln Leu Gln Tyr Cys Pro Ser Val
            500                 505                 510

Glu Ser Pro Tyr Ser Lys Ser Gly Pro Ala Leu Pro Pro Glu Gly Thr
        515                 520                 525

Leu Ala Arg Ser Pro Ser Ile Asp Ser Ile Gln Lys Asp Pro Arg Glu
530                 535                 540

Phe Gly Trp Arg Asp Pro Glu Leu Pro Glu Val Ile Gln Met Leu Gln
545                 550                 555                 560

His Gln Phe Pro Ser Val Gln Ser Asn Ala Ala Ala Tyr Leu Gln His
                565                 570                 575

Leu Cys Phe Gly Asp Asn Lys Ile Lys Ala Glu Ile Arg Arg Gln Gly
            580                 585                 590

Gly Ile Gln Leu Leu Val Asp Leu Leu Asp His Arg Met Thr Glu Val
        595                 600                 605

His Arg Ser Ala Cys Gly Ala Leu Arg Asn Leu Val Tyr Gly Lys Ala
610                 615                 620

Asn Asp Asp Asn Lys Ile Ala Leu Lys Asn Cys Gly Gly Ile Pro Ala
625                 630                 635                 640

Leu Val Arg Leu Leu Arg Lys Thr Thr Asp Leu Glu Ile Arg Glu Leu
                645                 650                 655

Val Thr Gly Val Leu Trp Asn Leu Ser Ser Cys Asp Ala Leu Lys Met
            660                 665                 670

Pro Ile Ile Gln Asp Ala Leu Ala Val Leu Thr Asn Ala Val Ile Ile
        675                 680                 685

Pro His Ser Gly Trp Glu Asn Ser Pro Leu Gln Asp Asp Arg Lys Ile
690                 695                 700

Gln Leu His Ser Ser Gln Val Leu Arg Asn Ala Thr Gly Cys Leu Arg
705                 710                 715                 720

Asn Val Ser Ser Ala Gly Glu Glu Ala Arg Arg Met Arg Glu Cys
                725                 730                 735

Asp Gly Leu Thr Asp Ala Leu Leu Tyr Val Ile Gln Ser Ala Leu Gly
            740                 745                 750

Ser Ser Glu Ile Asp Ser Lys Thr Val Glu Asn Cys Val Cys Ile Leu
        755                 760                 765

Arg Asn Leu Ser Tyr Arg Leu Ala Ala Glu Thr Ser Gln Gly Gln His
770                 775                 780

Met Gly Thr Asp Glu Leu Asp Gly Leu Leu Cys Gly Glu Ala Asn Gly
```

```
                785                 790                 795                 800
Lys Asp Ala Glu Ser Ser Gly Cys Trp Gly Lys Lys Lys Lys Lys
                    805                 810                 815
Lys Ser Gln Asp Gln Trp Ser Val Tyr Ile Arg Ala Ala Val Arg Lys
                820                 825                 830
Glu Lys Gly Leu Pro Ile Leu Val Glu Leu Arg Ile Asp Asn Asp
                835                 840                 845
Arg Val Val Cys Ala Val Ala Thr Ala Leu Arg Asn Met Ala Leu Asp
850                 855                 860
Val Arg Asn Lys Glu Leu Ile Gly Lys Tyr Ala Met Arg Asp Leu Val
865                 870                 875                 880
His Arg Leu Pro Gly Gly Asn Asn Ser Asn Asn Thr Ala Ser Lys Ala
                    885                 890                 895
Met Ser Asp Asp Thr Val Thr Ala Val Cys Cys Thr Leu His Glu Val
                900                 905                 910
Ile Thr Lys Asn Met Glu Asn Ala Lys Ala Leu Arg Asp Ala Gly Gly
                915                 920                 925
Ile Glu Lys Leu Val Gly Ile Ser Lys Ser Lys Gly Asp Lys His Ser
                930                 935                 940
Pro Lys Val Val Lys Ala Ala Ser Gln Val Leu Asn Ser Met Trp Gln
945                 950                 955                 960
Tyr Arg Asp Leu Arg Ser Leu Tyr Lys Lys Asp Gly Trp Ser Gln Tyr
                    965                 970                 975
His Phe Val Ala Ser Ser Thr Ile Glu Arg Asp Arg Gln Arg Pro
                980                 985                 990
Tyr Ser Ser Ser Arg Thr Pro Ser Ile Ser Pro Val Arg Val Ser Pro
                995                 1000                1005
Asn Asn Arg Ser Ala Ser Ala Pro Ala Ser Pro Arg Glu Met Ile
    1010                1015                1020
Ser Leu Lys Glu Arg Lys Thr Asp Tyr Glu Cys Thr Gly Ser Asn
    1025                1030                1035
Ala Thr Tyr His Gly Ala Lys Gly Glu His Thr Ser Arg Lys Asp
    1040                1045                1050
Ala Met Thr Ala Gln Asn Thr Gly Ile Ser Thr Leu Tyr Arg Asn
    1055                1060                1065
Ser Tyr Gly Ala Pro Ala Glu Asp Ile Lys His Asn Gln Val Ser
    1070                1075                1080
Ala Gln Pro Val Pro Gln Glu Pro Ser Arg Lys Asp Tyr Glu Thr
    1085                1090                1095
Tyr Gln Pro Phe Gln Asn Ser Thr Arg Asn Tyr Asp Glu Ser Phe
    1100                1105                1110
Phe Glu Asp Gln Val His His Arg Pro Pro Ala Ser Glu Tyr Thr
    1115                1120                1125
Met His Leu Gly Leu Lys Ser Thr Gly Asn Tyr Val Asp Phe Tyr
    1130                1135                1140
Ser Ala Ala Arg Pro Tyr Glu Leu Asn Tyr Glu Thr Ser His
    1145                1150                1155
Tyr Pro Ala Ser Pro Asp Ser Trp Val
    1160                1165

<210> SEQ ID NO 76
<211> LENGTH: 266
<212> TYPE: PRT
<213> ORGANISM: Human
```

<400> SEQUENCE: 76

```
Met Gln Gly Ser Thr Arg Arg Met Gly Val Met Thr Asp Val His Arg
1               5                   10                  15

Arg Phe Leu Gln Leu Leu Met Thr His Gly Val Leu Glu Glu Trp Asp
            20                  25                  30

Val Lys Arg Leu Gln Thr His Cys Tyr Lys Val His Asp Arg Asn Ala
        35                  40                  45

Thr Val Asp Lys Leu Glu Asp Phe Ile Asn Asn Ile Asn Ser Val Leu
    50                  55                  60

Glu Ser Leu Tyr Ile Glu Ile Lys Arg Gly Val Thr Glu Asp Asp Gly
65                  70                  75                  80

Arg Pro Ile Tyr Ala Leu Val Asn Leu Ala Thr Thr Ser Ile Ser Lys
                85                  90                  95

Met Ala Thr Asp Phe Ala Glu Asn Glu Leu Asp Leu Phe Arg Lys Ala
            100                 105                 110

Leu Glu Leu Ile Ile Asp Ser Glu Thr Gly Phe Ala Ser Ser Thr Asn
        115                 120                 125

Ile Leu Asn Leu Val Asp Gln Leu Lys Gly Lys Lys Met Arg Lys Lys
    130                 135                 140

Glu Ala Glu Gln Val Leu Gln Lys Phe Val Gln Asn Lys Trp Leu Ile
145                 150                 155                 160

Glu Lys Glu Gly Glu Phe Thr Leu His Gly Arg Ala Ile Leu Glu Met
                165                 170                 175

Glu Gln Tyr Ile Arg Glu Thr Tyr Pro Asp Ala Val Lys Ile Cys Asn
            180                 185                 190

Ile Cys His Ser Leu Leu Ile Gln Gly Gln Ser Cys Glu Thr Cys Gly
        195                 200                 205

Ile Arg Met His Leu Pro Cys Val Ala Lys Tyr Phe Gln Ser Asn Ala
    210                 215                 220

Glu Pro Arg Cys Pro His Cys Asn Asp Tyr Trp Pro His Glu Ile Pro
225                 230                 235                 240

Lys Val Phe Asp Pro Glu Lys Glu Arg Glu Ser Gly Val Leu Lys Ser
                245                 250                 255

Asn Lys Lys Ser Leu Arg Ser Arg Gln His
            260                 265
```

<210> SEQ ID NO 77
<211> LENGTH: 145
<212> TYPE: PRT
<213> ORGANISM: Human

<400> SEQUENCE: 77

```
Pro Tyr Pro Leu Ala Arg Trp Asp Ala Leu Gly Leu Pro Val Arg Ser
1               5                   10                  15

His Met Gln Gly Ser Thr Arg Arg Met Gly Val Met Thr Asp Val His
            20                  25                  30

Arg Arg Phe Leu Gln Leu Leu Met Thr His Gly Val Leu Glu Glu Trp
        35                  40                  45

Asp Val Lys Arg Leu Gln Thr His Cys Tyr Lys Val His Asp Arg Asn
    50                  55                  60

Ala Thr Val Asp Lys Leu Glu Asp Phe Ile Asn Asn Ile Asn Ser Val
65                  70                  75                  80

Leu Glu Ser Leu Tyr Ile Glu Ile Lys Arg Gly Val Thr Glu Asp Asp
                85                  90                  95
```

```
Gly Arg Pro Ile Tyr Ala Leu Val Asn Leu Ala Thr Thr Ser Ile Ser
                100                 105                 110

Lys Met Ala Thr Asp Phe Ala Glu Asn Glu Leu Asp Leu Phe Arg Lys
            115                 120                 125

Ala Leu Glu Leu Ile Ile Asp Ser Glu Thr Leu Arg Leu Pro Gln Thr
        130                 135                 140

Tyr
145

<210> SEQ ID NO 78
<211> LENGTH: 179
<212> TYPE: PRT
<213> ORGANISM: Human

<400> SEQUENCE: 78

Val His Leu Ala Thr Val Ser Ala Ser Ala Trp Asp Ala Leu Gly
1               5                   10                  15

Leu Pro Val Arg Ser His Met Gln Gly Ser Thr Arg Arg Met Gly Val
            20                  25                  30

Met Thr Asp Val His Arg Arg Phe Leu Gln Leu Leu Met Thr His Gly
        35                  40                  45

Val Leu Glu Glu Trp Asp Val Lys Arg Leu Gln Thr His Cys Tyr Lys
    50                  55                  60

Val His Asp Arg Asn Ala Thr Val Asp Lys Leu Glu Asp Phe Ile Asn
65                  70                  75                  80

Asn Ile Asn Ser Val Leu Glu Ser Leu Tyr Ile Glu Ile Lys Arg Gly
                85                  90                  95

Val Thr Glu Asp Asp Gly Arg Pro Ile Tyr Ala Leu Val Asn Leu Ala
            100                 105                 110

Thr Thr Ser Ile Ser Lys Met Ala Thr Asp Phe Ala Glu Asn Glu Leu
        115                 120                 125

Asp Leu Phe Arg Lys Ala Leu Glu Leu Ile Ile Asp Ser Glu Thr Gly
    130                 135                 140

Phe Ala Ser Ser Thr Asn Ile Leu Asn Leu Val Asp Gln Leu Lys Gly
145                 150                 155                 160

Lys Lys Met Arg Lys Lys Glu Ala Arg Cys Cys Arg Ser Leu Phe Lys
                165                 170                 175

Thr Ser Gly

<210> SEQ ID NO 79
<211> LENGTH: 392
<212> TYPE: PRT
<213> ORGANISM: Human

<400> SEQUENCE: 79

Met Glu Trp Trp Ala Ser Ser Pro Leu Arg Leu Trp Leu Leu Leu Phe
1               5                   10                  15

Leu Leu Pro Ser Ala Gln Gly Arg Gln Lys Glu Ser Gly Ser Lys Trp
            20                  25                  30

Lys Val Phe Ile Asp Gln Ile Asn Arg Ser Leu Glu Asn Tyr Glu Pro
        35                  40                  45

Cys Ser Ser Gln Asn Cys Ser Cys Tyr His Gly Val Ile Glu Glu Asp
    50                  55                  60

Leu Thr Pro Phe Arg Gly Gly Ile Ser Arg Lys Met Ala Glu Val
65                  70                  75                  80
```

Val Arg Arg Lys Leu Gly Thr His Tyr Gln Ile Thr Lys Asn Arg Leu
            85                  90                  95

Tyr Arg Glu Asn Asp Cys Met Phe Pro Ser Arg Cys Ser Gly Val Glu
            100                 105                 110

His Phe Ile Leu Glu Val Ile Gly Arg Leu Pro Asp Met Glu Met Val
            115                 120                 125

Ile Asn Val Arg Asp Tyr Pro Gln Val Pro Lys Trp Met Glu Pro Ala
            130                 135                 140

Ile Pro Val Phe Ser Phe Ser Lys Thr Ser Glu Tyr His Asp Ile Met
145                 150                 155                 160

Tyr Pro Ala Trp Thr Phe Trp Glu Gly Gly Pro Ala Val Trp Pro Ile
                165                 170                 175

Tyr Pro Thr Gly Leu Gly Arg Trp Asp Leu Phe Arg Glu Asp Leu Val
            180                 185                 190

Arg Ser Ala Ala Gln Trp Pro Trp Lys Lys Asn Ser Thr Ala Tyr
            195                 200                 205

Phe Arg Gly Ser Arg Thr Ser Pro Glu Arg Asp Pro Leu Ile Leu Leu
            210                 215                 220

Ser Arg Lys Asn Pro Lys Leu Val Asp Ala Glu Tyr Thr Lys Asn Gln
225                 230                 235                 240

Ala Trp Lys Ser Met Lys Asp Thr Leu Gly Lys Pro Ala Ala Lys Asp
                245                 250                 255

Val His Leu Val Asp His Cys Lys Tyr Lys Tyr Leu Phe Asn Phe Arg
            260                 265                 270

Gly Val Ala Ala Ser Phe Arg Phe Lys His Leu Phe Leu Cys Gly Ser
            275                 280                 285

Leu Val Phe His Val Gly Asp Glu Trp Leu Glu Phe Phe Tyr Pro Gln
            290                 295                 300

Leu Lys Pro Trp Val His Tyr Ile Pro Val Lys Thr Asp Leu Ser Asn
305                 310                 315                 320

Val Gln Glu Leu Leu Gln Phe Val Lys Ala Asn Asp Asp Val Ala Gln
                325                 330                 335

Glu Ile Ala Glu Arg Gly Ser Gln Phe Ile Arg Asn His Leu Gln Met
            340                 345                 350

Asp Asp Ile Thr Cys Tyr Trp Glu Asn Leu Leu Ser Glu Tyr Ser Lys
            355                 360                 365

Phe Leu Ser Tyr Asn Val Thr Arg Arg Lys Gly Tyr Asp Gln Ile Ile
            370                 375                 380

Pro Lys Met Leu Lys Thr Glu Leu
385                 390

<210> SEQ ID NO 80
<211> LENGTH: 411
<212> TYPE: PRT
<213> ORGANISM: Human

<400> SEQUENCE: 80

Met Arg Arg Arg Arg Ala Gly Gly Arg Thr Met Val Glu Arg Ala Ser
1               5                   10                  15

Lys Phe Val Leu Val Val Ala Gly Ser Val Cys Phe Met Leu Ile Leu
            20                  25                  30

Tyr Gln Tyr Ala Gly Pro Gly Leu Ser Leu Gly Ala Pro Gly Gly Arg
            35                  40                  45

Ala Pro Pro Asp Asp Leu Asp Leu Phe Pro Thr Pro Asp Pro His Tyr
            50                  55                  60

Glu Lys Lys Tyr Tyr Phe Pro Val Arg Glu Leu Gly Arg Ser Leu Arg
65                  70                  75                  80

Phe Asp Met Lys Gly Asp Val Ile Val Phe Leu His Ile Gln Lys
                85                  90                  95

Thr Gly Gly Thr Thr Phe Gly Arg His Leu Val Gln Asn Val Arg Leu
                100                 105                 110

Glu Val Pro Cys Asp Cys Arg Pro Gly Gln Lys Lys Cys Thr Cys Tyr
            115                 120                 125

Arg Pro Asn Arg Arg Glu Thr Trp Leu Phe Ser Arg Phe Ser Thr Gly
    130                 135                 140

Trp Ser Cys Gly Leu His Ala Asp Trp Thr Glu Leu Thr Asn Cys Val
145                 150                 155                 160

Pro Gly Val Leu Asp Arg Arg Asp Ser Ala Ala Leu Arg Thr Pro Arg
                165                 170                 175

Lys Phe Tyr Tyr Ile Thr Leu Leu Arg Asp Pro Val Ser Arg Tyr Leu
                180                 185                 190

Ser Glu Trp Arg His Val Gln Arg Gly Ala Thr Trp Lys Thr Ser Leu
            195                 200                 205

His Met Cys Asp Gly Arg Thr Pro Thr Pro Glu Glu Leu Pro Pro Cys
    210                 215                 220

Tyr Glu Gly Thr Asp Trp Ser Gly Cys Thr Leu Gln Glu Phe Met Asp
225                 230                 235                 240

Cys Pro Tyr Asn Leu Ala Asn Asn Arg Gln Val Arg Met Leu Ala Asp
                245                 250                 255

Leu Ser Leu Val Gly Cys Tyr Asn Leu Ser Phe Ile Pro Glu Gly Lys
                260                 265                 270

Arg Ala Gln Leu Leu Leu Glu Ser Ala Lys Lys Asn Leu Arg Gly Met
            275                 280                 285

Ala Phe Phe Gly Leu Thr Glu Phe Gln Arg Lys Thr Gln Tyr Leu Phe
    290                 295                 300

Glu Arg Thr Phe Asn Leu Lys Phe Ile Arg Pro Phe Met Gln Tyr Asn
305                 310                 315                 320

Ser Thr Arg Ala Gly Gly Val Glu Val Asp Gly Asp Thr Ile Arg Arg
                325                 330                 335

Ile Glu Glu Leu Asn Asp Leu Asp Met Gln Leu Tyr Asp Tyr Ala Lys
                340                 345                 350

Asp Leu Phe Gln Gln Arg Tyr Gln Tyr Lys Arg Gln Leu Glu Arg Arg
            355                 360                 365

Glu Gln Arg Leu Arg Ser Arg Glu Arg Leu Leu His Arg Ala Lys
    370                 375                 380

Glu Ala Leu Pro Arg Glu Asp Ala Asp Glu Pro Gly Arg Val Pro Thr
385                 390                 395                 400

Glu Asp Tyr Met Ser His Ile Ile Glu Lys Trp
                405                 410

<210> SEQ ID NO 81
<211> LENGTH: 464
<212> TYPE: PRT
<213> ORGANISM: Human

<400> SEQUENCE: 81

Met Thr Ser Cys Arg Cys Ser Val Thr Arg Ser Leu Trp Pro Ala
1               5                   10                  15

Leu Ala Pro Arg Arg Cys Gln His Thr Ser Pro Ala Ser Ala Gln Cys

-continued

```
                 20                  25                  30
Lys Gln Asp Lys Ala Cys Arg Phe Leu Ala Ala Gln Lys Gly Ala Tyr
             35                  40                  45
Pro Ile Ile Phe Thr Ala Trp Lys Leu Ala Thr Ala Gly Asp Gln Gly
         50                  55                  60
Leu Leu Leu Gln Ser Leu Asn Ala Leu Ser Val Leu Thr Asp Gly Gln
 65                  70                  75                  80
Pro Asp Leu Leu Asp Ala Gln Gly Leu Gln Leu Leu Val Ala Thr Leu
                 85                  90                  95
Thr Gln Asn Ala Asp Glu Ala Asp Leu Thr Cys Ser Gly Ile Arg Cys
            100                 105                 110
Val Arg His Ala Cys Leu Lys His Glu Gln Asn Arg Gln Asp Leu Val
            115                 120                 125
Lys Ala Gly Val Leu Pro Leu Leu Thr Gly Ala Ile Thr His His Gly
        130                 135                 140
His His Thr Asp Val Val Arg Glu Ala Cys Trp Ala Leu Arg Val Met
145                 150                 155                 160
Thr Phe Asp Asp Asp Ile Arg Val Pro Phe Gly His Ala His Asn His
                165                 170                 175
Ala Lys Met Ile Val Gln Glu Asn Lys Gly Leu Lys Val Leu Ile Glu
            180                 185                 190
Ala Thr Lys Ala Phe Leu Asp Asn Pro Gly Ile Leu Ser Glu Leu Cys
        195                 200                 205
Gly Thr Leu Ser Arg Leu Ala Ile Arg Asn Glu Phe Cys Gln Glu Val
    210                 215                 220
Val Asp Leu Gly Gly Leu Ser Ile Leu Val Ser Leu Ala Asp Cys
225                 230                 235                 240
Asn Asp His Gln Met Arg Asp Gln Ser Gly Val Gln Glu Leu Val Lys
                245                 250                 255
Gln Val Leu Ser Thr Leu Arg Ala Ile Ala Gly Asn Asp Asp Val Lys
            260                 265                 270
Asp Ala Ile Val Arg Ala Gly Gly Thr Glu Ser Ile Val Ala Ala Met
        275                 280                 285
Thr Gln His Leu Thr Ser Pro Gln Val Cys Glu Gln Ser Cys Ala Ala
    290                 295                 300
Leu Cys Phe Leu Ala Leu Arg Lys Pro Asp Asn Ser Arg Ile Ile Val
305                 310                 315                 320
Glu Gly Gly Gly Ala Val Ala Ala Leu Gln Ala Met Lys Ala His Pro
                325                 330                 335
Gln Lys Ala Gly Val Gln Lys Gln Ala Cys Met Leu Ile Arg Asn Leu
            340                 345                 350
Val Ala His Arg Pro Ser Arg Ser Pro Ser Trp Thr Trp Gly Leu Arg
        355                 360                 365
His Ser Ser Cys Arg Pro Asp Leu Pro Thr Val Thr Val Arg Thr Trp
    370                 375                 380
Pro Arg Pro Pro Cys Gly Thr Trp Val Val Met Ser Ser Ser Glu Ser
385                 390                 395                 400
Cys Gly Gln Ala Arg Gly Ala Thr Trp Arg His Asp Pro Arg Pro Ser
                405                 410                 415
Leu Val Thr Leu Gly Glu Ser Cys Asp Ser Gly Met Gly Val Asp Pro
            420                 425                 430
Cys Pro Pro Leu Ser Pro Ile Ser Ser Val Pro Phe Thr Met Arg Ser
        435                 440                 445
```

```
Val Phe Trp Gln Ala Leu Gly Lys Gly Ser Glu Gly Gly Ala Leu
        450                 455                 460

<210> SEQ ID NO 82
<211> LENGTH: 501
<212> TYPE: PRT
<213> ORGANISM: Human

<400> SEQUENCE: 82

Met Ser Glu Arg Cys Cys Ser Arg Tyr Ser Ser Gly Ala Ser Ile Gly
1               5                   10                  15

Cys Thr Pro Thr Ser Thr Gln Ala Lys Met Val Ser Lys Arg Ile Ala
            20                  25                  30

Gln Glu Thr Phe Asp Ala Ala Val Arg Glu Asn Ile Glu Glu Phe Ala
            35                  40                  45

Met Gly Pro Glu Glu Ala Val Lys Glu Ala Val Glu Gln Phe Glu Ser
        50                  55                  60

Gln Gly Val Asp Leu Ser Asn Ile Val Lys Thr Ala Pro Lys Val Ser
65                  70                  75                  80

Ala Asp Gly Ser Gln Glu Pro Thr His Asp Ile Leu Gln Met Leu Ser
                85                  90                  95

Asp Leu Gln Glu Ser Val Ala Ser Ser Arg Pro Gln Glu Val Ser Ala
            100                 105                 110

Tyr Leu Thr Arg Phe Cys Asp Gln Cys Lys Gln Asp Lys Ala Cys Arg
            115                 120                 125

Phe Leu Ala Ala Gln Lys Gly Ala Tyr Pro Ile Ile Phe Thr Ala Trp
        130                 135                 140

Lys Leu Ala Thr Ala Gly Asp Gln Gly Leu Leu Leu Gln Ser Leu Asn
145                 150                 155                 160

Ala Leu Ser Val Leu Thr Asp Gly Gln Pro Asp Leu Leu Asp Ala Gln
                165                 170                 175

Gly Leu Gln Leu Leu Val Ala Thr Leu Thr Gln Asn Ala Asp Glu Ala
            180                 185                 190

Asp Leu Thr Cys Ser Gly Ile Arg Cys Val Arg His Ala Cys Leu Lys
            195                 200                 205

His Glu Gln Asn Arg Gln Asp Leu Val Lys Ala Gly Val Leu Pro Leu
        210                 215                 220

Leu Thr Gly Ala Ile Thr His His Gly His His Thr Asp Val Val Arg
225                 230                 235                 240

Glu Ala Cys Trp Ala Leu Arg Val Met Thr Phe Asp Asp Ile Arg
                245                 250                 255

Val Pro Phe Gly His Ala His Asn His Ala Lys Met Ile Val Gln Glu
            260                 265                 270

Asn Lys Gly Leu Lys Val Leu Ile Glu Ala Thr Lys Ala Phe Leu Asp
        275                 280                 285

Asn Pro Gly Ile Leu Ser Glu Leu Cys Gly Thr Leu Ser Arg Leu Ala
        290                 295                 300

Ile Arg Asn Glu Phe Cys Gln Glu Val Val Asp Leu Gly Gly Leu Ser
305                 310                 315                 320

Ile Leu Val Ser Leu Leu Ala Asp Cys Asn Asp His Gln Met Arg Asp
                325                 330                 335

Gln Ser Gly Val Gln Glu Leu Val Lys Gln Val Leu Ser Thr Leu Arg
            340                 345                 350

Ala Ile Ala Gly Asn Asp Asp Val Lys Asp Ala Ile Val Arg Ala Gly
```

```
                355                 360                 365
Gly Thr Glu Ser Ile Val Ala Ala Met Thr Gln His Leu Thr Ser Pro
        370                 375                 380

Gln Val Cys Glu Gln Ser Cys Ala Ala Leu Cys Phe Leu Ala Leu Arg
385                 390                 395                 400

Lys Pro Asp Asn Ser Arg Ile Ile Val Glu Gly Gly Ala Val Ala
                405                 410                 415

Ala Leu Gln Ala Met Lys Ala His Pro Gln Lys Ala Gly Val Gln Lys
            420                 425                 430

Gln Ala Cys Met Leu Ile Arg Asn Leu Val Ala His Gly Gln Ala Phe
                435                 440                 445

Ser Lys Pro Ile Leu Asp Leu Gly Ala Glu Ala Leu Ile Met Gln Ala
        450                 455                 460

Arg Ser Ala His Arg Asp Cys Glu Asp Val Ala Lys Ala Leu Arg
465                 470                 475                 480

Asp Leu Gly Cys His Val Glu Leu Arg Glu Leu Trp Thr Gly Gln Arg
                485                 490                 495

Gly Asn Leu Ala Pro
            500

<210> SEQ ID NO 83
<211> LENGTH: 476
<212> TYPE: PRT
<213> ORGANISM: Human

<400> SEQUENCE: 83

Met Val Ser Lys Arg Ile Ala Gln Glu Thr Phe Asp Ala Ala Val Arg
1               5                   10                  15

Glu Asn Ile Glu Glu Phe Ala Met Gly Pro Glu Glu Ala Val Lys Glu
            20                  25                  30

Ala Val Glu Gln Phe Glu Ser Gln Gly Val Asp Leu Ser Asn Ile Val
        35                  40                  45

Lys Thr Ala Pro Lys Val Ser Ala Asp Gly Ser Gln Glu Pro Thr His
    50                  55                  60

Asp Ile Leu Gln Met Leu Ser Asp Leu Gln Glu Ser Val Ala Ser Ser
65                  70                  75                  80

Arg Pro Gln Glu Val Ser Ala Tyr Leu Thr Arg Phe Cys Asp Gln Cys
                85                  90                  95

Lys Gln Asp Lys Ala Cys Arg Phe Leu Ala Ala Gln Lys Gly Ala Tyr
            100                 105                 110

Pro Ile Ile Phe Thr Ala Trp Lys Leu Ala Thr Ala Gly Asp Gln Gly
        115                 120                 125

Leu Leu Leu Gln Ser Leu Asn Ala Leu Ser Val Leu Thr Asp Gly Gln
    130                 135                 140

Pro Asp Leu Leu Asp Ala Gln Gly Leu Gln Leu Leu Ala Thr Leu
145                 150                 155                 160

Thr Gln Asn Ala Asp Glu Ala Asp Leu Thr Cys Ser Gly Ile Arg Cys
                165                 170                 175

Val Arg His Ala Cys Leu Lys His Glu Gln Asn Arg Gln Asp Leu Val
            180                 185                 190

Lys Ala Gly Val Leu Pro Leu Leu Thr Gly Ala Ile Thr His His Gly
        195                 200                 205

His His Thr Asp Val Val Arg Glu Ala Cys Trp Ala Leu Arg Val Met
    210                 215                 220
```

Thr Phe Asp Asp Asp Ile Arg Val Pro Phe Gly His Ala His Asn His
225                 230                 235                 240

Ala Lys Met Ile Val Gln Glu Asn Lys Gly Leu Lys Val Leu Ile Glu
            245                 250                 255

Ala Thr Lys Ala Phe Leu Asp Asn Pro Gly Ile Leu Ser Glu Leu Cys
            260                 265                 270

Gly Thr Leu Ser Arg Leu Ala Ile Arg Asn Glu Phe Cys Gln Glu Val
            275                 280                 285

Val Asp Leu Gly Gly Leu Ser Ile Leu Val Ser Leu Leu Ala Asp Cys
            290                 295                 300

Asn Asp His Gln Met Arg Asp Gln Ser Gly Val Gln Glu Leu Val Lys
305                 310                 315                 320

Gln Val Leu Ser Thr Leu Arg Ala Ile Ala Gly Asn Asp Asp Val Lys
                325                 330                 335

Asp Ala Ile Val Arg Ala Gly Gly Thr Glu Ser Ile Val Ala Ala Met
                340                 345                 350

Thr Gln His Leu Thr Ser Pro Gln Val Cys Glu Gln Ser Cys Ala Ala
            355                 360                 365

Leu Cys Phe Leu Ala Leu Arg Lys Pro Asp Asn Ser Arg Ile Ile Val
370                 375                 380

Glu Gly Gly Gly Ala Val Ala Ala Leu Gln Ala Met Lys Ala His Pro
385                 390                 395                 400

Gln Lys Ala Gly Val Gln Lys Gln Ala Cys Met Leu Ile Arg Asn Leu
                405                 410                 415

Val Ala His Gly Gln Ala Phe Ser Lys Pro Ile Leu Asp Leu Gly Ala
            420                 425                 430

Glu Ala Leu Ile Met Gln Ala Arg Ser Ala His Arg Asp Cys Glu Asp
            435                 440                 445

Val Ala Lys Ala Ala Leu Arg Asp Leu Gly Cys His Val Glu Leu Arg
            450                 455                 460

Glu Leu Trp Thr Gly Gln Arg Gly Asn Leu Ala Pro
465                 470                 475

<210> SEQ ID NO 84
<211> LENGTH: 476
<212> TYPE: PRT
<213> ORGANISM: Human

<400> SEQUENCE: 84

Met Val Ser Lys Arg Ile Ala Gln Glu Thr Phe Asp Ala Ala Val Arg
1               5                   10                  15

Glu Asn Ile Glu Glu Phe Ala Met Gly Pro Glu Glu Ala Val Lys Glu
            20                  25                  30

Ala Val Glu Gln Phe Glu Ser Gln Gly Val Asp Leu Ser Asn Ile Val
            35                  40                  45

Lys Thr Ala Pro Lys Val Ser Ala Asp Gly Ser Gln Glu Pro Thr His
        50                  55                  60

Asp Ile Leu Gln Met Leu Ser Asp Leu Gln Glu Ser Val Ala Ser Ser
65                  70                  75                  80

Arg Pro Gln Glu Val Ser Ala Tyr Leu Thr Arg Phe Cys Asp Gln Cys
                85                  90                  95

Lys Gln Asp Lys Ala Cys Arg Phe Leu Ala Ala Gln Lys Gly Ala Tyr
            100                 105                 110

Pro Ile Ile Phe Thr Ala Trp Lys Leu Ala Thr Ala Gly Asp Gln Gly
        115                 120                 125

Leu Leu Leu Gln Ser Leu Asn Ala Leu Ser Val Leu Thr Asp Gly Gln
        130                 135                 140

Pro Asp Leu Leu Asp Ala Gln Gly Leu Gln Leu Val Ala Thr Leu
145                 150                 155                 160

Thr Gln Asn Ala Asp Glu Ala Asp Leu Thr Cys Ser Gly Ile Arg Cys
                165                 170                 175

Val Arg His Ala Cys Leu Lys His Glu Gln Asn Arg Gln Asp Leu Val
            180                 185                 190

Lys Ala Gly Val Leu Pro Leu Leu Thr Gly Ala Ile Thr His His Gly
        195                 200                 205

His His Thr Asp Val Val Arg Glu Ala Cys Trp Ala Leu Arg Val Met
    210                 215                 220

Thr Phe Asp Asp Ile Arg Val Pro Phe Gly His Ala His Asn His
225                 230                 235                 240

Ala Lys Met Ile Val Gln Glu Asn Lys Gly Leu Lys Val Leu Ile Glu
                245                 250                 255

Ala Thr Lys Ala Phe Leu Asp Asn Pro Gly Ile Leu Ser Glu Leu Cys
            260                 265                 270

Gly Thr Leu Ser Arg Leu Ala Ile Arg Asn Glu Phe Cys Gln Glu Val
        275                 280                 285

Val Asp Leu Gly Gly Leu Ser Ile Leu Val Ser Leu Leu Ala Asp Cys
    290                 295                 300

Asn Asp His Gln Met Arg Asp Gln Ser Gly Val Gln Glu Leu Val Lys
305                 310                 315                 320

Gln Val Leu Ser Thr Leu Arg Ala Ile Ala Gly Asn Asp Asp Val Lys
                325                 330                 335

Asp Ala Ile Val Arg Ala Gly Gly Thr Glu Ser Ile Val Ala Ala Met
            340                 345                 350

Thr Gln His Leu Thr Ser Pro Gln Val Cys Glu Gln Ser Cys Ala Ala
        355                 360                 365

Leu Cys Phe Leu Ala Leu Arg Lys Pro Asp Asn Ser Arg Ile Ile Val
    370                 375                 380

Glu Gly Gly Gly Ala Val Ala Ala Leu Gln Ala Met Lys Ala His Pro
385                 390                 395                 400

Gln Lys Ala Gly Val Gln Lys Gln Ala Cys Met Leu Ile Arg Asn Leu
                405                 410                 415

Val Ala His Gly Gln Ala Phe Ser Lys Pro Ile Leu Asp Leu Gly Ala
            420                 425                 430

Glu Ala Leu Ile Met Gln Ala Arg Ser Ala His Arg Asp Cys Glu Asp
        435                 440                 445

Val Ala Lys Ala Ala Leu Arg Asp Leu Gly Cys His Val Glu Leu Arg
    450                 455                 460

Glu Leu Trp Thr Gly Gln Arg Gly Asn Leu Ala Pro
465                 470                 475

<210> SEQ ID NO 85
<211> LENGTH: 590
<212> TYPE: PRT
<213> ORGANISM: Human

<400> SEQUENCE: 85

Met Ala Gly Ala Val Pro Gly Ala Ile Met Asp Glu Asp Tyr Tyr Gly
1               5                   10                  15

Ser Ala Ala Glu Trp Gly Asp Glu Ala Asp Gly Gly Gln Gln Glu Asp

```
            20                  25                  30
Asp Ser Gly Glu Gly Glu Asp Ala Glu Val Gln Gln Glu Cys Leu
        35                  40                  45
His Lys Phe Ser Thr Arg Asp Tyr Ile Met Glu Pro Ser Ile Phe Asn
50                  55                  60
Thr Leu Lys Arg Tyr Phe Gln Ala Gly Gly Ser Pro Glu Asn Val Ile
65                  70                  75                  80
Gln Leu Leu Ser Glu Asn Tyr Thr Ala Val Ala Gln Thr Val Asn Leu
                85                  90                  95
Leu Ala Glu Trp Leu Ile Gln Thr Gly Val Glu Pro Val Gln Val Gln
            100                 105                 110
Glu Thr Val Glu Asn His Leu Lys Ser Leu Leu Ile Lys His Phe Asp
        115                 120                 125
Pro Arg Lys Ala Asp Ser Ile Phe Thr Glu Gly Glu Thr Pro Ala
    130                 135                 140
Trp Leu Glu Gln Met Ile Ala His Thr Thr Trp Arg Asp Leu Phe Tyr
145                 150                 155                 160
Lys Leu Ala Glu Ala His Pro Asp Cys Leu Met Leu Asn Phe Thr Val
                165                 170                 175
Lys Leu Ile Ser Asp Ala Gly Tyr Gln Gly Glu Ile Thr Ser Val Ser
            180                 185                 190
Thr Ala Cys Gln Gln Leu Glu Val Phe Ser Arg Val Leu Arg Thr Ser
        195                 200                 205
Leu Ala Thr Ile Leu Asp Gly Gly Glu Glu Asn Leu Glu Lys Asn Leu
    210                 215                 220
Pro Glu Phe Ala Lys Met Val Cys His Gly Glu His Thr Tyr Leu Phe
225                 230                 235                 240
Ala Gln Ala Met Met Ser Val Leu Ala Gln Glu Glu Gln Gly Gly Ser
                245                 250                 255
Ala Val Arg Arg Ile Ala Gln Glu Val Gln Arg Phe Ala Gln Glu Lys
            260                 265                 270
Gly His Asp Ala Ser Gln Ile Thr Leu Ala Leu Gly Thr Ala Ala Ser
        275                 280                 285
Tyr Pro Arg Ala Cys Gln Ala Leu Gly Ala Met Leu Ser Lys Gly Ala
    290                 295                 300
Leu Asn Pro Ala Asp Ile Thr Val Leu Phe Lys Met Phe Thr Ser Met
305                 310                 315                 320
Asp Pro Pro Pro Val Glu Leu Ile Arg Val Pro Ala Phe Leu Asp Leu
                325                 330                 335
Phe Met Gln Ser Leu Phe Lys Pro Gly Ala Arg Ile Asn Gln Asp His
            340                 345                 350
Lys His Lys Tyr Ile His Ile Leu Ala Tyr Ala Ala Ser Val Val Glu
        355                 360                 365
Thr Trp Lys Lys Asn Lys Arg Val Ser Ile Asn Lys Asp Glu Leu Lys
    370                 375                 380
Ser Thr Ser Lys Ala Val Glu Thr Val His Asn Leu Cys Cys Asn Glu
385                 390                 395                 400
Asn Lys Gly Ala Ser Glu Leu Val Ala Glu Leu Ser Thr Leu Tyr Gln
                405                 410                 415
Cys Ile Arg Phe Pro Val Val Ala Met Gly Val Leu Lys Trp Val Asp
            420                 425                 430
Trp Thr Val Ser Glu Pro Arg Tyr Phe Gln Leu Gln Thr Asp His Thr
        435                 440                 445
```

```
Pro Val His Leu Ala Leu Leu Asp Glu Ile Ser Thr Cys His Gln Leu
    450                 455                 460

Leu His Pro Gln Val Leu Gln Leu Leu Val Lys Leu Phe Glu Thr Glu
465                 470                 475                 480

His Ser Gln Leu Asp Val Met Glu Gln Leu Glu Leu Lys Lys Thr Leu
                485                 490                 495

Leu Asp Arg Met Val His Leu Leu Ser Arg Gly Tyr Val Leu Pro Val
            500                 505                 510

Val Ser Tyr Ile Arg Lys Cys Leu Glu Lys Leu Asp Thr Asp Ile Ser
        515                 520                 525

Leu Ile Arg Tyr Phe Val Thr Glu Val Leu Asp Val Ile Ala Pro Pro
    530                 535                 540

Tyr Thr Ser Asp Phe Val Gln Leu Phe Leu Pro Ile Leu Glu Asn Asp
545                 550                 555                 560

Ser Ile Ala Gly Thr Ile Lys Thr Glu Gly Glu His Asp Pro Val Thr
                565                 570                 575

Glu Phe Ile Ala His Cys Lys Ser Asn Phe Ile Met Val Asn
            580                 585                 590

<210> SEQ ID NO 86
<211> LENGTH: 250
<212> TYPE: PRT
<213> ORGANISM: Human

<400> SEQUENCE: 86

Met Ala Met Leu Arg Val Gln Pro Glu Ala Gln Ala Lys Val Asp Val
1               5                   10                  15

Phe Arg Glu Asp Leu Cys Thr Lys Thr Glu Asn Leu Leu Gly Ser Tyr
            20                  25                  30

Phe Pro Lys Lys Ile Ser Glu Leu Asp Ala Phe Leu Lys Glu Pro Ala
        35                  40                  45

Leu Asn Glu Ala Asn Leu Ser Asn Leu Lys Ala Pro Leu Asp Ile Pro
    50                  55                  60

Val Pro Asp Pro Val Lys Glu Lys Glu Lys Glu Arg Lys Lys Gln
65                  70                  75                  80

Gln Glu Lys Glu Asp Lys Asp Glu Lys Lys Gly Glu Asp Glu Asp
                85                  90                  95

Lys Gly Pro Pro Cys Gly Pro Val Asn Cys Asn Glu Lys Ile Val Val
            100                 105                 110

Leu Leu Gln Arg Leu Lys Pro Glu Ile Lys Asp Val Ile Glu Gln Leu
        115                 120                 125

Asn Leu Val Thr Thr Trp Leu Gln Leu Gln Ile Pro Arg Ile Glu Asp
    130                 135                 140

Gly Asn Asn Phe Gly Val Ala Val Gln Glu Lys Val Phe Glu Leu Met
145                 150                 155                 160

Thr Ser Leu His Thr Lys Leu Glu Gly Phe His Thr Gln Ile Ser Lys
                165                 170                 175

Tyr Phe Ser Glu Arg Gly Asp Ala Val Thr Lys Ala Ala Lys Gln Pro
            180                 185                 190

His Val Gly Asp Tyr Arg Gln Leu Val His Glu Leu Asp Glu Ala Glu
        195                 200                 205

Tyr Arg Asp Ile Arg Leu Met Val Met Glu Ile Arg Asn Ala Tyr Val
    210                 215                 220

Arg Arg Gln Gly Gln Gly Arg Gly Gly Gln Arg Gln Leu Ser Gln Ala
```

```
            225                 230                 235                 240
Thr His Ser Leu Thr Leu Gln Ala Arg Gly
                245                 250

<210> SEQ ID NO 87
<211> LENGTH: 249
<212> TYPE: PRT
<213> ORGANISM: Human

<400> SEQUENCE: 87

Met Ala Met Leu Arg Val Gln Pro Glu Ala Gln Ala Lys Val Asp Val
1               5                   10                  15

Phe Arg Glu Asp Leu Cys Thr Lys Thr Glu Asn Leu Leu Gly Ser Tyr
            20                  25                  30

Phe Pro Lys Lys Ile Ser Glu Leu Asp Ala Phe Leu Lys Glu Pro Ala
        35                  40                  45

Leu Asn Glu Ala Asn Leu Ser Asn Leu Lys Ala Pro Leu Asp Ile Pro
    50                  55                  60

Val Pro Asp Pro Val Lys Glu Lys Glu Lys Glu Arg Lys Lys Gln
65                  70                  75                  80

Gln Glu Lys Glu Asp Lys Asp Glu Lys Lys Gly Glu Asp Glu Asp
                85                  90                  95

Lys Gly Pro Pro Cys Gly Pro Val Asn Cys Asn Glu Lys Ile Val Val
            100                 105                 110

Leu Leu Gln Arg Leu Lys Pro Glu Ile Lys Asp Val Ile Glu Gln Leu
        115                 120                 125

Asn Leu Val Thr Thr Trp Leu Gln Leu Gln Ile Pro Arg Ile Glu Asp
    130                 135                 140

Gly Asn Asn Phe Gly Val Ala Val Gln Glu Lys Val Phe Glu Leu Met
145                 150                 155                 160

Thr Ser Leu His Thr Lys Leu Glu Gly Phe His Thr Gln Ile Ser Lys
                165                 170                 175

Tyr Phe Ser Glu Arg Gly Asp Ala Val Thr Lys Ala Ala Lys Gln Pro
            180                 185                 190

His Val Gly Asp Tyr Arg Gln Leu Val His Glu Leu Asp Glu Ala Glu
        195                 200                 205

Tyr Arg Asp Ile Arg Leu Met Val Met Glu Ile Arg Asn Ala Tyr Ala
    210                 215                 220

Val Leu Tyr Asp Ile Ile Leu Lys Asn Phe Glu Lys Leu Lys Lys Pro
225                 230                 235                 240

Arg Gly Glu Thr Lys Gly Met Ile Tyr
                245

<210> SEQ ID NO 88
<211> LENGTH: 558
<212> TYPE: PRT
<213> ORGANISM: Human

<400> SEQUENCE: 88

Met Glu Leu Arg Ala Arg Gly Trp Trp Leu Leu Cys Ala Ala Ala Ala
1               5                   10                  15

Leu Val Ala Cys Ala Arg Gly Asp Pro Ala Ser Lys Ser Arg Ser Cys
            20                  25                  30

Gly Glu Val Arg Gln Ile Tyr Gly Ala Lys Gly Phe Ser Leu Ser Asp
        35                  40                  45

Val Pro Gln Ala Glu Ile Ser Gly Glu His Leu Arg Ile Cys Pro Gln
```

-continued

```
            50                  55                  60
Gly Tyr Thr Cys Cys Thr Ser Glu Met Glu Glu Asn Leu Ala Asn Arg
 65                  70                  75                  80

Ser His Ala Glu Leu Glu Thr Ala Leu Arg Asp Ser Ser Arg Val Leu
                 85                  90                  95

Gln Ala Met Leu Ala Thr Gln Leu Arg Ser Phe Asp Asp His Phe Gln
            100                 105                 110

His Leu Leu Asn Asp Ser Glu Arg Thr Leu Gln Ala Thr Phe Pro Gly
            115                 120                 125

Ala Phe Gly Glu Leu Tyr Thr Gln Asn Ala Arg Ala Phe Arg Asp Leu
            130                 135                 140

Tyr Ser Glu Leu Arg Leu Tyr Arg Gly Ala Asn Leu His Leu Glu
145                 150                 155                 160

Glu Thr Leu Ala Glu Phe Trp Ala Arg Leu Leu Glu Arg Leu Phe Lys
                165                 170                 175

Gln Leu His Pro Gln Leu Leu Leu Pro Asp Asp Tyr Leu Asp Cys Leu
            180                 185                 190

Gly Lys Gln Ala Glu Ala Leu Arg Pro Phe Gly Glu Ala Pro Arg Glu
            195                 200                 205

Leu Arg Leu Arg Ala Thr Arg Ala Phe Val Ala Ala Arg Ser Phe Val
210                 215                 220

Gln Gly Leu Gly Val Ala Ser Asp Val Val Arg Lys Val Ala Gln Val
225                 230                 235                 240

Pro Leu Gly Pro Glu Cys Ser Arg Ala Val Met Lys Leu Val Tyr Cys
                245                 250                 255

Ala His Cys Leu Gly Val Pro Gly Ala Arg Pro Cys Pro Asp Tyr Cys
            260                 265                 270

Arg Asn Val Leu Lys Gly Cys Leu Ala Asn Gln Ala Asp Leu Asp Ala
            275                 280                 285

Glu Trp Arg Asn Leu Leu Asp Ser Met Val Leu Ile Thr Asp Lys Phe
            290                 295                 300

Trp Gly Thr Ser Gly Val Glu Ser Val Ile Gly Ser Val His Thr Trp
305                 310                 315                 320

Leu Ala Glu Ala Ile Asn Ala Leu Gln Asp Asn Arg Asp Thr Leu Thr
                325                 330                 335

Ala Lys Val Ile Gln Gly Cys Gly Asn Pro Lys Val Asn Pro Gln Gly
            340                 345                 350

Pro Gly Pro Glu Glu Lys Arg Arg Gly Lys Leu Ala Pro Arg Glu
            355                 360                 365

Arg Pro Pro Ser Gly Thr Leu Glu Lys Leu Val Ser Glu Ala Lys Ala
370                 375                 380

Gln Leu Arg Asp Val Gln Asp Phe Trp Ile Ser Leu Pro Gly Thr Leu
385                 390                 395                 400

Cys Ser Glu Lys Met Ala Leu Ser Thr Ala Ser Asp Asp Arg Cys Trp
                405                 410                 415

Asn Gly Met Ala Arg Gly Arg Tyr Leu Pro Glu Val Met Gly Asp Gly
            420                 425                 430

Leu Ala Asn Gln Ile Asn Asn Pro Glu Val Glu Val Asp Ile Thr Lys
            435                 440                 445

Pro Asp Met Thr Ile Arg Gln Gln Ile Met Gln Leu Lys Ile Met Thr
            450                 455                 460

Asn Arg Leu Arg Ser Ala Tyr Asn Gly Asn Asp Val Asp Phe Gln Asp
465                 470                 475                 480
```

-continued

```
Ala Ser Asp Asp Gly Ser Gly Ser Gly Asp Gly Cys Leu Asp
                485             490             495

Asp Leu Cys Ser Arg Lys Val Ser Arg Lys Ser Ser Ser Arg Thr
            500             505             510

Pro Leu Thr His Ala Leu Pro Gly Leu Ser Glu Gln Glu Gly Gln Lys
        515             520             525

Thr Ser Ala Ala Ser Cys Pro Gln Pro Pro Thr Phe Leu Leu Pro Leu
    530             535             540

Leu Leu Phe Leu Ala Leu Thr Val Ala Arg Pro Arg Trp Arg
545             550             555

<210> SEQ ID NO 89
<211> LENGTH: 1214
<212> TYPE: PRT
<213> ORGANISM: Human

<400> SEQUENCE: 89

Met Ala Ser Cys Ala Ser Ile Asp Ile Glu Asp Ala Thr Gln His Leu
1               5                   10                  15

Arg Asp Ile Leu Lys Leu Asp Arg Pro Ala Gly Gly Pro Ser Ala Glu
            20                  25                  30

Ser Pro Arg Pro Ser Ser Ala Tyr Asn Gly Asp Leu Asn Gly Leu Leu
        35                  40                  45

Val Pro Asp Pro Leu Cys Ser Gly Asp Ser Thr Ser Ala Asn Lys Thr
    50                  55                  60

Gly Leu Arg Thr Met Pro Pro Ile Asn Leu Gln Glu Lys Gln Val Ile
65                  70                  75                  80

Cys Leu Ser Gly Asp Asp Ser Ser Thr Cys Ile Gly Ile Leu Ala Lys
                85                  90                  95

Glu Val Glu Ile Val Ala Ser Ser Asp Ser Ser Ile Ser Ser Lys Ala
            100                 105                 110

Arg Gly Ser Asn Lys Val Lys Ile Gln Pro Val Ala Lys Tyr Asp Trp
        115                 120                 125

Glu Gln Lys Tyr Tyr Tyr Gly Asn Leu Ile Ala Val Ser Asn Ser Phe
    130                 135                 140

Leu Ala Tyr Ala Ile Arg Ala Ala Asn Asn Gly Ser Ala Met Val Arg
145                 150                 155                 160

Val Ile Ser Val Ser Thr Ser Glu Arg Thr Leu Leu Lys Gly Phe Thr
                165                 170                 175

Gly Ser Val Ala Asp Leu Ala Phe Ala His Leu Asn Ser Pro Gln Leu
            180                 185                 190

Ala Cys Leu Asp Glu Ala Gly Asn Leu Phe Val Trp Arg Leu Ala Leu
        195                 200                 205

Val Asn Gly Lys Ile Gln Glu Ile Leu Val His Ile Arg Gln Pro
    210                 215                 220

Glu Gly Thr Pro Leu Asn His Phe Arg Arg Ile Ile Trp Cys Pro Phe
225                 230                 235                 240

Ile Pro Glu Glu Ser Glu Asp Cys Cys Glu Glu Ser Ser Pro Thr Val
                245                 250                 255

Ala Leu Leu His Glu Asp Arg Ala Glu Val Trp Asp Leu Asp Met Leu
            260                 265                 270

Arg Ser Ser His Ser Thr Trp Pro Val Asp Val Ser Gln Ile Lys Gln
        275                 280                 285

Gly Phe Ile Val Val Lys Gly His Ser Thr Cys Leu Ser Glu Gly Ala
```

```
            290                 295                 300

Leu Ser Pro Asp Gly Thr Val Leu Ala Thr Ala Ser His Asp Gly Tyr
305                 310                 315                 320

Val Lys Phe Trp Gln Ile Tyr Ile Glu Gly Gln Asp Glu Pro Arg Cys
                325                 330                 335

Leu His Glu Trp Lys Pro His Asp Gly Arg Pro Leu Ser Cys Leu Leu
                340                 345                 350

Phe Cys Asp Asn His Lys Lys Gln Asp Pro Asp Val Pro Phe Trp Arg
                355                 360                 365

Phe Leu Ile Thr Gly Ala Asp Gln Asn Arg Glu Leu Lys Met Trp Cys
                370                 375                 380

Thr Val Ser Trp Thr Cys Leu Gln Thr Ile Arg Phe Ser Pro Asp Ile
385                 390                 395                 400

Phe Ser Ser Val Ser Val Pro Pro Ser Leu Lys Val Cys Leu Asp Leu
                405                 410                 415

Ser Ala Glu Tyr Leu Ile Leu Ser Asp Val Gln Arg Lys Val Leu Tyr
                420                 425                 430

Val Met Glu Leu Leu Gln Asn Gln Glu Glu Gly His Ala Cys Phe Ser
                435                 440                 445

Ser Ile Ser Glu Phe Leu Leu Thr His Pro Val Leu Ser Phe Gly Ile
                450                 455                 460

Gln Val Val Ser Arg Cys Arg Leu Arg His Thr Glu Val Leu Pro Ala
465                 470                 475                 480

Glu Glu Glu Asn Asp Ser Leu Gly Ala Asp Gly Thr His Gly Ala Gly
                485                 490                 495

Ala Met Glu Ser Ala Ala Gly Val Leu Ile Lys Leu Phe Cys Val His
                500                 505                 510

Thr Lys Ala Leu Gln Asp Val Gln Ile Arg Phe Gln Pro Gln Leu Asn
                515                 520                 525

Pro Asp Val Val Ala Pro Leu Pro Thr His Thr Ala His Glu Asp Phe
                530                 535                 540

Thr Phe Gly Glu Ser Arg Pro Glu Leu Gly Ser Glu Gly Leu Gly Ser
545                 550                 555                 560

Ala Ala His Gly Ser Gln Pro Asp Leu Arg Arg Ile Val Glu Leu Pro
                565                 570                 575

Ala Pro Ala Asp Phe Leu Ser Leu Ser Ser Glu Thr Lys Pro Lys Leu
                580                 585                 590

Met Thr Pro Asp Ala Phe Met Thr Pro Ser Ala Ser Leu Gln Gln Ile
                595                 600                 605

Thr Ala Ser Pro Ser Ser Ser Ser Gly Ser Ser Ser Ser Ser Ser Ser
                610                 615                 620

Ser Ser Ser Ser Ser Leu Thr Ala Val Ser Ala Met Ser Ser Thr Ser
625                 630                 635                 640

Ala Val Asp Pro Ser Leu Thr Arg Pro Pro Glu Glu Leu Thr Leu Ser
                645                 650                 655

Pro Lys Leu Gln Leu Asp Gly Ser Leu Thr Met Ser Ser Ser Gly Ser
                660                 665                 670

Leu Gln Ala Ser Pro Arg Gly Leu Leu Pro Gly Leu Leu Pro Ala Pro
                675                 680                 685

Ala Asp Lys Leu Thr Pro Lys Gly Pro Gly Gln Val Pro Thr Ala Thr
                690                 695                 700

Ser Ala Leu Ser Leu Glu Leu Gln Glu Val Glu Pro Leu Gly Leu Pro
705                 710                 715                 720
```

```
Gln Ala Ser Pro Ser Arg Thr Arg Ser Pro Asp Val Ile Ser Ser Ala
                725                 730                 735

Ser Thr Ala Leu Ser Gln Asp Ile Pro Glu Ile Ala Ser Glu Ala Leu
            740                 745                 750

Ser Arg Gly Phe Gly Ser Ser Ala Pro Glu Gly Leu Glu Pro Asp Ser
        755                 760                 765

Met Ala Ser Ala Ala Ser Ala Leu His Leu Leu Ser Pro Arg Pro Arg
770                 775                 780

Pro Gly Pro Glu Leu Gly Pro Gln Leu Gly Leu Asp Gly Gly Pro Gly
785                 790                 795                 800

Asp Gly Asp Arg His Asn Thr Pro Ser Leu Leu Glu Ala Ala Leu Thr
                805                 810                 815

Gln Glu Ala Ser Thr Pro Asp Ser Gln Val Trp Pro Thr Ala Pro Asp
            820                 825                 830

Ile Thr Arg Glu Thr Cys Ser Thr Leu Ala Glu Ser Pro Arg Asn Gly
        835                 840                 845

Leu Gln Glu Lys His Lys Ser Leu Ala Phe His Arg Pro Pro Tyr His
850                 855                 860

Leu Leu Gln Gln Arg Asp Ser Gln Asp Ala Ser Ala Glu Gln Ser Asp
865                 870                 875                 880

His Asp Asp Glu Val Ala Ser Leu Ala Ser Ala Ser Gly Gly Phe Gly
                885                 890                 895

Thr Lys Val Pro Ala Pro Arg Leu Pro Ala Lys Asp Trp Lys Thr Lys
            900                 905                 910

Gly Ser Pro Arg Thr Ser Pro Lys Leu Lys Arg Lys Ser Lys Lys Asp
        915                 920                 925

Asp Gly Asp Ala Ala Met Gly Ser Arg Leu Thr Glu His Gln Val Ala
930                 935                 940

Glu Pro Pro Glu Asp Trp Pro Ala Leu Ile Trp Gln Gln Arg Glu
945                 950                 955                 960

Leu Ala Glu Leu Arg His Ser Gln Glu Glu Leu Leu Gln Arg Leu Cys
                965                 970                 975

Thr Gln Leu Glu Gly Leu Gln Ser Thr Val Thr Gly His Val Glu Arg
            980                 985                 990

Ala Leu Glu Thr Arg His Glu Gln Glu Gln Arg Arg Leu Glu Arg Ala
            995                 1000                1005

Leu Ala Glu Gly Gln Gln Arg Gly Gly Gln Leu Gln Glu Gln Leu
    1010                1015                1020

Thr Gln Gln Leu Ser Gln Ala Leu Ser Ser Ala Val Ala Gly Arg
    1025                1030                1035

Leu Glu Arg Ser Ile Arg Asp Glu Ile Lys Lys Thr Val Pro Pro
    1040                1045                1050

Cys Val Ser Arg Ser Leu Glu Pro Met Ala Gly Gln Leu Ser Asn
    1055                1060                1065

Ser Val Ala Thr Lys Leu Thr Ala Val Glu Gly Ser Met Lys Glu
    1070                1075                1080

Asn Ile Ser Lys Leu Leu Lys Ser Lys Asn Leu Thr Asp Ala Ile
    1085                1090                1095

Ala Arg Ala Ala Ala Asp Thr Leu Gln Gly Pro Met Gln Ala Ala
    1100                1105                1110

Tyr Arg Glu Ala Phe Gln Ser Val Val Leu Pro Ala Phe Glu Lys
    1115                1120                1125
```

```
Ser Cys Gln Ala Met Phe Gln Gln Ile Asn Asp Ser Phe Arg Leu
    1130                1135                1140

Gly Thr Gln Glu Tyr Leu Gln Leu Glu Ser His Met Lys Ser
    1145                1150                1155

Arg Lys Ala Arg Glu Gln Glu Ala Arg Glu Pro Val Leu Ala Gln
    1160                1165                1170

Leu Arg Gly Leu Val Ser Thr Leu Gln Ser Ala Thr Glu Gln Met
    1175                1180                1185

Pro Pro Trp Pro Ala Val Phe Val Leu Arg Cys Ser Thr Ser Cys
    1190                1195                1200

Met Trp Leu Trp Ala Ala Cys Arg Ser Pro Phe
    1205                1210

<210> SEQ ID NO 90
<211> LENGTH: 1401
<212> TYPE: PRT
<213> ORGANISM: Human

<400> SEQUENCE: 90

Met Ala Ser Cys Ala Ser Ile Asp Ile Glu Asp Ala Thr Gln His Leu
1               5                   10                  15

Arg Asp Ile Leu Lys Leu Asp Arg Pro Ala Gly Gly Pro Ser Ala Glu
                20                  25                  30

Ser Pro Arg Pro Ser Ser Ala Tyr Asn Gly Asp Leu Asn Gly Leu Leu
            35                  40                  45

Val Pro Asp Pro Leu Cys Ser Gly Asp Ser Thr Ser Ala Asn Lys Thr
        50                  55                  60

Gly Leu Arg Thr Met Pro Pro Ile Asn Leu Gln Glu Lys Gln Val Ile
65                  70                  75                  80

Cys Leu Ser Gly Asp Asp Ser Ser Thr Cys Ile Gly Ile Leu Ala Lys
                85                  90                  95

Glu Val Glu Ile Val Ala Ser Ser Asp Ser Ser Ile Ser Ser Lys Ala
                100                 105                 110

Arg Gly Ser Asn Lys Val Lys Ile Gln Pro Val Ala Lys Tyr Asp Trp
            115                 120                 125

Glu Gln Lys Tyr Tyr Tyr Gly Asn Leu Ile Ala Val Ser Asn Ser Phe
        130                 135                 140

Leu Ala Tyr Ala Ile Arg Ala Asn Asn Gly Ser Ala Met Val Arg
145                 150                 155                 160

Val Ile Ser Val Ser Thr Ser Glu Arg Thr Leu Leu Lys Gly Phe Thr
                165                 170                 175

Gly Ser Val Ala Asp Leu Ala Phe Ala His Leu Asn Ser Pro Gln Leu
            180                 185                 190

Ala Cys Leu Asp Glu Ala Gly Asn Leu Phe Val Trp Arg Leu Ala Leu
        195                 200                 205

Val Asn Gly Lys Ile Gln Glu Glu Ile Leu Val His Ile Arg Gln Pro
    210                 215                 220

Glu Gly Thr Pro Leu Asn His Phe Arg Arg Ile Ile Trp Cys Pro Phe
225                 230                 235                 240

Ile Pro Glu Glu Ser Glu Asp Cys Cys Glu Glu Ser Pro Thr Val
                245                 250                 255

Ala Leu Leu His Glu Asp Arg Ala Glu Val Trp Asp Leu Asp Met Leu
            260                 265                 270

Arg Ser Ser His Ser Thr Trp Pro Val Asp Val Ser Gln Ile Lys Gln
        275                 280                 285
```

-continued

```
Gly Phe Ile Val Val Lys Gly His Ser Thr Cys Leu Ser Glu Gly Ala
    290                 295                 300
Leu Ser Pro Asp Gly Thr Val Leu Ala Thr Ala Ser His Asp Gly Tyr
305                 310                 315                 320
Val Lys Phe Trp Gln Ile Tyr Ile Glu Gly Gln Asp Glu Pro Arg Cys
                325                 330                 335
Leu His Glu Trp Lys Pro His Asp Gly Arg Pro Leu Ser Cys Leu Leu
            340                 345                 350
Phe Cys Asp Asn His Lys Lys Gln Asp Pro Asp Val Pro Phe Trp Arg
        355                 360                 365
Phe Leu Ile Thr Gly Ala Asp Gln Asn Arg Glu Leu Lys Met Trp Cys
    370                 375                 380
Thr Val Ser Trp Thr Cys Leu Gln Thr Ile Arg Phe Ser Pro Asp Ile
385                 390                 395                 400
Phe Ser Ser Val Ser Val Pro Pro Ser Leu Lys Val Cys Leu Asp Leu
                405                 410                 415
Ser Ala Glu Tyr Leu Ile Leu Ser Asp Val Gln Arg Lys Val Leu Tyr
            420                 425                 430
Val Met Glu Leu Leu Gln Asn Gln Glu Glu Gly His Ala Cys Phe Ser
        435                 440                 445
Ser Ile Ser Glu Phe Leu Leu Thr His Pro Val Leu Ser Phe Gly Ile
    450                 455                 460
Gln Val Val Ser Arg Cys Arg Leu Arg His Thr Glu Val Leu Pro Ala
465                 470                 475                 480
Glu Glu Glu Asn Asp Ser Leu Gly Ala Asp Gly Thr His Gly Ala Gly
                485                 490                 495
Ala Met Glu Ser Ala Ala Gly Val Leu Ile Lys Leu Phe Cys Val His
            500                 505                 510
Thr Lys Ala Leu Gln Asp Val Gln Ile Arg Phe Gln Pro Gln Leu Asn
        515                 520                 525
Pro Asp Val Val Ala Pro Leu Pro Thr His Thr Ala His Glu Asp Phe
    530                 535                 540
Thr Phe Gly Glu Ser Arg Pro Glu Leu Gly Ser Glu Gly Leu Gly Ser
545                 550                 555                 560
Ala Ala His Gly Ser Gln Pro Asp Leu Arg Arg Ile Val Glu Leu Pro
                565                 570                 575
Ala Pro Ala Asp Phe Leu Ser Leu Ser Ser Glu Thr Lys Pro Lys Leu
            580                 585                 590
Met Thr Pro Asp Ala Phe Met Thr Pro Ser Ala Ser Leu Gln Gln Ile
        595                 600                 605
Thr Ala Ser Pro Ser Ser Ser Ser Gly Ser Ser Ser Ser Ser Ser Ser
    610                 615                 620
Ser Ser Ser Ser Ser Leu Thr Ala Val Ser Ala Met Ser Ser Thr Ser
625                 630                 635                 640
Ala Val Asp Pro Ser Leu Thr Arg Pro Pro Glu Glu Leu Thr Leu Ser
                645                 650                 655
Pro Lys Leu Gln Leu Asp Gly Ser Leu Thr Met Ser Ser Ser Gly Ser
            660                 665                 670
Leu Gln Ala Ser Pro Arg Gly Leu Leu Pro Gly Leu Leu Pro Ala Pro
        675                 680                 685
Ala Asp Lys Leu Thr Pro Lys Gly Pro Gly Gln Val Pro Thr Ala Thr
    690                 695                 700
```

-continued

```
Ser Ala Leu Ser Leu Glu Leu Gln Glu Val Glu Pro Leu Gly Leu Pro
705                 710                 715                 720

Gln Ala Ser Pro Ser Arg Thr Arg Ser Pro Asp Val Ile Ser Ser Ala
            725                 730                 735

Ser Thr Ala Leu Ser Gln Asp Ile Pro Glu Ile Ala Ser Glu Ala Leu
            740                 745                 750

Ser Arg Gly Phe Gly Ser Ser Ala Pro Glu Gly Leu Glu Pro Asp Ser
            755                 760                 765

Met Ala Ser Ala Ala Ser Ala Leu His Leu Leu Ser Pro Arg Pro Arg
            770                 775                 780

Pro Gly Pro Glu Leu Gly Pro Gln Leu Gly Leu Asp Gly Gly Pro Gly
785                 790                 795                 800

Asp Gly Asp Arg His Asn Thr Pro Ser Leu Leu Glu Ala Ala Leu Thr
            805                 810                 815

Gln Glu Ala Ser Thr Pro Asp Ser Gln Val Trp Pro Thr Ala Pro Asp
            820                 825                 830

Ile Thr Arg Glu Thr Cys Ser Thr Leu Ala Glu Ser Pro Arg Asn Gly
            835                 840                 845

Leu Gln Glu Lys His Lys Ser Leu Ala Phe His Arg Pro Pro Tyr His
850                 855                 860

Leu Leu Gln Gln Arg Asp Ser Gln Asp Ala Ser Ala Glu Gln Ser Asp
865                 870                 875                 880

His Asp Asp Glu Val Ala Ser Leu Ala Ser Ala Ser Gly Gly Phe Gly
                885                 890                 895

Thr Lys Val Pro Ala Pro Arg Leu Pro Ala Lys Asp Trp Lys Thr Lys
            900                 905                 910

Gly Ser Pro Arg Thr Ser Pro Lys Leu Lys Arg Lys Ser Lys Lys Asp
            915                 920                 925

Asp Gly Asp Ala Ala Met Gly Ser Arg Leu Thr Glu His Gln Val Ala
            930                 935                 940

Glu Pro Pro Glu Asp Trp Pro Ala Leu Ile Trp Gln Gln Arg Glu
945                 950                 955                 960

Leu Ala Glu Leu Arg His Ser Gln Glu Glu Leu Leu Gln Arg Leu Cys
            965                 970                 975

Thr Gln Leu Glu Gly Leu Gln Ser Thr Val Thr Gly His Val Glu Arg
            980                 985                 990

Ala Leu Glu Thr Arg His Glu Gln Glu Gln Arg Arg Leu Glu Arg Ala
            995                 1000                1005

Leu Ala Glu Gly Gln Gln Arg Gly Gly Gln Leu Gln Glu Gln Leu
    1010                1015                1020

Thr Gln Gln Leu Ser Gln Ala Leu Ser Ser Ala Val Ala Gly Arg
    1025                1030                1035

Leu Glu Arg Ser Ile Arg Asp Glu Ile Lys Lys Thr Val Pro Pro
    1040                1045                1050

Cys Val Ser Arg Ser Leu Glu Pro Met Ala Gly Gln Leu Ser Asn
    1055                1060                1065

Ser Val Ala Thr Lys Leu Thr Ala Val Glu Gly Ser Met Lys Glu
    1070                1075                1080

Asn Ile Ser Lys Leu Leu Lys Ser Lys Asn Leu Thr Asp Ala Ile
    1085                1090                1095

Ala Arg Ala Ala Ala Asp Thr Leu Gln Gly Pro Met Gln Ala Ala
    1100                1105                1110

Tyr Arg Glu Ala Phe Gln Ser Val Val Leu Pro Ala Phe Glu Lys
```

```
                 1115                1120                1125

Ser Cys Gln Ala Met Phe Gln Gln Ile Asn Asp Ser Phe Arg Leu
    1130                1135                1140

Gly Thr Gln Glu Tyr Leu Gln Leu Glu Ser His Met Lys Ser
    1145                1150                1155

Arg Lys Ala Arg Glu Gln Glu Ala Arg Glu Pro Val Leu Ala Gln
    1160                1165                1170

Leu Arg Gly Leu Val Ser Thr Leu Gln Ser Ala Thr Glu Gln Met
    1175                1180                1185

Ala Ala Thr Val Ala Gly Ser Val Arg Ala Glu Val Gln His Gln
    1190                1195                1200

Leu His Val Ala Val Gly Ser Leu Gln Glu Ser Ile Leu Ala Gln
    1205                1210                1215

Val Gln Arg Ile Val Lys Gly Glu Val Ser Val Ala Leu Lys Glu
    1220                1225                1230

Gln Gln Ala Ala Val Thr Ser Ser Ile Met Gln Ala Met Arg Ser
    1235                1240                1245

Ala Ala Gly Thr Pro Val Pro Ser Ala His Leu Asp Cys Gln Ala
    1250                1255                1260

Gln Gln Ala His Ile Leu Gln Leu Leu Gln Gln Gly His Leu Asn
    1265                1270                1275

Gln Ala Phe Gln Gln Ala Leu Thr Ala Ala Asp Leu Asn Leu Val
    1280                1285                1290

Leu Tyr Val Cys Glu Thr Val Asp Pro Ala Gln Val Phe Gly Gln
    1295                1300                1305

Pro Pro Cys Pro Leu Ser Gln Pro Val Leu Leu Ser Leu Ile Gln
    1310                1315                1320

Gln Leu Ala Ser Asp Leu Gly Thr Arg Thr Asp Leu Lys Leu Ser
    1325                1330                1335

Tyr Leu Glu Glu Ala Val Met His Leu Asp His Ser Asp Pro Ile
    1340                1345                1350

Thr Arg Asp His Met Gly Ser Val Met Ala Gln Val Arg Gln Lys
    1355                1360                1365

Leu Phe Gln Phe Leu Gln Ala Glu Pro His Asn Ser Leu Gly Lys
    1370                1375                1380

Ala Ala Arg Arg Leu Ser Leu Met Leu His Gly Leu Val Thr Pro
    1385                1390                1395

Ser Leu Pro
    1400

<210> SEQ ID NO 91
<211> LENGTH: 620
<212> TYPE: PRT
<213> ORGANISM: Human

<400> SEQUENCE: 91

Met Arg Arg Ser Glu Val Leu Ala Glu Glu Ser Ile Val Cys Leu Gln
1               5                   10                  15

Lys Ala Leu Asn His Leu Arg Glu Ile Trp Glu Leu Ile Gly Ile Pro
            20                  25                  30

Glu Asp Gln Arg Leu Gln Arg Thr Glu Val Val Lys Lys His Ile Lys
        35                  40                  45

Glu Leu Leu Asp Met Met Ile Ala Glu Glu Glu Ser Leu Lys Glu Arg
    50                  55                  60
```

```
Leu Ile Lys Ser Ile Ser Val Cys Gln Lys Glu Leu Asn Thr Leu Cys
 65                  70                  75                  80

Ser Glu Leu His Val Glu Pro Phe Gln Glu Gly Glu Thr Thr Ile
                 85                  90                  95

Leu Gln Leu Glu Lys Asp Leu Arg Thr Gln Val Glu Leu Met Arg Lys
                100                 105                 110

Gln Lys Lys Glu Arg Lys Gln Glu Leu Lys Leu Leu Gln Glu Gln Asp
                115                 120                 125

Gln Glu Leu Cys Glu Ile Leu Cys Met Pro His Tyr Asp Ile Asp Ser
            130                 135                 140

Ala Ser Val Pro Ser Leu Glu Glu Leu Asn Gln Phe Arg Gln His Val
145                 150                 155                 160

Thr Thr Leu Arg Glu Thr Lys Ala Ser Arg Arg Glu Glu Phe Val Ser
                165                 170                 175

Ile Lys Arg Gln Ile Ile Leu Cys Met Glu Ala Leu Asp His Thr Pro
                180                 185                 190

Asp Thr Ser Phe Glu Arg Asp Val Val Cys Glu Asp Glu Asp Ala Phe
            195                 200                 205

Cys Leu Ser Leu Glu Asn Ile Ala Thr Leu Gln Lys Leu Leu Arg Gln
210                 215                 220

Leu Glu Met Gln Lys Ser Gln Asn Glu Ala Val Cys Glu Gly Leu Arg
225                 230                 235                 240

Thr Gln Ile Arg Glu Leu Trp Asp Arg Leu Gln Ile Pro Glu Glu Glu
                245                 250                 255

Arg Glu Ala Val Ala Thr Ile Met Ser Gly Ser Lys Ala Lys Val Arg
                260                 265                 270

Lys Ala Leu Gln Leu Glu Val Asp Arg Leu Glu Glu Leu Lys Met Gln
                275                 280                 285

Asn Met Lys Lys Val Ile Glu Ala Ile Arg Val Glu Leu Val Gln Tyr
            290                 295                 300

Trp Asp Gln Cys Phe Tyr Ser Gln Glu Gln Arg Gln Ala Phe Ala Pro
305                 310                 315                 320

Phe Cys Ala Glu Asp Tyr Thr Glu Ser Leu Leu Gln Leu His Asp Ala
                325                 330                 335

Glu Ile Val Arg Leu Lys Asn Tyr Tyr Glu Val His Lys Glu Leu Phe
                340                 345                 350

Glu Gly Val Gln Lys Trp Glu Glu Thr Trp Arg Leu Phe Leu Glu Phe
            355                 360                 365

Glu Arg Lys Ala Ser Asp Pro Asn Arg Phe Thr Asn Arg Gly Gly Asn
            370                 375                 380

Leu Leu Lys Glu Glu Lys Gln Arg Ala Lys Leu Gln Lys Met Leu Pro
385                 390                 395                 400

Lys Leu Glu Glu Glu Leu Lys Ala Arg Ile Glu Leu Trp Glu Gln Glu
                405                 410                 415

His Ser Lys Ala Phe Met Val Asn Gly Gln Lys Phe Met Glu Tyr Val
                420                 425                 430

Ala Glu Gln Trp Glu Met His Arg Leu Glu Lys Glu Arg Ala Lys Gln
            435                 440                 445

Glu Arg Gln Leu Lys Asn Lys Lys Gln Thr Glu Thr Glu Met Leu Tyr
            450                 455                 460

Gly Ser Ala Pro Arg Thr Pro Ser Lys Arg Arg Gly Leu Ala Pro Asn
465                 470                 475                 480

Thr Pro Gly Lys Ala Arg Lys Leu Asn Thr Thr Thr Met Ser Asn Ala
```

```
                    485              490                   495
Thr Ala Asn Ser Ser Ile Arg Pro Ile Phe Gly Gly Thr Val Tyr His
            500                 505                 510

Ser Pro Val Ser Arg Leu Pro Pro Ser Gly Ser Lys Pro Val Ala Ala
            515                 520                 525

Ser Thr Cys Ser Gly Lys Lys Thr Pro Arg Thr Gly Arg His Gly Ala
            530                 535                 540

Asn Lys Glu Asn Leu Glu Leu Asn Gly Ser Ile Leu Ser Gly Gly Tyr
545                 550                 555                 560

Pro Gly Ser Ala Pro Leu Gln Arg Asn Phe Ser Ile Asn Ser Val Ala
                565                 570                 575

Ser Thr Tyr Ser Glu Phe Ala Lys Asp Pro Ser Leu Ser Asp Ser Ser
            580                 585                 590

Thr Val Gly Leu Gln Arg Glu Leu Ser Lys Ala Ser Lys Ser Asp Ala
            595                 600                 605

Thr Ser Gly Ile Leu Asn Ser Thr Asn Ile Gln Ser
            610                 615                 620
```

<210> SEQ ID NO 92
<211> LENGTH: 674
<212> TYPE: PRT
<213> ORGANISM: Human

<400> SEQUENCE: 92

```
Thr Arg Leu Arg Pro Val Ala Arg Phe Glu Ile Leu Arg Gly Ser Thr
1               5                   10                  15

Ala Arg Gly Ala Ala Thr Arg Ser Asp Ile Ala Gly Val Cys Gly Trp
            20                  25                  30

Leu Leu Leu Ser Gly Pro Cys Gly Val Gly Leu Asp Leu Asp Ser Arg
            35                  40                  45

Leu Leu Gly Ala Ser Ala Met Arg Arg Ser Glu Val Leu Ala Glu Glu
        50                  55                  60

Ser Ile Val Cys Leu Gln Lys Ala Leu Asn His Leu Arg Glu Ile Trp
65                  70                  75                  80

Glu Leu Ile Gly Ile Pro Glu Asp Gln Arg Leu Gln Arg Thr Glu Val
                85                  90                  95

Val Lys Lys His Ile Lys Glu Leu Leu Asp Met Met Ile Ala Glu Glu
            100                 105                 110

Glu Ser Leu Lys Glu Arg Leu Ile Lys Ser Ile Ser Val Cys Gln Lys
            115                 120                 125

Glu Leu Asn Thr Leu Cys Ser Glu Leu His Val Glu Pro Phe Gln Glu
        130                 135                 140

Glu Gly Glu Thr Thr Ile Leu Gln Leu Glu Lys Asp Leu Arg Thr Gln
145                 150                 155                 160

Val Glu Leu Met Arg Lys Gln Lys Lys Glu Arg Lys Gln Glu Leu Lys
                165                 170                 175

Leu Leu Gln Glu Gln Asp Gln Glu Leu Cys Glu Ile Leu Cys Met Pro
            180                 185                 190

His Tyr Asp Ile Asp Ser Ala Ser Val Pro Ser Leu Glu Glu Leu Asn
            195                 200                 205

Gln Phe Arg Gln His Val Thr Thr Leu Arg Glu Thr Lys Ala Ser Arg
        210                 215                 220

Arg Glu Glu Phe Val Ser Ile Lys Arg Gln Ile Ile Leu Cys Met Glu
225                 230                 235                 240
```

```
Ala Leu Asp His Thr Pro Asp Thr Ser Phe Glu Arg Asp Val Val Cys
                245                 250                 255

Glu Asp Glu Asp Ala Phe Cys Leu Ser Leu Glu Asn Ile Ala Thr Leu
            260                 265                 270

Gln Lys Leu Leu Arg Gln Leu Glu Met Gln Lys Ser Gln Asn Glu Ala
        275                 280                 285

Val Cys Glu Gly Leu Arg Thr Gln Ile Arg Glu Leu Trp Asp Arg Leu
    290                 295                 300

Gln Ile Pro Glu Glu Arg Glu Ala Val Ala Thr Ile Met Ser Gly
305                 310                 315                 320

Ser Lys Ala Lys Val Arg Lys Ala Leu Gln Leu Glu Val Asp Arg Leu
                325                 330                 335

Glu Glu Leu Lys Met Gln Asn Met Lys Lys Val Ile Glu Ala Ile Arg
            340                 345                 350

Val Glu Leu Val Gln Tyr Trp Asp Gln Cys Phe Tyr Ser Gln Glu Gln
        355                 360                 365

Arg Gln Ala Phe Ala Pro Phe Cys Ala Glu Asp Tyr Thr Glu Ser Leu
    370                 375                 380

Leu Gln Leu His Asp Ala Glu Ile Val Arg Leu Lys Asn Tyr Tyr Glu
385                 390                 395                 400

Val His Lys Glu Leu Phe Glu Gly Val Gln Lys Trp Glu Glu Thr Trp
                405                 410                 415

Arg Leu Phe Leu Glu Phe Glu Arg Lys Ala Ser Asp Pro Asn Arg Phe
            420                 425                 430

Thr Asn Arg Gly Gly Asn Leu Leu Lys Glu Lys Gln Arg Ala Lys
        435                 440                 445

Leu Gln Lys Met Leu Pro Lys Leu Glu Glu Leu Lys Ala Arg Ile
    450                 455                 460

Glu Leu Trp Glu Gln Glu His Ser Lys Ala Phe Met Val Asn Gly Gln
465                 470                 475                 480

Lys Phe Met Glu Tyr Val Ala Glu Gln Trp Glu Met His Arg Leu Glu
                485                 490                 495

Lys Glu Arg Ala Lys Gln Glu Arg Gln Leu Lys Asn Lys Lys Gln Thr
            500                 505                 510

Glu Thr Glu Met Leu Tyr Gly Ser Ala Pro Arg Thr Pro Ser Lys Arg
        515                 520                 525

Arg Gly Leu Ala Pro Asn Thr Pro Gly Lys Ala Arg Lys Leu Asn Thr
    530                 535                 540

Thr Thr Met Ser Asn Ala Thr Ala Asn Ser Ser Ile Arg Pro Ile Phe
545                 550                 555                 560

Gly Gly Thr Val Tyr His Ser Pro Val Ser Arg Leu Pro Pro Ser Gly
                565                 570                 575

Ser Lys Pro Val Ala Ala Ser Thr Cys Ser Gly Lys Lys Thr Pro Arg
            580                 585                 590

Thr Gly Arg His Gly Ala Asn Lys Glu Asn Leu Glu Leu Asn Gly Ser
        595                 600                 605

Ile Leu Ser Gly Gly Tyr Pro Gly Ser Ala Pro Leu Gln Arg Asn Phe
    610                 615                 620

Ser Ile Asn Ser Val Ala Ser Thr Tyr Ser Glu Phe Ala Lys Asp Pro
625                 630                 635                 640

Ser Leu Ser Asp Ser Ser Thr Val Gly Leu Gln Arg Glu Leu Ser Lys
                645                 650                 655

Ala Ser Lys Ser Asp Ala Thr Ser Gly Ile Leu Asn Ser Thr Asn Ile
```

Gln Ser

<210> SEQ ID NO 93
<211> LENGTH: 660
<212> TYPE: PRT
<213> ORGANISM: Human

<400> SEQUENCE: 93

Thr Arg Leu Arg Pro Val Ala Arg Phe Glu Ile Leu Arg Gly Ser Thr
1               5                   10                  15

Ala Arg Gly Ala Ala Thr Arg Ser Asp Ile Ala Gly Val Cys Gly Trp
            20                  25                  30

Leu Leu Leu Ser Gly Pro Cys Gly Val Gly Leu Asp Leu Asp Ser Arg
        35                  40                  45

Leu Leu Gly Ala Ser Ala Met Arg Arg Ser Glu Val Leu Ala Glu Glu
    50                  55                  60

Ser Ile Val Cys Leu Gln Lys Ala Leu Asn His Leu Arg Glu Ile Trp
65                  70                  75                  80

Glu Leu Ile Gly Ile Pro Glu Asp Gln Arg Leu Gln Arg Thr Glu Val
                85                  90                  95

Val Lys Lys His Ile Lys Glu Leu Leu Asp Met Met Ile Ala Glu Glu
            100                 105                 110

Glu Ser Leu Lys Glu Arg Leu Ile Lys Ser Ile Ser Val Cys Gln Lys
        115                 120                 125

Glu Leu Asn Thr Leu Cys Ser Glu Leu His Val Glu Pro Phe Gln Glu
    130                 135                 140

Glu Gly Glu Thr Thr Ile Leu Gln Leu Glu Lys Asp Leu Arg Thr Gln
145                 150                 155                 160

Val Glu Leu Met Arg Lys Gln Lys Lys Glu Arg Lys Gln Glu Leu Lys
                165                 170                 175

Leu Leu Gln Glu Gln Asp Gln Glu Leu Cys Glu Ile Leu Cys Met Pro
            180                 185                 190

His Tyr Asp Ile Asp Ser Ala Ser Val Pro Ser Leu Glu Glu Leu Asn
        195                 200                 205

Gln Phe Arg Gln His Val Thr Thr Leu Arg Glu Thr Lys Ala Ser Arg
    210                 215                 220

Arg Glu Glu Phe Val Ser Ile Lys Arg Gln Ile Ile Leu Cys Met Glu
225                 230                 235                 240

Ala Leu Asp His Thr Pro Asp Thr Ser Phe Glu Arg Asp Val Val Cys
                245                 250                 255

Glu Asp Glu Asp Ala Phe Cys Leu Ser Leu Glu Asn Ile Ala Thr Leu
            260                 265                 270

Gln Lys Leu Leu Arg Gln Leu Glu Met Gln Lys Ser Gln Asn Glu Ala
    275                 280                 285

Val Cys Glu Gly Leu Arg Thr Gln Ile Arg Glu Leu Trp Asp Arg Leu
290                 295                 300

Gln Ile Pro Glu Glu Glu Arg Glu Ala Val Ala Thr Ile Met Ser Gly
305                 310                 315                 320

Ser Lys Ala Lys Val Arg Lys Ala Leu Gln Leu Glu Val Asp Arg Leu
                325                 330                 335

Glu Glu Leu Lys Met Gln Asn Met Lys Lys Val Ile Glu Ala Ile Arg
            340                 345                 350

Val Glu Leu Val Gln Tyr Trp Asp Gln Cys Phe Tyr Ser Gln Glu Gln

-continued

```
                355                 360                 365
Arg Gln Ala Phe Ala Pro Phe Cys Ala Glu Asp Tyr Thr Glu Ser Leu
            370                 375                 380

Leu Gln Leu His Asp Ala Glu Ile Val Arg Leu Lys Asn Tyr Tyr Glu
385                 390                 395                 400

Val His Lys Glu Leu Phe Glu Gly Val Gln Lys Trp Glu Glu Thr Trp
                405                 410                 415

Arg Leu Phe Leu Glu Phe Glu Arg Lys Ala Ser Asp Pro Asn Arg Phe
            420                 425                 430

Thr Asn Arg Gly Gly Asn Leu Leu Lys Glu Lys Gln Arg Ala Lys
        435                 440                 445

Leu Gln Lys Met Leu Pro Lys Leu Glu Glu Glu Leu Lys Ala Arg Ile
    450                 455                 460

Glu Leu Trp Glu Gln His Ser Lys Ala Phe Met Val Asn Gly Gln
465                 470                 475                 480

Lys Phe Met Glu Tyr Val Ala Glu Gln Trp Glu Met His Arg Leu Glu
                485                 490                 495

Lys Glu Arg Ala Lys Gln Glu Arg Gln Leu Lys Asn Lys Lys Gln Thr
            500                 505                 510

Glu Thr Glu Met Leu Tyr Gly Ser Ala Pro Arg Thr Pro Ser Lys Arg
        515                 520                 525

Arg Gly Leu Ala Pro Asn Thr Pro Gly Lys Ala Arg Lys Leu Asn Thr
    530                 535                 540

Thr Thr Met Ser Asn Ala Thr Ala Asn Ser Ser Ile Arg Pro Ile Phe
545                 550                 555                 560

Gly Gly Thr Val Tyr His Ser Pro Val Ser Arg Leu Pro Pro Ser Gly
                565                 570                 575

Ser Lys Pro Val Ala Ala Ser Thr Cys Ser Gly Lys Lys Thr Pro Arg
            580                 585                 590

Thr Gly Arg His Gly Ala Asn Lys Glu Asn Leu Glu Leu Asn Gly Ser
        595                 600                 605

Ile Leu Ser Gly Gly Tyr Pro Gly Ser Ala Pro Leu Gln Arg Asn Phe
    610                 615                 620

Ser Ile Asn Ser Val Ala Ser Thr Tyr Ser Glu Phe Ala Arg Glu Leu
625                 630                 635                 640

Ser Lys Ala Ser Lys Ser Asp Ala Thr Ser Gly Ile Leu Asn Ser Thr
                645                 650                 655

Asn Ile Gln Ser
            660

<210> SEQ ID NO 94
<211> LENGTH: 417
<212> TYPE: PRT
<213> ORGANISM: Human

<400> SEQUENCE: 94

Met Thr Thr Gln Leu Gly Pro Ala Leu Val Leu Gly Val Ala Leu Cys
1               5                   10                  15

Leu Gly Cys Gly Gln Pro Leu Pro Gln Val Pro Glu Arg Pro Phe Ser
            20                  25                  30

Val Leu Trp Asn Val Pro Ser Ala His Cys Glu Ala Arg Phe Gly Val
        35                  40                  45

His Leu Pro Leu Asn Ala Leu Gly Ile Ile Ala Asn Arg Gly Gln His
    50                  55                  60
```

```
Phe His Gly Gln Asn Met Thr Ile Phe Tyr Lys Asn Gln Leu Gly Leu
 65                  70                  75                  80

Tyr Pro Tyr Phe Gly Pro Arg Gly Thr Ala His Asn Gly Gly Ile Pro
                 85                  90                  95

Gln Ala Leu Pro Leu Asp Arg His Leu Ala Leu Ala Ala Tyr Gln Ile
            100                 105                 110

His His Ser Leu Arg Pro Gly Phe Ala Gly Pro Ala Val Leu Asp Trp
        115                 120                 125

Glu Glu Trp Cys Pro Leu Trp Ala Gly Asn Trp Gly Arg Arg Arg Ala
    130                 135                 140

Tyr Gln Ala Ala Ser Trp Ala Trp Ala Gln Gln Val Phe Pro Asp Leu
145                 150                 155                 160

Asp Pro Gln Glu Gln Leu Tyr Lys Ala Tyr Thr Gly Phe Glu Gln Ala
                165                 170                 175

Ala Arg Ala Leu Met Glu Asp Thr Leu Arg Val Ala Gln Ala Leu Arg
            180                 185                 190

Pro His Gly Leu Trp Gly Phe Tyr His Tyr Pro Ala Cys Gly Asn Gly
        195                 200                 205

Trp His Ser Met Ala Ser Asn Tyr Thr Gly Arg Cys His Ala Ala Thr
    210                 215                 220

Leu Ala Arg Asn Thr Gln Leu His Trp Leu Trp Ala Ala Ser Ser Ala
225                 230                 235                 240

Leu Phe Pro Ser Ile Tyr Leu Pro Pro Arg Leu Pro Pro Ala His His
                245                 250                 255

Gln Ala Phe Val Arg His Arg Leu Glu Glu Ala Phe Arg Val Ala Leu
            260                 265                 270

Val Gly His Arg His Pro Leu Pro Val Leu Ala Tyr Val Arg Leu Thr
        275                 280                 285

His Arg Arg Ser Gly Arg Phe Leu Ser Gln Asp Asp Leu Val Gln Ser
    290                 295                 300

Ile Gly Val Ser Ala Ala Leu Gly Ala Ala Gly Val Val Leu Trp Gly
305                 310                 315                 320

Asp Leu Ser Leu Ser Ser Ser Glu Glu Glu Cys Trp His Leu His Asp
                325                 330                 335

Tyr Leu Val Asp Thr Leu Gly Pro Tyr Val Ile Asn Val Thr Arg Ala
            340                 345                 350

Ala Met Ala Cys Ser His Gln Arg Cys His Gly His Gly Arg Cys Ala
        355                 360                 365

Arg Arg Asp Pro Gly Gln Met Glu Ala Phe Leu His Leu Trp Pro Asp
    370                 375                 380

Gly Ser Leu Gly Asp Trp Lys Ser Phe Ser Cys His Cys Tyr Trp Gly
385                 390                 395                 400

Trp Ala Gly Pro Thr Cys Gln Glu Pro Arg Pro Gly Pro Lys Glu Ala
                405                 410                 415

Val

<210> SEQ ID NO 95
<211> LENGTH: 462
<212> TYPE: PRT
<213> ORGANISM: Human

<400> SEQUENCE: 95

Met Thr Thr Gln Leu Gly Pro Ala Leu Val Leu Gly Val Ala Leu Cys
 1               5                  10                  15
```

```
Leu Gly Cys Gly Gln Pro Leu Pro Gln Val Pro Glu Arg Pro Phe Ser
            20                  25                  30

Val Leu Trp Asn Val Pro Ser Ala His Cys Glu Ala Arg Phe Gly Val
        35                  40                  45

His Leu Pro Leu Asn Ala Leu Gly Ile Ile Ala Asn Arg Gly Gln His
    50                  55                  60

Phe His Gly Gln Asn Met Thr Ile Phe Tyr Lys Asn Gln Leu Gly Leu
 65                  70                  75                  80

Tyr Pro Tyr Phe Gly Pro Arg Gly Thr Ala His Asn Gly Gly Ile Pro
                85                  90                  95

Gln Ala Leu Pro Leu Asp Arg His Leu Ala Leu Ala Ala Tyr Gln Ile
            100                 105                 110

His His Ser Leu Arg Pro Gly Phe Ala Gly Pro Ala Val Leu Asp Trp
        115                 120                 125

Glu Glu Trp Cys Pro Leu Trp Ala Gly Asn Trp Gly Arg Arg Arg Ala
    130                 135                 140

Tyr Gln Ala Ala Ser Trp Ala Trp Ala Gln Gln Val Phe Pro Asp Leu
145                 150                 155                 160

Asp Pro Gln Glu Gln Leu Tyr Lys Ala Tyr Thr Gly Phe Glu Gln Ala
                165                 170                 175

Ala Arg Ala Leu Met Glu Asp Thr Leu Arg Val Ala Gln Ala Leu Arg
            180                 185                 190

Pro His Gly Leu Trp Gly Phe Tyr His Tyr Pro Ala Cys Gly Asn Gly
        195                 200                 205

Trp His Ser Met Ala Ser Asn Tyr Thr Gly Arg Cys His Ala Ala Thr
    210                 215                 220

Leu Ala Arg Asn Thr Gln Leu His Trp Leu Trp Ala Ala Ser Ser Ala
225                 230                 235                 240

Leu Phe Pro Ser Ile Tyr Leu Pro Pro Arg Leu Pro Pro Ala His His
                245                 250                 255

Gln Ala Phe Val Arg His Arg Leu Glu Glu Ala Phe Arg Val Ala Leu
            260                 265                 270

Val Gly His Arg His Pro Leu Pro Val Leu Ala Tyr Val Arg Leu Thr
        275                 280                 285

His Arg Arg Ser Gly Arg Phe Leu Ser Gln Asp Asp Leu Val Gln Ser
    290                 295                 300

Ile Gly Val Ser Ala Ala Leu Gly Ala Ala Gly Val Val Leu Trp Gly
305                 310                 315                 320

Asp Leu Ser Leu Ser Ser Glu Glu Glu Cys Trp His Leu His Asp
                325                 330                 335

Tyr Leu Val Asp Thr Leu Gly Pro Tyr Val Ile Asn Val Thr Arg Ala
            340                 345                 350

Ala Met Ala Cys Ser His Gln Arg Cys His Gly His Gly Arg Cys Ala
        355                 360                 365

Arg Arg Asp Pro Gly Gln Met Glu Ala Phe Leu His Leu Trp Pro Asp
    370                 375                 380

Gly Ser Leu Gly Asp Trp Lys Ser Phe Ser Cys His Cys Tyr Trp Gly
385                 390                 395                 400

Trp Ala Gly Pro Thr Cys Gln Glu Pro Leu Gly Leu Lys Lys Gln Tyr
                405                 410                 415

Lys Ala Arg Ala Pro Ala Thr Ala Ser Ser Phe Pro Cys Cys His Phe
            420                 425                 430

Ser Ser Pro Gly Thr Thr Leu Ser His Ser Cys Ser Ile Gln Phe Thr
```

```
                      435                 440                 445
Val Asn Pro Pro Lys His Thr Pro Arg Phe Pro Trp Asn Pro
        450                 455                 460

<210> SEQ ID NO 96
<211> LENGTH: 387
<212> TYPE: PRT
<213> ORGANISM: Human

<400> SEQUENCE: 96

Met Thr Thr Gln Leu Gly Pro Ala Leu Val Leu Gly Val Ala Leu Cys
1               5                   10                  15

Leu Gly Cys Gly Gln Pro Leu Pro Gln Val Pro Glu Arg Pro Phe Ser
            20                  25                  30

Val Leu Trp Asn Val Pro Ser Ala His Cys Glu Ala Arg Phe Gly Val
        35                  40                  45

His Leu Pro Leu Asn Ala Leu Gly Ile Ile Ala Asn Arg Gly Gln His
    50                  55                  60

Phe His Gly Gln Asn Met Thr Ile Phe Tyr Lys Asn Gln Leu Gly Leu
65                  70                  75                  80

Tyr Pro Tyr Phe Gly Pro Arg Gly Thr Ala His Asn Gly Gly Ile Pro
                85                  90                  95

Gln Ala Leu Pro Leu Asp Arg His Leu Ala Leu Ala Ala Tyr Gln Ile
            100                 105                 110

His His Ser Leu Arg Pro Gly Phe Ala Gly Pro Ala Val Leu Asp Trp
        115                 120                 125

Glu Glu Trp Cys Pro Leu Trp Ala Gly Asn Trp Gly Arg Arg Arg Ala
    130                 135                 140

Tyr Gln Ala Ala Ser Trp Ala Trp Ala Gln Gln Val Phe Pro Asp Leu
145                 150                 155                 160

Asp Pro Gln Glu Gln Leu Tyr Lys Ala Tyr Thr Gly Phe Glu Gln Ala
                165                 170                 175

Ala Arg Ala Leu Met Glu Asp Thr Leu Arg Val Ala Gln Ala Leu Arg
            180                 185                 190

Pro His Gly Leu Trp Gly Phe Tyr His Tyr Pro Ala Cys Gly Asn Gly
        195                 200                 205

Trp His Ser Met Ala Ser Asn Tyr Thr Gly Arg Cys His Ala Ala Thr
    210                 215                 220

Leu Ala Arg Asn Thr Gln Leu His Trp Leu Trp Ala Ala Ser Ser Ala
225                 230                 235                 240

Leu Phe Pro Ser Ile Tyr Leu Pro Pro Arg Leu Pro Pro Ala His His
                245                 250                 255

Gln Ala Phe Val Arg His Arg Leu Glu Glu Ala Phe Arg Val Ala Leu
            260                 265                 270

Val Gly His Arg His Pro Leu Pro Val Leu Ala Tyr Val Arg Leu Thr
        275                 280                 285

His Arg Arg Ser Gly Arg Phe Leu Ser Gln Glu Glu Cys Trp His Leu
    290                 295                 300

His Asp Tyr Leu Val Asp Thr Leu Gly Pro Tyr Val Ile Asn Val Thr
305                 310                 315                 320

Arg Ala Ala Met Ala Cys Ser His Gln Arg Cys His Gly His Gly Arg
                325                 330                 335

Cys Ala Arg Arg Asp Pro Gly Gln Met Glu Ala Phe Leu His Leu Trp
            340                 345                 350
```

```
Pro Asp Gly Ser Leu Gly Asp Trp Lys Ser Phe Ser Cys His Cys Tyr
            355                 360                 365

Trp Gly Trp Ala Gly Pro Thr Cys Gln Glu Pro Arg Pro Gly Pro Lys
    370                 375                 380

Glu Ala Val
385

<210> SEQ ID NO 97
<211> LENGTH: 462
<212> TYPE: PRT
<213> ORGANISM: Human

<400> SEQUENCE: 97

Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
            20                  25                  30

Gly Ile Asp Lys Arg Thr Ile Glu Lys Phe Glu Lys Glu Ala Ala Glu
        35                  40                  45

Met Gly Lys Gly Ser Phe Lys Tyr Ala Trp Val Leu Asp Lys Leu Lys
    50                  55                  60

Ala Glu Arg Glu Arg Gly Ile Thr Ile Asp Ile Ser Leu Trp Lys Phe
65                  70                  75                  80

Glu Thr Ser Lys Tyr Tyr Val Thr Ile Ile Asp Ala Pro Gly His Arg
                85                  90                  95

Asp Phe Ile Lys Asn Met Ile Thr Gly Thr Ser Gln Ala Asp Cys Ala
            100                 105                 110

Val Leu Ile Val Ala Ala Gly Val Gly Glu Phe Glu Ala Gly Ile Ser
        115                 120                 125

Lys Asn Gly Gln Thr Arg Glu His Ala Leu Leu Ala Tyr Thr Leu Gly
    130                 135                 140

Val Lys Gln Leu Ile Val Gly Val Asn Lys Met Asp Ser Thr Glu Pro
145                 150                 155                 160

Pro Tyr Ser Gln Lys Arg Tyr Glu Glu Ile Val Lys Glu Val Ser Thr
                165                 170                 175

Tyr Ile Lys Lys Ile Gly Tyr Asn Pro Asp Thr Val Ala Phe Val Pro
            180                 185                 190

Ile Ser Gly Trp Asn Gly Asp Asn Met Leu Glu Pro Ser Ala Asn Met
        195                 200                 205

Pro Trp Phe Lys Gly Trp Lys Val Thr Arg Lys Asp Gly Asn Ala Ser
    210                 215                 220

Gly Thr Thr Leu Leu Glu Ala Leu Asp Cys Ile Leu Pro Pro Thr Arg
225                 230                 235                 240

Pro Thr Asp Lys Pro Leu Arg Leu Pro Leu Gln Asp Val Tyr Lys Ile
                245                 250                 255

Gly Gly Ile Gly Thr Val Pro Val Gly Arg Val Glu Thr Gly Val Leu
            260                 265                 270

Lys Pro Gly Met Val Val Thr Phe Ala Pro Val Asn Val Thr Thr Glu
        275                 280                 285

Val Lys Ser Val Glu Met His His Glu Ala Leu Ser Glu Ala Leu Pro
    290                 295                 300

Gly Asp Asn Val Gly Phe Lys Val Lys Asn Val Ser Val Lys Asp Val
305                 310                 315                 320

Arg Arg Gly Asn Val Ala Gly Asp Ser Lys Asn Asp Pro Pro Met Glu
                325                 330                 335
```

```
Ala Ala Gly Phe Thr Ala Gln Val Ile Ile Leu Asn His Pro Gly Gln
            340                 345                 350

Ile Ser Ala Gly Tyr Ala Pro Val Leu Asp Cys His Met Ala His Ile
            355                 360                 365

Ala Cys Lys Phe Ala Glu Leu Lys Glu Lys Ile Asp Arg Arg Ser Gly
            370                 375                 380

Lys Lys Leu Glu Asp Gly Pro Lys Phe Leu Lys Ser Gly Asp Ala Ala
385                 390                 395                 400

Ile Val Asp Met Val Pro Gly Lys Pro Met Cys Val Glu Ser Phe Ser
            405                 410                 415

Asp Tyr Pro Pro Leu Gly Arg Phe Ala Val Arg Asp Met Arg Gln Thr
            420                 425                 430

Val Ala Val Gly Val Ile Lys Ala Val Asp Lys Ala Ala Gly Ala
            435                 440                 445

Gly Lys Val Thr Lys Ser Ala Gln Lys Ala Gln Lys Ala Lys
            450                 455                 460

<210> SEQ ID NO 98
<211> LENGTH: 381
<212> TYPE: PRT
<213> ORGANISM: Human

<400> SEQUENCE: 98

Met Ala Leu Lys Ala Glu Gly Ala Ala Leu Asp Cys Phe Glu Val Thr
1               5                   10                  15

Leu Lys Cys Glu Glu Gly Glu Asp Glu Glu Ala Met Val Val Ala
            20                  25                  30

Val Ile Pro Arg Pro Glu Pro Met Leu Arg Val Thr Gln Gln Glu Lys
            35                  40                  45

Thr Pro Pro Arg Pro Ser Pro Leu Glu Ala Gly Ser Asp Gly Cys
            50                  55                  60

Glu Glu Pro Lys Gln Gln Val Ser Trp Glu Gln Glu Phe Leu Val Gly
65                  70                  75                  80

Ser Ser Pro Gly Gly Ser Gly Arg Ala Leu Cys Met Val Cys Gly Ala
            85                  90                  95

Glu Ile Arg Ala Pro Ser Ala Asp Thr Ala Arg Ser His Ile Leu Glu
            100                 105                 110

Gln His Pro His Thr Leu Asp Leu Ser Pro Ser Glu Lys Ser Asn Ile
            115                 120                 125

Leu Glu Ala Trp Ser Gly Val Ala Leu Leu Gln Asp Val Arg Ala
            130                 135                 140

Glu Gln Pro Ser Pro Asn Ser Asp Ser Gly Gln Asp Ala His Pro
145                 150                 155                 160

Asp Pro Asp Ala Asn Pro Asp Ala Ala Arg Met Pro Ala Glu Ile Val
            165                 170                 175

Val Leu Leu Asp Ser Glu Asp Asn Pro Ser Leu Pro Arg Ser Arg
            180                 185                 190

Pro Arg Gly Leu Arg Pro Leu Glu Leu Pro Ala Val Pro Ala Thr Glu
            195                 200                 205

Pro Gly Asn Lys Lys Pro Arg Gly Gln Arg Trp Lys Glu Pro Gly
            210                 215                 220

Glu Glu Pro Val Arg Lys Lys Arg Gly Arg Pro Met Thr Lys Asn Leu
225                 230                 235                 240

Asp Pro Asp Pro Glu Pro Pro Ser Pro Asp Ser Pro Thr Glu Thr Phe
```

```
                245                 250                 255
Ala Ala Pro Ala Glu Val Arg His Phe Thr Asp Gly Ser Phe Pro Ala
            260                 265                 270
Gly Phe Val Leu Gln Leu Phe Ser His Thr Gln Leu Arg Gly Pro Asp
            275                 280                 285
Ser Lys Asp Ser Pro Lys Asp Arg Glu Val Ala Glu Gly Gly Leu Pro
            290                 295                 300
Arg Ala Glu Ser Pro Ser Pro Ala Pro Pro Gly Leu Arg Gly Thr
305                 310                 315                 320
Leu Asp Leu Gln Val Ile Arg Val Arg Met Glu Glu Pro Pro Ala Val
                325                 330                 335
Ser Leu Leu Gln Asp Trp Ser Arg His Pro Gln Gly Thr Lys Arg Val
                340                 345                 350
Gly Ala Gly Asp Thr Ser Asp Trp Pro Thr Val Leu Ser Glu Ser Ser
                355                 360                 365
Thr Thr Val Ala Gly Lys Pro Glu Lys Gly Asn Gly Val
                370                 375                 380

<210> SEQ ID NO 99
<211> LENGTH: 1909
<212> TYPE: PRT
<213> ORGANISM: Human

<400> SEQUENCE: 99

Met Ser Thr His Arg Ser Arg Leu Leu Thr Ala Ala Pro Leu Ser Met
1               5                   10                  15
Glu Gln Arg Arg Pro Trp Pro Arg Ala Leu Glu Val Asp Ser Arg Ser
            20                  25                  30
Val Val Leu Leu Ser Val Val Trp Val Leu Leu Ala Pro Pro Ala Ala
            35                  40                  45
Gly Met Pro Gln Phe Ser Thr Phe His Ser Glu Asn Arg Asp Trp Thr
        50                  55                  60
Phe Asn His Leu Thr Val His Gln Gly Thr Gly Ala Val Tyr Val Gly
65                  70                  75                  80
Ala Ile Asn Arg Val Tyr Lys Leu Thr Gly Asn Leu Thr Ile Gln Val
                85                  90                  95
Ala His Lys Thr Gly Pro Glu Glu Asp Asn Lys Ser Cys Tyr Pro Pro
            100                 105                 110
Leu Ile Val Gln Pro Cys Ser Glu Val Leu Thr Leu Thr Asn Asn Val
            115                 120                 125
Asn Lys Leu Leu Ile Ile Asp Tyr Ser Glu Asn Arg Leu Leu Ala Cys
        130                 135                 140
Gly Ser Leu Tyr Gln Gly Val Cys Lys Leu Leu Arg Leu Asp Asp Leu
145                 150                 155                 160
Phe Ile Leu Val Glu Pro Ser His Lys Lys Glu His Tyr Leu Ser Ser
                165                 170                 175
Val Asn Lys Thr Gly Thr Met Tyr Gly Val Ile Val Arg Ser Glu Gly
            180                 185                 190
Glu Asp Gly Lys Leu Phe Ile Gly Thr Ala Val Asp Gly Lys Gln Asp
            195                 200                 205
Tyr Phe Pro Thr Leu Ser Ser Arg Lys Leu Pro Arg Asp Pro Glu Ser
        210                 215                 220
Ser Ala Met Leu Asp Tyr Glu Leu His Ser Asp Phe Val Ser Ser Leu
225                 230                 235                 240
```

```
Ile Lys Ile Pro Ser Asp Thr Leu Ala Leu Val Ser His Phe Asp Ile
            245                 250                 255

Phe Tyr Ile Tyr Gly Phe Ala Ser Gly Gly Phe Val Tyr Phe Leu Thr
        260                 265                 270

Val Gln Pro Glu Thr Pro Glu Gly Val Ala Ile Asn Ser Ala Gly Asp
    275                 280                 285

Leu Phe Tyr Thr Ser Arg Ile Val Arg Leu Cys Lys Asp Asp Pro Lys
290                 295                 300

Phe His Ser Tyr Val Ser Leu Pro Phe Gly Cys Thr Arg Ala Gly Val
305                 310                 315                 320

Glu Tyr Arg Leu Leu Gln Ala Ala Tyr Leu Ala Lys Pro Gly Asp Ser
            325                 330                 335

Leu Ala Gln Ala Phe Asn Ile Thr Ser Gln Asp Asp Val Leu Phe Ala
        340                 345                 350

Ile Phe Ser Lys Gly Gln Lys Gln Tyr His His Pro Asp Asp Ser
        355                 360                 365

Ala Leu Cys Ala Phe Pro Ile Arg Ala Ile Asn Leu Gln Ile Lys Glu
    370                 375                 380

Arg Leu Gln Ser Cys Tyr Gln Gly Gly Asn Leu Glu Leu Asn Trp
385                 390                 395                 400

Leu Leu Gly Lys Asp Val Gln Cys Thr Lys Ala Pro Val Pro Ile Asp
            405                 410                 415

Asp Asn Phe Cys Gly Leu Asp Ile Asn Gln Pro Leu Gly Gly Ser Thr
        420                 425                 430

Pro Val Glu Gly Leu Thr Leu Tyr Thr Thr Ser Arg Asp Arg Met Thr
    435                 440                 445

Ser Val Ala Ser Tyr Val Tyr Asn Gly Tyr Ser Val Val Phe Val Gly
450                 455                 460

Thr Lys Ser Gly Lys Leu Lys Lys Ile Arg Ala Asp Gly Pro Pro His
465                 470                 475                 480

Gly Gly Val Gln Tyr Glu Met Val Ser Val Leu Lys Asp Gly Ser Pro
            485                 490                 495

Ile Leu Arg Asp Met Ala Phe Ser Ile Asp Gln Arg Tyr Leu Tyr Val
        500                 505                 510

Met Ser Glu Arg Gln Val Thr Arg Val Pro Val Glu Ser Cys Glu Gln
    515                 520                 525

Tyr Thr Thr Cys Gly Glu Cys Leu Ser Ser Gly Asp Pro His Cys Gly
530                 535                 540

Trp Cys Ala Leu His Asn Met Cys Ser Arg Arg Asp Lys Cys Gln Gln
545                 550                 555                 560

Ala Trp Glu Pro Asn Arg Phe Ala Ala Ser Ile Ser Gln Cys Val Ser
            565                 570                 575

Leu Ala Val His Pro Ser Ser Ile Ser Val Ser Glu His Ser Arg Leu
        580                 585                 590

Leu Ser Leu Val Val Ser Asp Ala Pro Asp Leu Ser Ala Gly Ile Ala
    595                 600                 605

Cys Ala Phe Gly Asn Leu Thr Glu Val Glu Gly Gln Val Ser Gly Ser
610                 615                 620

Gln Val Ile Cys Ile Ser Pro Gly Pro Lys Asp Val Pro Val Ile Pro
625                 630                 635                 640

Leu Asp Gln Asp Trp Phe Gly Leu Glu Leu Gln Leu Arg Ser Lys Glu
            645                 650                 655

Thr Gly Lys Ile Phe Val Ser Thr Glu Phe Lys Phe Tyr Asn Cys Ser
```

```
                   660                665                670
Ala His Gln Leu Cys Leu Ser Cys Val Asn Ser Ala Phe Arg Cys His
            675                680                685

Trp Cys Lys Tyr Arg Asn Leu Cys Thr His Asp Pro Thr Thr Cys Ser
            690                695                700

Phe Gln Glu Gly Arg Ile Asn Ile Ser Glu Asp Cys Pro Gln Leu Val
705                710                715                720

Pro Thr Glu Glu Ile Leu Ile Pro Val Gly Glu Val Lys Pro Ile Thr
                725                730                735

Leu Lys Ala Arg Asn Leu Pro Gln Pro Gln Ser Gly Gln Arg Gly Tyr
            740                745                750

Glu Cys Val Leu Asn Ile Gln Gly Ala Ile His Arg Val Pro Ala Leu
            755                760                765

Arg Phe Asn Ser Ser Val Gln Cys Gln Asn Ser Ser Tyr Gln Tyr
            770                775                780

Asp Gly Met Asp Ile Ser Asn Leu Ala Val Asp Phe Ala Val Val Trp
785                790                795                800

Asn Gly Asn Phe Ile Ile Asp Asn Pro Gln Asp Leu Lys Val His Leu
                805                810                815

Tyr Lys Cys Ala Ala Gln Arg Glu Ser Cys Gly Leu Cys Leu Lys Ala
            820                825                830

Asp Arg Lys Phe Glu Cys Gly Trp Cys Ser Gly Glu Arg Arg Cys Thr
            835                840                845

Leu His Gln His Cys Thr Ser Pro Ser Ser Pro Trp Leu Asp Trp Ser
850                855                860

Ser His Asn Val Lys Cys Ser Asn Pro Gln Ile Thr Glu Ile Leu Thr
865                870                875                880

Val Ser Gly Pro Pro Glu Gly Gly Thr Arg Val Thr Ile His Gly Val
                885                890                895

Asn Leu Gly Leu Asp Phe Ser Glu Ile Ala His His Val Gln Val Ala
            900                905                910

Gly Val Pro Cys Thr Pro Leu Pro Gly Glu Tyr Ile Ile Ala Glu Gln
            915                920                925

Ile Val Cys Glu Met Gly His Ala Leu Val Gly Thr Thr Ser Gly Pro
            930                935                940

Val Arg Leu Cys Ile Gly Glu Cys Lys Pro Glu Phe Met Thr Lys Ser
945                950                955                960

His Gln Gln Tyr Thr Phe Val Asn Pro Ser Val Leu Ser Leu Asn Pro
                965                970                975

Ile Arg Gly Pro Glu Ser Gly Gly Thr Met Val Thr Ile Thr Gly His
            980                985                990

Tyr Leu Gly Ala Gly Ser Ser Val Ala Val Tyr Leu Gly Asn Gln Thr
            995               1000               1005

Cys Glu Phe Tyr Gly Arg Ser Met Ser Glu Ile Val Cys Val Ser
            1010               1015               1020

Pro Pro Ser Ser Asn Gly Leu Gly Pro Val Pro Val Ser Val Ser
            1025               1030               1035

Val Asp Arg Ala His Val Asp Ser Asn Leu Gln Phe Glu Tyr Ile
            1040               1045               1050

Asp Asp Pro Arg Val Gln Arg Ile Glu Pro Glu Trp Ser Ile Ala
            1055               1060               1065

Ser Gly His Thr Pro Leu Thr Ile Thr Gly Phe Asn Leu Asp Val
            1070               1075               1080
```

```
Ile Gln Glu Pro Arg Ile Arg Val Lys Phe Asn Gly Lys Glu Ser
1085                1090                1095

Val Asn Val Cys Lys Val Val Asn Thr Thr Thr Leu Thr Cys Leu
1100                1105                1110

Ala Pro Ser Leu Thr Thr Asp Tyr Arg Pro Gly Leu Asp Thr Val
1115                1120                1125

Glu Arg Pro Asp Glu Phe Gly Phe Val Phe Asn Asn Val Gln Ser
1130                1135                1140

Leu Leu Ile Tyr Asn Asp Thr Lys Phe Ile Tyr Tyr Pro Asn Pro
1145                1150                1155

Thr Phe Glu Leu Leu Ser Pro Thr Gly Val Leu Asp Gln Lys Pro
1160                1165                1170

Gly Ser Pro Ile Ile Leu Lys Gly Lys Asn Leu Cys Pro Pro Ala
1175                1180                1185

Ser Gly Gly Ala Lys Leu Asn Tyr Thr Val Leu Ile Gly Glu Thr
1190                1195                1200

Pro Cys Ala Val Thr Val Ser Glu Thr Gln Leu Leu Cys Glu Pro
1205                1210                1215

Pro Asn Leu Thr Gly Gln His Lys Val Met Val His Val Gly Gly
1220                1225                1230

Met Val Phe Ser Pro Gly Ser Val Ser Val Ile Ser Asp Ser Leu
1235                1240                1245

Leu Thr Leu Pro Ala Ile Val Ser Ile Ala Ala Gly Gly Ser Leu
1250                1255                1260

Leu Leu Ile Ile Val Ile Ile Val Leu Ile Ala Tyr Lys Arg Lys
1265                1270                1275

Ser Arg Glu Asn Asp Leu Thr Leu Lys Arg Leu Gln Met Gln Met
1280                1285                1290

Asp Asn Leu Glu Ser Arg Val Ala Leu Glu Cys Lys Glu Ala Phe
1295                1300                1305

Ala Glu Leu Gln Thr Asp Ile Asn Glu Leu Thr Ser Asp Leu Asp
1310                1315                1320

Arg Ser Gly Ile Pro Tyr Leu Asp Tyr Arg Thr Tyr Ala Met Arg
1325                1330                1335

Val Leu Phe Pro Gly Ile Glu Asp His Pro Val Leu Arg Glu Leu
1340                1345                1350

Glu Val Gln Gly Asn Gly Gln Gln His Val Glu Lys Ala Leu Lys
1355                1360                1365

Leu Phe Ala Gln Leu Ile Asn Asn Lys Val Phe Leu Leu Thr Phe
1370                1375                1380

Ile Arg Thr Leu Glu Leu Gln Arg Ser Phe Ser Met Arg Asp Arg
1385                1390                1395

Gly Asn Val Ala Ser Leu Ile Met Thr Gly Leu Gln Gly Arg Leu
1400                1405                1410

Glu Tyr Ala Thr Asp Val Leu Lys Gln Leu Leu Ser Asp Leu Ile
1415                1420                1425

Asp Lys Asn Leu Glu Asn Lys Asn His Pro Lys Leu Leu Leu Arg
1430                1435                1440

Arg Thr Glu Ser Val Ala Glu Lys Met Leu Thr Asn Trp Phe Ala
1445                1450                1455

Phe Leu Leu His Lys Phe Leu Lys Glu Cys Ala Gly Glu Pro Leu
1460                1465                1470
```

-continued

Phe Met Leu Tyr Cys Ala Ile Lys Gln Gln Met Glu Lys Gly Pro
1475                 1480                 1485

Ile Asp Ala Ile Thr Gly Glu Ala Arg Tyr Ser Leu Ser Glu Asp
1490                 1495                 1500

Lys Leu Ile Arg Gln Gln Ile Glu Tyr Lys Thr Leu Ile Leu Asn
1505                 1510                 1515

Cys Val Asn Pro Asp Asn Glu Asn Ser Pro Glu Ile Pro Val Lys
1520                 1525                 1530

Val Leu Asn Cys Asp Thr Ile Thr Gln Val Lys Glu Lys Ile Leu
1535                 1540                 1545

Asp Ala Val Tyr Lys Asn Val Pro Tyr Ser Gln Arg Pro Arg Ala
1550                 1555                 1560

Val Asp Met Asp Leu Glu Trp Arg Gln Gly Arg Ile Ala Arg Val
1565                 1570                 1575

Val Leu Gln Asp Glu Asp Ile Thr Thr Lys Ile Glu Gly Asp Trp
1580                 1585                 1590

Lys Arg Leu Asn Thr Leu Met His Tyr Gln Val Ser Asp Arg Ser
1595                 1600                 1605

Val Val Ala Leu Val Pro Lys Gln Thr Ser Ser Tyr Asn Ile Pro
1610                 1615                 1620

Ala Ser Ala Ser Ile Ser Arg Thr Ser Ile Ser Arg Tyr Asp Ser
1625                 1630                 1635

Ser Phe Arg Tyr Thr Gly Ser Pro Asp Ser Leu Arg Ser Arg Ala
1640                 1645                 1650

Pro Met Ile Thr Pro Asp Leu Glu Ser Gly Val Lys Val Trp His
1655                 1660                 1665

Leu Val Lys Asn His Asp His Gly Asp Gln Lys Glu Gly Asp Arg
1670                 1675                 1680

Gly Ser Lys Met Val Ser Glu Ile Tyr Leu Thr Arg Leu Leu Ala
1685                 1690                 1695

Thr Lys Gly Thr Leu Gln Lys Phe Val Asp Asp Leu Phe Glu Thr
1700                 1705                 1710

Leu Phe Ser Thr Val His Arg Gly Ser Ala Leu Pro Leu Ala Ile
1715                 1720                 1725

Lys Tyr Met Phe Asp Phe Leu Asp Glu Gln Ala Asp Arg His Ser
1730                 1735                 1740

Ile His Asp Thr Asp Val Arg His Thr Trp Lys Ser Asn Cys Leu
1745                 1750                 1755

Pro Leu Arg Phe Trp Val Asn Val Ile Lys Asn Pro Gln Phe Val
1760                 1765                 1770

Phe Asp Ile His Lys Gly Ser Ile Thr Asp Ala Cys Leu Ser Val
1775                 1780                 1785

Val Ala Gln Thr Phe Met Asp Ser Cys Ser Thr Ser Glu His Arg
1790                 1795                 1800

Leu Gly Lys Asp Ser Pro Ser Asn Lys Leu Leu Tyr Ala Lys Asp
1805                 1810                 1815

Ile Pro Ser Tyr Lys Ser Trp Val Glu Arg Tyr Tyr Ala Asp Ile
1820                 1825                 1830

Ala Lys Leu Pro Ala Ile Ser Asp Gln Asp Met Asn Ala Tyr Leu
1835                 1840                 1845

Ala Glu Gln Ser Arg Leu His Ala Val Glu Phe Asn Met Leu Ser
1850                 1855                 1860

Ala Leu Asn Glu Ile Tyr Ser Tyr Val Ser Lys Tyr Ser Glu Glu

```
                    1865                1870                1875

Leu Ile  Gly Ala Leu Glu Gln  Asp Glu Gln Ala Arg  Arg Gln Arg
         1880                1885                1890

Leu Ala  Tyr Lys Val Glu Gln  Leu Ile Asn Ala Met  Ser Ile Glu
         1895                1900                1905

Ser

<210> SEQ ID NO 100
<211> LENGTH: 1894
<212> TYPE: PRT
<213> ORGANISM: Human

<400> SEQUENCE: 100

Met Glu Gln Arg Arg Pro Trp Pro Arg Ala Leu Glu Val Asp Ser Arg
1               5                   10                  15

Ser Val Val Leu Leu Ser Val Val Trp Val Leu Leu Ala Pro Pro Ala
                20                  25                  30

Ala Gly Met Pro Gln Phe Ser Thr Phe His Ser Glu Asn Arg Asp Trp
            35                  40                  45

Thr Phe Asn His Leu Thr Val His Gln Gly Thr Gly Ala Val Tyr Val
    50                  55                  60

Gly Ala Ile Asn Arg Val Tyr Lys Leu Thr Gly Asn Leu Thr Ile Gln
65                  70                  75                  80

Val Ala His Lys Thr Gly Pro Glu Glu Asp Asn Lys Ser Cys Tyr Pro
                85                  90                  95

Pro Leu Ile Val Gln Pro Cys Ser Glu Val Leu Thr Leu Thr Asn Asn
            100                 105                 110

Val Asn Lys Leu Leu Ile Ile Asp Tyr Ser Glu Asn Arg Leu Leu Ala
        115                 120                 125

Cys Gly Ser Leu Tyr Gln Gly Val Cys Lys Leu Leu Arg Leu Asp Asp
    130                 135                 140

Leu Phe Ile Leu Val Glu Pro Ser His Lys Lys Glu His Tyr Leu Ser
145                 150                 155                 160

Ser Val Asn Lys Thr Gly Thr Met Tyr Gly Val Ile Val Arg Ser Glu
                165                 170                 175

Gly Glu Asp Gly Lys Leu Phe Ile Gly Thr Ala Val Asp Gly Lys Gln
            180                 185                 190

Asp Tyr Phe Pro Thr Leu Ser Ser Arg Lys Leu Pro Arg Asp Pro Glu
        195                 200                 205

Ser Ser Ala Met Leu Asp Tyr Glu Leu His Ser Asp Phe Val Ser Ser
    210                 215                 220

Leu Ile Lys Ile Pro Ser Asp Thr Leu Ala Leu Val Ser His Phe Asp
225                 230                 235                 240

Ile Phe Tyr Ile Tyr Gly Phe Ala Ser Gly Gly Phe Val Tyr Phe Leu
                245                 250                 255

Thr Val Gln Pro Glu Thr Pro Glu Gly Val Ala Ile Asn Ser Ala Gly
            260                 265                 270

Asp Leu Phe Tyr Thr Ser Arg Ile Val Arg Leu Cys Lys Asp Asp Pro
        275                 280                 285

Lys Phe His Ser Tyr Val Ser Leu Pro Phe Gly Cys Thr Arg Ala Gly
    290                 295                 300

Val Glu Tyr Arg Leu Leu Gln Ala Ala Tyr Leu Ala Lys Pro Gly Asp
305                 310                 315                 320

Ser Leu Ala Gln Ala Phe Asn Ile Thr Ser Gln Asp Asp Val Leu Phe
```

-continued

```
                325                 330                 335
Ala Ile Phe Ser Lys Gly Gln Lys Gln Tyr His His Pro Pro Asp Asp
            340                 345                 350
Ser Ala Leu Cys Ala Phe Pro Ile Arg Ala Ile Asn Leu Gln Ile Lys
            355                 360                 365
Glu Arg Leu Gln Ser Cys Tyr Gln Gly Glu Gly Asn Leu Glu Leu Asn
        370                 375                 380
Trp Leu Leu Gly Lys Asp Val Gln Cys Thr Lys Ala Pro Val Pro Ile
385                 390                 395                 400
Asp Asp Asn Phe Cys Gly Leu Asp Ile Asn Gln Pro Leu Gly Gly Ser
                405                 410                 415
Thr Pro Val Glu Gly Leu Thr Leu Tyr Thr Thr Ser Arg Asp Arg Met
            420                 425                 430
Thr Ser Val Ala Ser Tyr Val Tyr Asn Gly Tyr Ser Val Val Phe Val
            435                 440                 445
Gly Thr Lys Ser Gly Lys Leu Lys Lys Ile Arg Ala Asp Gly Pro Pro
        450                 455                 460
His Gly Gly Val Gln Tyr Glu Met Val Ser Val Leu Lys Asp Gly Ser
465                 470                 475                 480
Pro Ile Leu Arg Asp Met Ala Phe Ser Ile Asp Gln Arg Tyr Leu Tyr
                485                 490                 495
Val Met Ser Glu Arg Gln Val Thr Arg Val Pro Val Glu Ser Cys Glu
            500                 505                 510
Gln Tyr Thr Thr Cys Gly Glu Cys Leu Ser Ser Gly Asp Pro His Cys
            515                 520                 525
Gly Trp Cys Ala Leu His Asn Met Cys Ser Arg Arg Asp Lys Cys Gln
        530                 535                 540
Gln Ala Trp Glu Pro Asn Arg Phe Ala Ala Ser Ile Ser Gln Cys Val
545                 550                 555                 560
Ser Leu Ala Val His Pro Ser Ser Ile Ser Val Ser Glu His Ser Arg
                565                 570                 575
Leu Leu Ser Leu Val Val Ser Asp Ala Pro Asp Leu Ser Ala Gly Ile
            580                 585                 590
Ala Cys Ala Phe Gly Asn Leu Thr Glu Val Glu Gly Gln Val Ser Gly
            595                 600                 605
Ser Gln Val Ile Cys Ile Ser Pro Gly Pro Lys Asp Val Pro Val Ile
        610                 615                 620
Pro Leu Asp Gln Asp Trp Phe Gly Leu Glu Leu Gln Leu Arg Ser Lys
625                 630                 635                 640
Glu Thr Gly Lys Ile Phe Val Ser Thr Glu Phe Lys Phe Tyr Asn Cys
                645                 650                 655
Ser Ala His Gln Leu Cys Leu Ser Cys Val Asn Ser Ala Phe Arg Cys
            660                 665                 670
His Trp Cys Lys Tyr Arg Asn Leu Cys Thr His Asp Pro Thr Thr Cys
            675                 680                 685
Ser Phe Gln Glu Gly Arg Ile Asn Ile Ser Glu Asp Cys Pro Gln Leu
        690                 695                 700
Val Pro Thr Glu Glu Ile Leu Ile Pro Val Gly Glu Val Lys Pro Ile
705                 710                 715                 720
Thr Leu Lys Ala Arg Asn Leu Pro Gln Pro Gln Ser Gly Gln Arg Gly
                725                 730                 735
Tyr Glu Cys Val Leu Asn Ile Gln Gly Ala Ile His Arg Val Pro Ala
            740                 745                 750
```

-continued

```
Leu Arg Phe Asn Ser Ser Val Gln Cys Gln Asn Ser Tyr Gln
        755                 760                 765
Tyr Asp Gly Met Asp Ile Ser Asn Leu Ala Val Asp Phe Ala Val Val
770                 775                 780
Trp Asn Gly Asn Phe Ile Ile Asp Asn Pro Gln Asp Leu Lys Val His
785                 790                 795                 800
Leu Tyr Lys Cys Ala Ala Gln Arg Glu Ser Cys Gly Leu Cys Leu Lys
                805                 810                 815
Ala Asp Arg Lys Phe Glu Cys Gly Trp Cys Ser Gly Glu Arg Arg Cys
                820                 825                 830
Thr Leu His Gln His Cys Thr Ser Pro Ser Ser Pro Trp Leu Asp Trp
                835                 840                 845
Ser Ser His Asn Val Lys Cys Ser Asn Pro Gln Ile Thr Glu Ile Leu
        850                 855                 860
Thr Val Ser Gly Pro Pro Glu Gly Gly Thr Arg Val Thr Ile His Gly
865                 870                 875                 880
Val Asn Leu Gly Leu Asp Phe Ser Glu Ile Ala His His Val Gln Val
                885                 890                 895
Ala Gly Val Pro Cys Thr Pro Leu Pro Gly Glu Tyr Ile Ile Ala Glu
                900                 905                 910
Gln Ile Val Cys Glu Met Gly His Ala Leu Val Gly Thr Thr Ser Gly
                915                 920                 925
Pro Val Arg Leu Cys Ile Gly Glu Cys Lys Pro Glu Phe Met Thr Lys
        930                 935                 940
Ser His Gln Gln Tyr Thr Phe Val Asn Pro Ser Val Leu Ser Leu Asn
945                 950                 955                 960
Pro Ile Arg Gly Pro Glu Ser Gly Gly Thr Met Val Thr Ile Thr Gly
                965                 970                 975
His Tyr Leu Gly Ala Gly Ser Ser Val Ala Val Tyr Leu Gly Asn Gln
                980                 985                 990
Thr Cys Glu Phe Tyr Gly Arg Ser Met Ser Glu Ile Val Cys Val Ser
        995                 1000                1005
Pro Pro Ser Ser Asn Gly Leu Gly Pro Val Pro Val Ser Val Ser
        1010                1015                1020
Val Asp Arg Ala His Val Asp Ser Asn Leu Gln Phe Glu Tyr Ile
        1025                1030                1035
Asp Asp Pro Arg Val Gln Arg Ile Glu Pro Glu Trp Ser Ile Ala
        1040                1045                1050
Ser Gly His Thr Pro Leu Thr Ile Thr Gly Phe Asn Leu Asp Val
        1055                1060                1065
Ile Gln Glu Pro Arg Ile Arg Val Lys Phe Asn Gly Lys Glu Ser
        1070                1075                1080
Val Asn Val Cys Lys Val Val Asn Thr Thr Thr Leu Thr Cys Leu
        1085                1090                1095
Ala Pro Ser Leu Thr Thr Asp Tyr Arg Pro Gly Leu Asp Thr Val
        1100                1105                1110
Glu Arg Pro Asp Glu Phe Gly Phe Val Phe Asn Asn Val Gln Ser
        1115                1120                1125
Leu Leu Ile Tyr Asn Asp Thr Lys Phe Ile Tyr Tyr Pro Asn Pro
        1130                1135                1140
Thr Phe Glu Leu Leu Ser Pro Thr Gly Val Leu Asp Gln Lys Pro
        1145                1150                1155
```

```
Gly Ser Pro Ile Ile Leu Lys Gly Lys Asn Leu Cys Pro Pro Ala
    1160                1165                1170

Ser Gly Gly Ala Lys Leu Asn Tyr Thr Val Leu Ile Gly Glu Thr
    1175                1180                1185

Pro Cys Ala Val Thr Val Ser Glu Thr Gln Leu Leu Cys Glu Pro
    1190                1195                1200

Pro Asn Leu Thr Gly Gln His Lys Val Met Val His Val Gly Gly
    1205                1210                1215

Met Val Phe Ser Pro Gly Ser Val Ser Val Ile Ser Asp Ser Leu
    1220                1225                1230

Leu Thr Leu Pro Ala Ile Val Ser Ile Ala Ala Gly Gly Ser Leu
    1235                1240                1245

Leu Leu Ile Ile Val Ile Ile Val Leu Ile Ala Tyr Lys Arg Lys
    1250                1255                1260

Ser Arg Glu Asn Asp Leu Thr Leu Lys Arg Leu Gln Met Gln Met
    1265                1270                1275

Asp Asn Leu Glu Ser Arg Val Ala Leu Glu Cys Lys Glu Ala Phe
    1280                1285                1290

Ala Glu Leu Gln Thr Asp Ile Asn Glu Leu Thr Ser Asp Leu Asp
    1295                1300                1305

Arg Ser Gly Ile Pro Tyr Leu Asp Tyr Arg Thr Tyr Ala Met Arg
    1310                1315                1320

Val Leu Phe Pro Gly Ile Glu Asp His Pro Val Leu Arg Glu Leu
    1325                1330                1335

Glu Val Gln Gly Asn Gly Gln Gln His Val Glu Lys Ala Leu Lys
    1340                1345                1350

Leu Phe Ala Gln Leu Ile Asn Asn Lys Val Phe Leu Leu Thr Phe
    1355                1360                1365

Ile Arg Thr Leu Glu Leu Gln Arg Ser Phe Ser Met Arg Asp Arg
    1370                1375                1380

Gly Asn Val Ala Ser Leu Ile Met Thr Gly Leu Gln Gly Arg Leu
    1385                1390                1395

Glu Tyr Ala Thr Asp Val Leu Lys Gln Leu Leu Ser Asp Leu Ile
    1400                1405                1410

Asp Lys Asn Leu Glu Asn Lys Asn His Pro Lys Leu Leu Leu Arg
    1415                1420                1425

Arg Thr Glu Ser Val Ala Glu Lys Met Leu Thr Asn Trp Phe Ala
    1430                1435                1440

Phe Leu Leu His Lys Phe Leu Lys Glu Cys Ala Gly Glu Pro Leu
    1445                1450                1455

Phe Met Leu Tyr Cys Ala Ile Lys Gln Gln Met Glu Lys Gly Pro
    1460                1465                1470

Ile Asp Ala Ile Thr Gly Glu Ala Arg Tyr Ser Leu Ser Glu Asp
    1475                1480                1485

Lys Leu Ile Arg Gln Gln Ile Glu Tyr Lys Thr Leu Ile Leu Asn
    1490                1495                1500

Cys Val Asn Pro Asp Asn Glu Asn Ser Pro Glu Ile Pro Val Lys
    1505                1510                1515

Val Leu Asn Cys Asp Thr Ile Thr Gln Val Lys Glu Lys Ile Leu
    1520                1525                1530

Asp Ala Val Tyr Lys Asn Val Pro Tyr Ser Gln Arg Pro Arg Ala
    1535                1540                1545

Val Asp Met Asp Leu Glu Trp Arg Gln Gly Arg Ile Ala Arg Val
```

| | | 1550 | | | | | 1555 | | | | | 1560 | | |
|---|---|---|---|---|---|---|---|---|---|---|---|---|---|---|

Val Leu Gln Asp Glu Asp Ile Thr Thr Lys Ile Glu Gly Asp Trp
　　1565　　　　　　　　1570　　　　　　　　1575

Lys Arg Leu Asn Thr Leu Met His Tyr Gln Val Ser Asp Arg Ser
　　1580　　　　　　　　1585　　　　　　　　1590

Val Val Ala Leu Val Pro Lys Gln Thr Ser Ser Tyr Asn Ile Pro
　　1595　　　　　　　　1600　　　　　　　　1605

Ala Ser Ala Ser Ile Ser Arg Thr Ser Ile Ser Arg Tyr Asp Ser
　　1610　　　　　　　　1615　　　　　　　　1620

Ser Phe Arg Tyr Thr Gly Ser Pro Asp Ser Leu Arg Ser Arg Ala
　　1625　　　　　　　　1630　　　　　　　　1635

Pro Met Ile Thr Pro Asp Leu Glu Ser Gly Val Lys Val Trp His
　　1640　　　　　　　　1645　　　　　　　　1650

Leu Val Lys Asn His Asp His Gly Asp Gln Lys Glu Gly Asp Arg
　　1655　　　　　　　　1660　　　　　　　　1665

Gly Ser Lys Met Val Ser Glu Ile Tyr Leu Thr Arg Leu Leu Ala
　　1670　　　　　　　　1675　　　　　　　　1680

Thr Lys Gly Thr Leu Gln Lys Phe Val Asp Asp Leu Phe Glu Thr
　　1685　　　　　　　　1690　　　　　　　　1695

Leu Phe Ser Thr Val His Arg Gly Ser Ala Leu Pro Leu Ala Ile
　　1700　　　　　　　　1705　　　　　　　　1710

Lys Tyr Met Phe Asp Phe Leu Asp Glu Gln Ala Asp Arg His Ser
　　1715　　　　　　　　1720　　　　　　　　1725

Ile His Asp Thr Asp Val Arg His Thr Trp Lys Ser Asn Cys Leu
　　1730　　　　　　　　1735　　　　　　　　1740

Pro Leu Arg Phe Trp Val Asn Val Ile Lys Asn Pro Gln Phe Val
　　1745　　　　　　　　1750　　　　　　　　1755

Phe Asp Ile His Lys Gly Ser Ile Thr Asp Ala Cys Leu Ser Val
　　1760　　　　　　　　1765　　　　　　　　1770

Val Ala Gln Thr Phe Met Asp Ser Cys Ser Thr Ser Glu His Arg
　　1775　　　　　　　　1780　　　　　　　　1785

Leu Gly Lys Asp Ser Pro Ser Asn Lys Leu Leu Tyr Ala Lys Asp
　　1790　　　　　　　　1795　　　　　　　　1800

Ile Pro Ser Tyr Lys Ser Trp Val Glu Arg Tyr Tyr Ala Asp Ile
　　1805　　　　　　　　1810　　　　　　　　1815

Ala Lys Leu Pro Ala Ile Ser Asp Gln Asp Met Asn Ala Tyr Leu
　　1820　　　　　　　　1825　　　　　　　　1830

Ala Glu Gln Ser Arg Leu His Ala Val Glu Phe Asn Met Leu Ser
　　1835　　　　　　　　1840　　　　　　　　1845

Ala Leu Asn Glu Ile Tyr Ser Tyr Val Ser Lys Tyr Ser Glu Glu
　　1850　　　　　　　　1855　　　　　　　　1860

Leu Ile Gly Ala Leu Glu Gln Asp Glu Gln Ala Arg Arg Gln Arg
　　1865　　　　　　　　1870　　　　　　　　1875

Leu Ala Tyr Lys Val Glu Gln Leu Ile Asn Ala Met Ser Ile Glu
　　1880　　　　　　　　1885　　　　　　　　1890

Ser

<210> SEQ ID NO 101
<211> LENGTH: 720
<212> TYPE: PRT
<213> ORGANISM: Human

<400> SEQUENCE: 101

Met Pro Pro Pro Ser Asp Ile Val Lys Val Ala Ile Glu Trp Pro Gly

-continued

```
1               5                   10                  15
Ala Asn Ala Gln Leu Leu Glu Ile Asp Gln Lys Arg Pro Leu Ala Ser
            20                  25                  30

Ile Ile Lys Glu Val Cys Asp Gly Trp Ser Leu Pro Asn Pro Glu Tyr
            35                  40                  45

Tyr Thr Leu Arg Tyr Ala Asp Gly Pro Gln Leu Tyr Ile Thr Glu Gln
            50                  55                  60

Thr Arg Ser Asp Ile Lys Asn Gly Thr Ile Leu Gln Leu Ala Ile Ser
65                  70                  75                  80

Pro Ser Arg Ala Ala Arg Gln Leu Met Glu Arg Thr Gln Ser Ser Asn
                85                  90                  95

Met Glu Thr Arg Leu Asp Ala Met Lys Glu Leu Ala Lys Leu Ser Ala
                100                 105                 110

Asp Val Thr Phe Ala Thr Glu Phe Ile Asn Met Asp Gly Ile Ile Val
                115                 120                 125

Leu Thr Arg Leu Val Glu Ser Gly Thr Lys Leu Leu Ser His Tyr Ser
            130                 135                 140

Glu Met Leu Ala Phe Thr Leu Thr Ala Phe Leu Glu Leu Met Asp His
145                 150                 155                 160

Gly Ile Val Ser Trp Asp Met Val Ser Ile Thr Phe Ile Lys Gln Ile
                165                 170                 175

Ala Gly Tyr Val Ser Gln Pro Met Val Asp Val Ser Ile Leu Gln Arg
                180                 185                 190

Ser Leu Ala Ile Leu Glu Ser Met Val Leu Asn Ser Gln Ser Leu Tyr
            195                 200                 205

Gln Lys Ile Ala Glu Glu Ile Thr Val Gly Gln Leu Ile Ser His Leu
    210                 215                 220

Gln Val Ser Asn Gln Glu Ile Gln Thr Tyr Ala Ile Ala Leu Ile Asn
225                 230                 235                 240

Ala Leu Phe Leu Lys Ala Pro Glu Asp Lys Arg Gln Asp Met Ala Asn
                245                 250                 255

Ala Phe Ala Gln Lys His Leu Arg Ser Ile Ile Leu Asn His Val Ile
                260                 265                 270

Arg Gly Asn Arg Pro Ile Lys Thr Glu Met Ala His Gln Leu Tyr Val
            275                 280                 285

Leu Gln Val Leu Thr Phe Asn Leu Leu Glu Glu Arg Met Met Thr Lys
    290                 295                 300

Met Asp Pro Asn Asp Gln Ala Gln Arg Asp Ile Ile Phe Glu Leu Arg
305                 310                 315                 320

Arg Ile Ala Phe Asp Ala Glu Ser Asp Pro Ser Asn Ala Pro Gly Ser
                325                 330                 335

Gly Thr Glu Lys Arg Lys Ala Met Tyr Thr Lys Asp Tyr Lys Met Leu
            340                 345                 350

Gly Phe Thr Asn His Ile Asn Pro Ala Met Asp Phe Thr Gln Thr Pro
            355                 360                 365

Pro Gly Met Leu Ala Leu Asp Asn Met Leu Tyr Leu Ala Lys Val His
    370                 375                 380

Gln Asp Thr Tyr Ile Arg Ile Val Leu Glu Asn Ser Ser Arg Glu Asp
385                 390                 395                 400

Lys His Glu Cys Pro Phe Gly Arg Ser Ala Ile Glu Leu Thr Lys Met
                405                 410                 415

Leu Cys Glu Ile Leu Gln Val Gly Glu Leu Pro Asn Glu Gly Arg Asn
            420                 425                 430
```

Asp Tyr His Pro Met Phe Phe Thr His Asp Arg Ala Phe Glu Glu Leu
            435                 440                 445

Phe Gly Ile Cys Ile Gln Leu Leu Asn Lys Thr Trp Lys Glu Met Arg
450                 455                 460

Ala Thr Ala Glu Asp Phe Asn Lys Val Met Gln Val Val Arg Glu Gln
465                 470                 475                 480

Ile Thr Arg Ala Leu Pro Ser Lys Pro Asn Ser Leu Asp Gln Phe Lys
            485                 490                 495

Ser Lys Leu Arg Ser Leu Ser Tyr Ser Glu Ile Leu Arg Leu Arg Gln
            500                 505                 510

Ser Glu Arg Met Ser Gln Asp Asp Phe Gln Ser Pro Ile Val Glu
            515                 520                 525

Leu Arg Glu Lys Ile Gln Pro Glu Ile Leu Glu Leu Ile Lys Gln Gln
530                 535                 540

Arg Leu Asn Arg Leu Cys Glu Gly Ser Ser Phe Arg Lys Ile Gly Asn
545                 550                 555                 560

Arg Arg Arg Gln Glu Arg Phe Trp Tyr Cys Arg Leu Ala Leu Asn His
            565                 570                 575

Lys Val Leu His Tyr Gly Asp Leu Asp Asp Asn Pro Gln Gly Glu Val
            580                 585                 590

Thr Phe Glu Ser Leu Gln Glu Lys Ile Pro Val Ala Asp Ile Lys Ala
            595                 600                 605

Ile Val Thr Gly Lys Asp Cys Pro His Met Lys Glu Lys Ser Ala Leu
            610                 615                 620

Lys Gln Asn Lys Glu Val Leu Glu Leu Ala Phe Ser Ile Leu Tyr Asp
625                 630                 635                 640

Pro Asp Glu Thr Leu Asn Phe Ile Ala Pro Asn Lys Tyr Glu Tyr Cys
            645                 650                 655

Ile Trp Ile Asp Gly Leu Ser Ala Leu Leu Gly Lys Asp Met Ser Ser
            660                 665                 670

Glu Leu Thr Lys Ser Asp Leu Asp Thr Leu Leu Ser Met Glu Met Lys
            675                 680                 685

Leu Arg Leu Leu Asp Leu Glu Asn Ile Gln Ile Pro Glu Ala Pro Pro
            690                 695                 700

Pro Ile Pro Lys Glu Pro Ser Ser Tyr Asp Phe Val Tyr His Tyr Gly
705                 710                 715                 720

<210> SEQ ID NO 102
<211> LENGTH: 720
<212> TYPE: PRT
<213> ORGANISM: Human

<400> SEQUENCE: 102

Met Pro Pro Pro Ser Asp Ile Val Lys Val Ala Ile Glu Trp Pro Gly
1               5                   10                  15

Ala Asn Ala Gln Leu Leu Glu Ile Asp Gln Lys Arg Pro Leu Ala Ser
            20                  25                  30

Ile Ile Lys Glu Val Cys Asp Gly Trp Ser Leu Pro Asn Pro Glu Tyr
        35                  40                  45

Tyr Thr Leu Arg Tyr Ala Asp Gly Pro Gln Leu Tyr Ile Thr Glu Gln
    50                  55                  60

Thr Arg Ser Asp Ile Lys Asn Gly Thr Ile Leu Gln Leu Ala Ile Ser
65                  70                  75                  80

Pro Ser Arg Ala Ala Arg Gln Leu Met Glu Arg Thr Gln Ser Ser Asn

-continued

```
                85                  90                  95
Met Glu Thr Arg Leu Asp Ala Met Lys Glu Leu Ala Lys Leu Ser Ala
                100                 105                 110

Asp Val Thr Phe Ala Thr Glu Phe Ile Asn Met Asp Gly Ile Ile Val
            115                 120                 125

Leu Thr Arg Leu Val Glu Ser Gly Thr Lys Leu Leu Ser His Tyr Ser
130                 135                 140

Glu Met Leu Ala Phe Thr Leu Thr Ala Phe Leu Glu Leu Met Asp His
145                 150                 155                 160

Gly Ile Val Ser Trp Asp Met Val Ser Ile Thr Phe Ile Lys Gln Ile
                165                 170                 175

Ala Gly Tyr Val Ser Gln Pro Met Val Asp Val Ser Ile Leu Gln Arg
            180                 185                 190

Ser Leu Ala Ile Leu Glu Ser Met Val Leu Asn Ser Gln Ser Leu Tyr
                195                 200                 205

Gln Lys Ile Ala Glu Glu Ile Thr Val Gly Gln Leu Ile Ser His Leu
            210                 215                 220

Gln Val Ser Asn Gln Glu Ile Gln Thr Tyr Ala Ile Ala Leu Ile Asn
225                 230                 235                 240

Ala Leu Phe Leu Lys Ala Pro Glu Asp Lys Arg Gln Asp Met Ala Asn
                245                 250                 255

Ala Phe Ala Gln Lys His Leu Arg Ser Ile Ile Leu Asn His Val Ile
            260                 265                 270

Arg Gly Asn Arg Pro Ile Lys Thr Glu Met Ala His Gln Leu Tyr Val
                275                 280                 285

Leu Gln Val Leu Thr Phe Asn Leu Leu Glu Glu Arg Met Met Thr Lys
            290                 295                 300

Met Asp Pro Asn Asp Gln Ala Gln Arg Asp Ile Ile Phe Glu Leu Arg
305                 310                 315                 320

Arg Ile Ala Phe Asp Ala Glu Ser Asp Pro Ser Asn Ala Pro Gly Ser
                325                 330                 335

Gly Thr Glu Lys Arg Lys Ala Met Tyr Thr Lys Asp Tyr Lys Met Leu
            340                 345                 350

Gly Phe Thr Asn His Ile Asn Pro Ala Met Asp Phe Thr Gln Thr Pro
                355                 360                 365

Pro Gly Met Leu Ala Leu Asp Asn Met Leu Tyr Leu Ala Lys Val His
            370                 375                 380

Gln Asp Thr Tyr Ile Arg Ile Val Leu Glu Asn Ser Ser Arg Glu Asp
385                 390                 395                 400

Lys His Glu Cys Pro Phe Gly Arg Ser Ala Ile Glu Leu Thr Lys Met
                405                 410                 415

Leu Cys Glu Ile Leu Gln Val Gly Glu Leu Pro Asn Glu Gly Arg Asn
            420                 425                 430

Asp Tyr His Pro Met Phe Phe Thr His Asp Arg Ala Phe Glu Glu Leu
                435                 440                 445

Phe Gly Ile Cys Ile Gln Leu Leu Asn Lys Thr Trp Lys Glu Met Arg
            450                 455                 460

Ala Thr Ala Glu Asp Phe Asn Lys Val Met Gln Val Val Arg Glu Gln
465                 470                 475                 480

Ile Thr Arg Ala Leu Pro Ser Lys Pro Asn Ser Leu Asp Gln Phe Lys
                485                 490                 495

Ser Lys Leu Arg Ser Leu Ser Tyr Ser Glu Ile Leu Arg Leu Arg Gln
            500                 505                 510
```

```
Ser Glu Arg Met Ser Gln Asp Phe Gln Ser Pro Pro Ile Val Glu
    515                 520                 525

Leu Arg Glu Lys Ile Gln Pro Glu Ile Leu Glu Leu Ile Lys Gln Gln
530                 535                 540

Arg Leu Asn Arg Leu Cys Glu Gly Ser Ser Phe Arg Lys Ile Gly Asn
545                 550                 555                 560

Arg Arg Arg Gln Glu Arg Phe Trp Tyr Cys Arg Leu Ala Leu Asn His
                565                 570                 575

Lys Val Leu His Tyr Gly Asp Leu Asp Asp Asn Pro Gln Gly Glu Val
                580                 585                 590

Thr Phe Glu Ser Leu Gln Glu Lys Ile Pro Val Ala Asp Ile Lys Ala
                595                 600                 605

Ile Val Thr Gly Lys Asp Cys Pro His Met Lys Glu Lys Ser Ala Leu
                610                 615                 620

Lys Gln Asn Lys Glu Val Leu Glu Leu Ala Phe Ser Ile Leu Tyr Asp
625                 630                 635                 640

Pro Asp Glu Thr Leu Asn Phe Ile Ala Pro Asn Lys Tyr Glu Tyr Cys
                645                 650                 655

Ile Trp Ile Asp Gly Leu Ser Ala Leu Leu Gly Lys Asp Met Ser Ser
                660                 665                 670

Glu Leu Thr Lys Ser Asp Leu Asp Thr Leu Ser Met Glu Met Lys
                675                 680                 685

Leu Arg Leu Leu Asp Leu Glu Asn Ile Gln Ile Pro Glu Ala Pro Pro
690                 695                 700

Pro Ile Pro Lys Glu Pro Ser Ser Tyr Asp Phe Val Tyr His Tyr Gly
705                 710                 715                 720

<210> SEQ ID NO 103
<211> LENGTH: 718
<212> TYPE: PRT
<213> ORGANISM: Human

<400> SEQUENCE: 103

Met Pro Pro Pro Ser Asp Ile Val Lys Val Ala Ile Glu Trp Pro Gly
1               5                   10                  15

Ala Asn Ala Gln Leu Leu Glu Ile Asp Gln Lys Arg Pro Leu Ala Ser
                20                  25                  30

Ile Ile Lys Glu Val Cys Asp Gly Trp Ser Leu Pro Asn Pro Glu Tyr
                35                  40                  45

Tyr Thr Leu Arg Tyr Ala Asp Gly Pro Gln Leu Tyr Ile Thr Glu Gln
    50                  55                  60

Thr Arg Ser Asp Ile Lys Asn Gly Thr Ile Leu Gln Leu Ala Ile Ser
65                  70                  75                  80

Pro Ser Arg Ala Ala Arg Gln Leu Met Glu Arg Thr Gln Ser Ser Asn
                85                  90                  95

Met Glu Thr Arg Leu Asp Ala Met Lys Glu Leu Ala Lys Leu Ser Ala
                100                 105                 110

Asp Val Thr Phe Ala Thr Glu Phe Ile Asn Met Asp Gly Ile Ile Val
                115                 120                 125

Leu Thr Arg Leu Val Glu Ser Gly Thr Lys Leu Leu Ser His Glu Met
    130                 135                 140

Leu Ala Phe Thr Leu Thr Ala Phe Leu Glu Leu Met Asp His Gly Ile
145                 150                 155                 160

Val Ser Trp Asp Met Val Ser Ile Thr Phe Ile Lys Gln Ile Ala Gly
```

-continued

```
            165                 170                 175
Tyr Val Ser Gln Pro Met Val Asp Val Ser Ile Leu Gln Arg Ser Leu
            180                 185                 190
Ala Ile Leu Glu Ser Met Val Leu Asn Ser Gln Ser Leu Tyr Gln Lys
            195                 200                 205
Ile Ala Glu Glu Ile Thr Val Gly Gln Leu Ile Ser His Leu Gln Val
            210                 215                 220
Ser Asn Gln Glu Ile Gln Thr Tyr Ala Ile Ala Leu Ile Asn Ala Leu
225                 230                 235                 240
Phe Leu Lys Ala Pro Glu Asp Lys Arg Gln Asp Met Ala Asn Ala Phe
            245                 250                 255
Ala Gln Lys His Leu Arg Ser Ile Ile Leu Asn His Val Ile Arg Gly
            260                 265                 270
Asn Arg Pro Ile Lys Thr Glu Met Ala His Gln Leu Tyr Val Leu Gln
            275                 280                 285
Val Leu Thr Phe Asn Leu Leu Glu Glu Arg Met Met Thr Lys Met Asp
            290                 295                 300
Pro Asn Asp Gln Ala Gln Arg Asp Ile Ile Phe Glu Leu Arg Arg Ile
305                 310                 315                 320
Ala Phe Asp Ala Glu Ser Asp Pro Ser Asn Ala Pro Gly Ser Gly Thr
            325                 330                 335
Glu Lys Arg Lys Ala Met Tyr Thr Lys Asp Tyr Lys Met Leu Gly Phe
            340                 345                 350
Thr Asn His Ile Asn Pro Ala Met Asp Phe Thr Gln Thr Pro Pro Gly
            355                 360                 365
Met Leu Ala Leu Asp Asn Met Leu Tyr Leu Ala Lys Val His Gln Asp
370                 375                 380
Thr Tyr Ile Arg Ile Val Leu Glu Asn Ser Ser Arg Glu Asp Lys His
385                 390                 395                 400
Glu Cys Pro Phe Gly Arg Ser Ala Ile Glu Leu Thr Lys Met Leu Cys
            405                 410                 415
Glu Ile Leu Gln Val Gly Glu Leu Pro Asn Glu Gly Arg Asn Asp Tyr
            420                 425                 430
His Pro Met Phe Phe Thr His Asp Arg Ala Phe Glu Glu Leu Phe Gly
            435                 440                 445
Ile Cys Ile Gln Leu Leu Asn Lys Thr Trp Lys Glu Met Arg Ala Thr
            450                 455                 460
Ala Glu Asp Phe Asn Lys Val Met Gln Val Val Arg Glu Gln Ile Thr
465                 470                 475                 480
Arg Ala Leu Pro Ser Lys Pro Asn Ser Leu Asp Gln Phe Lys Ser Lys
            485                 490                 495
Leu Arg Ser Leu Ser Tyr Ser Glu Ile Leu Arg Leu Arg Gln Ser Glu
            500                 505                 510
Arg Met Ser Gln Asp Asp Phe Gln Ser Pro Ile Val Glu Leu Arg
            515                 520                 525
Glu Lys Ile Gln Pro Glu Ile Leu Glu Leu Ile Lys Gln Gln Arg Leu
            530                 535                 540
Asn Arg Leu Cys Glu Gly Ser Ser Phe Arg Lys Ile Gly Asn Arg Arg
545                 550                 555                 560
Arg Gln Glu Arg Phe Trp Tyr Cys Arg Leu Ala Leu Asn His Lys Val
            565                 570                 575
Leu His Tyr Gly Asp Leu Asp Asp Asn Pro Gln Gly Glu Val Thr Phe
            580                 585                 590
```

```
Glu Ser Leu Gln Glu Lys Ile Pro Val Ala Asp Ile Lys Ala Ile Val
            595                 600                 605

Thr Gly Lys Asp Cys Pro His Met Lys Glu Lys Ser Ala Leu Lys Gln
        610                 615                 620

Asn Lys Glu Val Leu Glu Leu Ala Phe Ser Ile Leu Tyr Asp Pro Asp
625                 630                 635                 640

Glu Thr Leu Asn Phe Ile Ala Pro Asn Lys Tyr Glu Tyr Cys Ile Trp
                645                 650                 655

Ile Asp Gly Leu Ser Ala Leu Leu Gly Lys Asp Met Ser Ser Glu Leu
            660                 665                 670

Thr Lys Ser Asp Leu Asp Thr Leu Leu Ser Met Glu Met Lys Leu Arg
        675                 680                 685

Leu Leu Asp Leu Glu Asn Ile Gln Ile Pro Glu Ala Pro Pro Pro Ile
690                 695                 700

Pro Lys Glu Pro Ser Ser Tyr Asp Phe Val Tyr His Tyr Gly
705                 710                 715

<210> SEQ ID NO 104
<211> LENGTH: 632
<212> TYPE: PRT
<213> ORGANISM: Human

<400> SEQUENCE: 104

Met Glu Arg Thr Gln Ser Ser Asn Met Glu Thr Arg Leu Asp Ala Met
1               5                  10                   15

Lys Glu Leu Ala Lys Leu Ser Ala Asp Val Thr Phe Ala Thr Glu Phe
            20                  25                  30

Ile Asn Met Asp Gly Ile Ile Val Leu Thr Arg Leu Val Glu Ser Gly
        35                  40                  45

Thr Lys Leu Leu Ser His Tyr Ser Glu Met Leu Ala Phe Thr Leu Thr
    50                  55                  60

Ala Phe Leu Glu Leu Met Asp His Gly Ile Val Ser Trp Asp Met Val
65                  70                  75                  80

Ser Ile Thr Phe Ile Lys Gln Ile Ala Gly Tyr Val Ser Gln Pro Met
                85                  90                  95

Val Asp Val Ser Ile Leu Gln Arg Ser Leu Ala Ile Leu Glu Ser Met
            100                 105                 110

Val Leu Asn Ser Gln Ser Leu Tyr Gln Lys Ile Ala Glu Glu Ile Thr
        115                 120                 125

Val Gly Gln Leu Ile Ser His Leu Gln Val Ser Asn Gln Glu Ile Gln
    130                 135                 140

Thr Tyr Ala Ile Ala Leu Ile Asn Ala Leu Phe Leu Lys Ala Pro Glu
145                 150                 155                 160

Asp Lys Arg Gln Asp Met Ala Asn Ala Phe Ala Gln Lys His Leu Arg
                165                 170                 175

Ser Ile Ile Leu Asn His Val Ile Arg Gly Asn Arg Pro Ile Lys Thr
            180                 185                 190

Glu Met Ala His Gln Leu Tyr Val Leu Gln Val Leu Thr Phe Asn Leu
        195                 200                 205

Leu Glu Glu Arg Met Met Thr Lys Met Asp Pro Asn Asp Gln Ala Gln
    210                 215                 220

Arg Asp Ile Ile Phe Glu Leu Arg Arg Ile Ala Phe Asp Ala Glu Ser
225                 230                 235                 240

Asp Pro Ser Asn Ala Pro Gly Ser Gly Thr Glu Lys Arg Lys Ala Met
```

```
                  245                 250                 255
Tyr Thr Lys Asp Tyr Lys Met Leu Gly Phe Thr Asn His Ile Asn Pro
            260                 265                 270

Ala Met Asp Phe Thr Gln Thr Pro Pro Gly Met Leu Ala Leu Asp Asn
            275                 280                 285

Met Leu Tyr Leu Ala Lys Val His Gln Asp Thr Tyr Ile Arg Ile Val
            290                 295                 300

Leu Glu Asn Ser Ser Arg Glu Asp Lys His Glu Cys Pro Phe Gly Arg
305                 310                 315                 320

Ser Ala Ile Glu Leu Thr Lys Met Leu Cys Glu Ile Leu Gln Val Gly
                325                 330                 335

Glu Leu Pro Asn Glu Gly Arg Asn Asp Tyr His Pro Met Phe Phe Thr
            340                 345                 350

His Asp Arg Ala Phe Glu Glu Leu Phe Gly Ile Cys Ile Gln Leu Leu
            355                 360                 365

Asn Lys Thr Trp Lys Glu Met Arg Ala Thr Ala Glu Asp Phe Asn Lys
            370                 375                 380

Val Met Gln Val Val Arg Glu Gln Ile Thr Arg Ala Leu Pro Ser Lys
385                 390                 395                 400

Pro Asn Ser Leu Asp Gln Phe Lys Ser Lys Leu Arg Ser Leu Ser Tyr
                405                 410                 415

Ser Glu Ile Leu Arg Leu Arg Gln Ser Glu Arg Met Ser Gln Asp Asp
            420                 425                 430

Phe Gln Ser Pro Pro Ile Val Glu Leu Arg Glu Lys Ile Gln Pro Glu
            435                 440                 445

Ile Leu Glu Leu Ile Lys Gln Gln Arg Leu Asn Arg Leu Cys Glu Gly
            450                 455                 460

Ser Ser Phe Arg Lys Ile Gly Asn Arg Arg Gln Glu Arg Phe Trp
465                 470                 475                 480

Tyr Cys Arg Leu Ala Leu Asn His Lys Val Leu His Tyr Gly Asp Leu
                485                 490                 495

Asp Asp Asn Pro Gln Gly Glu Val Thr Phe Glu Ser Leu Gln Glu Lys
            500                 505                 510

Ile Pro Val Ala Asp Ile Lys Ala Ile Val Thr Gly Lys Asp Cys Pro
            515                 520                 525

His Met Lys Glu Lys Ser Ala Leu Lys Gln Asn Lys Glu Val Leu Glu
            530                 535                 540

Leu Ala Phe Ser Ile Leu Tyr Asp Pro Asp Glu Thr Leu Asn Phe Ile
545                 550                 555                 560

Ala Pro Asn Lys Tyr Glu Tyr Cys Ile Trp Ile Asp Gly Leu Ser Ala
                565                 570                 575

Leu Leu Gly Lys Asp Met Ser Ser Glu Leu Thr Lys Ser Asp Leu Asp
            580                 585                 590

Thr Leu Leu Ser Met Glu Met Lys Leu Arg Leu Leu Asp Leu Glu Asn
            595                 600                 605

Ile Gln Ile Pro Glu Ala Pro Pro Ile Pro Lys Glu Pro Ser Ser
            610                 615                 620

Tyr Asp Phe Val Tyr His Tyr Gly
625                 630

<210> SEQ ID NO 105
<211> LENGTH: 463
<212> TYPE: PRT
<213> ORGANISM: Human
```

<400> SEQUENCE: 105

```
Met Ala Ala Leu Arg Ala Leu Cys Gly Phe Arg Gly Val Ala Ala Gln
1               5                   10                  15

Val Leu Arg Pro Gly Ala Gly Val Arg Leu Pro Ile Gln Pro Ser Arg
            20                  25                  30

Gly Val Arg Gln Trp Gln Pro Asp Val Glu Trp Ala Gln Gln Phe Gly
        35                  40                  45

Gly Ala Val Met Tyr Pro Ser Lys Glu Thr Ala His Trp Lys Pro Pro
    50                  55                  60

Pro Trp Asn Asp Val Asp Pro Lys Asp Thr Ile Val Lys Asn Ile
65                  70                  75                  80

Thr Leu Asn Phe Gly Pro Gln His Pro Ala Ala His Gly Val Leu Arg
                85                  90                  95

Leu Val Met Glu Leu Ser Gly Glu Met Val Arg Lys Cys Asp Pro His
                100                 105                 110

Ile Gly Leu Leu His Arg Gly Thr Glu Lys Leu Ile Glu Tyr Lys Thr
            115                 120                 125

Tyr Leu Gln Ala Leu Pro Tyr Phe Asp Arg Leu Asp Tyr Val Ser Met
130                 135                 140

Met Cys Asn Glu Gln Ala Tyr Ser Leu Ala Val Glu Lys Leu Leu Asn
145                 150                 155                 160

Ile Arg Pro Pro Arg Ala Gln Trp Ile Arg Val Leu Phe Gly Glu
            165                 170                 175

Ile Thr Arg Leu Leu Asn His Ile Met Ala Val Thr Thr His Ala Leu
            180                 185                 190

Asp Leu Gly Ala Met Thr Pro Phe Phe Trp Leu Phe Glu Glu Arg Glu
        195                 200                 205

Lys Met Phe Glu Phe Tyr Glu Arg Val Ser Gly Ala Arg Met His Ala
    210                 215                 220

Ala Tyr Ile Arg Pro Gly Gly Val His Gln Asp Leu Pro Leu Gly Leu
225                 230                 235                 240

Met Asp Asp Ile Tyr Gln Phe Ser Lys Asn Phe Ser Leu Arg Leu Asp
                245                 250                 255

Glu Leu Glu Glu Leu Leu Thr Asn Asn Arg Ile Trp Arg Asn Arg Thr
            260                 265                 270

Ile Asp Ile Gly Val Val Thr Ala Glu Glu Ala Leu Asn Tyr Gly Phe
        275                 280                 285

Ser Gly Val Met Leu Arg Gly Ser Gly Ile Gln Trp Asp Leu Arg Lys
    290                 295                 300

Thr Gln Pro Tyr Asp Val Tyr Asp Gln Val Glu Phe Asp Val Pro Val
305                 310                 315                 320

Gly Ser Arg Gly Asp Cys Tyr Asp Arg Tyr Leu Cys Arg Val Glu Glu
                325                 330                 335

Met Arg Gln Ser Leu Arg Ile Ile Ala Gln Cys Leu Asn Lys Met Pro
            340                 345                 350

Pro Gly Glu Ile Lys Val Asp Asp Ala Lys Val Ser Pro Pro Lys Arg
        355                 360                 365

Ala Glu Met Lys Thr Ser Met Glu Ser Leu Ile His His Phe Lys Leu
    370                 375                 380

Tyr Thr Glu Gly Tyr Gln Val Pro Pro Gly Ala Thr Tyr Thr Ala Ile
385                 390                 395                 400

Glu Ala Pro Lys Gly Glu Phe Gly Val Tyr Leu Val Ser Asp Gly Ser
```

```
                         405                 410                 415
Ser Arg Pro Tyr Arg Cys Lys Ile Lys Ala Pro Gly Phe Ala His Leu
            420                 425                 430

Ala Gly Leu Asp Lys Met Ser Lys Gly His Met Leu Ala Asp Val Val
            435                 440                 445

Ala Ile Ile Gly Thr Gln Asp Ile Val Phe Gly Glu Val Asp Arg
450                 455                 460

<210> SEQ ID NO 106
<211> LENGTH: 463
<212> TYPE: PRT
<213> ORGANISM: Human

<400> SEQUENCE: 106

Met Ala Ala Leu Arg Ala Leu Cys Gly Phe Arg Gly Val Ala Ala Gln
1               5                   10                  15

Val Leu Arg Pro Gly Ala Gly Val Arg Leu Pro Ile Gln Pro Ser Arg
            20                  25                  30

Gly Val Arg Gln Trp Gln Pro Asp Val Glu Trp Ala Gln Gln Phe Gly
        35                  40                  45

Gly Ala Val Met Tyr Pro Ser Lys Glu Thr Ala His Trp Lys Pro Pro
50                  55                  60

Pro Trp Asn Asp Val Asp Pro Lys Asp Thr Ile Val Lys Asn Ile
65              70                  75                  80

Thr Leu Asn Phe Gly Pro Gln His Pro Ala Ala His Gly Val Leu Arg
                85                  90                  95

Leu Val Met Glu Leu Ser Gly Glu Met Val Arg Lys Cys Asp Pro His
            100                 105                 110

Ile Gly Leu Leu His Arg Gly Thr Glu Lys Leu Ile Glu Tyr Lys Thr
        115                 120                 125

Tyr Leu Gln Ala Leu Pro Tyr Phe Asp Arg Leu Asp Tyr Val Ser Met
130                 135                 140

Met Cys Asn Glu Gln Ala Tyr Ser Leu Ala Val Glu Lys Leu Leu Asn
145                 150                 155                 160

Ile Arg Pro Pro Arg Ala Gln Trp Ile Arg Val Leu Phe Gly Glu
                165                 170                 175

Ile Thr Arg Leu Leu Asn His Ile Met Ala Val Thr Thr His Ala Leu
            180                 185                 190

Asp Leu Gly Ala Met Thr Pro Phe Phe Trp Leu Phe Glu Glu Arg Glu
        195                 200                 205

Lys Met Phe Glu Phe Tyr Glu Arg Val Ser Gly Ala Arg Met His Ala
    210                 215                 220

Ala Tyr Ile Arg Pro Gly Gly Val His Gln Asp Leu Pro Leu Gly Leu
225                 230                 235                 240

Met Asp Asp Ile Tyr Gln Phe Ser Lys Asn Phe Ser Leu Arg Leu Asp
                245                 250                 255

Glu Leu Glu Glu Leu Leu Thr Asn Asn Arg Ile Trp Arg Asn Arg Thr
            260                 265                 270

Ile Asp Ile Gly Val Val Thr Ala Glu Glu Ala Leu Asn Tyr Gly Phe
        275                 280                 285

Ser Gly Val Met Leu Arg Gly Ser Gly Ile Gln Trp Asp Leu Arg Lys
    290                 295                 300

Thr Gln Pro Tyr Asp Val Tyr Asp Gln Val Glu Phe Asp Val Pro Val
305                 310                 315                 320
```

```
Gly Ser Arg Gly Asp Cys Tyr Asp Arg Tyr Leu Cys Arg Val Glu Glu
            325                 330                 335

Met Arg Gln Ser Leu Arg Ile Ile Ala Gln Cys Leu Asn Lys Met Pro
        340                 345                 350

Pro Gly Glu Ile Lys Val Asp Asp Ala Lys Val Ser Pro Pro Lys Arg
            355                 360                 365

Ala Glu Met Lys Thr Ser Met Glu Ser Leu Ile His His Phe Lys Leu
        370                 375                 380

Tyr Thr Glu Gly Tyr Gln Val Pro Pro Gly Ala Thr Tyr Thr Ala Ile
385                 390                 395                 400

Glu Ala Pro Lys Gly Glu Phe Gly Val Tyr Leu Val Ser Asp Gly Ser
            405                 410                 415

Ser Arg Pro Tyr Arg Cys Lys Ile Lys Ala Pro Gly Phe Ala His Leu
        420                 425                 430

Ala Gly Leu Asp Lys Met Ser Lys Gly His Met Leu Ala Asp Val Val
        435                 440                 445

Ala Ile Ile Gly Thr Gln Asp Ile Val Phe Gly Glu Val Asp Arg
        450                 455                 460

<210> SEQ ID NO 107
<211> LENGTH: 693
<212> TYPE: PRT
<213> ORGANISM: Human

<400> SEQUENCE: 107

Met Ala Gly Gly Pro Gly Pro Gly Glu Pro Ala Ala Pro Gly Ala Gln
1               5                   10                  15

His Phe Leu Tyr Glu Val Pro Pro Trp Val Met Cys Arg Phe Tyr Lys
            20                  25                  30

Val Met Asp Ala Leu Glu Pro Ala Asp Trp Cys Gln Phe Gly Gly Trp
        35                  40                  45

Arg Arg Ala Ala Gly Gly Arg Glu Ala Arg Gly Leu Leu Ala Pro Thr
    50                  55                  60

Pro Asp Ala Pro Arg Pro Ala Ala Leu Ile Val Arg Asp Gln Thr
65              70                  75                  80

Glu Leu Arg Leu Cys Glu Arg Ser Gly Gln Arg Thr Ala Ser Val Leu
            85                  90                  95

Trp Pro Trp Ile Asn Arg Asn Ala Arg Val Ala Asp Leu Val His Ile
            100                 105                 110

Leu Thr His Leu Gln Leu Leu Arg Ala Arg Asp Ile Ile Thr Ala Trp
        115                 120                 125

His Pro Pro Ala Pro Leu Pro Ser Pro Gly Thr Thr Ala Pro Arg Pro
    130                 135                 140

Ser Ser Ile Pro Ala Pro Ala Glu Ala Glu Ala Trp Ser Pro Arg Lys
145                 150                 155                 160

Leu Pro Ser Ser Ala Ser Thr Phe Leu Ser Pro Ala Phe Pro Gly Ser
                165                 170                 175

Gln Thr His Ser Gly Pro Glu Leu Gly Leu Val Pro Ser Pro Ala Ser
            180                 185                 190

Leu Trp Pro Pro Pro Ser Ala Pro Ser Thr Lys Pro Gly
        195                 200                 205

Pro Glu Ser Ser Val Ser Leu Leu Gln Gly Ala Arg Pro Phe Pro Phe
    210                 215                 220

Cys Trp Pro Leu Cys Glu Ile Ser Arg Gly Thr His Asn Phe Ser Glu
225                 230                 235                 240
```

-continued

```
Glu Leu Lys Ile Gly Glu Gly Phe Gly Cys Val Tyr Arg Ala Val
            245             250             255

Met Arg Asn Thr Val Tyr Ala Val Lys Arg Leu Lys Glu Asn Ala Asp
        260                 265                 270

Leu Glu Trp Thr Ala Val Lys Gln Ser Phe Leu Thr Gly Val Glu Gln
        275                 280             285

Leu Ser Arg Phe Arg His Pro Asn Ile Val Asp Phe Ala Gly Tyr Cys
        290                 295                 300

Ala Gln Asn Gly Phe Tyr Cys Leu Val Tyr Gly Phe Leu Pro Asn Gly
305                 310                 315                 320

Ser Leu Glu Asp Arg Leu His Cys Gln Thr Gln Ala Cys Pro Pro Leu
                325                 330                 335

Ser Trp Pro Gln Arg Leu Asp Ile Leu Leu Gly Thr Ala Arg Ala Ile
                340                 345                 350

Gln Phe Leu His Gln Asp Ser Pro Ser Leu Ile His Gly Asp Ile Lys
            355                 360                 365

Ser Ser Asn Val Leu Leu Asp Glu Arg Leu Thr Pro Lys Leu Gly Asp
        370                 375                 380

Phe Gly Leu Ala Arg Phe Ser Arg Phe Ala Gly Ser Ser Pro Ser Gln
385                 390                 395                 400

Ser Ser Met Val Ala Arg Thr Gln Thr Val Arg Gly Thr Leu Ala Tyr
                405                 410                 415

Leu Pro Glu Glu Tyr Ile Lys Thr Gly Arg Leu Ala Val Asp Thr Asp
                420                 425                 430

Thr Phe Ser Phe Gly Val Val Leu Glu Thr Leu Ala Gly Gln Arg
            435                 440                 445

Ala Val Lys Thr His Gly Ala Arg Thr Lys Tyr Leu Lys Asp Leu Val
        450                 455                 460

Glu Glu Glu Ala Glu Glu Ala Gly Val Ala Leu Arg Ser Thr Gln Ser
465                 470                 475                 480

Thr Leu Gln Ala Gly Leu Ala Ala Asp Ala Trp Ala Ala Pro Ile Ala
                485                 490                 495

Met Gln Ile Tyr Lys Lys His Leu Gly Gln Leu Ala Cys Cys Cys Leu
                500                 505                 510

His Arg Arg Ala Lys Arg Pro Pro Met Thr Gln Glu Asn Ser Tyr
        515                 520                 525

Val Ser Ser Thr Gly Arg Ala His Ser Gly Ala Ala Pro Trp Gln Pro
        530                 535                 540

Leu Ala Ala Pro Ser Gly Ala Ser Ala Gln Ala Ala Glu Gln Leu Gln
545                 550                 555                 560

Arg Gly Pro Asn Gln Pro Val Glu Ser Asp Glu Ser Leu Gly Gly Leu
                565                 570                 575

Ser Ala Ala Leu Arg Ser Trp His Leu Thr Pro Ser Cys Pro Leu Asp
                580                 585                 590

Pro Ala Pro Leu Arg Glu Ala Gly Cys Pro Gln Gly Asp Thr Ala Gly
            595                 600                 605

Glu Ser Ser Trp Gly Ser Gly Pro Gly Ser Arg Pro Thr Ala Val Glu
        610                 615                 620

Gly Leu Ala Leu Gly Ser Ser Ala Ser Ser Ser Glu Pro Pro Gln
625                 630                 635                 640

Ile Ile Ile Asn Pro Ala Arg Gln Lys Met Val Gln Lys Leu Ala Leu
                645                 650                 655
```

-continued

```
Tyr Glu Asp Gly Ala Leu Asp Ser Leu Gln Leu Leu Ser Ser Ser
            660                 665                 670

Leu Pro Gly Leu Gly Leu Glu Gln Asp Arg Gln Gly Pro Glu Glu Ser
        675                 680                 685

Asp Glu Phe Gln Ser
    690

<210> SEQ ID NO 108
<211> LENGTH: 712
<212> TYPE: PRT
<213> ORGANISM: Human

<400> SEQUENCE: 108

Met Ala Gly Gly Pro Gly Pro Gly Glu Pro Ala Ala Pro Gly Ala Gln
1               5                   10                  15

His Phe Leu Tyr Glu Val Pro Pro Trp Val Met Cys Arg Phe Tyr Lys
            20                  25                  30

Val Met Asp Ala Leu Glu Pro Ala Asp Trp Cys Gln Phe Ala Ala Leu
        35                  40                  45

Ile Val Arg Asp Gln Thr Glu Leu Arg Leu Cys Glu Arg Ser Gly Gln
    50                  55                  60

Arg Thr Ala Ser Val Leu Trp Pro Trp Ile Asn Arg Asn Ala Arg Val
65                  70                  75                  80

Ala Asp Leu Val His Ile Leu Thr His Leu Gln Leu Leu Arg Ala Arg
                85                  90                  95

Asp Ile Ile Thr Ala Trp His Pro Pro Ala Pro Leu Pro Ser Pro Gly
            100                 105                 110

Thr Thr Ala Pro Arg Pro Ser Ser Ile Pro Ala Pro Ala Glu Ala Glu
        115                 120                 125

Ala Trp Ser Pro Arg Lys Leu Pro Ser Ser Ala Ser Thr Phe Leu Ser
    130                 135                 140

Pro Ala Phe Pro Gly Ser Gln Thr His Ser Gly Pro Glu Leu Gly Leu
145                 150                 155                 160

Val Pro Ser Pro Ala Ser Leu Trp Pro Pro Pro Ser Pro Ala Pro
                165                 170                 175

Ser Ser Thr Lys Pro Gly Pro Glu Ser Ser Val Ser Leu Leu Gln Gly
            180                 185                 190

Ala Arg Pro Phe Pro Phe Cys Trp Pro Leu Cys Glu Ile Ser Arg Gly
        195                 200                 205

Thr His Asn Phe Ser Glu Glu Leu Lys Ile Gly Glu Gly Gly Phe Gly
    210                 215                 220

Cys Val Tyr Arg Ala Val Met Arg Asn Thr Val Tyr Ala Val Lys Arg
225                 230                 235                 240

Leu Lys Glu Asn Ala Asp Leu Glu Trp Thr Ala Val Lys Gln Ser Phe
                245                 250                 255

Leu Thr Glu Val Glu Gln Leu Ser Arg Phe Arg His Pro Asn Ile Val
            260                 265                 270

Asp Phe Ala Gly Tyr Cys Ala Gln Asn Gly Phe Tyr Cys Leu Val Tyr
        275                 280                 285

Gly Phe Leu Pro Asn Gly Ser Leu Glu Asp Arg Leu His Cys Gln Thr
    290                 295                 300

Gln Ala Cys Pro Pro Leu Ser Trp Pro Gln Arg Leu Asp Ile Leu Leu
305                 310                 315                 320

Gly Thr Ala Arg Ala Ile Gln Phe Leu His Gln Asp Ser Pro Ser Leu
                325                 330                 335
```

Ile His Gly Asp Ile Lys Ser Ser Asn Val Leu Leu Asp Glu Arg Leu
            340                 345                 350

Thr Pro Lys Leu Gly Asp Phe Gly Leu Ala Arg Phe Ser Arg Phe Ala
            355                 360                 365

Gly Ser Ser Pro Ser Gln Ser Ser Met Val Ala Arg Thr Gln Thr Val
370                 375                 380

Arg Gly Thr Leu Ala Tyr Leu Pro Glu Glu Tyr Ile Lys Thr Gly Arg
385                 390                 395                 400

Leu Ala Val Asp Thr Asp Thr Phe Ser Phe Gly Val Val Leu Glu
            405                 410                 415

Thr Leu Ala Gly Gln Arg Ala Val Lys Thr His Gly Ala Arg Thr Lys
            420                 425                 430

Tyr Leu Lys Asp Leu Val Glu Glu Ala Glu Ala Gly Val Ala
            435                 440                 445

Leu Arg Ser Thr Gln Ser Thr Leu Gln Ala Gly Leu Ala Ala Asp Ala
            450                 455                 460

Trp Ala Ala Pro Ile Ala Met Gln Ile Tyr Lys Lys His Leu Asp Pro
465                 470                 475                 480

Arg Pro Gly Pro Cys Pro Pro Glu Leu Gly Leu Gly Leu Gly Gln Leu
            485                 490                 495

Ala Cys Cys Cys Leu His Arg Arg Ala Lys Arg Arg Pro Pro Met Thr
            500                 505                 510

Gln Val Tyr Glu Arg Leu Glu Lys Leu Gln Ala Val Val Ala Gly Val
            515                 520                 525

Pro Gly His Ser Glu Ala Ala Ser Cys Ile Pro Pro Ser Pro Gln Glu
            530                 535                 540

Asn Ser Tyr Val Ser Ser Thr Gly Arg Ala His Ser Gly Ala Ala Pro
545                 550                 555                 560

Trp Gln Pro Leu Ala Ala Pro Ser Gly Ala Ser Ala Gln Ala Ala Glu
            565                 570                 575

Gln Leu Gln Arg Gly Pro Asn Gln Pro Val Glu Ser Asp Glu Ser Leu
            580                 585                 590

Gly Gly Leu Ser Ala Ala Leu Arg Ser Trp His Leu Thr Pro Ser Cys
            595                 600                 605

Pro Leu Asp Pro Ala Pro Leu Arg Glu Ala Gly Cys Pro Gln Gly Asp
            610                 615                 620

Thr Ala Gly Glu Ser Ser Trp Gly Ser Gly Pro Gly Ser Arg Pro Thr
625                 630                 635                 640

Ala Val Glu Gly Leu Ala Leu Gly Ser Ser Ala Ser Ser Ser Ser Glu
            645                 650                 655

Pro Pro Gln Ile Ile Ile Asn Pro Ala Arg Gln Lys Met Val Gln Lys
            660                 665                 670

Leu Ala Leu Tyr Glu Asp Gly Ala Leu Asp Ser Leu Gln Leu Leu Ser
            675                 680                 685

Ser Ser Ser Leu Pro Gly Leu Gly Leu Glu Gln Asp Arg Gln Gly Pro
            690                 695                 700

Glu Glu Ser Asp Glu Phe Gln Ser
705                 710

<210> SEQ ID NO 109
<211> LENGTH: 682
<212> TYPE: PRT
<213> ORGANISM: Human

```
<400> SEQUENCE: 109

Met Ala Gly Gly Pro Gly Pro Gly Glu Pro Ala Ala Pro Gly Ala Gln
1               5                   10                  15

His Phe Leu Tyr Glu Val Pro Pro Trp Val Met Cys Arg Phe Tyr Lys
            20                  25                  30

Val Met Asp Ala Leu Glu Pro Ala Asp Trp Cys Gln Phe Ala Ala Leu
        35                  40                  45

Ile Val Arg Asp Gln Thr Glu Leu Arg Leu Cys Glu Arg Ser Gly Gln
    50                  55                  60

Arg Thr Ala Ser Val Leu Trp Pro Trp Ile Asn Arg Asn Ala Arg Val
65                  70                  75                  80

Ala Asp Leu Val His Ile Leu Thr His Leu Gln Leu Leu Arg Ala Arg
                85                  90                  95

Asp Ile Ile Thr Ala Trp His Pro Ala Pro Leu Pro Ser Pro Gly
            100                 105                 110

Thr Thr Ala Pro Arg Pro Ser Ser Ile Pro Ala Pro Ala Glu Ala Glu
        115                 120                 125

Ala Trp Ser Pro Arg Lys Leu Pro Ser Ser Ala Ser Thr Phe Leu Ser
    130                 135                 140

Pro Ala Phe Pro Gly Ser Gln Thr His Ser Gly Pro Glu Leu Gly Leu
145                 150                 155                 160

Val Pro Ser Pro Ala Ser Leu Trp Pro Pro Pro Ser Pro Ala Pro
                165                 170                 175

Ser Ser Thr Lys Pro Gly Pro Glu Ser Ser Val Ser Leu Leu Gln Gly
            180                 185                 190

Ala Arg Pro Phe Pro Phe Cys Trp Pro Leu Cys Glu Ile Ser Arg Gly
        195                 200                 205

Thr His Asn Phe Ser Glu Glu Leu Lys Ile Gly Glu Gly Gly Phe Gly
    210                 215                 220

Cys Val Tyr Arg Ala Val Met Arg Asn Thr Val Tyr Ala Val Lys Arg
225                 230                 235                 240

Leu Lys Glu Asn Ala Asp Leu Glu Trp Thr Ala Val Lys Gln Ser Phe
                245                 250                 255

Leu Thr Glu Val Glu Gln Leu Ser Arg Phe Arg His Pro Asn Ile Val
            260                 265                 270

Asp Phe Ala Gly Tyr Cys Ala Gln Asn Gly Phe Tyr Cys Leu Val Tyr
        275                 280                 285

Gly Phe Leu Pro Asn Gly Ser Leu Glu Asp Arg Leu His Cys Gln Thr
    290                 295                 300

Gln Ala Cys Pro Pro Leu Ser Trp Pro Gln Arg Leu Asp Ile Leu Leu
305                 310                 315                 320

Gly Thr Ala Arg Ala Ile Gln Phe Leu His Gln Asp Ser Pro Ser Leu
                325                 330                 335

Ile His Gly Asp Ile Lys Ser Ser Asn Val Leu Leu Asp Glu Arg Leu
            340                 345                 350

Thr Pro Lys Leu Gly Asp Phe Gly Leu Ala Arg Phe Ser Arg Phe Ala
        355                 360                 365

Gly Ser Ser Pro Ser Gln Ser Ser Met Val Ala Arg Thr Gln Thr Val
    370                 375                 380

Arg Gly Thr Leu Ala Tyr Leu Pro Glu Glu Tyr Ile Lys Thr Gly Arg
385                 390                 395                 400

Leu Ala Val Asp Thr Asp Thr Phe Ser Phe Gly Val Val Val Leu Glu
                405                 410                 415
```

```
Thr Leu Ala Gly Gln Arg Ala Val Lys Thr His Gly Ala Arg Thr Lys
            420                 425                 430

Tyr Leu Lys Asp Leu Val Glu Glu Ala Glu Ala Gly Val Ala
            435                 440                 445

Leu Arg Ser Thr Gln Ser Thr Leu Gln Ala Gly Leu Ala Ala Asp Ala
450                 455                 460

Trp Ala Ala Pro Ile Ala Met Gln Ile Tyr Lys Lys His Leu Asp Pro
465                 470                 475                 480

Arg Pro Gly Pro Cys Pro Pro Glu Leu Gly Leu Gly Leu Gly Gln Leu
                    485                 490                 495

Ala Cys Cys Cys Leu His Arg Arg Ala Lys Arg Arg Pro Pro Met Thr
                500                 505                 510

Gln Glu Asn Ser Tyr Val Ser Ser Thr Gly Arg Ala His Ser Gly Ala
            515                 520                 525

Ala Pro Trp Gln Pro Leu Ala Ala Pro Ser Gly Ala Ser Ala Gln Ala
        530                 535                 540

Ala Glu Gln Leu Gln Arg Gly Pro Asn Gln Pro Val Glu Ser Asp Glu
545                 550                 555                 560

Ser Leu Gly Gly Leu Ser Ala Ala Leu Arg Ser Trp His Leu Thr Pro
                565                 570                 575

Ser Cys Pro Leu Asp Pro Ala Pro Leu Arg Glu Ala Gly Cys Pro Gln
                580                 585                 590

Gly Asp Thr Ala Gly Glu Ser Ser Trp Gly Ser Gly Pro Gly Ser Arg
            595                 600                 605

Pro Thr Ala Val Glu Gly Leu Ala Leu Gly Ser Ser Ala Ser Ser Ser
        610                 615                 620

Ser Glu Pro Pro Gln Ile Ile Ile Asn Pro Ala Arg Gln Lys Met Val
625                 630                 635                 640

Gln Lys Leu Ala Leu Tyr Glu Asp Gly Ala Leu Asp Ser Leu Gln Leu
                645                 650                 655

Leu Ser Ser Ser Ser Leu Pro Gly Leu Gly Leu Glu Gln Asp Arg Gln
                660                 665                 670

Gly Pro Glu Glu Ser Asp Glu Phe Gln Ser
            675                 680

<210> SEQ ID NO 110
<211> LENGTH: 633
<212> TYPE: PRT
<213> ORGANISM: Human

<400> SEQUENCE: 110

Met Ala Gly Gly Pro Gly Pro Gly Glu Pro Ala Ala Pro Gly Ala Gln
1               5                   10                  15

His Phe Leu Tyr Glu Val Pro Pro Trp Val Met Cys Arg Phe Tyr Lys
            20                  25                  30

Val Met Asp Ala Leu Glu Pro Ala Asp Trp Cys Gln Phe Ala Ala Leu
        35                  40                  45

Ile Val Arg Asp Gln Thr Glu Leu Arg Leu Cys Glu Arg Ser Gly Gln
    50                  55                  60

Arg Thr Ala Ser Val Leu Trp Pro Trp Ile Asn Arg Asn Ala Arg Val
65                  70                  75                  80

Ala Asp Leu Val His Ile Leu Thr His Leu Gln Leu Leu Arg Ala Arg
                85                  90                  95

Asp Ile Ile Thr Ala Trp His Pro Pro Ala Pro Leu Pro Ser Pro Gly
```

```
            100                 105                 110
Thr Thr Ala Pro Arg Pro Ser Ser Ile Pro Ala Pro Ala Glu Ala Glu
            115                 120                 125

Ala Trp Ser Pro Arg Lys Leu Pro Ser Ser Ala Ser Thr Phe Leu Ser
            130                 135                 140

Pro Ala Phe Pro Gly Ser Gln Thr His Ser Gly Pro Glu Leu Gly Leu
145                 150                 155                 160

Val Pro Ser Pro Ala Ser Leu Trp Pro Pro Pro Ser Pro Ala Pro
                165                 170                 175

Ser Ser Thr Lys Pro Gly Pro Glu Ser Ser Val Ser Leu Leu Gln Gly
            180                 185                 190

Ala Arg Pro Phe Pro Phe Cys Trp Pro Leu Cys Glu Ile Ser Arg Gly
            195                 200                 205

Thr His Asn Phe Ser Glu Glu Leu Lys Ile Gly Glu Gly Gly Phe Gly
            210                 215                 220

Cys Val Tyr Arg Ala Val Met Arg Asn Thr Val Tyr Ala Val Lys Arg
225                 230                 235                 240

Leu Lys Glu Asn Ala Asp Leu Glu Trp Thr Ala Val Lys Gln Ser Phe
                245                 250                 255

Leu Thr Glu Val Glu Gln Leu Ser Arg Phe Arg His Pro Asn Ile Val
            260                 265                 270

Asp Phe Ala Gly Tyr Cys Ala Gln Asn Gly Phe Tyr Cys Leu Val Tyr
            275                 280                 285

Gly Phe Leu Pro Asn Gly Ser Leu Glu Asp Arg Leu His Cys Gln Thr
            290                 295                 300

Gln Ala Cys Pro Pro Leu Ser Trp Pro Gln Arg Leu Asp Ile Leu Leu
305                 310                 315                 320

Gly Thr Ala Arg Ala Ile Gln Phe Leu His Gln Asp Ser Pro Ser Leu
            325                 330                 335

Ile His Gly Asp Ile Lys Ser Ser Asn Val Leu Leu Asp Glu Arg Leu
            340                 345                 350

Thr Pro Lys Leu Gly Asp Phe Gly Leu Ala Arg Phe Ser Arg Phe Ala
            355                 360                 365

Gly Ser Ser Pro Ser Gln Ser Ser Met Val Ala Arg Thr Gln Thr Val
            370                 375                 380

Arg Gly Thr Leu Ala Tyr Leu Pro Glu Glu Tyr Ile Lys Thr Gly Arg
385                 390                 395                 400

Leu Ala Val Asp Thr Asp Thr Phe Ser Phe Gly Val Val Leu Glu
                405                 410                 415

Thr Leu Ala Gly Gln Arg Ala Val Lys Thr His Gly Ala Arg Thr Lys
            420                 425                 430

Tyr Leu Val Tyr Glu Arg Leu Lys Leu Gln Ala Val Ala Gly
            435                 440                 445

Val Pro Gly His Ser Glu Ala Ala Ser Cys Ile Pro Pro Ser Pro Gln
            450                 455                 460

Glu Asn Ser Tyr Val Ser Ser Thr Gly Arg Ala His Ser Gly Ala Ala
465                 470                 475                 480

Pro Trp Gln Pro Leu Ala Ala Pro Ser Gly Ala Ser Ala Gln Ala Ala
                485                 490                 495

Glu Gln Leu Gln Arg Gly Pro Asn Gln Pro Val Glu Ser Asp Glu Ser
            500                 505                 510

Leu Gly Gly Leu Ser Ala Ala Leu Arg Ser Trp His Leu Thr Pro Ser
            515                 520                 525
```

```
Cys Pro Leu Asp Pro Ala Pro Leu Arg Glu Ala Gly Cys Pro Gln Gly
        530                 535                 540

Asp Thr Ala Gly Glu Ser Ser Trp Gly Ser Gly Pro Gly Ser Arg Pro
545                 550                 555                 560

Thr Ala Val Glu Gly Leu Ala Leu Gly Ser Ser Ala Ser Ser Ser Ser
                565                 570                 575

Glu Pro Pro Gln Ile Ile Ile Asn Pro Ala Arg Gln Lys Met Val Gln
                580                 585                 590

Lys Leu Ala Leu Tyr Glu Asp Gly Ala Leu Asp Ser Leu Gln Leu Leu
                595                 600                 605

Ser Ser Ser Ser Leu Pro Gly Leu Gly Leu Glu Gln Asp Arg Gln Gly
                610                 615                 620

Pro Glu Glu Ser Asp Glu Phe Gln Ser
625                 630

<210> SEQ ID NO 111
<211> LENGTH: 708
<212> TYPE: PRT
<213> ORGANISM: Human

<400> SEQUENCE: 111

Met Ala Gly Gly Pro Gly Pro Gly Glu Pro Ala Ala Pro Gly Ala Gln
1                   5                   10                  15

His Phe Leu Tyr Glu Val Pro Pro Trp Val Met Cys Arg Phe Tyr Lys
                20                  25                  30

Val Met Asp Ala Leu Glu Pro Ala Asp Trp Cys Gln Phe Gly Gly Trp
            35                  40                  45

Arg Arg Ala Ala Gly Gly Arg Glu Ala Arg Gly Leu Leu Ala Pro Thr
        50                  55                  60

Pro Asp Ala Pro Arg Pro Ala Ala Leu Ile Val Arg Asp Gln Thr
65                  70                  75                  80

Glu Leu Arg Leu Cys Glu Arg Ser Gly Gln Arg Thr Ala Ser Val Leu
                85                  90                  95

Trp Pro Trp Ile Asn Arg Asn Ala Arg Val Ala Asp Leu Val His Ile
                100                 105                 110

Leu Thr His Leu Gln Leu Leu Arg Ala Arg Asp Ile Ile Thr Ala Trp
            115                 120                 125

His Pro Pro Ala Pro Leu Pro Ser Pro Gly Thr Thr Ala Pro Arg Pro
        130                 135                 140

Ser Ser Ile Pro Ala Pro Ala Glu Ala Glu Ala Trp Ser Pro Arg Lys
145                 150                 155                 160

Leu Pro Ser Ser Ala Ser Thr Phe Leu Ser Pro Ala Phe Pro Gly Ser
                165                 170                 175

Gln Thr His Ser Gly Pro Glu Leu Gly Leu Val Pro Ser Pro Ala Ser
                180                 185                 190

Leu Trp Pro Pro Pro Ser Pro Ala Pro Ser Ser Thr Lys Pro Gly
            195                 200                 205

Pro Glu Ser Ser Val Ser Leu Leu Gln Gly Ala Arg Pro Phe Pro Phe
        210                 215                 220

Cys Trp Pro Leu Cys Glu Ile Ser Arg Gly Thr His Asn Phe Ser Glu
225                 230                 235                 240

Glu Leu Lys Ile Gly Glu Gly Gly Phe Gly Cys Val Tyr Arg Ala Val
                245                 250                 255

Met Arg Asn Thr Val Tyr Ala Val Lys Arg Leu Lys Glu Asn Ala Asp
```

```
              260                 265                 270
Leu Glu Trp Thr Ala Val Lys Gln Ser Phe Leu Thr Glu Val Glu Gln
            275                 280                 285

Leu Ser Arg Phe Arg His Pro Asn Ile Val Asp Phe Ala Gly Tyr Cys
            290                 295                 300

Ala Gln Asn Gly Phe Tyr Cys Leu Val Tyr Gly Phe Leu Pro Asn Gly
305                 310                 315                 320

Ser Leu Glu Asp Arg Leu His Cys Gln Thr Gln Ala Cys Pro Pro Leu
            325                 330                 335

Ser Trp Pro Gln Arg Leu Asp Ile Leu Leu Gly Thr Ala Arg Ala Ile
            340                 345                 350

Gln Phe Leu His Gln Asp Ser Pro Ser Leu Ile His Gly Asp Ile Lys
            355                 360                 365

Ser Ser Asn Val Leu Leu Asp Glu Arg Leu Thr Pro Lys Leu Gly Asp
            370                 375                 380

Phe Gly Leu Ala Arg Phe Ser Arg Phe Ala Gly Ser Ser Pro Ser Gln
385                 390                 395                 400

Ser Ser Met Val Ala Arg Thr Gln Thr Val Arg Gly Thr Leu Ala Tyr
                405                 410                 415

Leu Pro Glu Glu Tyr Ile Lys Thr Gly Arg Leu Ala Val Asp Thr Asp
            420                 425                 430

Thr Phe Ser Phe Gly Val Val Leu Glu Thr Leu Ala Gly Gln Arg
            435                 440                 445

Ala Val Lys Thr His Gly Ala Arg Thr Lys Tyr Leu Lys Asp Leu Val
            450                 455                 460

Glu Glu Glu Ala Glu Glu Ala Gly Val Ala Leu Arg Ser Thr Gln Ser
465                 470                 475                 480

Thr Leu Gln Ala Gly Leu Ala Ala Asp Ala Trp Ala Ala Pro Ile Ala
                485                 490                 495

Met Gln Ile Tyr Lys Lys His Leu Asp Pro Arg Pro Gly Pro Cys Pro
                500                 505                 510

Pro Glu Leu Gly Leu Gly Leu Gly Gln Leu Ala Cys Cys Cys Leu His
            515                 520                 525

Arg Arg Ala Lys Arg Arg Pro Pro Met Thr Gln Glu Asn Ser Tyr Val
530                 535                 540

Ser Ser Thr Gly Arg Ala His Ser Gly Ala Ala Pro Trp Gln Pro Leu
545                 550                 555                 560

Ala Ala Pro Ser Gly Ala Ser Ala Gln Ala Ala Glu Gln Leu Gln Arg
                565                 570                 575

Gly Pro Asn Gln Pro Val Glu Ser Asp Glu Ser Leu Gly Gly Leu Ser
            580                 585                 590

Ala Ala Leu Arg Ser Trp His Leu Thr Pro Ser Cys Pro Leu Asp Pro
            595                 600                 605

Ala Pro Leu Arg Glu Ala Gly Cys Pro Gln Gly Asp Thr Ala Gly Glu
            610                 615                 620

Ser Ser Trp Gly Ser Gly Pro Gly Ser Arg Pro Thr Ala Val Glu Gly
625                 630                 635                 640

Leu Ala Leu Gly Ser Ser Ala Ser Ser Ser Glu Pro Pro Gln Ile
                645                 650                 655

Ile Ile Asn Pro Ala Arg Gln Lys Met Val Gln Lys Leu Ala Leu Tyr
            660                 665                 670

Glu Asp Gly Ala Leu Asp Ser Leu Gln Leu Leu Ser Ser Ser Ser Leu
            675                 680                 685
```

```
Pro Gly Leu Gly Leu Glu Gln Asp Arg Gln Gly Pro Glu Glu Ser Asp
    690                 695                 700
Glu Phe Gln Ser
705

<210> SEQ ID NO 112
<211> LENGTH: 140
<212> TYPE: PRT
<213> ORGANISM: Human

<400> SEQUENCE: 112

Met Ala Ala Ile Pro Ser Ser Gly Ser Leu Val Ala Thr His Asp Tyr
1               5                   10                  15

Tyr Arg Arg Arg Leu Gly Ser Thr Ser Ser Asn Ser Ser Cys Ser Ser
                20                  25                  30

Thr Glu Cys Pro Gly Glu Ala Ile Pro His Pro Pro Gly Glu Cys Arg
            35                  40                  45

Ile Ala Pro Phe Ser Pro Arg Ser Ser Arg Ser Trp Gln His Gln Asp
        50                  55                  60

Pro Thr Ser Leu Leu Ser Gly Leu Pro Lys Ala Asp Pro Gly His Trp
65                  70                  75                  80

Trp Ala Ser Phe Phe Phe Gly Lys Ser Thr Leu Pro Phe Met Ala Thr
                85                  90                  95

Val Leu Glu Ser Ala Glu His Ser Glu Pro Pro Gln Ala Ser Ser Ser
                100                 105                 110

Met Thr Ala Cys Gly Leu Ala Arg Asp Ala Pro Arg Lys Gln Pro Gly
            115                 120                 125

Gly Gln Ser Ser Thr Ala Ser Ala Gly Pro Pro Ser
        130                 135                 140

<210> SEQ ID NO 113
<211> LENGTH: 70
<212> TYPE: PRT
<213> ORGANISM: Human

<400> SEQUENCE: 113

Met Ala Ala Ile Pro Ser Ser Gly Ser Leu Val Ala Thr His Asp Tyr
1               5                   10                  15

Tyr Arg Arg Arg Leu Gly Ser Thr Ser Ser Asn Ser Ser Cys Ser Ser
                20                  25                  30

Thr Glu Cys Pro Gly Glu Ala Ile Pro His Pro Pro Gly Leu Pro Lys
            35                  40                  45

Ala Asp Pro Gly His Trp Trp Ala Ser Phe Phe Phe Gly Lys Ser Thr
        50                  55                  60

Leu Pro Pro Pro Thr Leu
65                  70

<210> SEQ ID NO 114
<211> LENGTH: 114
<212> TYPE: PRT
<213> ORGANISM: Human

<400> SEQUENCE: 114

Met Ala Ala Ile Pro Ser Ser Gly Ser Leu Val Ala Thr His Asp Tyr
1               5                   10                  15

Tyr Arg Arg Arg Leu Gly Ser Thr Ser Ser Asn Ser Ser Cys Ser Ser
                20                  25                  30
```

```
Thr Glu Cys Pro Gly Glu Ala Ile Pro His Pro Gly Leu Pro Lys
         35                  40                  45

Ala Asp Pro Gly His Trp Trp Ala Ser Phe Phe Gly Lys Ser Thr
 50                  55                  60

Leu Pro Phe Met Ala Thr Val Leu Glu Ser Ala Glu His Ser Glu Pro
 65                  70                  75                  80

Pro Gln Ala Ser Ser Ser Met Thr Ala Cys Gly Leu Ala Arg Asp Ala
                 85                  90                  95

Pro Arg Lys Gln Pro Gly Gly Gln Ser Ser Thr Ala Ser Ala Gly Pro
            100                 105                 110

Pro Ser
```

<210> SEQ ID NO 115
<211> LENGTH: 400
<212> TYPE: PRT
<213> ORGANISM: Human

<400> SEQUENCE: 115

```
Met Glu Asp Gly Val Tyr Glu Pro Pro Asp Leu Thr Pro Glu Glu Arg
 1               5                  10                  15

Met Glu Leu Glu Asn Ile Arg Arg Lys Gln Glu Leu Leu Val Glu
             20                  25                  30

Ile Gln Arg Leu Arg Glu Glu Leu Ser Glu Ala Met Ser Glu Val Glu
             35                  40                  45

Gly Leu Glu Ala Asn Glu Gly Ser Lys Thr Leu Gln Arg Asn Arg Lys
         50                  55                  60

Met Ala Met Gly Arg Lys Lys Phe Asn Met Asp Pro Lys Lys Gly Ile
 65                  70                  75                  80

Gln Phe Leu Val Glu Asn Glu Leu Leu Gln Asn Thr Pro Glu Glu Ile
                 85                  90                  95

Ala Arg Phe Leu Tyr Lys Gly Glu Gly Leu Asn Lys Thr Ala Ile Gly
             100                 105                 110

Asp Tyr Leu Gly Glu Arg Glu Glu Leu Asn Leu Ala Val Leu His Ala
             115                 120                 125

Phe Val Asp Leu His Glu Phe Thr Asp Leu Asn Leu Val Gln Ala Leu
 130                 135                 140

Arg Gln Phe Leu Trp Ser Phe Arg Leu Pro Gly Glu Ala Gln Lys Ile
145                 150                 155                 160

Asp Arg Met Met Glu Ala Phe Ala Gln Arg Tyr Cys Leu Cys Asn Pro
                165                 170                 175

Gly Val Phe Gln Ser Thr Asp Thr Cys Tyr Val Leu Ser Phe Ala Val
             180                 185                 190

Ile Met Leu Asn Thr Ser Leu His Asn Pro Asn Val Arg Asp Lys Pro
         195                 200                 205

Gly Leu Glu Arg Phe Val Ala Met Asn Arg Gly Ile Asn Glu Gly Gly
     210                 215                 220

Asp Leu Pro Glu Glu Leu Leu Arg Asn Leu Tyr Asp Ser Ile Arg Asn
225                 230                 235                 240

Glu Pro Phe Lys Ile Pro Glu Asp Asp Gly Asn Asp Leu Thr His Thr
                245                 250                 255

Phe Phe Asn Pro Asp Arg Glu Gly Trp Leu Leu Lys Leu Gly Arg Gly
             260                 265                 270

Arg Val Lys Thr Trp Lys Arg Arg Trp Phe Ile Leu Thr Asp Asn Cys
         275                 280                 285
```

```
Leu Tyr Tyr Phe Glu Tyr Thr Thr Asp Lys Glu Pro Arg Gly Ile Ile
        290                 295                 300

Pro Leu Glu Asn Leu Ser Ile Arg Glu Val Asp Asp Pro Arg Lys Pro
305                 310                 315                 320

Asn Cys Phe Glu Leu Tyr Ile Pro Asn Asn Lys Gly Gln Leu Ile Lys
                325                 330                 335

Ala Cys Lys Thr Glu Ala Asp Gly Arg Val Glu Gly Asn His Met
                340                 345                 350

Val Tyr Arg Ile Ser Ala Pro Thr Gln Glu Glu Lys Asp Glu Trp Ile
        355                 360                 365

Lys Ser Ile Gln Ala Ala Val Ser Val Asp Pro Phe Tyr Glu Met Leu
370                 375                 380

Ala Ala Arg Lys Lys Arg Ile Ser Val Lys Lys Lys Gln Glu Gln Pro
385                 390                 395                 400

<210> SEQ ID NO 116
<211> LENGTH: 399
<212> TYPE: PRT
<213> ORGANISM: Human

<400> SEQUENCE: 116

Met Glu Asp Gly Val Tyr Glu Pro Pro Asp Leu Thr Pro Glu Glu Arg
1               5                   10                  15

Met Glu Leu Glu Asn Ile Arg Arg Arg Lys Gln Glu Leu Leu Val Glu
                20                  25                  30

Ile Gln Arg Leu Arg Glu Glu Leu Ser Glu Ala Met Ser Glu Val Glu
            35                  40                  45

Gly Leu Glu Ala Asn Glu Gly Ser Lys Thr Leu Gln Arg Asn Arg Lys
        50                  55                  60

Met Ala Met Gly Arg Lys Lys Phe Asn Met Asp Pro Lys Lys Gly Ile
65                  70                  75                  80

Gln Phe Leu Val Glu Asn Glu Leu Leu Gln Asn Thr Pro Glu Glu Ile
                85                  90                  95

Ala Arg Phe Leu Tyr Lys Gly Glu Gly Leu Asn Lys Thr Ala Ile Gly
            100                 105                 110

Asp Tyr Leu Gly Glu Arg Glu Glu Leu Asn Leu Ala Val Leu His Ala
        115                 120                 125

Phe Val Asp Leu His Glu Phe Thr Asp Leu Asn Leu Val Gln Ala Leu
130                 135                 140

Arg Gln Phe Leu Trp Ser Phe Arg Leu Pro Gly Glu Ala Gln Lys Ile
145                 150                 155                 160

Asp Arg Met Met Glu Ala Phe Ala Gln Arg Tyr Cys Leu Cys Asn Pro
                165                 170                 175

Gly Val Phe Gln Ser Thr Asp Thr Cys Tyr Val Leu Ser Phe Ala Val
            180                 185                 190

Ile Met Leu Asn Thr Ser Leu His Asn Pro Asn Val Arg Asp Lys Pro
        195                 200                 205

Gly Leu Glu Arg Phe Val Ala Met Asn Arg Gly Ile Asn Glu Gly Gly
210                 215                 220

Asp Leu Pro Glu Glu Leu Leu Arg Asn Leu Tyr Asp Ser Ile Arg Asn
225                 230                 235                 240

Glu Pro Phe Lys Ile Pro Glu Asp Asp Gly Asn Asp Leu Thr His Thr
                245                 250                 255

Phe Phe Asn Pro Asp Arg Glu Gly Trp Leu Leu Lys Leu Gly Gly Arg
            260                 265                 270
```

```
Val Lys Thr Trp Lys Arg Arg Trp Phe Ile Leu Thr Asp Asn Cys Leu
            275                 280                 285

Tyr Tyr Phe Glu Tyr Thr Thr Asp Lys Glu Pro Arg Gly Ile Ile Pro
        290                 295                 300

Leu Glu Asn Leu Ser Ile Arg Glu Val Asp Asp Pro Arg Lys Pro Asn
305                 310                 315                 320

Cys Phe Glu Leu Tyr Ile Pro Asn Asn Lys Gly Gln Leu Ile Lys Ala
            325                 330                 335

Cys Lys Thr Glu Ala Asp Gly Arg Val Val Glu Gly Asn His Met Val
            340                 345                 350

Tyr Arg Ile Ser Ala Pro Thr Gln Glu Glu Lys Asp Glu Trp Ile Lys
            355                 360                 365

Ser Ile Gln Ala Ala Val Ser Val Asp Pro Phe Tyr Glu Met Leu Ala
            370                 375                 380

Ala Arg Lys Lys Arg Ile Ser Val Lys Lys Lys Gln Glu Gln Pro
385                 390                 395

<210> SEQ ID NO 117
<211> LENGTH: 165
<212> TYPE: PRT
<213> ORGANISM: Human

<400> SEQUENCE: 117

Met Val Asn Pro Thr Val Phe Phe Asp Ile Ala Val Asp Gly Glu Pro
1               5                   10                  15

Leu Gly Arg Val Ser Phe Glu Leu Phe Ala Asp Lys Val Pro Lys Thr
            20                  25                  30

Ala Glu Asn Phe Arg Ala Leu Ser Thr Gly Glu Lys Gly Phe Gly Tyr
            35                  40                  45

Lys Gly Ser Cys Phe His Arg Ile Ile Pro Gly Phe Met Cys Gln Gly
        50                  55                  60

Gly Asp Phe Thr Arg His Asn Gly Thr Gly Lys Ser Ile Tyr Gly
65                  70                  75                  80

Glu Lys Phe Glu Asp Glu Asn Phe Ile Leu Lys His Thr Gly Pro Gly
            85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val
            115                 120                 125

Phe Gly Lys Val Lys Glu Gly Met Asn Ile Val Glu Ala Met Glu Arg
        130                 135                 140

Phe Gly Ser Arg Asn Gly Lys Thr Ser Lys Lys Ile Thr Ile Ala Asp
145                 150                 155                 160

Cys Gly Gln Leu Glu
                165

<210> SEQ ID NO 118
<211> LENGTH: 44
<212> TYPE: PRT
<213> ORGANISM: Human

<400> SEQUENCE: 118

Thr Ala Glu Glu Glu Ala Ser Ser Glu Ala Cys Ala Gly Pro Ala Thr
1               5                   10                  15

Arg Ser Pro Gly Trp Gly Asp Pro Gly Ile Ser His Arg Asp Cys Cys
            20                  25                  30
```

```
Arg Arg Lys Ala Glu Trp Gly Thr Ala Glu Ser Arg
        35                  40

<210> SEQ ID NO 119
<211> LENGTH: 97
<212> TYPE: PRT
<213> ORGANISM: Human

<400> SEQUENCE: 119

Glu Ala Glu Leu Pro Asp Arg Gly Gly Ala Ala Val Gln Val Ser Ser
1               5                   10                  15

Pro Lys His Cys Gly Leu Cys Trp Leu Leu Cys Ser Glu Arg Leu Leu
            20                  25                  30

Leu Pro Gly Val Arg Leu Pro Ala Gln Arg Leu Pro Gly Gly Pro Ser
        35                  40                  45

Pro Leu Pro Asp Pro Gly Leu Pro Thr Ser Leu Leu Ala Ser Ala Thr
    50                  55                  60

Gly His Pro Ser Gly Tyr Ser Pro Gly Asn Ser Val Thr Ser Thr Gly
65                  70                  75                  80

Gln Pro Gln Pro His Pro Trp Arg His Gln Glu Phe Gln Arg Pro Ser
                85                  90                  95

Gly

<210> SEQ ID NO 120
<211> LENGTH: 81
<212> TYPE: PRT
<213> ORGANISM: Human

<400> SEQUENCE: 120

Leu Arg Gly Leu Ala Pro Pro Ser Pro Pro Val Ile Val Arg Arg
1               5                   10                  15

Gly Pro Arg Gly Val Ala Ala Gln Ile Pro Ala Ser Lys Leu Lys
            20                  25                  30

His Gly Gly His Pro Leu Gln Arg Leu Ala Arg Gly His Pro Arg Leu
        35                  40                  45

Leu Pro Ala Pro Pro Gly Phe His Phe Gln Gln Gln Leu Leu Gln
    50                  55                  60

Tyr Arg Val Pro Arg Gly Ser His Ser Pro Pro Arg Ser Pro Gln
65                  70                  75                  80

Gly

<210> SEQ ID NO 121
<211> LENGTH: 119
<212> TYPE: PRT
<213> ORGANISM: Human

<400> SEQUENCE: 121

Ala Pro Trp Pro Ser Ala Pro Val Pro Ala Thr Arg Asp Arg Ala Pro
1               5                   10                  15

Arg Pro Ala Arg Gly Arg Arg Pro Asp Pro Thr Ser Gln Gln Ala Lys
            20                  25                  30

Ala Trp Arg Pro Ser Pro Pro Ala Ala Arg Ser Trp Pro Pro Thr Thr
        35                  40                  45

Thr Thr Gly Ala Ala Trp Val Pro Leu Pro Ala Thr Ala Pro Ala Ala
    50                  55                  60

Val Pro Ser Ala Pro Gly Lys Pro Phe Pro Thr Pro Gln Val Ser Pro
65                  70                  75                  80
```

```
Arg Leu Thr Arg Val Ile Gly Gly Pro Ala Ser Phe Ser Gly Ser Pro
                85              90              95

Pro Ser Arg Ser Trp Pro Arg Cys Trp Ser Pro Gln Ser Thr Arg Asn
            100             105             110

Leu Pro Arg Pro Pro Ala Ala
        115

<210> SEQ ID NO 122
<211> LENGTH: 29
<212> TYPE: PRT
<213> ORGANISM: Human

<400> SEQUENCE: 122

Trp Thr Cys Ser Pro His Pro Thr Pro Thr Thr Arg Arg Ser Thr Thr
1               5                   10                  15

Ser Arg Ser Ala Ser Trp Ser Ala Arg Cys Ala Ser Thr
                20                  25
```